US012473297B2

(12) United States Patent
Lee et al.

(10) Patent No.: US 12,473,297 B2
(45) Date of Patent: Nov. 18, 2025

(54) HETEROCYCLIC COMPOUND AND ORGANIC LIGHT EMITTING DIODE COMPRISING SAME

(71) Applicant: LT MATERIALS CO., LTD., Yongin (KR)

(72) Inventors: Nam-Jin Lee, Osan-si (KR); Young-Jin Lee, Osan-si (KR); Won-Jang Jeong, Hwaseong-si (KR)

(73) Assignee: LT MATERIALS CO., LTD., Yongin (KR)

( * ) Notice: Subject to any disclaimer, the term of this patent is extended or adjusted under 35 U.S.C. 154(b) by 903 days.

(21) Appl. No.: 17/288,701

(22) PCT Filed: Nov. 12, 2019

(86) PCT No.: PCT/KR2019/015309

§ 371 (c)(1),
(2) Date: Apr. 26, 2021

(87) PCT Pub. No.: WO2020/101314

PCT Pub. Date: May 22, 2020

(65) Prior Publication Data

US 2022/0013729 A1 Jan. 13, 2022

(30) Foreign Application Priority Data

Nov. 12, 2018 (KR) ........................ 10-2018-0138490

(51) Int. Cl.
*C07D 491/107* (2006.01)
*C07D 471/10* (2006.01)
(Continued)

(52) U.S. Cl.
CPC ....... *C07D 491/107* (2013.01); *C07D 471/10* (2013.01); *C07D 495/10* (2013.01);
(Continued)

(58) Field of Classification Search
CPC .. C07D 471/10; C07D 471/40; C07D 495/04; C07D 495/10; C07D 519/00; C07F 9/53;
(Continued)

(56) References Cited

U.S. PATENT DOCUMENTS

| | | | |
|---|---|---|---|
| 4,356,429 | A | 10/1982 | Tang |
| 10,177,319 | B2 | 1/2019 | No et al. |

(Continued)

FOREIGN PATENT DOCUMENTS

| | | | |
|---|---|---|---|
| CN | 105906640 | A | 8/2016 |
| CN | 108864146 | A | 11/2018 |

(Continued)

OTHER PUBLICATIONS

International Search Report for PCT/KR2019/015309 mailed on Feb. 21, 2020.

(Continued)

*Primary Examiner* — Elizabeth M. Dahlburg
(74) *Attorney, Agent, or Firm* — Birch, Stewart, Kolasch & Birch, LLP

(57) ABSTRACT

The present specification relates to a heterocyclic compound represented by Chemical Formula 1, and an organic light emitting device comprising the same.
(Continued)

[Chemical Formula 1]

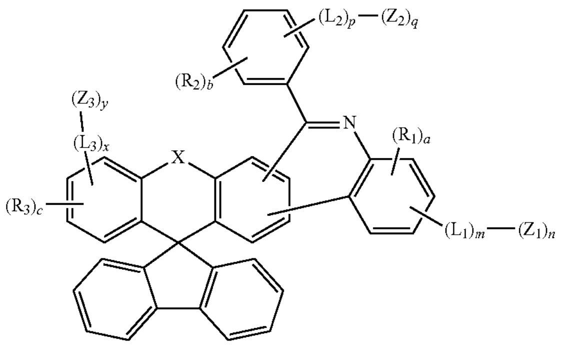

17 Claims, 3 Drawing Sheets

(51) Int. Cl.

| | |
|---|---|
| ***C07D 495/10*** | (2006.01) |
| ***C07D 519/00*** | (2006.01) |
| ***C09K 11/06*** | (2006.01) |
| ***H10K 50/16*** | (2023.01) |
| ***H10K 50/17*** | (2023.01) |
| ***H10K 50/18*** | (2023.01) |
| ***H10K 50/19*** | (2023.01) |
| ***H10K 85/60*** | (2023.01) |
| *H10K 50/15* | (2023.01) |

(52) U.S. Cl.

CPC ............ *C07D 519/00* (2013.01); *C09K 11/06* (2013.01); *H10K 85/615* (2023.02); *H10K 85/624* (2023.02); *H10K 85/654* (2023.02); *H10K 85/657* (2023.02); *H10K 85/6572* (2023.02); *H10K 85/6574* (2023.02); *H10K 85/6576* (2023.02); *C09K 2211/1018* (2013.01); *H10K 50/15* (2023.02); *H10K 50/16* (2023.02); *H10K 50/17* (2023.02); *H10K 50/171* (2023.02); *H10K 50/18* (2023.02); *H10K 50/19* (2023.02)

(58) Field of Classification Search

CPC .................. C07F 9/5325; C09K 11/06; C09K 2211/1018; H01L 51/0052; H01L 51/0056; H01L 51/0067; H01L 51/0073; H01L 51/0074; H01L 51/5056; H01L 51/5072; H01L 51/5076; H01L 51/5088; H01L 51/5092; H01L 51/5096; H10K 50/00; H10K 50/15; H10K 50/16; H10K 50/165; H10K 50/17; H10K 50/171; H10K 50/18; H10K 50/19; H10K 85/615; H10K 85/624; H10K 85/654; H10K 85/657; H10K 85/6572; H10K 85/6574; H10K 85/6576

See application file for complete search history.

(56) References Cited

U.S. PATENT DOCUMENTS

| | | | | |
|---|---|---|---|---|
| 2003/0189401 | A1* | 10/2003 | Kido ...................... | H10K 50/15 313/506 |
| 2017/0179395 | A1 | 6/2017 | Kim et al. | |
| 2017/0317295 | A1* | 11/2017 | No ........................ | C07F 9/5765 |
| 2019/0010164 | A1 | 1/2019 | Cha et al. | |

FOREIGN PATENT DOCUMENTS

| | | | |
|---|---|---|---|
| JP | 2003-96072 | A | 4/2003 |
| KR | 10-2017-0075123 | A | 7/2017 |
| KR | 10-2017-0089785 | A | 8/2017 |
| KR | 10-2018-0037695 | A | 4/2018 |
| WO | WO 2016/068633 | A2 | 5/2016 |

OTHER PUBLICATIONS

Kuwabara et al., "Thermally Stable Multilayered Organic Electroluminescent Devices Using Novel Starburst Molecules, 4,4',4"-Tri(N-carbazolyl)triphenylamine (TCTA) and 4,4',4"-Tris(3-methylphenylphenyl-amino)triphenylamine (m-MTDATA), as Hole-Transport Materials", Advanced Material, 1994, vol. 6, No. 9, pp. 677-679.

* cited by examiner

【FIG. 1】
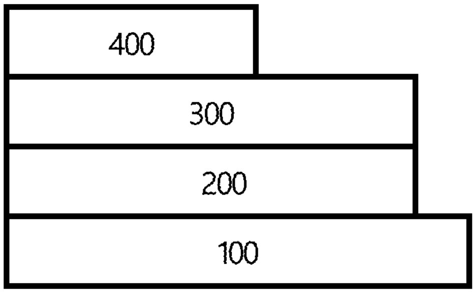
【FIG. 2】
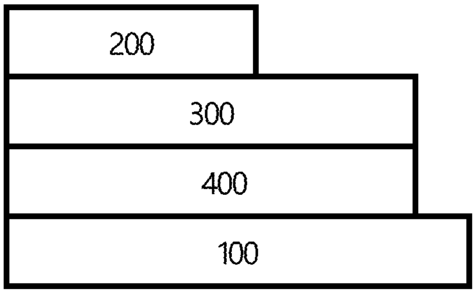

【FIG. 3】
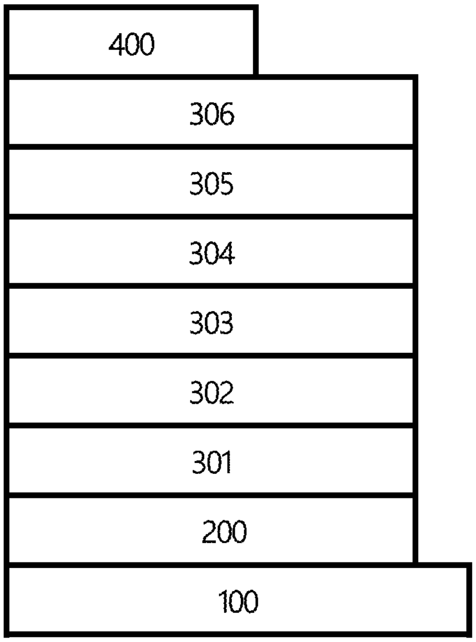

【FIG. 4】
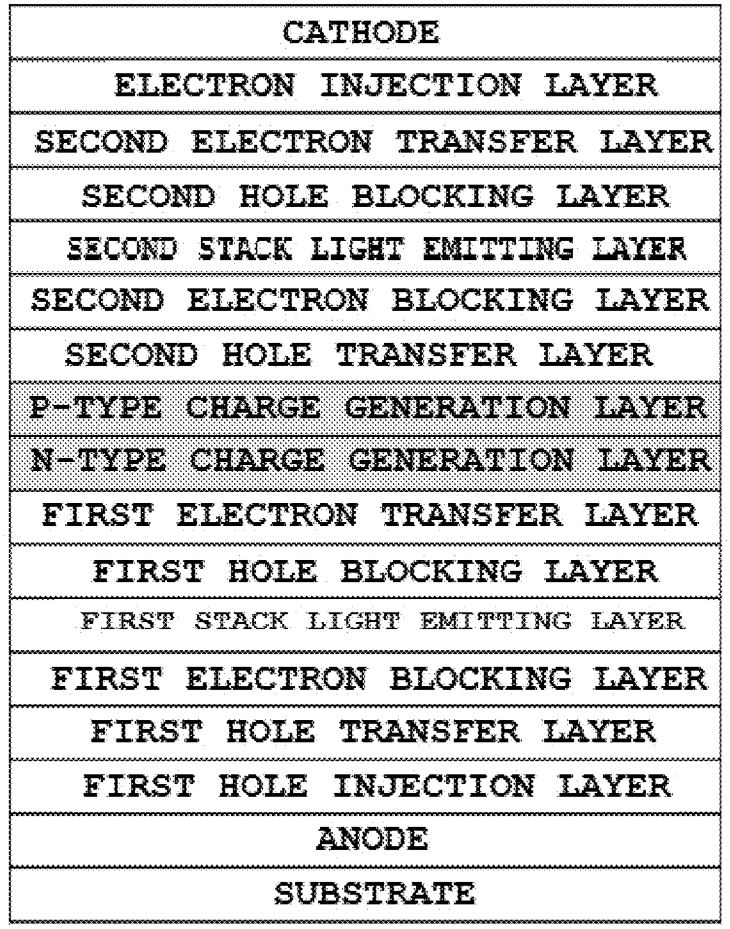

HETEROCYCLIC COMPOUND AND ORGANIC LIGHT EMITTING DIODE COMPRISING SAME

TECHNICAL FIELD

This application claims priority to and the benefits of Korean Patent Application No. 10-2018-0138490, filed with the Korean Intellectual Property Office on Nov. 12, 2018, the entire contents of which are incorporated herein by reference.

The present specification relates to a heterocyclic compound, and an organic light emitting device comprising the same.

BACKGROUND ART

An electroluminescent device is one type of self-emissive display devices, and has an advantage of having a wide viewing angle, and a high response speed as well as having an excellent contrast.

An organic light emitting device has a structure disposing an organic thin film between two electrodes. When a voltage is applied to an organic light emitting device having such a structure, electrons and holes injected from the two electrodes bind and pair in the organic thin film, and light emits as these annihilate. The organic thin film may be formed in a single layer or a multilayer as necessary.

A material of the organic thin film may have a light emitting function as necessary. For example, as a material of the organic thin film, compounds capable of forming a light emitting layer themselves alone may be used, or compounds capable of performing a role of a host or a dopant of a host-dopant-based light emitting layer may also be used. In addition thereto, compounds capable of performing roles of hole injection, hole transfer, electron blocking, hole blocking, electron transfer, electron injection and the like may also be used as a material of the organic thin film.

Development of an organic thin film material has been continuously required for enhancing performance, lifetime or efficiency of an organic light emitting device.

PRIOR ART DOCUMENTS

Patent Documents

U.S. Pat. No. 4,356,429

DISCLOSURE

Technical Problem

The present specification is directed to providing a heterocyclic compound, and an organic light emitting device comprising the same.

Technical Solution

One embodiment of the present specification provides a heterocyclic compound represented by the following Chemical Formula 1.

[Chemical Formula 1]

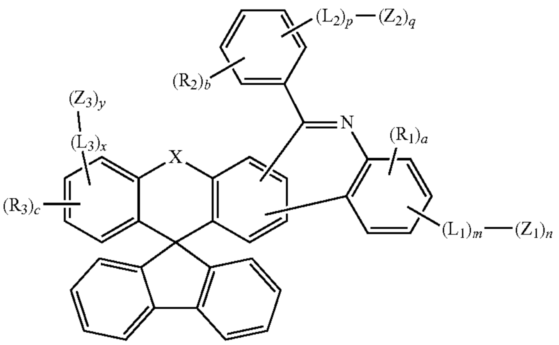

In Chemical Formula 1,

X is O; S; or $NR_{21}$, $L_1$ to $L_3$ are the same as or different from each other, and each independently a direct bond; a substituted or unsubstituted arylene group; or a substituted or unsubstituted heteroarylene group, $Z_1$ to $Z_3$ are the same as or different from each other, and each independently selected from the group consisting of hydrogen; deuterium; a halogen group; a cyano group; a substituted or unsubstituted alkyl group; a substituted or unsubstituted alkenyl group; a substituted or unsubstituted alkynyl group; a substituted or unsubstituted alkoxy group; a substituted or unsubstituted cycloalkyl group; a substituted or unsubstituted heterocycloalkyl group; a substituted or unsubstituted aryl group; a substituted or unsubstituted heteroaryl group; a substituted or unsubstituted phosphine oxide group; and a substituted or unsubstituted amine group, $R_1$ to $R_3$ are the same as or different from each other, and each independently selected from the group consisting of hydrogen; deuterium; a halogen group; a cyano group; a substituted or unsubstituted alkyl group; a substituted or unsubstituted alkenyl group; a substituted or unsubstituted alkynyl group; a substituted or unsubstituted alkoxy group; a substituted or unsubstituted cycloalkyl group; a substituted or unsubstituted heterocycloalkyl group; a substituted or unsubstituted aryl group; a substituted or unsubstituted heteroaryl group; a substituted or unsubstituted phosphine oxide group; and a substituted or unsubstituted amine group, or two or more groups adjacent to each other bond to each other to form a substituted or unsubstituted aliphatic or aromatic hydrocarbon ring or heteroring, $R_{21}$ is hydrogen; or a substituted or unsubstituted aryl group, m, p, x, n, q and y are each an integer of 1 to 5, a is an integer of 1 to 3, b is an integer of 1 to 4, c is an integer of 1 to 3, and when m, p, x, n, q, y, a, b and c are an integer of 2 or greater, substituents in the parentheses are the same as or different from each other.

Another embodiment of the present specification provides an organic light emitting device comprising a first electrode; a second electrode; and one or more organic material layers provided between the first electrode and the second electrode, wherein one or more layers of the organic material layers comprise the heterocyclic compound represented by Chemical Formula 1.

Advantageous Effects

A compound described in the present specification can be used as a material of an organic material layer of an organic light emitting device. The compound is capable of performing a role of a hole injection material, a hole transfer material, a light emitting material, an electron transfer material, an electron injection material and the like. Particularly, the compound can be used as an electron transfer layer material, a hole blocking layer material or a charge generation layer material of an organic light emitting device.

Specifically, when using the compound represented by Chemical Formula 1 in an organic material layer, a device driving voltage can be lowered, light efficiency can be enhanced, and device lifetime properties can be enhanced.

DESCRIPTION OF DRAWINGS

FIG. 1 to FIG. 4 are diagrams each illustrating a lamination structure of an organic light emitting device according to one embodiment of the present specification.

REFERENCE NUMERAL

100: Substrate
200: Anode
300: Organic Material Layer
301: Hole Injection Layer
302: Hole Transfer Layer
303: Light Emitting Layer
304: Hole Blocking Layer
305: Electron Transfer Layer
306: Electron Injection Layer
400: Cathode

MODE FOR DISCLOSURE

Hereinafter, the present specification will be described in more detail.

In the present specification, a certain part "comprising" certain constituents means capable of further comprising other constituents, and does not exclude other constituents unless particularly stated on the contrary.

A term "substitution" means a hydrogen atom bonding to a carbon atom of a compound is changed to another substituent, and the position of substitution is not limited as long as it is a position at which the hydrogen atom is substituted, that is, a position at which a substituent can substitute, and when two or more substituents substitute, the two or more substituents may be the same as or different from each other.

In the present specification, the halogen may be fluorine, chlorine, bromine or iodine.

In the present specification, the alkyl group comprises linear or branched having 1 to 60 carbon atoms, and may be further substituted with other substituents. The number of carbon atoms of the alkyl group may be from 1 to 60, specifically from 1 to 40 and more specifically from 1 to 20. Specific examples thereof may comprise a methyl group, an ethyl group, a propyl group, an n-propyl group, an isopropyl group, a butyl group, an n-butyl group, an isobutyl group, a tert-butyl group, a sec-butyl group, a 1-methyl-butyl group, a 1-ethylbutyl group, a pentyl group, an n-pentyl group, an isopentyl group, a neopentyl group, a tert-pentyl group, a hexyl group, an n-hexyl group, a 1-methylpentyl group, a 2-methylpentyl group, a 4-methyl-2-pentyl group, a 3,3-dimethylbutyl group, a 2-ethylbutyl group, a heptyl group, an n-heptyl group, a 1-methylhexyl group, a cyclopentylmethyl group, a cyclohexylmethyl group, an octyl group, an n-octyl group, a tert-octyl group, a 1-methylheptyl group, a 2-ethylhexyl group, a 2-propylpentyl group, an n-nonyl group, a 2,2-dimethylheptyl group, a 1-ethyl-propyl group, a 1,1-dimethyl-propyl group, an isohexyl group, a 2-methylpentyl group, a 4-methylhexyl group, a 5-methylhexyl group and the like, but are not limited thereto.

In the present specification, the alkenyl group comprises linear or branched having 2 to 60 carbon atoms, and may be further substituted with other substituents. The number of carbon atoms of the alkenyl group may be from 2 to 60, specifically from 2 to 40 and more specifically from 2 to 20. Specific examples thereof may comprise a vinyl group, a 1-propenyl group, an isopropenyl group, a 1-butenyl group, a 2-butenyl group, a 3-butenyl group, a 1-pentenyl group, a 2-pentenyl group, a 3-pentenyl group, a 3-methyl-1-butenyl group, a 1,3-butadienyl group, an allyl group, a 1-phenylvinyl-1-yl group, a 2-phenylvinyl-1-yl group, a 2,2-diphenylvinyl-1-yl group, a 2-phenyl-2-(naphthyl-1-yl)vinyl-1-yl group, a 2,2-bis(diphenyl-1-yl)vinyl-1-yl group, a stilbenyl group, a styrenyl group and the like, but are not limited thereto.

In the present specification, the alkynyl group comprises linear or branched having 2 to 60 carbon atoms, and may be further substituted with other substituents. The number of carbon atoms of the alkynyl group may be from 2 to 60, specifically from 2 to 40 and more specifically from 2 to 20.

In the present specification, the alkoxy group may be linear, branched or cyclic. The number of carbon atoms of the alkoxy group is not particularly limited, but is preferably from 1 to 20. Specific examples thereof may comprise methoxy, ethoxy, n-propoxy, isopropoxy, i-propyloxy, n-butoxy, isobutoxy, tert-butoxy, sec-butoxy, n-pentyloxy, neopentyloxy, isopentyloxy, n-hexyloxy, 3,3-dimethylbutyloxy, 2-ethylbutyloxy, n-octyloxy, n-nonyloxy, n-decyloxy, benzyloxy, p-methylbenzyloxy and the like, but are not limited thereto.

In the present specification, the cycloalkyl group comprises monocyclic or polycyclic having 3 to 60 carbon atoms, and may be further substituted with other substituents. Herein, the polycyclic means a group in which the cycloalkyl group is directly linked to or fused with other cyclic groups. Herein, the other cyclic groups may be a cycloalkyl group, but may also be different types of cyclic groups such as a heterocycloalkyl group, an aryl group and a heteroaryl group. The number of carbon groups of the cycloalkyl group may be from 3 to 60, specifically from 3 to 40 and more specifically from 5 to 20. Specific examples thereof may comprise a cyclopropyl group, a cyclobutyl group, a cyclopentyl group, a 3-methylcyclopentyl group, a 2,3-dimethylcyclopentyl group, a cyclohexyl group, a 3-methylcyclohexyl group, a 4-methylcyclohexyl group, a 2,3-dimethylcyclohexyl group, a 3,4,5-trimethylcyclohexyl group, a 4-tert-butylcyclohexyl group, a cycloheptyl group, a cyclooctyl group and the like, but are not limited thereto.

In the present specification, the heterocycloalkyl group comprises O, S, Se, N or Si as a heteroatom, comprises monocyclic or polycyclic having 2 to 60 carbon atoms, and may be further substituted with other substituents. Herein, the polycyclic means a group in which the heterocycloalkyl group is directly linked to or fused with other cyclic groups. Herein, the other cyclic groups may be a heterocycloalkyl group, but may also be different types of cyclic groups such as a cycloalkyl group, an aryl group and a heteroaryl group. The number of carbon atoms of the heterocycloalkyl group may be from 2 to 60, specifically from 2 to 40 and more specifically from 3 to 20.

In the present specification, the aryl group comprises monocyclic or polycyclic having 6 to 60 carbon atoms, and may be further substituted with other substituents. Herein, the polycyclic means a group in which the aryl group is directly linked to or fused with other cyclic groups. Herein, the other cyclic groups may be an aryl group, but may also be different types of cyclic groups such as a cycloalkyl group, a heterocycloalkyl group and a heteroaryl group. The aryl group comprises a spiro group. The number of carbon atoms of the aryl group may be from 6 to 60, specifically from 6 to 40 and more specifically from 6 to 25. Specific examples of the aryl group may comprise a phenyl group, a biphenyl group, a triphenyl group, a naphthyl group, an anthryl group, a chrysenyl group, a phenanthrenyl group, a perylenyl group, a fluoranthenyl group, a triphenylenyl group, a phenalenyl group, a pyrenyl group, a tetracenyl group, a pentacenyl group, a fluorenyl group, an indenyl group, an acenaphthylenyl group, a benzofluorenyl group, a spirobifluorenyl group, a 2,3-dihydro-1H-indenyl group, a fused ring thereof, and the like, but are not limited thereto.

In the present specification, the silyl group is a substituent comprising Si, having the Si atom directly linked as a radical, and is represented by $—SiR_{104}R_{105}R_{106}$. $R_{104}$ to $R_{106}$ are the same as or different from each other, and may be each independently a substituent formed with at least one of hydrogen; deuterium; a halogen group; an alkyl group; an alkenyl group; an alkoxy group; a cycloalkyl group; an aryl group; and a heterocyclic group. Specific examples of the silyl group may comprise a trimethylsilyl group, a triethylsilyl group, a t-butyldimethylsilyl group, a vinyldimethylsilyl group, a propyldimethylsilyl group, a triphenylsilyl group, a diphenylsilyl group, a phenylsilyl group and the like, but are not limited thereto.

In the present specification, the fluorenyl group may be substituted, and adjacent substituents may bond to each other to form a ring.

When the fluorenyl group is substituted,

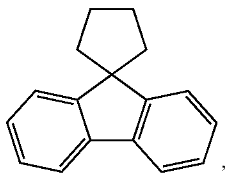
,
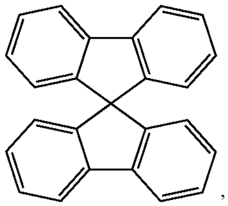
,
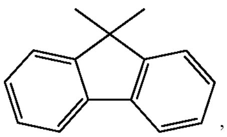
,
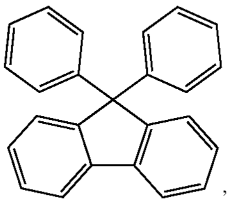
,
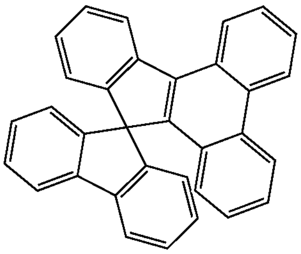
,

-continued

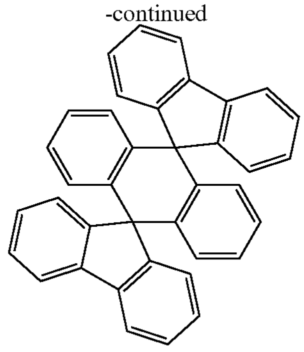

and the like may be included, however, the structure is not limited thereto.

In the present specification, the heteroaryl group comprises O, S, Se, N or Si as a heteroatom, comprises monocyclic or polycyclic having 2 to 60 carbon atoms, and may be further substituted with other substituents. Herein, the polycyclic means a group in which the heteroaryl group is directly linked to or fused with other cyclic groups. Herein, the other cyclic groups may be a heteroaryl group, but may also be different types of cyclic groups such as a cycloalkyl group, a heterocycloalkyl group and an aryl group. The number of carbon atoms of the heteroaryl group may be from 2 to 60, specifically from 2 to 40 and more specifically from 3 to 25. Specific examples of the heteroaryl group may comprise a pyridyl group, a pyrrolyl group, a pyrimidyl group, a pyridazinyl group, a furanyl group, a thiophene group, an imidazolyl group, a pyrazolyl group, an oxazolyl group, an isoxazolyl group, a thiazolyl group, an isothiazolyl group, a triazolyl group, a furazanyl group, an oxadiazolyl group, a thiadiazolyl group, a dithiazolyl group, a tetrazolyl group, a pyranyl group, a thiopyranyl group, a diazinyl group, an oxazinyl group, a thiazinyl group, a dioxynyl group, a triazinyl group, a tetrazinyl group, a quinolyl group, an isoquinolyl group, a quinazolinyl group, an isoquinazolinyl group, a qninozolinyl group, a naphthyridyl group, an acridinyl group, a phenanthridinyl group, an imidazopyridinyl group, a diazanaphthalenyl group, a triazaindene group, an indolyl group, an indolizinyl group, a benzothiazolyl group, a benzoxazolyl group, a benzimidazolyl group, a benzothiophene group, a benzofuran group, a dibenzothiophene group, a dibenzofuran group, a carbazolyl group, a benzocarbazolyl group, a dibenzocarbazolyl group, a phenazinyl group, a dibenzosilole group, spirobi(dibenzosilole), a dihydrophenazinyl group, a phenoxazinyl group, a phenanthridyl group, an imidazopyridinyl group, a thienyl group, an indolo[2,3-a]carbazolyl group, an indolo[2,3-b]carbazolyl group, an indolinyl group, a 10,11-dihydrodibenzo[b,f]azepine group, a 9,10-dihydroacridinyl group, a phenanthrazinyl group, a phenothiathiazinyl group, a phthalazinyl group, a naphthylidinyl group, a phenanthrolinyl group, a benzo[c][1,2,5]thiadiazolyl group, a 5,10-dihydrobenzo[b,e][1,4]azasilinyl, a pyrazolo[1,5-c]quinazolinyl group, a pyrido[1,2-b]indazolyl group, a pyrido[1,2-a]imidazo[1,2-e]indolinyl group, a 5,11-dihydroindeno[1,2-b]carbazolyl group and the like, but are not limited thereto.

In the present specification, the phosphine oxide group may be specifically substituted with an aryl group, and as the aryl group, examples described above may be used. Examples of the phosphine oxide group may comprise a diphenylphosphine oxide group, a dinaphthylphosphine oxide group and the like, but are not limited thereto.

In the present specification, the amine group may be selected from the group consisting of a monoalkylamine group; a monoarylamine group; a monoheteroarylamine group; —$NH_2$; a dialkylamine group; a diarylamine group; a diheteroarylamine group; an alkylarylamine group; an alkylheteroarylamine group; and an arylheteroarylamine group, and although not particularly limited thereto, the number of carbon atoms is preferably from 1 to 30. Specific examples of the amine group may comprise a methylamine group, a dimethylamine group, an ethylamine group, a diethylamine group, a phenylamine group, a naphthylamine group, a biphenylamine group, a dibiphenylamine group, an anthracenylamine group, a 9-methyl-anthracenylamine group, a diphenylamine group, a phenylnaphthylamine group, a ditolylamine group, a phenyltolylamine group, a triphenylamine group, a biphenylnaphthylamine group, a phenylbiphenylamine group, a biphenylfluorenylamine group, a phenyltriphenylenylamine group, a biphenyltriphenylenylamine group and the like, but are not limited thereto.

In the present specification, an "adjacent" group may mean a substituent substituting an atom directly linked to an atom substituted by the corresponding substituent, a substituent sterically most closely positioned to the corresponding substituent, or another substituent substituting an atom substituted by the corresponding substituent. For example, two substituents substituting ortho positions in a benzene ring, and two substituents substituting the same carbon in an aliphatic ring may be interpreted as groups "adjacent" to each other.

As the aliphatic or aromatic hydrocarbon ring or heteroring that the adjacent groups may form, the structures illustrated as the cycloalkyl group, the cycloheteroalkyl group, the aryl group and the heteroaryl group may be used except for those that are not monovalent.

In the present specification, "substituted or unsubstituted" means being substituted with one or more substituents selected from the group consisting of C1 to C60 linear or branched alkyl; C2 to C60 linear or branched alkenyl; C2 to C60 linear or branched alkynyl; C3 to C60 monocyclic or polycyclic cycloalkyl; C2 to C60 monocyclic or polycyclic heterocycloalkyl; C6 to C60 monocyclic or polycyclic aryl; C2 to C60 monocyclic or polycyclic heteroaryl; —SiRR'R"; —P(=O)RR'; C1 to C20 alkylamine; C6 to C60 monocyclic or polycyclic arylamine; and C2 to C60 monocyclic or polycyclic heteroarylamine, or being unsubstituted, or being substituted with a substituent linking two or more substituents selected from among the substituents illustrated above, or being unsubstituted. R, R' and R" are the same as or different from each other, and each independently hydrogen; deuterium; a cyano group; a substituted or unsubstituted alkyl group; a substituted or unsubstituted cycloalkyl group; a substituted or unsubstituted aryl group; or a substituted or unsubstituted heteroaryl group.

One embodiment of the present specification provides a compound represented by Chemical Formula 1.

By having a structure in which a heteroring is fused to spirofluorene, Chemical Formula 1 has an excellent electron transfer ability as a hopping ability is enhanced by an expansion of conjugation, and as a result, driving and efficiency may be improved when used in a device.

In the heterocyclic compound provided in one embodiment of the present specification, Chemical Formula 1 is represented by any one of the following Chemical Formulae 2 to 5.

[Chemical Formula 2]

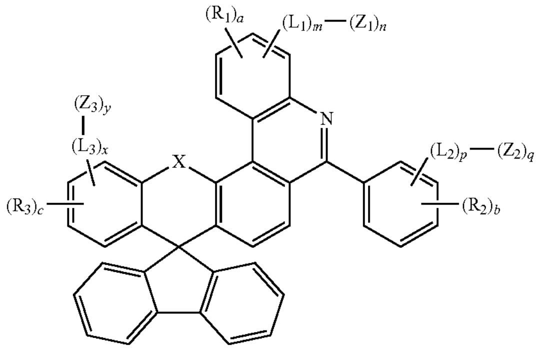

[Chemical Formula 3]

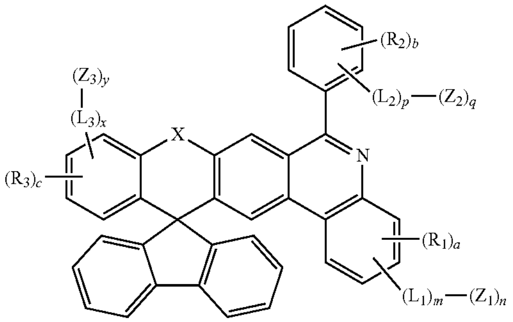

[Chemical Formula 4]

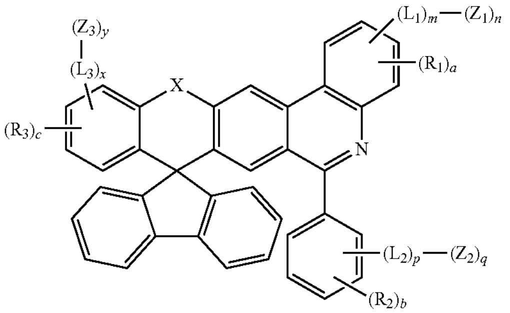

[Chemical Formula 5]

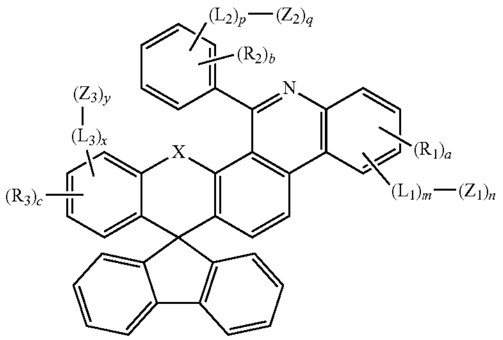

In Chemical Formula 2 to Chemical Formula 5, each substituent has the same definition as in Chemical Formula 1.

In one embodiment of the present specification, X may be O; S; or $NR_{21}$.

In another embodiment, X may be O.

In another embodiment, X may be S.

In another embodiment, X may be $NR_{21}$.

In one embodiment of the present specification, $R_{21}$ may be hydrogen; or a substituted or unsubstituted aryl group.

In another embodiment, $R_{21}$ may be a substituted or unsubstituted aryl group.

In another embodiment, $R_{21}$ may be a phenyl group.

In one embodiment of the present specification, $L_1$ to $L_3$ are the same as or different from each other, and may be each independently a direct bond; a substituted or unsubstituted arylene group; or a substituted or unsubstituted heteroarylene group.

In another embodiment, $L_1$ to $L_3$ are the same as or different from each other, and may be each independently a direct bond; a substituted or unsubstituted C6 to C60 arylene group; or a substituted or unsubstituted C2 to C60 heteroarylene group.

In another embodiment, $L_1$ to $L_3$ are the same as or different from each other, and may be each independently a direct bond; a substituted or unsubstituted C6 to C40 arylene group; or a substituted or unsubstituted C2 to C40 heteroarylene group.

In another embodiment, $L_1$ to $L_3$ are the same as or different from each other, and may be each independently a direct bond; a substituted or unsubstituted C6 to C20 arylene group; or a substituted or unsubstituted C2 to C20 heteroarylene group.

In another embodiment, $L_1$ to $L_3$ are the same as or different from each other, and may be each independently a direct bond; a C6 to C20 arylene group; or a C2 to C20 heteroarylene group.

In another embodiment, $L_1$ to $L_3$ are the same as or different from each other, and may be each independently a direct bond; a phenylene group; a biphenylene group; a naphthylene group; an anthracene group; a phenanthrene group; a divalent pyrimidine group; a divalent triazine group; a divalent pyridine group; a divalent quinazoline group; or a divalent quinoxaline group.

In one embodiment of the present specification, $Z_1$ to $Z_3$ are the same as or different from each other, and may be each independently selected from the group consisting of hydrogen; deuterium; a halogen group; a cyano group; a substituted or unsubstituted alkyl group; a substituted or unsubstituted alkenyl group; a substituted or unsubstituted alkynyl group; a substituted or unsubstituted alkoxy group; a substituted or unsubstituted cycloalkyl group; a substituted or unsubstituted heterocycloalkyl group; a substituted or unsubstituted aryl group; a substituted or unsubstituted heteroaryl group; a substituted or unsubstituted phosphine oxide group; and a substituted or unsubstituted amine group.

In another embodiment, $Z_1$ to $Z_3$ are the same as or different from each other, and may be each independently hydrogen; deuterium; a cyano group; a substituted or unsubstituted aryl group; a substituted or unsubstituted heteroaryl group; or a substituted or unsubstituted phosphine oxide group.

In another embodiment, $Z_1$ to $Z_3$ are the same as or different from each other, and may be each independently hydrogen; deuterium; a cyano group; a substituted or unsubstituted C6 to C60 aryl group; a substituted or unsubstituted C2 to C60 heteroaryl group; or a substituted or unsubstituted phosphine oxide group.

In another embodiment, $Z_1$ to $Z_3$ are the same as or different from each other, and may be each independently hydrogen; deuterium; a cyano group; a substituted or unsubstituted C6 to C40 aryl group; a substituted or unsubstituted C2 to C40 heteroaryl group; or a substituted or unsubstituted phosphine oxide group.

In another embodiment, $Z_1$ to $Z_3$ are the same as or different from each other, and may be each independently hydrogen; deuterium; a cyano group; a C6 to C40 aryl group unsubstituted or substituted with one or more substituents selected from the group consisting of a C6 to C40 aryl group, a C2 to C40 heteroaryl group and a C1 to C40 alkyl group; a C2 to C40 heteroaryl group unsubstituted or substituted with one or more substituents selected from the group consisting of a C6 to C40 aryl group and a C1 to C40 alkyl group; or a substituted or unsubstituted phosphine oxide group.

In another embodiment, $Z_1$ to $Z_3$ are the same as or different from each other, and may be each independently hydrogen; deuterium; a cyano group; a phenyl group; a biphenyl group; an anthracene group; a triphenylene group; a dibenzofuran group; a dibenzothiophene group; a pyrimidine group unsubstituted or substituted with one or more substituents selected from the group consisting of a phenyl group, a biphenyl group, a dibenzofuran group and a dibenzothiophene group; a triazine group unsubstituted or substituted with one or more substituents selected from the group consisting of a phenyl group, a biphenyl group, a dibenzofuran group and a dibenzothiophene group; a phenanthroline group unsubstituted or substituted with a phenyl group; a quinazoline group unsubstituted or substituted with a phenyl group; a quinoxaline group unsubstituted or substituted with a phenyl group; a carbazole group unsubstituted or substituted with one or more substituents selected from the group consisting of a phenyl group and a cyano group; an imidazole group unsubstituted or substituted with a phenyl group; a pyridine group unsubstituted or substituted with a pyridine group; a benzo[4,5]thieno[3,2-d]pyrimidine group unsubstituted or substituted with a phenyl group; or a phosphine oxide group unsubstituted or substituted with a phenyl group.

In one embodiment of the present specification, $R_1$ to $R_3$ are the same as or different from each other, and each independently selected from the group consisting of hydrogen; deuterium; a halogen group; a cyano group; a substituted or unsubstituted alkyl group; a substituted or unsubstituted alkenyl group; a substituted or unsubstituted alkynyl group; a substituted or unsubstituted alkoxy group; a substituted or unsubstituted cycloalkyl group; a substituted or unsubstituted heterocycloalkyl group; a substituted or unsubstituted aryl group; a substituted or unsubstituted heteroaryl group; a substituted or unsubstituted phosphine oxide group; and a substituted or unsubstituted amine group, or two or more groups adjacent to each other may bond to each other to form a substituted or unsubstituted aliphatic or aromatic hydrocarbon ring or heteroring.

In another embodiment, $R_1$ to $R_3$ may be hydrogen.

In the heterocyclic compound provided in one embodiment of the present specification, Chemical Formula 1 is represented by any one of the following Chemical Formulae 6 to 8.

[Chemical Formula 6]

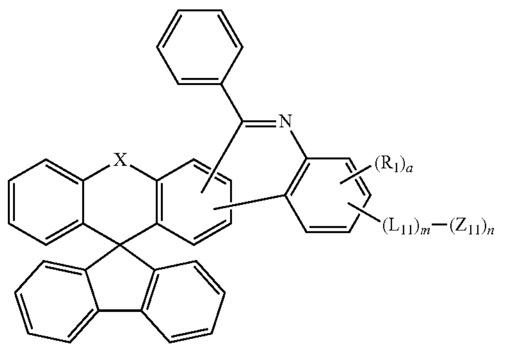

[Chemical Formula 7]

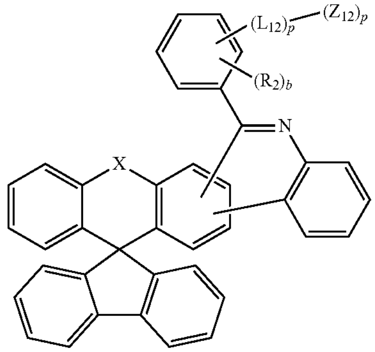

[Chemical Formula 8]

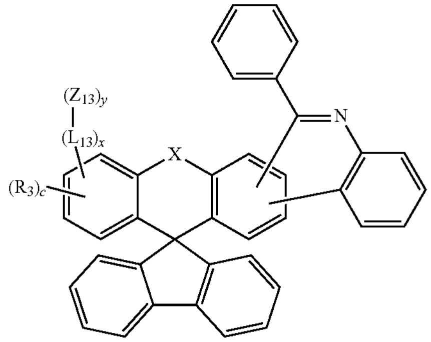

in Chemical Formulae 6 to 8,

X, $R_1$ to $R_3$, m, p, x, n, q, y, a, b and c have the same definitions as in Chemical Formula 1.

In one embodiment of the present specification, $L_{11}$ to $L_{13}$ are the same as or different from each other, and may be each independently a direct bond; a substituted or unsubstituted arylene group; or a substituted or unsubstituted heteroarylene group.

In another embodiment, $L_{11}$ to $L_{13}$ are the same as or different from each other, and may be each independently a direct bond; a substituted or unsubstituted C6 to C60 arylene group; or a substituted or unsubstituted C2 to C60 heteroarylene group.

In another embodiment, $L_{11}$ to $L_{13}$ are the same as or different from each other, and may be each independently a direct bond; a substituted or unsubstituted C6 to C40 arylene group; or a substituted or unsubstituted C2 to C40 heteroarylene group.

In another embodiment, $L_{11}$ to $L_{13}$ are the same as or different from each other, and may be each independently a direct bond; a substituted or unsubstituted C6 to C20 arylene group; or a substituted or unsubstituted C2 to C20 heteroarylene group.

In another embodiment, $L_{11}$ to $L_{13}$ are the same as or different from each other, and may be each independently a direct bond; a C6 to C20 arylene group; or a C2 to C20 heteroarylene group.

In another embodiment, $L_{11}$ to $L_{13}$ are the same as or different from each other, and may be each independently a direct bond; a phenylene group; a biphenylene group; a naphthylene group; an anthracene group; a phenanthrene group; a divalent pyrimidine group; a divalent triazine group; a divalent pyridine group; a divalent quinazoline group; or a divalent quinoxaline group.

In one embodiment of the present specification, $Z_{11}$ to $Z_{13}$ are the same as or different from each other, and may be each independently selected from the group consisting of a cyano group; a substituted or unsubstituted aryl group; a substituted or unsubstituted heteroaryl group; and a substituted or unsubstituted phosphine oxide group.

In another embodiment, $Z_{11}$ to $Z_{13}$ are the same as or different from each other, and may be each independently a cyano group; a substituted or unsubstituted C6 to C60 aryl group; a substituted or unsubstituted C2 to C60 heteroaryl group; or a substituted or unsubstituted phosphine oxide group.

In another embodiment, $Z_{11}$ to $Z_{13}$ are the same as or different from each other, and may be each independently a cyano group; a substituted or unsubstituted C6 to C40 aryl group; a substituted or unsubstituted C2 to C40 heteroaryl group; or a substituted or unsubstituted phosphine oxide group.

In another embodiment, $Z_{11}$ to $Z_{13}$ are the same as or different from each other, and may be each independently a cyano group; a C6 to C40 aryl group unsubstituted or substituted with one or more substituents selected from the group consisting of a C6 to C40 aryl group, a C2 to C40 heteroaryl group and a C1 to C40 alkyl group; a C2 to C40 heteroaryl group unsubstituted or substituted with one or more substituents selected from the group consisting of a C6 to C40 aryl group and a C1 to C40 alkyl group; or a substituted or unsubstituted phosphine oxide group.

In another embodiment, $Z_{11}$ to $Z_{13}$ are the same as or different from each other, and may be each independently a cyano group; a phenyl group; a biphenyl group; an anthracene group; a triphenylene group; a dibenzofuran group; a dibenzothiophene group; a pyrimidine group unsubstituted or substituted with one or more substituents selected from the group consisting of a phenyl group, a biphenyl group, a dibenzofuran group and a dibenzothiophene group; a triazine group unsubstituted or substituted with one or more substituents selected from the group consisting of a phenyl group, a biphenyl group, a dibenzofuran group and a dibenzothiophene group; a phenanthroline group unsubstituted or substituted with a phenyl group; a quinazoline group unsubstituted or substituted with a phenyl group; a quinoxaline group unsubstituted or substituted with a phenyl group; a carbazole group unsubstituted or substituted with one or more substituents selected from the group consisting of a phenyl group and a cyano group; an imidazole group unsubstituted or substituted with a phenyl group; a pyridine group unsubstituted or substituted with a pyridine group; a benzo[4,5]thieno[3,2-d]pyrimidine group unsubstituted or substituted with a phenyl group; or a phosphine oxide group unsubstituted or substituted with a phenyl group.

In the heterocyclic compound provided in one embodiment of the present specification, Chemical Formula 1 is represented by any one of the following compounds.

-continued
1
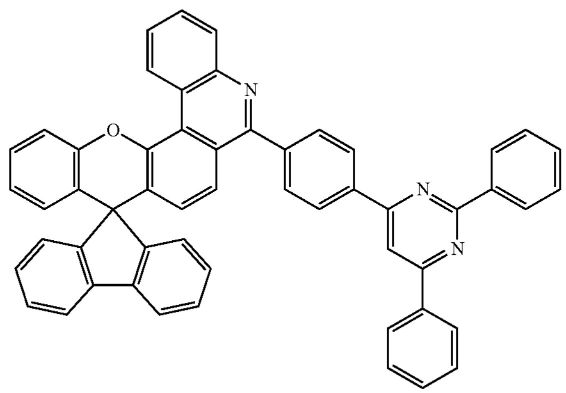
2
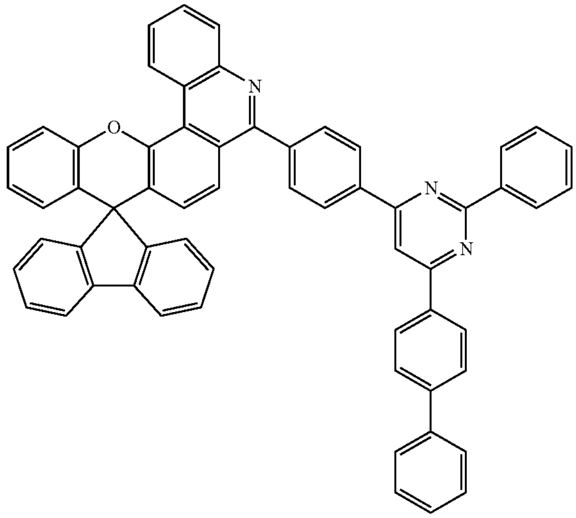
3
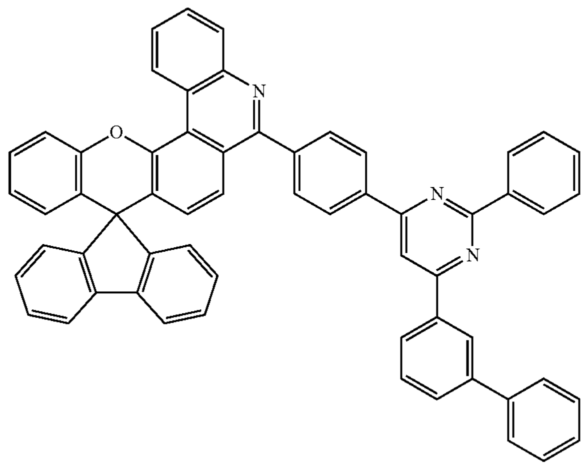
4
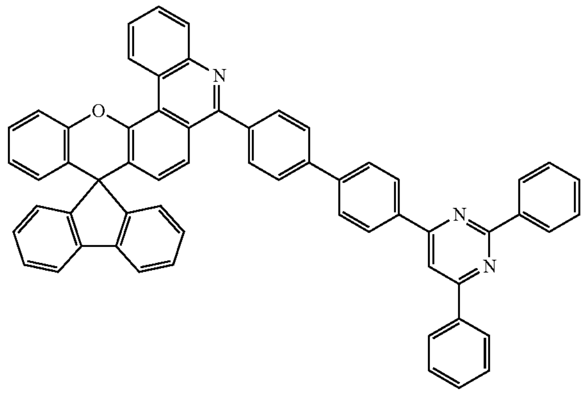
5
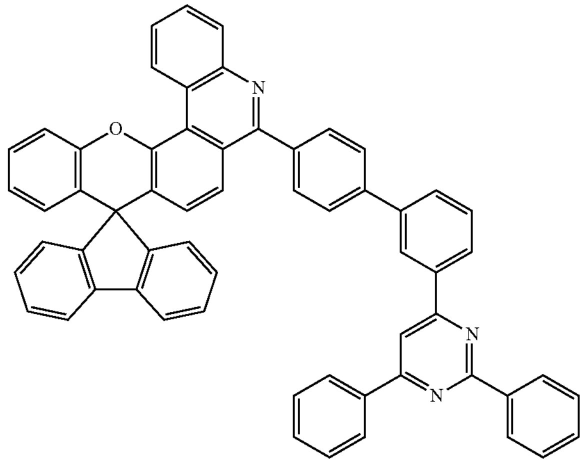
6
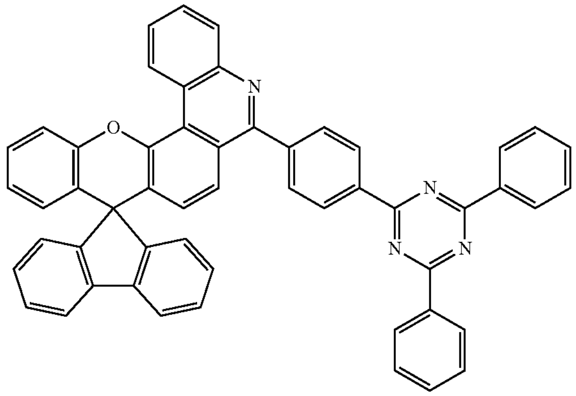

-continued
7
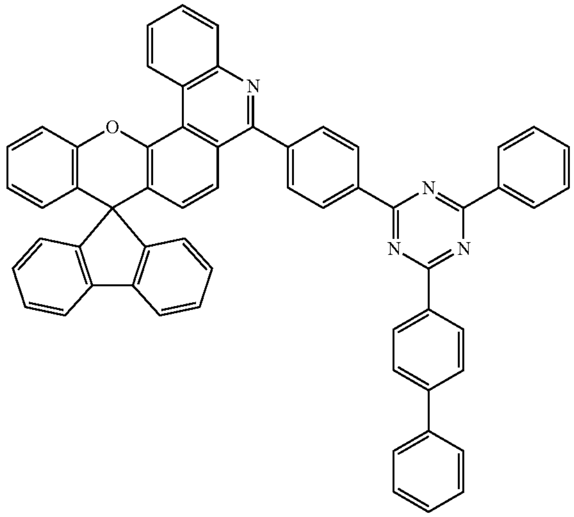
8
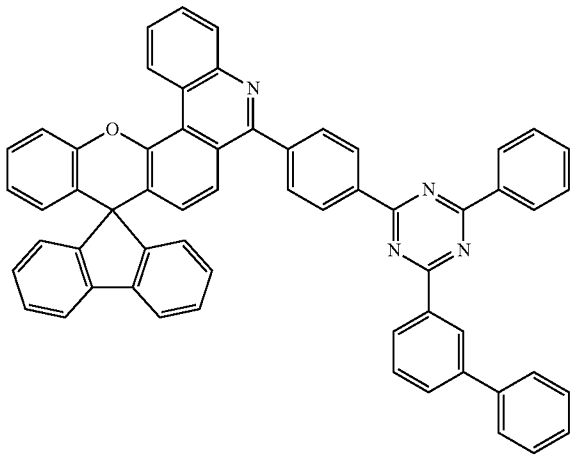
9
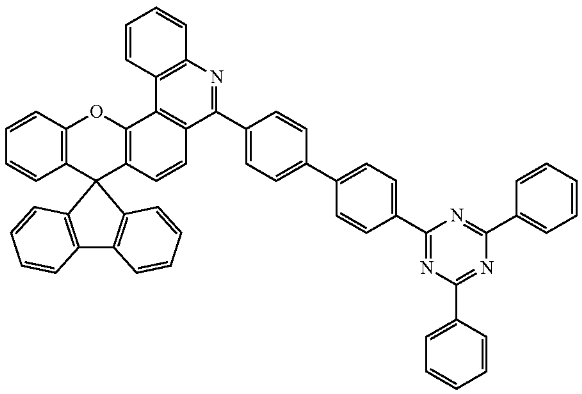
-continued
10
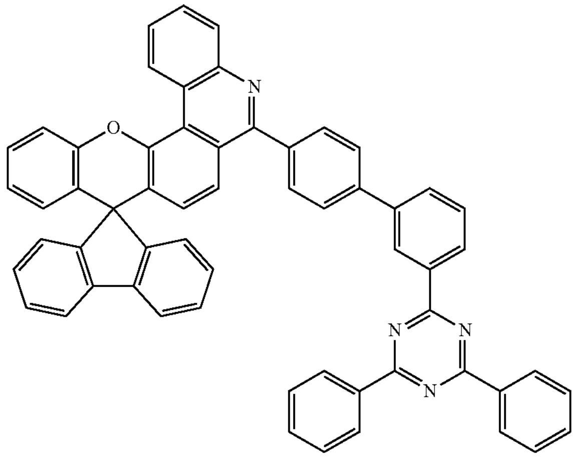
11
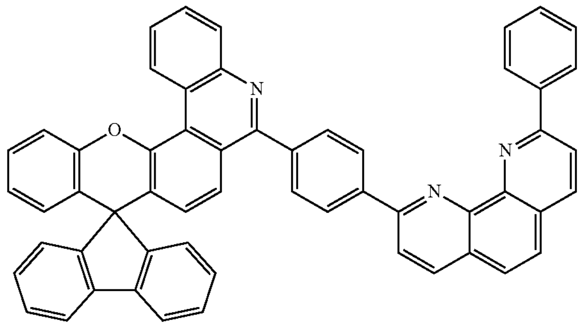
12
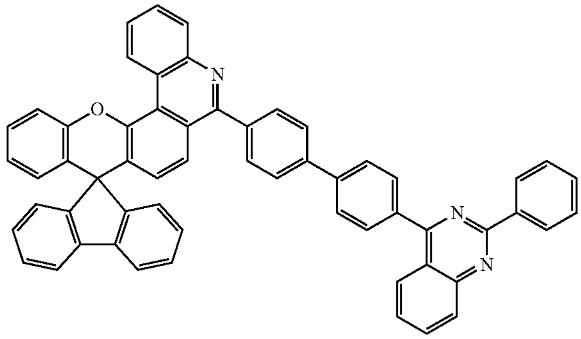
13
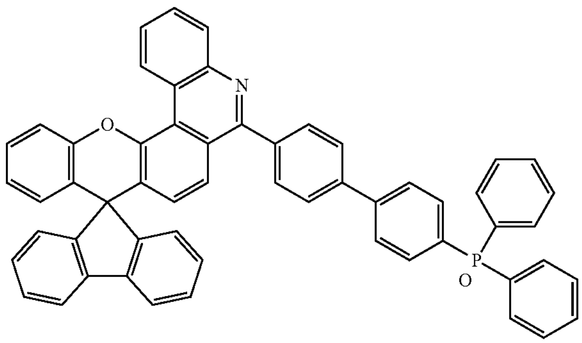

-continued
14
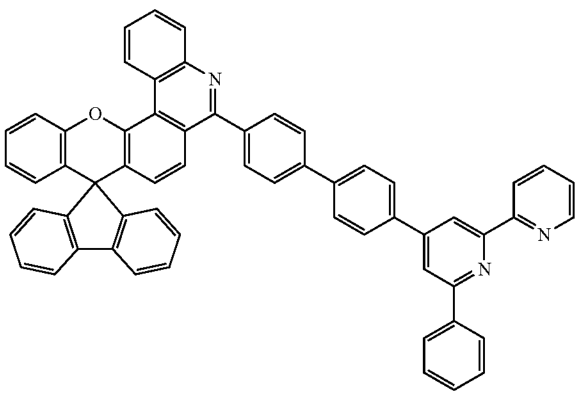
15
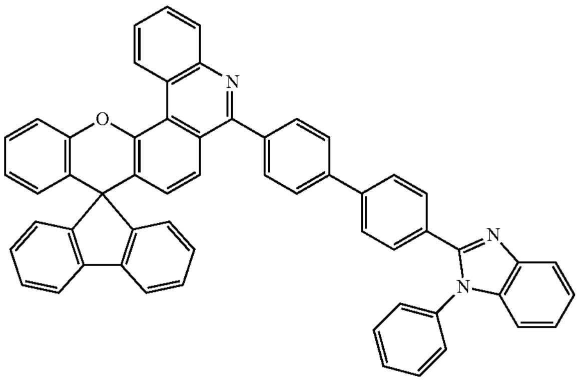
16
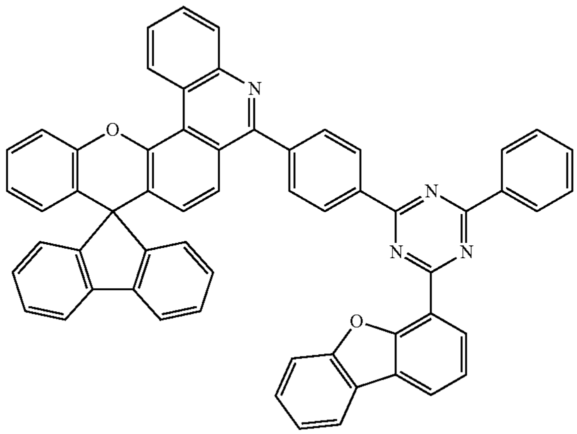
-continued
17
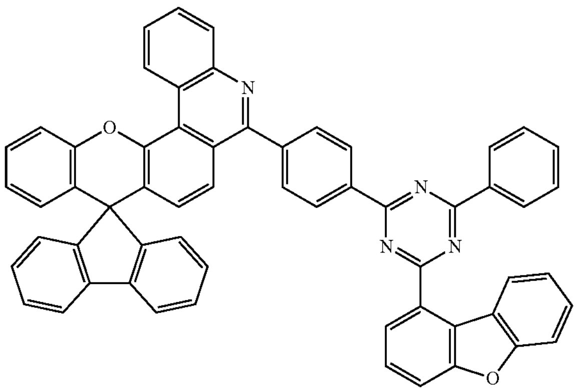
18
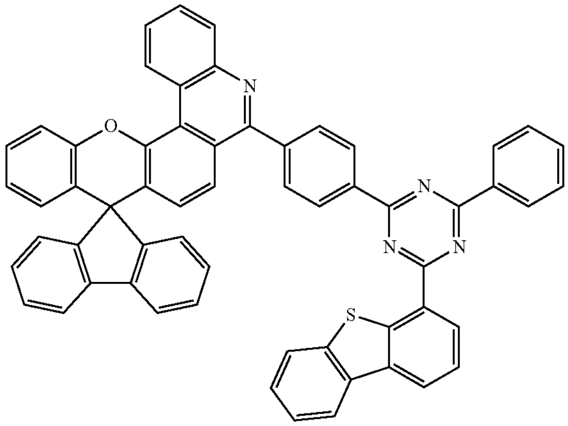
19
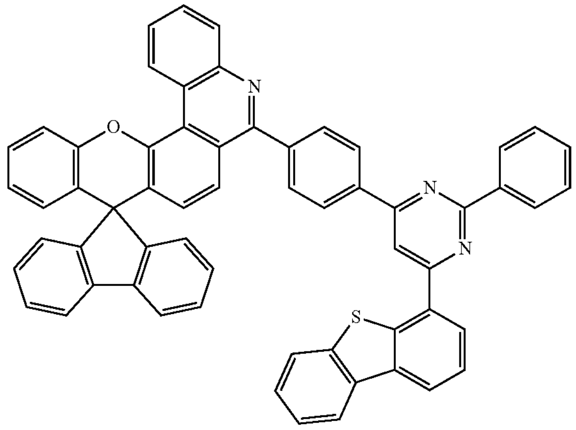

-continued
20
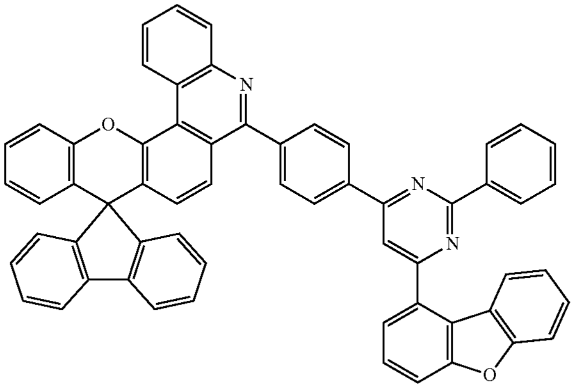
21
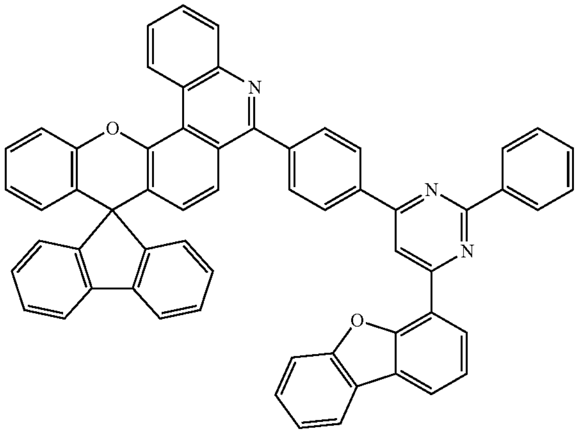
22
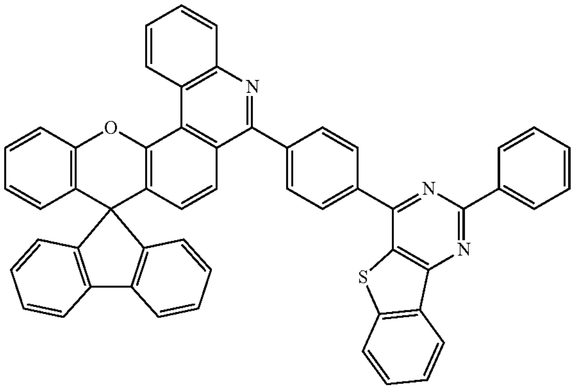
23
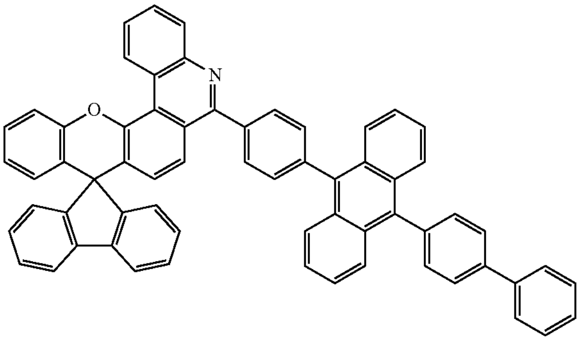
-continued
24
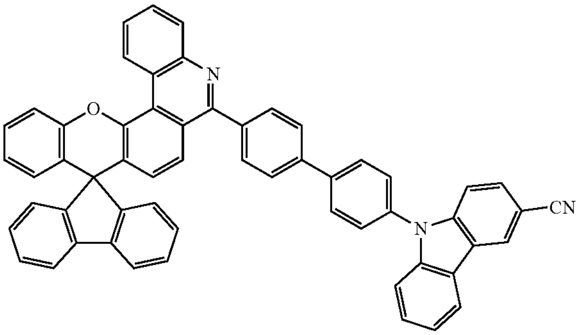
25
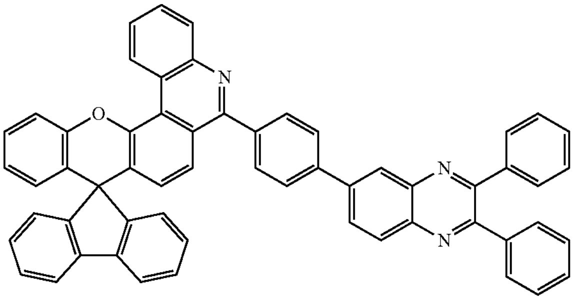
26
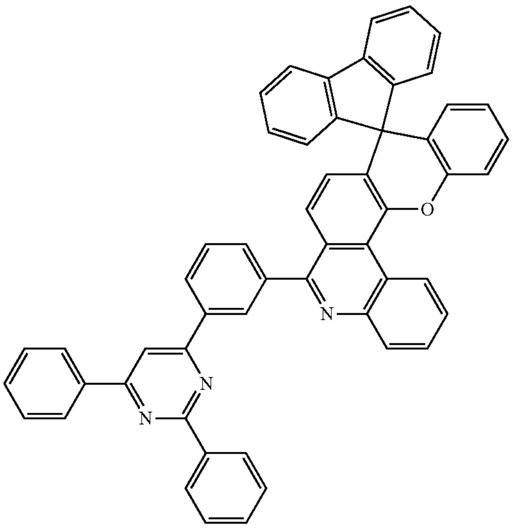

-continued
27
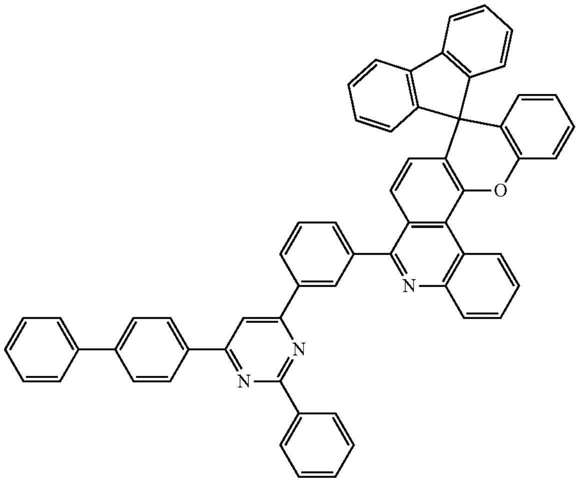
28
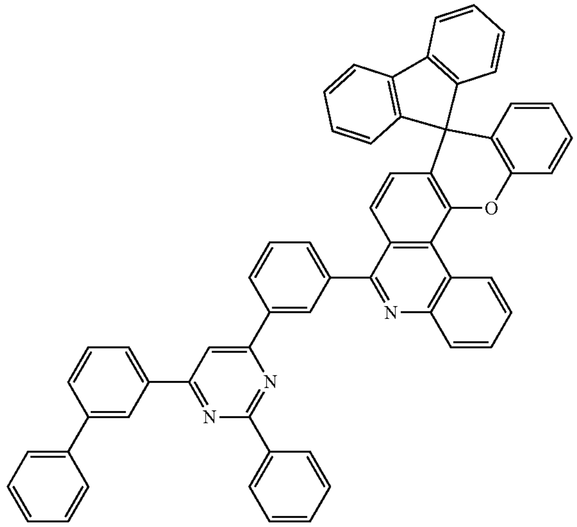
-continued
29
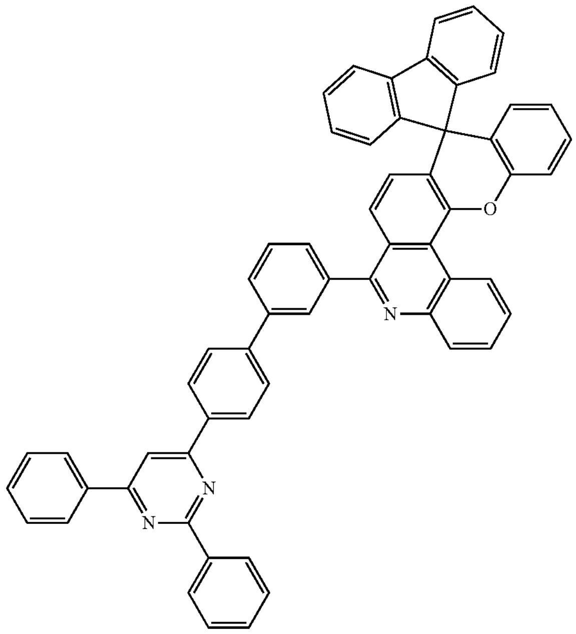
30
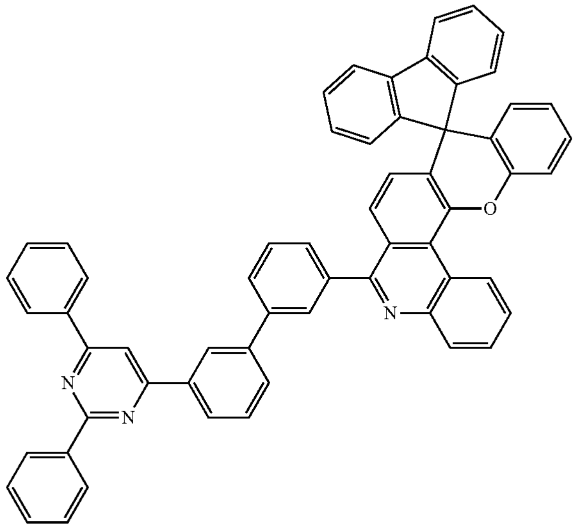

-continued
31
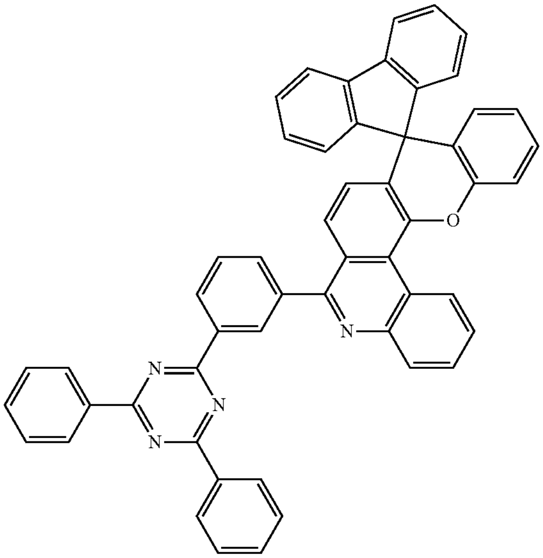
32
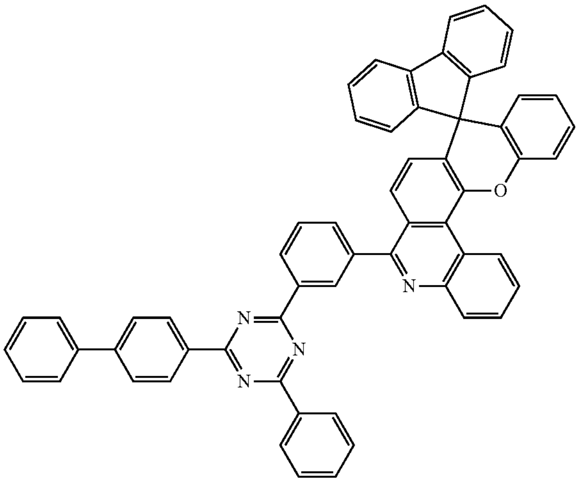
33
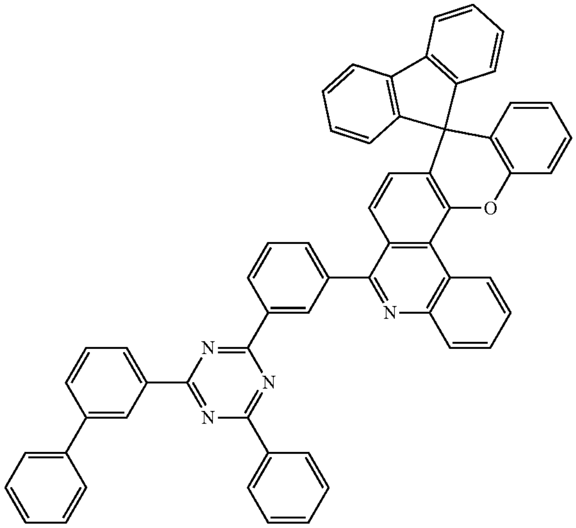
-continued
34
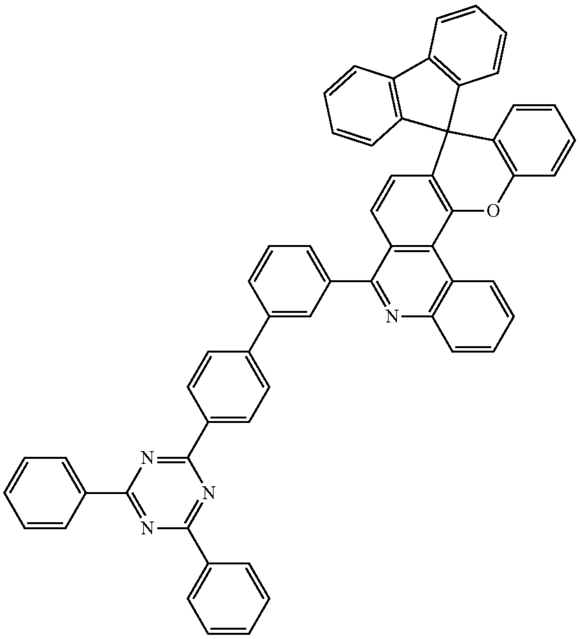
35
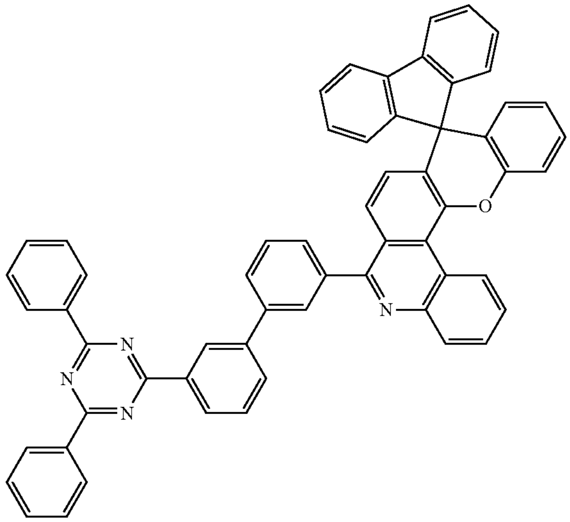

36
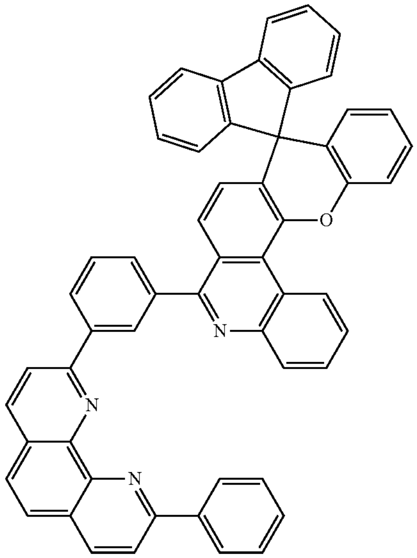
38
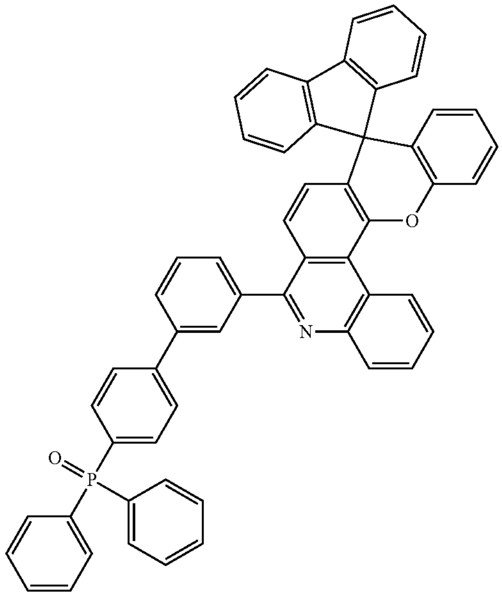
37
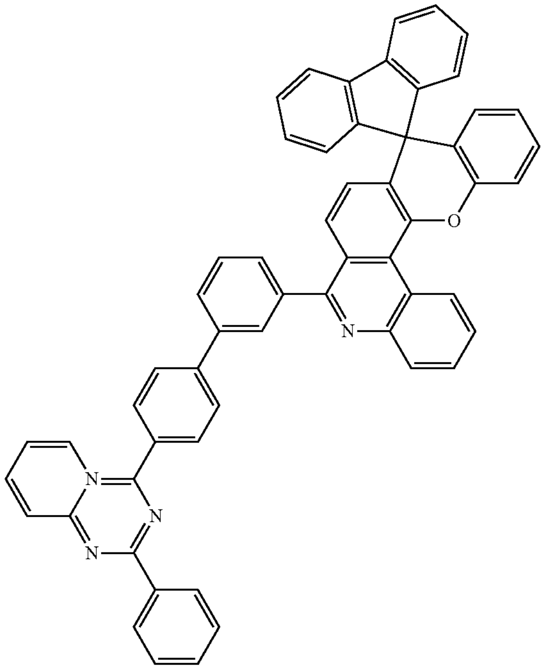
39
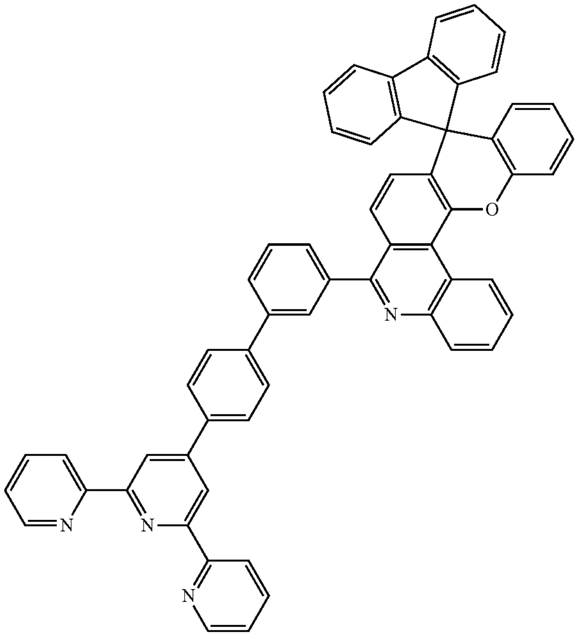

-continued
40
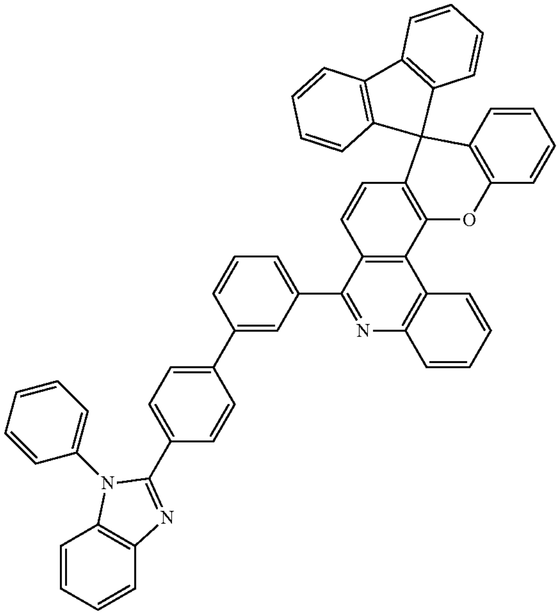
41
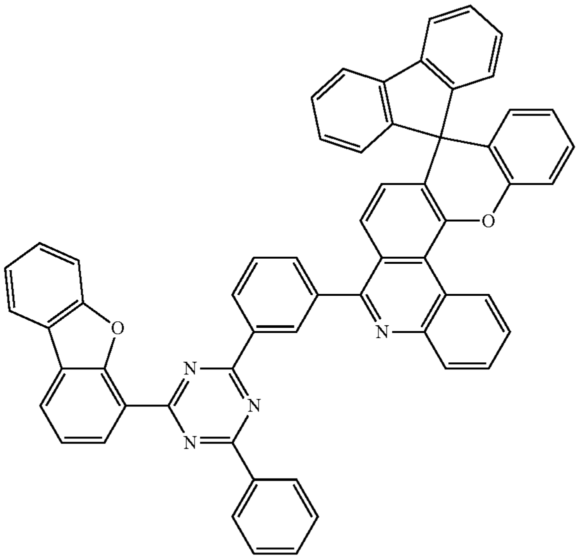
-continued
42
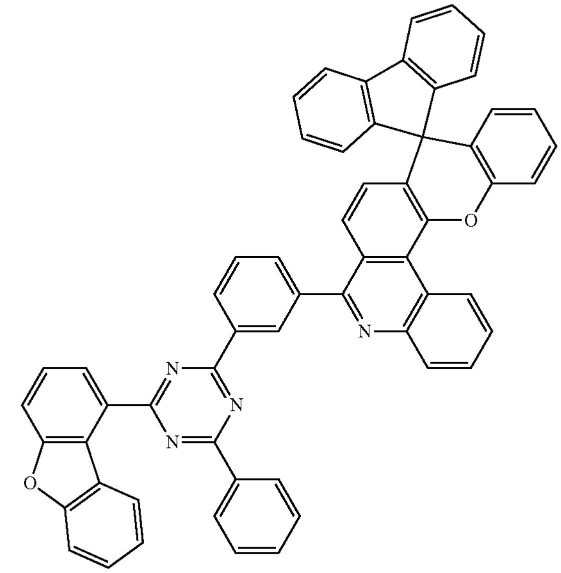
43
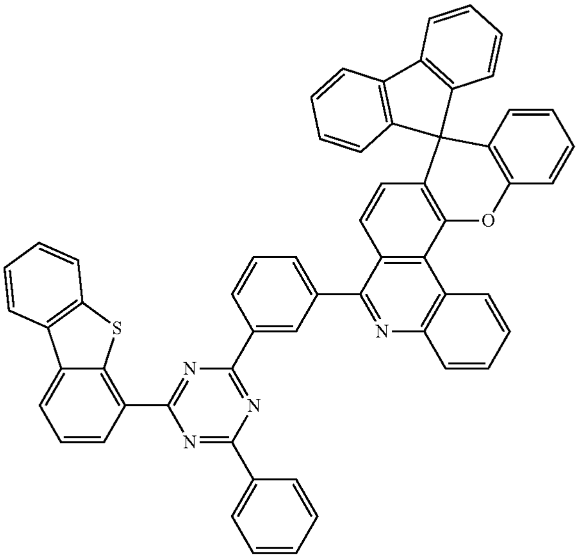

-continued
44
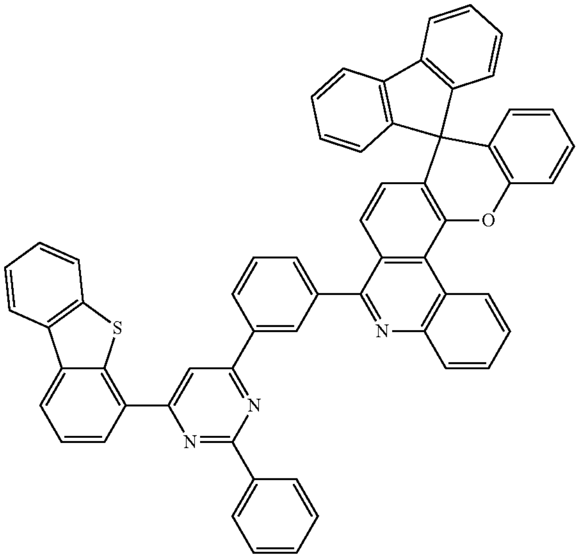
-continued
46
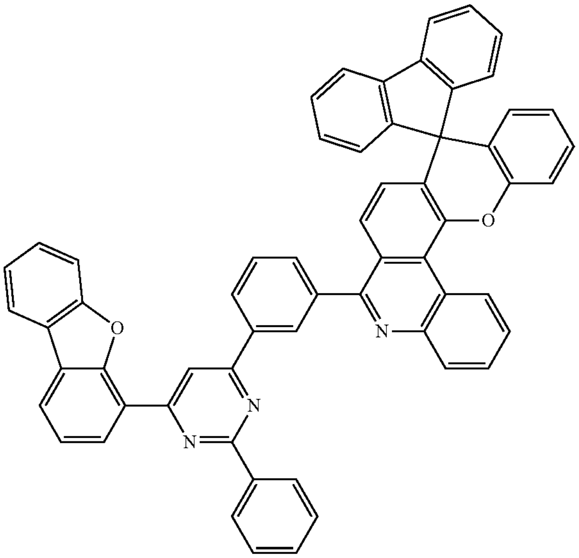
45
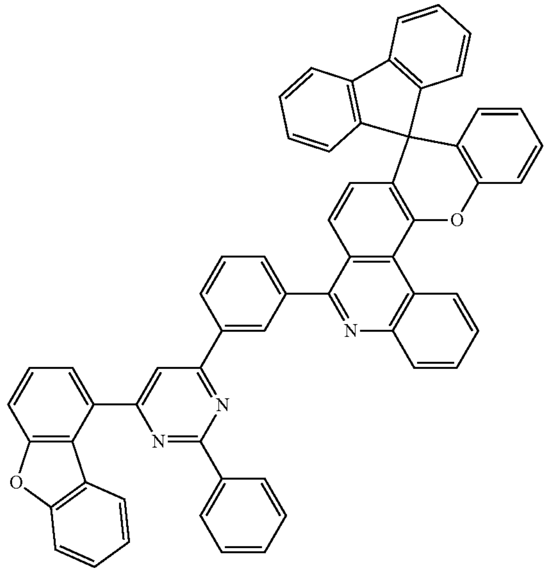
47
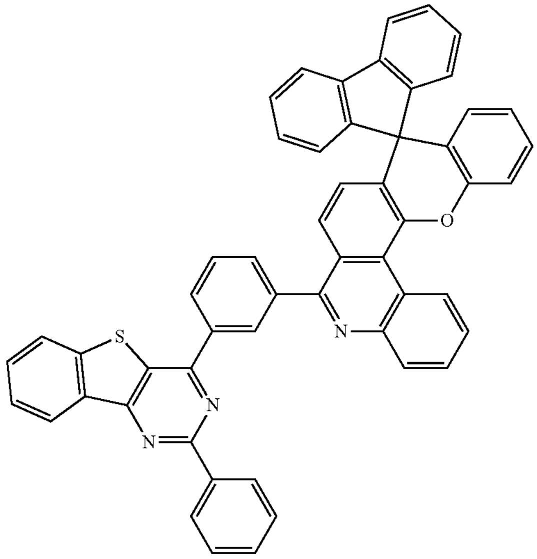

-continued
48
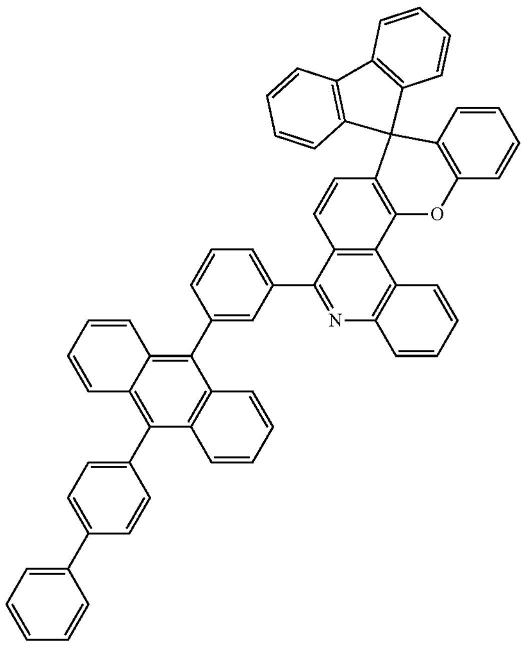
50
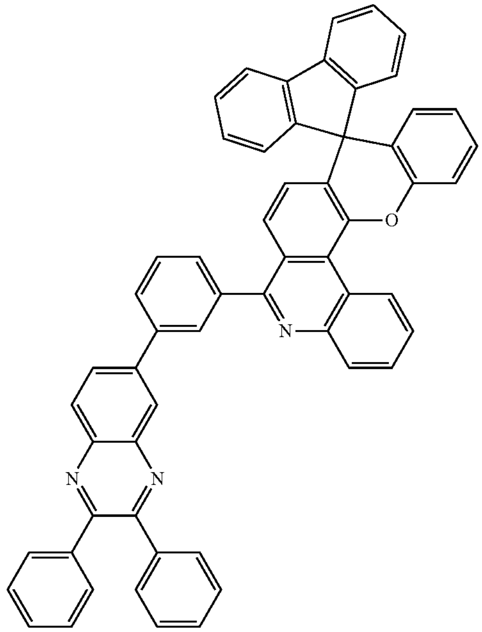
49
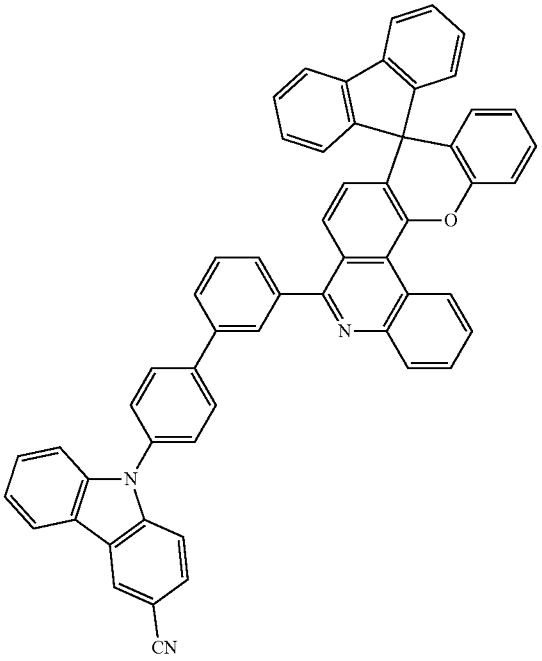
51
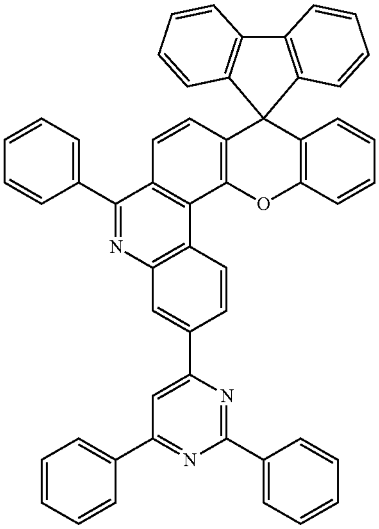

-continued
52
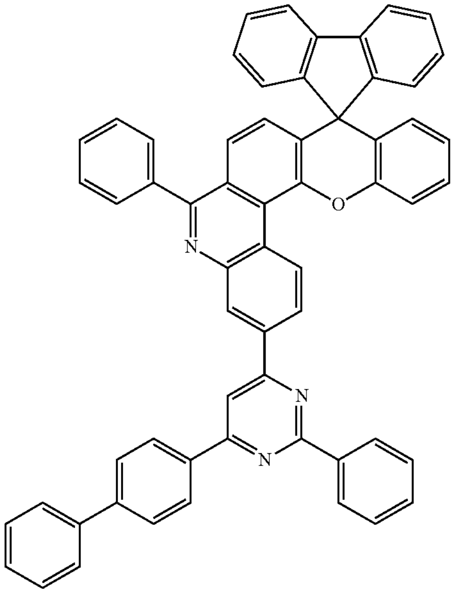
53
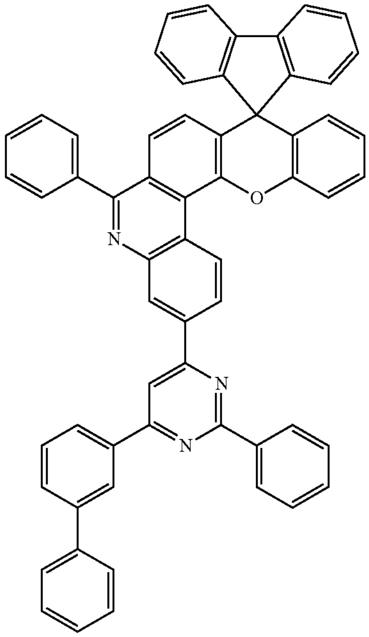
-continued
54
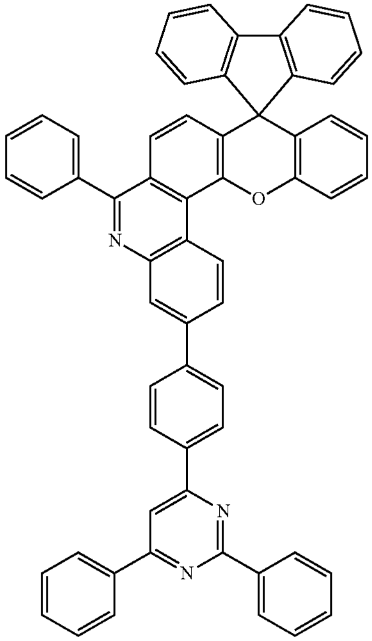
55
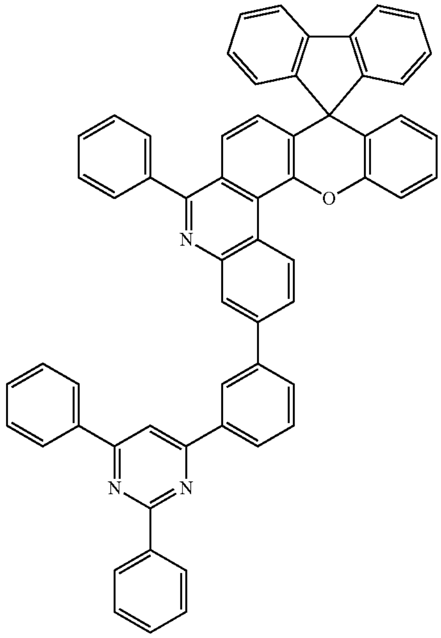

-continued
56
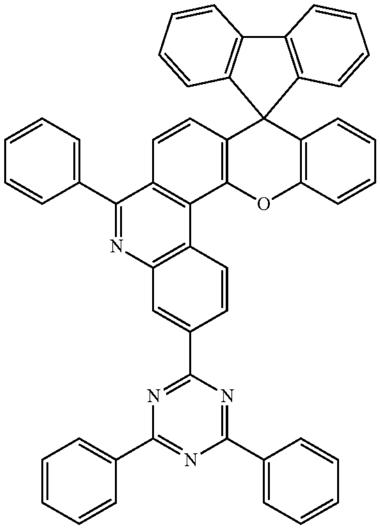
57
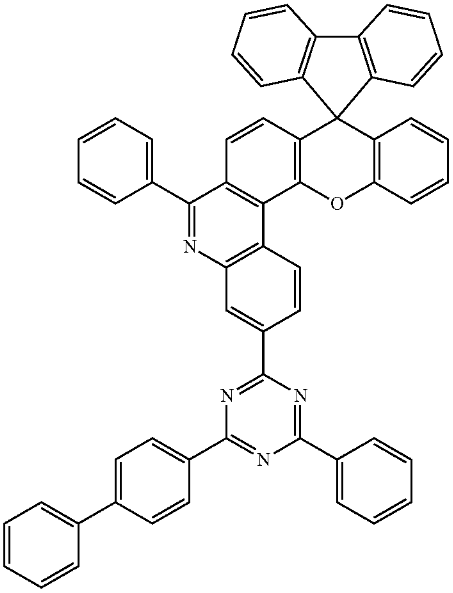
-continued
58
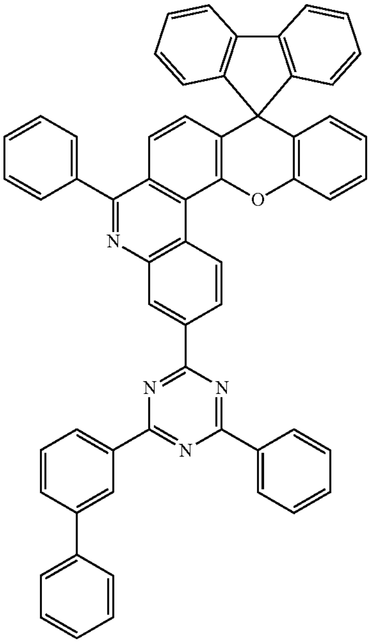
59
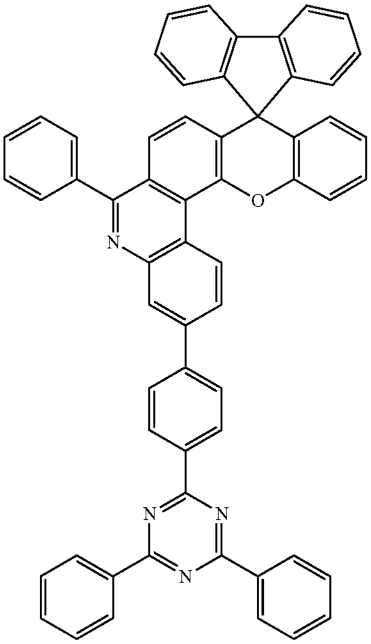

-continued
60
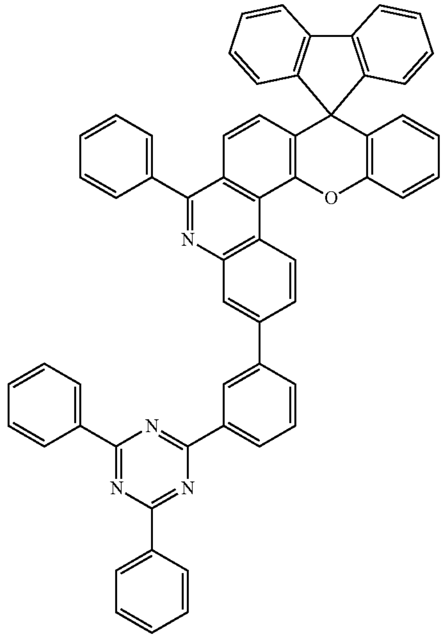
62
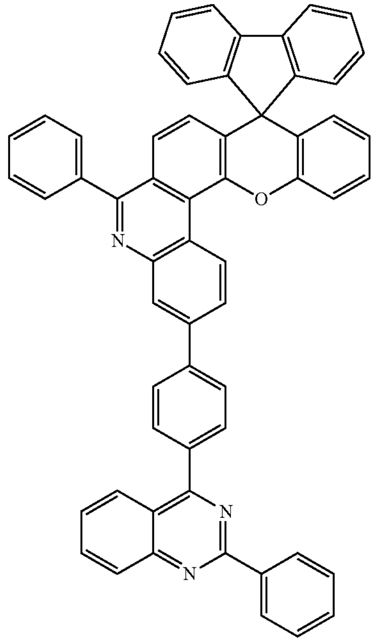
61
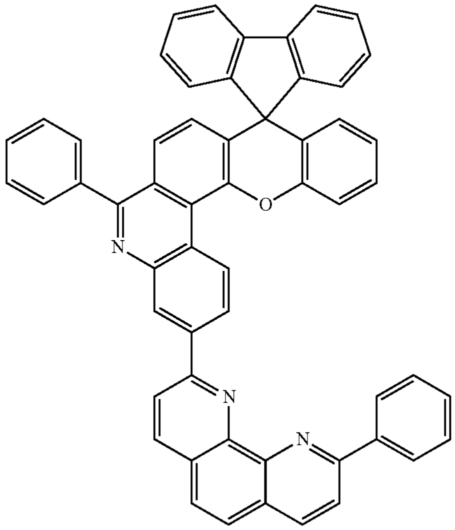
63
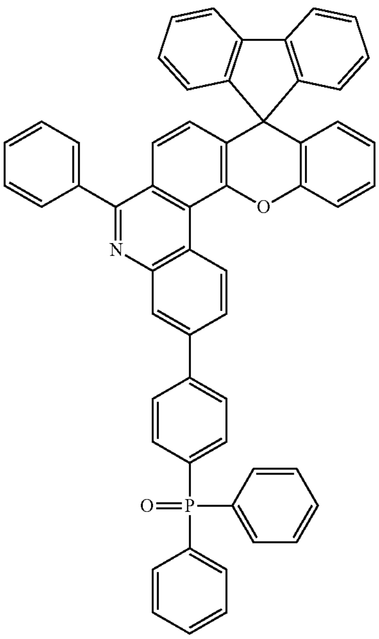

-continued
64
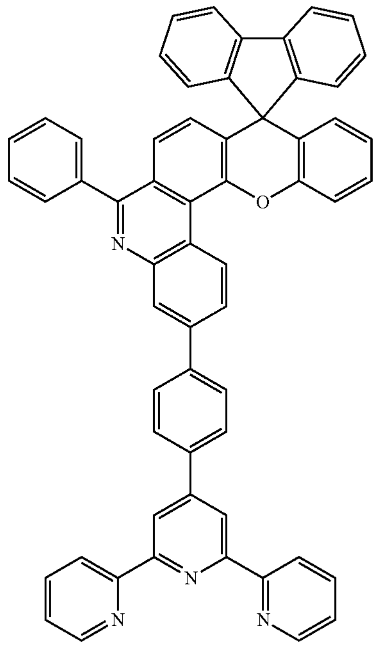
65
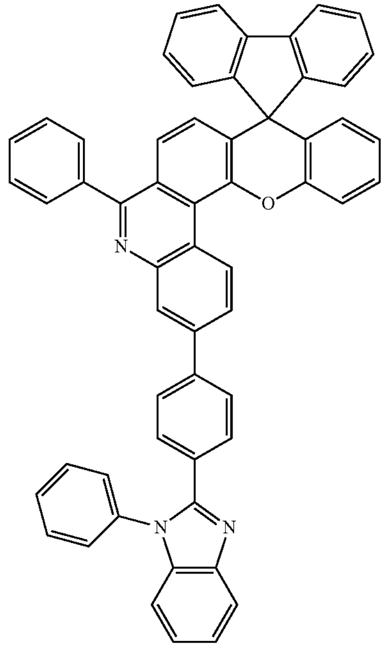
-continued
66
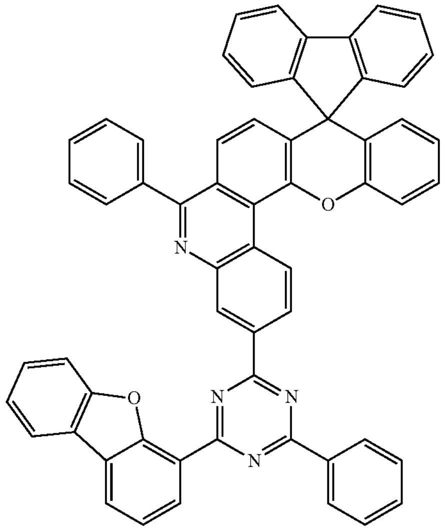
67
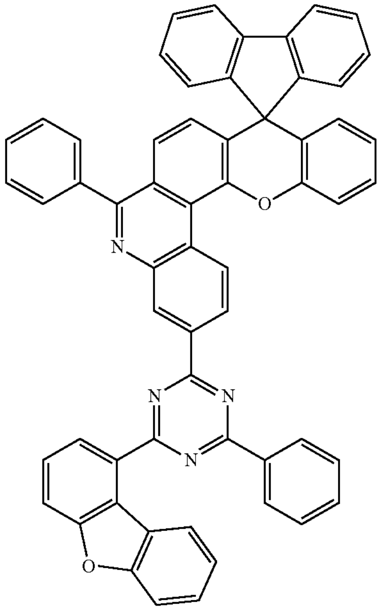
68
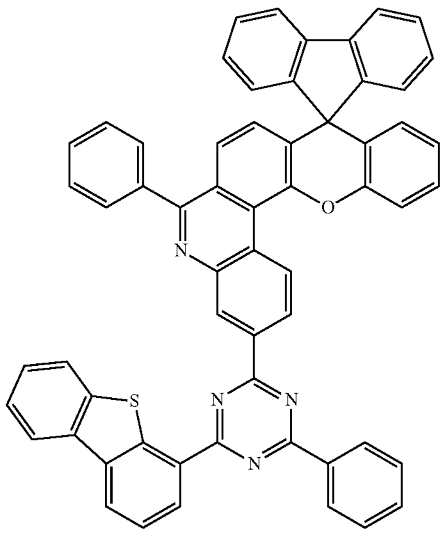

69
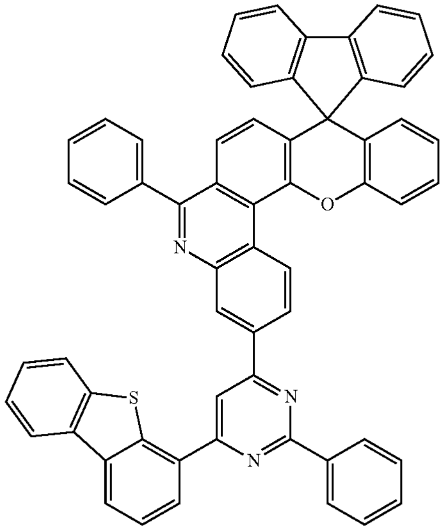
70
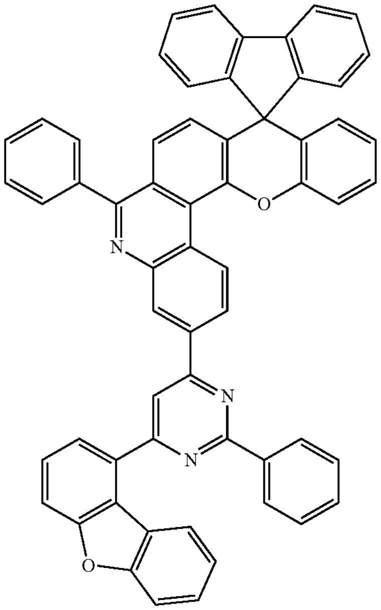
71
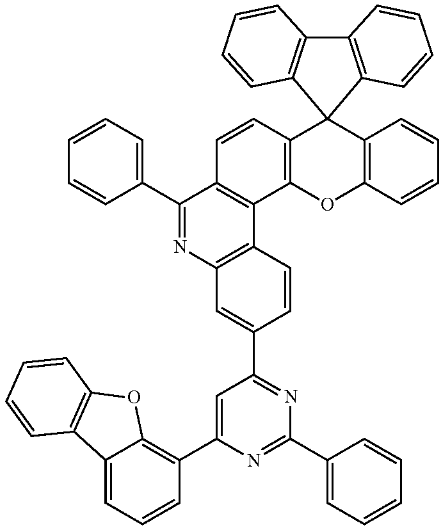
72
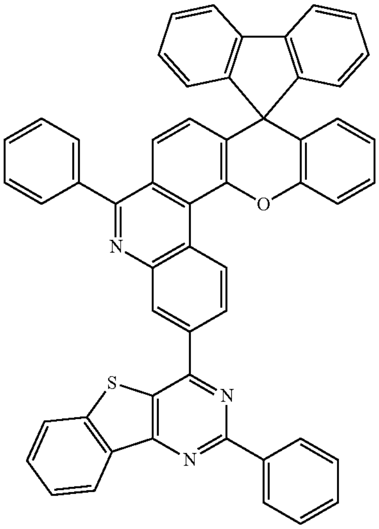
73
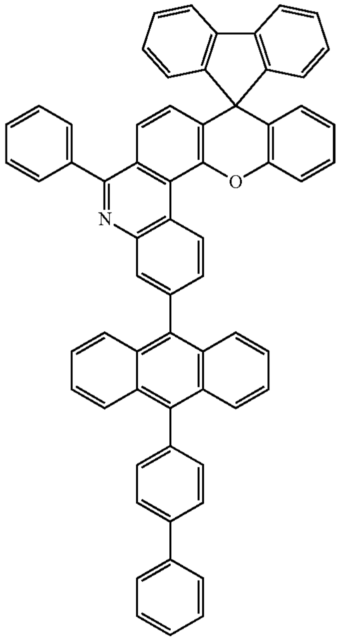

-continued
74
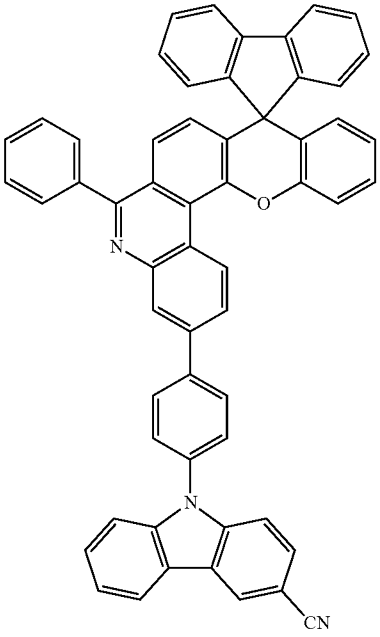
75
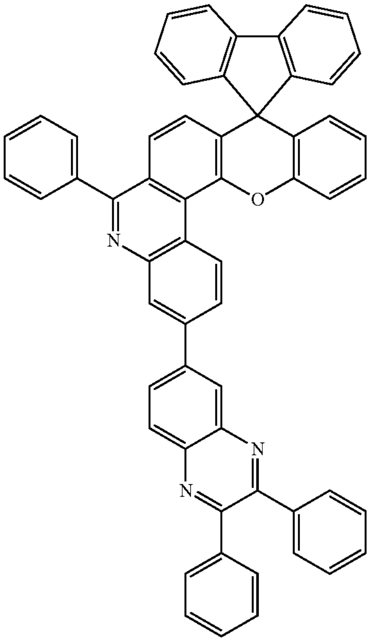
-continued
76
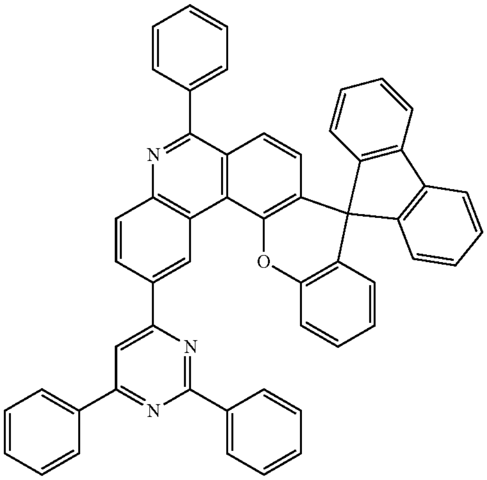
77
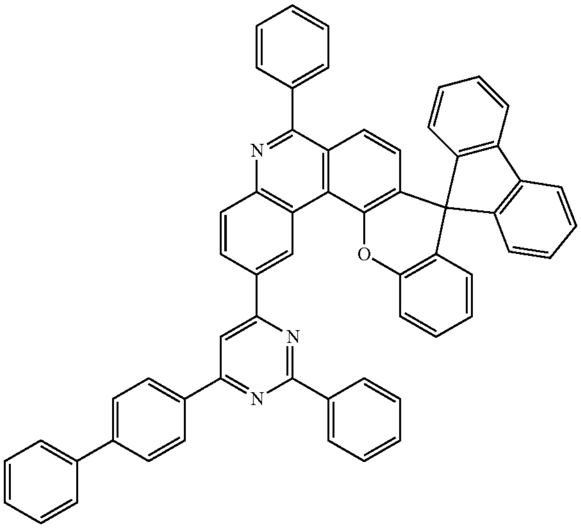
78
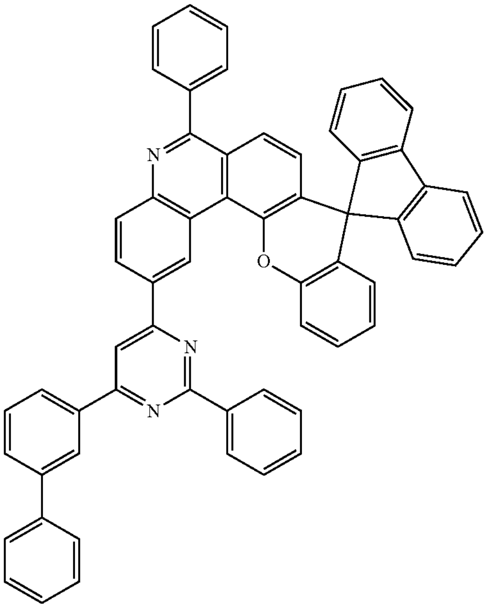

-continued
79
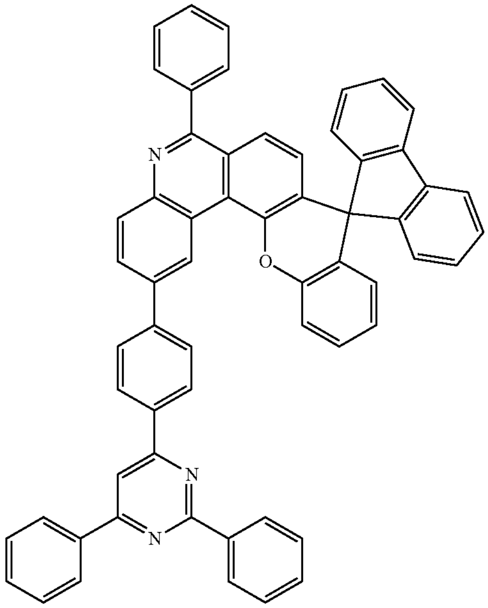
80
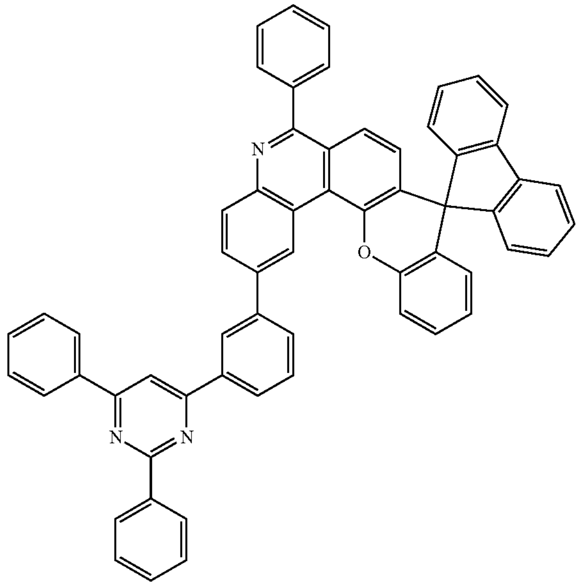
-continued
81
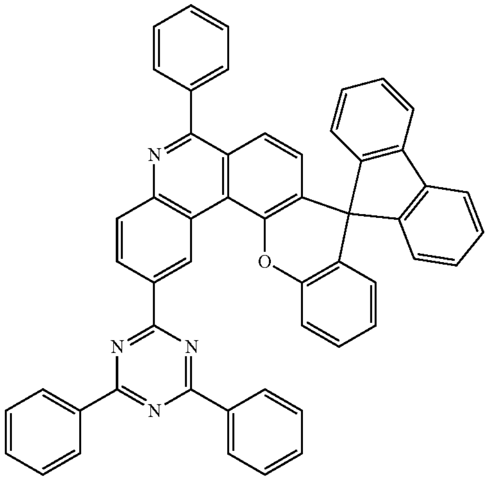
82
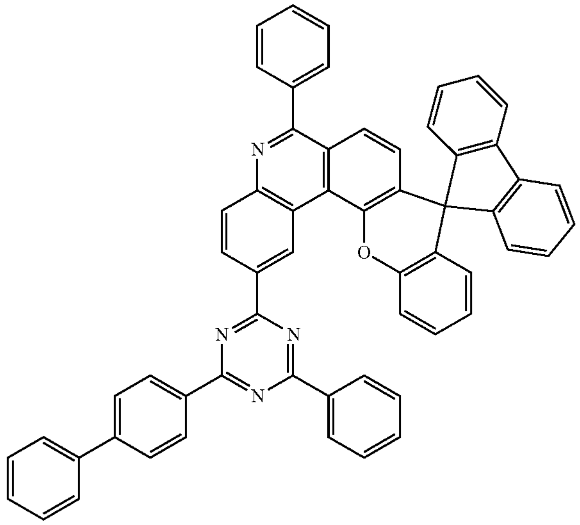
83
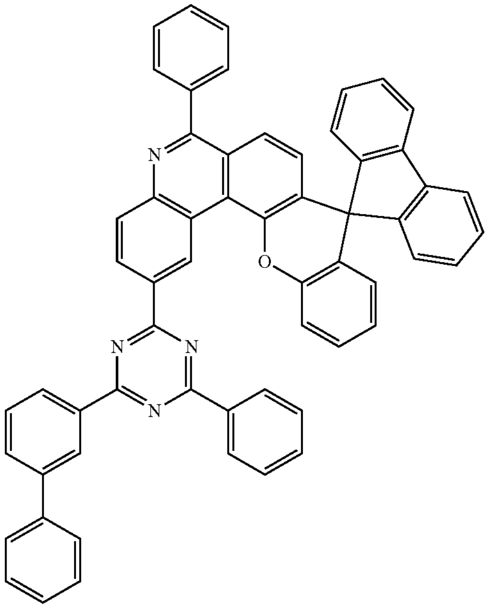

-continued
84
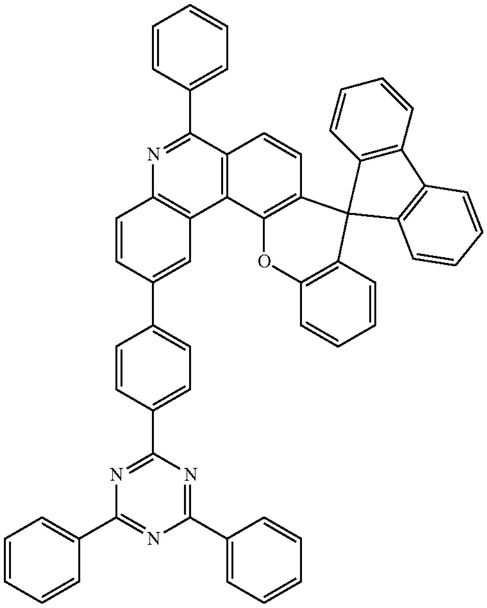
85
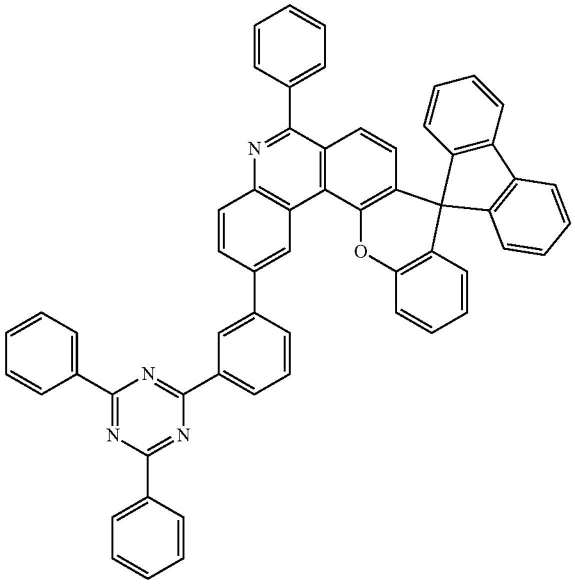
-continued
86
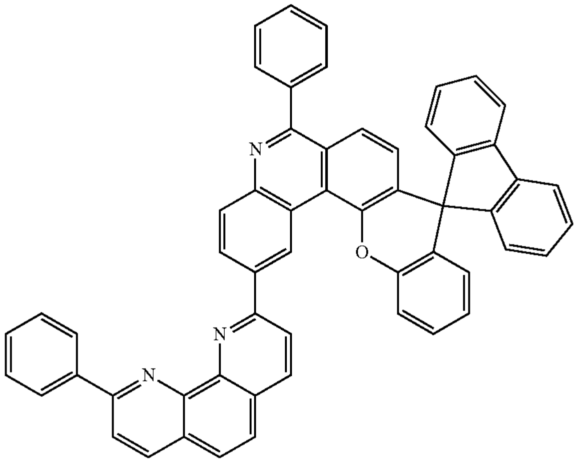
87
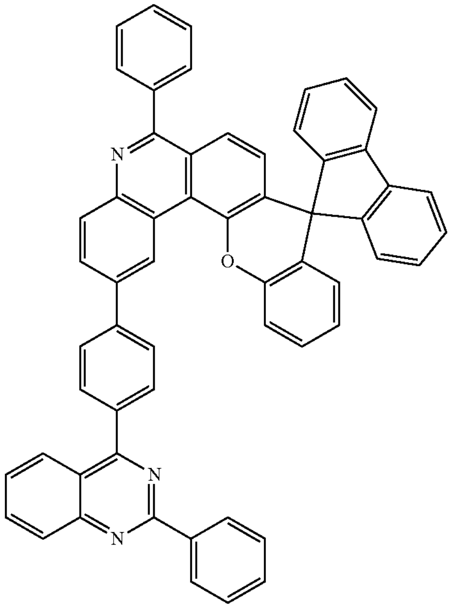

-continued
88
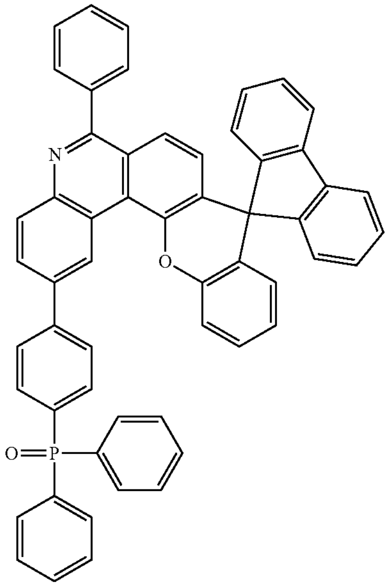
89
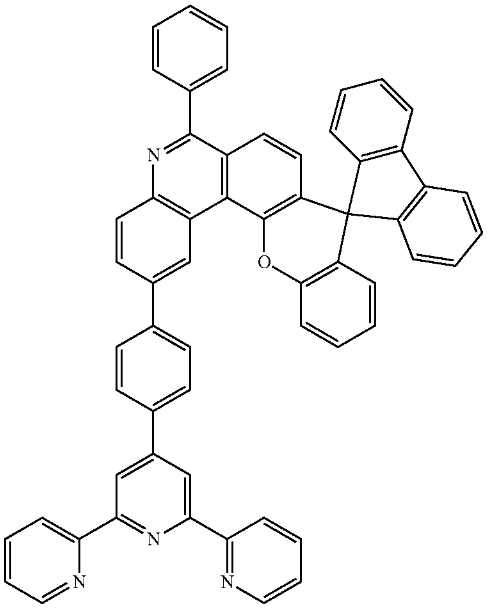
-continued
90
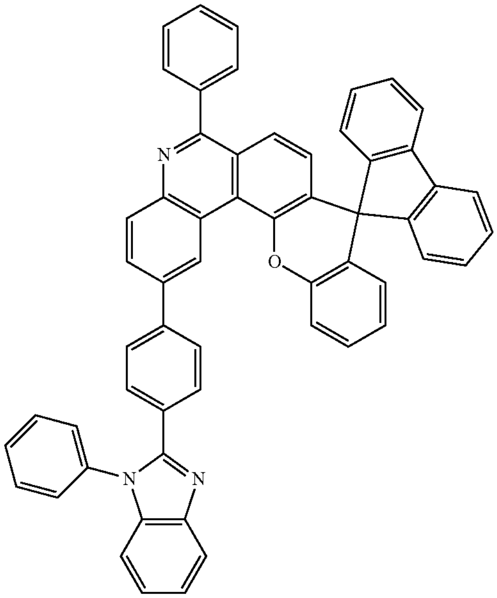
91
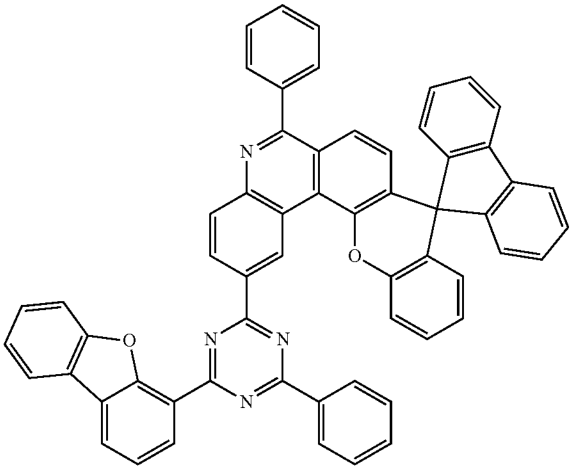
92
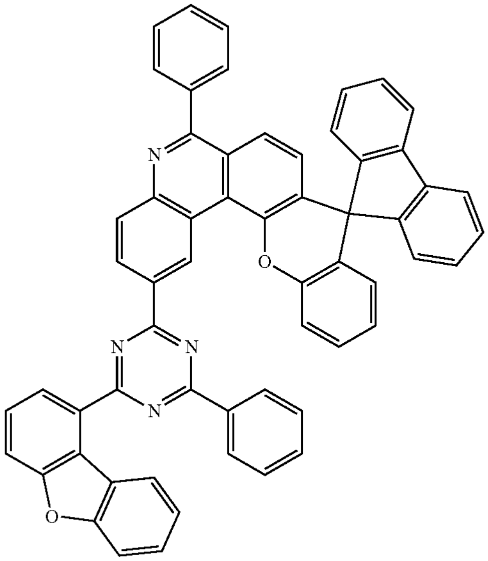

-continued
93
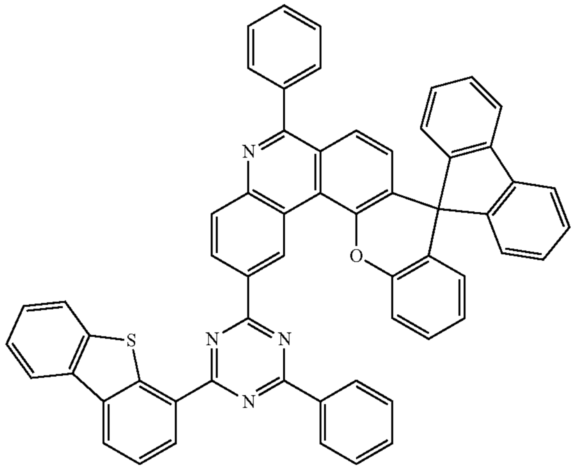
94
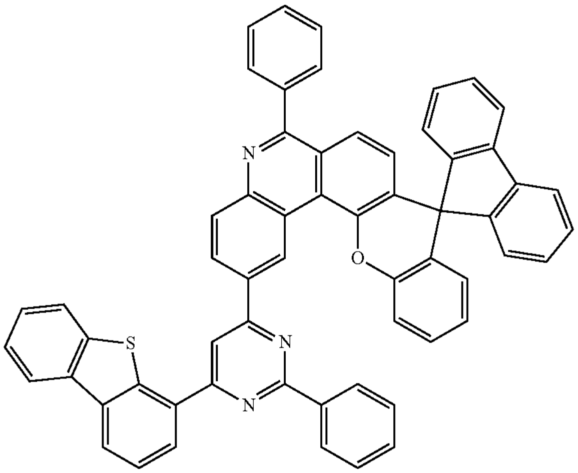
95
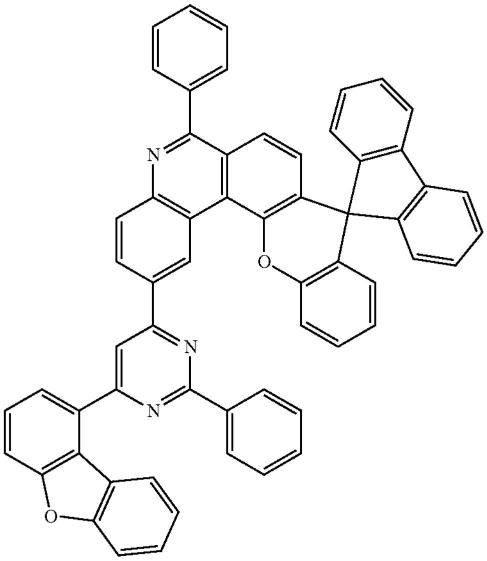
-continued
96
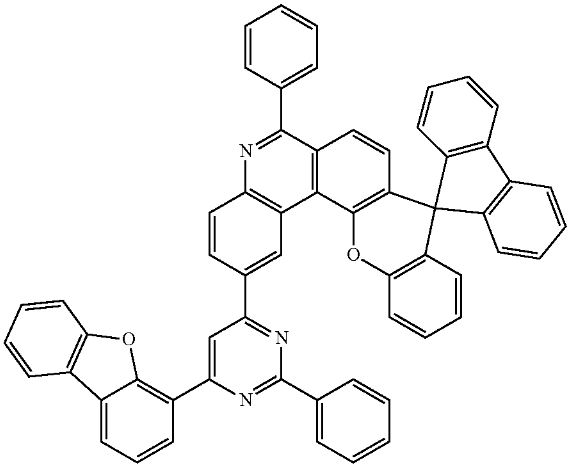
97
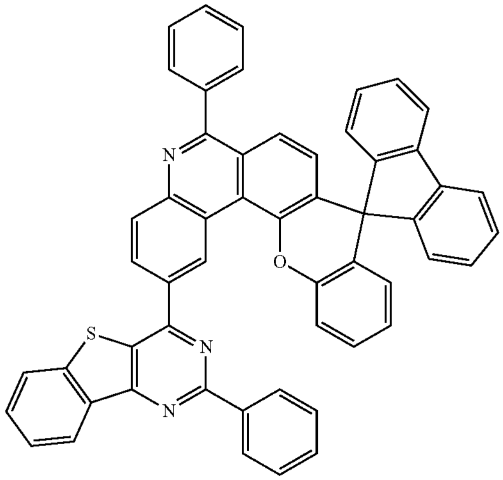
98
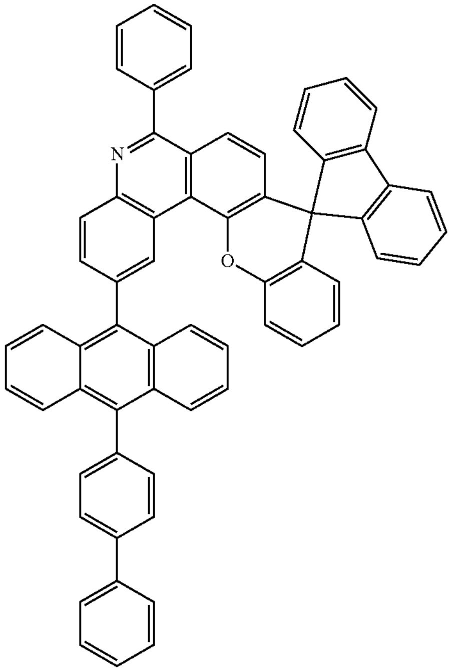

99
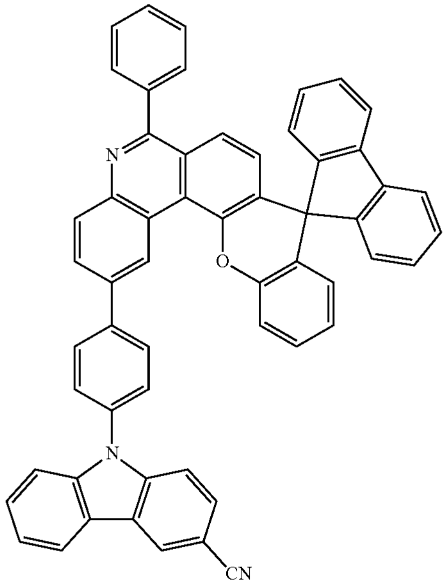
100
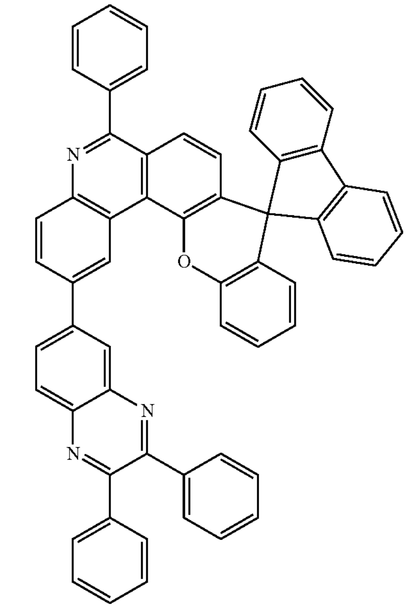
101
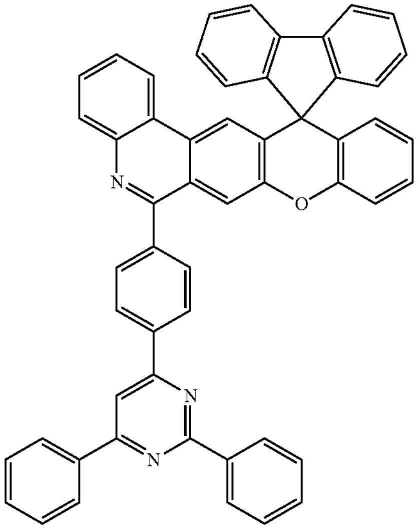
102
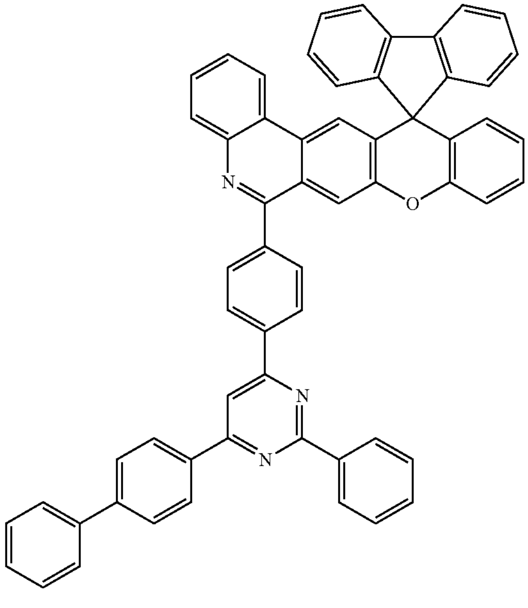

-continued
103
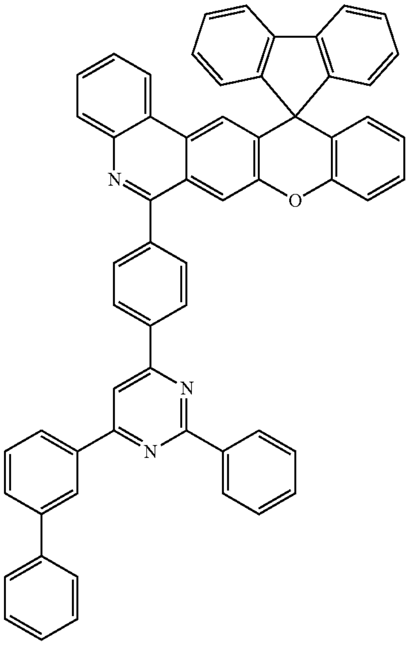
104
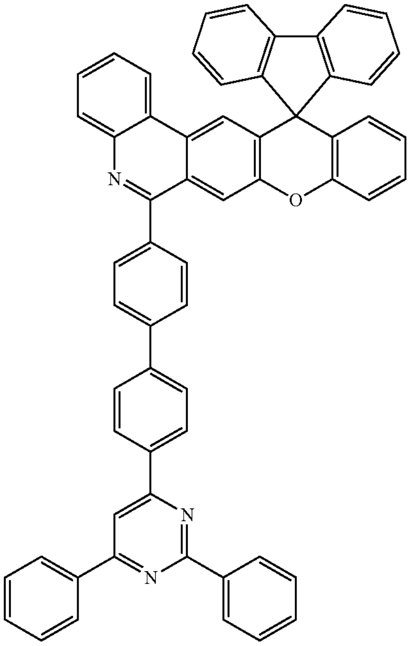
-continued
105
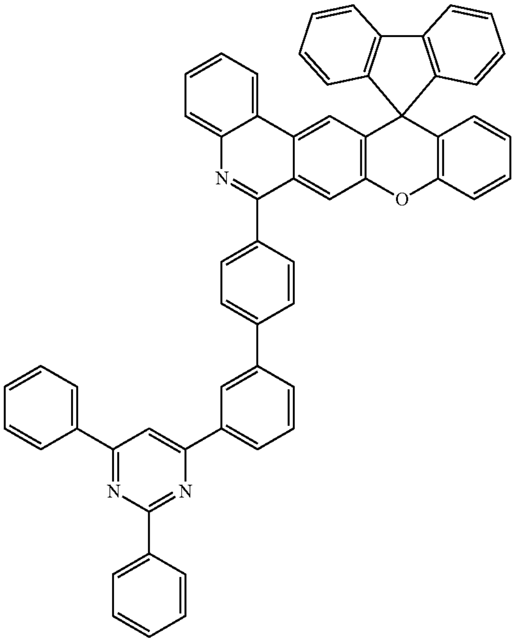
106
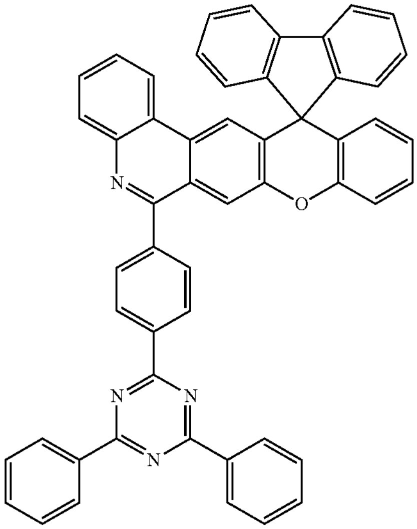

-continued
107
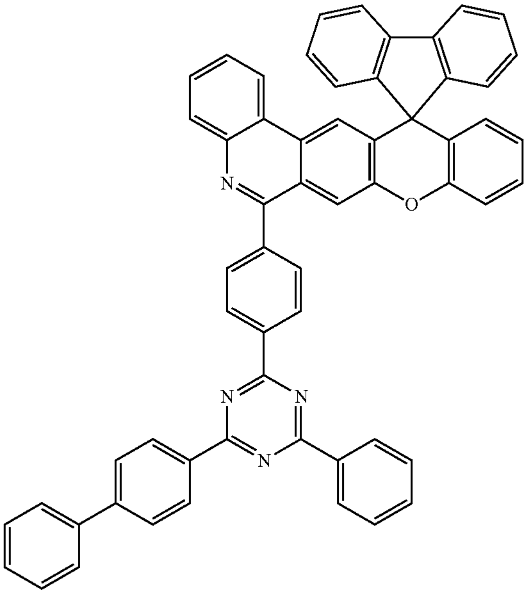
108
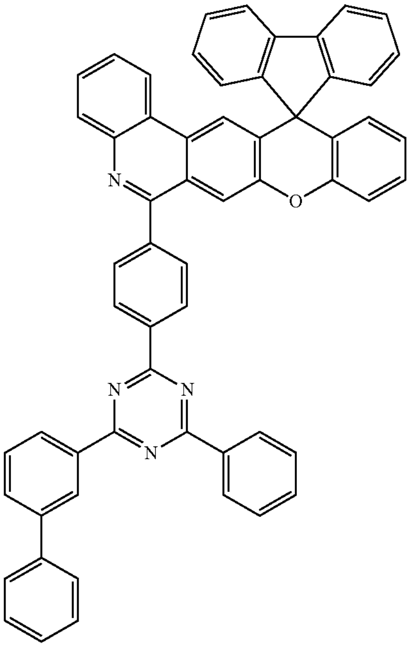
-continued
109
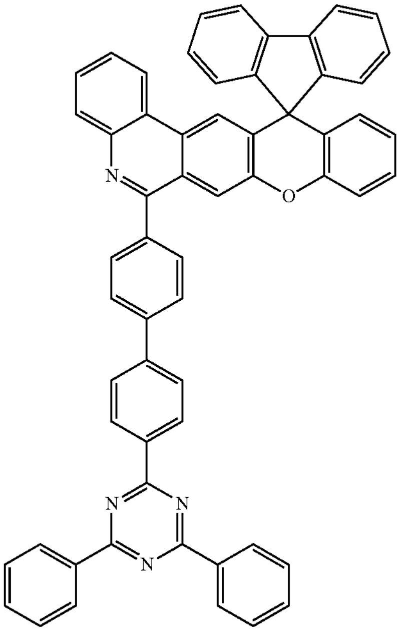
110
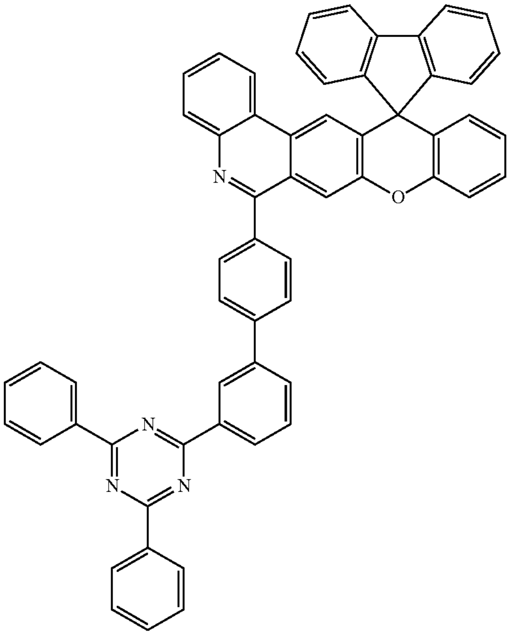

-continued
111
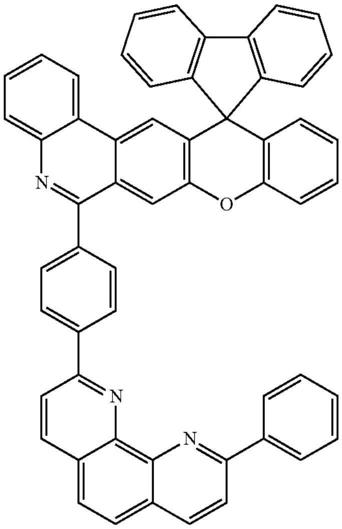
112
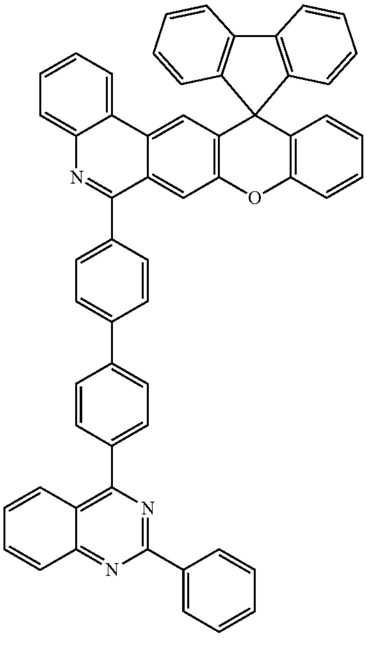
-continued
113
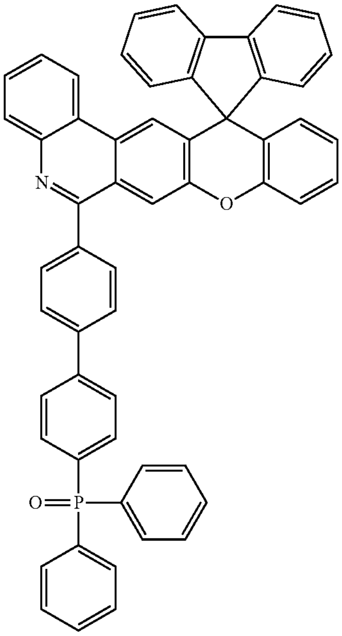
114
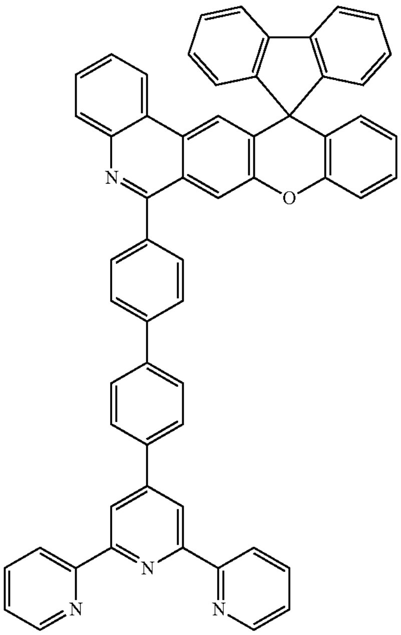

-continued
115
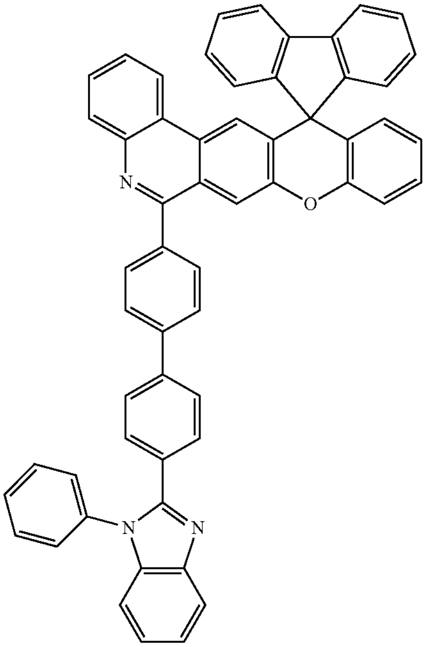
116
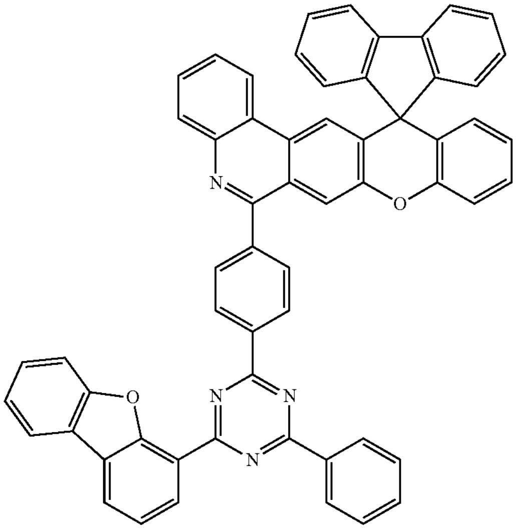
-continued
117
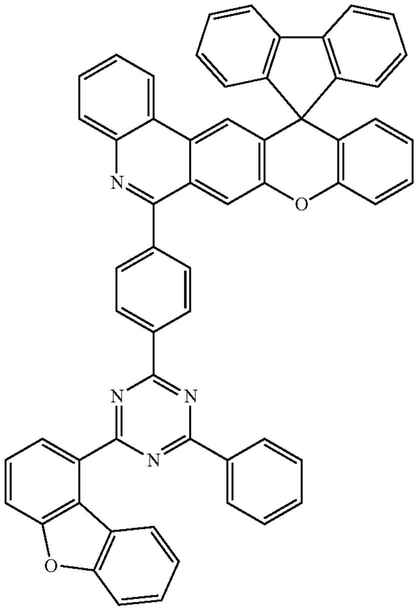
118
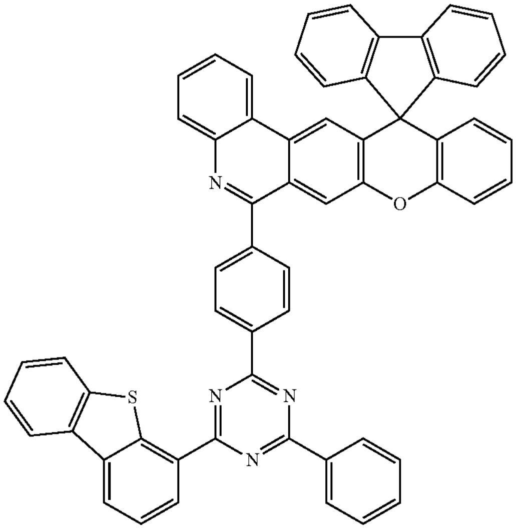
119
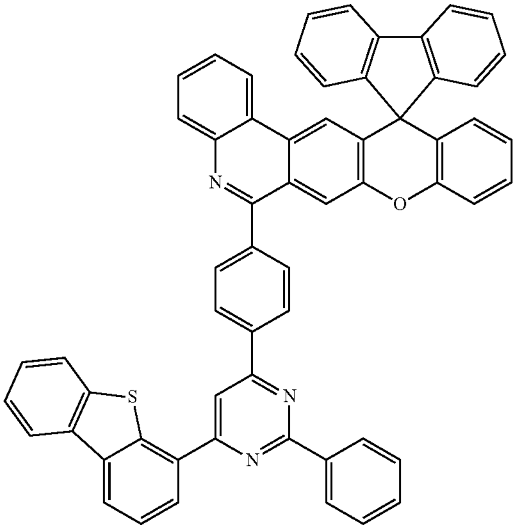

-continued
120
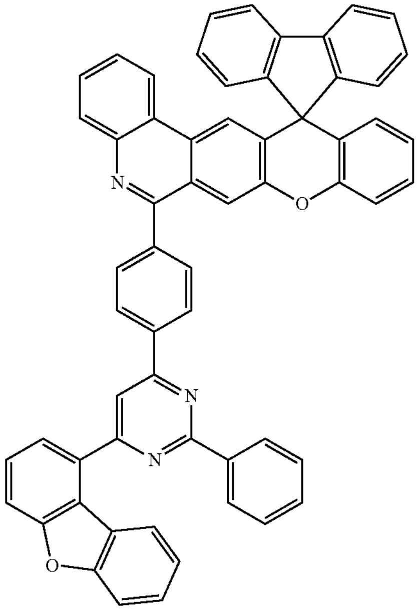
121
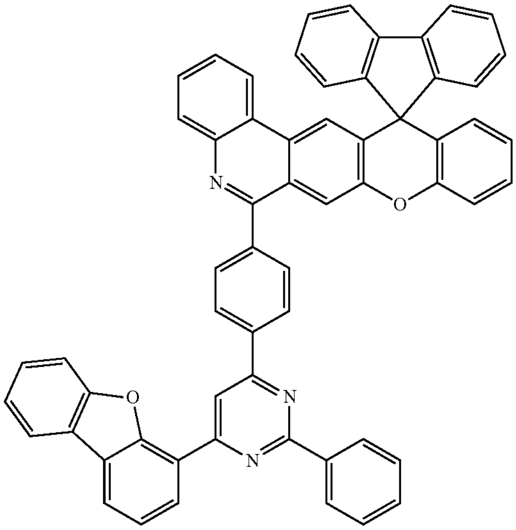
122
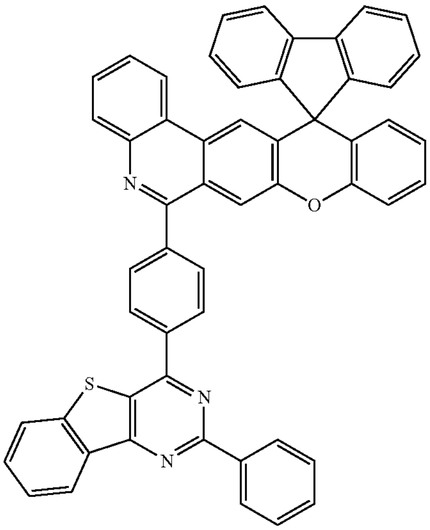
-continued
123
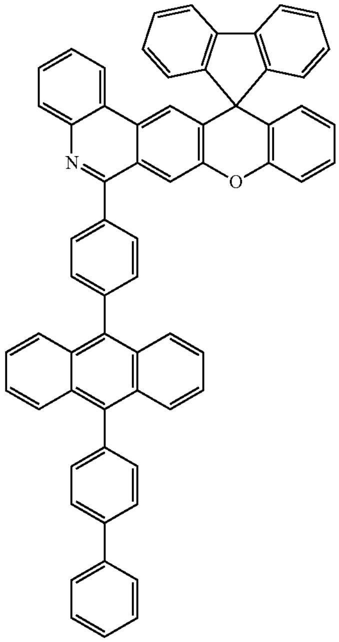
124
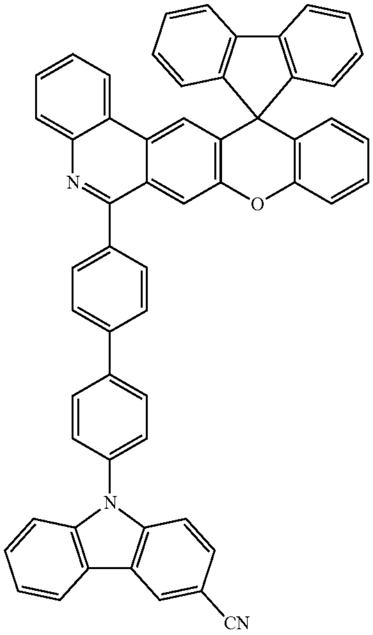

-continued
125
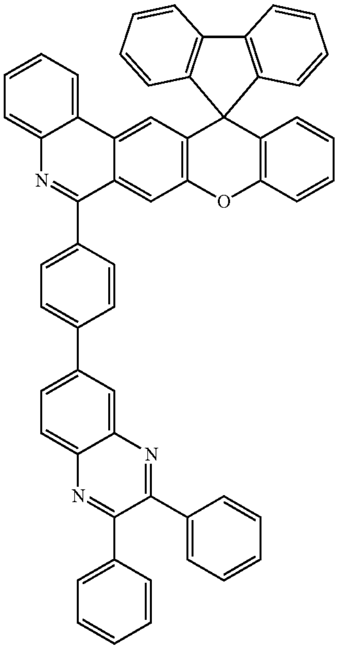
126
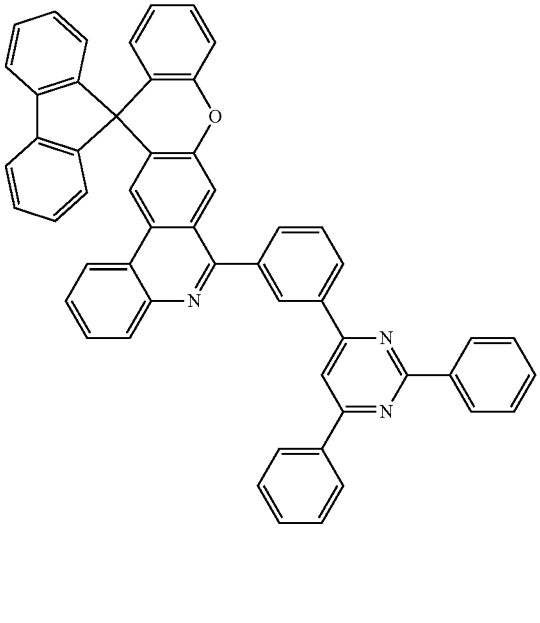
-continued
127
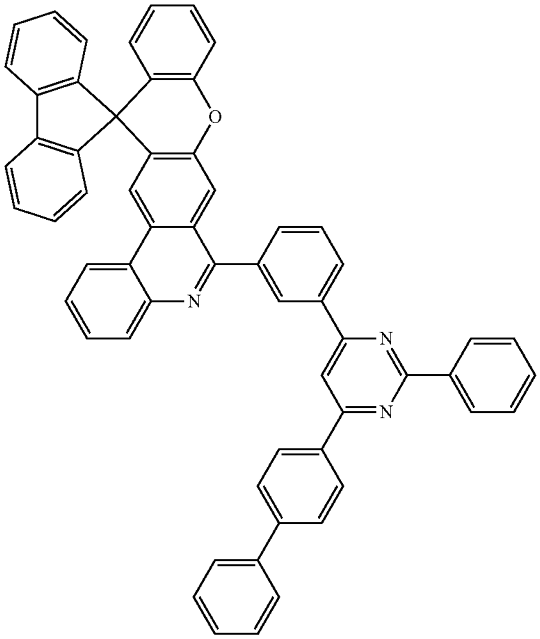
128
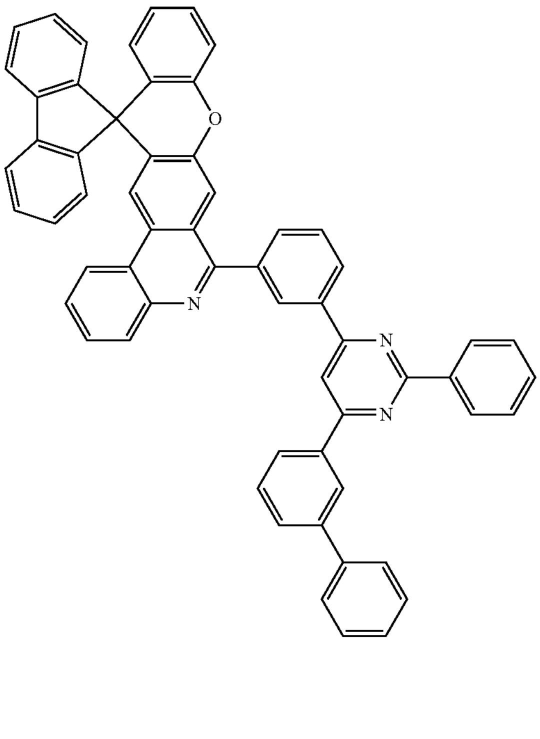

-continued
129
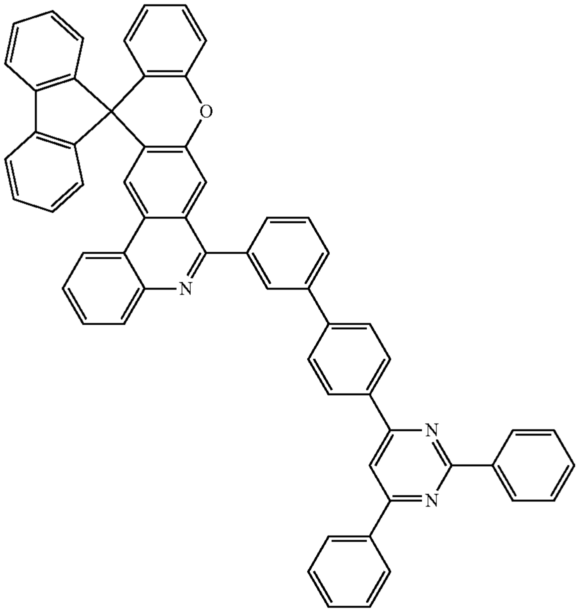
131
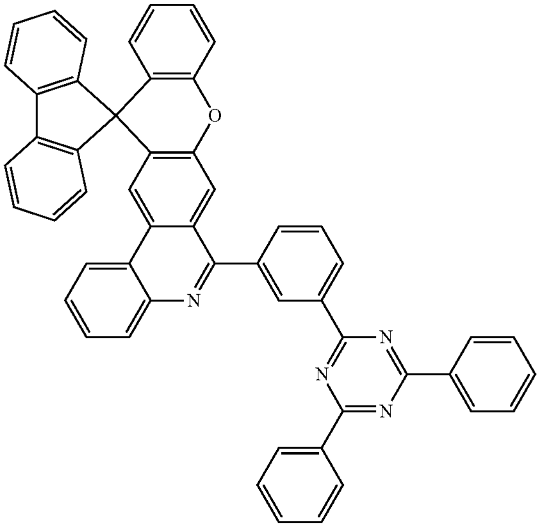
130
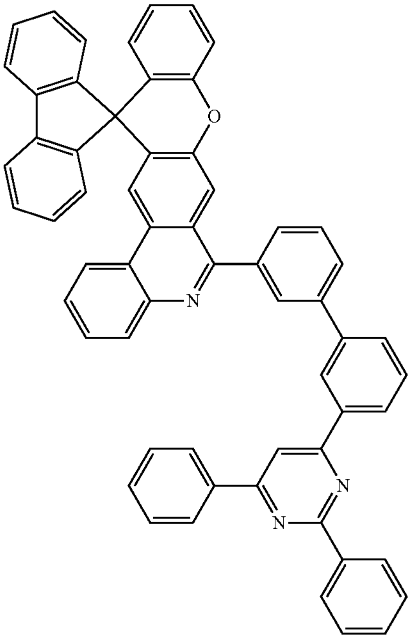
132
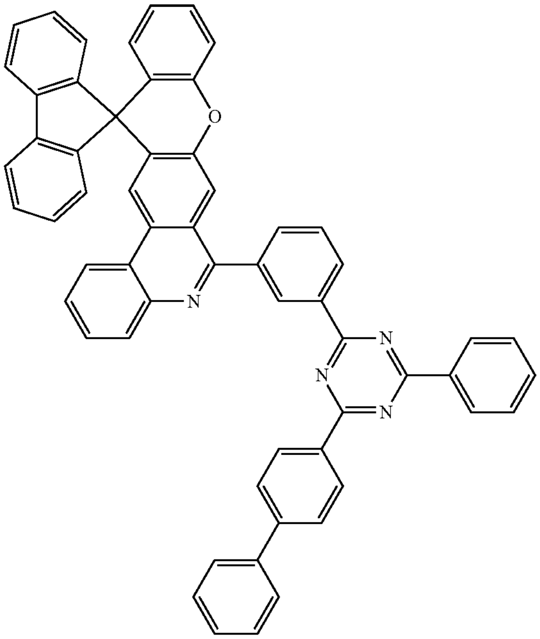

-continued
133
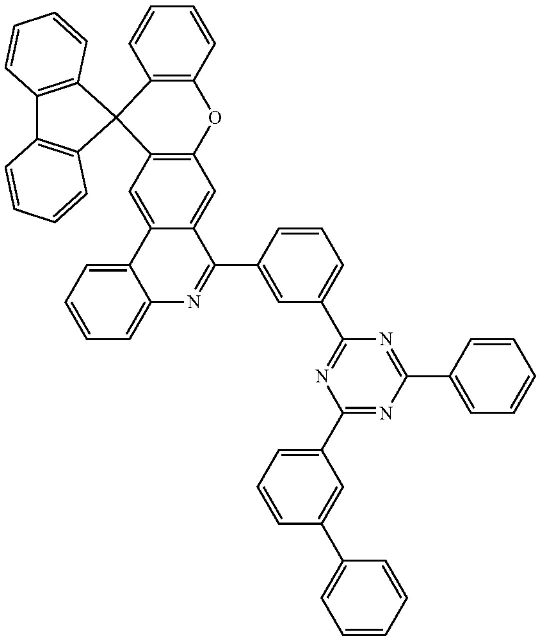
134
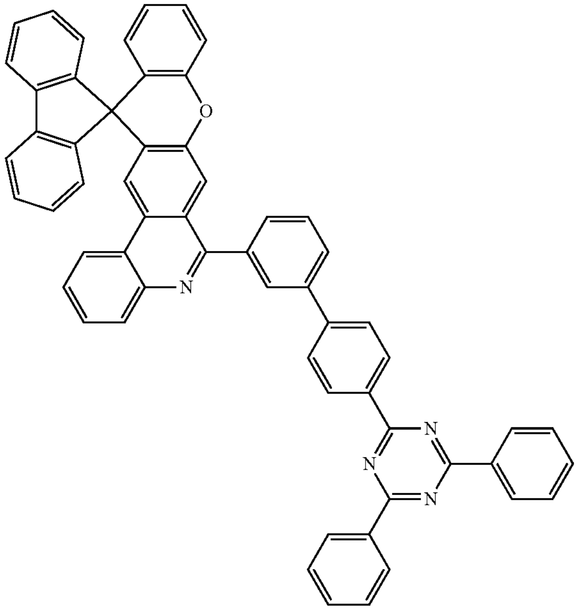
-continued
135
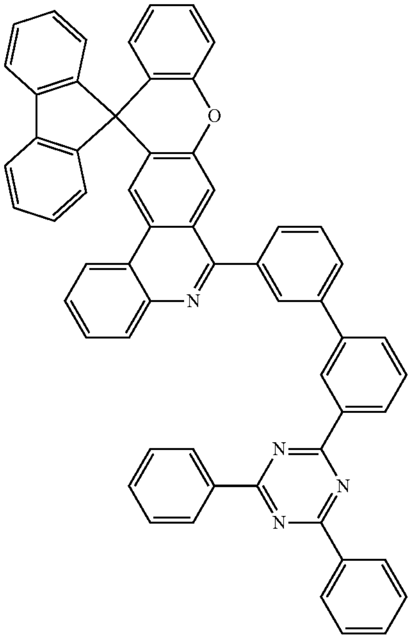
136
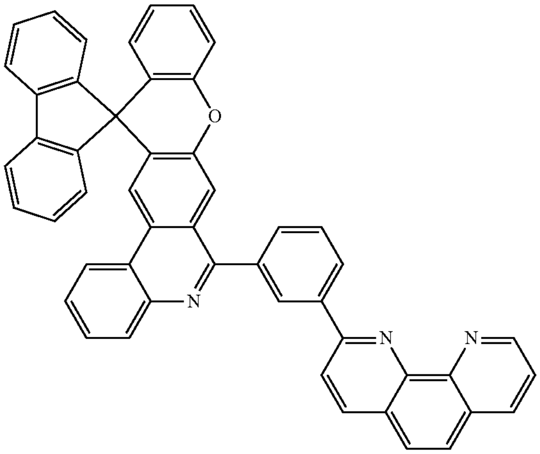

-continued
137
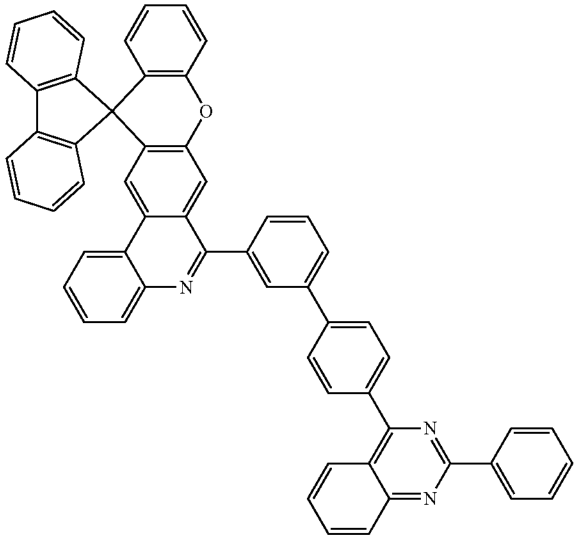
138
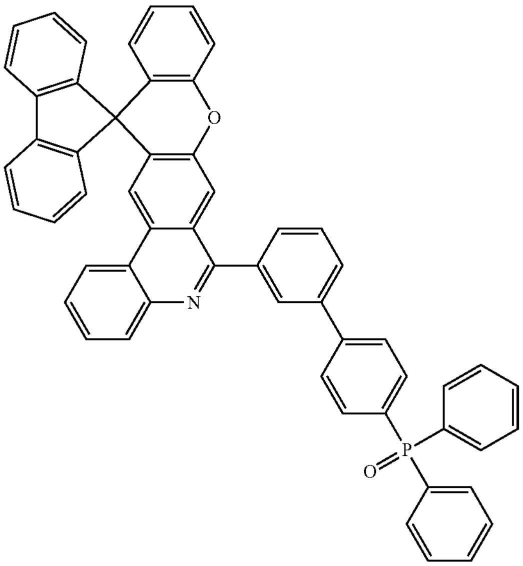
-continued
139
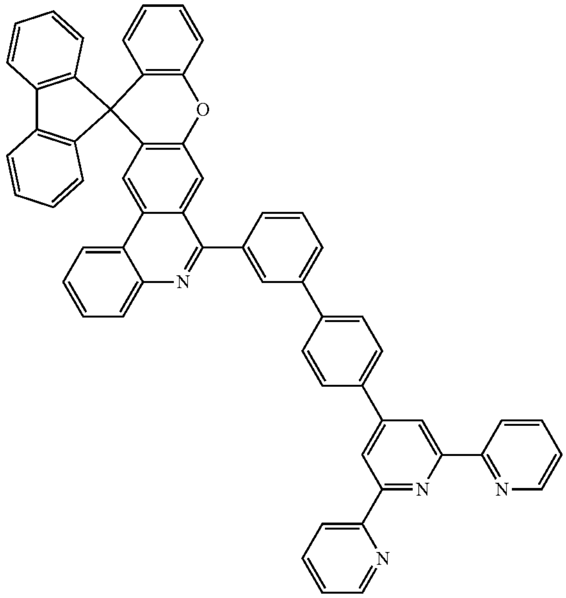
140
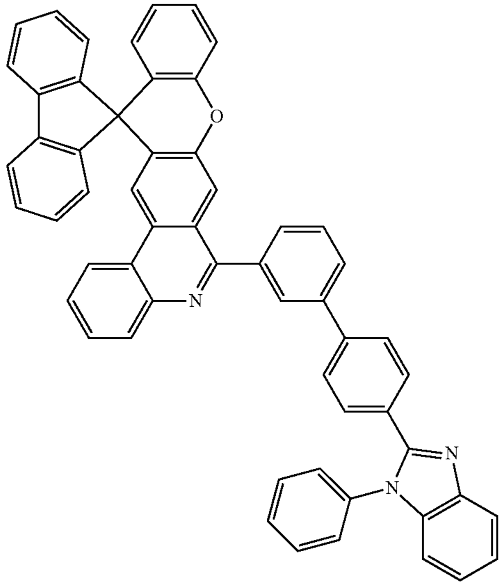

-continued
141
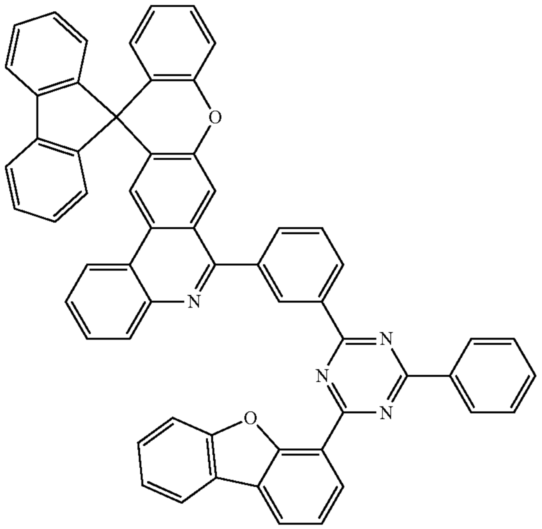
143
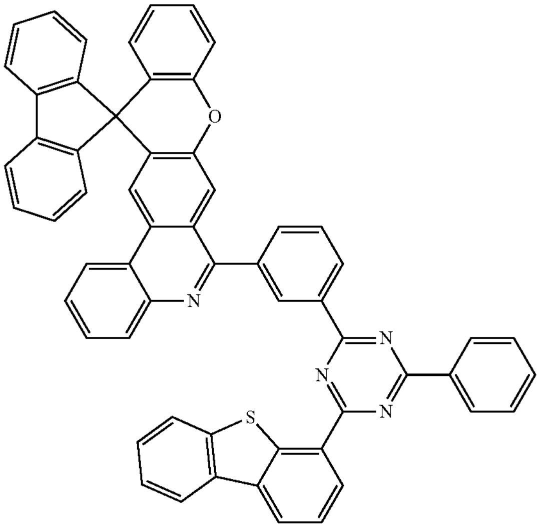
142
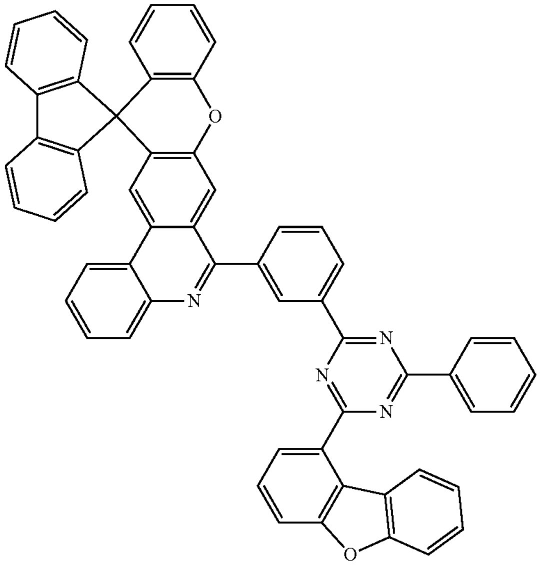
144
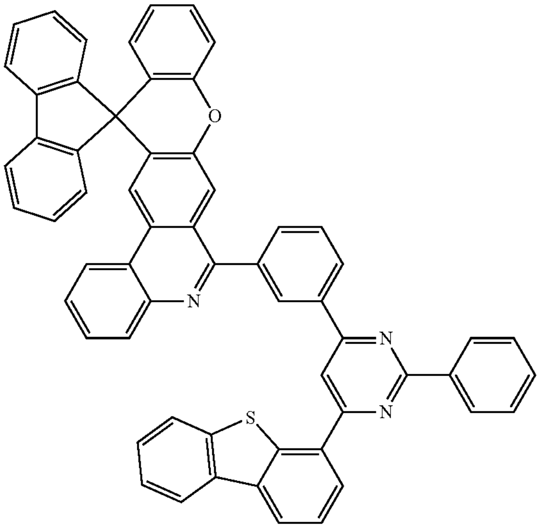

-continued
145
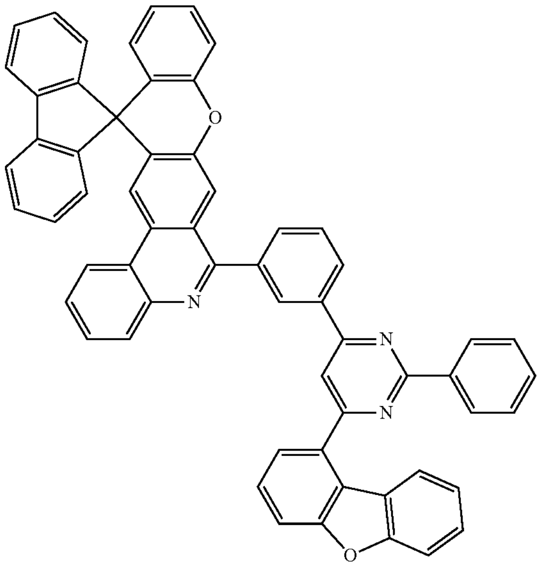
146
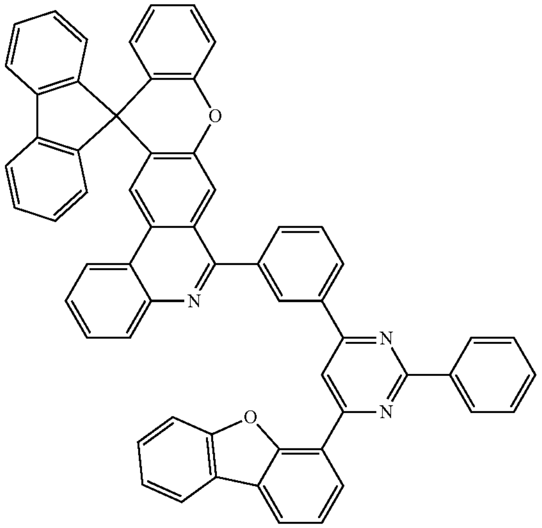
147
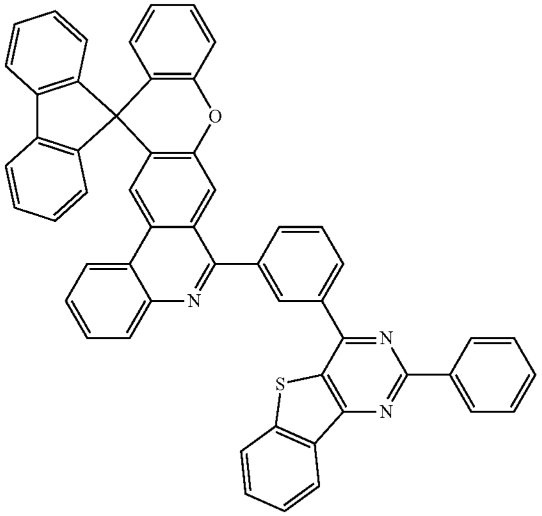
-continued
148
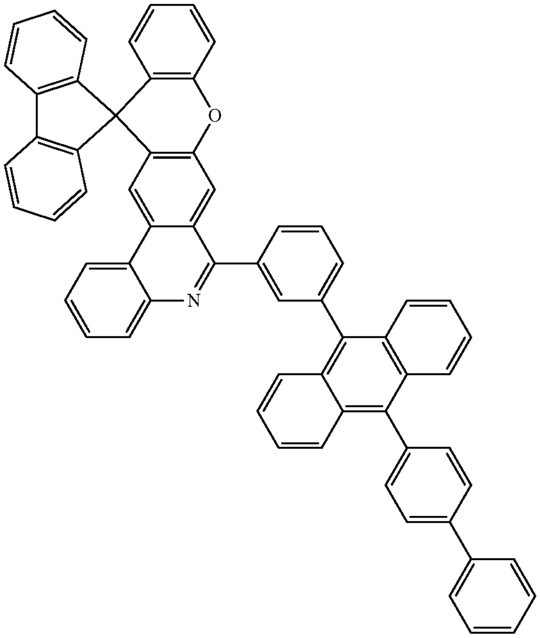
149
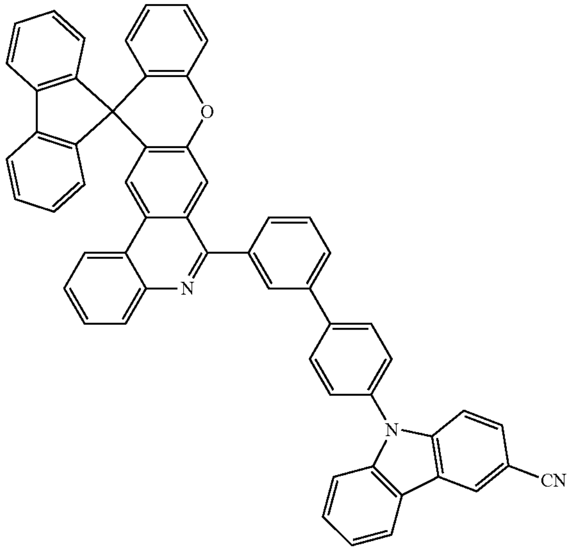

-continued
150
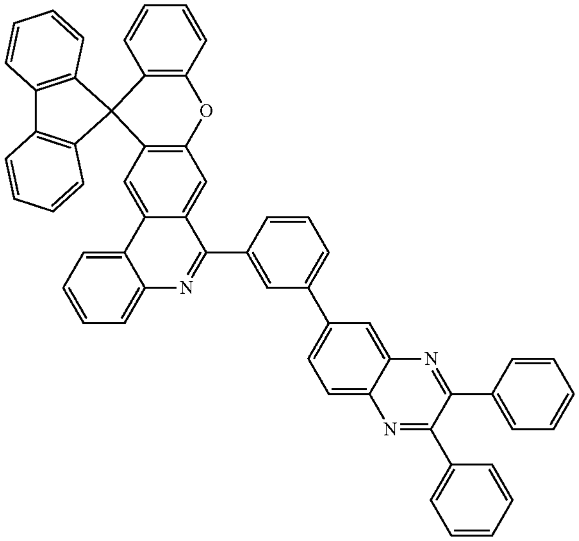
151
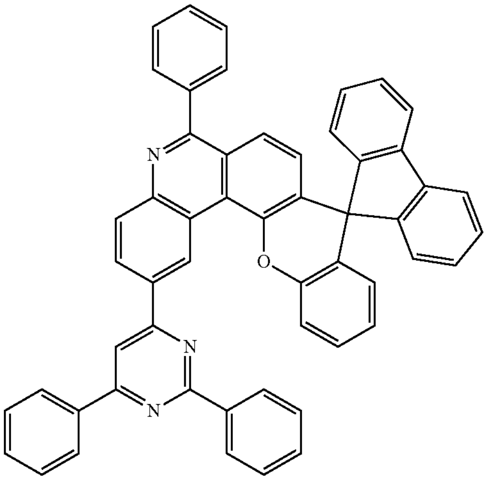
152
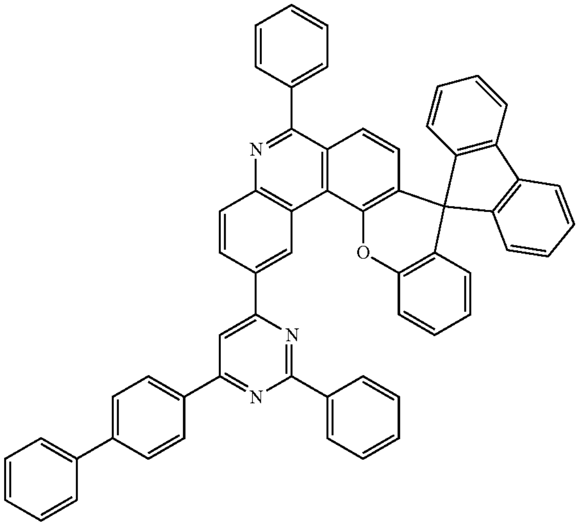
-continued
153
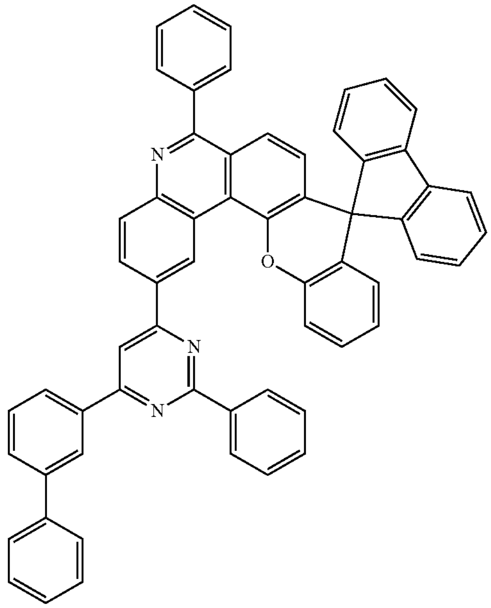
154
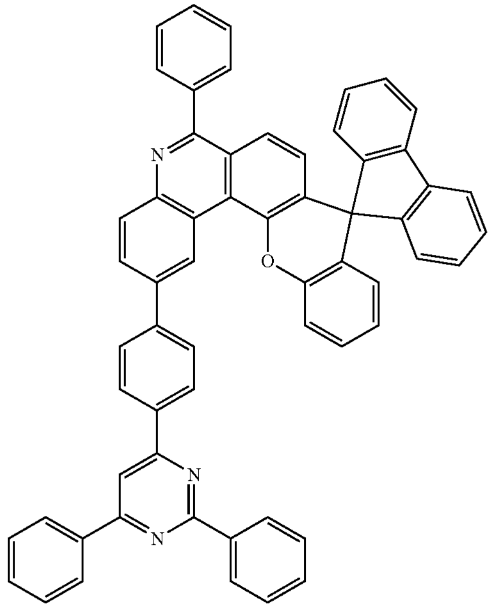

-continued
155
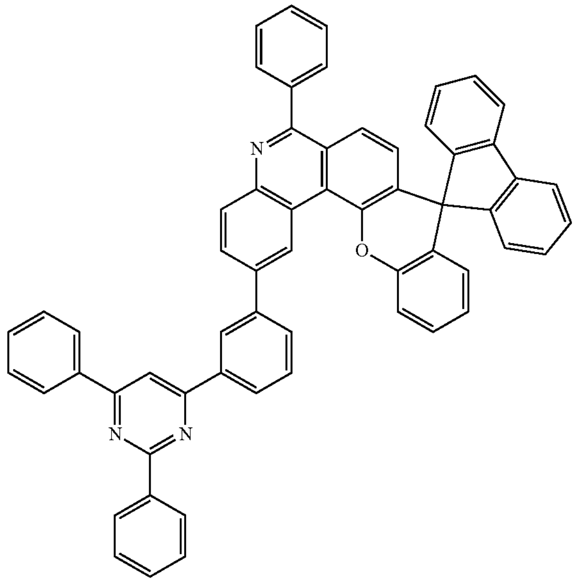
156
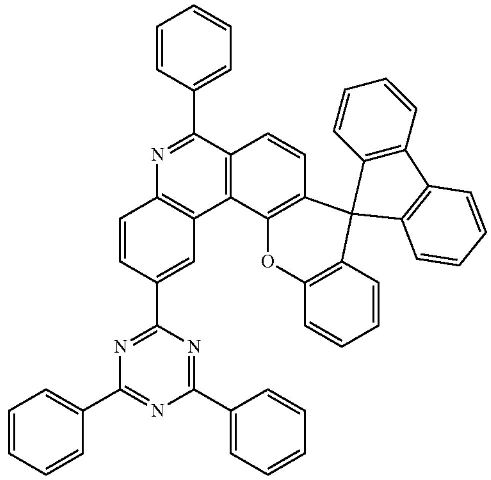
157
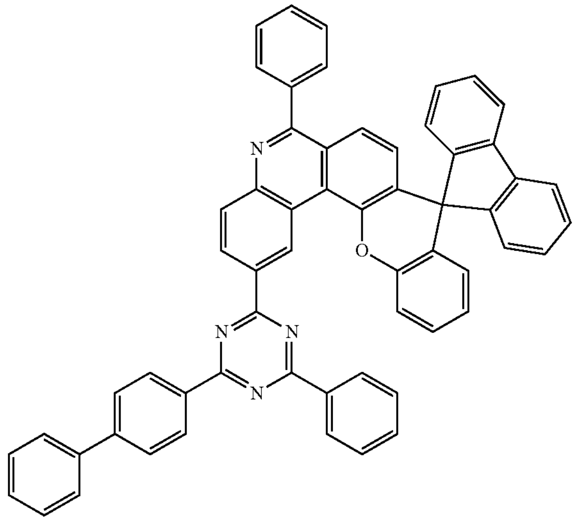
-continued
158
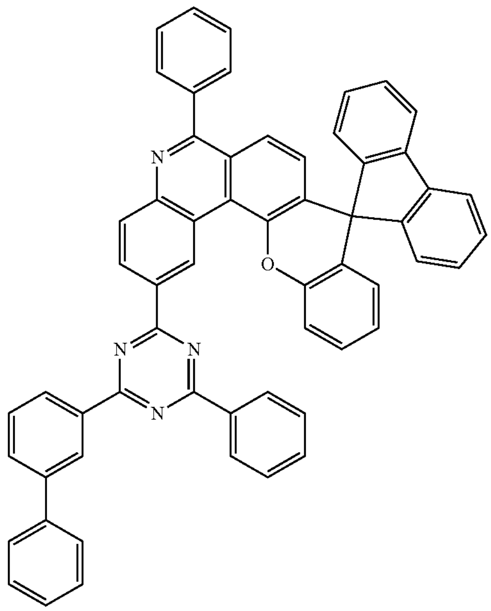
159
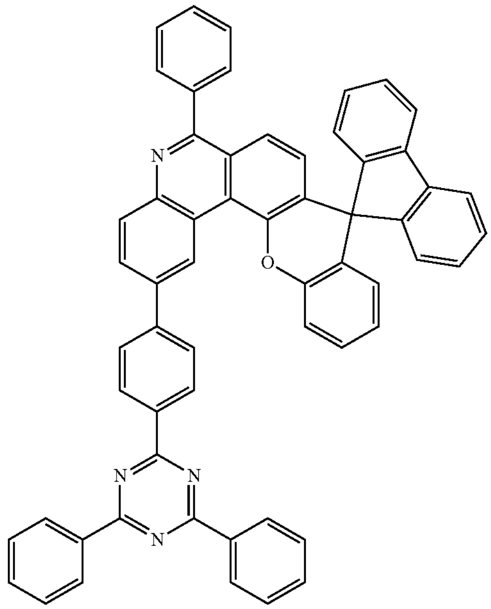

-continued
160
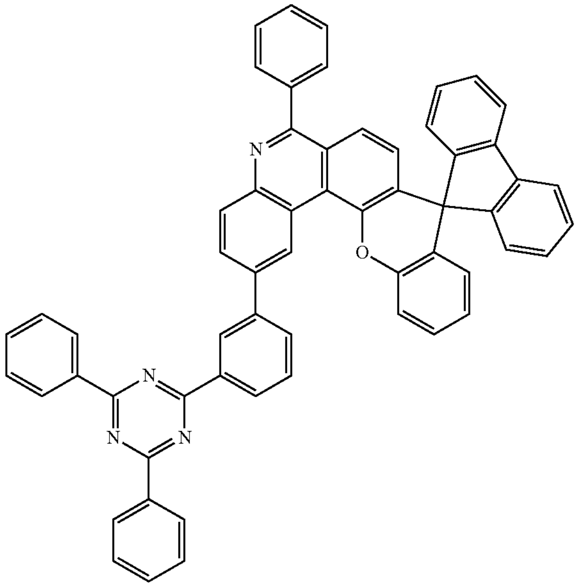
162
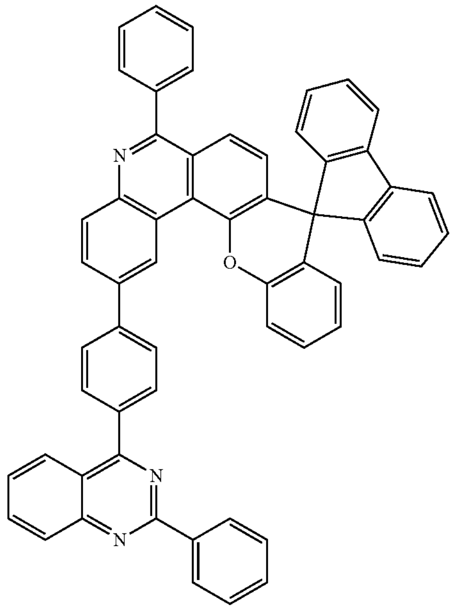
161
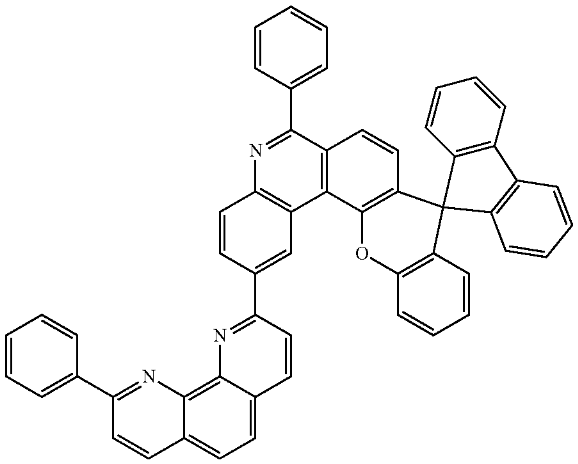
163
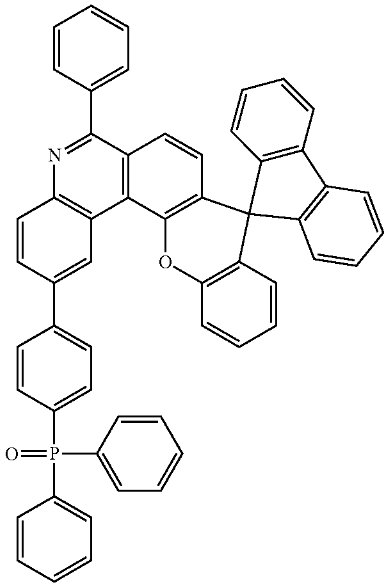

-continued
164
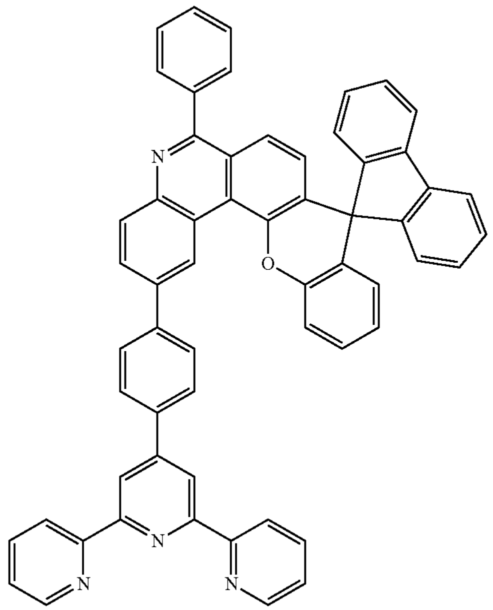
165
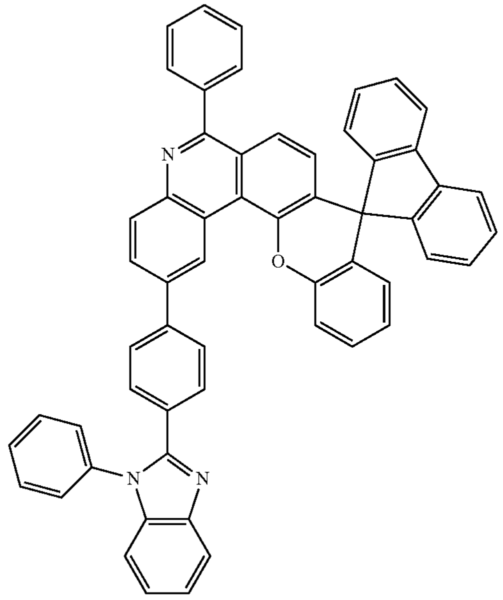
-continued
166
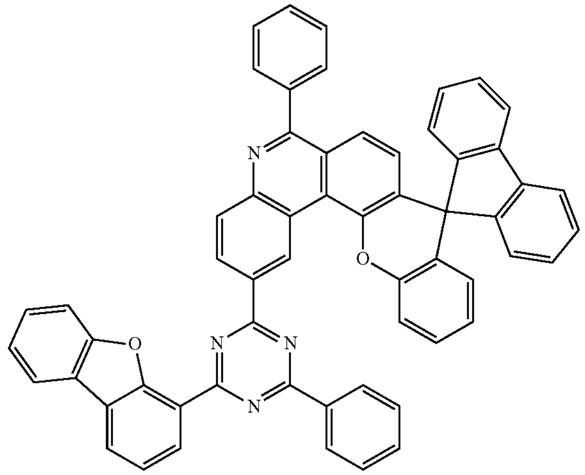
167
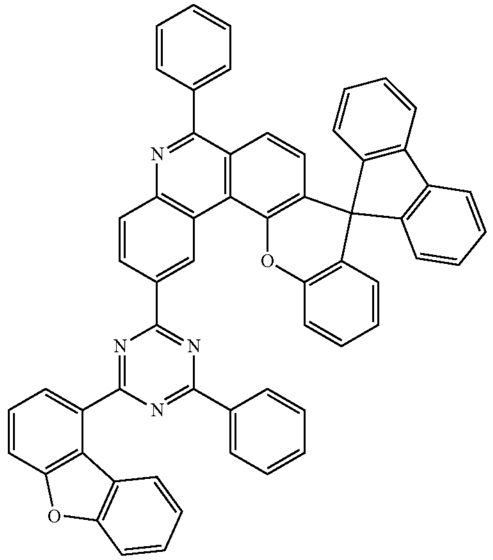
168
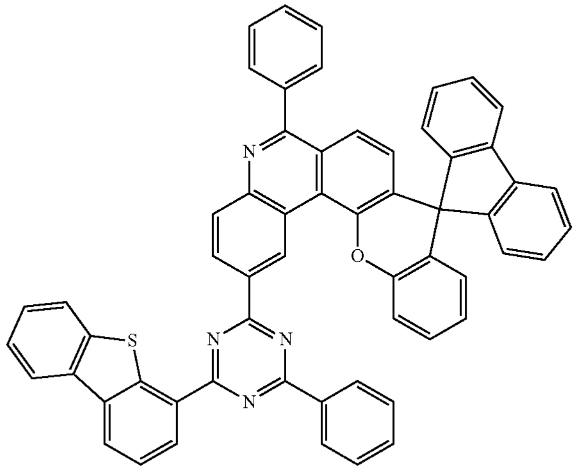

-continued
169
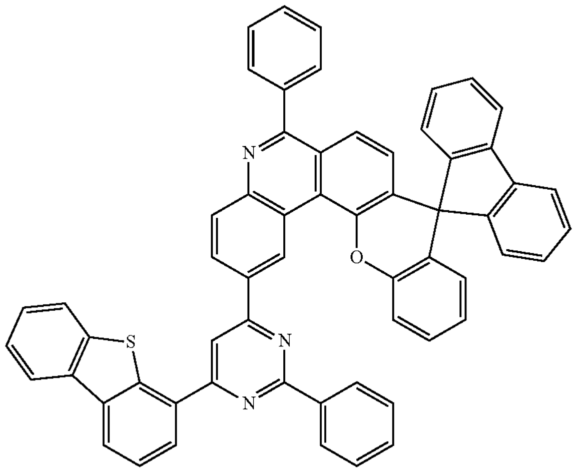
170
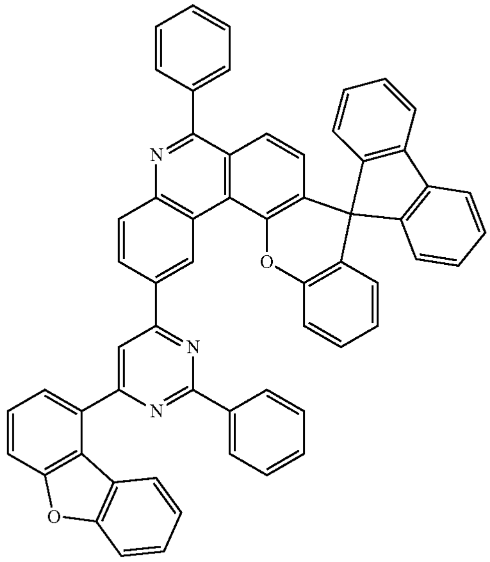
171
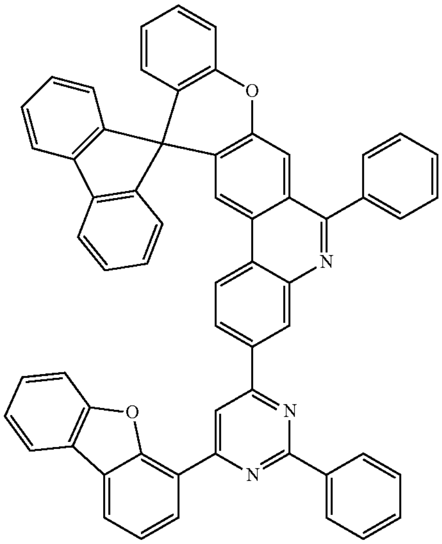
-continued
172
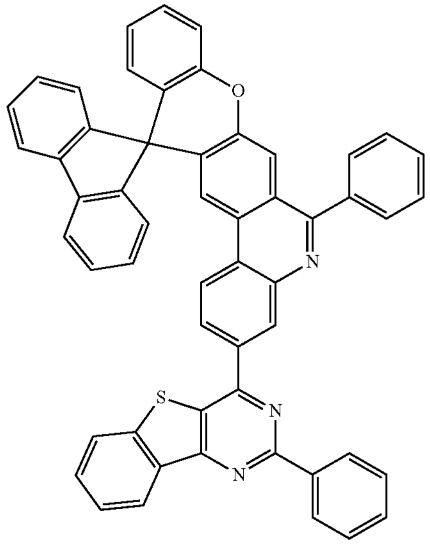
173
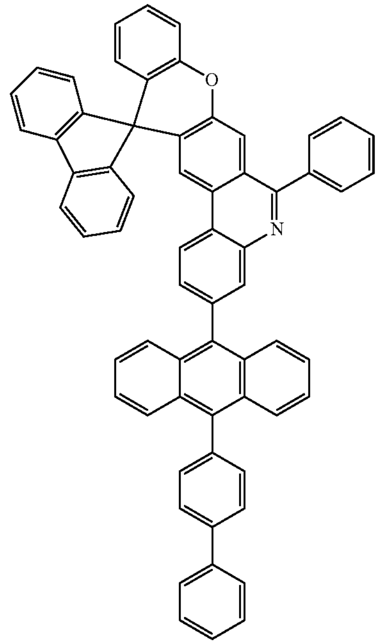

-continued
174
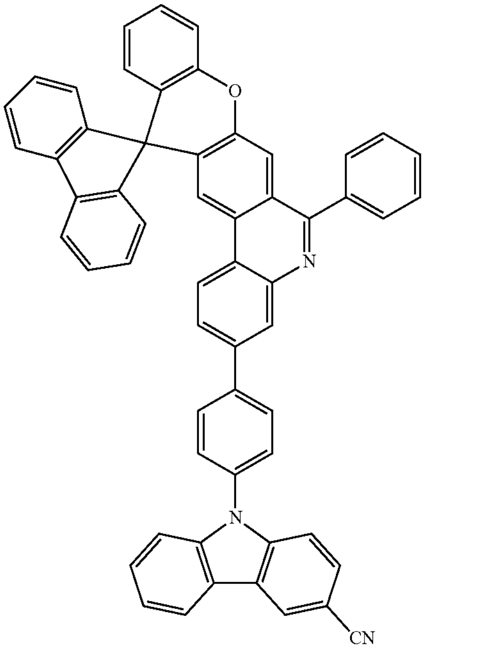
175
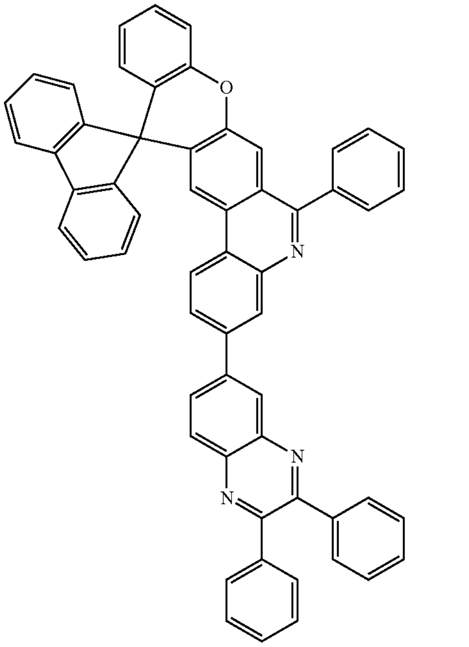
-continued
176
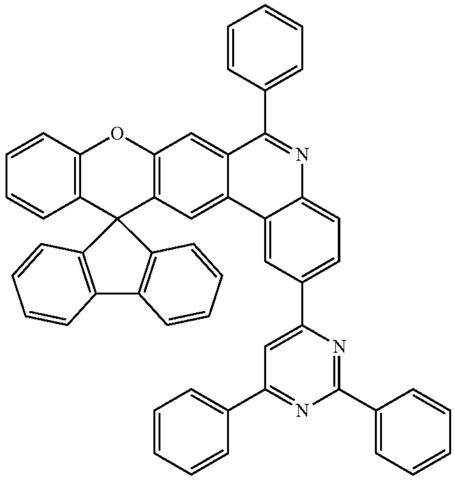
177
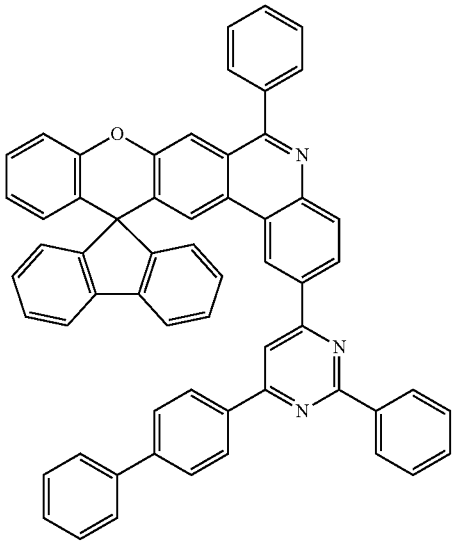
178
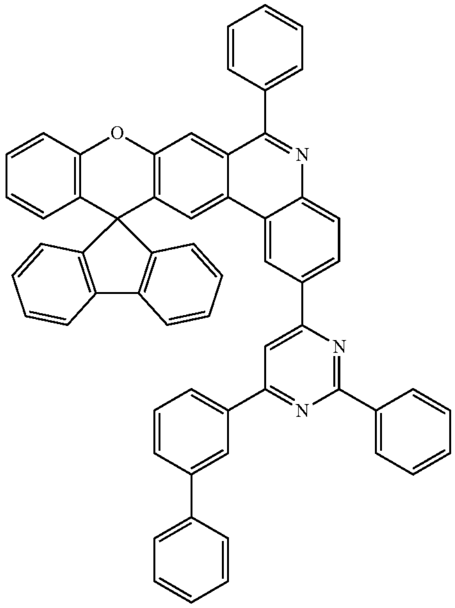

-continued
179
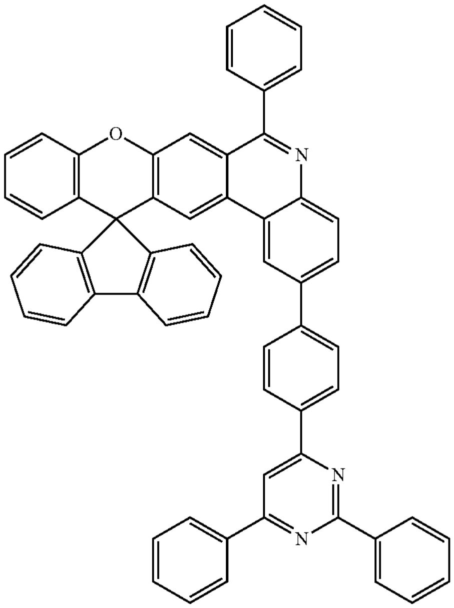
180
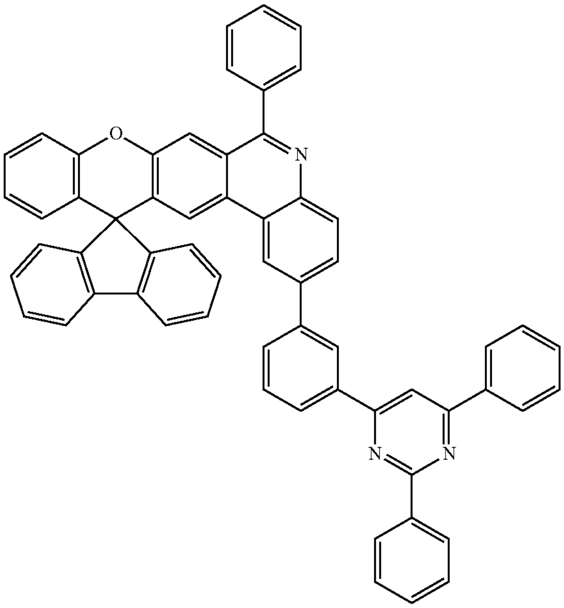
-continued
181
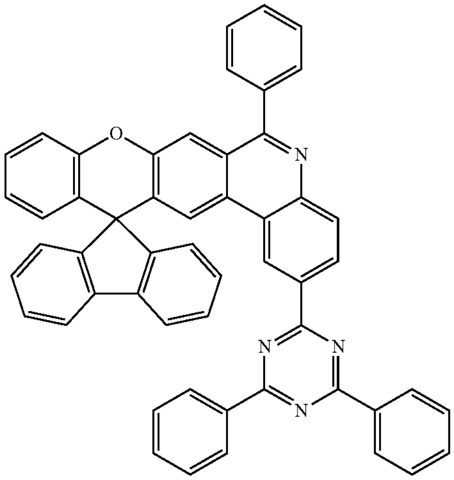
182
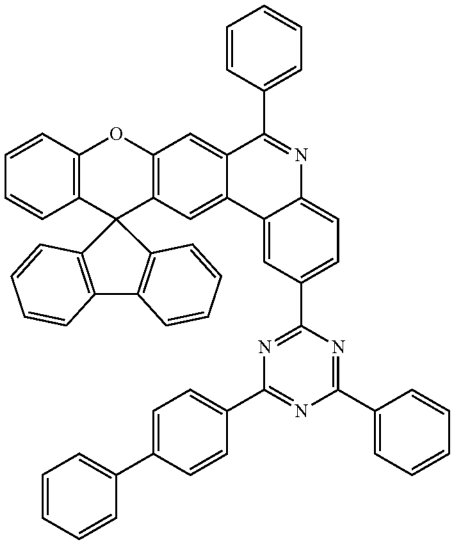
183
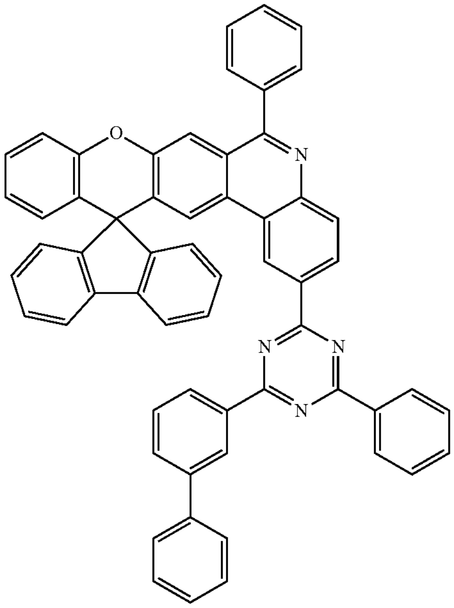

-continued
184
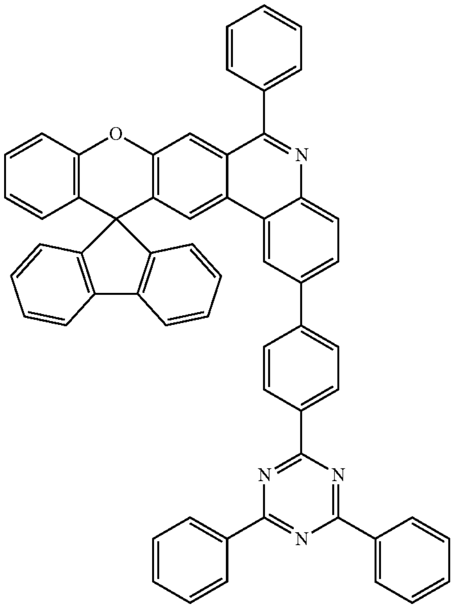
186
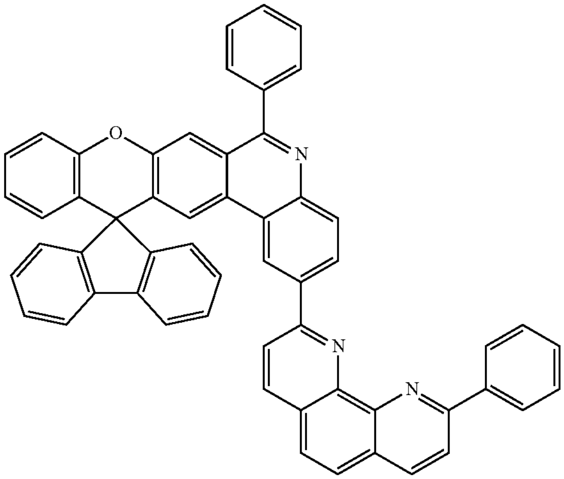
185
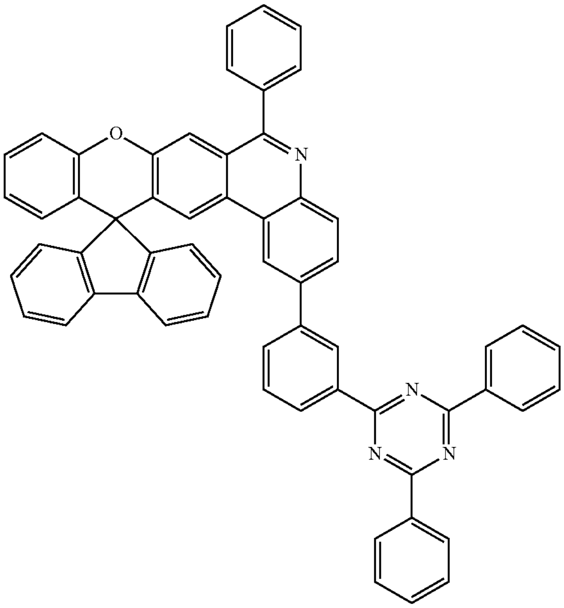
187
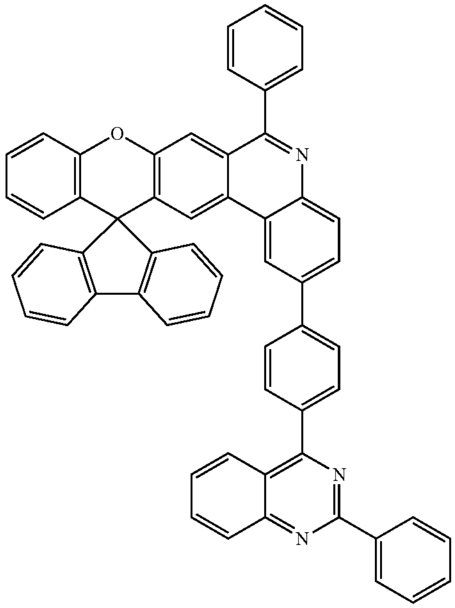

-continued
188
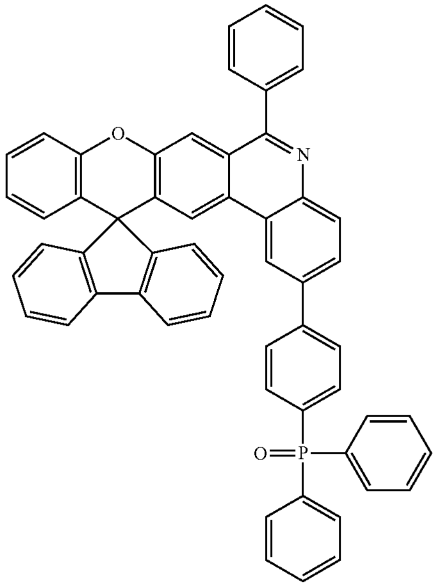
189
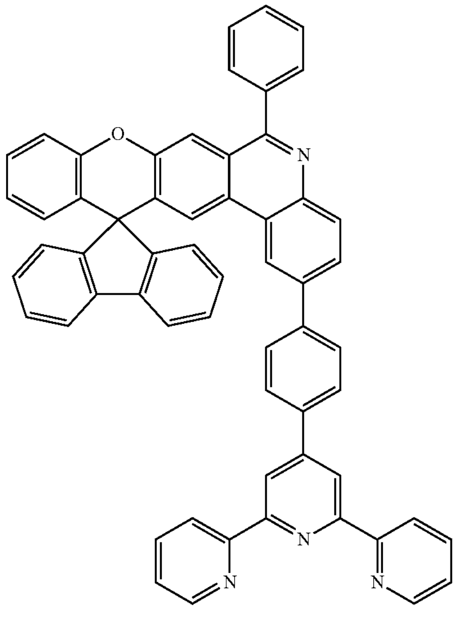
-continued
190
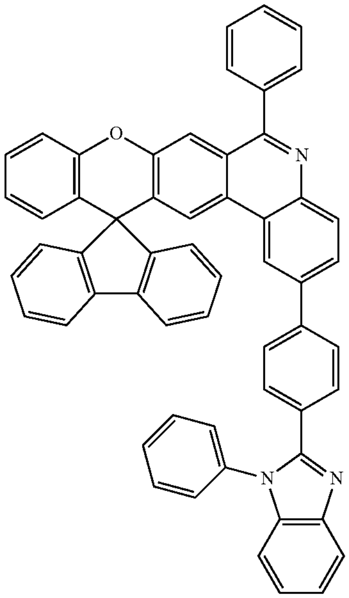
191
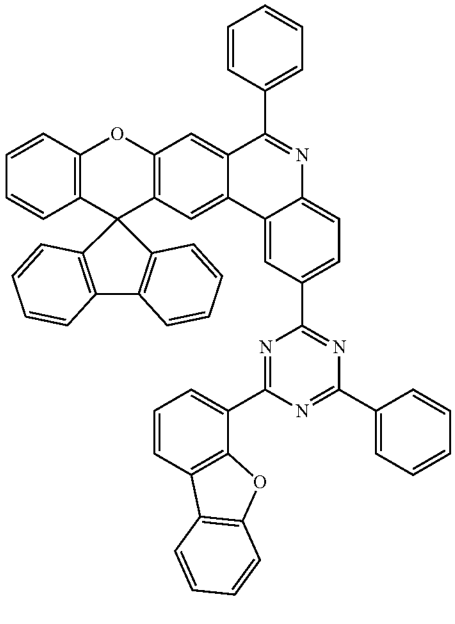

-continued
192
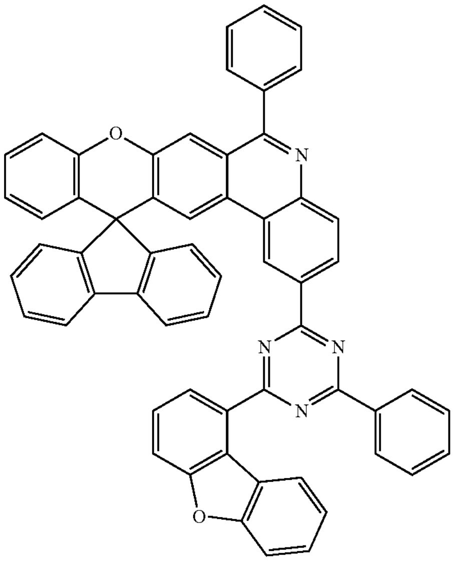
193
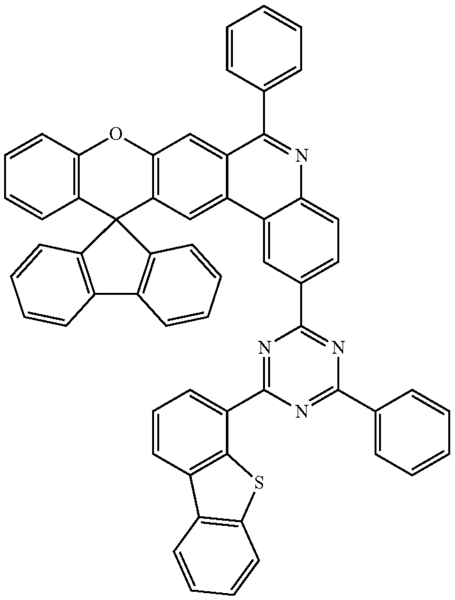
-continued
194
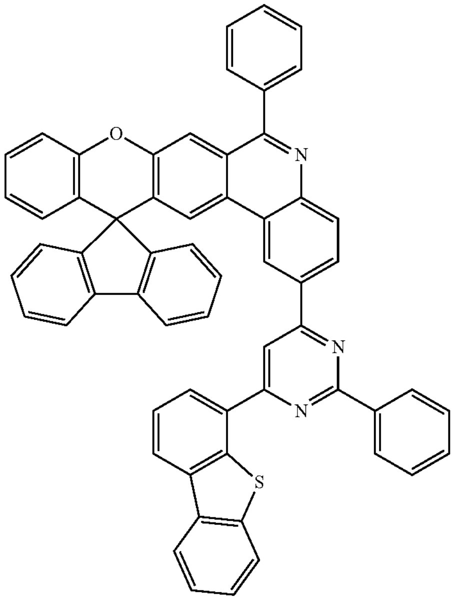
195
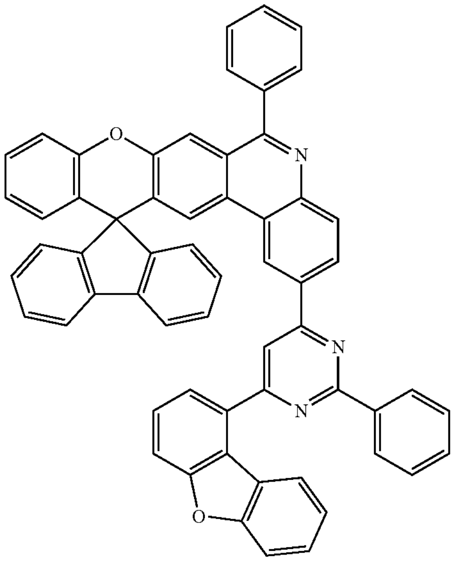

-continued
196
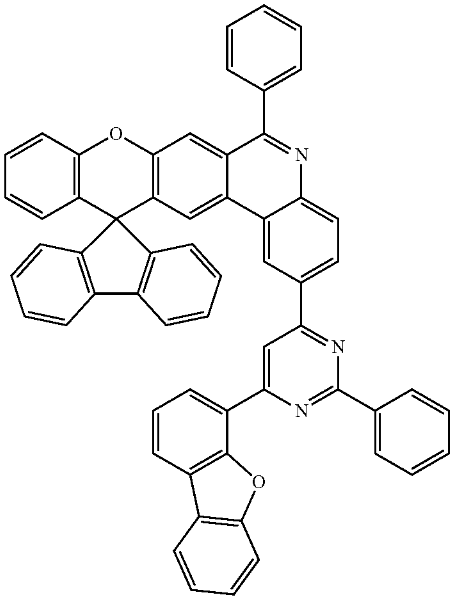
197
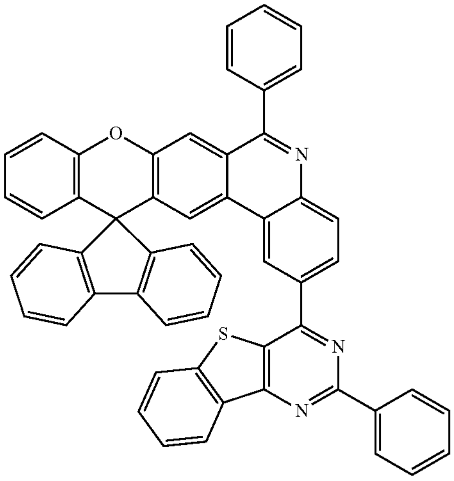
-continued
198
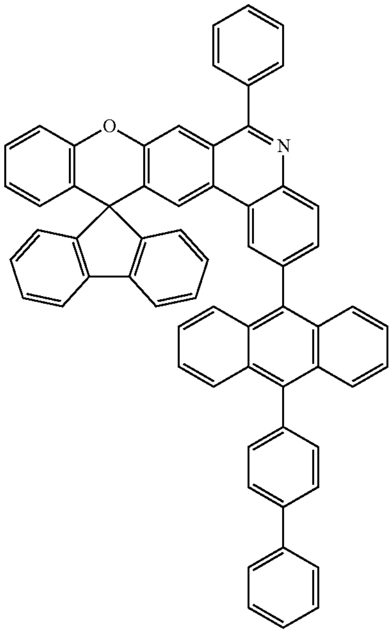
199
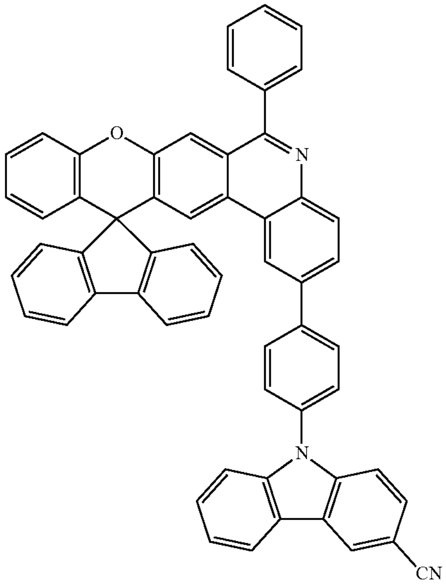

-continued
200
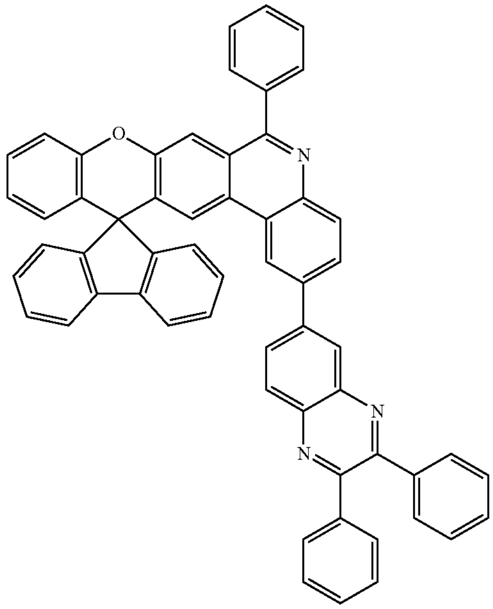
201
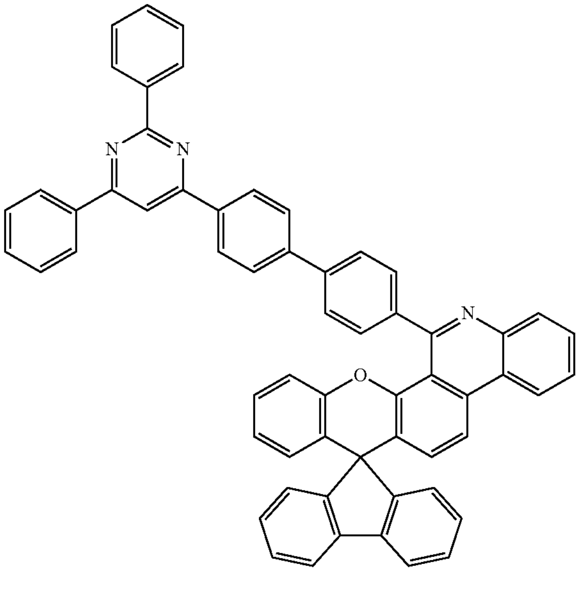
-continued
202
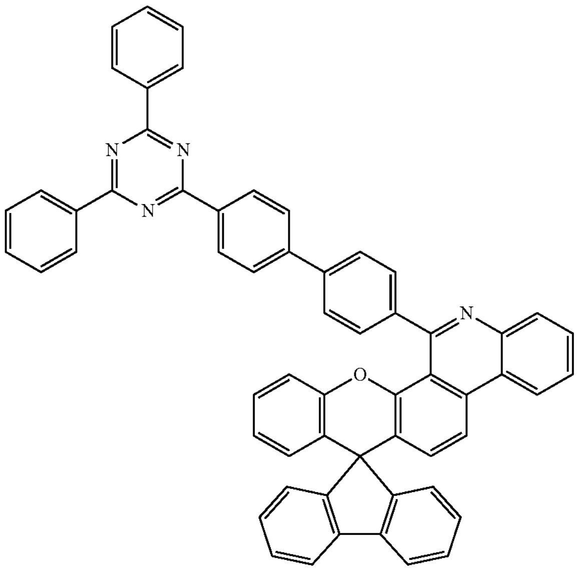
203
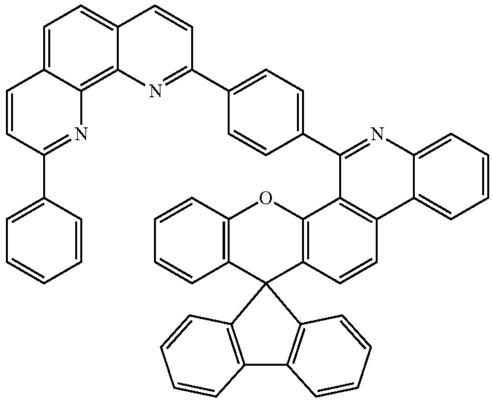
204
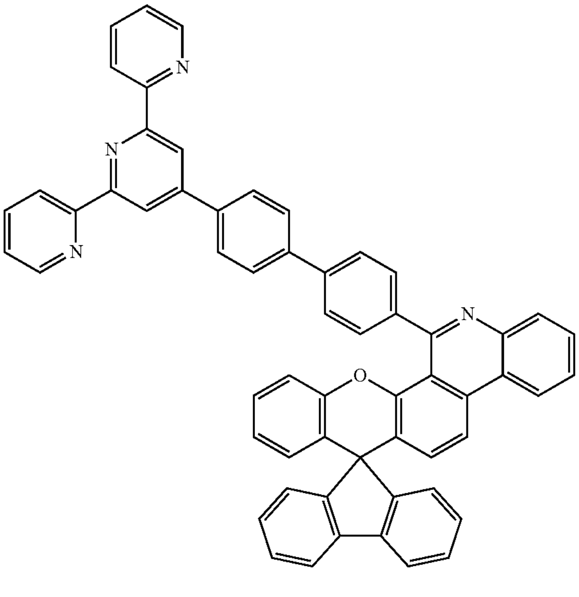

-continued
205
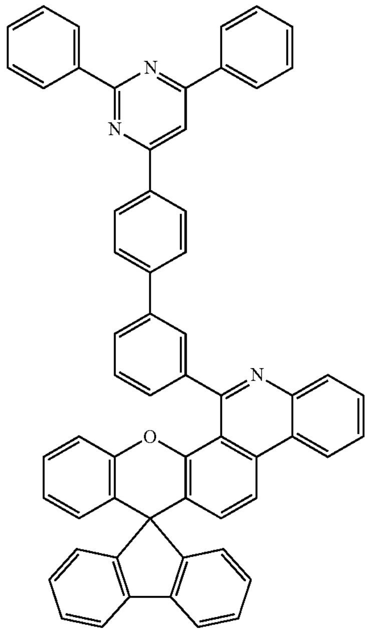
206
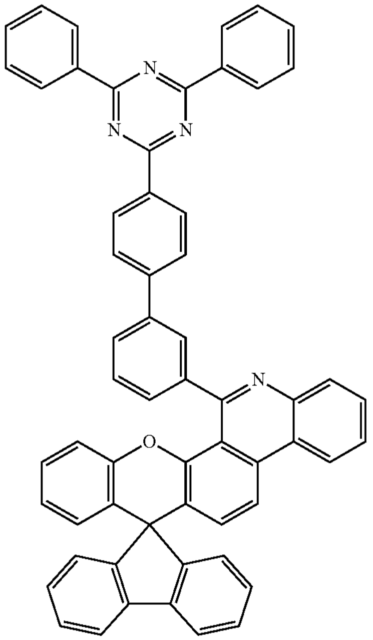
-continued
207
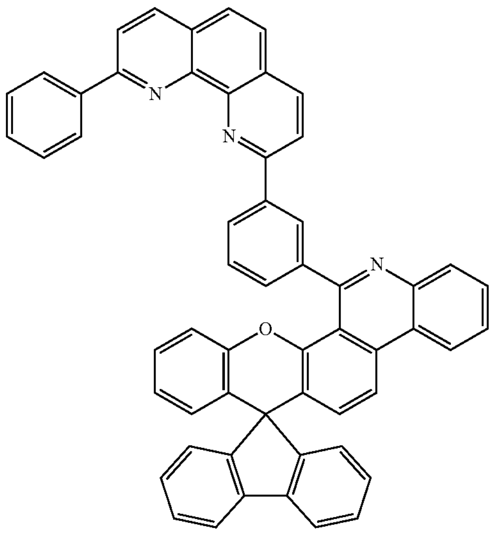
208
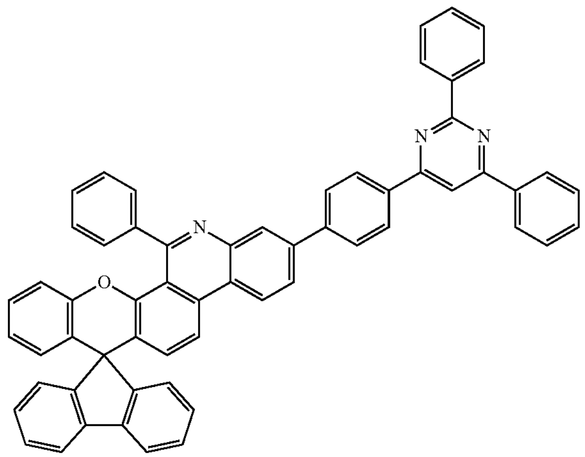
209
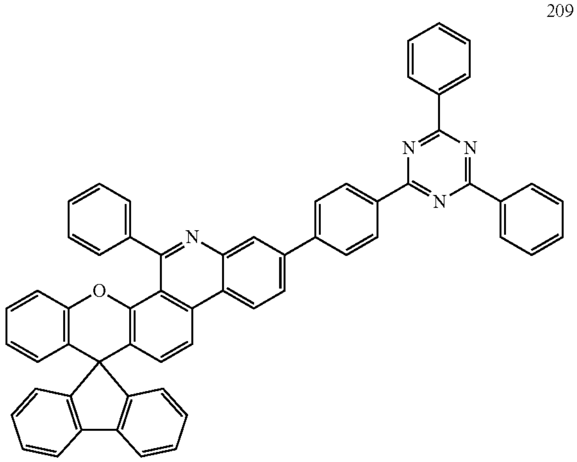

210
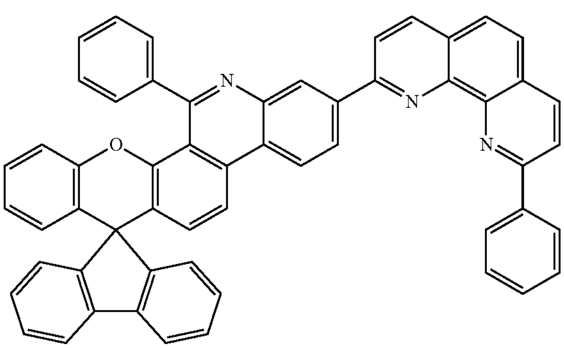
211
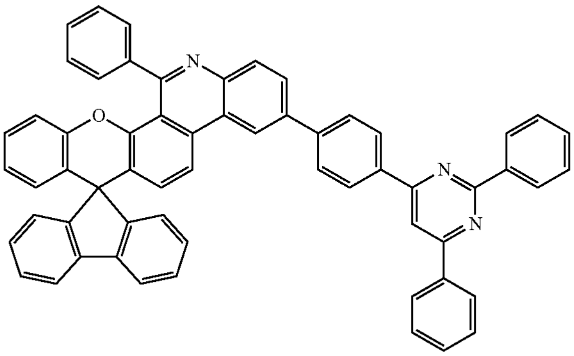
212
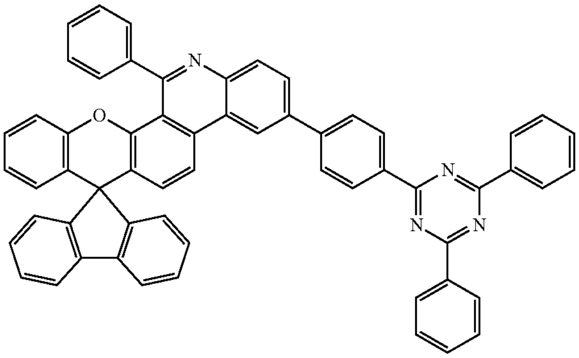
213
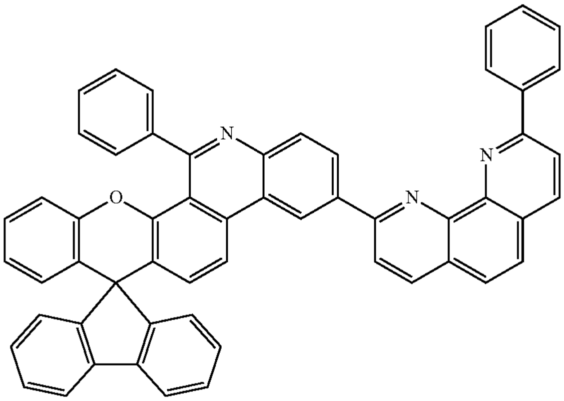
214
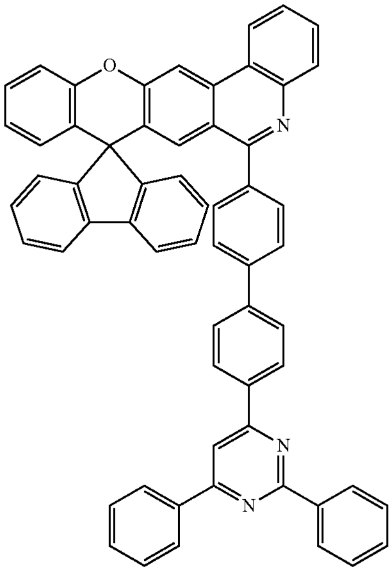
215
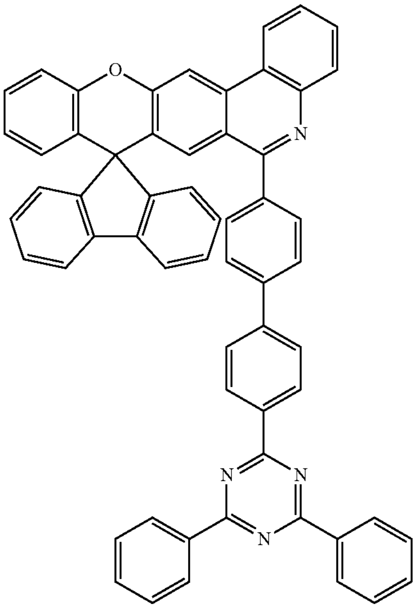
216
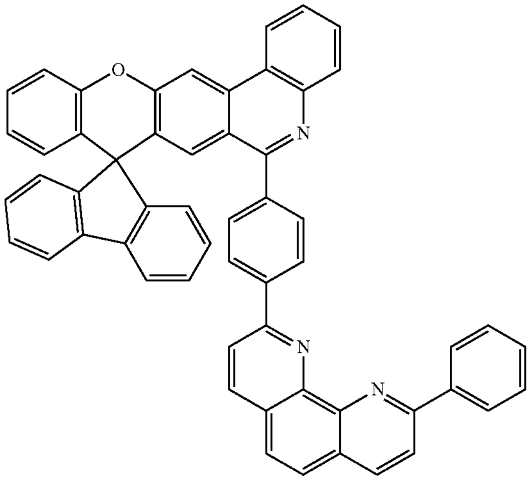

-continued
217
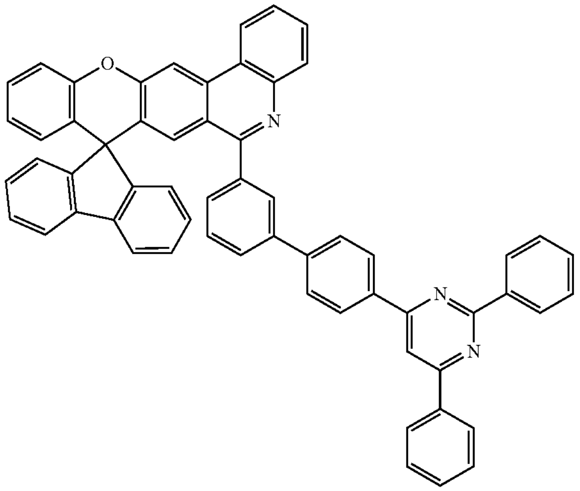
218
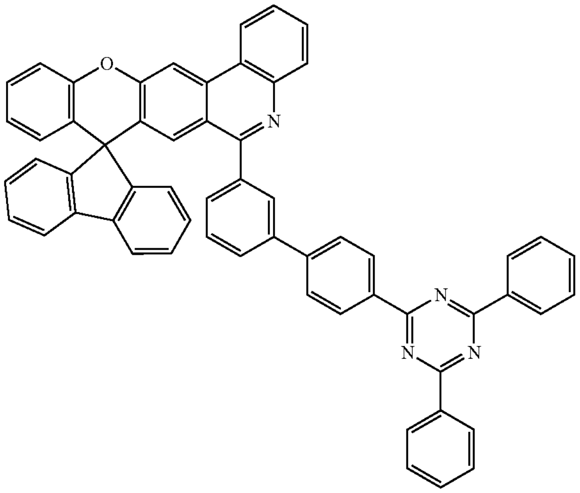
219
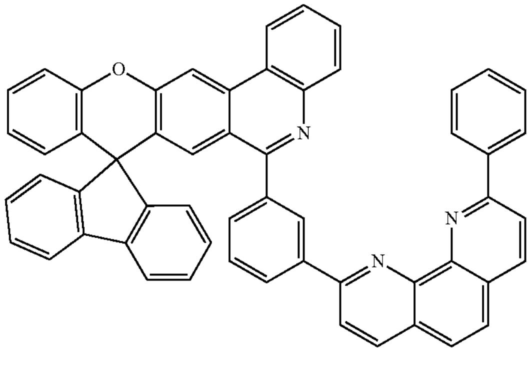
-continued
220
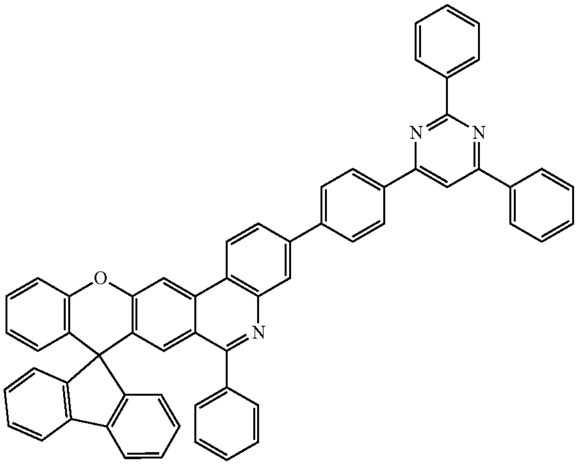
221
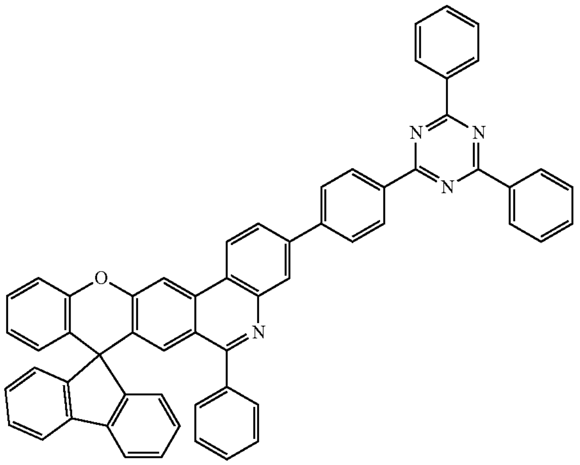
222
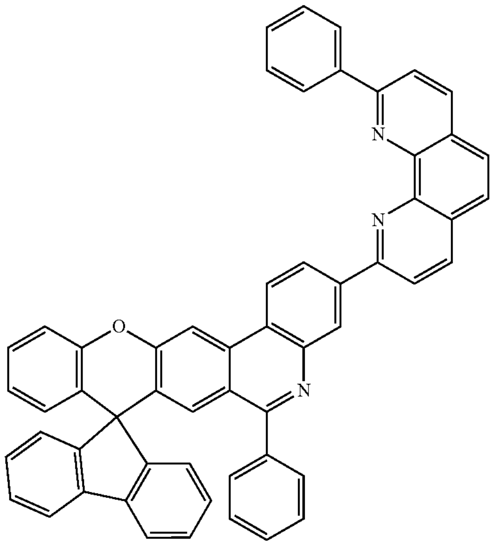

223
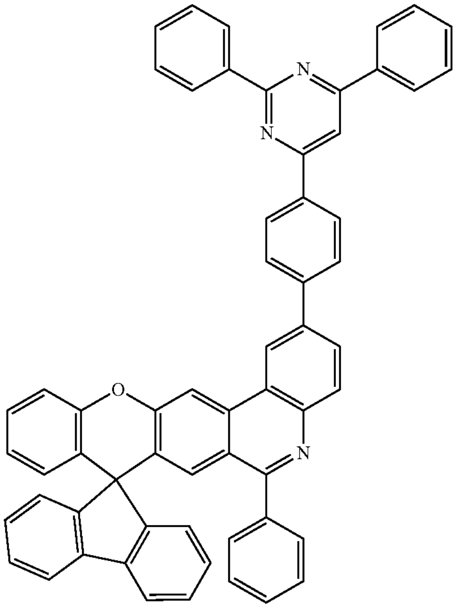
224
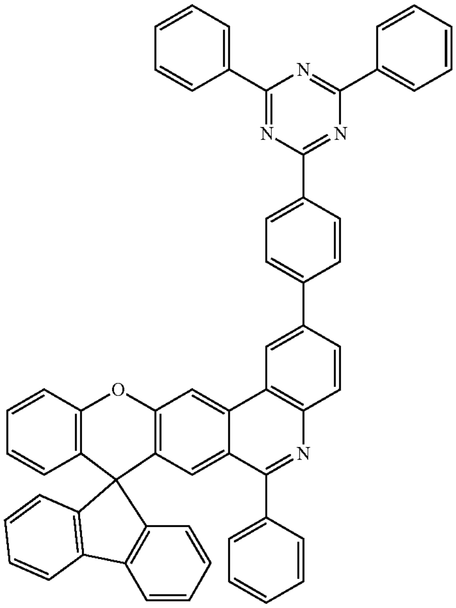
225
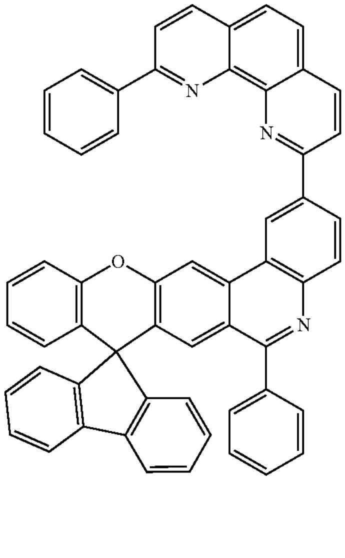
226
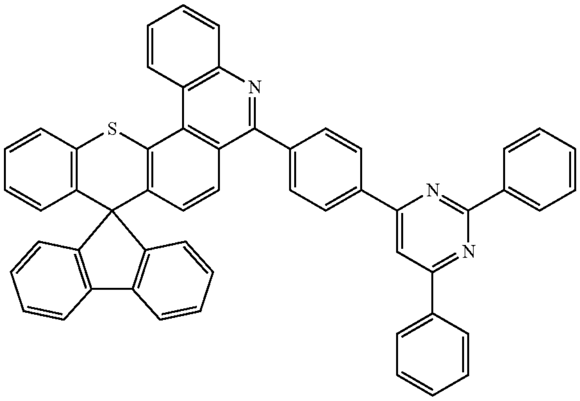
227
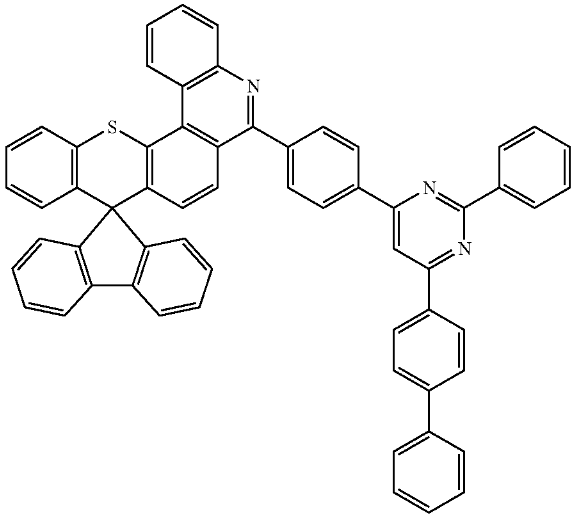

-continued
228
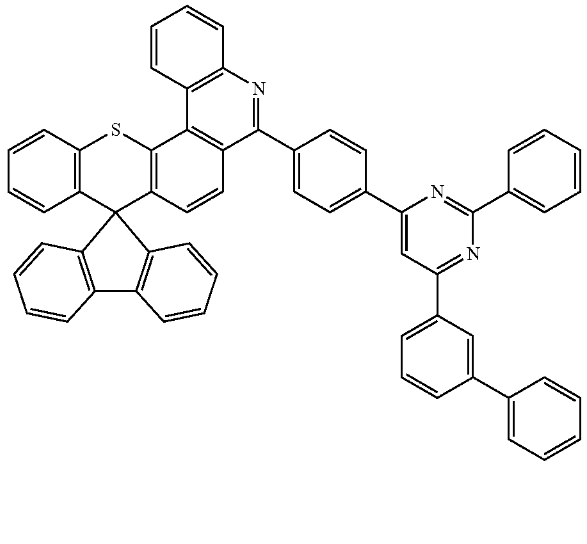
229
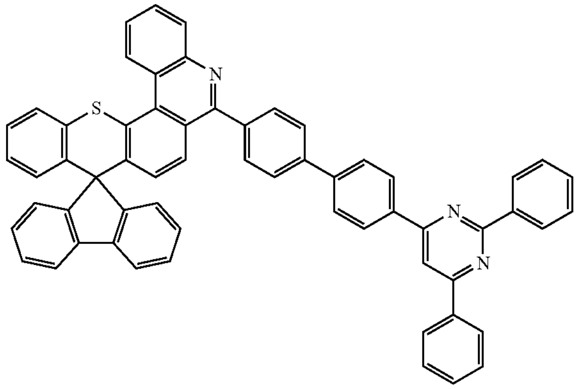
230
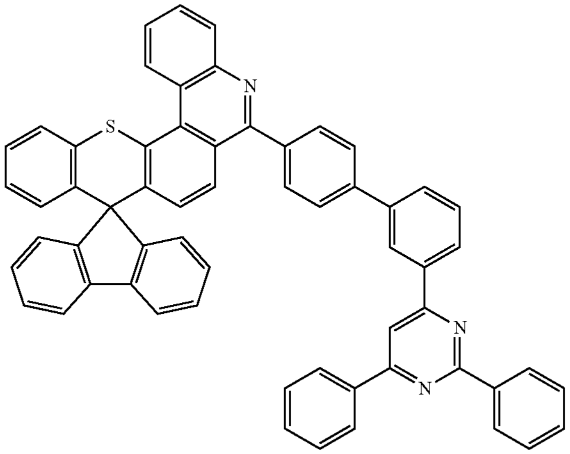
-continued
231
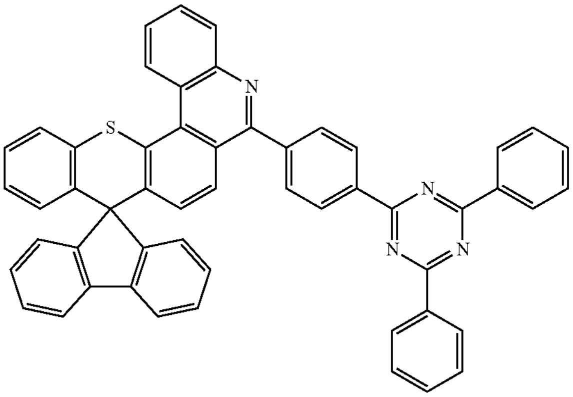
232
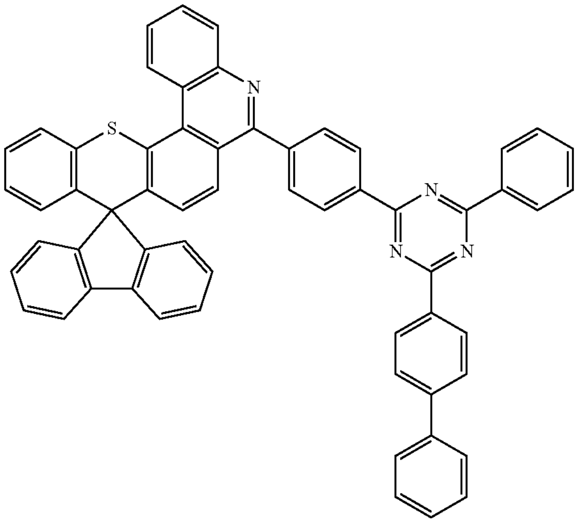
233
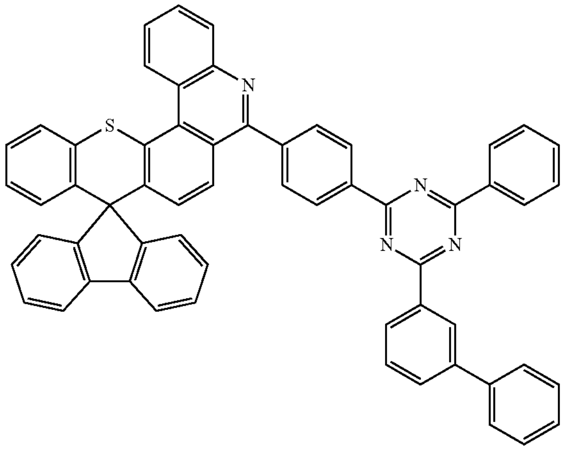

-continued
234
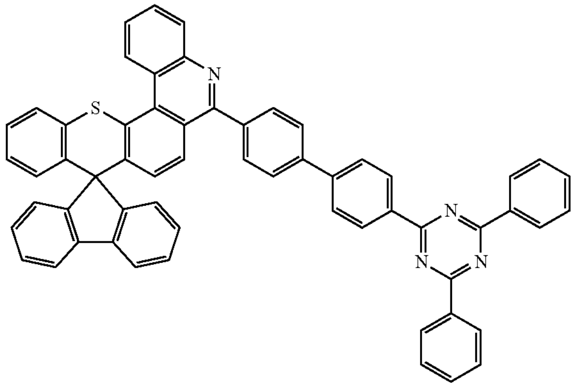
235
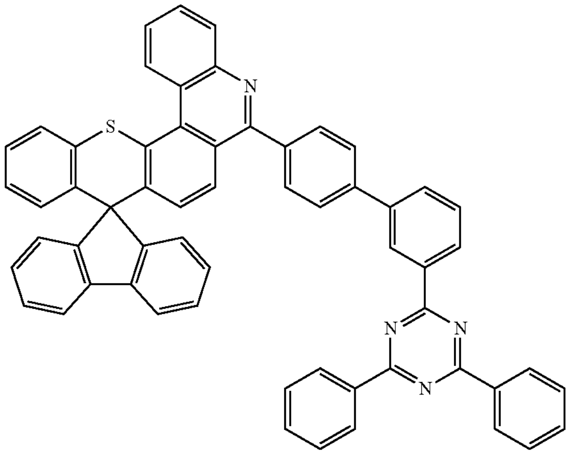
236
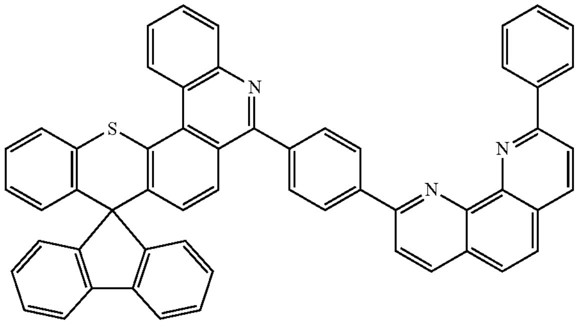
237
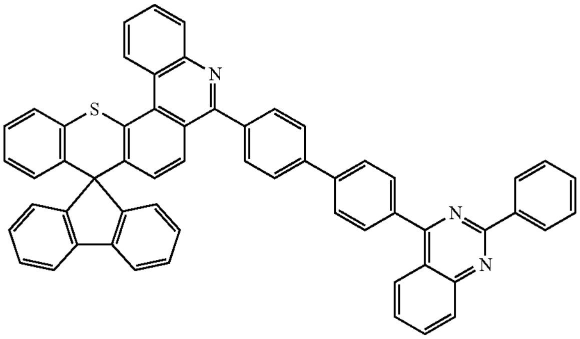
-continued
238
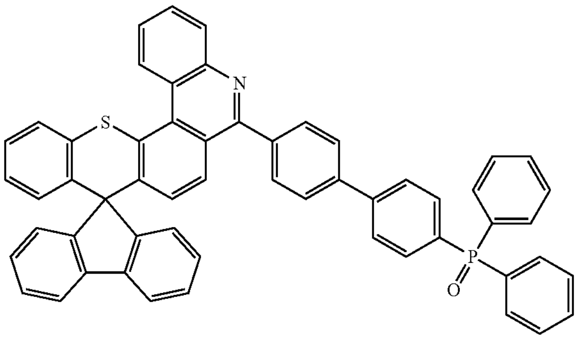
239
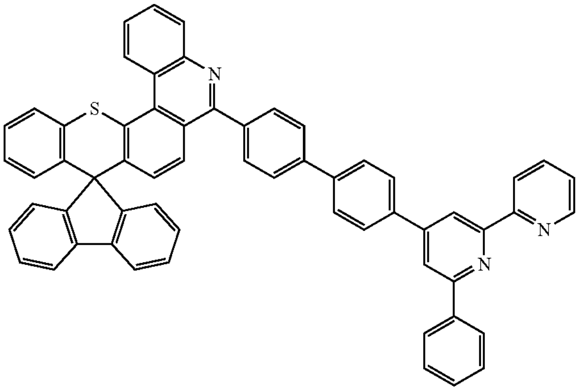
240
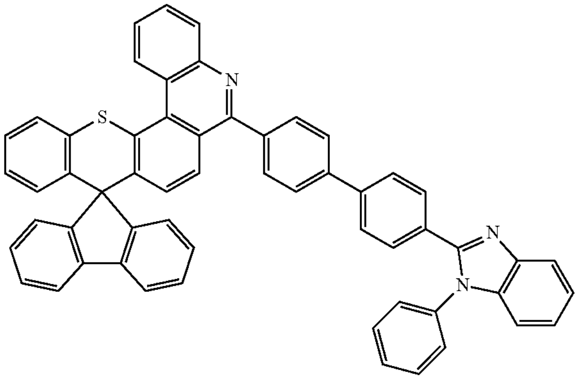
241
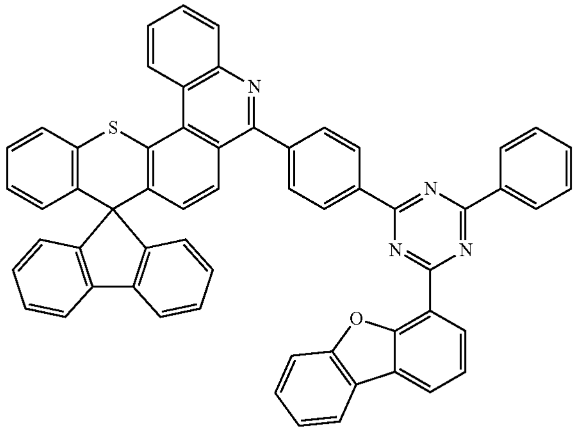

-continued
242
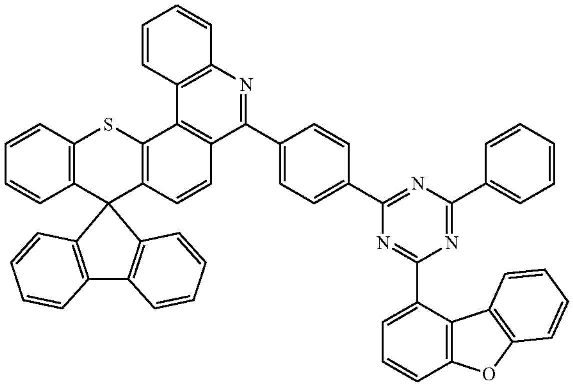
243
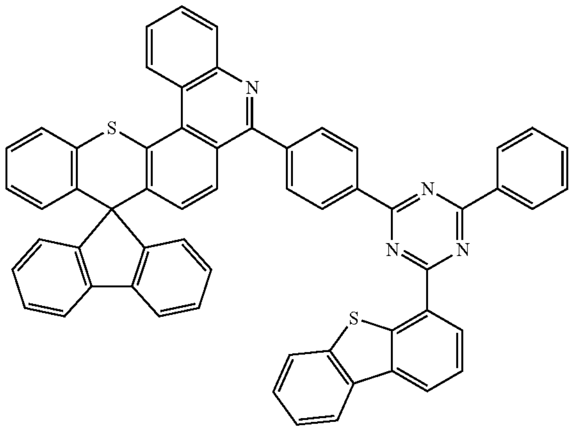
244
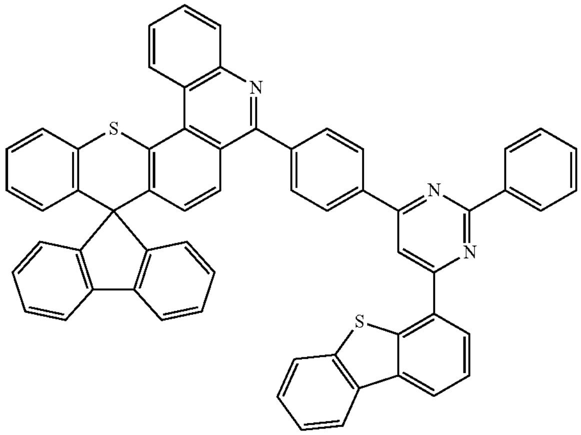
-continued
245
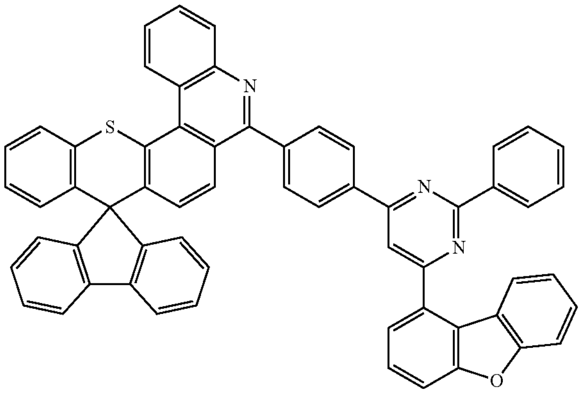
246
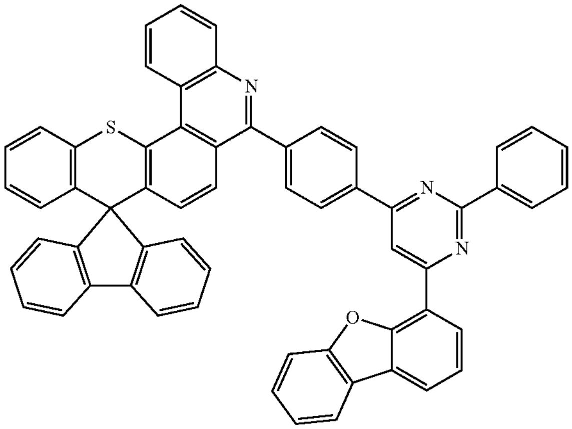
247
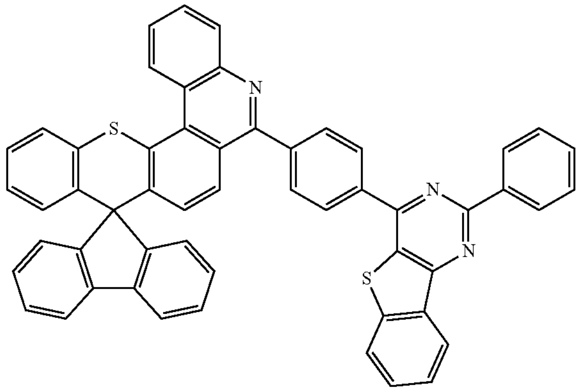
248
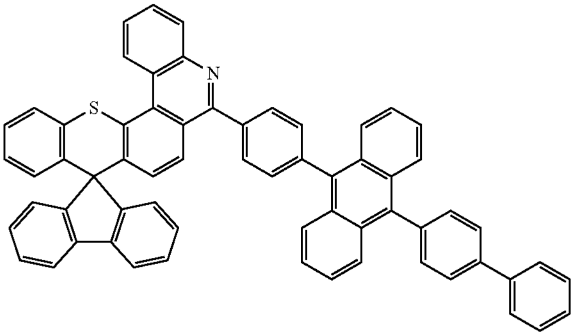

-continued
249
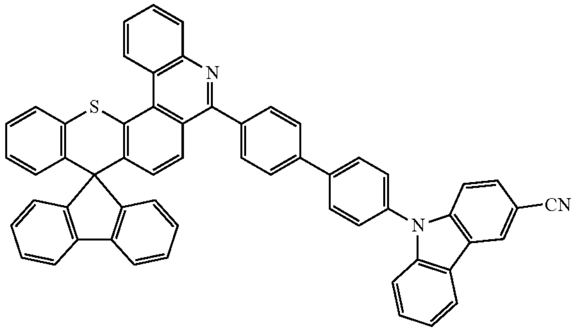
250
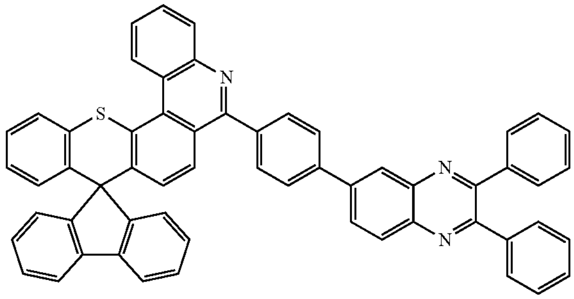
251
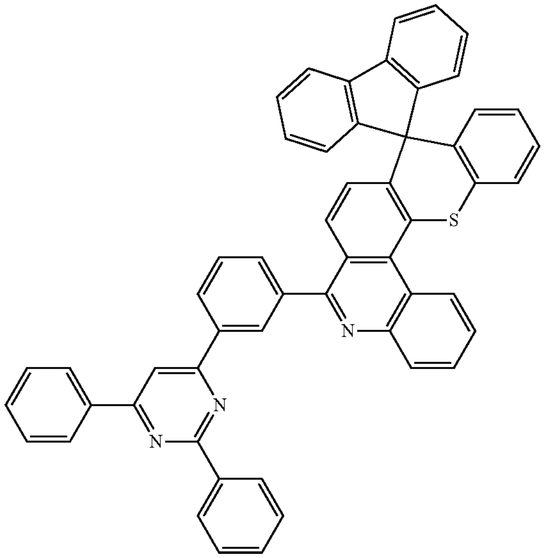
-continued
252
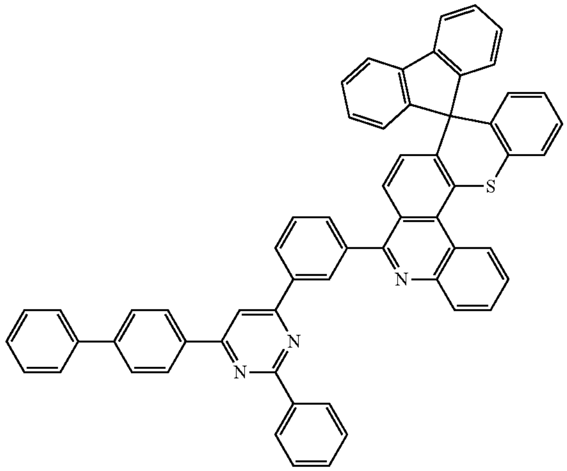
253
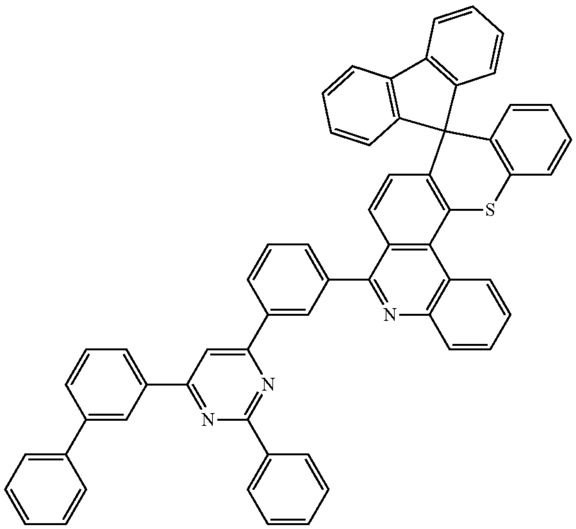

-continued
254
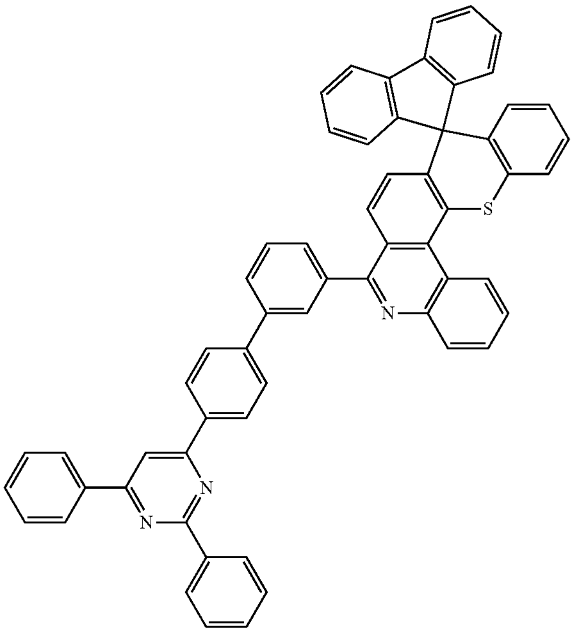
255
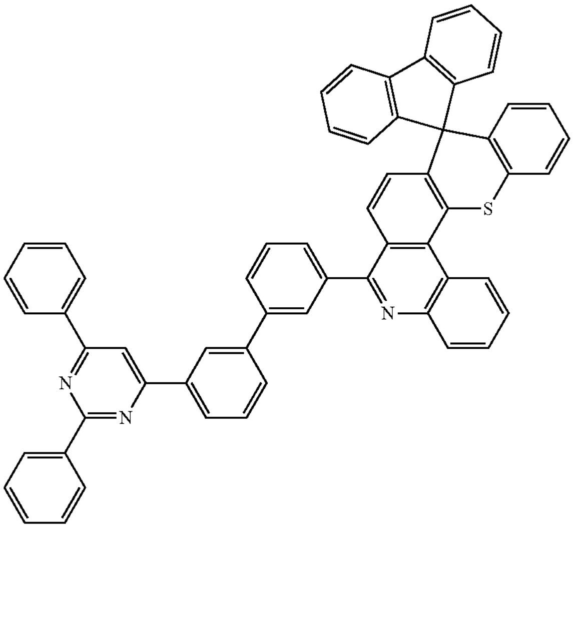
-continued
256
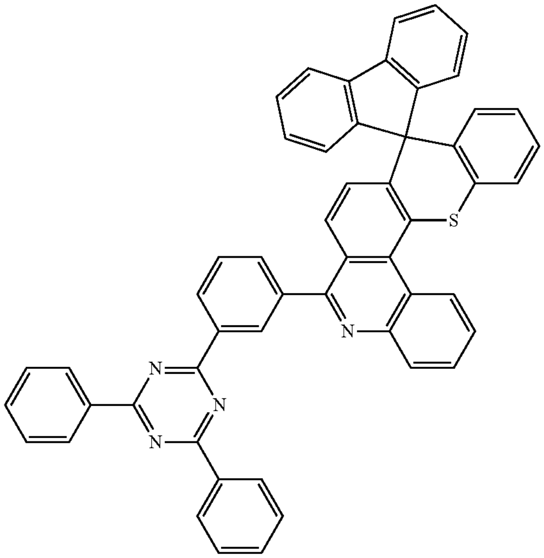
257
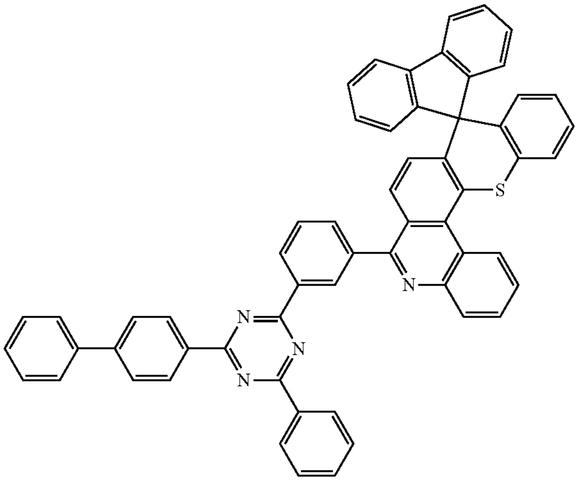
258
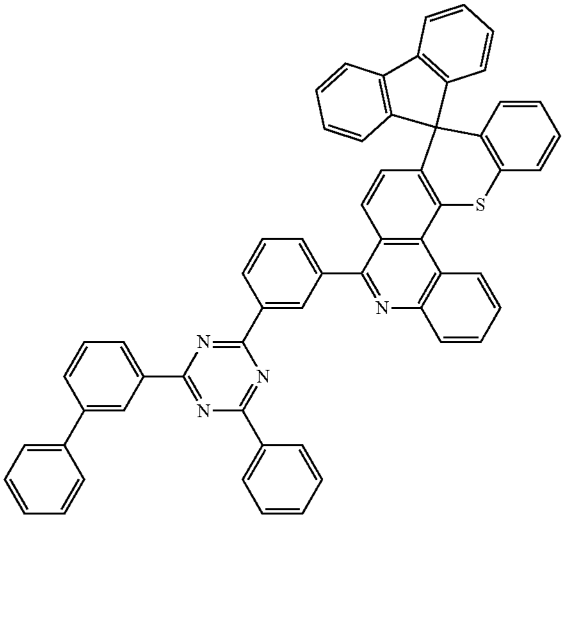

-continued
259
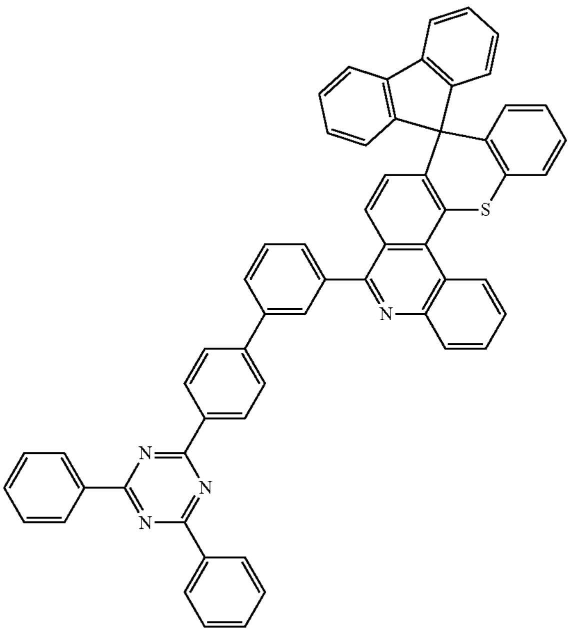
260
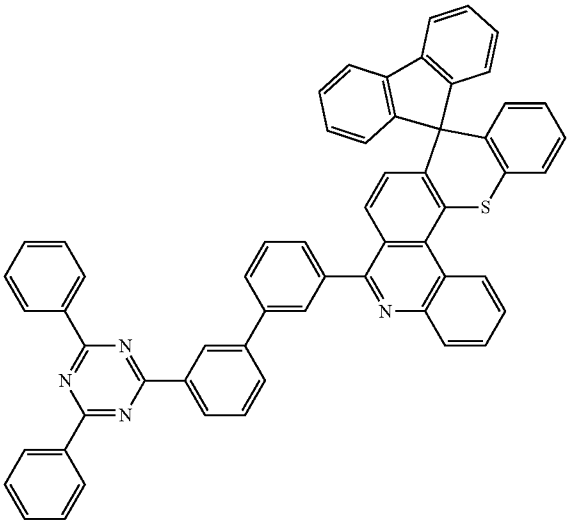
-continued
261
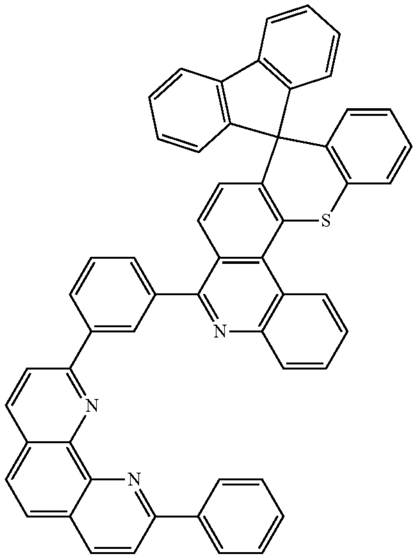
262
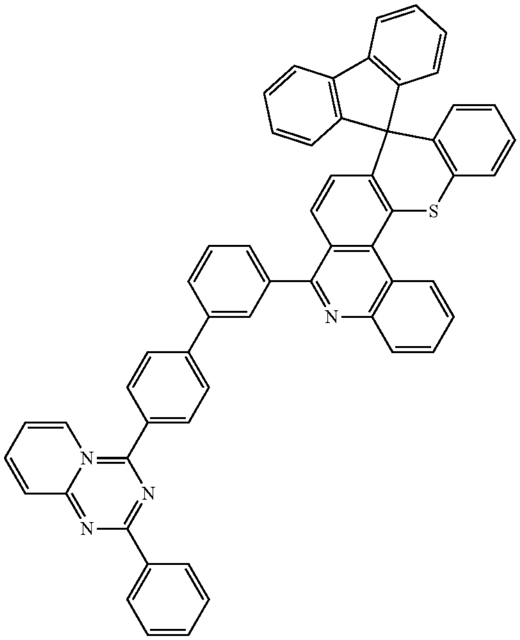

-continued
263
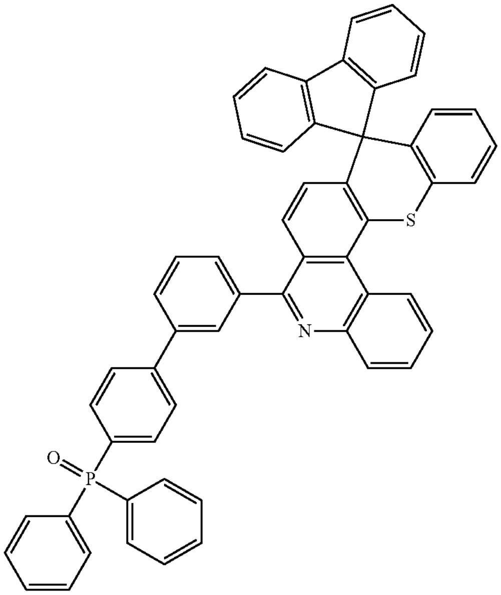
264
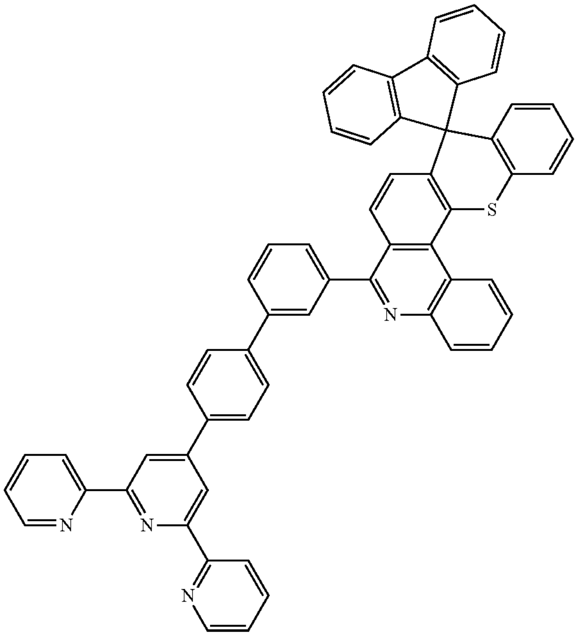
-continued
265
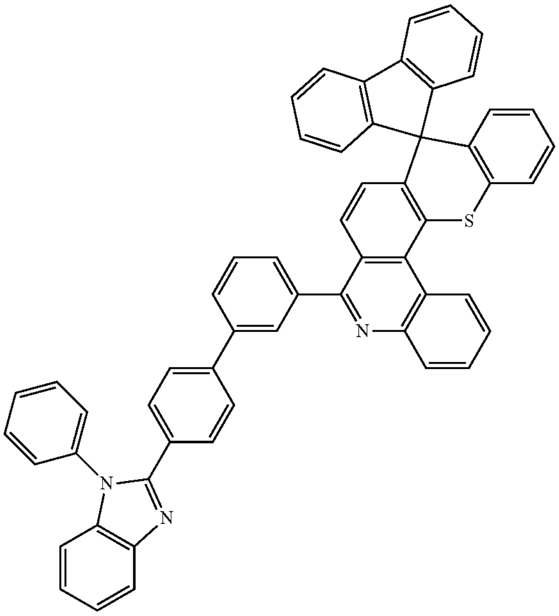
266
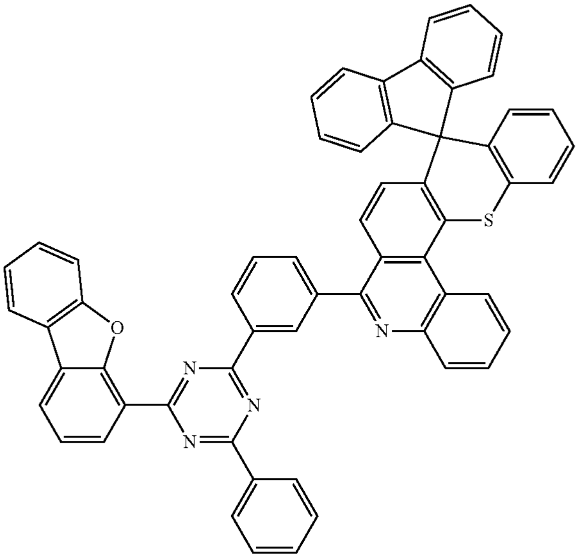

-continued
267
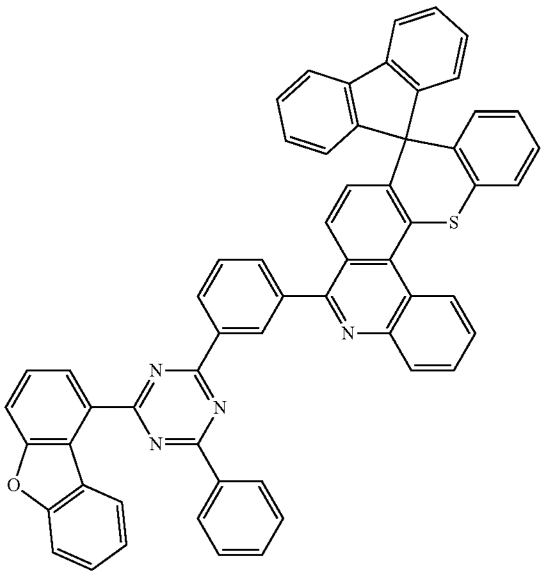
268
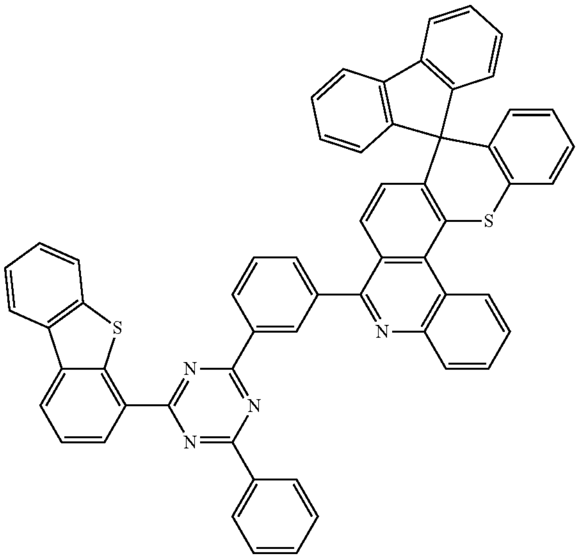
-continued
269
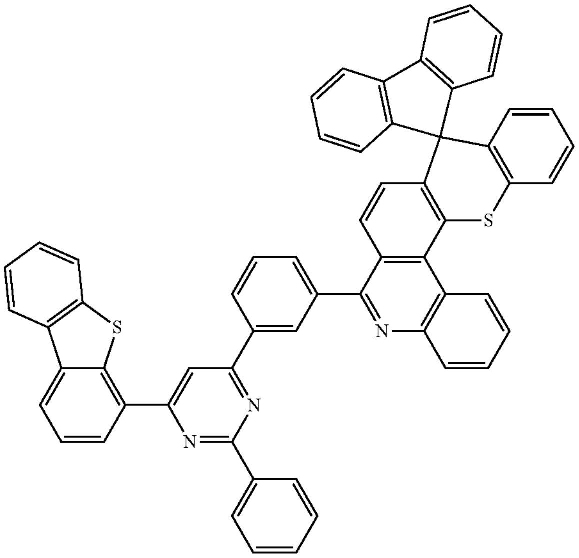
270
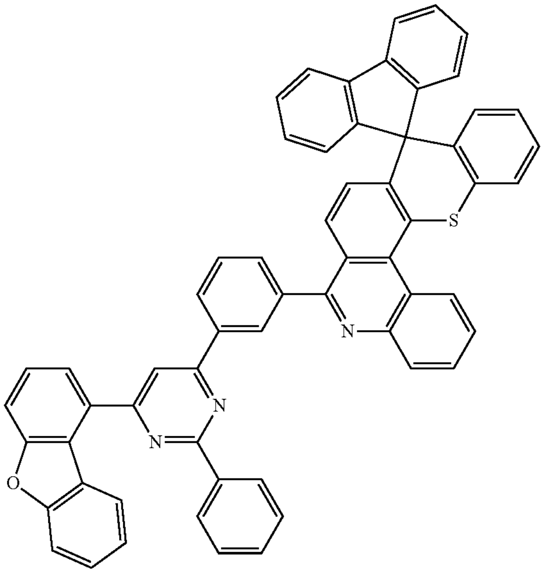

-continued
271
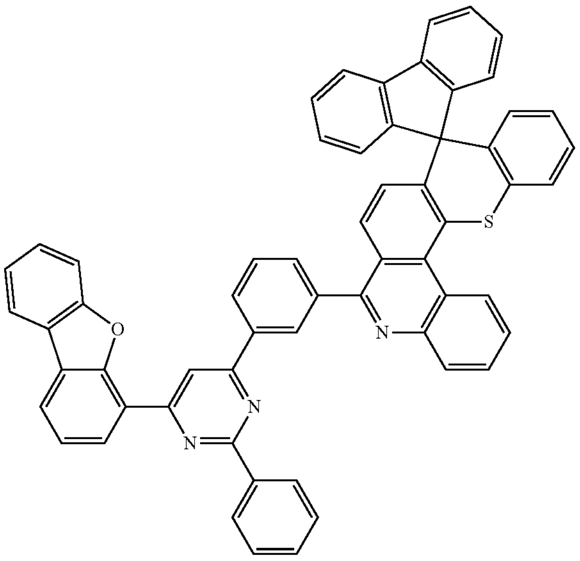
272
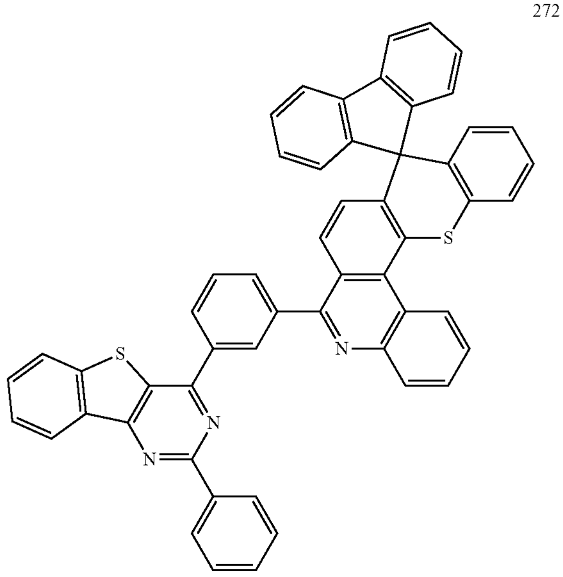
-continued
273
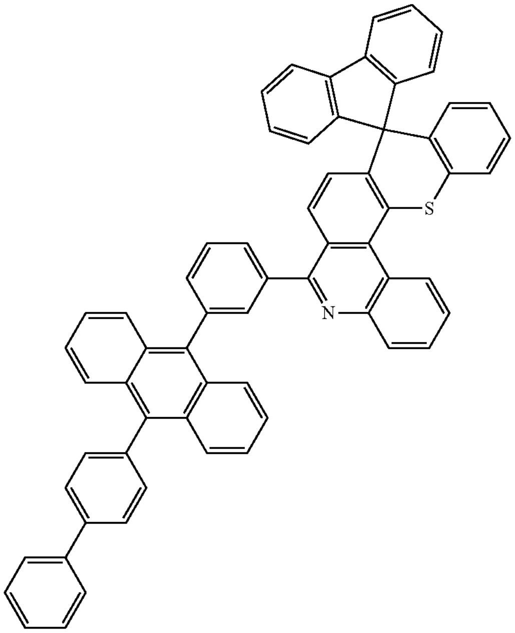
274
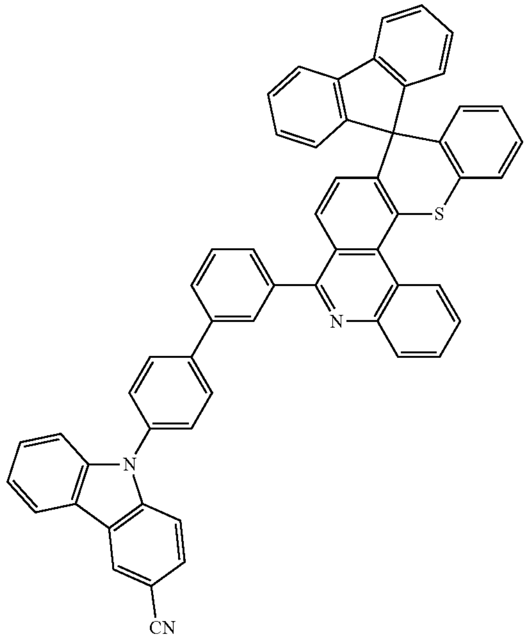

-continued
275
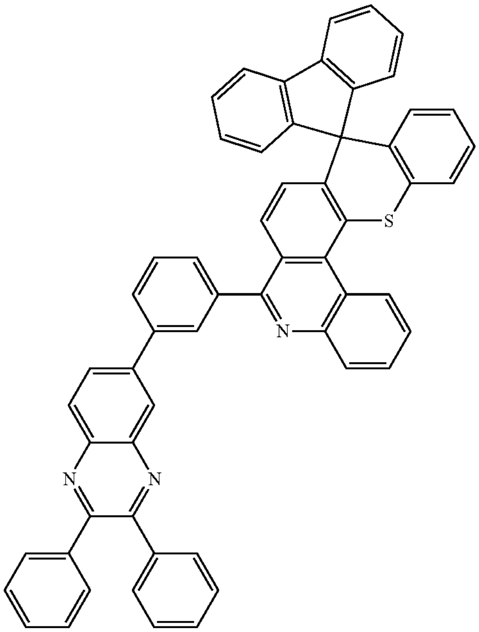
276
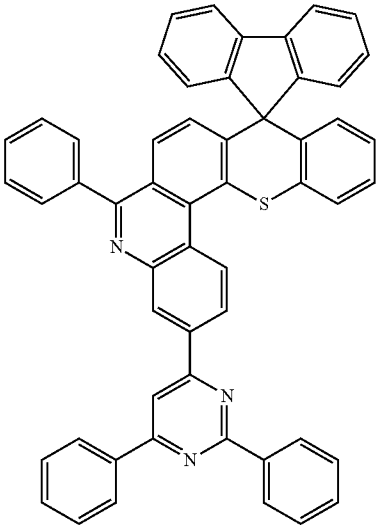
-continued
277
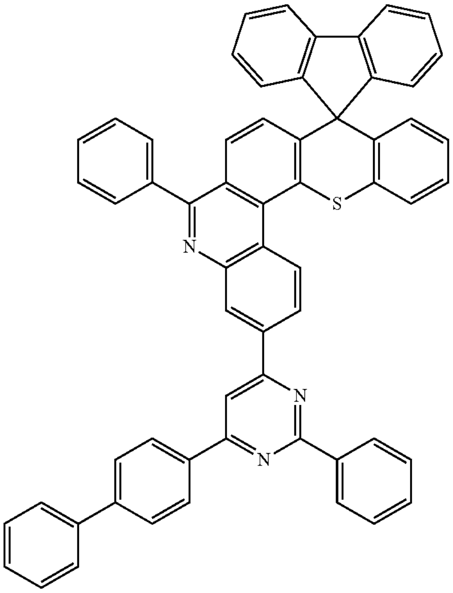
278
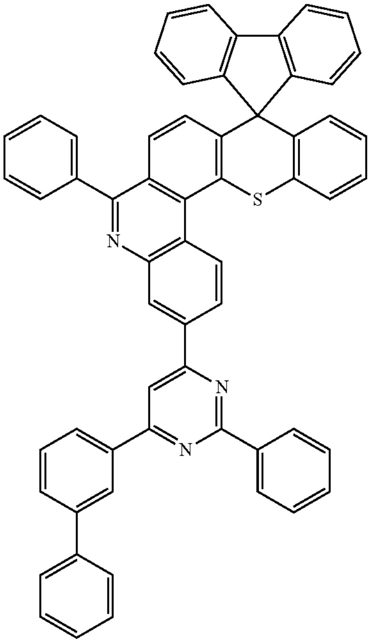

279
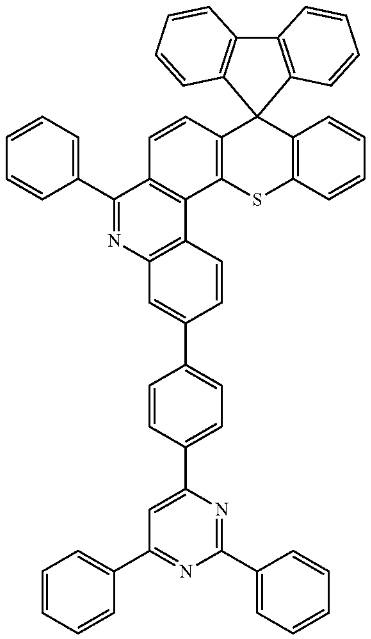
280
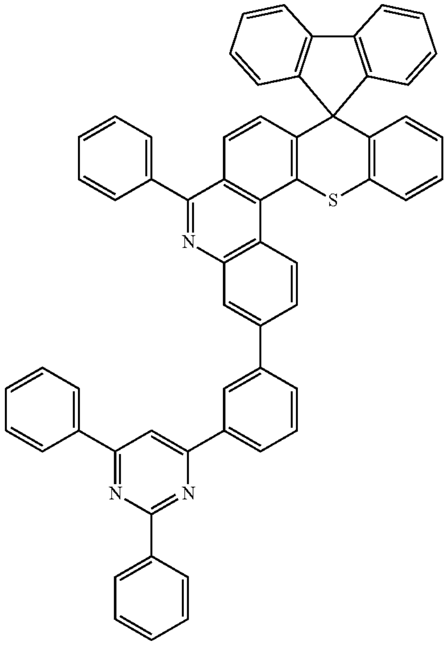
281
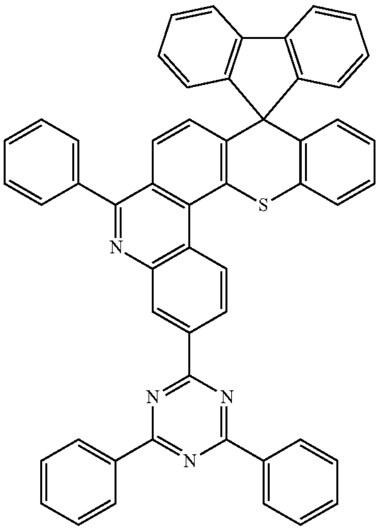
282
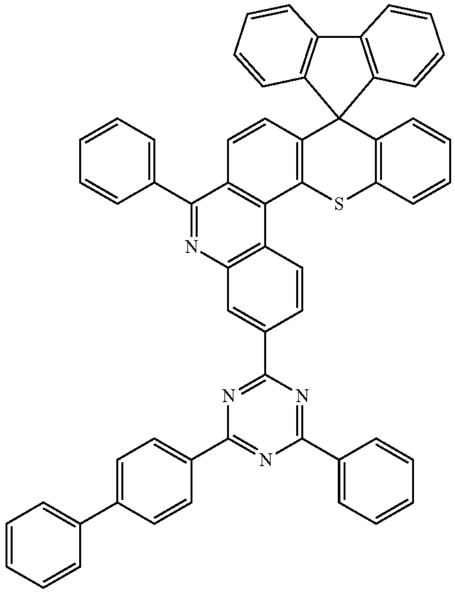

-continued
283
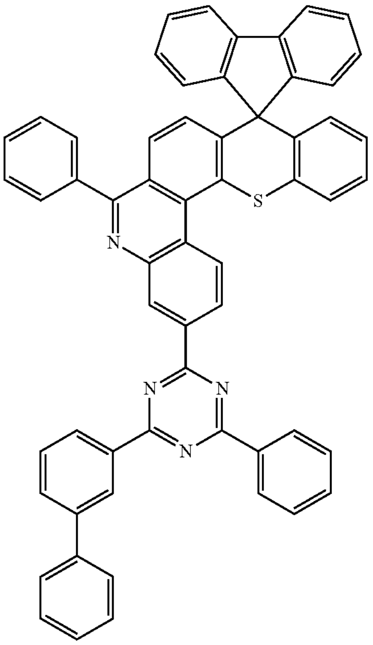
284
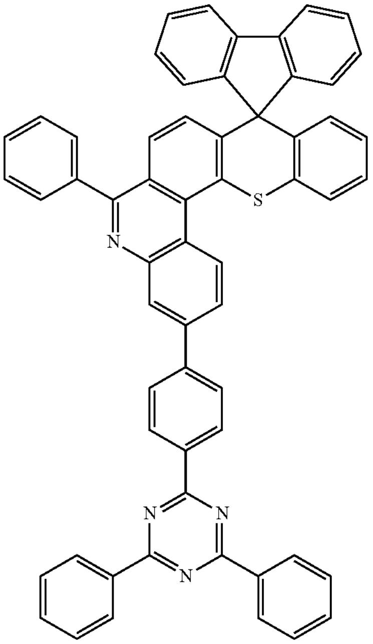
-continued
285
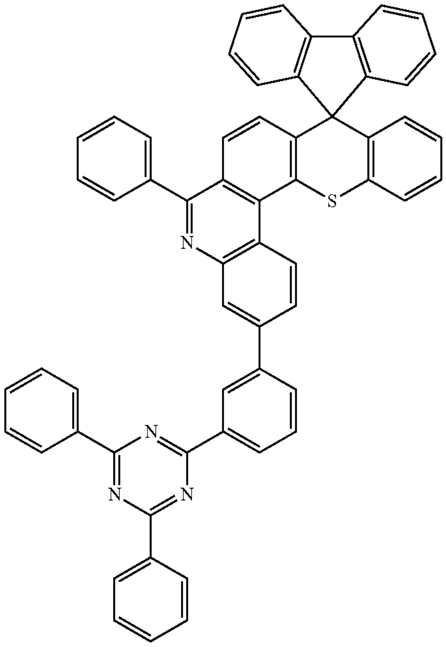
286
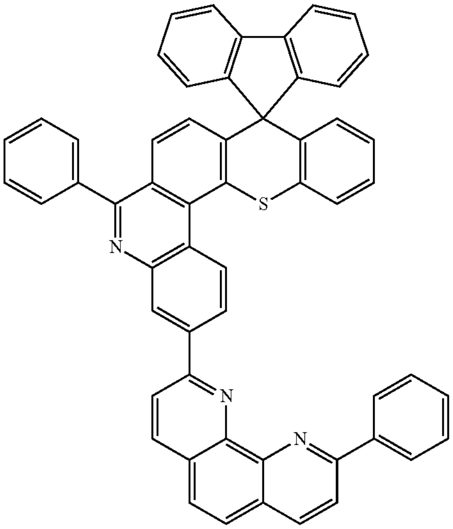

-continued
287
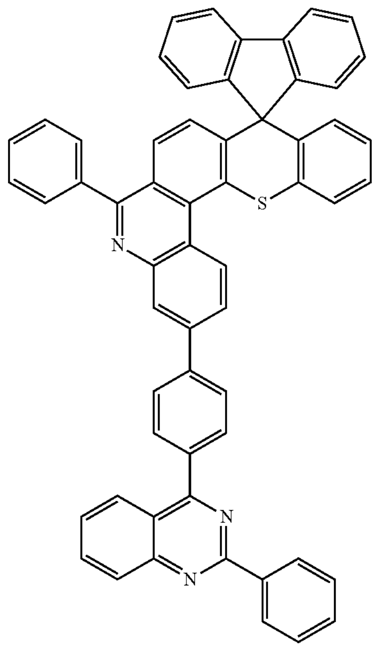
288
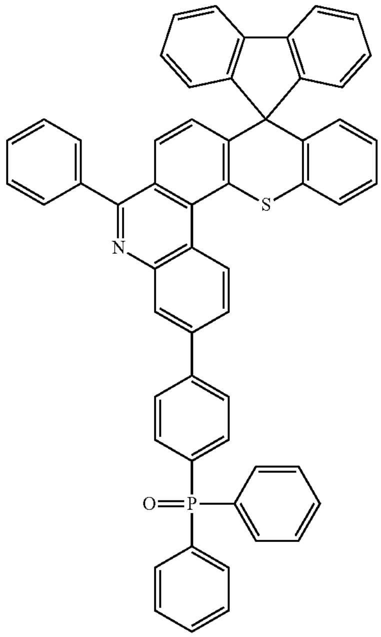
-continued
289
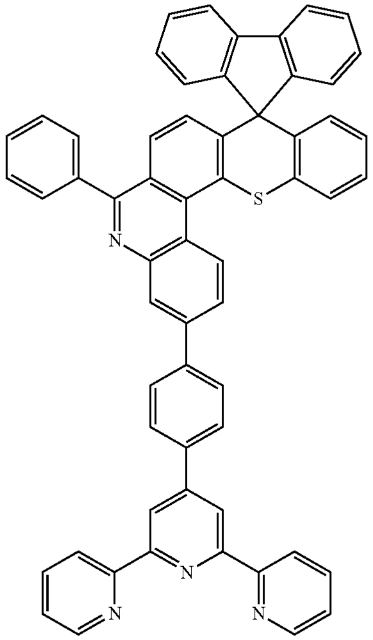
290
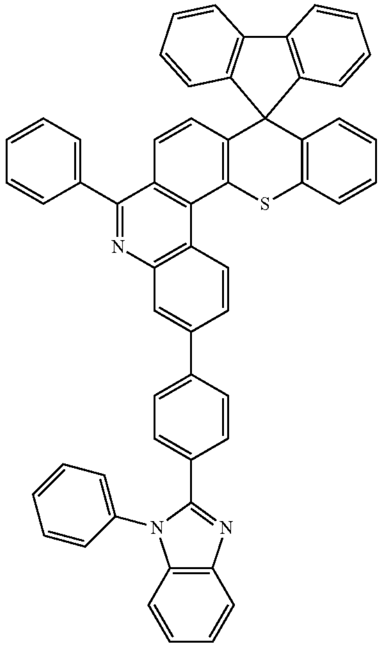

-continued
291
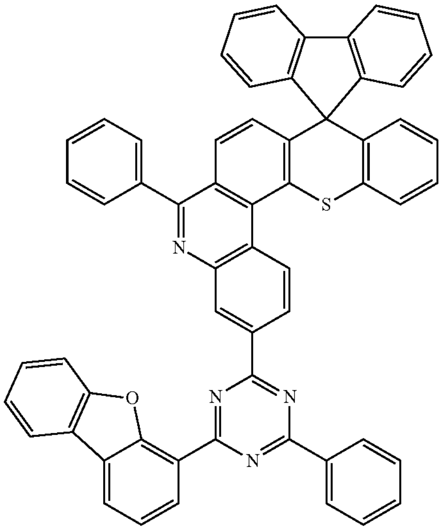
292
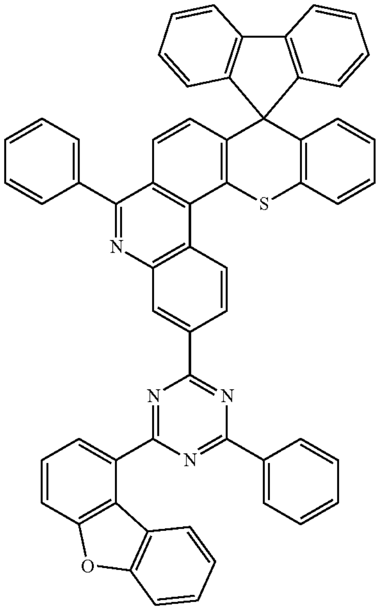
293
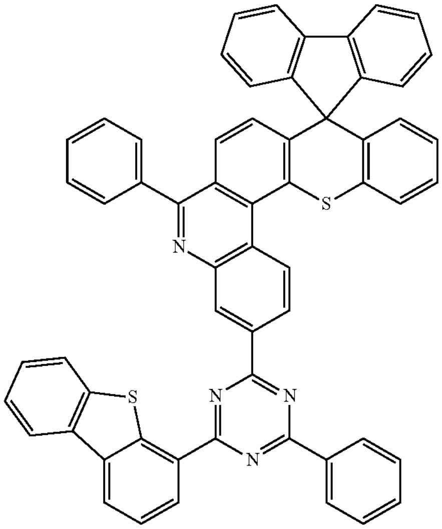
-continued
294
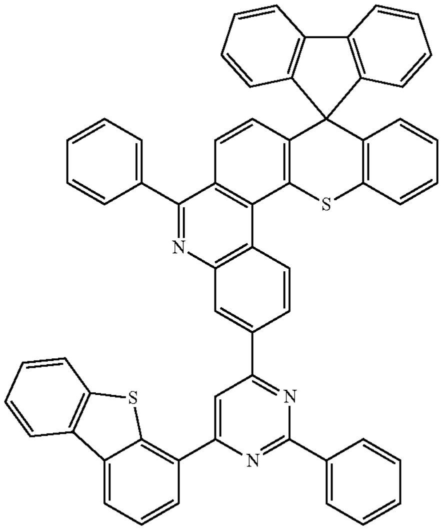
295
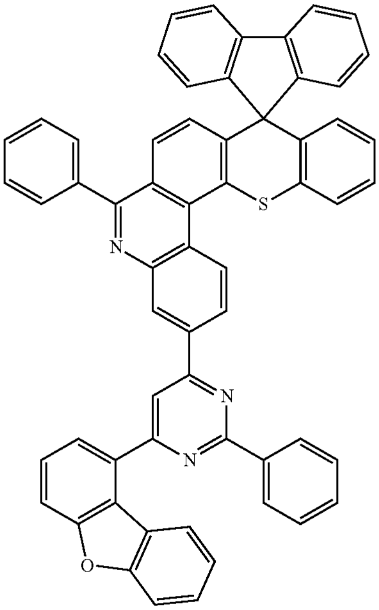
296
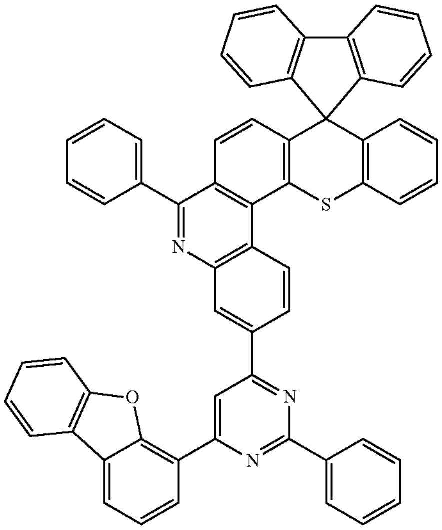

297
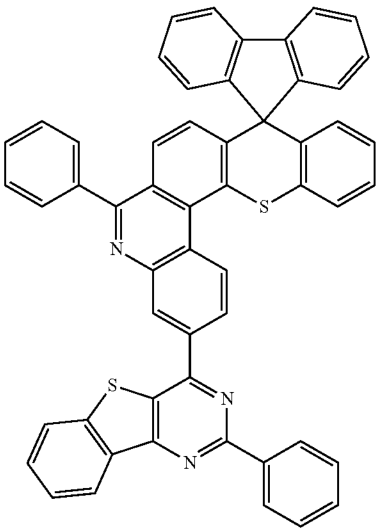
298
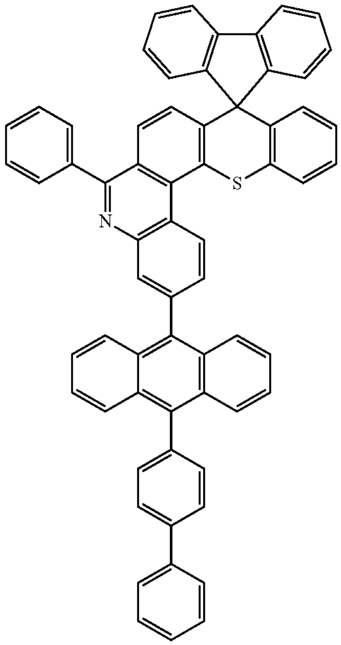
299
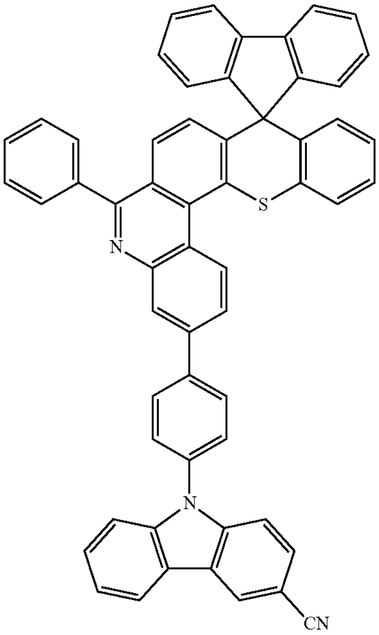
300
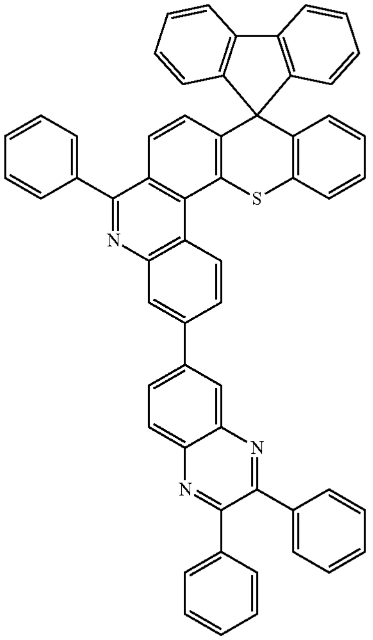

-continued
301
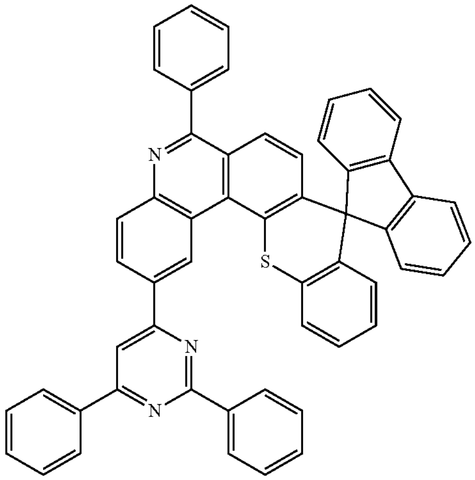
302
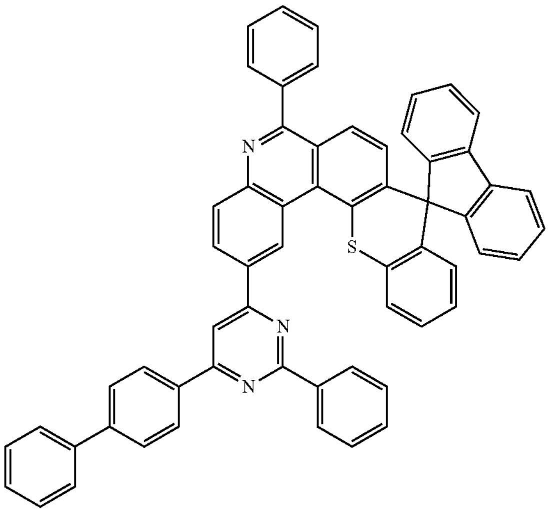
303
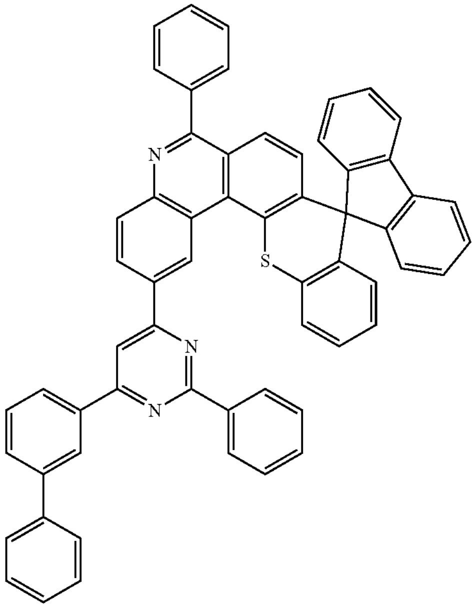
304
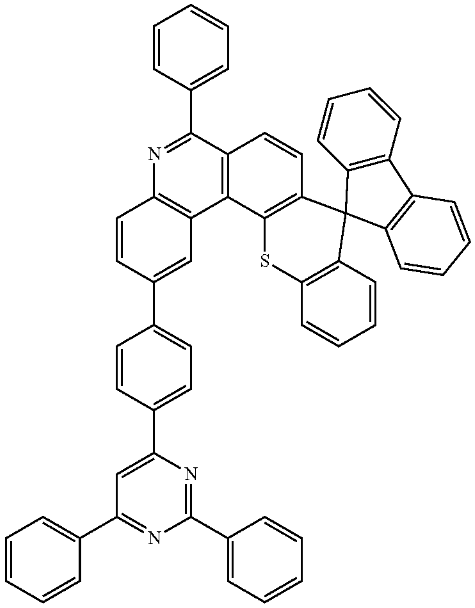
305
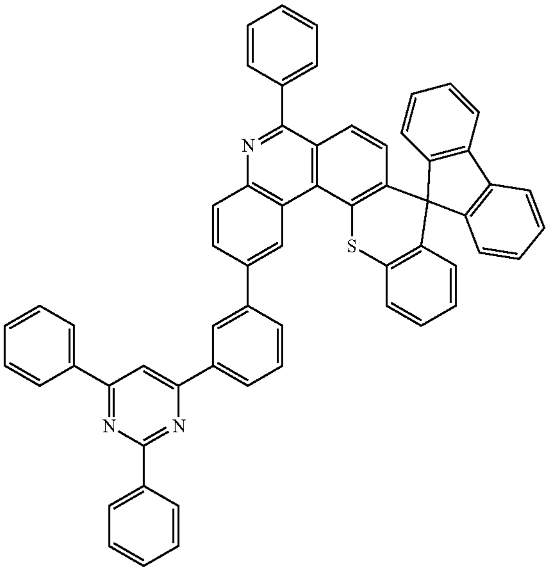

-continued
306
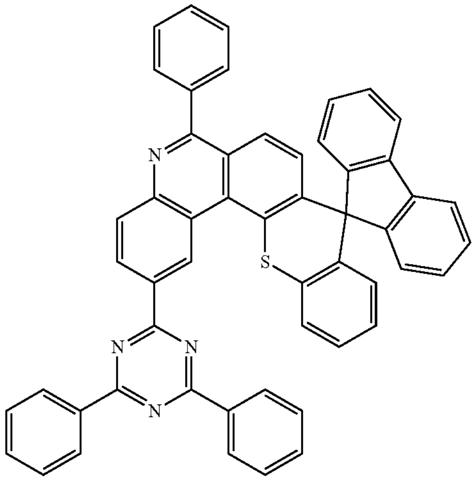
307
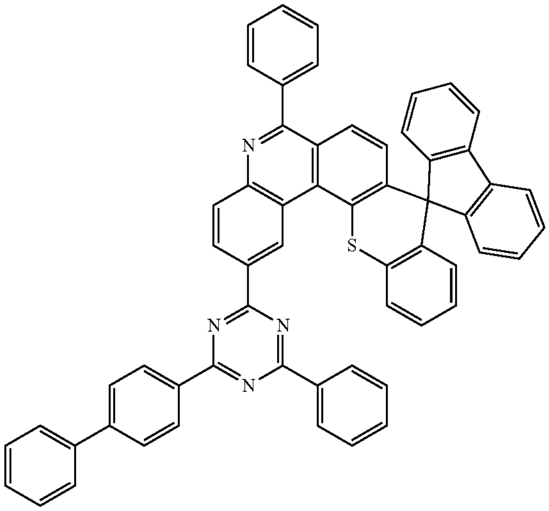
308
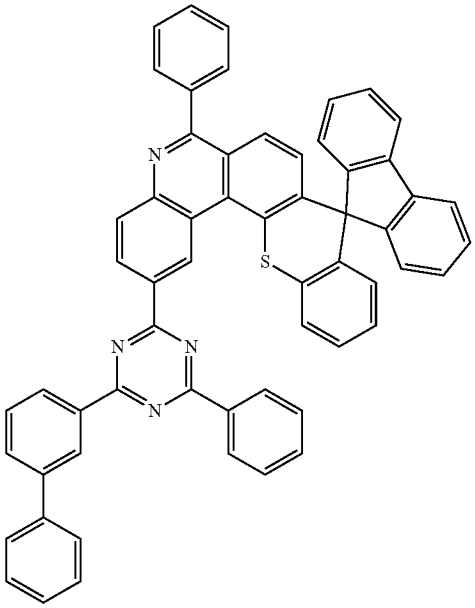
-continued
309
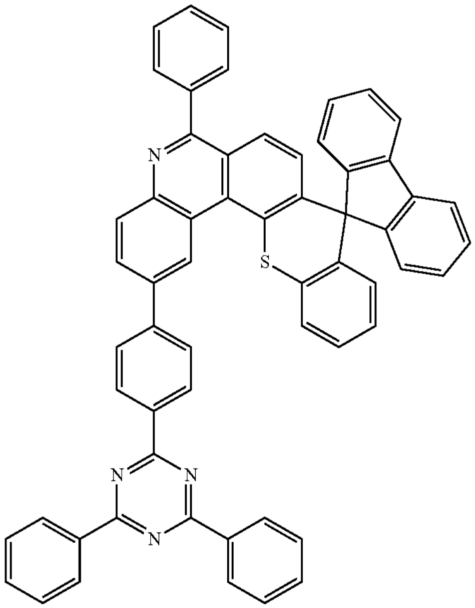
310
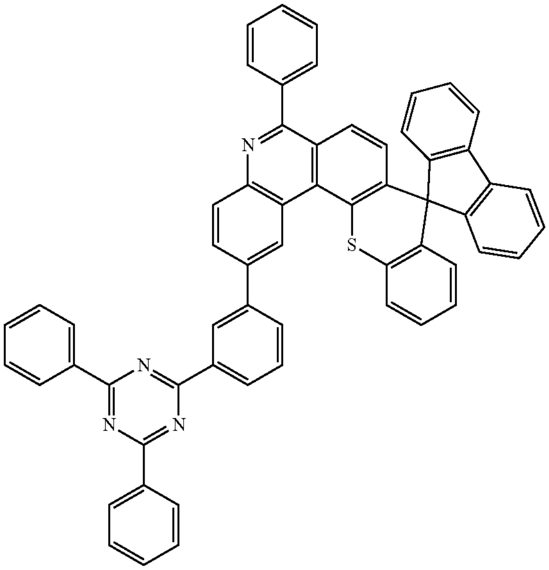
311
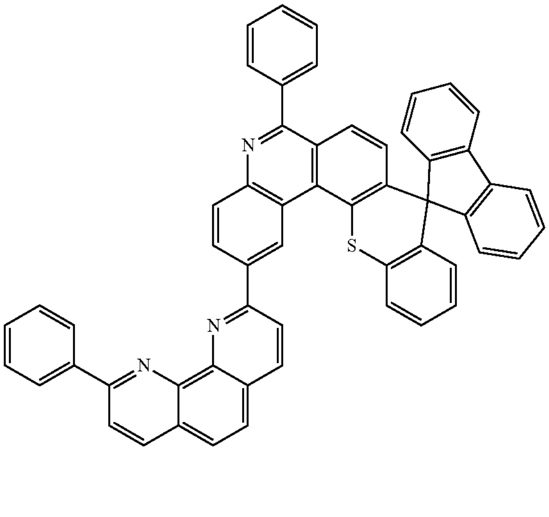

-continued
312
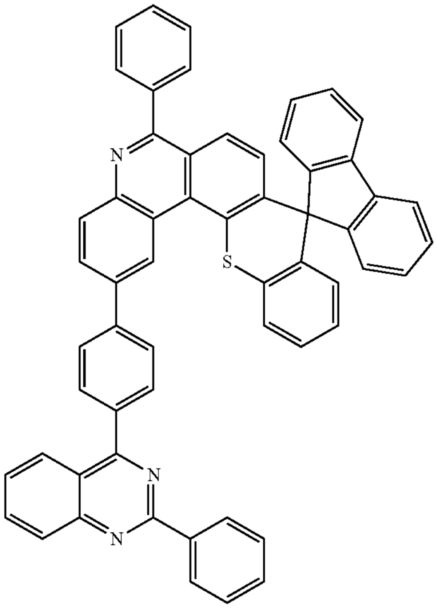
313
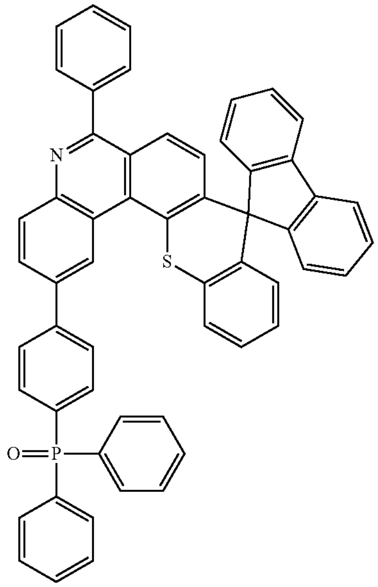
-continued
314
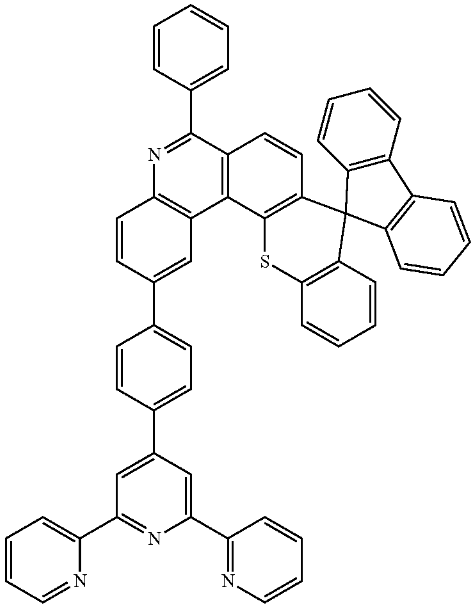
315
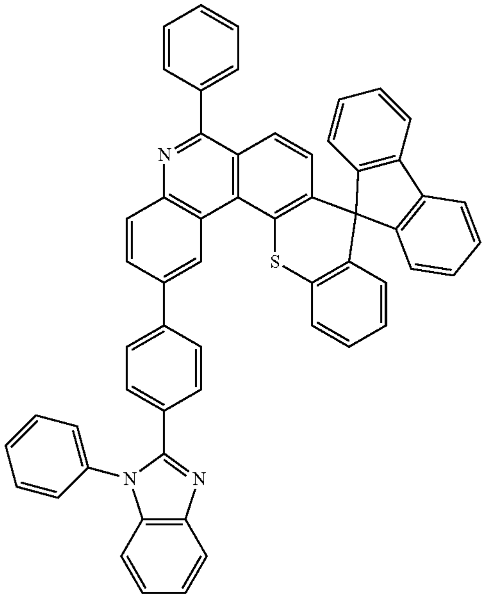

-continued
316
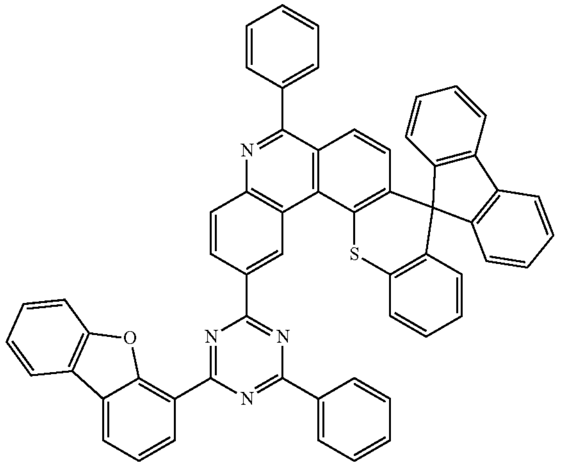
317
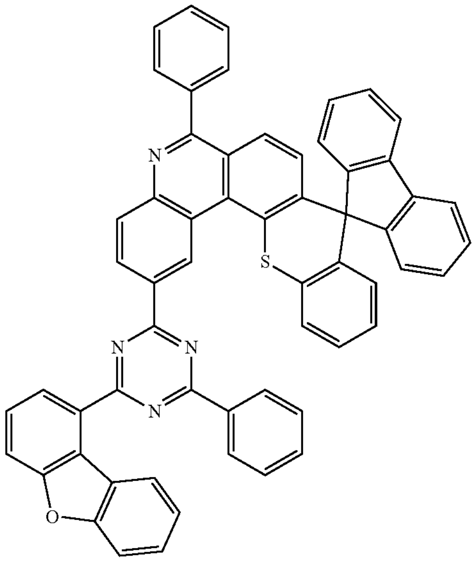
318
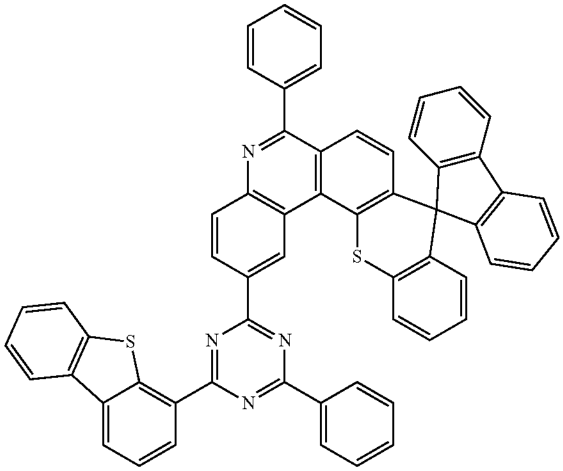
-continued
319
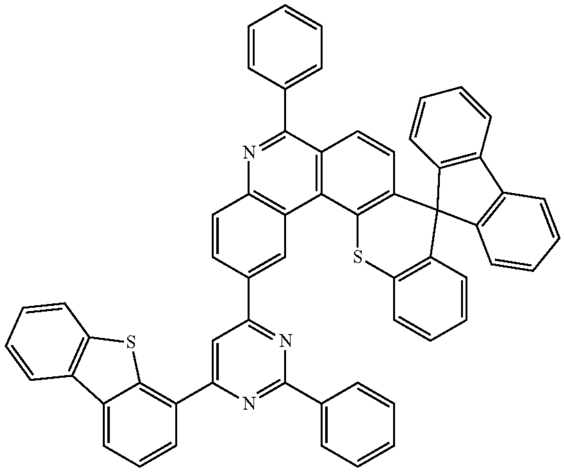
320
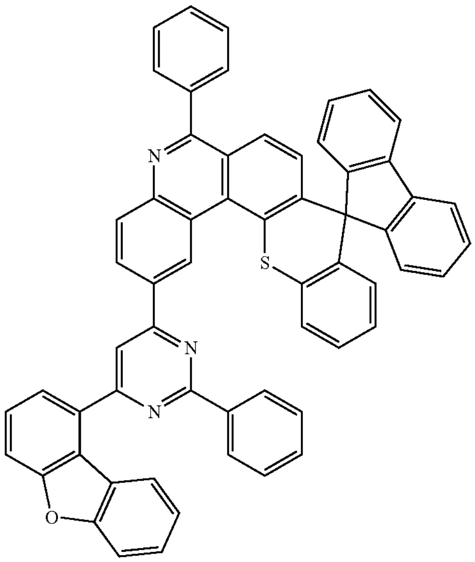
321
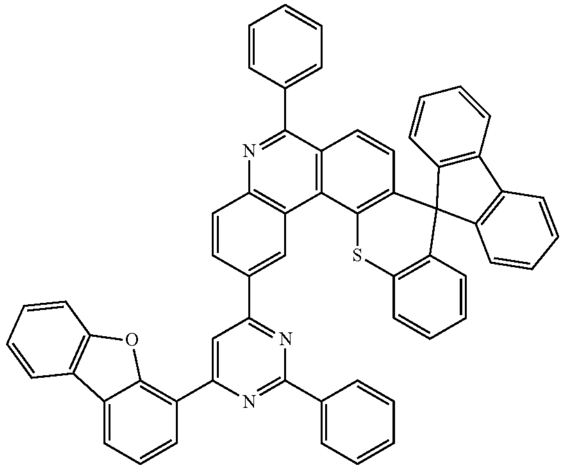

-continued
322
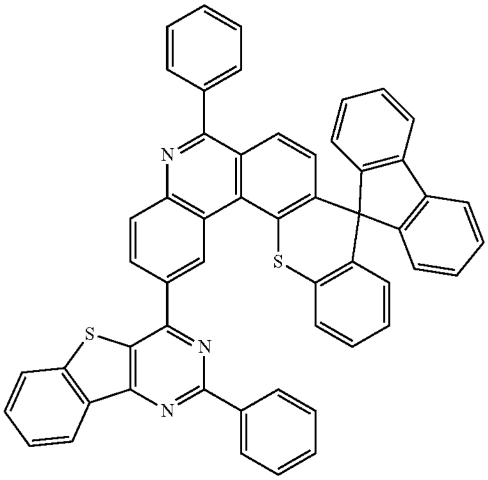
-continued
324
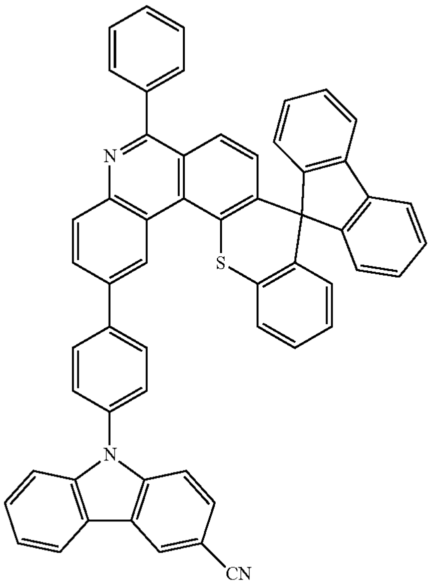
323
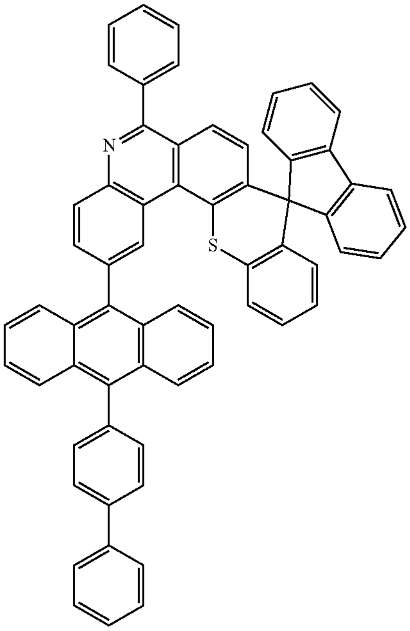
325
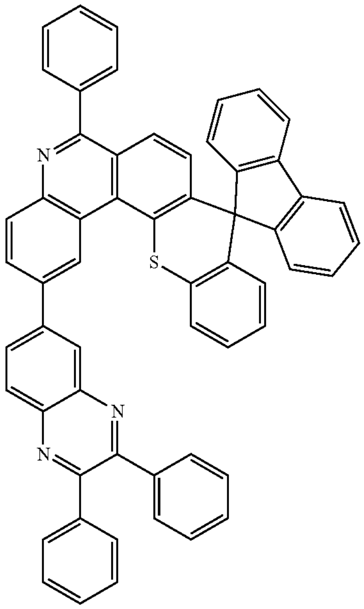

-continued
326
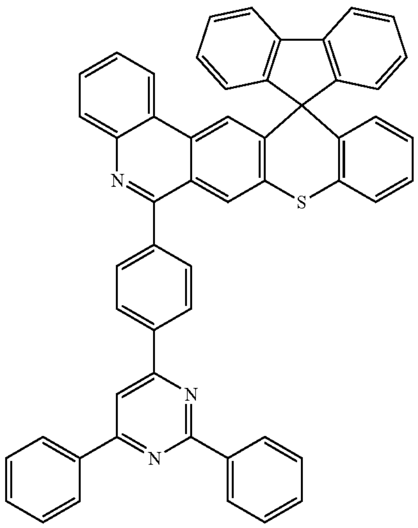
327
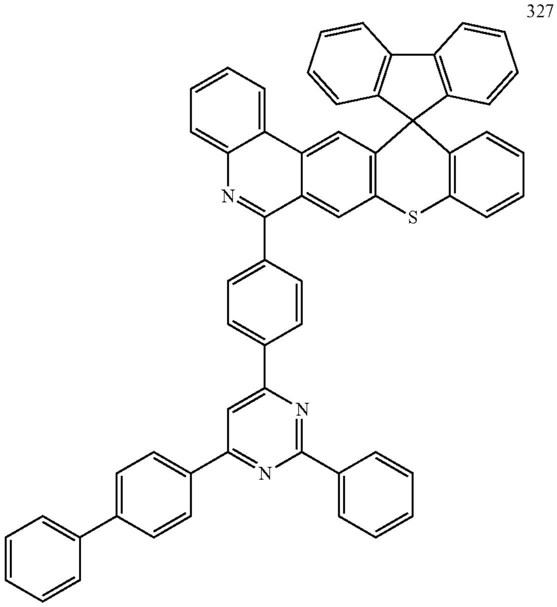
-continued
328
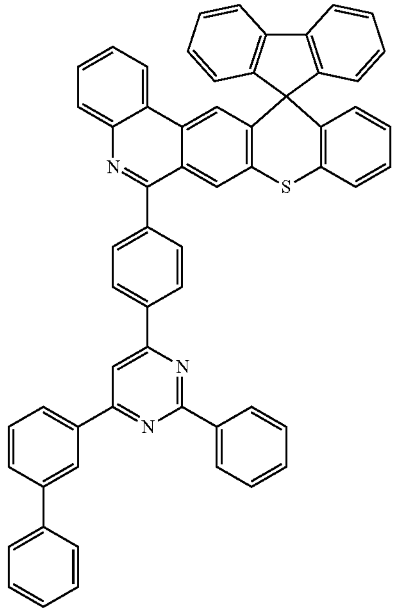
329
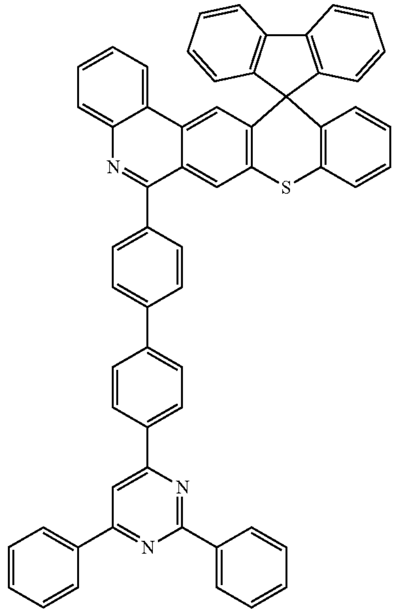

-continued
330
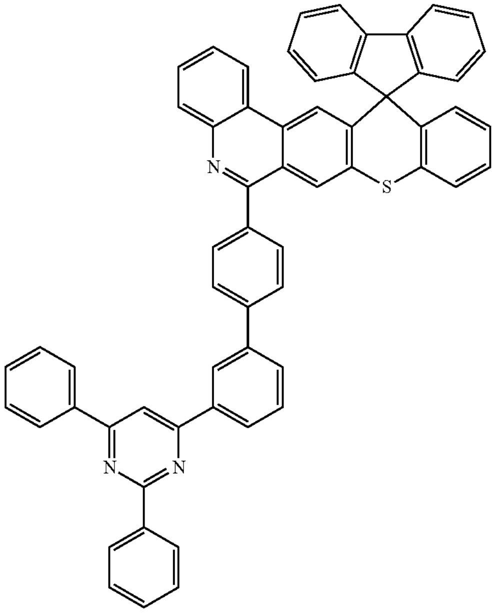
331
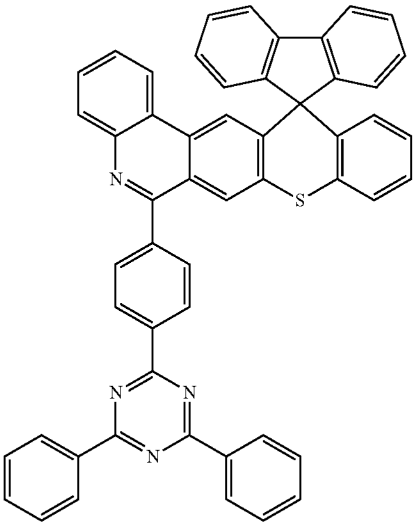
-continued
332
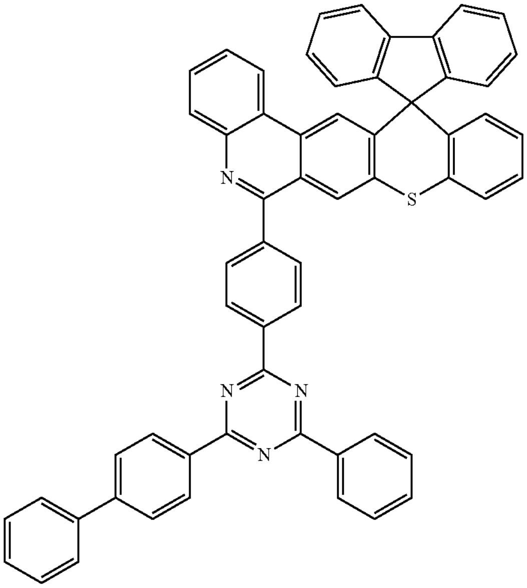
333
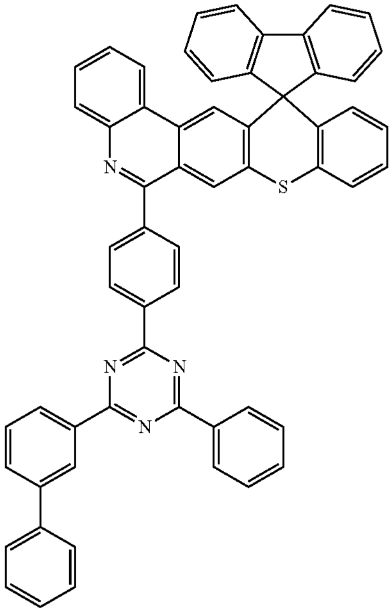

-continued
334
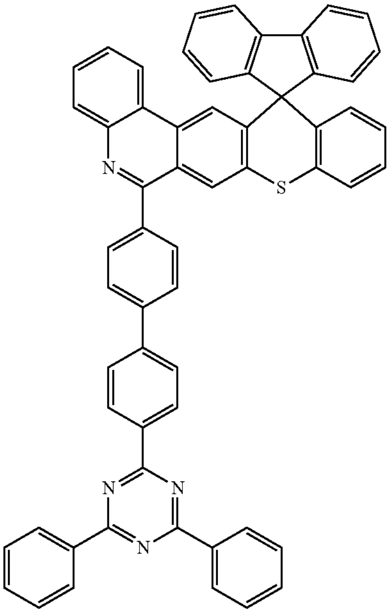
335
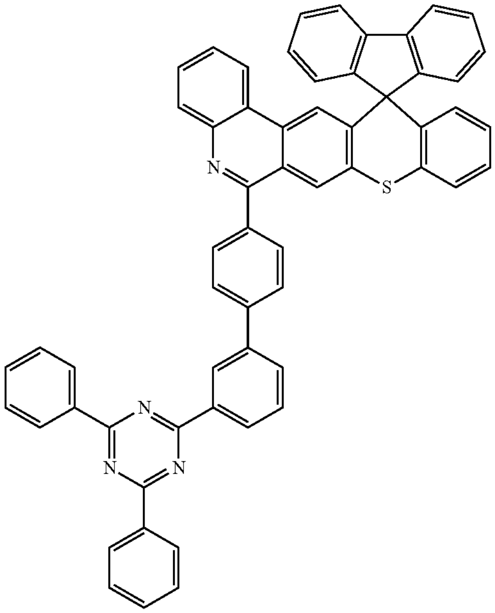
-continued
336
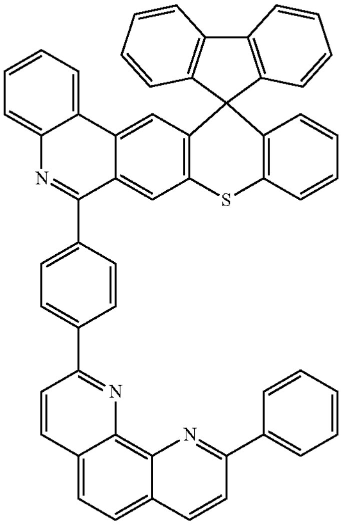
337
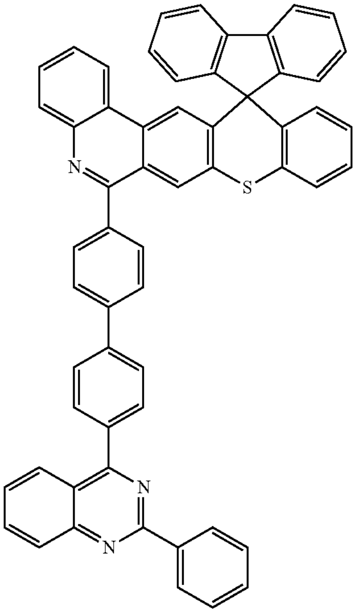

-continued
338
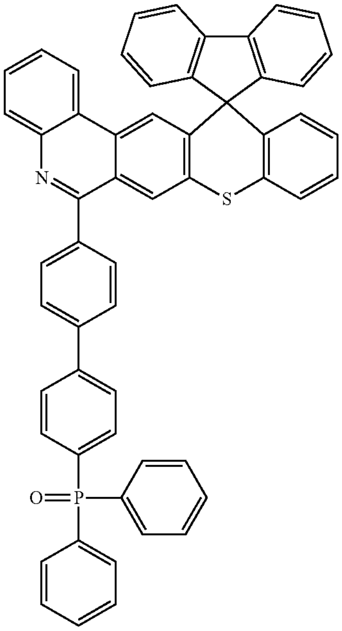
339
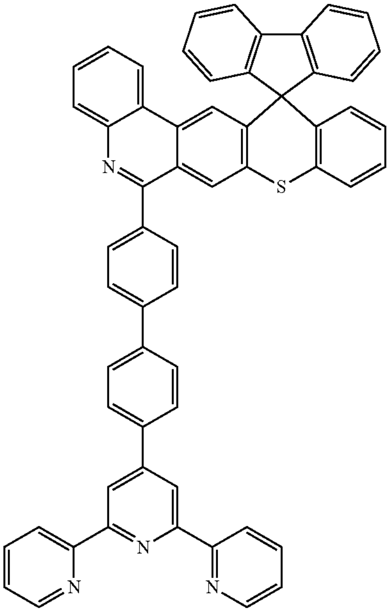
-continued
340
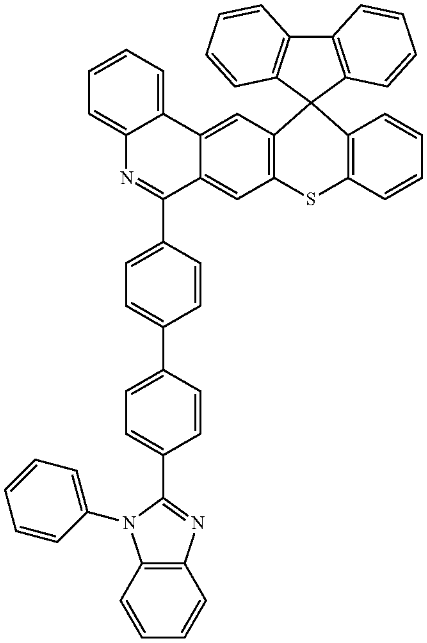
341
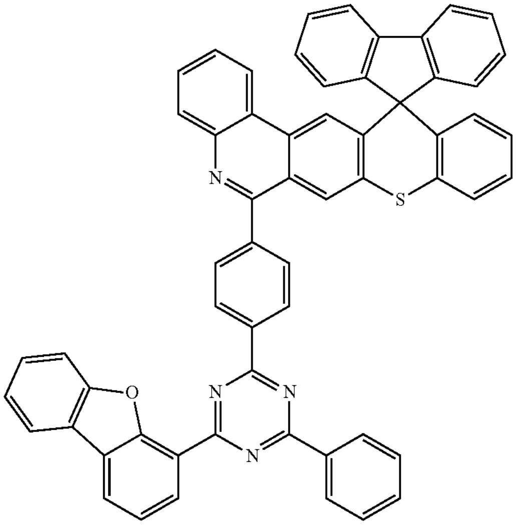

342
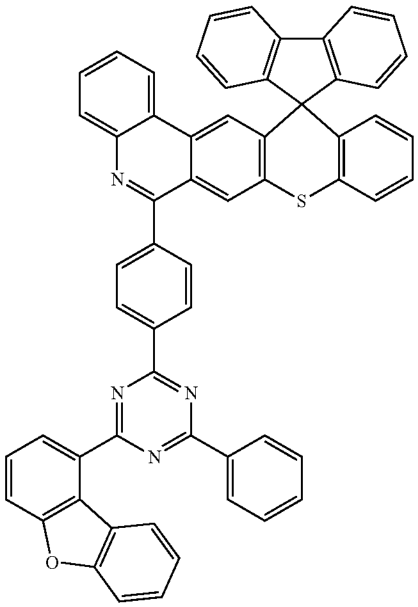
343
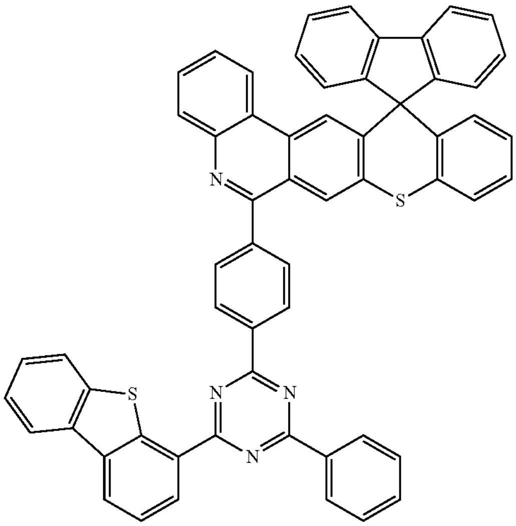
344
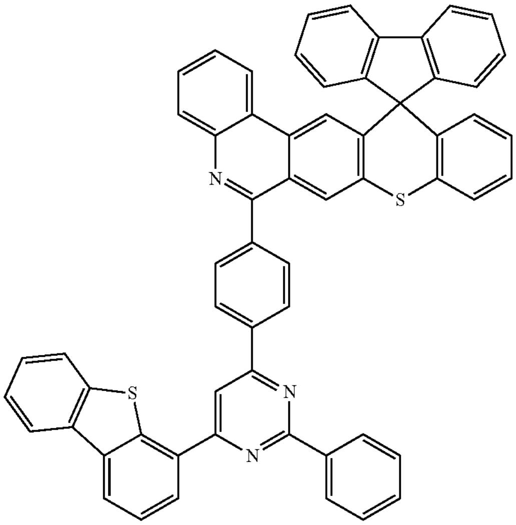
345
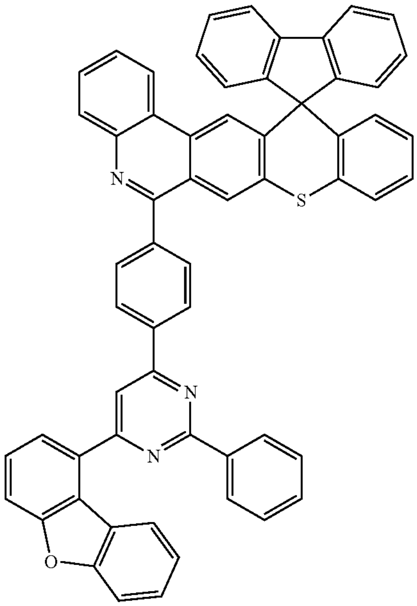

-continued
346
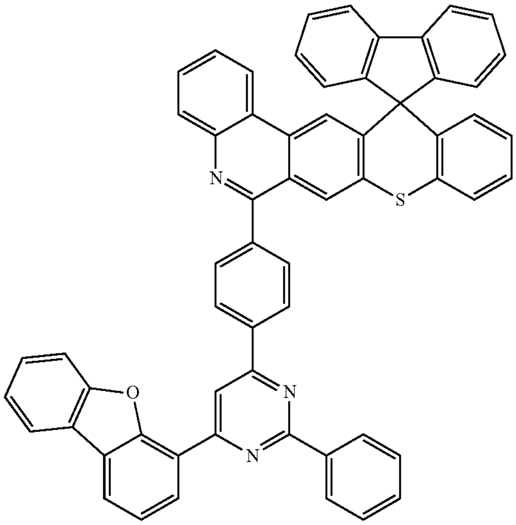
348
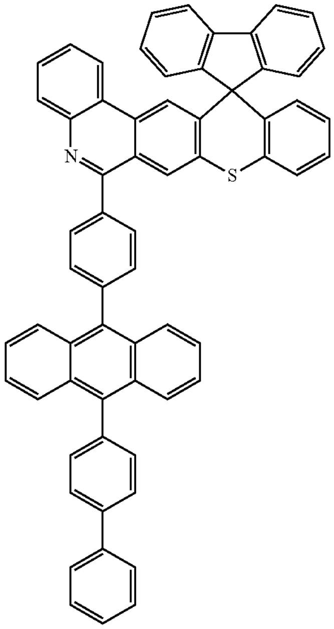
347
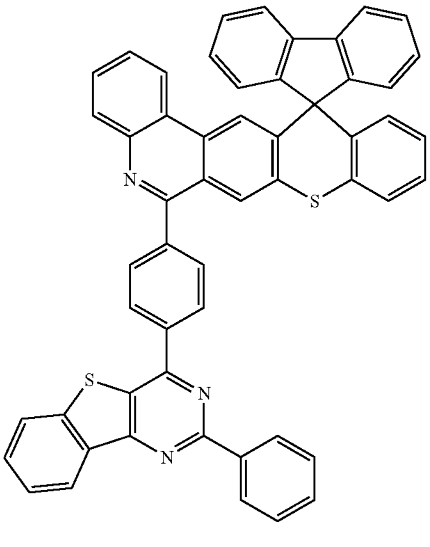
349
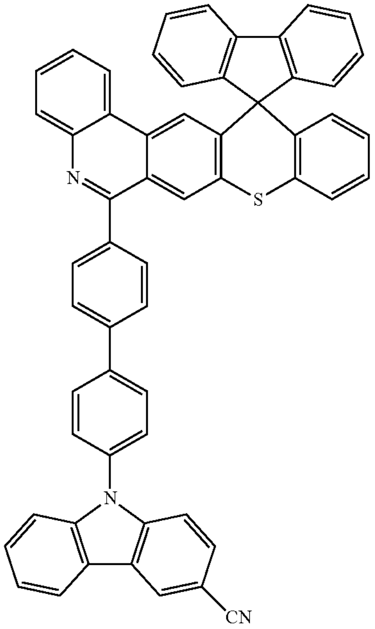

-continued
350
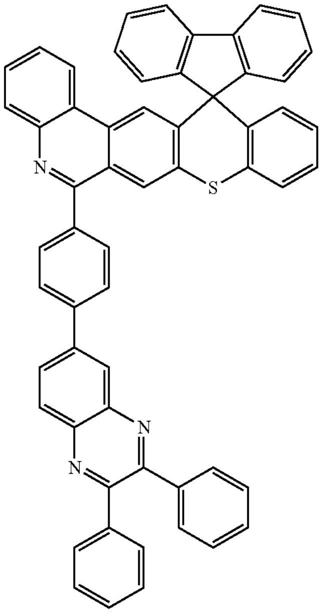
351
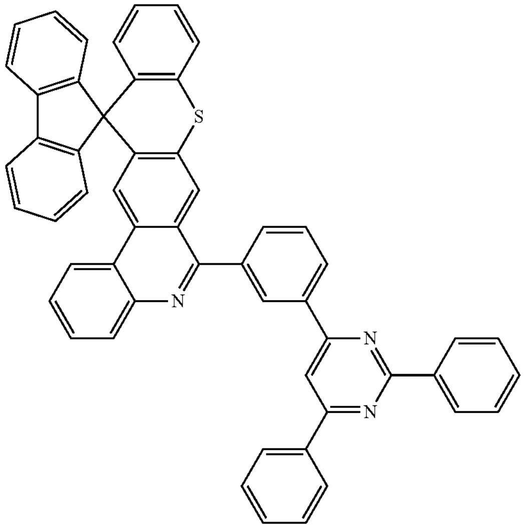
-continued
352
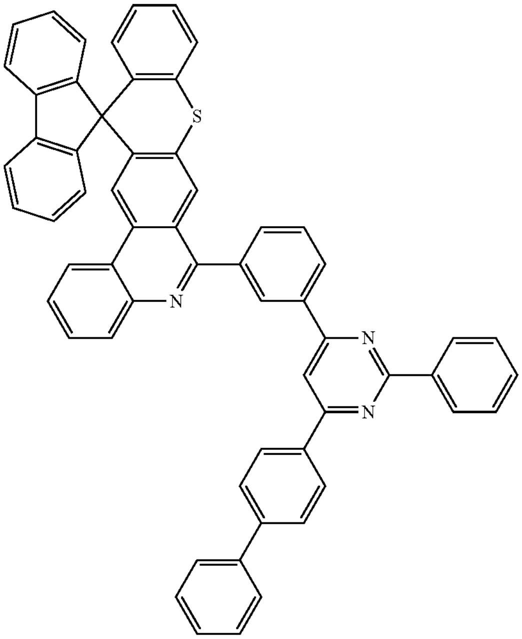
353
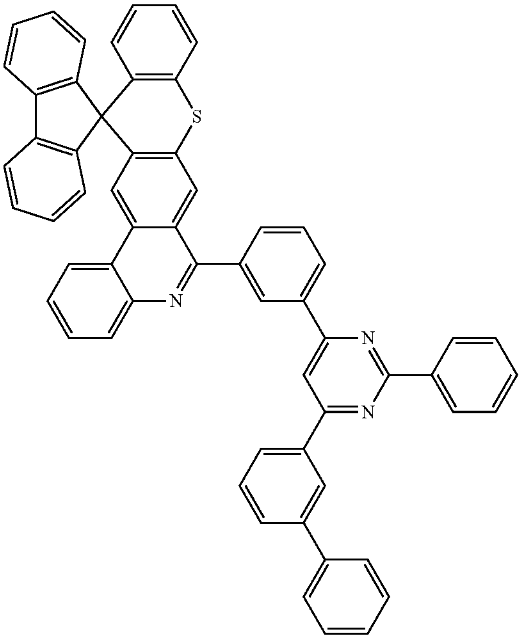

-continued
354
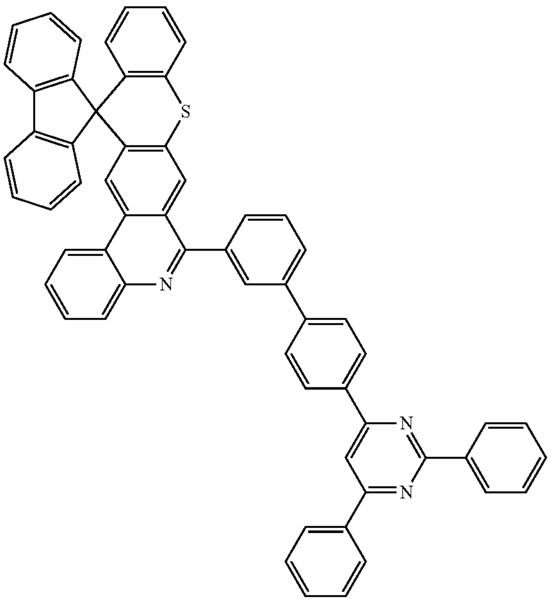
355
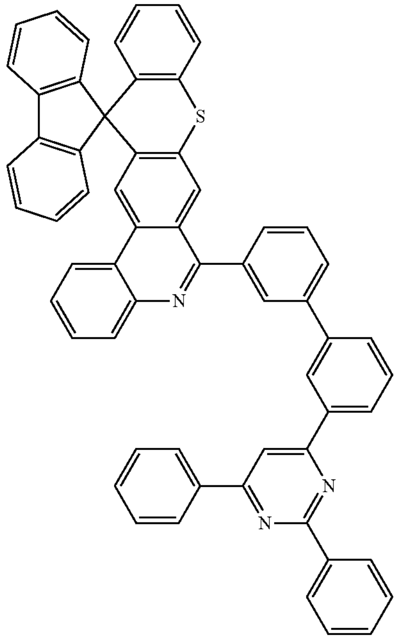
-continued
356
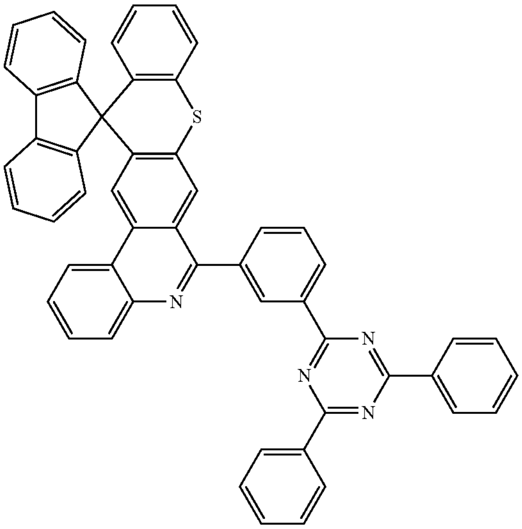
357
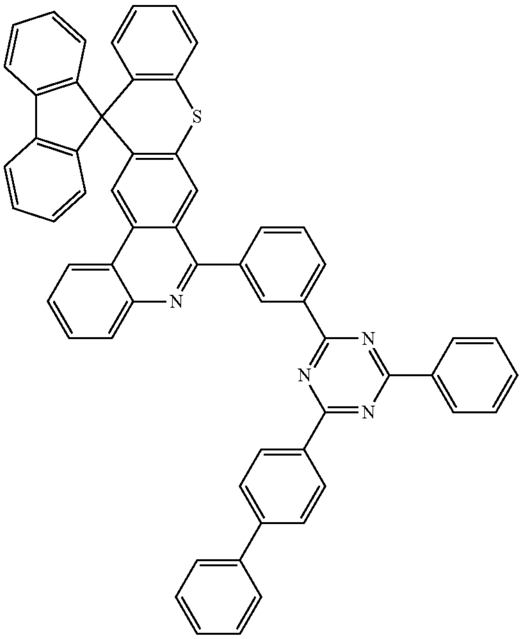

-continued
358
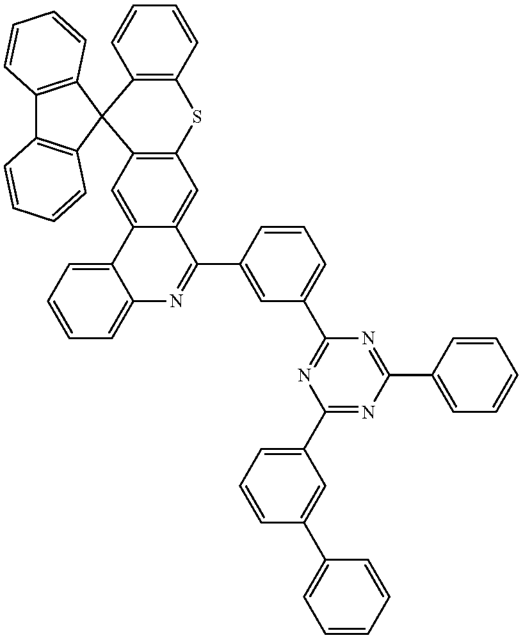
359
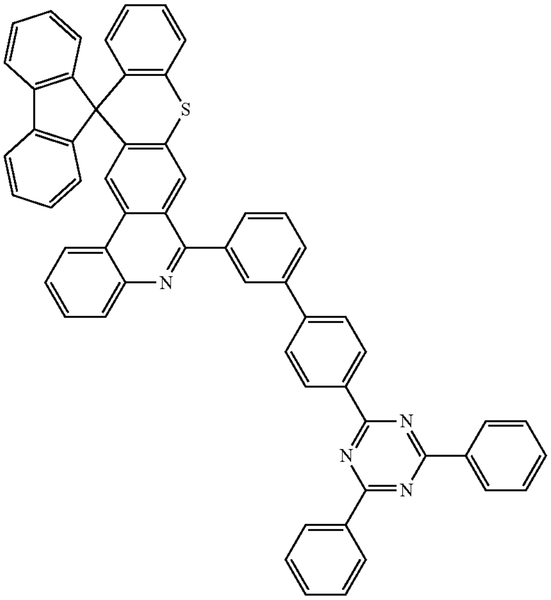
-continued
360
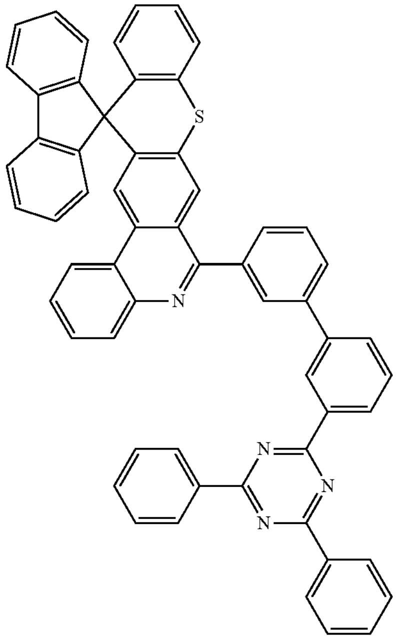
361
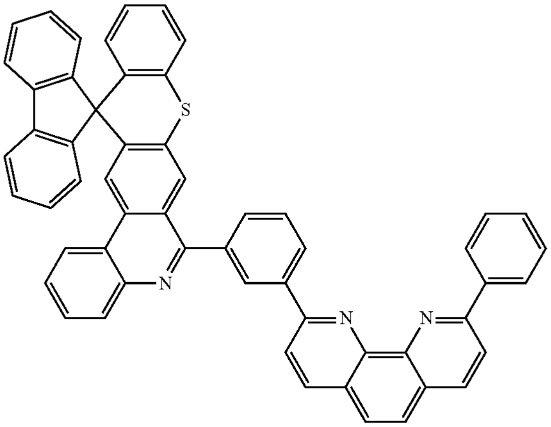
362
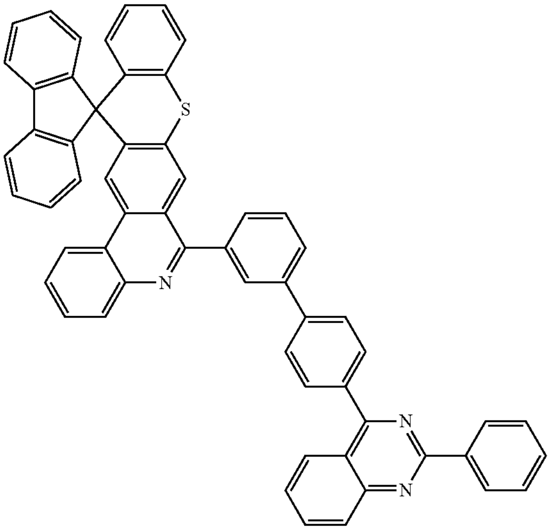

-continued
363
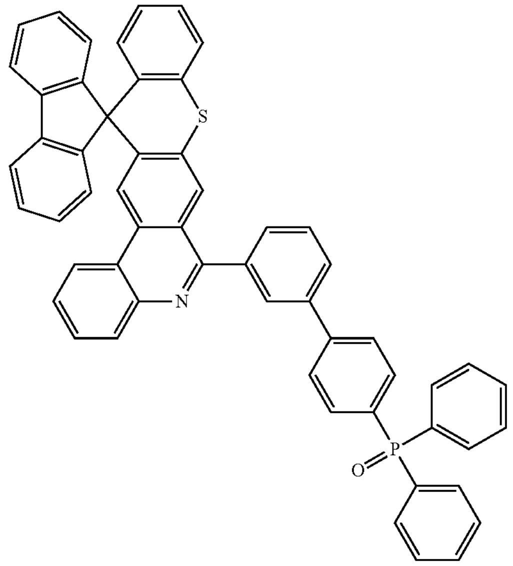
364
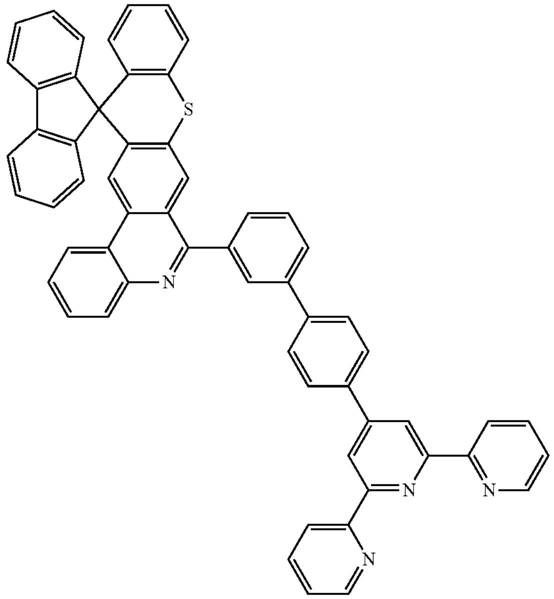
-continued
365
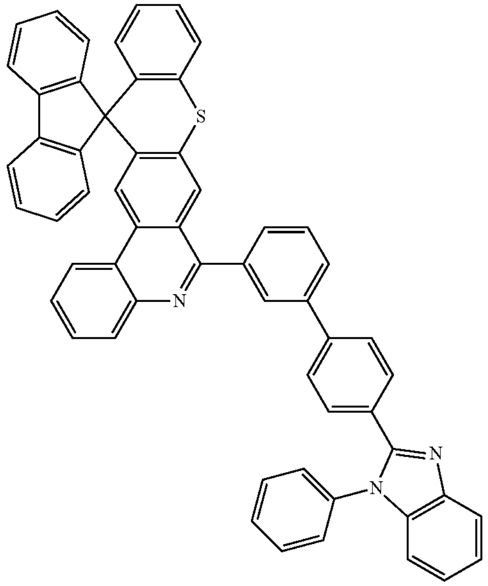
366
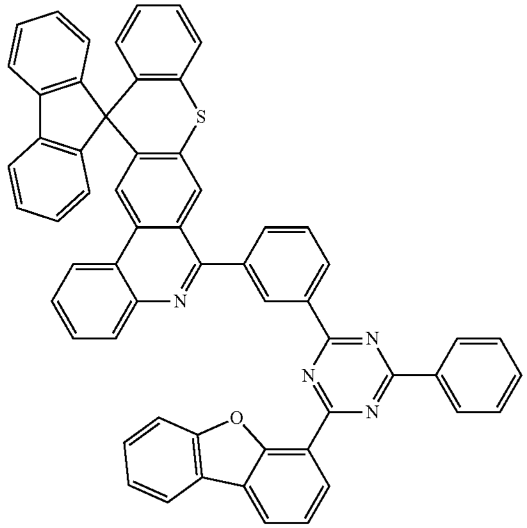

-continued
367
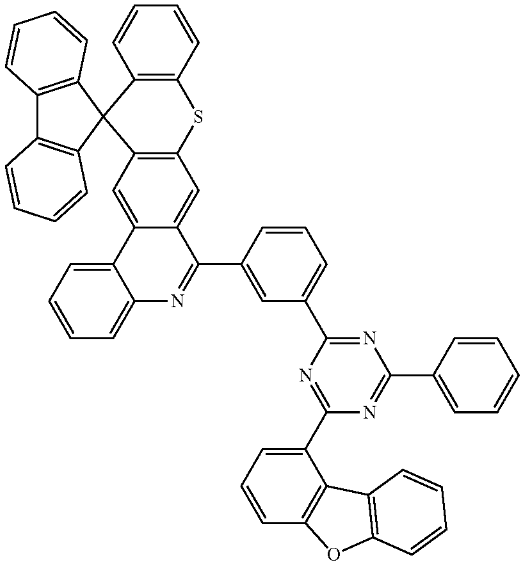
368
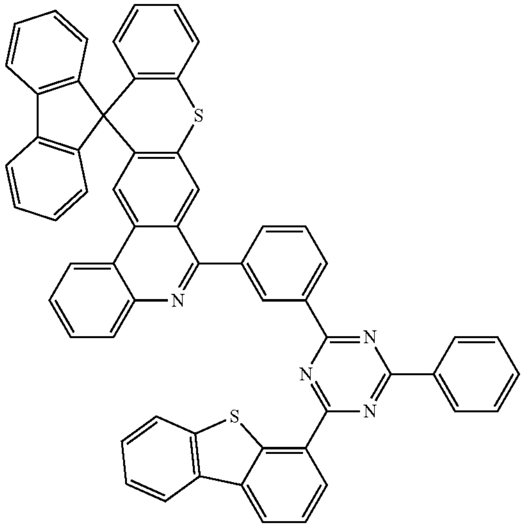
369
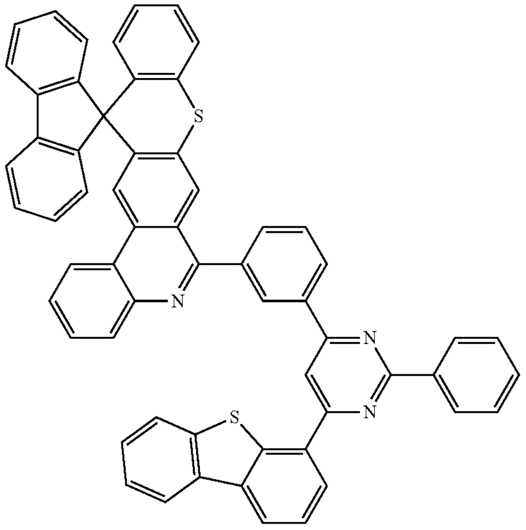
-continued
370
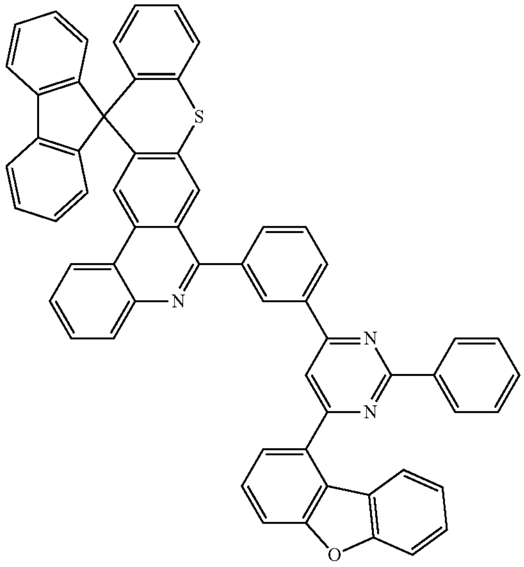
371
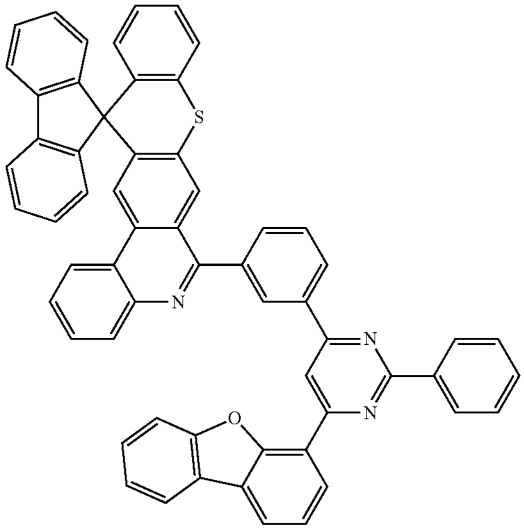
372
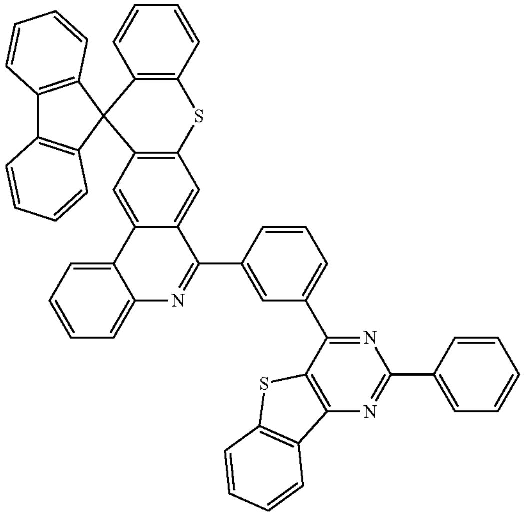

-continued
373
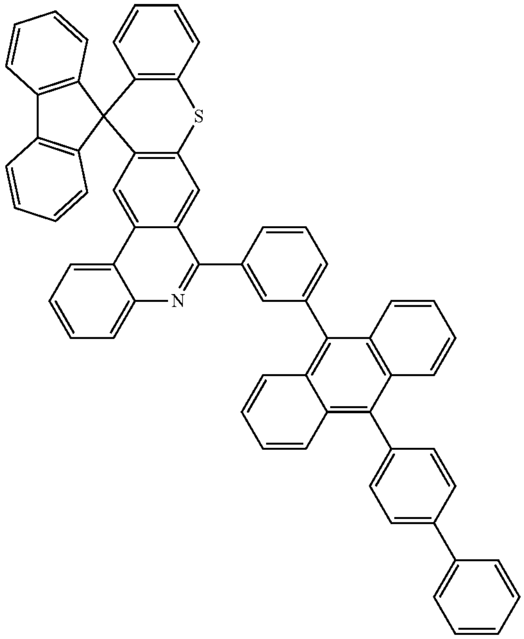
374
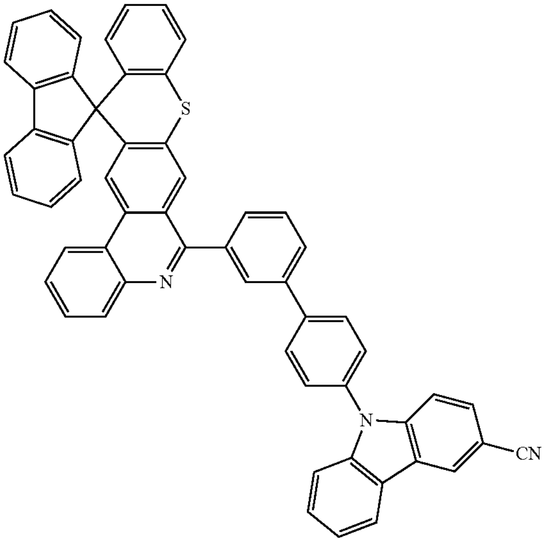
-continued
375
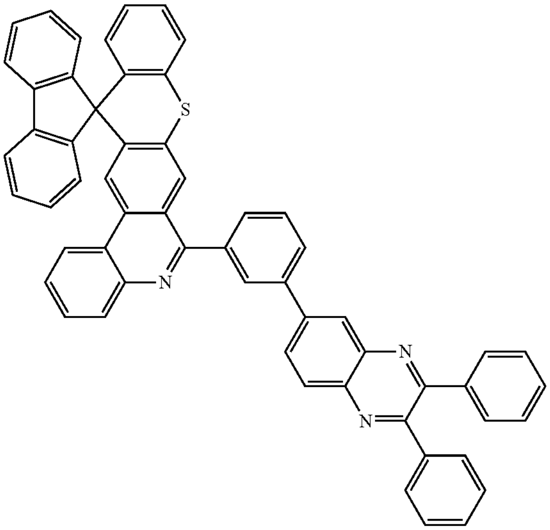
376
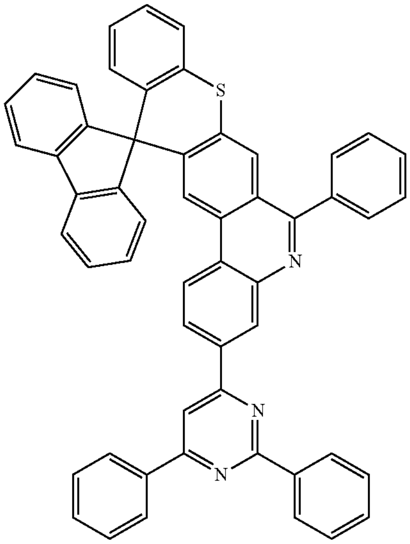

-continued
377
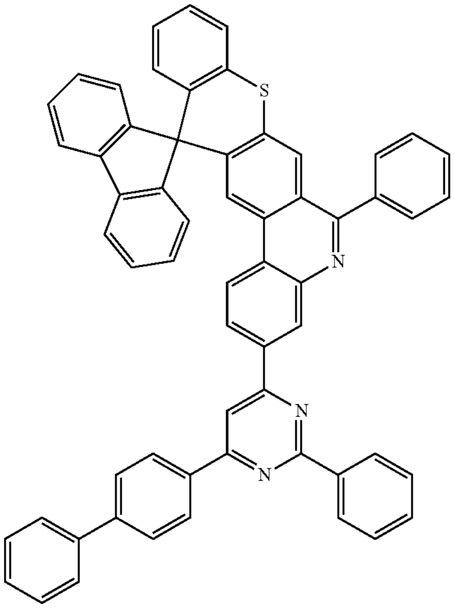
379
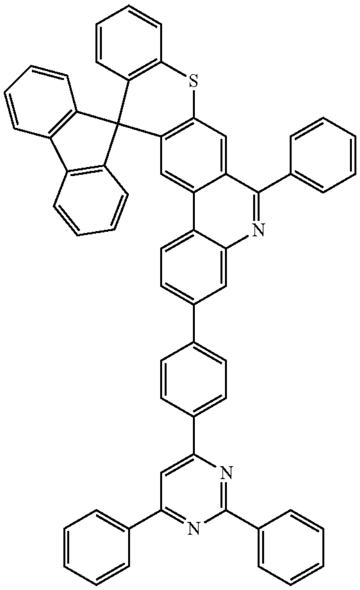
378
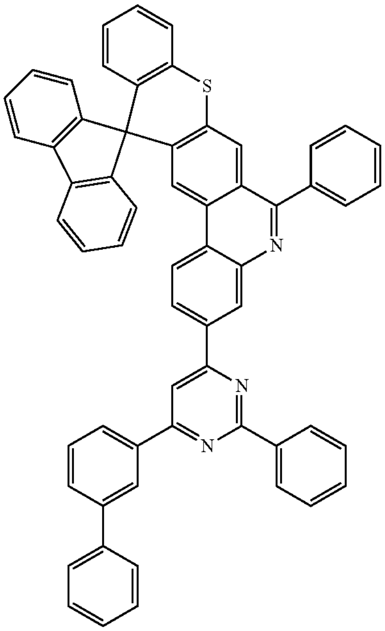
380
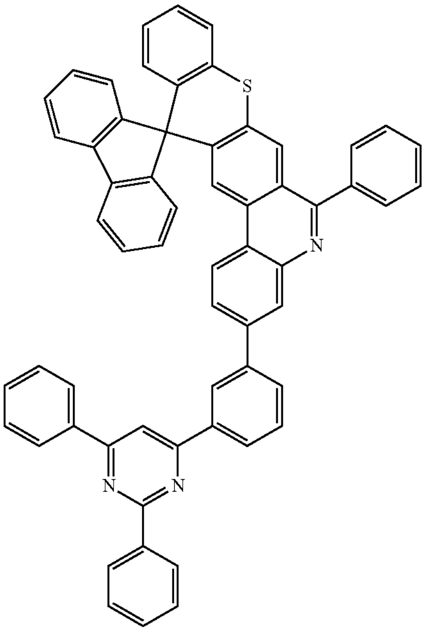

-continued
381
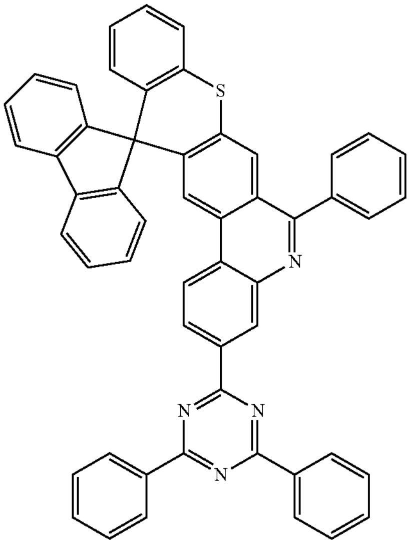
383
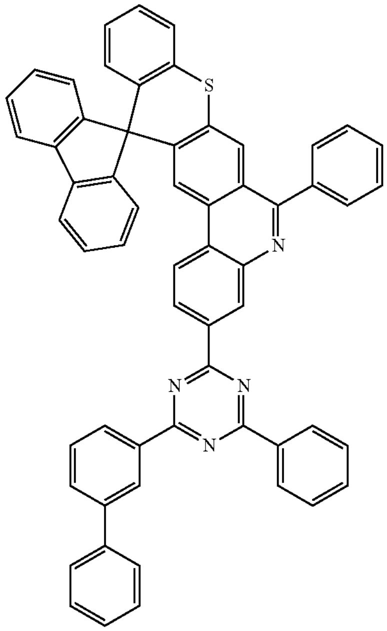
382
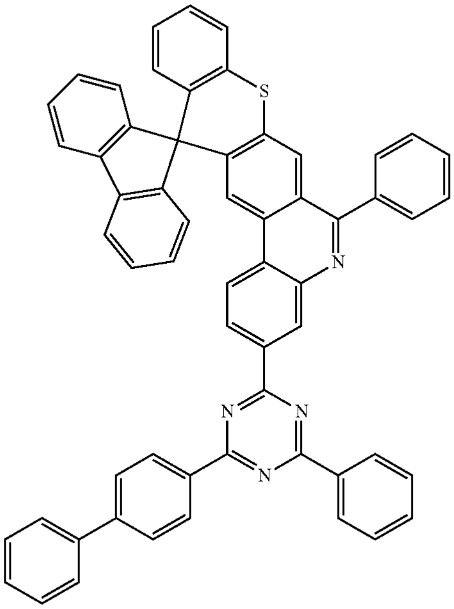
384
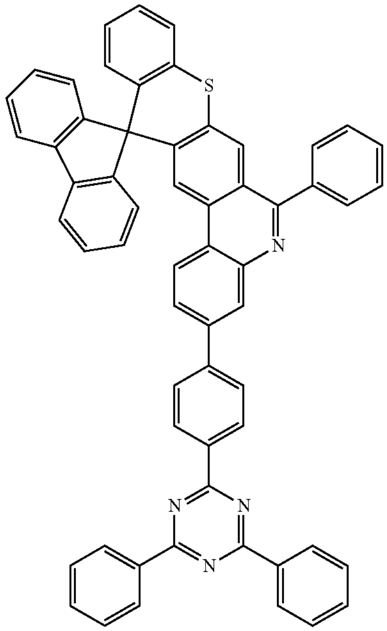

-continued
385
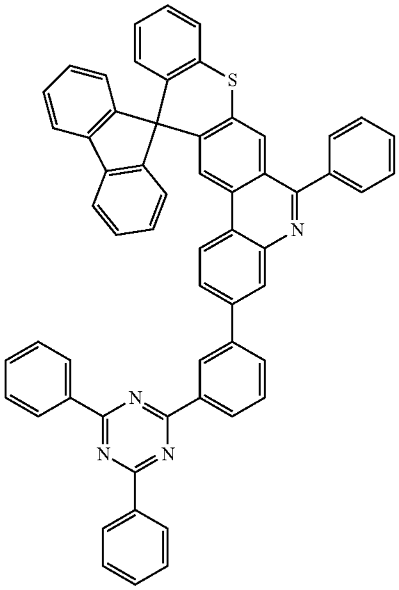
386
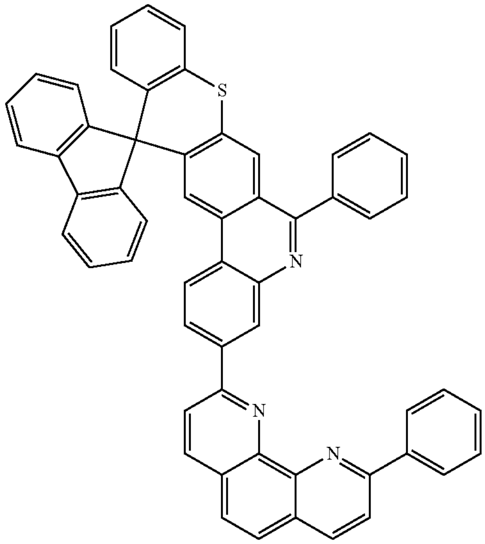
-continued
387
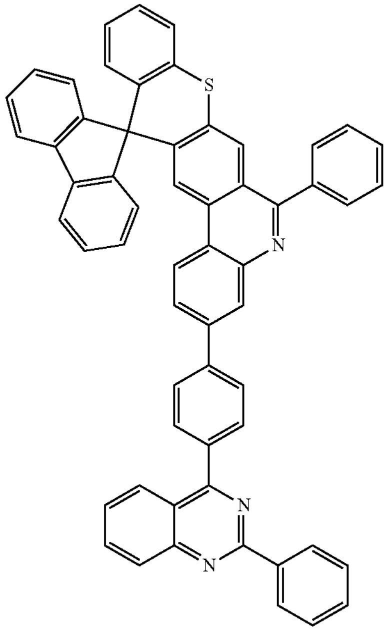
388
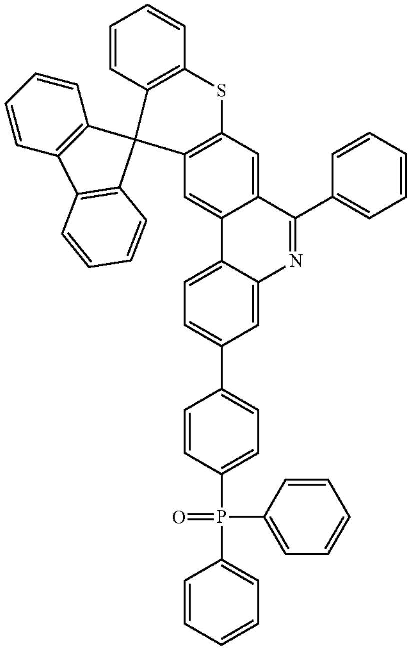

-continued
389
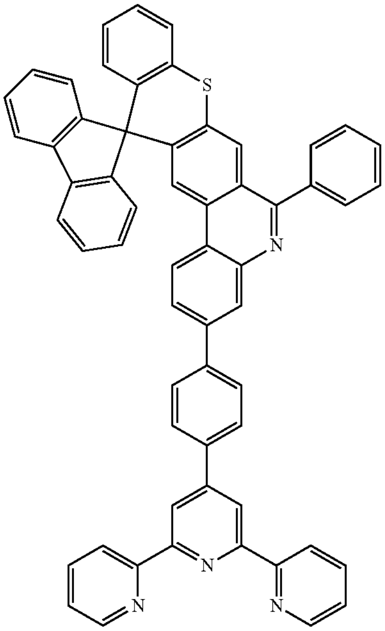
390
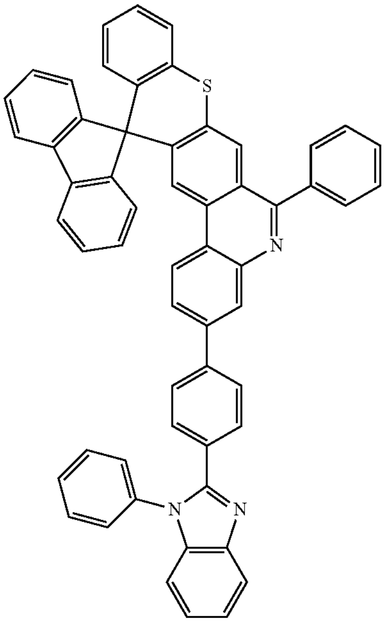
-continued
391
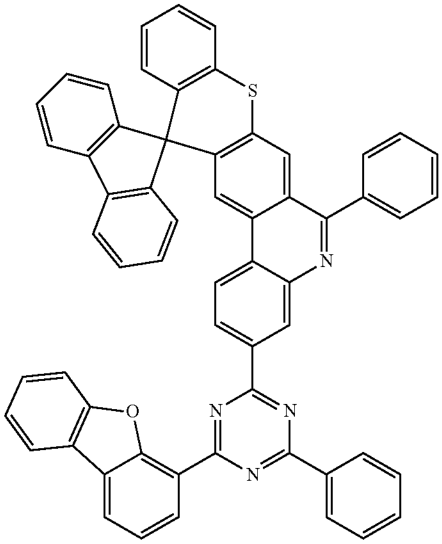
392
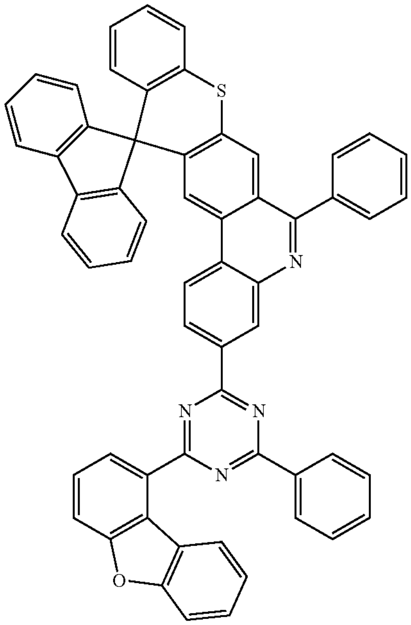

-continued
393
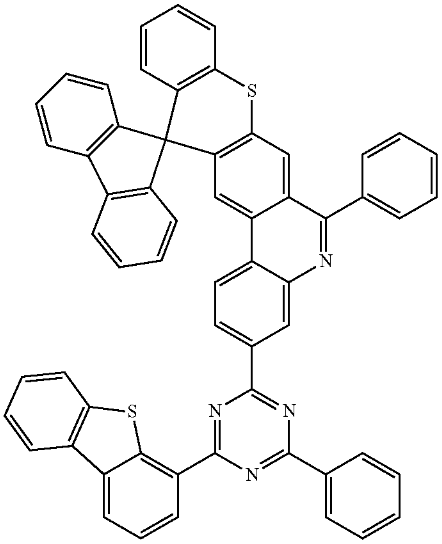
394
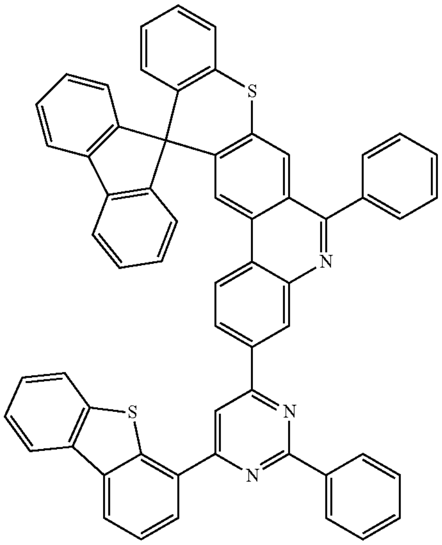
-continued
395
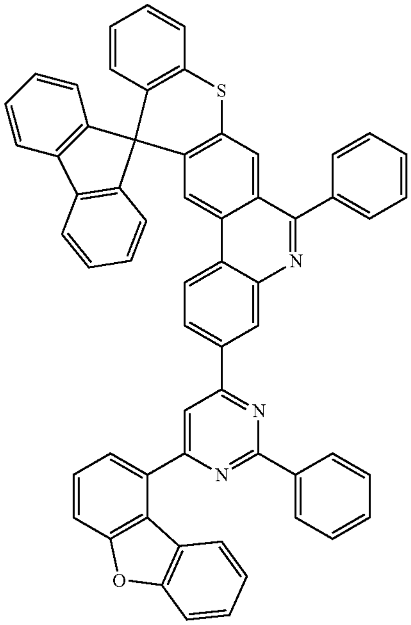
396
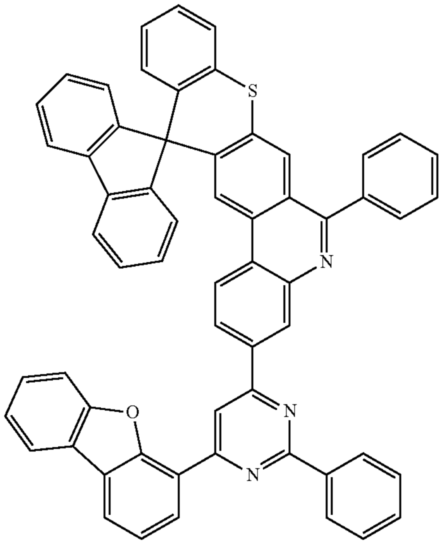

-continued
397
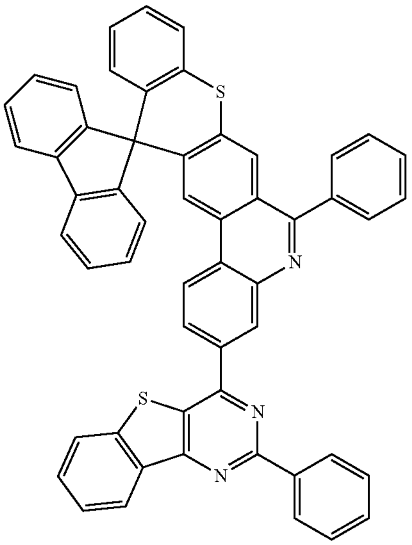
398
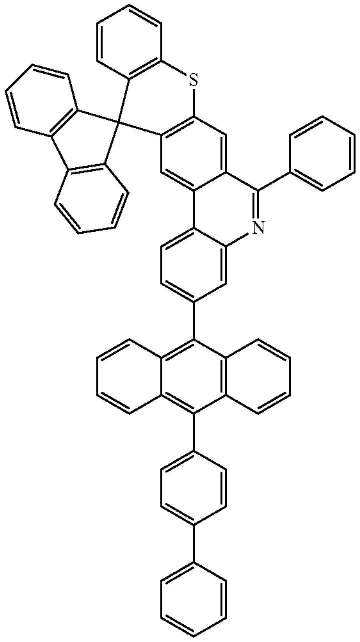
-continued
399
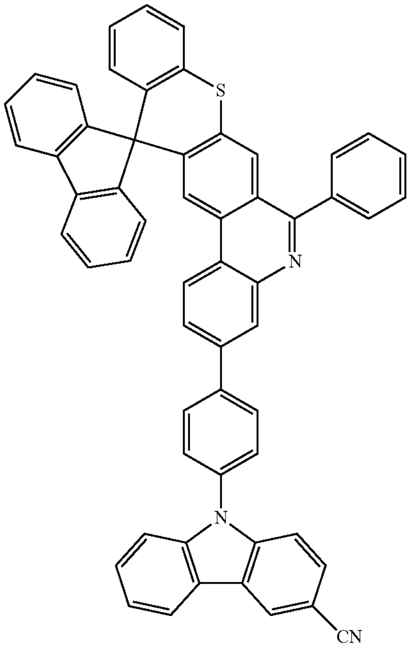
400
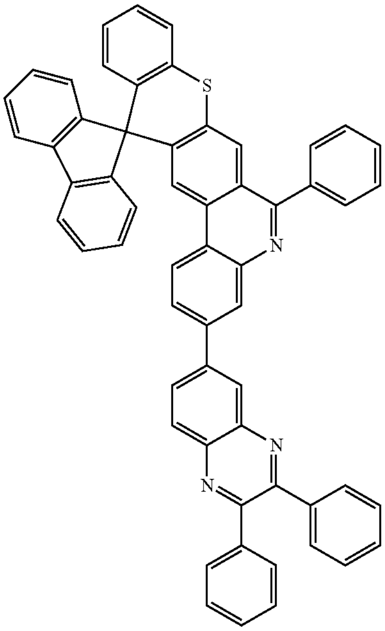

-continued
401
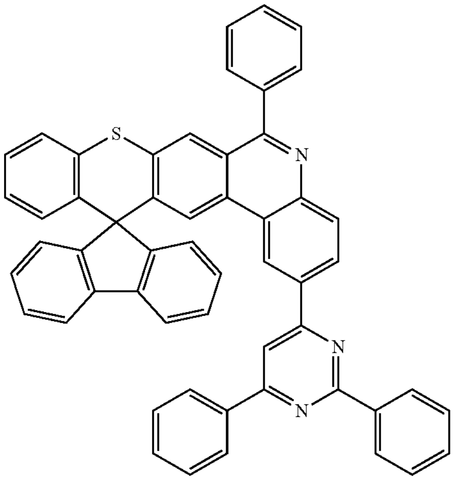
402
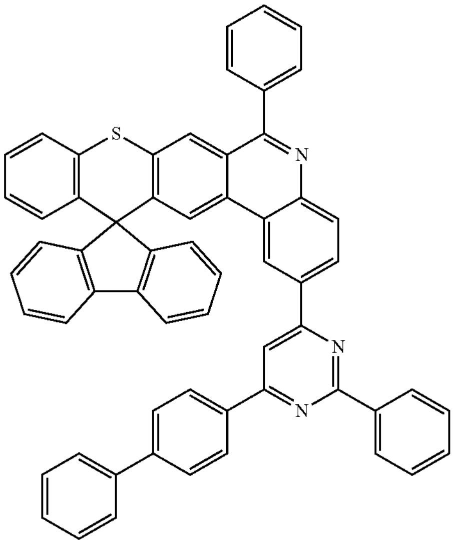
403
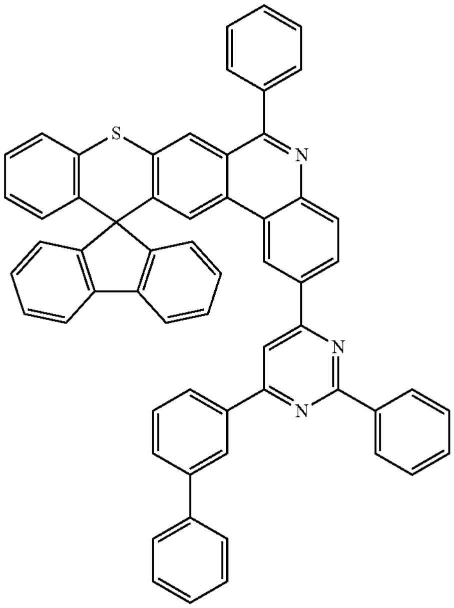
404
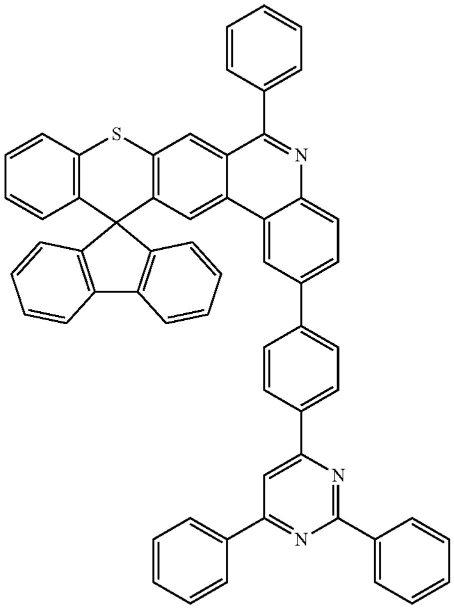
405
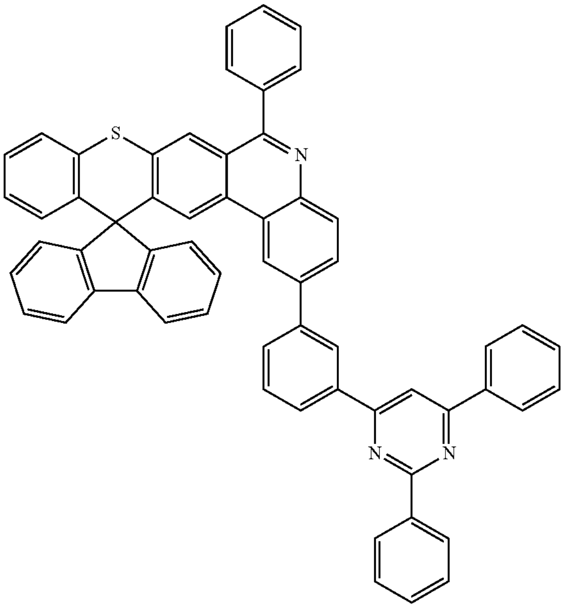

-continued
406
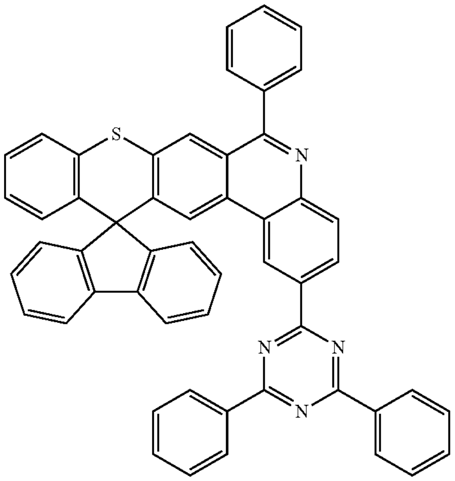
407
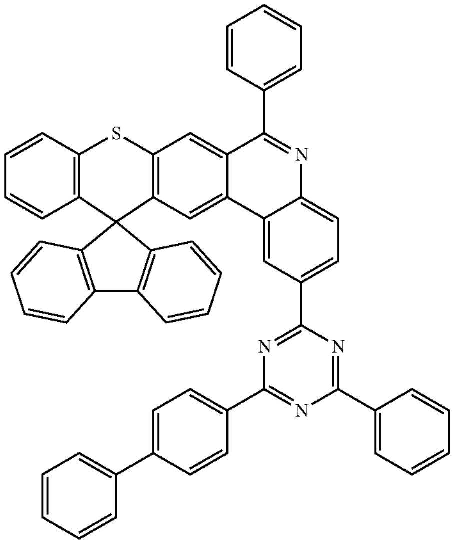
408
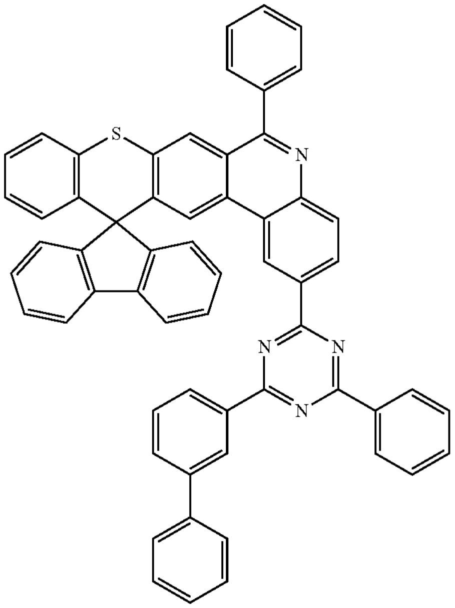
-continued
409
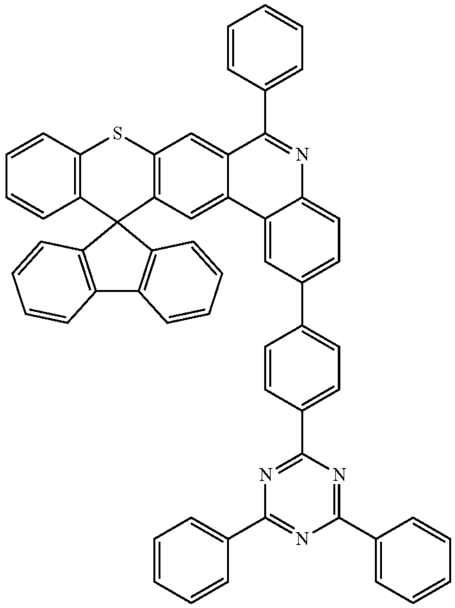
410
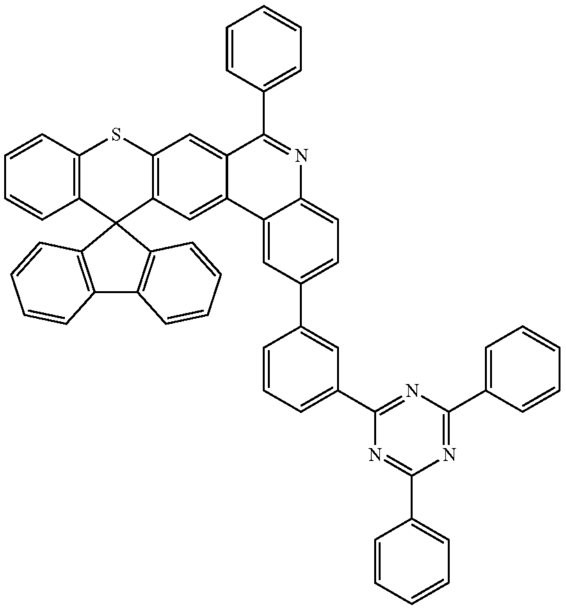

-continued
411
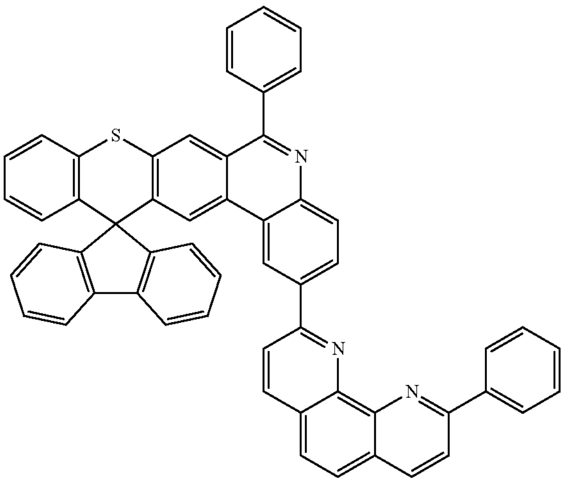
-continued
413
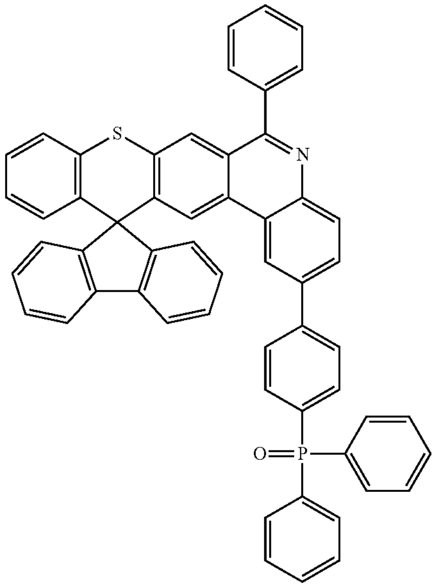
412
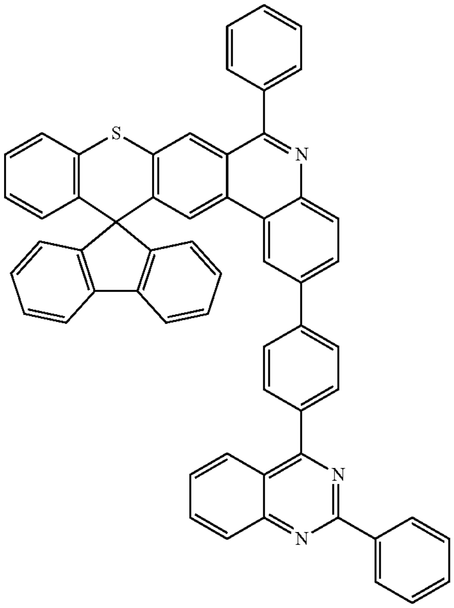
414
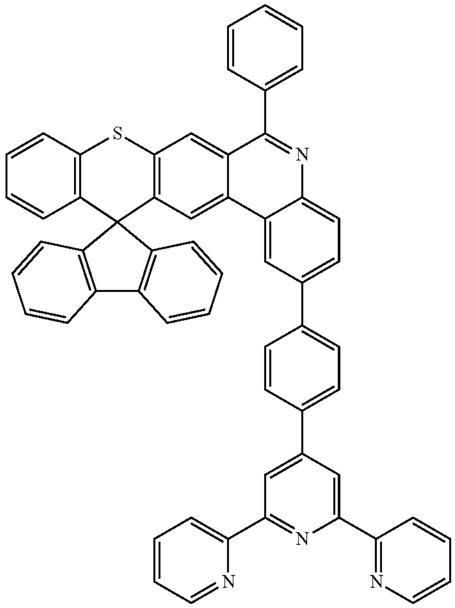

-continued
415
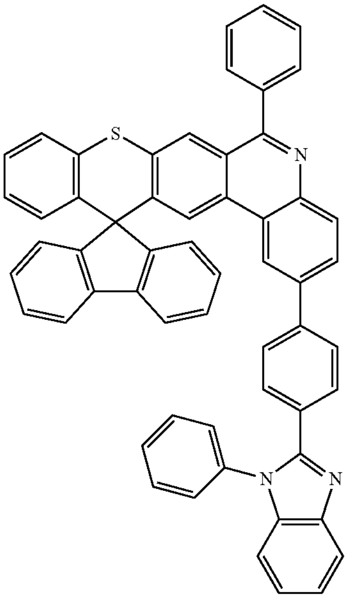
417
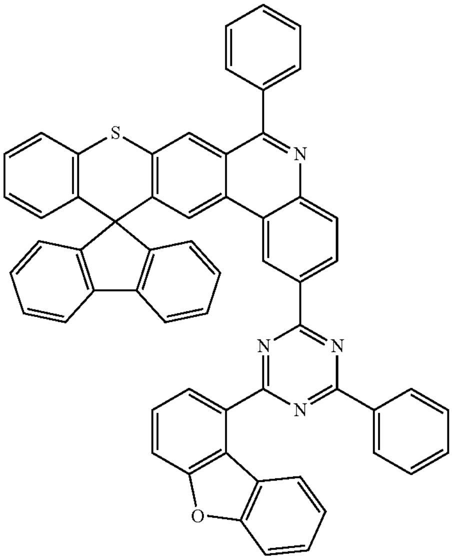
416
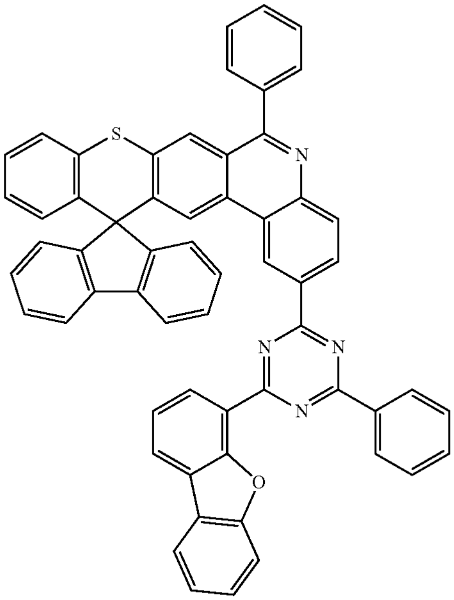
418
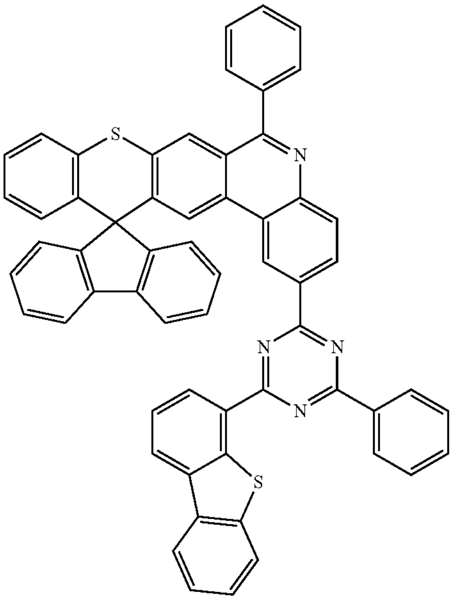

-continued
419
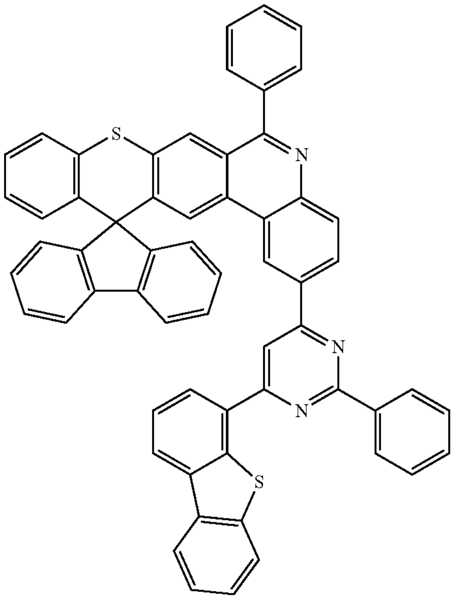
420
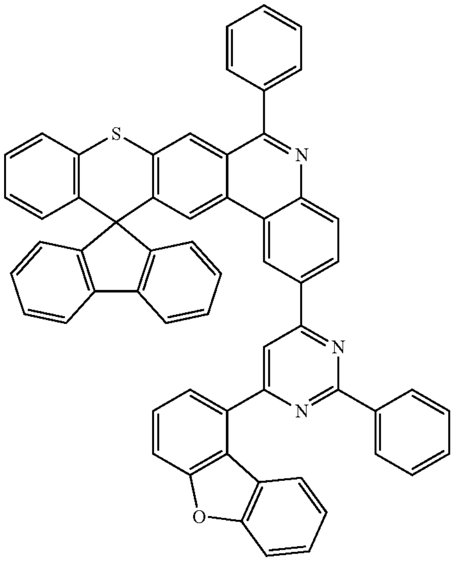
-continued
421
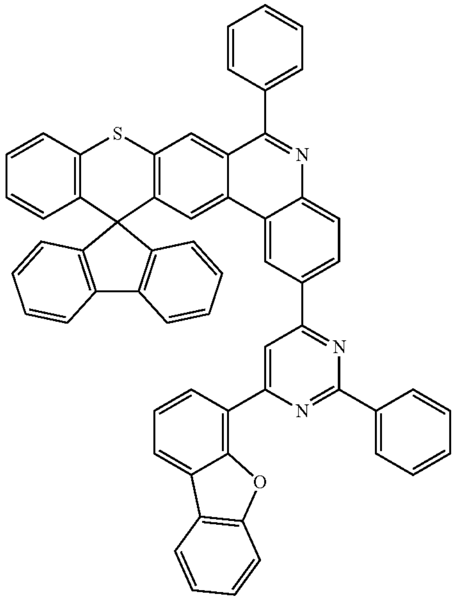
422
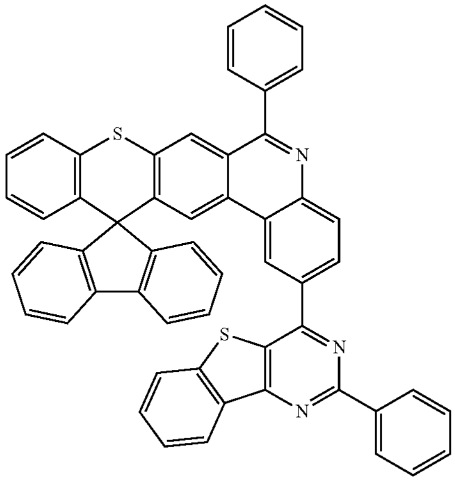

423
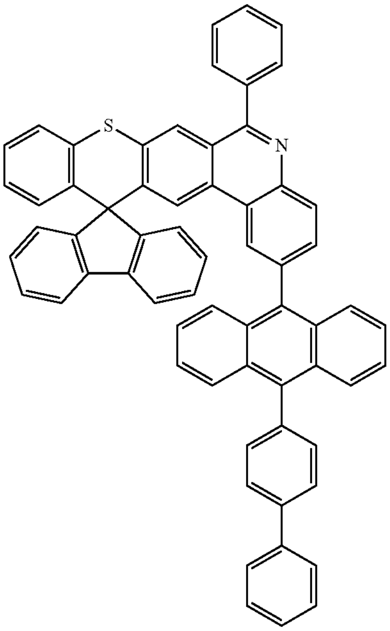
425
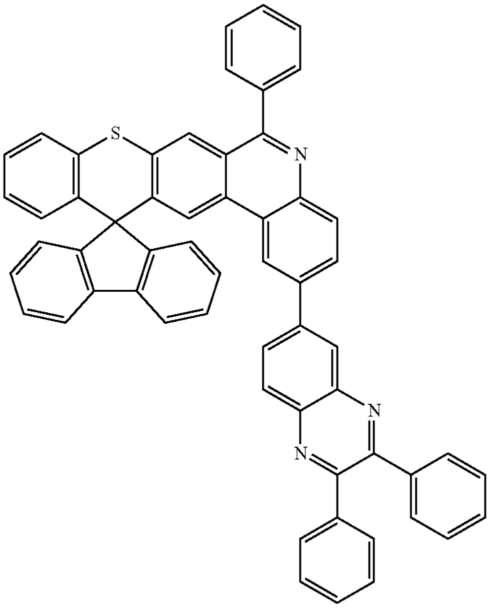
424
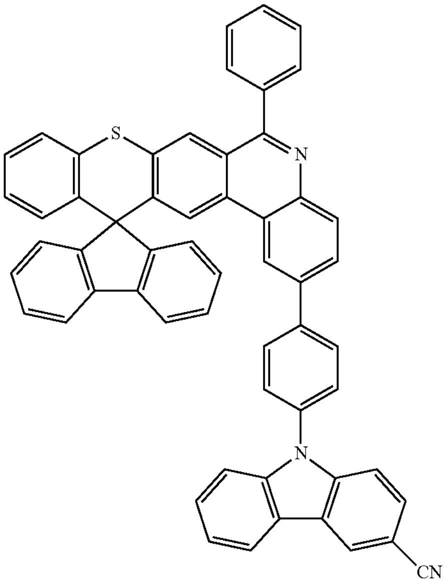
426
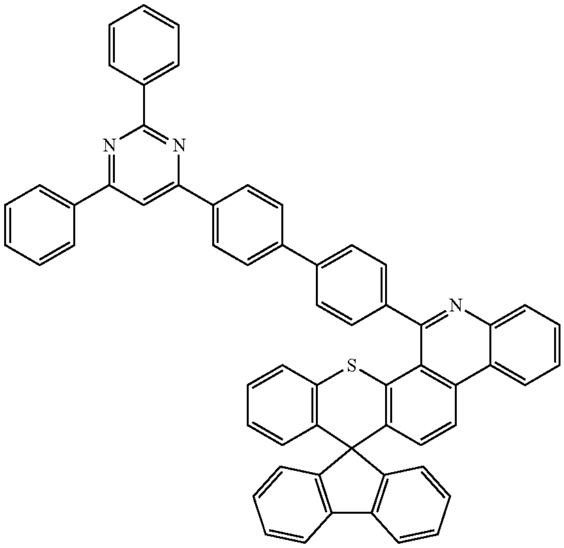

-continued
427
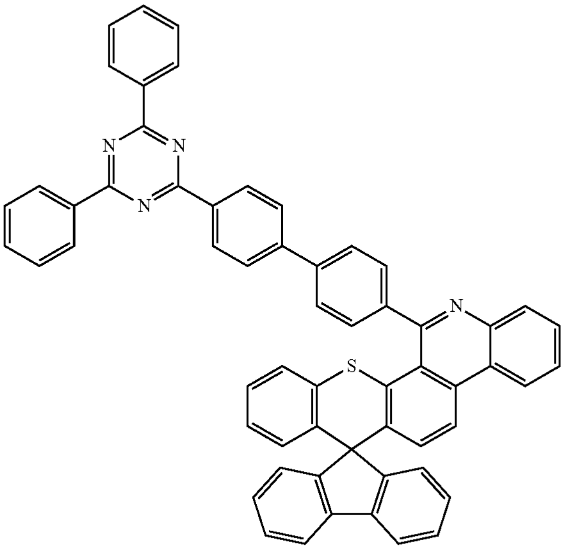
428
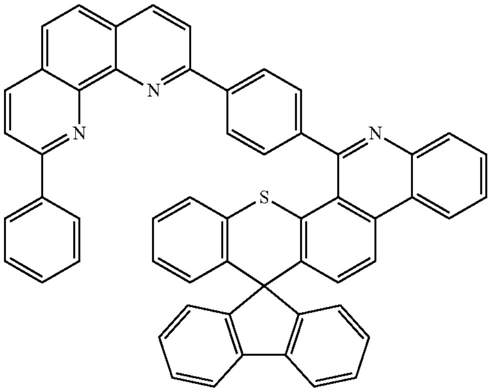
429
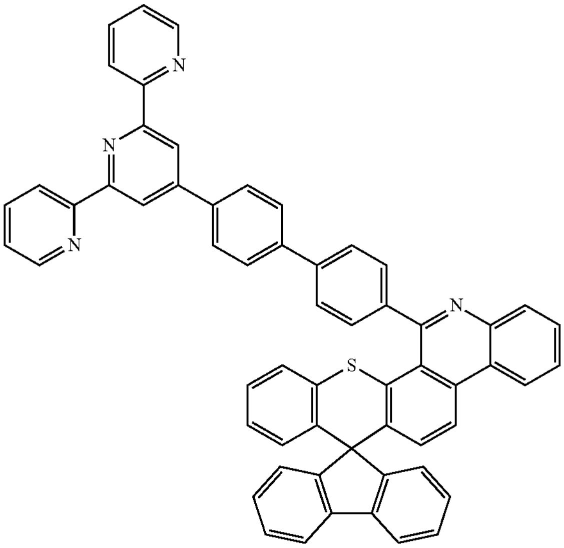
-continued
430
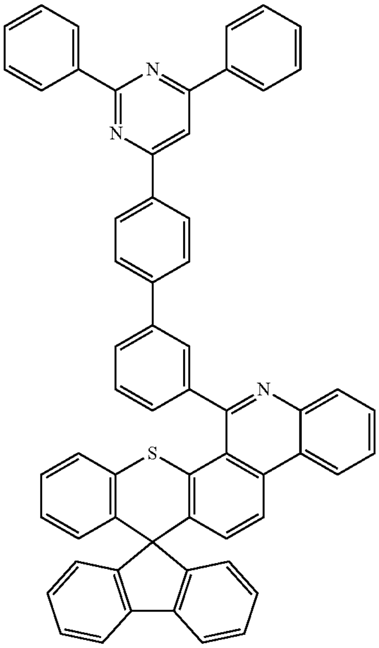
431
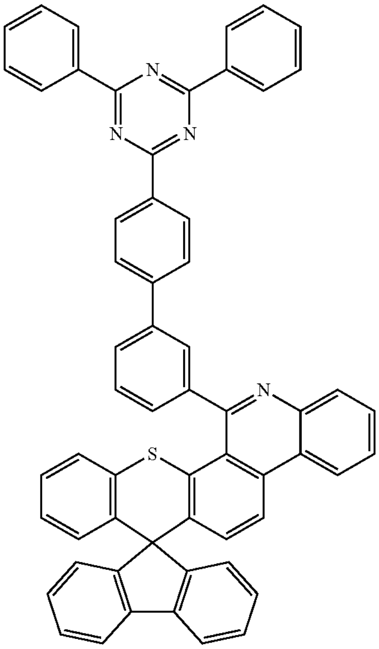

432
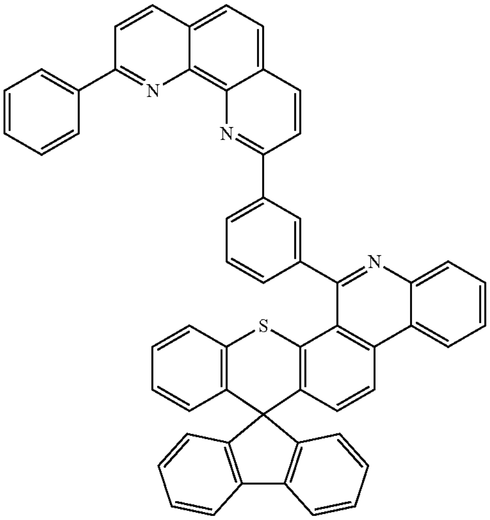
433
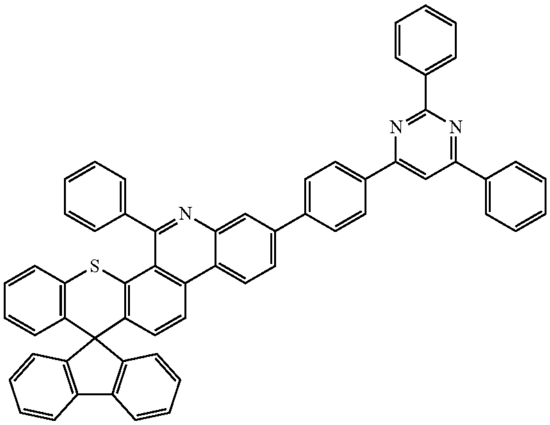
434
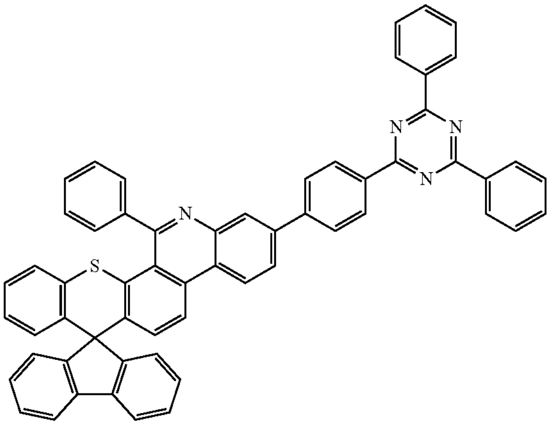
435
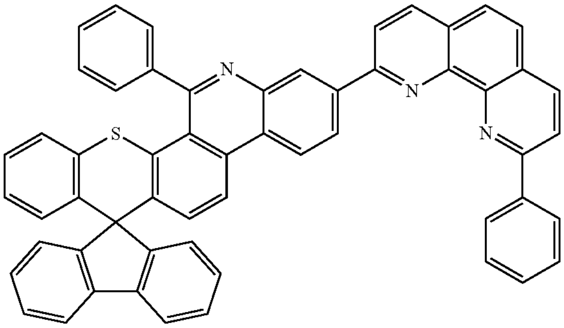
436
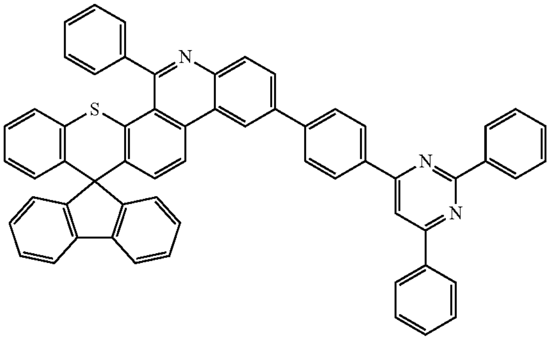
437
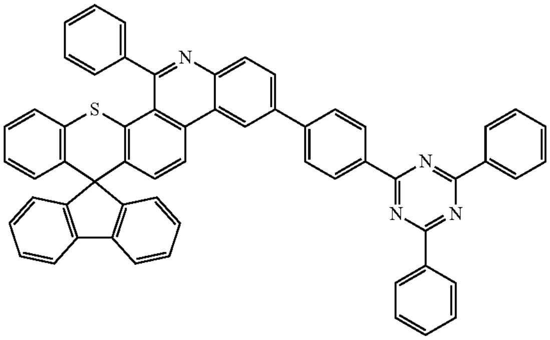
438
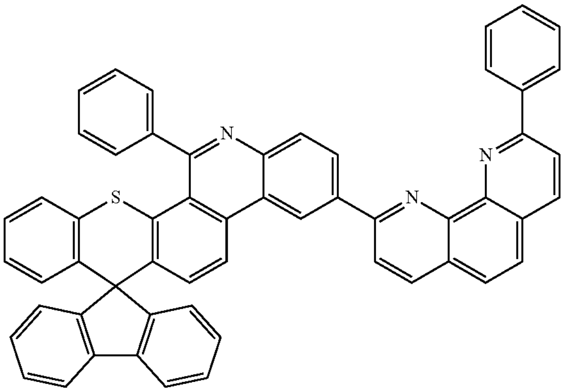

-continued
439
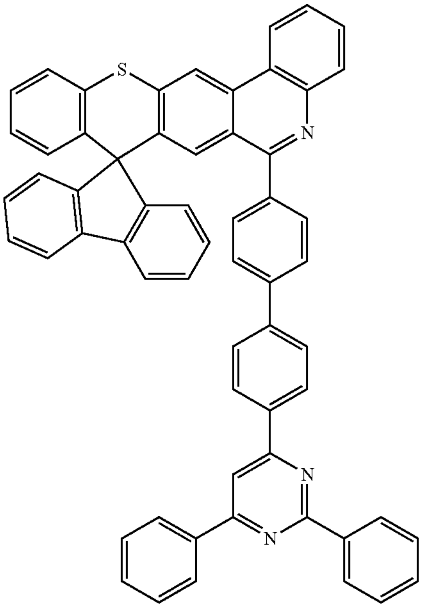
440
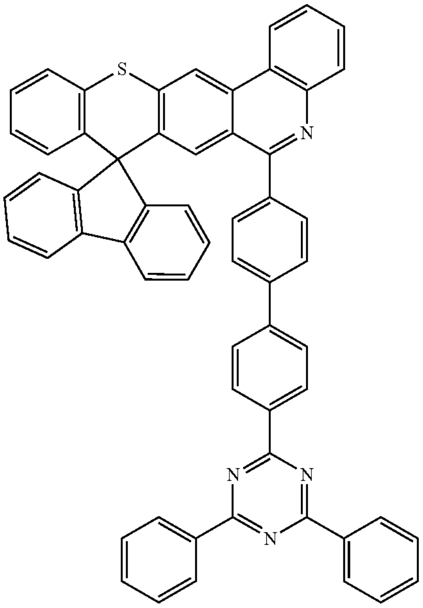
-continued
441
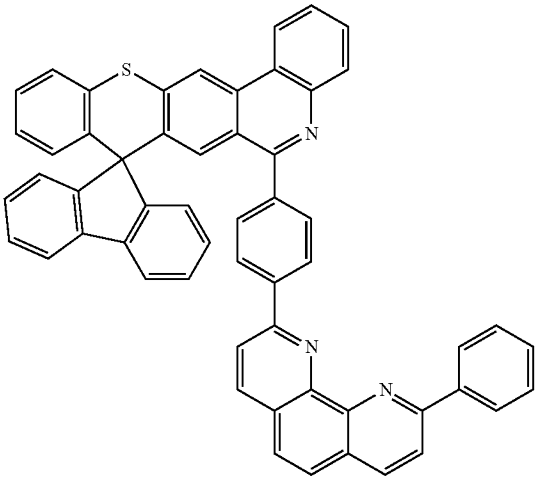
442
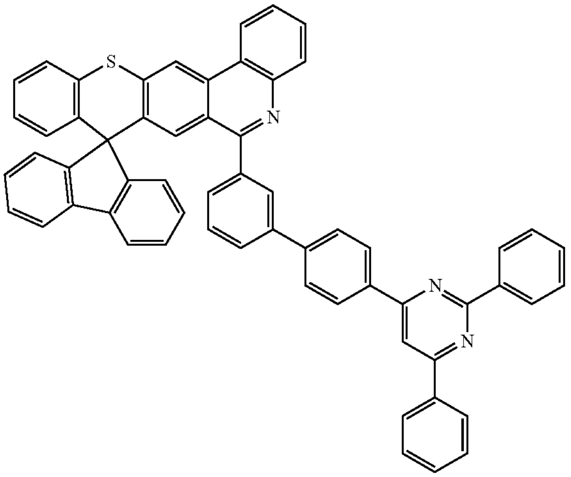
443
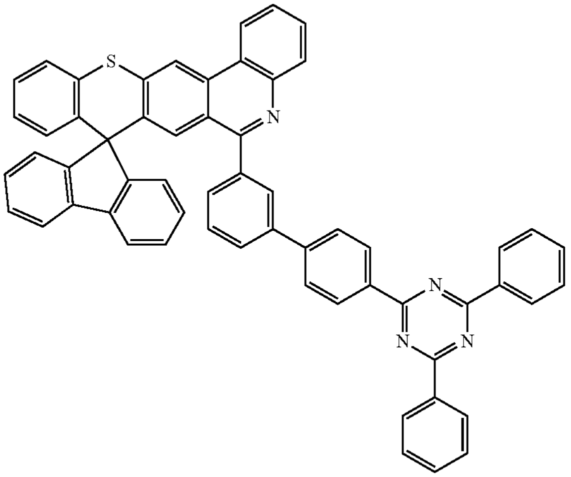

-continued
444
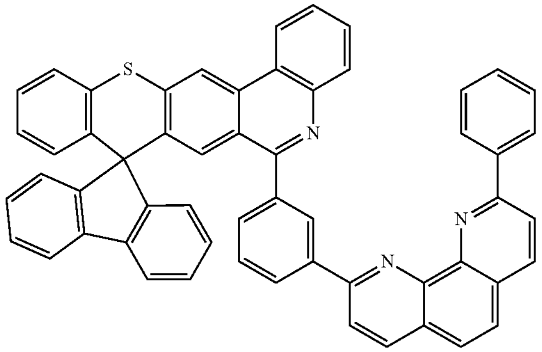
445
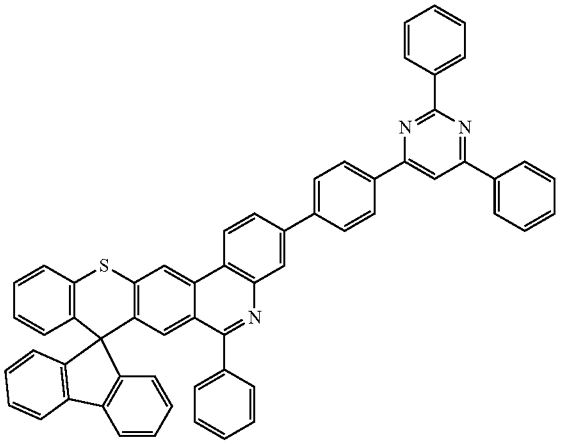
446
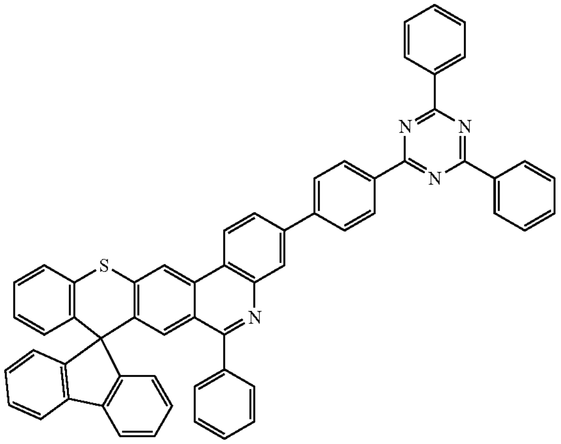
-continued
447
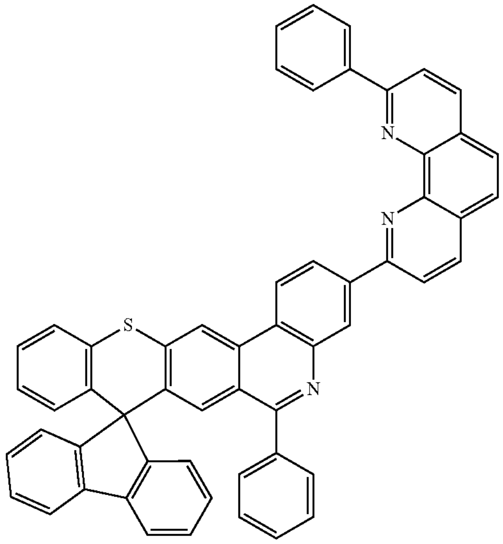
448
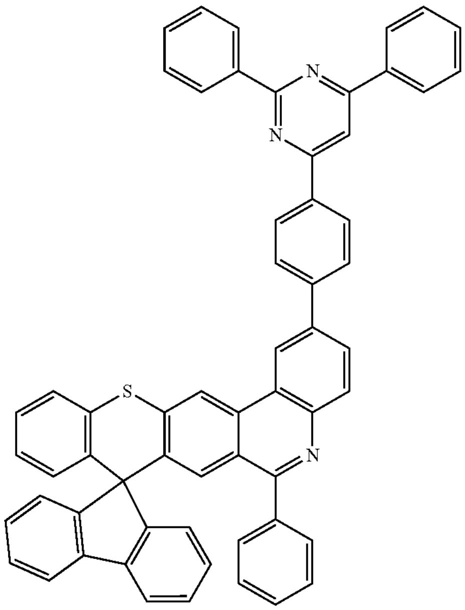

-continued
449
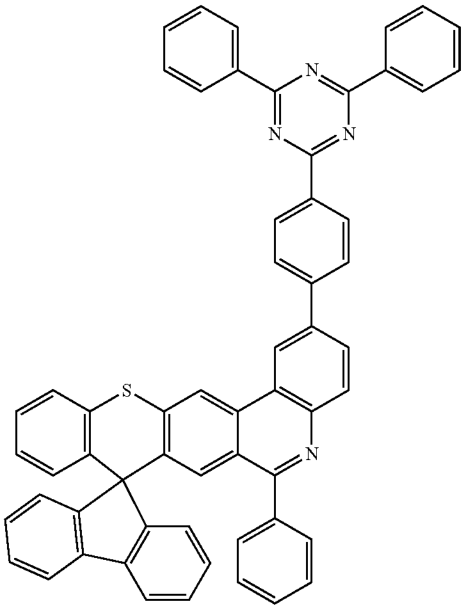
450
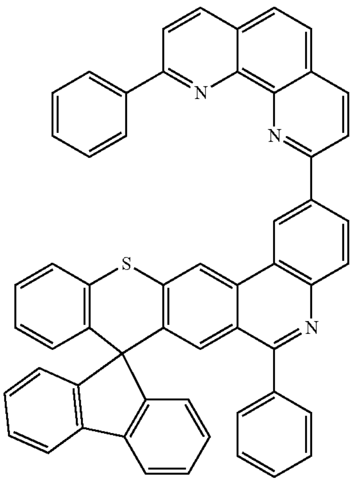
451
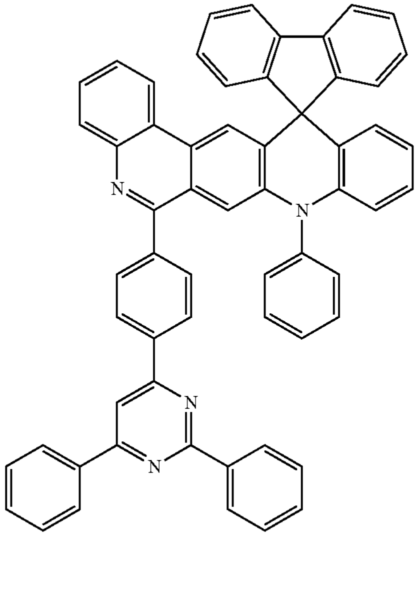
-continued
452
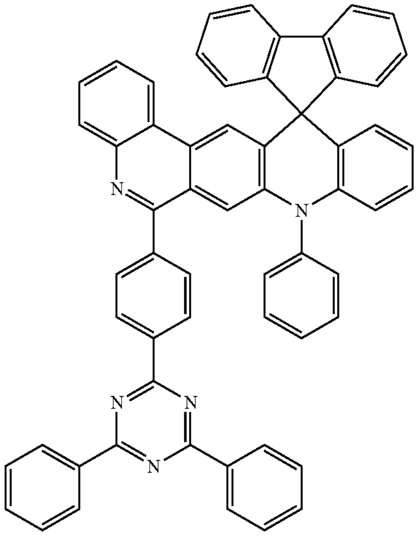
453
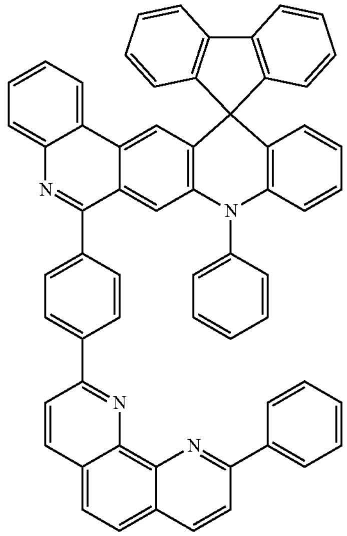
454
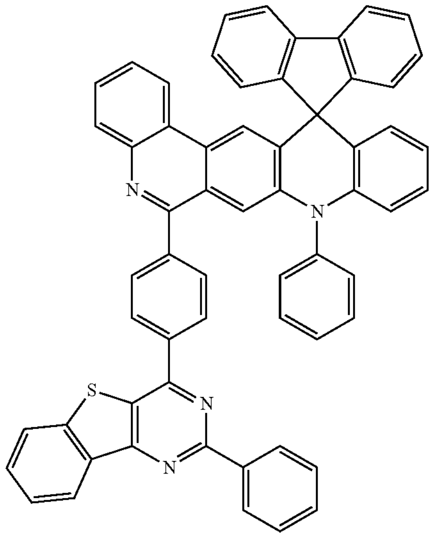

-continued
455
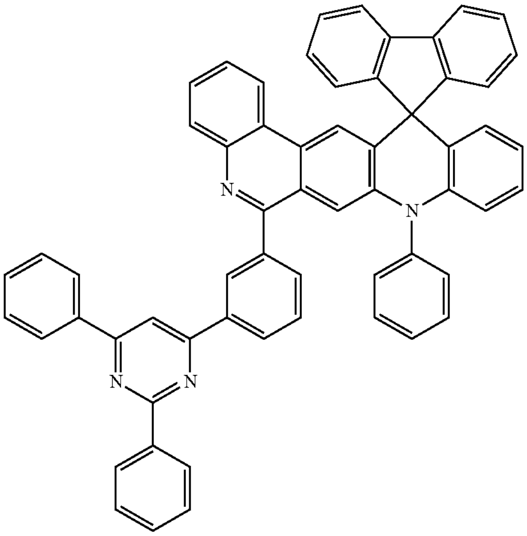
456
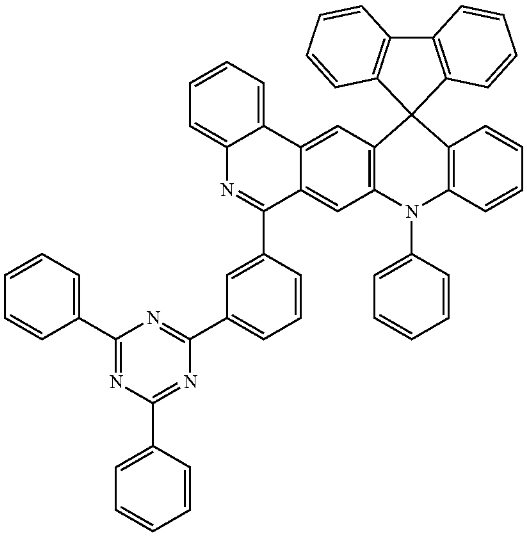
-continued
457
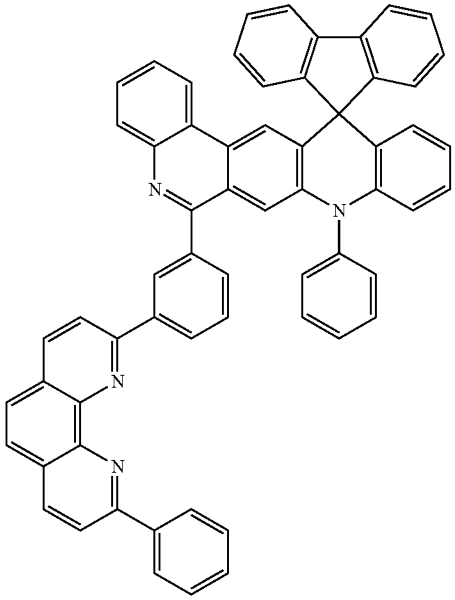
458
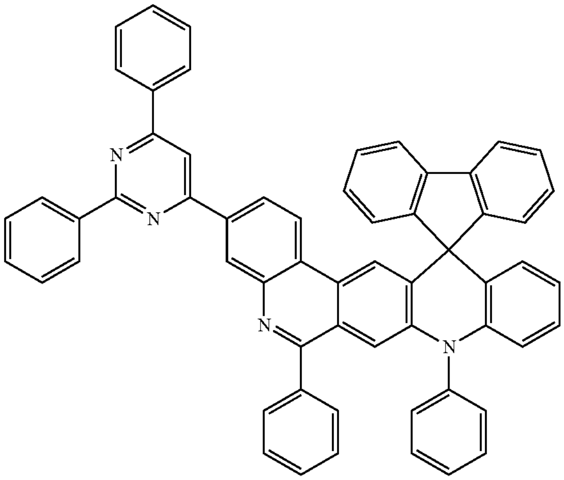
459
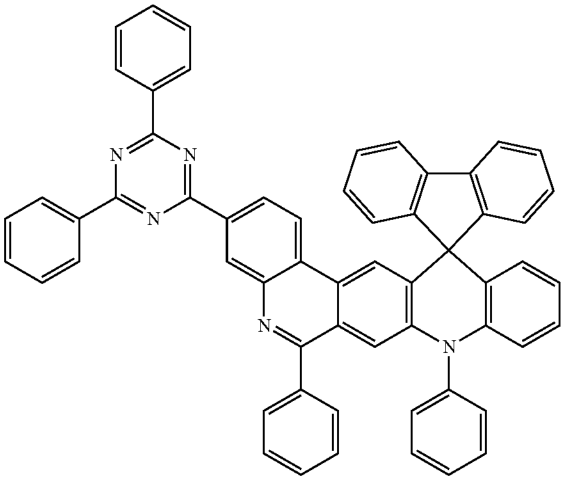

-continued
460
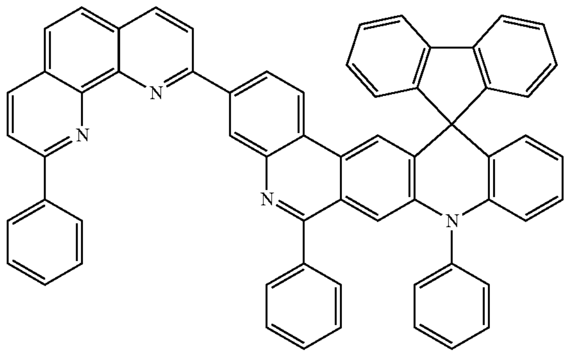
461
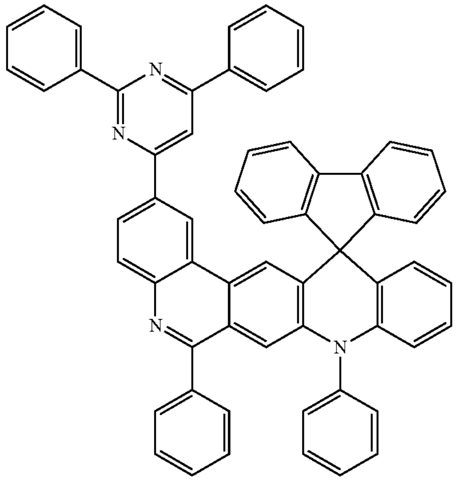
462
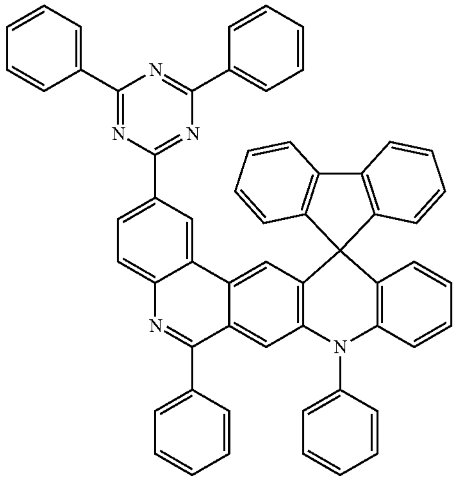
-continued
463
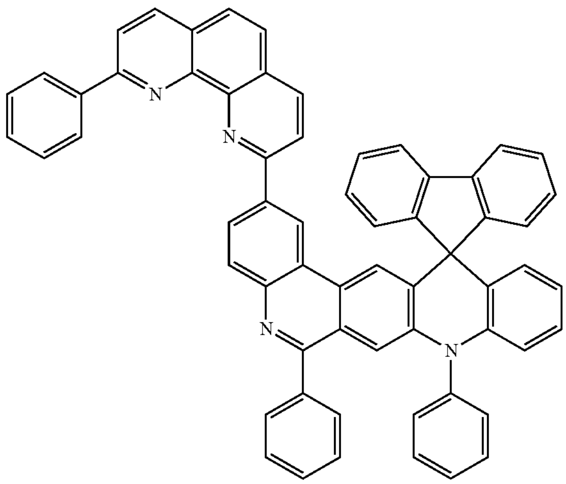
464
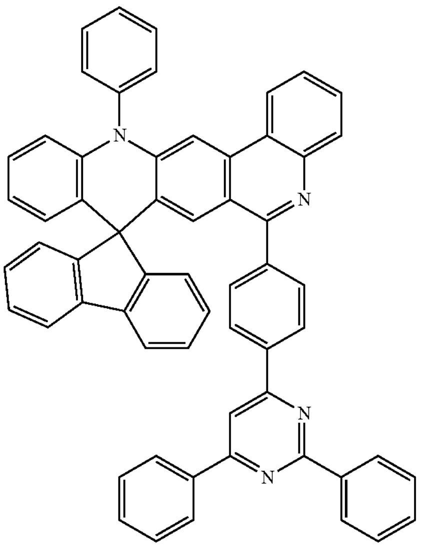
465
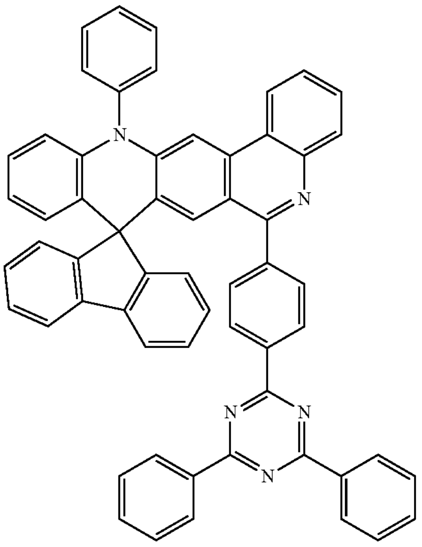

466
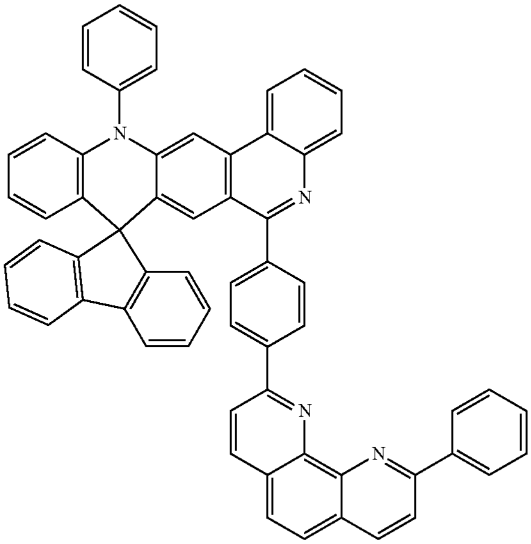
467
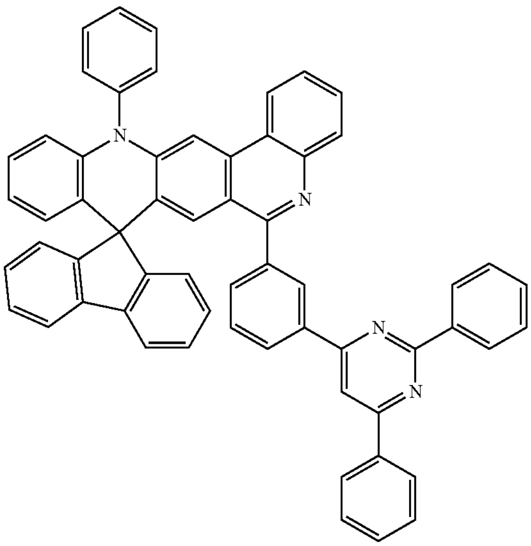
468
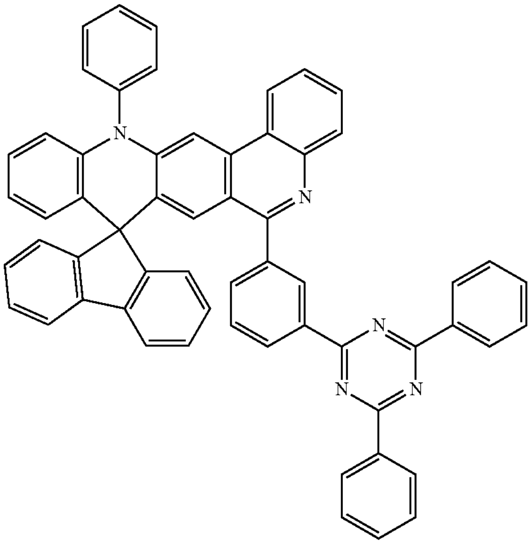
469
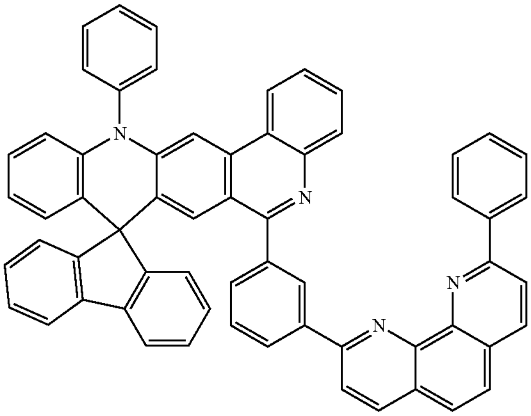
470
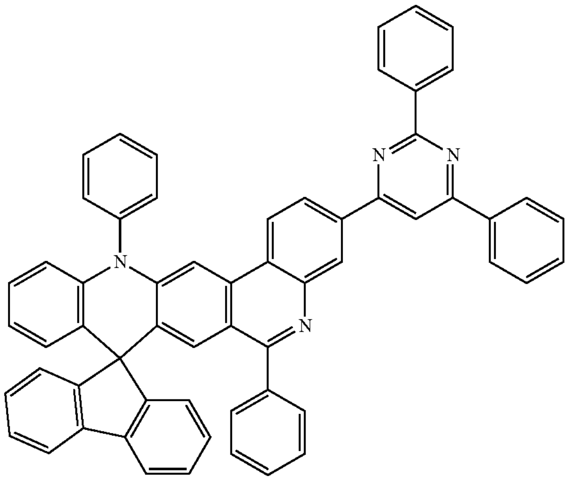

-continued
471
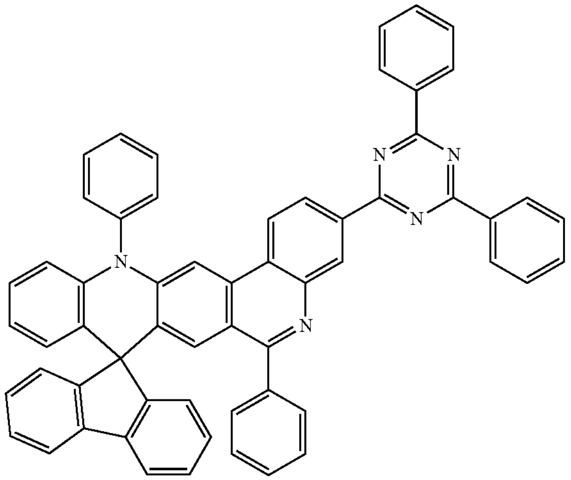
472
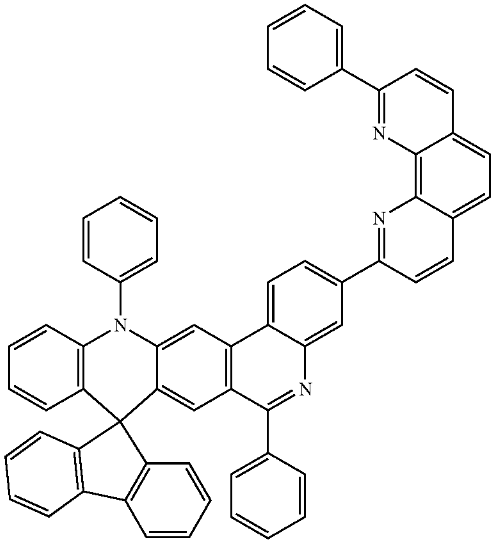
473
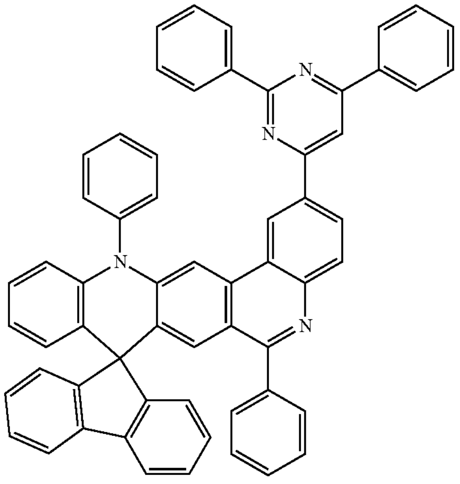
-continued
474
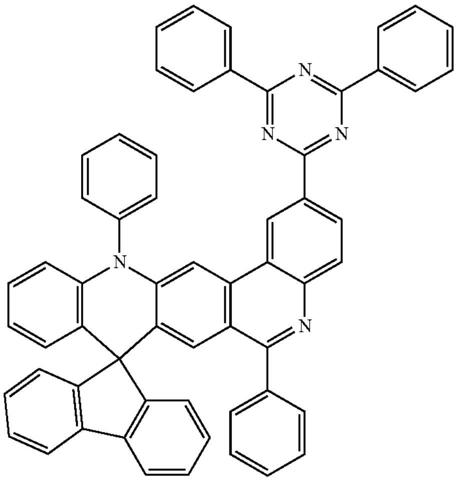
475
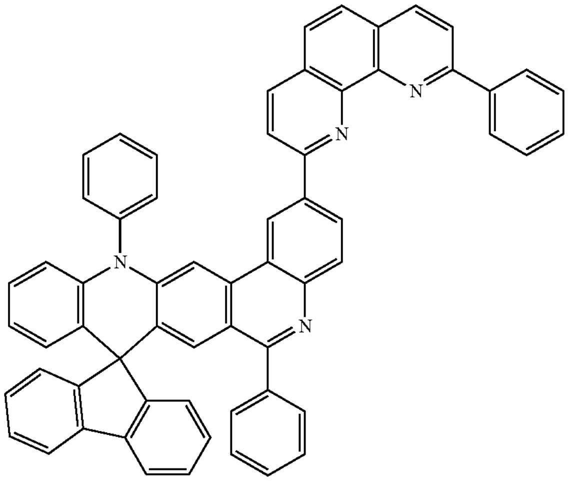
476
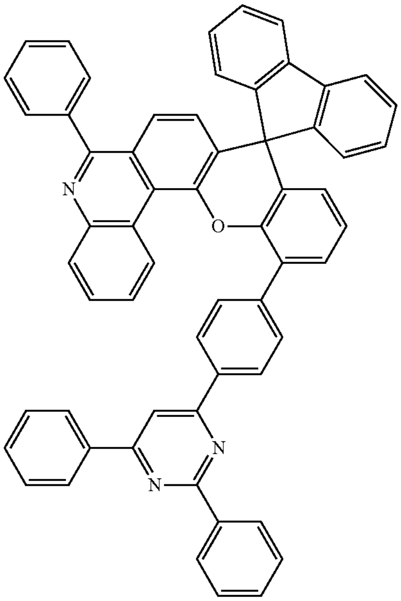

-continued
477
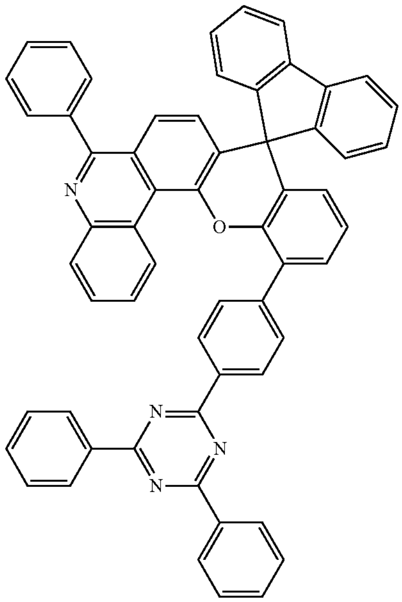
478
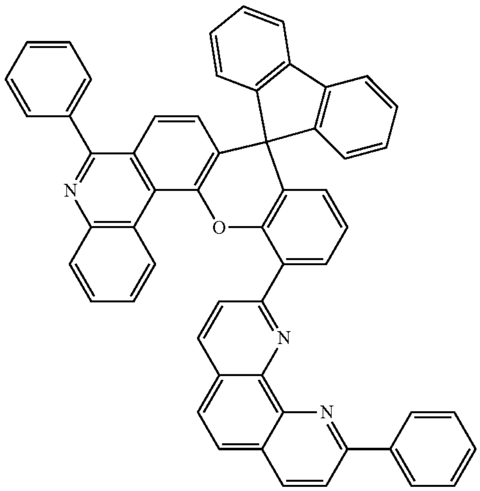
-continued
479
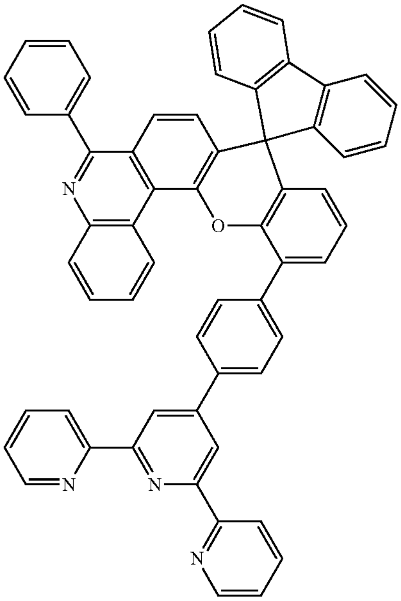
480
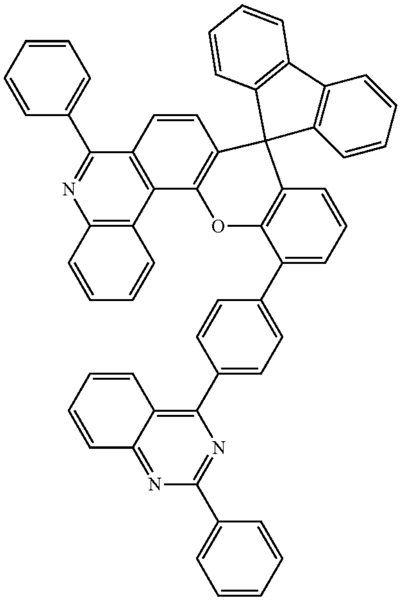

-continued
481
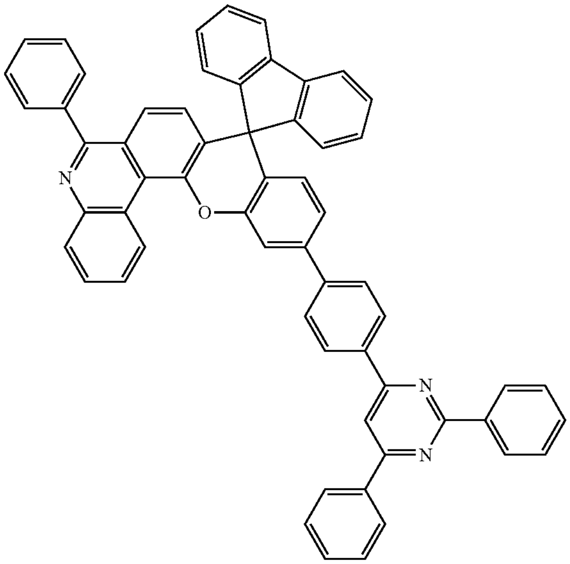
482
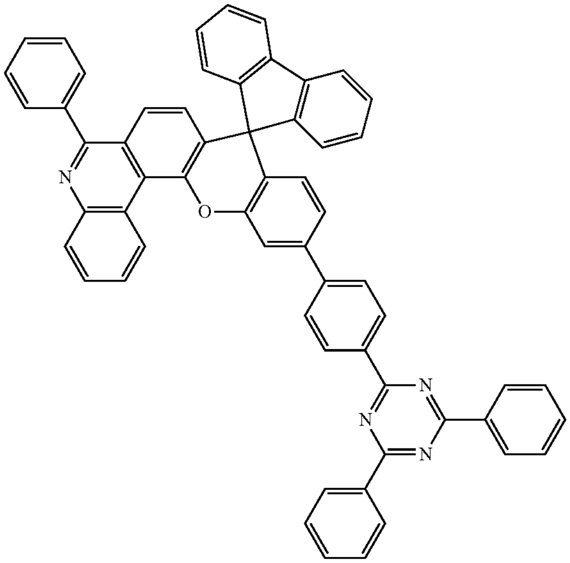
483
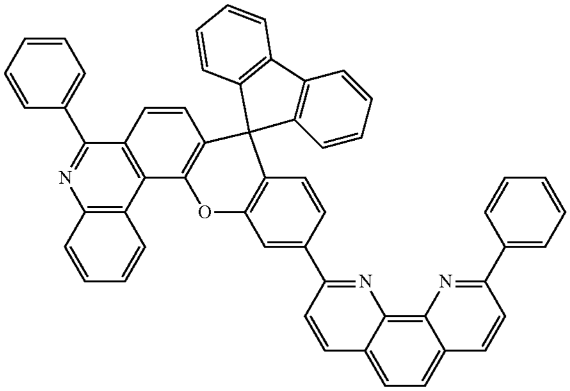
-continued
484
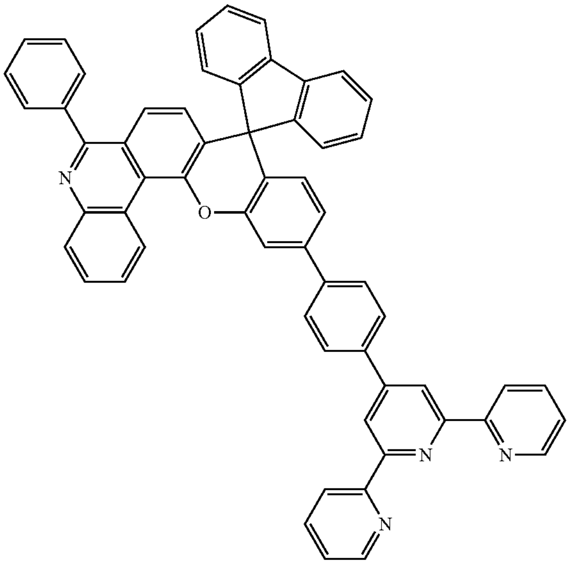
485
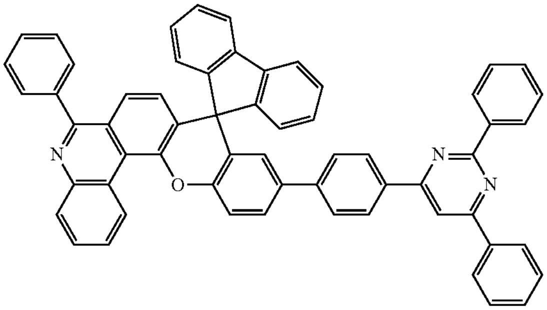
486
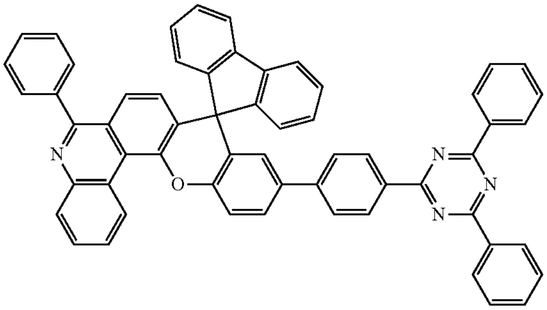
487
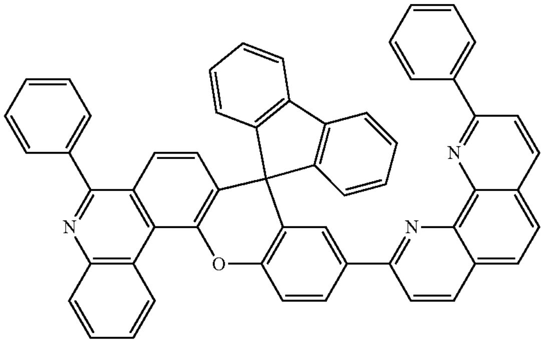

-continued
488
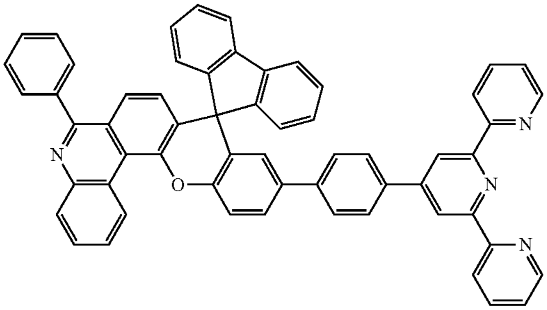
489
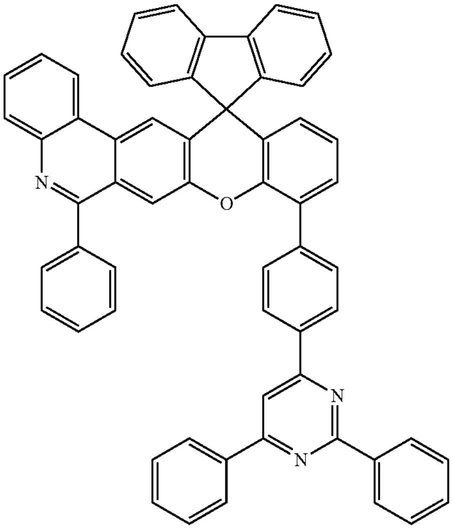
490
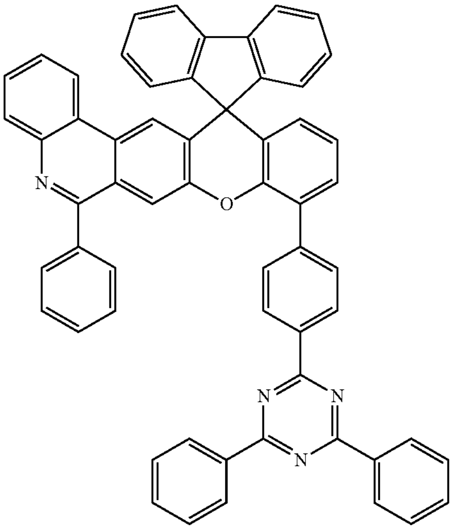
-continued
491
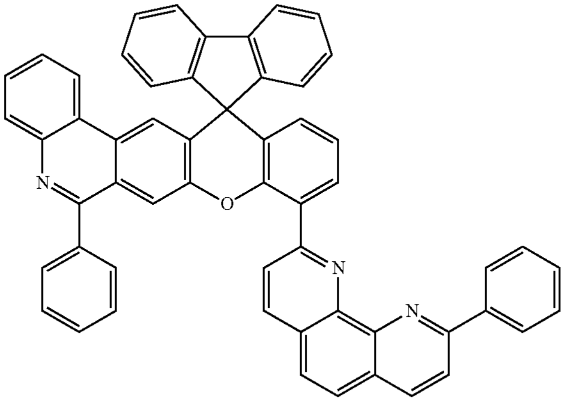
492
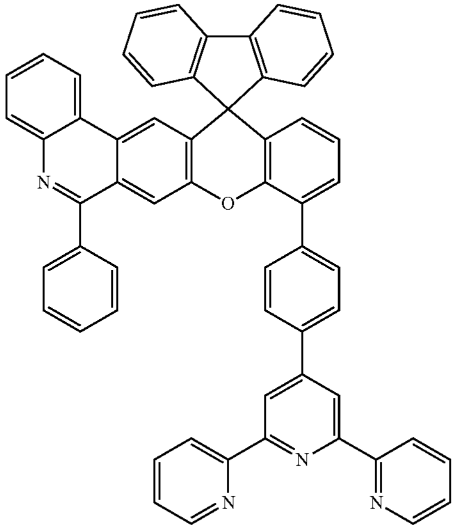
493
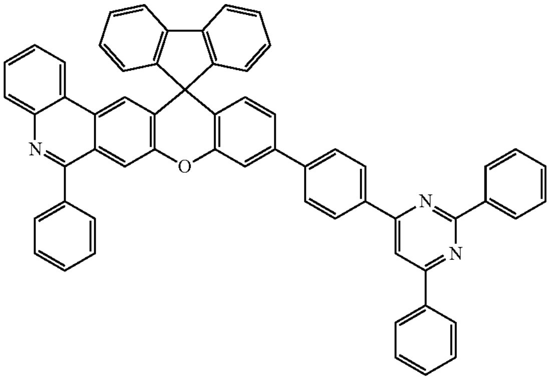

-continued
494
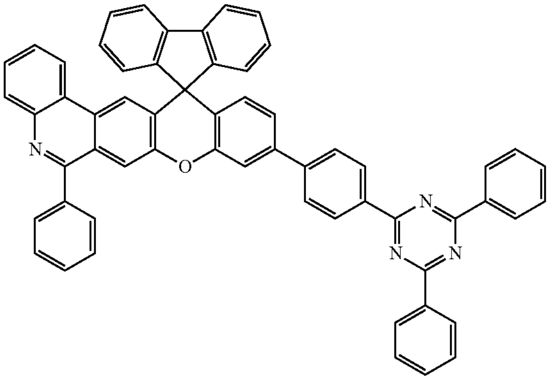
495
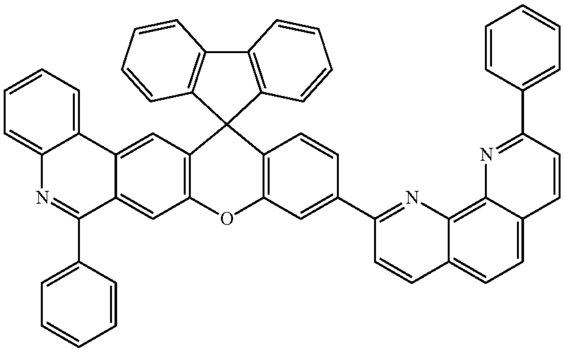
496
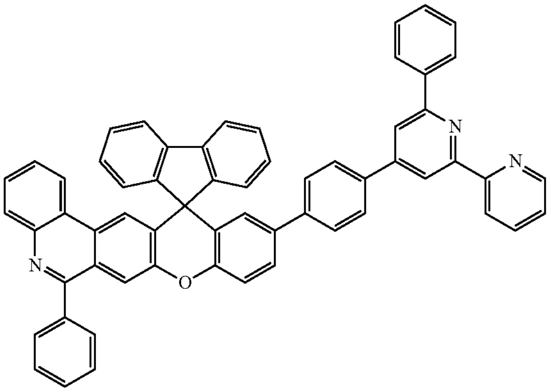
497
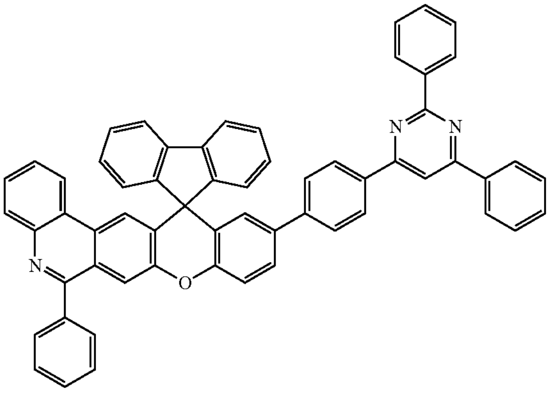
-continued
498
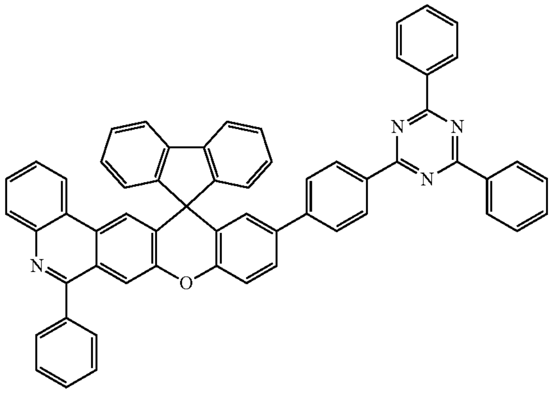
499
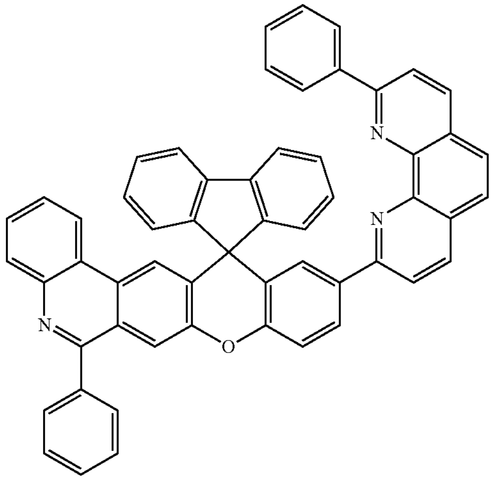
500
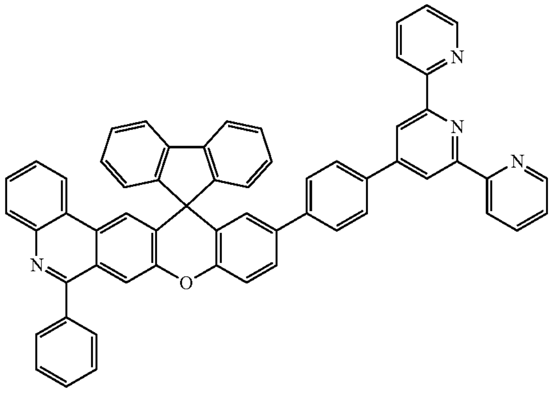

-continued
501
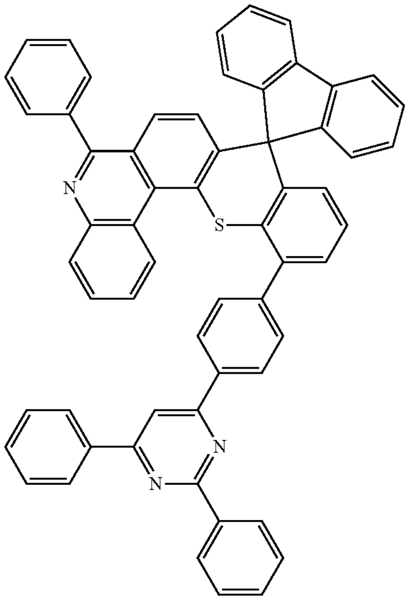
502
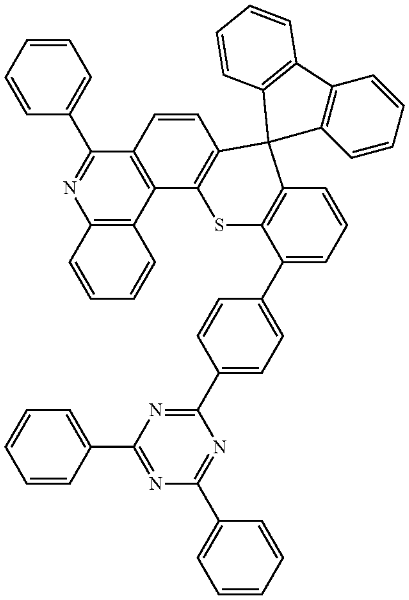
-continued
503
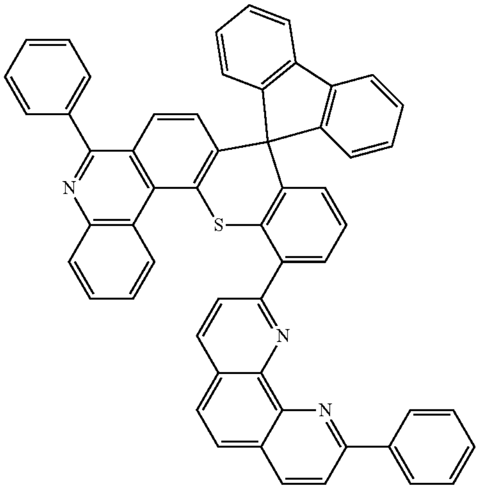
504
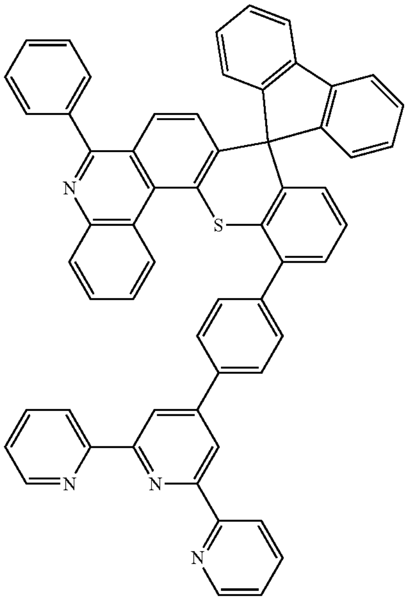

-continued
505
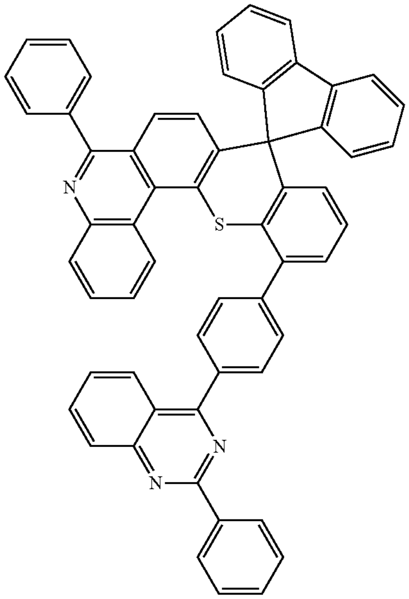
506
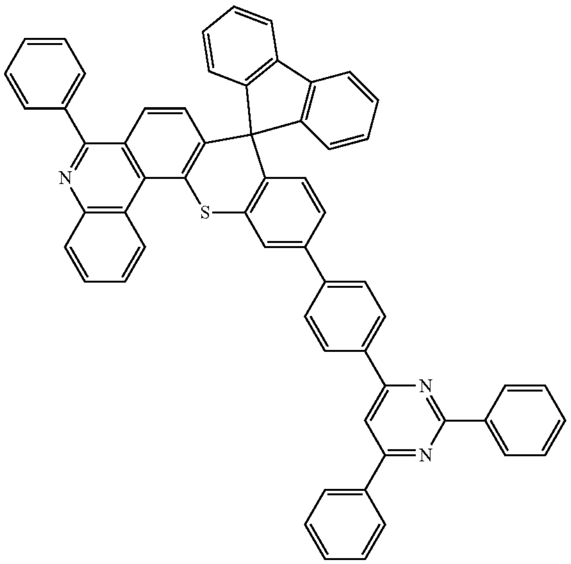
-continued
507
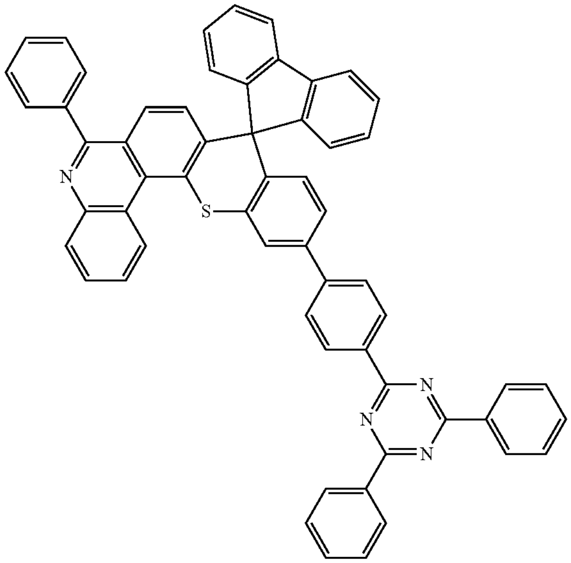
508
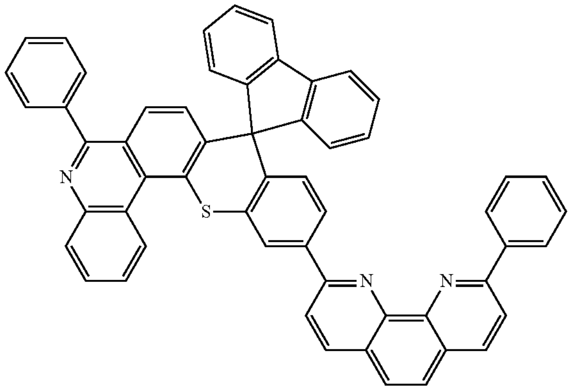
509
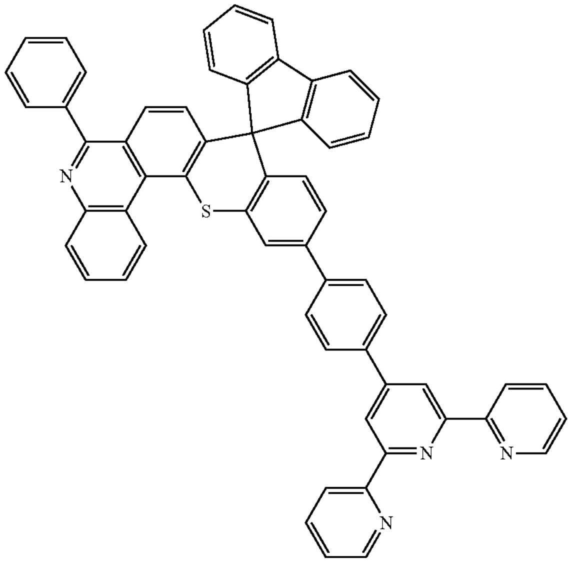

-continued
510
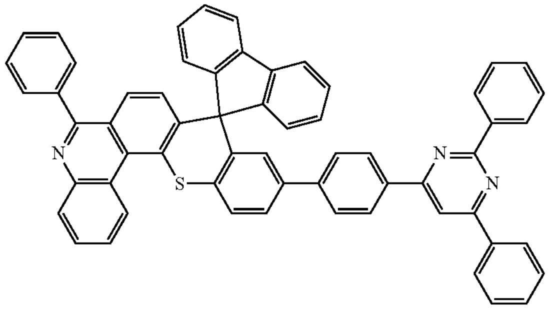
511
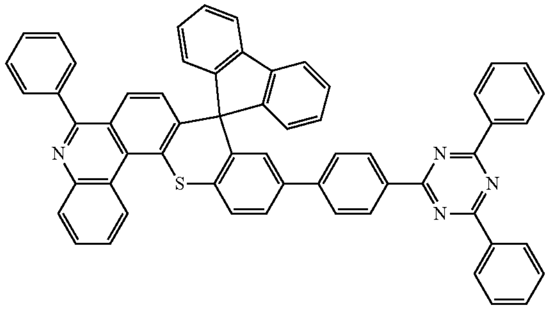
512
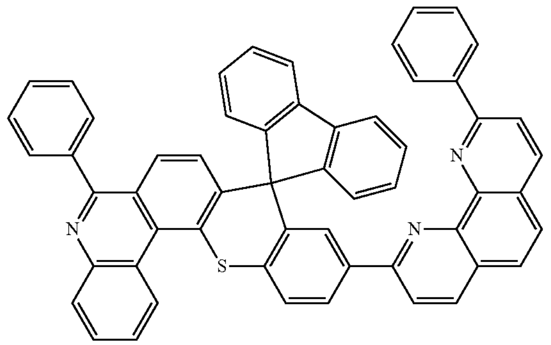
513
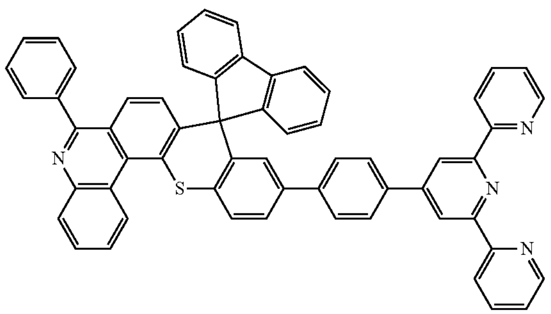
-continued
514
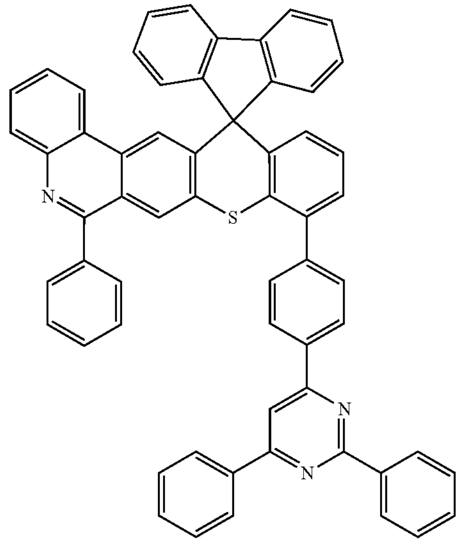
515
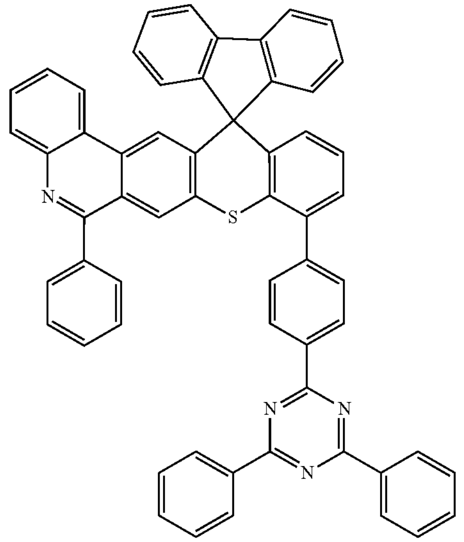
516
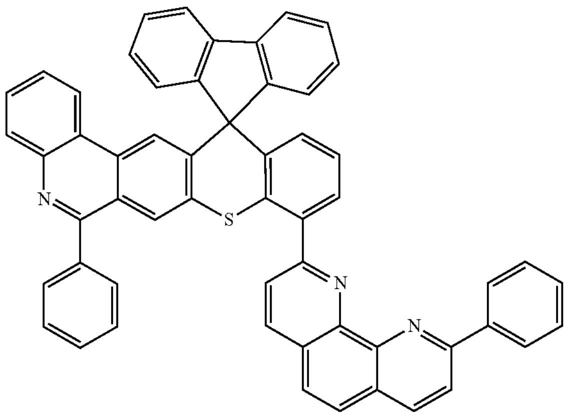

-continued
517
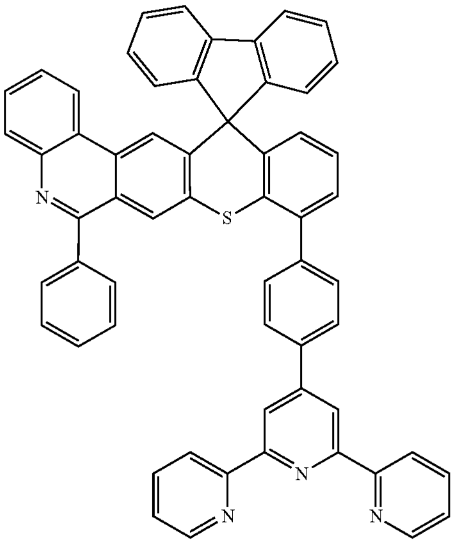
518
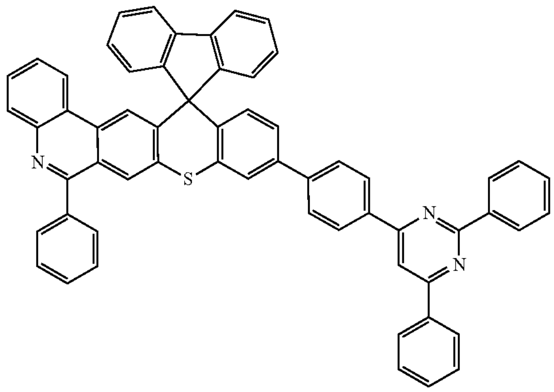
519
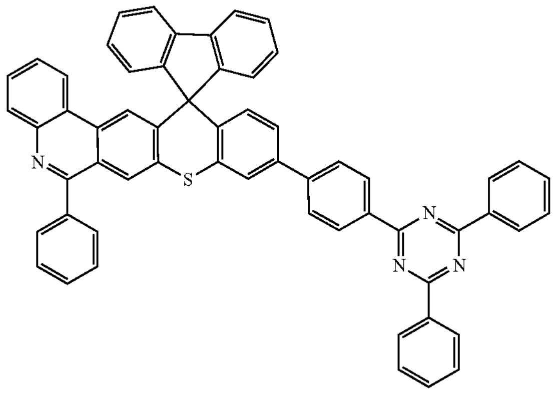
-continued
520
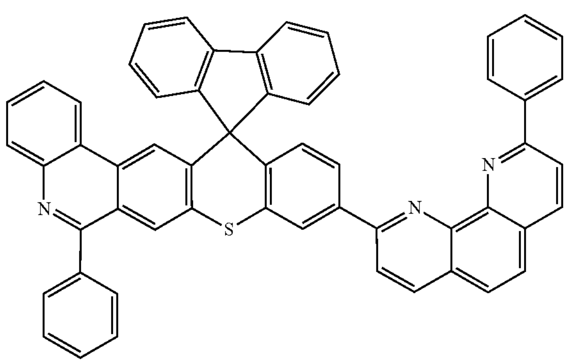
521
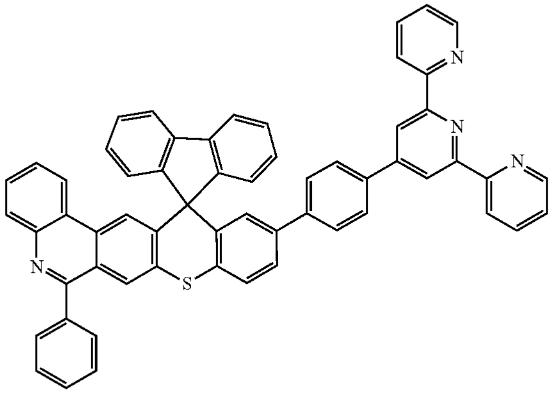
522
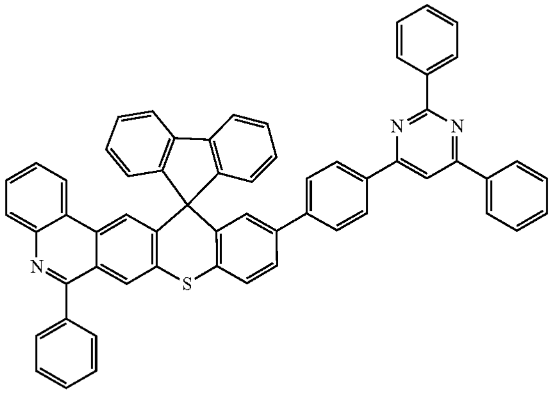
523
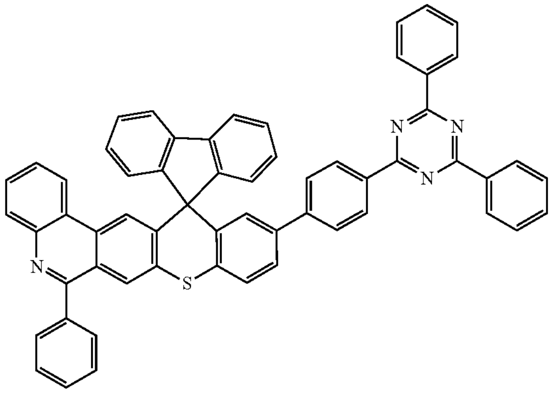

-continued
524
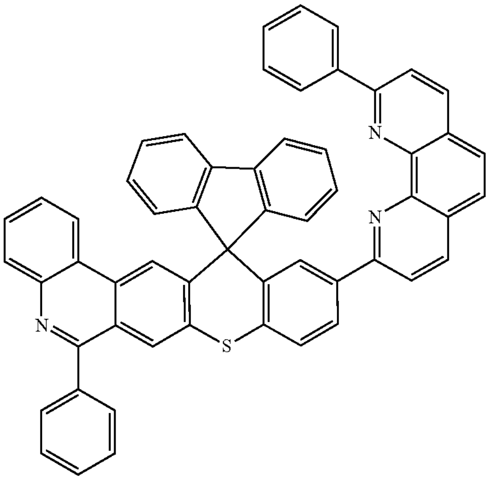
525
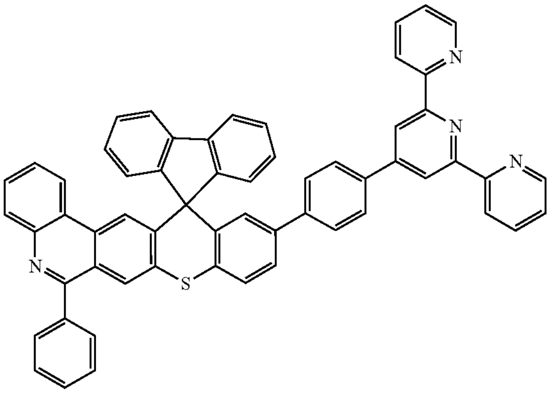
526
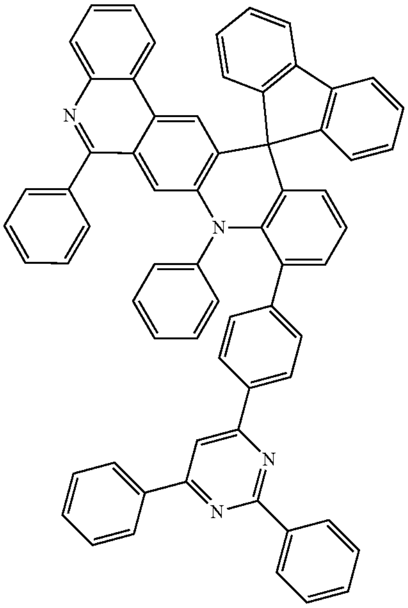
-continued
527
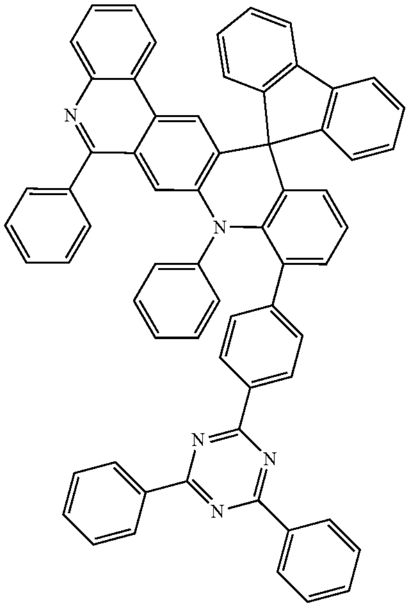
528
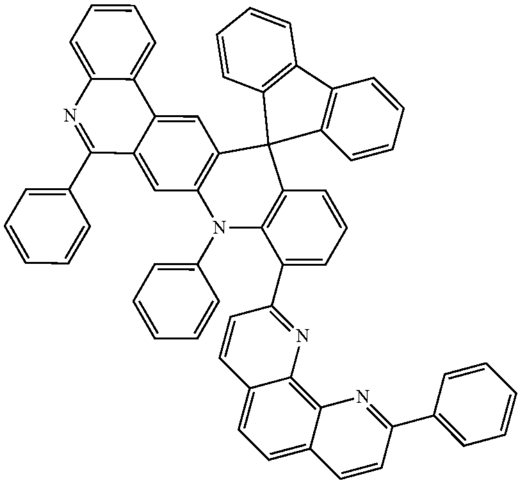

-continued
529
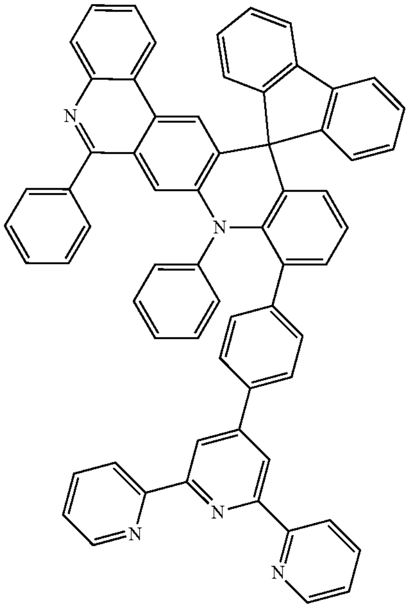
530
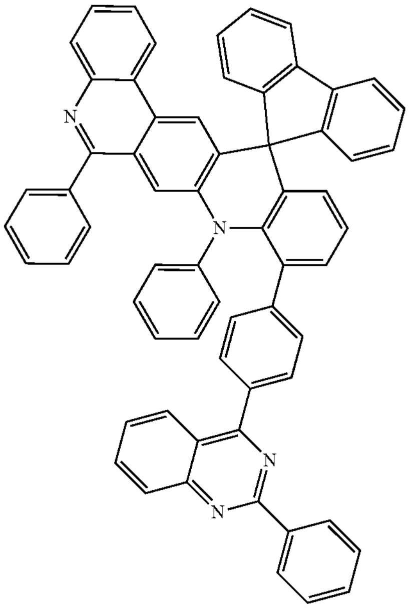
-continued
531
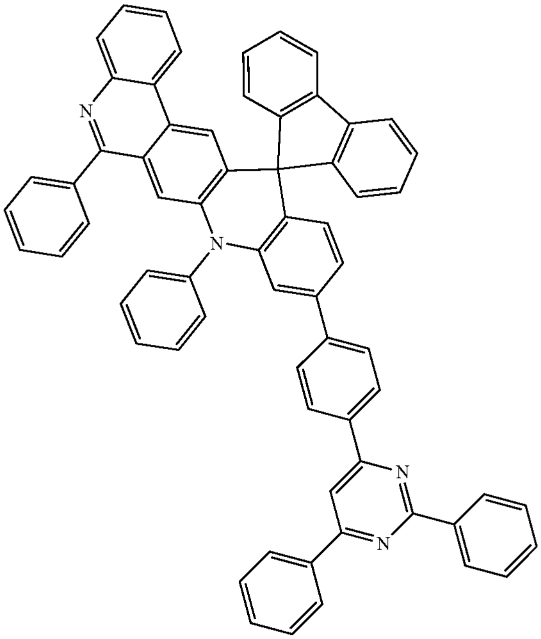
532
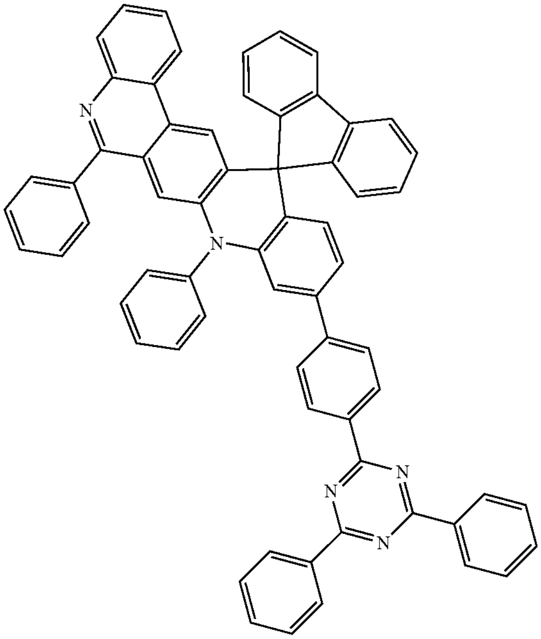

-continued
533
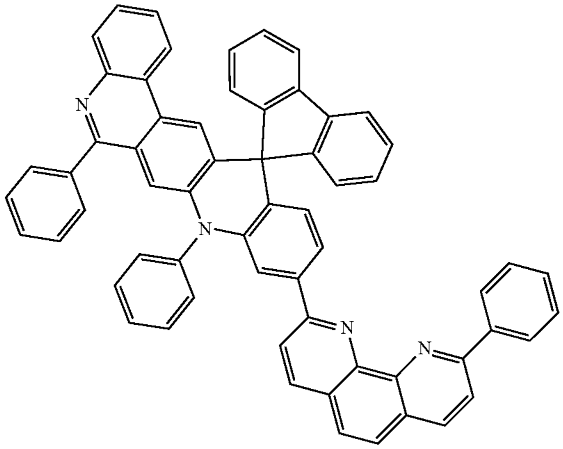
534
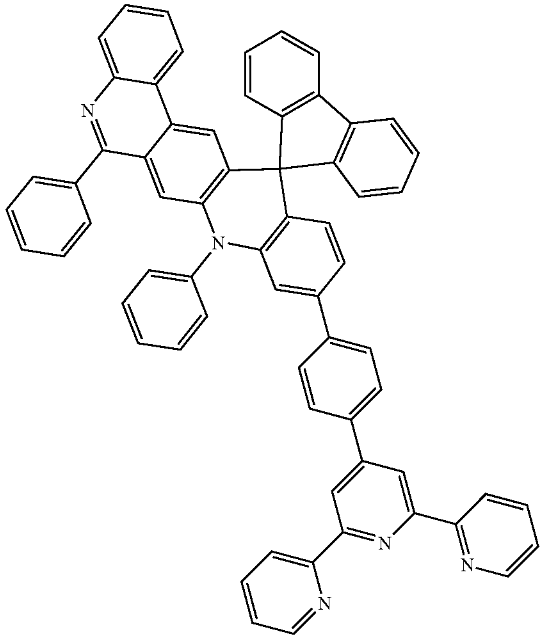
-continued
535
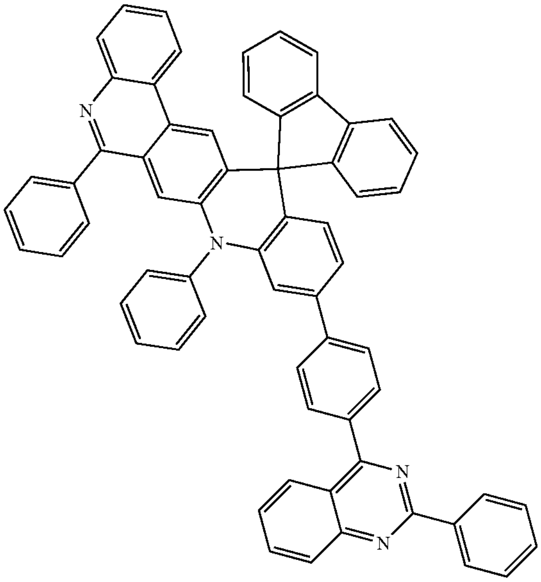
536
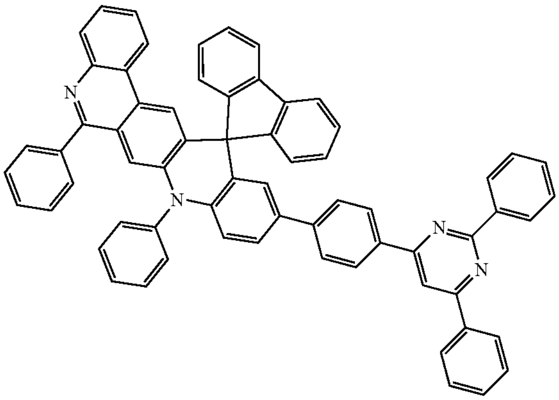
537
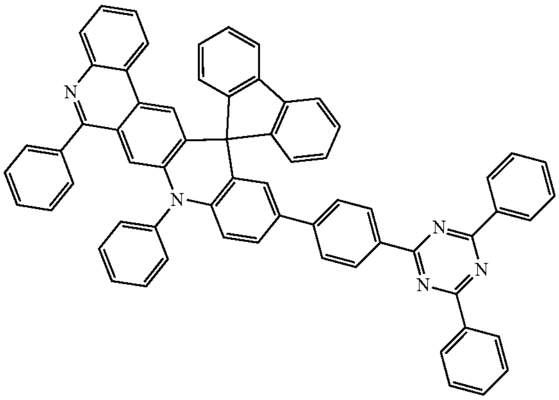

-continued
538
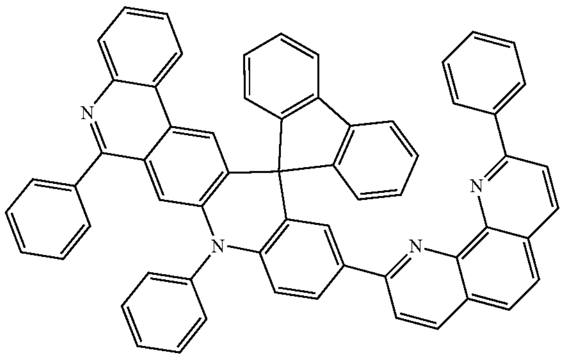
539
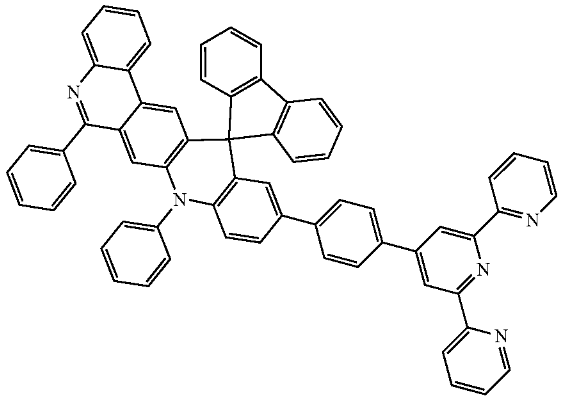
540
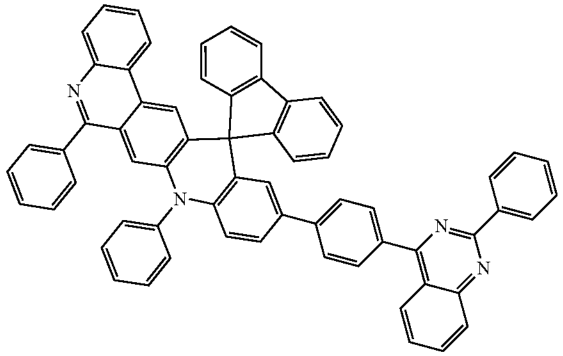
541
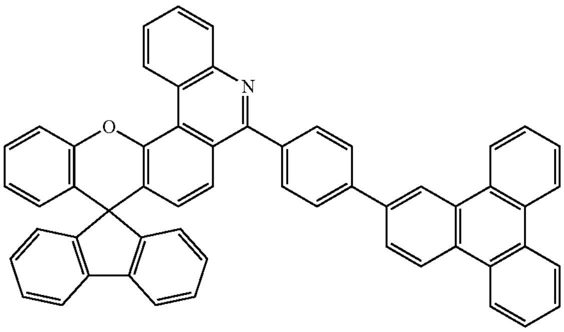
-continued
542
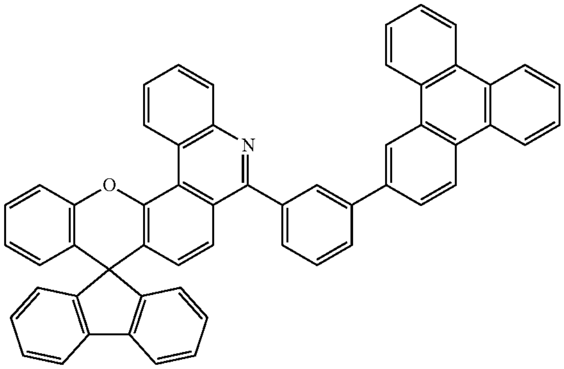
543
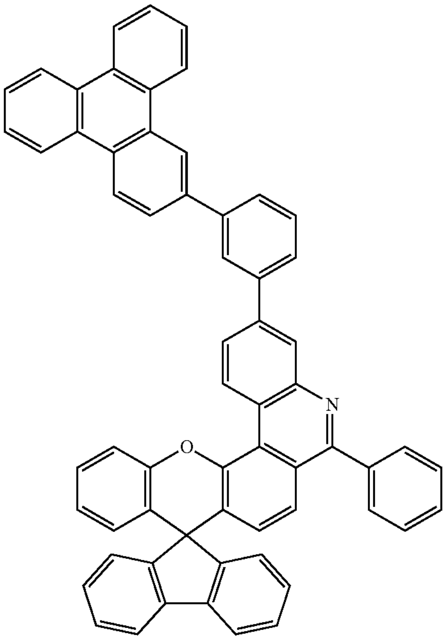
544
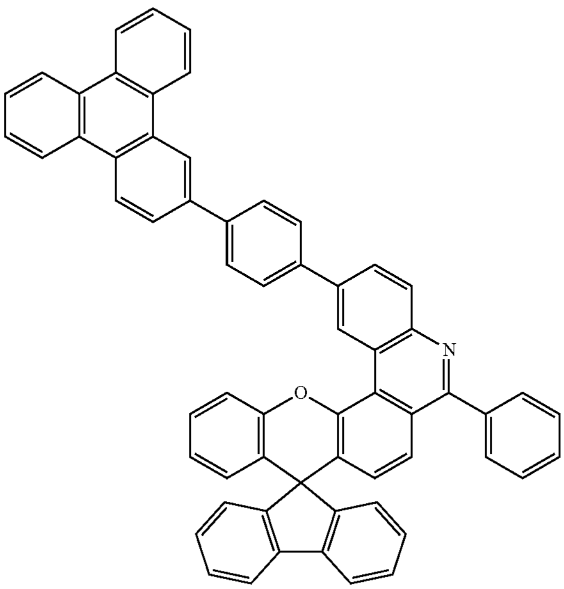

-continued
545
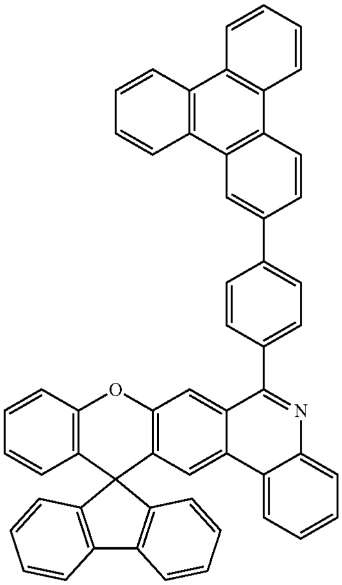
546
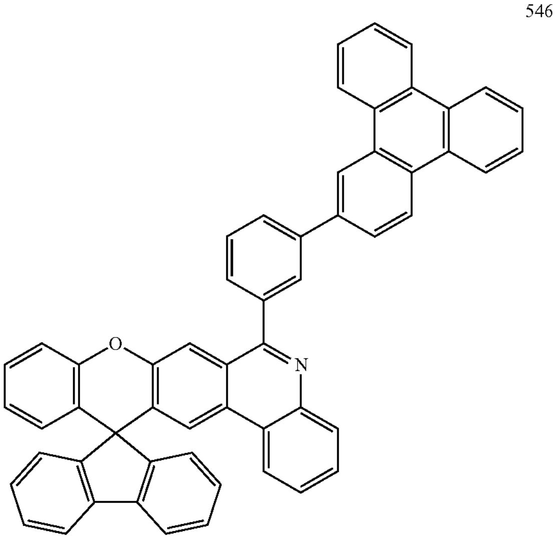
547
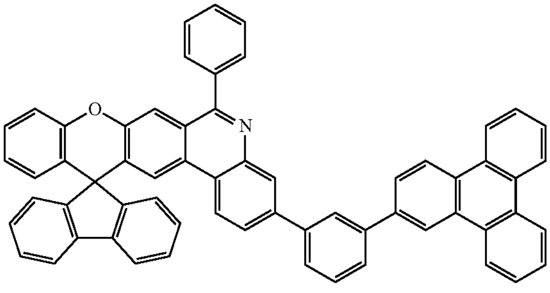
-continued
548
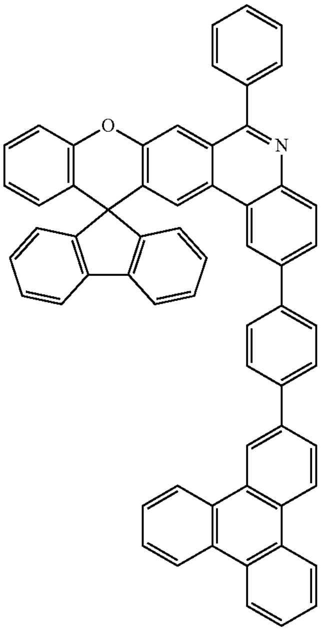
549
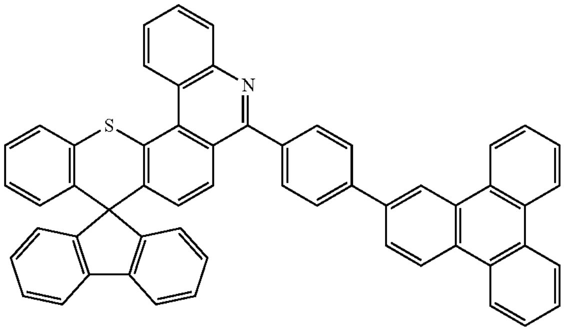
550
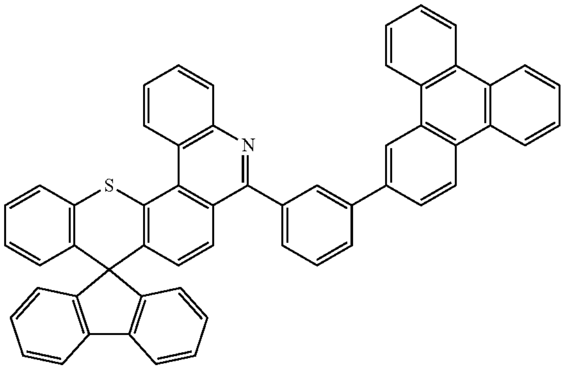

-continued

551

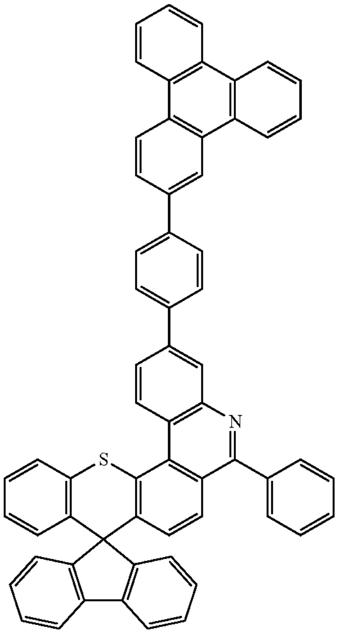

552

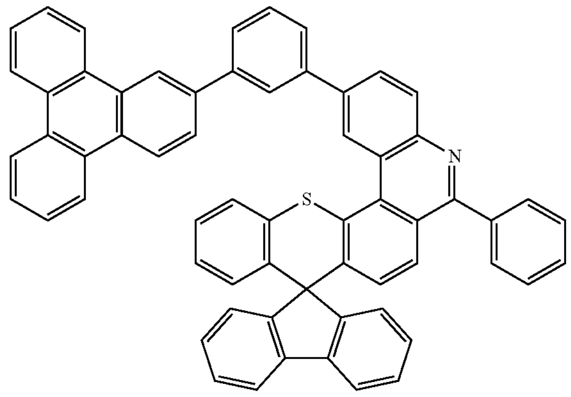

553

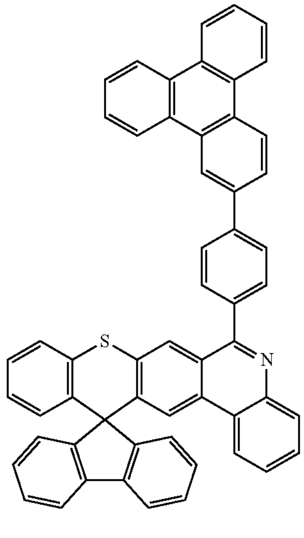

-continued

554

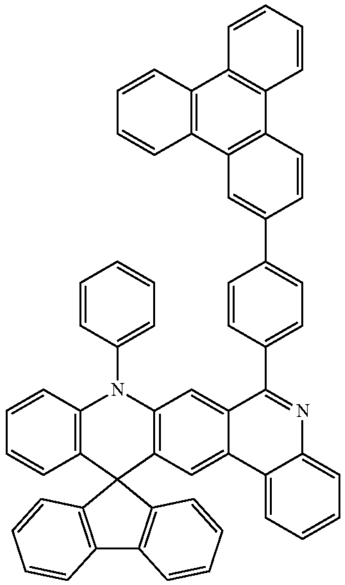

555

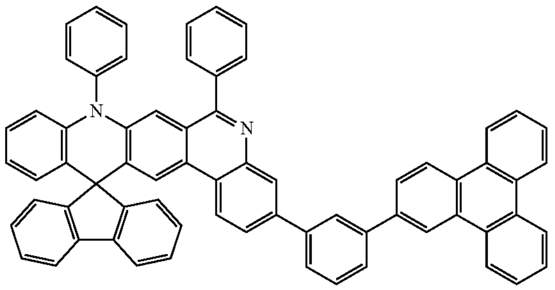

In addition, by introducing various substituents to the structure of Chemical Formula 1, compounds having unique properties of the introduced substituents may be synthesized. For example, by introducing substituents normally used as hole injection layer materials, hole transfer layer materials, light emitting layer materials, electron transfer layer materials and charge generation layer materials used for manufacturing an organic light emitting device to the core structure, materials satisfying conditions required for each organic material layer may be synthesized.

In addition, by introducing various substituents to the structure of Chemical Formula 1, the energy band gap may be finely controlled, and meanwhile, properties at interfaces between organic materials are enhanced, and material applications may become diverse.

Another embodiment of the present specification provides an organic light emitting device comprising a first electrode; a second electrode; and one or more organic material layers provided between the first electrode and the second electrode, wherein one or more layers of the organic material layers comprise the heterocyclic compound represented by Chemical Formula 1.

In one embodiment of the present specification, the first electrode may be an anode, and the second electrode may be a cathode.

In another embodiment of the present specification, the first electrode may be a cathode, and the second electrode may be an anode.

In one embodiment of the present specification, the organic light emitting device may be a blue organic light emitting device, and the heterocyclic compound according to Chemical Formula 1 may be used as a material of the blue organic light emitting device.

In another embodiment of the present specification, the organic light emitting device may be a green organic light emitting device, and the heterocyclic compound according to Chemical Formula 1 may be used as a material of the green organic light emitting device.

In another embodiment of the present specification, the organic light emitting device may be a red organic light emitting device, and the heterocyclic compound according to Chemical Formula 1 may be used as a material of the red organic light emitting device.

Specific details on the heterocyclic compound represented by Chemical Formula 1 are the same as the descriptions provided above.

The organic light emitting device of the present specification may be manufactured using common organic light emitting device manufacturing methods and materials except that one or more organic material layers are formed using the heterocyclic compound described above.

The heterocyclic compound may be formed into an organic material layer through a solution coating method as well as a vacuum deposition method when manufacturing the organic light emitting device. Herein, the solution coating method means spin coating, dip coating, inkjet printing, screen printing, a spray method, roll coating and the like, but is not limited thereto.

The organic material layer of the organic light emitting device of the present specification may be formed in a single layer structure, or may also be formed in a multilayer structure in which two or more organic material layers are laminated. For example, the organic light emitting device according to one embodiment of the present disclosure may have a structure comprising a hole injection layer, a hole transfer layer, a light emitting layer, an electron transfer layer, an electron injection layer and the like as the organic material layer. However, the structure of the organic light emitting device is not limited thereto, and may comprise a smaller number of organic material layers.

In the organic light emitting device of the present specification, the organic material layer comprises an electron transfer layer, and the electron transfer layer may comprise the heterocyclic compound.

In another organic light emitting device of the present specification, the organic material layer comprises a hole blocking layer, and the hole blocking layer may comprise the heterocyclic compound.

The organic light emitting device of the present disclosure may further comprise one, two or more layers selected from the group consisting of a light emitting layer, a hole injection layer, a hole transfer layer, an electron injection layer, an electron transfer layer, an electron blocking layer and a hole blocking layer.

FIGS. 1 to 3 illustrate a lamination order of electrodes and organic material layers of an organic light emitting device according to one embodiment of the present specification. However, the scope of the present application is not limited to these diagrams, and structures of organic light emitting devices known in the art may also be used in the present application.

FIG. 1 illustrates an organic light emitting device in which an anode (200), an organic material layer (300) and a cathode (400) are consecutively laminated on a substrate (100). However, the structure is not limited to such a structure, and as illustrated in FIG. 2, an organic light emitting device in which a cathode, an organic material layer and an anode are consecutively laminated on a substrate may also be obtained.

FIG. 3 illustrates a case of the organic material layer being a multilayer. The organic light emitting device according to FIG. 3 comprises a hole injection layer (301), a hole transfer layer (302), a light emitting layer (303), a hole blocking layer (304), an electron transfer layer (305) and an electron injection layer (306). However, the scope of the present application is not limited to such a lamination structure, and as necessary, other layers except the light emitting layer may not be included, and other necessary functional layers may be further included.

The organic material layer comprising the compound represented by Chemical Formula 1 may further comprise other materials as necessary.

In addition, the organic light emitting device according to one embodiment of the present specification comprises an anode, a cathode, and two or more stacks provided between the anode and the cathode, and the two or more stacks each independently comprise a light emitting layer, a charge generation layer is included between the two or more stacks, and the charge generation layer comprises the heterocyclic compound represented by Chemical Formula 1.

In addition, the organic light emitting device according to one embodiment of the present specification comprises an anode, a first stack provided on the anode and comprising a first light emitting layer, a charge generation layer provided on the first stack, a second stack provided on the charge generation layer and comprising a second light emitting layer, and a cathode provided on the second stack. Herein, the charge generation layer may comprise the heterocyclic compound represented by Chemical Formula 1. In addition, the first stack and the second stack may each independently further comprise one or more types of the hole injection layer, the hole transfer layer, the hole blocking layer, the electron transfer layer, the electron injection layer and the like described above.

The charge generation layer may be an N-type charge generation layer, and the charge generation layer may further comprise a dopant known in the art in addition to the heterocyclic compound represented by Chemical Formula 1.

As the organic light emitting device according to one embodiment of the present specification, an organic light emitting device having a 2-stack tandem structure is illustrated in FIG. 4.

Herein, the first electron blocking layer, the first hole blocking layer, the second hole blocking layer and the like described in FIG. 4 may not be included in some cases.

In the organic light emitting device according to one embodiment of the present specification, materials other than the compound of Chemical Formula 1 are illustrated below, however, these are for illustrative purposes only and not for limiting the scope of the present application, and may be replaced by materials known in the art.

As the anode material, materials having relatively large work function may be used, and transparent conductive oxides, metals, conductive polymers or the like may be used. Specific examples of the anode material comprise metals such as vanadium, chromium, copper, zinc and gold, or alloys thereof; metal oxides such as zinc oxide, indium oxide, indium tin oxide (ITO) and indium zinc oxide (IZO); combinations of metals and oxides such as ZnO:Al or $SnO_2$:Sb; conductive polymers such as poly(3-methylthiophene), poly[3,4-(ethylene-1,2-dioxy)thiophene] (PEDOT), polypyrrole and polyaniline, and the like, but are not limited thereto.

As the cathode material, materials having relatively small work function may be used, and metals, metal oxides, conductive polymers or the like may be used. Specific examples of the cathode material comprise metals such as magnesium, calcium, sodium, potassium, titanium, indium, yttrium, lithium, gadolinium, aluminum, silver, tin and lead, or alloys thereof; multilayer structure materials such as LiF/Al or $LiO_2$/Al, and the like, but are not limited thereto.

As the hole injection material, known hole injection materials may be used, and for example, phthalocyanine compounds such as copper phthalocyanine disclosed in U.S. Pat. No. 4,356,429, or starburst-type amine derivatives such as tris(4-carbazoyl-9-ylphenyl)amine (TCTA), 4,4', 4"-tri[phenyl(m-tolyl)amino]triphenylamine (m-MTDATA) or 1,3,5-tris[4-(3-methylphenylphenylamino)phenyl]benzene (m-MTDAPB) described in the literature [Advanced Material, 6, p. 677 (1994)], polyaniline/dodecylbenzene sulfonic acid, poly(3,4-ethylenedioxythiophene)/poly(4-styrene-sulfonate), polyaniline/camphor sulfonic acid or polyaniline/poly(4-styrene-sulfonate) that are conductive polymers having solubility, and the like, may be used.

As the hole transfer material, pyrazoline derivatives, arylamine-based derivatives, stilbene derivatives, triphenyldiamine derivatives and the like may be used, and low molecular or high molecular materials may also be used.

As the electron transfer material, metal complexes of oxadiazole derivatives, anthraquinodimethane and derivatives thereof, benzoquinone and derivatives thereof, naphthoquinone and derivatives thereof, anthraquinone and derivatives thereof, tetracyanoanthraquinodimethane and derivatives thereof, fluorenone derivatives, diphenyldicyanoethylene and derivatives thereof, diphenoquinone derivatives, 8-hydroxyquinoline and derivatives thereof, and the like, may be used, and high molecular materials may also be used as well as low molecular materials.

As examples of the electron injection material, LiF is typically used in the art, however, the present application is not limited thereto.

As the light emitting material, red, green or blue light emitting materials may be used, and as necessary, two or more light emitting materials may be mixed and used. Herein, two or more light emitting materials may be used by being deposited as individual sources of supply or by being premixed and deposited as one source of supply. In addition, fluorescent materials may also be used as the light emitting material, however, phosphorescent materials may also be used. As the light emitting material, materials emitting light by bonding electrons and holes injected from an anode and a cathode, respectively, may be used alone, however, materials having a host material and a dopant material involving in light emission together may also be used.

When mixing light emitting material hosts, same series hosts may be mixed, or different series hosts may be mixed. For example, any two or more types of materials among n-type host materials or p-type host materials may be selected, and used as a host material of a light emitting layer.

The organic light emitting device according to one embodiment of the present specification may be a top-emission type, a bottom-emission type or a dual-emission type depending on the materials used.

The heterocyclic compound according to one embodiment of the present specification may also be used in an organic electronic device comprising an organic solar cell, an organic photo conductor, an organic transistor and the like under a similar principle used in the organic light emitting device.

Hereinafter, the present specification will be described in more detail with reference to examples, however, these are for illustrative purposes only, and the scope of the present application is not limited thereto.

Preparation Example

<Preparation Example 1> Preparation of Intermediates A and B

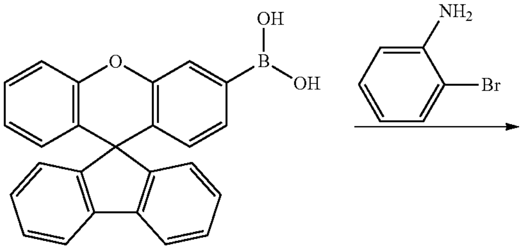

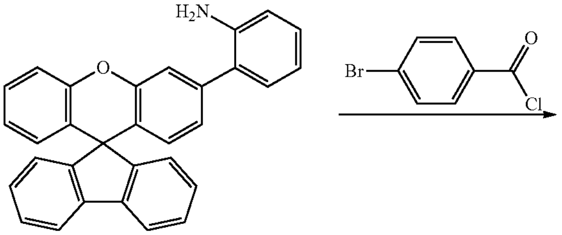

A-2

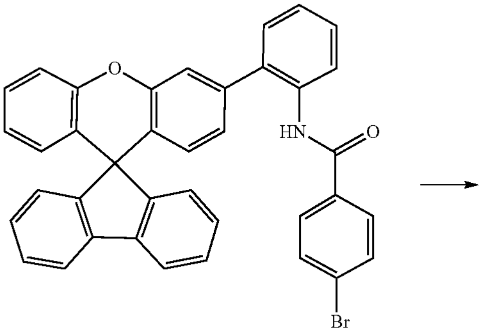

A-1

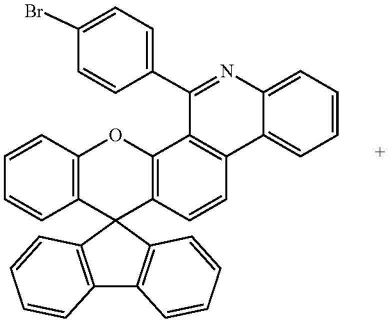

A

-continued

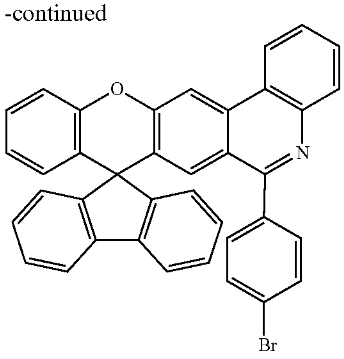

B

1) Preparation of Intermediate A-2

After dissolving spiro[fluorene-9,9'-xanthen]-3'-ylboronic acid (50 g, 132.90 mmol) and 2-bromoaniline (25.15 g, 146.19 mmol) in dioxane/water ($H_2O$) (500 ml/100 ml), $Pd(PPh_3)_4$ (7.68 g, 6.65 mmol) and $NaHCO_3$ (33.50 g, 398.71 mmol) were introduced thereto, and the result was stirred for 15 hours under reflux. After the reaction was completed, methylene chloride (MC) was introduced to dissolve the reaction solution, and then the result was extracted with distilled water. The organic layer was dried with anhydrous $MgSO_4$, and, after removing the solvent using a rotary evaporator, purified with column chromatography using dichloromethane and hexane as a developing solvent to obtain Intermediate A-2 (41 g, yield: 72%).

2) Preparation of Intermediate A-1

After dissolving Intermediate A-2 (41 g, 96.81 mmol) in methylene chloride (MC) (500 ml), TEA (29.39 g, 290.44 mmol) was introduced thereto. The temperature was lowered from room temperature to 0° C., and 4-bromobenzoyl chloride (23.37 g, 106.49 mmol) dissolved in methylene chloride (MC) was slowly added dropwise thereto. After the reaction was completed, the result was extracted with methylene chloride (MC) and distilled water. The organic layer was dried with anhydrous $MgSO_4$, and, after removing the solvent using a rotary evaporator, purified with column chromatography using dichloromethane and hexane as a developing solvent to obtain Intermediate A-1 (52 g, yield: 88%).

3) Preparation of Intermediates A and B

After dissolving Intermediate A-1 (52 g, 85.74 mmol) in nitrobenzene (500 ml), $POCl_3$ (14.46 g, 94.31 mmol) was slowly added dropwise thereto, and the result was stirred for 4 hours at 150° C. After the reaction was completed, the result was neutralized with an aqueous $NaHCO_3$ solution, and then extracted with methylene chloride (MC) and distilled water. The organic layer was dried with anhydrous $MgSO_4$, and, after removing the solvent using a rotary evaporator, purified with column chromatography using dichloromethane and hexane as a developing solvent to obtain Intermediate A (18 g, yield: 35%) and Intermediate B (20 g, yield: 39%).

<Preparation Example 2> Preparation of Compound 1

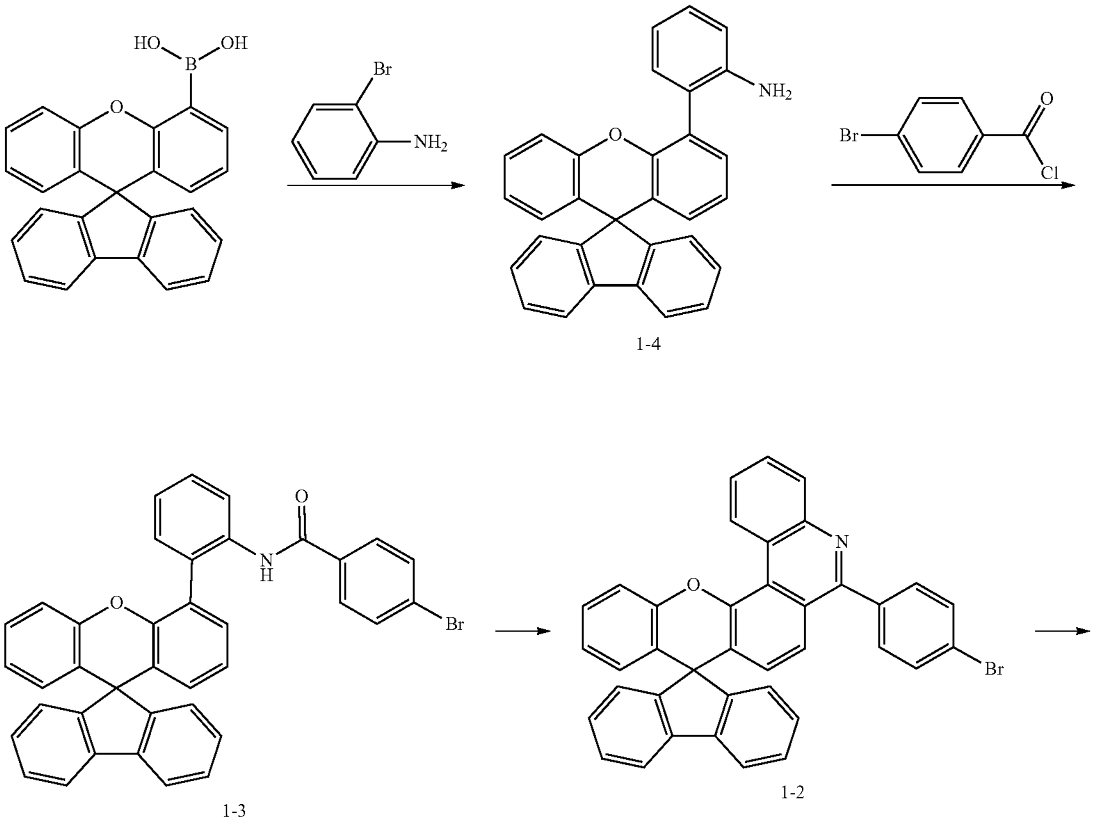

1-4

1-3

1-2

-continued

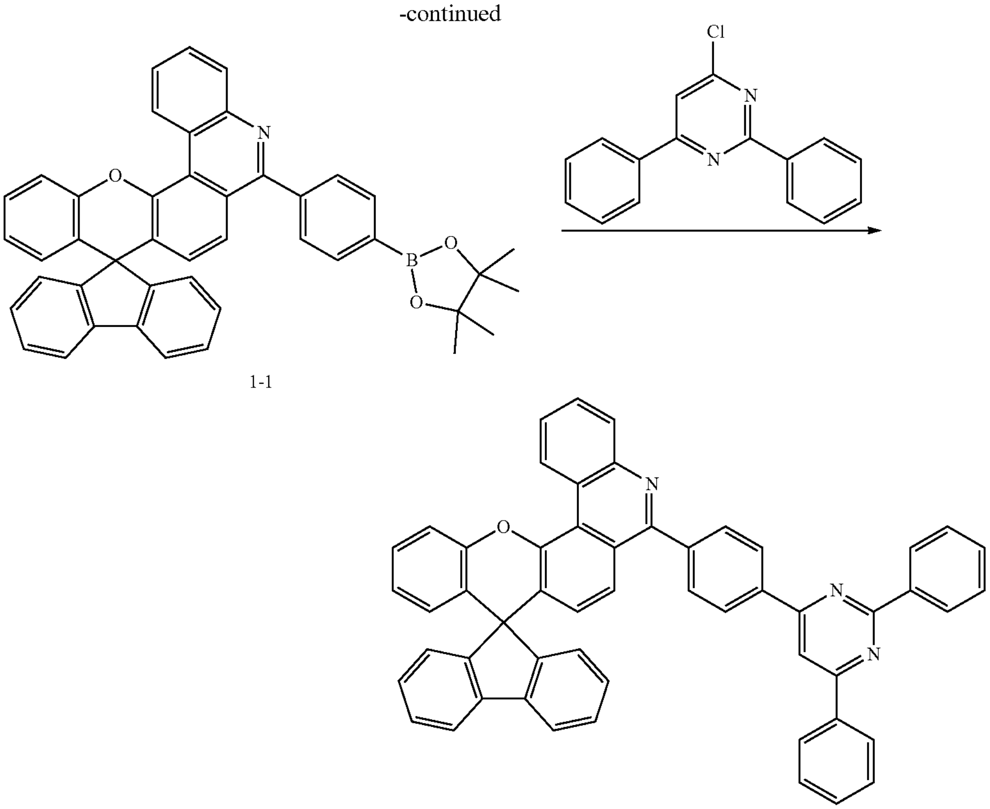

1-1

1

1) Preparation of Compound 1-4

After dissolving spiro[fluorene-9,9'-xanthen]-4'-ylboronic acid (50 g, 132.90 mmol) and 2-bromoaniline (25.15 g, 146.19 mmol) in dioxane/water ($H_2O$) (500 ml/100 ml), $Pd(PPh_3)_4$ (7.68 g, 6.65 mmol) and $NaHCO_3$ (33.50 g, 398.71 mmol) were introduced thereto, and the result was stirred for 15 hours under reflux. After the reaction was completed, methylene chloride (MC) was introduced to dissolve the reaction solution, and then the result was extracted with distilled water. The organic layer was dried with anhydrous $MgSO_4$, and, after removing the solvent using a rotary evaporator, purified with column chromatography using dichloromethane and hexane as a developing solvent to obtain Compound 1-4 (41 g, yield: 72%).

2) Preparation of Compound 1-3

After dissolving Compound 1-4 (41 g, 96.81 mmol) in methylene chloride (MC) (500 ml), TEA (29.39 g, 290.44 mmol) was introduced thereto. The temperature was lowered from room temperature to 0° C., and 4-bromobenzoyl chloride (23.37 g, 106.49 mmol) dissolved in methylene chloride (MC) was slowly added dropwise thereto. After the reaction was completed, the result was extracted with methylene chloride (MC) and distilled water. The organic layer was dried with anhydrous $MgSO_4$, and, after removing the solvent using a rotary evaporator, purified with column chromatography using dichloromethane and hexane as a developing solvent to obtain Compound 1-3 (52 g, yield: 88%).

3) Preparation of Compound 1-2

After dissolving Compound 1-3 (52 g, 85.74 mmol) in nitrobenzene (500 ml), $POCl_3$ (14.46 g, 94.31 mmol) was slowly added dropwise thereto, and the result was stirred for 4 hours at 150° C. After the reaction was completed, the result was neutralized with an aqueous $NaHCO_3$ solution, and then extracted with methylene chloride (MC) and distilled water. The organic layer was dried with anhydrous $MgSO_4$, and, after removing the solvent using a rotary evaporator, purified with column chromatography using dichloromethane and hexane as a developing solvent to obtain Compound 1-2 (43 g, yield: 85%).

4) Preparation of Compound 1-1

After dissolving Compound 1-2 (43 g, 73.07 mmol) and bis(pinacolato)diboron (27.83 g, 109.60 mmol) in 1,4-dioxane (400 ml), $Pd(dppf)Cl_2$ (2.14 g, 2.92 mmol) and KOAc (21.51 g, 219.21 mmol) were introduced thereto, and the result was stirred for 5 hours under reflux. After the reaction was completed, the result was extracted with methylene chloride (MC) and water. The organic layer was dried with anhydrous $MgSO_4$, and then silica gel filtered. The result was precipitated using methylene chloride (MC)/methanol (MeOH), and then filtered to obtained Compound 1-1 (42 g, yield: 90%).

5) Preparation of Compound 1

After dissolving Compound 1-1 (10 g, 15.73 mmol) and 4-chloro-2,6-diphenylpyrimidine (4.41 g, 16.52 mmol) in toluene/ethanol/water (100 ml/20 ml/20 ml), $Pd(PPh_3)_4$(0.91 g, 0.79 mmol) and $K_3PO_4$ (10.02 g, 47.20 mmol) were introduced thereto, and the result was stirred for 5 hours under reflux. After the reaction was completed, the result was cooled to room temperature, and produced solids were filtered and then washed with ethyl acetate (EA) and methanol (MeOH). After that, the solids were all dissolved in an excess amount of dichloromethane, and then silica gel filtered to obtain Compound 1 (9 g, yield: 77%).

<Preparation Example 3> Syntheses of Target Compounds

Target compounds were synthesized in the same manner as in Preparation Example 1 except that Intermediate C of the following Table 1 was used instead of spiro[fluorene-9, 9'-xanthen]-4'-ylboronic acid, Intermediate D of the following Table 1 was used instead of 2-bromoaniline, Intermediate E of the following Table 1 was used instead of 4-bromobenzoyl chloride, and Intermediate F of the following Table 1 was used instead of 4-chloro-2,6-diphenylpyrimidine.

TABLE 1

| Compound | Intermediate C | Intermediate D | Intermediate E | Intermediate F |
|---|---|---|---|---|
| 6 | 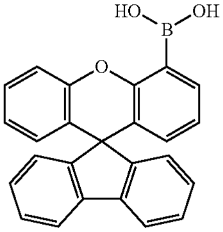 | 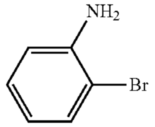 | 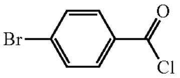 | 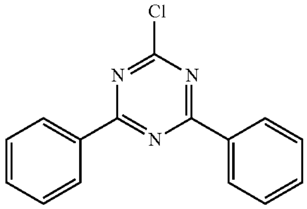 [SMILES: Clc1nc(-c2ccccc2)nc(-c2ccccc2)n1] |
| 11 | 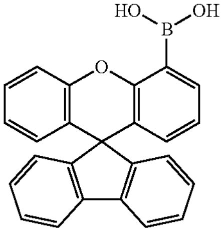 [SMILES: OB(O)c1cccc2c1Oc1ccccc1C21c2ccccc2-c2ccccc21] | 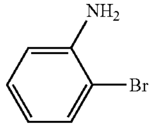 | 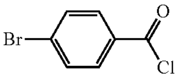 | 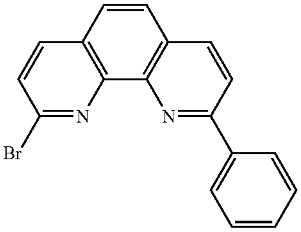 [SMILES: Brc1ccc2ccc3ccc(-c4ccccc4)nc3c2n1] |
| 12 | 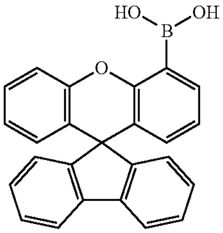 | 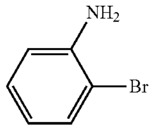 | 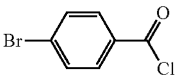 | 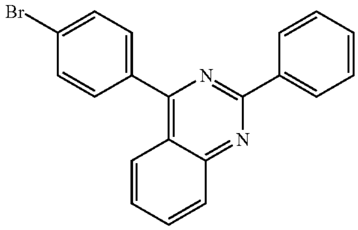 [SMILES: Brc1ccc(-c2nc(-c3ccccc3)nc3ccccc23)cc1] |
| 15 | 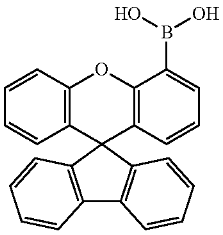 [SMILES: OB(O)c1cccc2c1Oc1ccccc1C21c2ccccc2-c2ccccc21] | 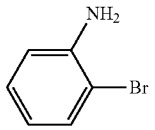 | 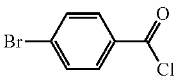 | 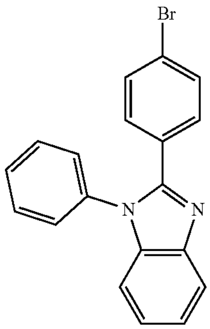 [SMILES: Brc1ccc(-c2nc3ccccc3n2-c2ccccc2)cc1] |

TABLE 1-continued
| | | | | |
|---|---|---|---|---|
| 23 | 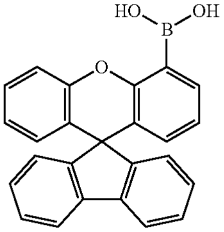 [SMILES: OB(O)c1cccc2c1Oc1ccccc1C21c2ccccc2-c2ccccc21] | 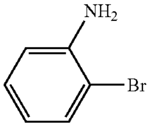 | 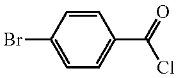 | 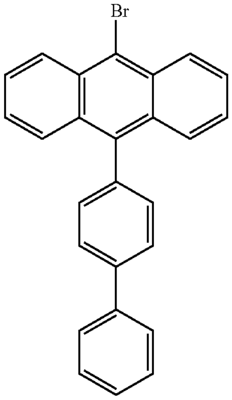 [SMILES: Brc1c2ccccc2c(-c2ccc(-c3ccccc3)cc2)c2ccccc12] |
| 26 | 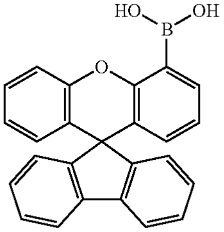 [SMILES: OB(O)c1cccc2c1Oc1ccccc1C21c2ccccc2-c2ccccc21] | 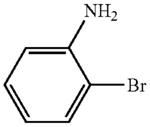 | 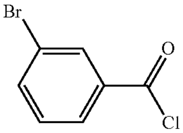 | 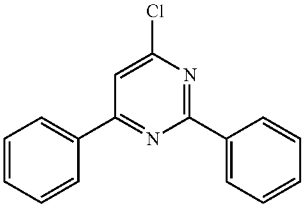 [SMILES: Clc1cc(-c2ccccc2)nc(-c2ccccc2)n1] |
| 31 | 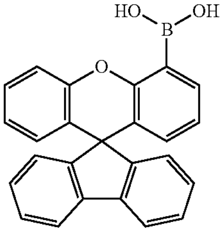 | 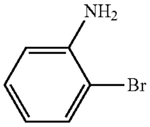 | 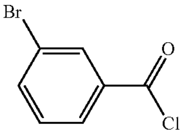 | 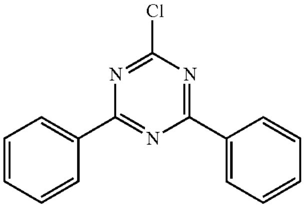 [SMILES: Clc1nc(-c2ccccc2)nc(-c2ccccc2)n1] |
| 36 | 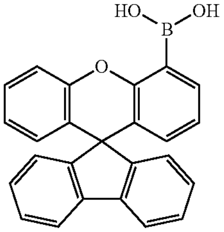 | 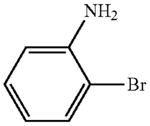 | 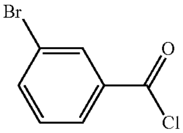 | 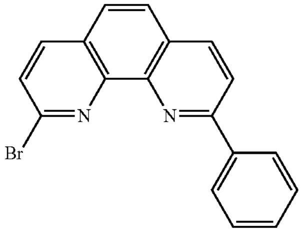 [SMILES: Brc1ccc2ccc3ccc(-c4ccccc4)nc3c2n1] |
| 42 | 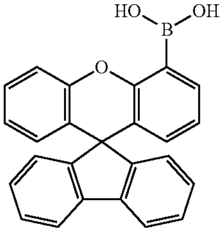 [SMILES: OB(O)c1cccc2c1Oc1ccccc1C21c2ccccc2-c2ccccc21] | 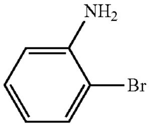 | 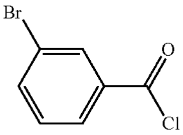 | 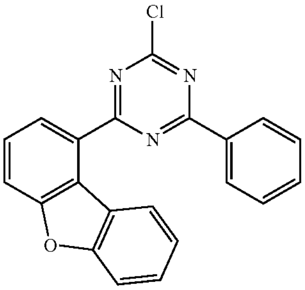 [SMILES: Clc1nc(-c2ccccc2)nc(-c2cccc3oc4ccccc4c23)n1] |

TABLE 1-continued
| | | | | |
|---|---|---|---|---|
| 56 | 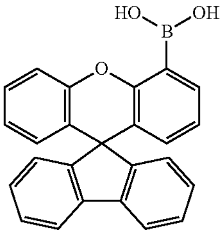 | 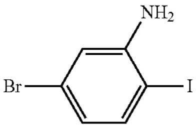 | 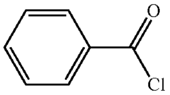 | 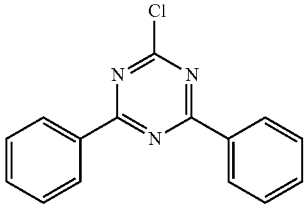 [SMILES: Clc1nc(-c2ccccc2)nc(-c2ccccc2)n1] |
| 62 | 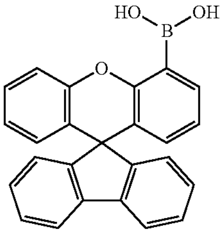 [SMILES: OB(O)c1cccc2c1Oc1ccccc1C21c2ccccc2-c2ccccc21] | 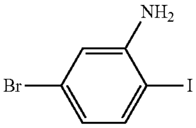 | 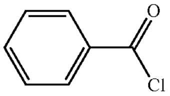 | 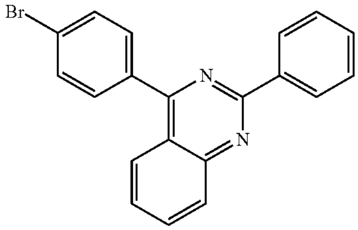 [SMILES: Brc1ccc(-c2nc(-c3ccccc3)nc3ccccc23)cc1] |
| 71 | 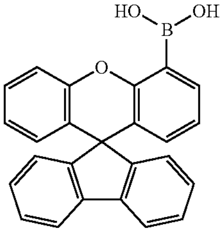 [SMILES: OB(O)c1cccc2c1Oc1ccccc1C21c2ccccc2-c2ccccc21] | 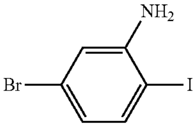 | 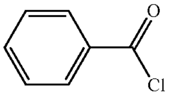 | 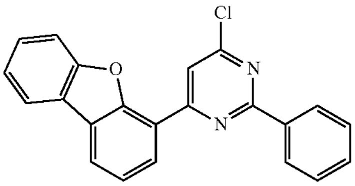 |
| 77 | 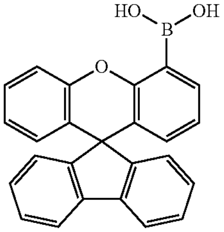 | 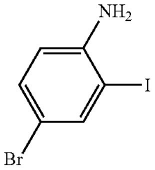 | 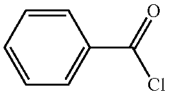 | 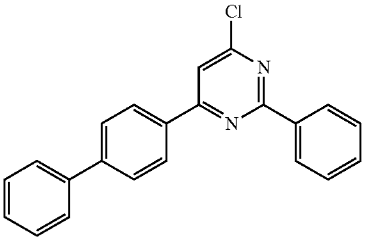 [SMILES: Clc1cc(-c2ccc(-c3ccccc3)cc2)nc(-c2ccccc2)n1] |
| 91 | 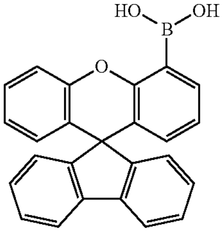 | 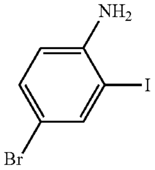 | 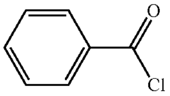 | 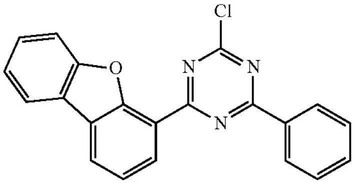 |
| 93 | 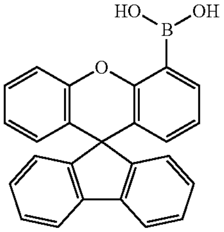 [SMILES: OB(O)c1cccc2c1Oc1ccccc1C21c2ccccc2-c2ccccc21] | 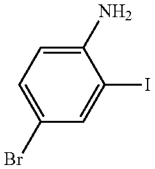 | 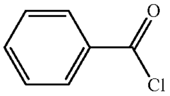 | 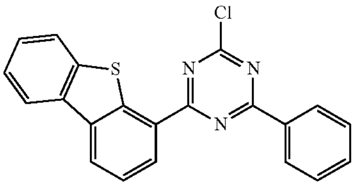 |

TABLE 1-continued
| | | | | |
|---|---|---|---|---|
| 104 | 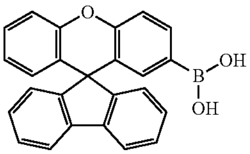 [SMILES: OB(O)c1ccc2c(c1)C1(c3ccccc3O2)c2ccccc2-c2ccccc21] | 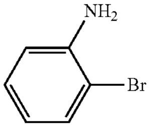 | 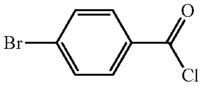 | 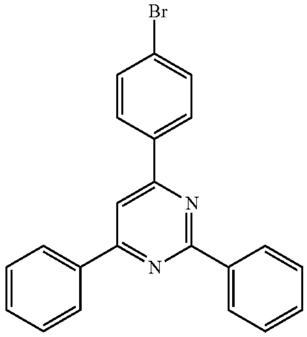 [SMILES: Brc1ccc(-c2cc(-c3ccccc3)nc(-c3ccccc3)n2)cc1] |
| 105 | 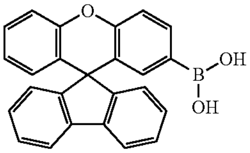 [SMILES: OB(O)c1ccc2c(c1)C1(c3ccccc3O2)c2ccccc2-c2ccccc21] | 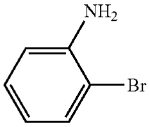 | 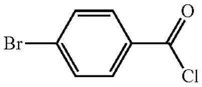 | 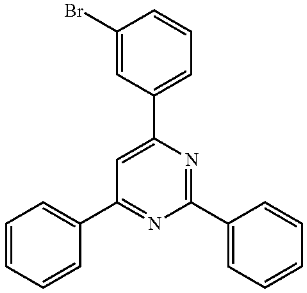 [SMILES: Brc1cccc(-c2cc(-c3ccccc3)nc(-c3ccccc3)n2)c1] |
| 111 | 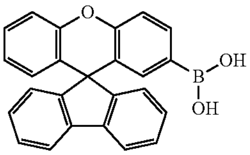 | 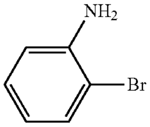 | 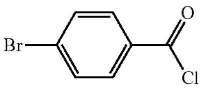 | 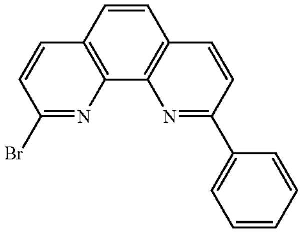 [SMILES: Brc1ccc2ccc3ccc(-c4ccccc4)nc3c2n1] |
| 124 | 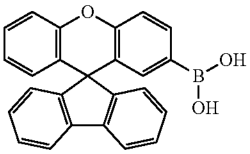 | 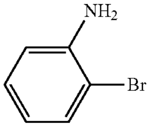 | 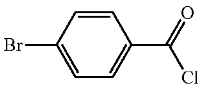 | 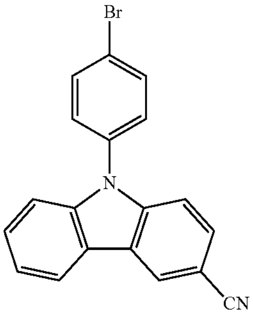 [SMILES: N#Cc1ccc2c(c1)c1ccccc1n2-c1ccc(Br)cc1] |
| 134 | 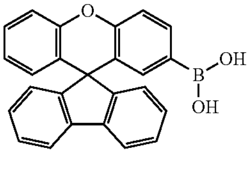 | 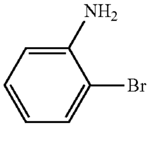 | 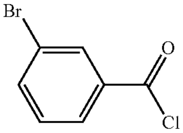 | 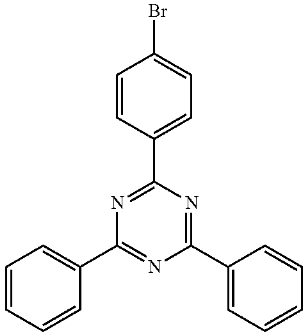 [SMILES: Brc1ccc(-c2nc(-c3ccccc3)nc(-c3ccccc3)n2)cc1] |

TABLE 1-continued
| | | | | |
|---|---|---|---|---|
| 146 | 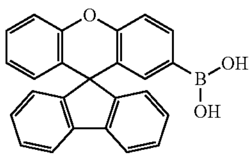 [SMILES: OB(O)c1ccc2c(c1)C1(c3ccccc3O2)c2ccccc2-c2ccccc21] | 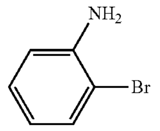 | 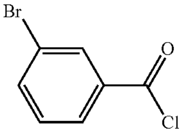 | 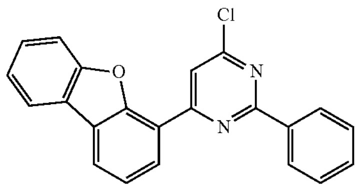 |
| 151 | 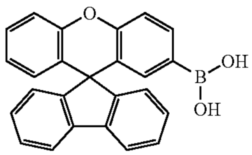 [SMILES: OB(O)c1ccc2c(c1)C1(c3ccccc3O2)c2ccccc2-c2ccccc21] | 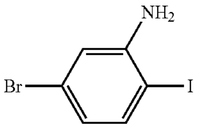 | 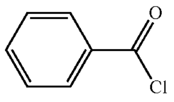 | 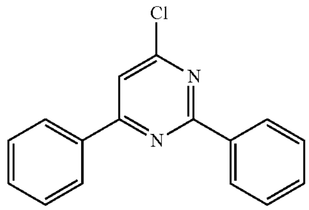 |
| 156 | 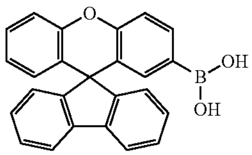 [SMILES: OB(O)c1ccc2c(c1)C1(c3ccccc3O2)c2ccccc2-c2ccccc21] | 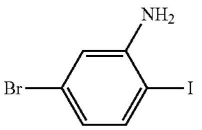 | 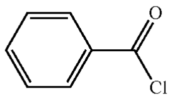 | 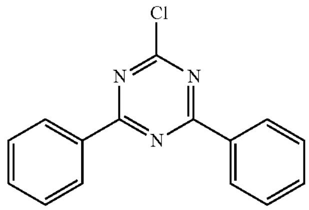 |
| 161 | 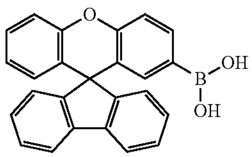 | 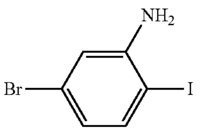 | 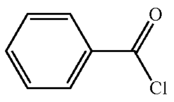 | 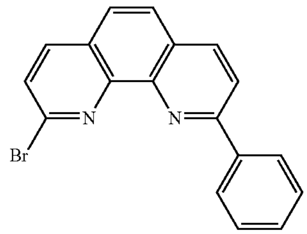 [SMILES: Brc1ccc2ccc3ccc(-c4ccccc4)nc3c2n1] |
| 168 | 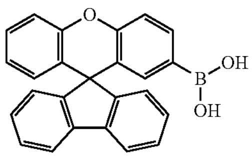 | 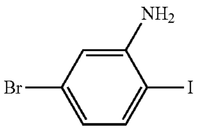 | 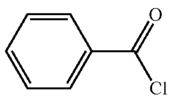 | 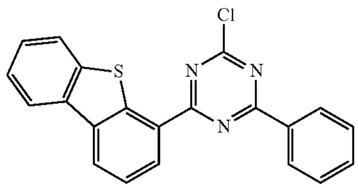 |
| 179 | 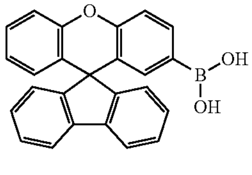 | 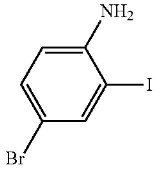 | 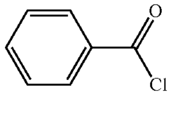 | 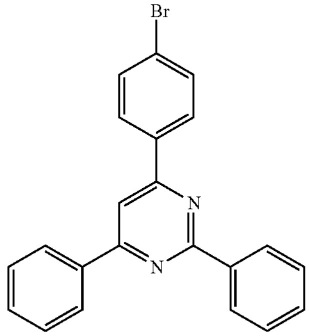 [SMILES: Brc1ccc(-c2cc(-c3ccccc3)nc(-c3ccccc3)n2)cc1] |

TABLE 1-continued
| | | | | |
|---|---|---|---|---|
| 183 | 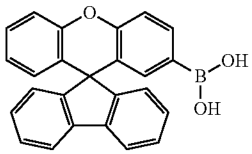 [SMILES: OB(O)c1ccc2c(c1)C1(c3ccccc3O2)c2ccccc2-c2ccccc21] | 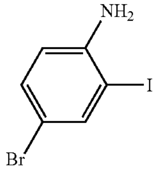 | 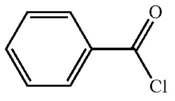 | 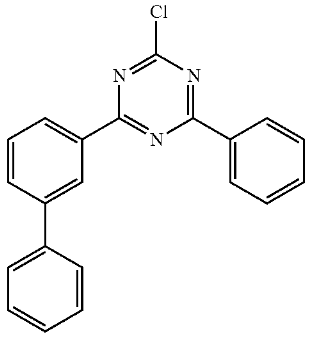 [SMILES: Clc1nc(-c2ccccc2)nc(-c2cccc(-c3ccccc3)c2)n1] |
| 215 | 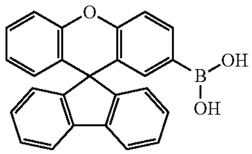 [SMILES: OB(O)c1ccc2c(c1)C1(c3ccccc3O2)c2ccccc2-c2ccccc21] | 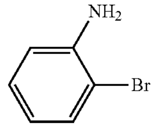 | 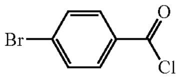 | 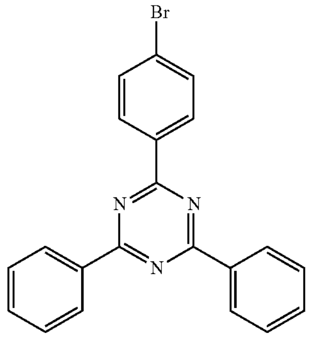 [SMILES: Brc1ccc(-c2nc(-c3ccccc3)nc(-c3ccccc3)n2)cc1] |
| 251 | 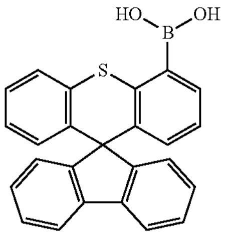 [SMILES: OB(O)c1cccc2c1Sc1ccccc1C21c2ccccc2-c2ccccc21] | 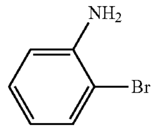 | 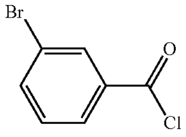 | 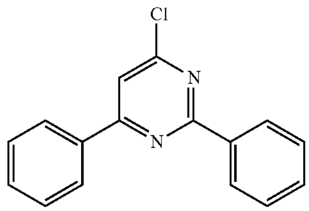 [SMILES: Clc1cc(-c2ccccc2)nc(-c2ccccc2)n1] |
| 256 | 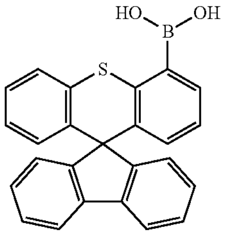 | 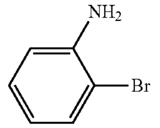 | 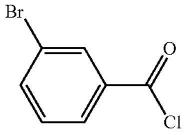 | 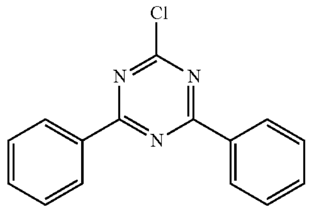 |
| 266 | 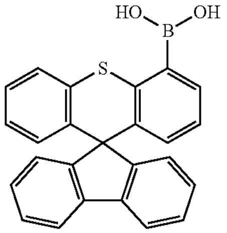 [SMILES: OB(O)c1cccc2c1Sc1ccccc1C21c2ccccc2-c2ccccc21] | 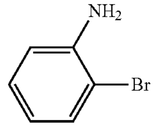 | 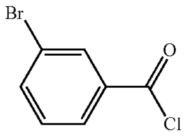 | 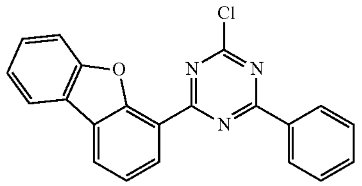 |
| 268 | 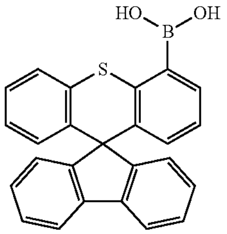 [SMILES: OB(O)c1cccc2c1Sc1ccccc1C21c2ccccc2-c2ccccc21] | 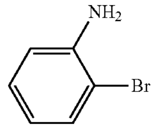 | 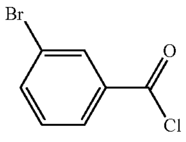 | 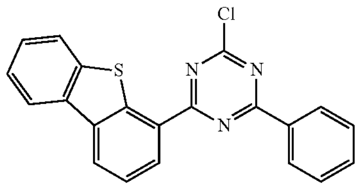 |

TABLE 1-continued
| | | | | |
|---|---|---|---|---|
| 279 | 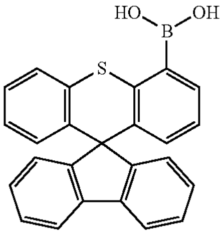 [SMILES: OB(O)c1cccc2c1Sc1ccccc1C21c2ccccc2-c2ccccc21] | 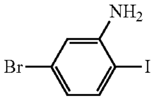 | 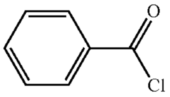 | 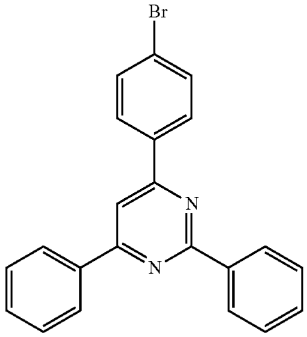 |
| 284 | 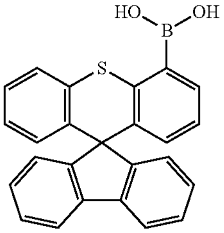 | 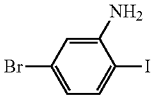 | 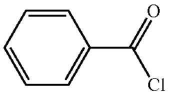 | 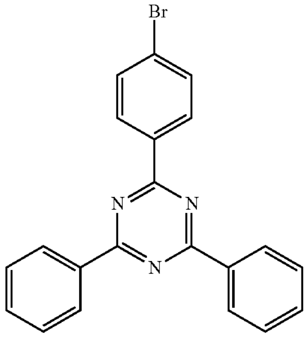 [SMILES: Brc1ccc(-c2nc(-c3ccccc3)nc(-c3ccccc3)n2)cc1] |
| 288 | 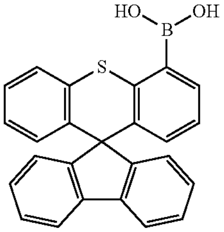 [SMILES: OB(O)c1cccc2c1Sc1ccccc1C21c2ccccc2-c2ccccc21] | 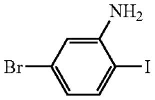 | 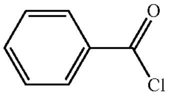 | 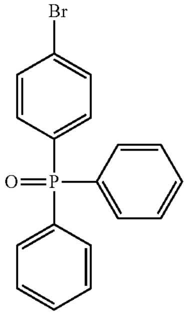 [SMILES: O=P(c1ccccc1)(c1ccccc1)c1ccc(Br)cc1] |
| 307 | 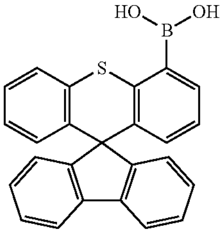 [SMILES: OB(O)c1cccc2c1Sc1ccccc1C21c2ccccc2-c2ccccc21] | 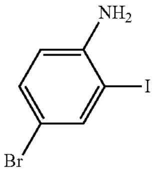 | 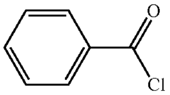 | 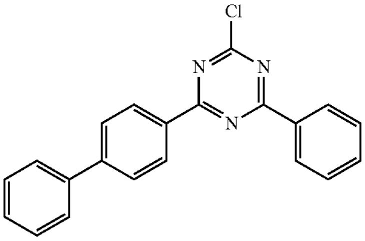 [SMILES: Clc1nc(-c2ccccc2)nc(-c2ccc(-c3ccccc3)cc2)n1] |
| 324 | 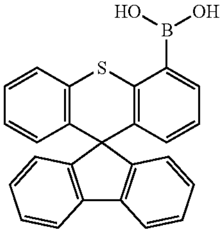 [SMILES: OB(O)c1cccc2c1Sc1ccccc1C21c2ccccc2-c2ccccc21] | 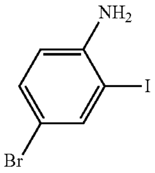 | 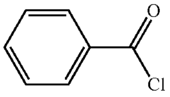 | 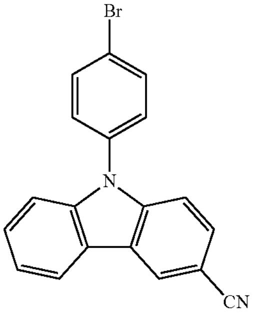 [SMILES: N#Cc1ccc2c(c1)c1ccccc1n2-c1ccc(Br)cc1] |

TABLE 1-continued
| | | | | |
|---|---|---|---|---|
| 336 | 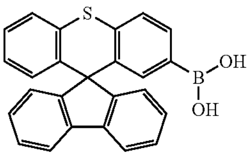 [SMILES: OB(O)c1ccc2c(c1)C1(c3ccccc3S2)c2ccccc2-c2ccccc21] | 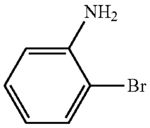 | 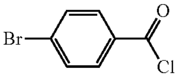 | 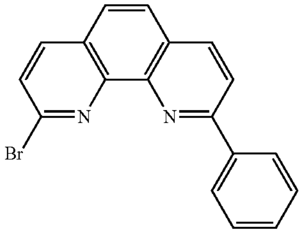 [SMILES: Brc1ccc2ccc3ccc(-c4ccccc4)nc3c2n1] |
| 337 | 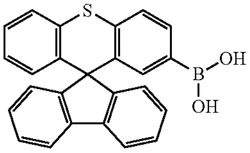 [SMILES: OB(O)c1ccc2c(c1)C1(c3ccccc3S2)c2ccccc2-c2ccccc21] | 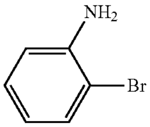 | 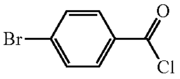 | 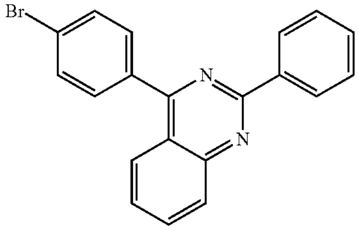 [SMILES: Brc1ccc(-c2nc(-c3ccccc3)nc3ccccc23)cc1] |
| 351 | 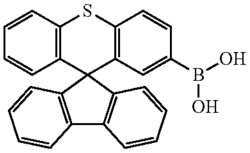 [SMILES: OB(O)c1ccc2c(c1)C1(c3ccccc3S2)c2ccccc2-c2ccccc21] | 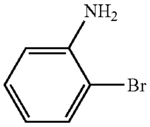 | 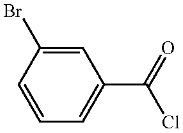 | 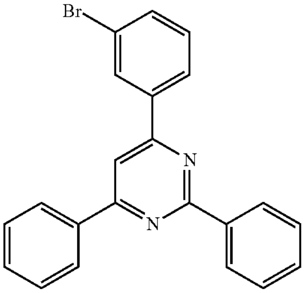 [SMILES: Brc1cccc(-c2cc(-c3ccccc3)nc(-c3ccccc3)n2)c1] |
| 356 | 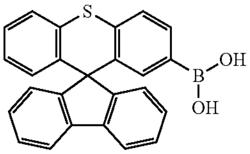 [SMILES: OB(O)c1ccc2c(c1)C1(c3ccccc3S2)c2ccccc2-c2ccccc21] | 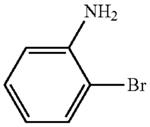 | 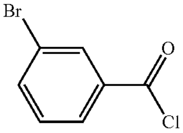 | 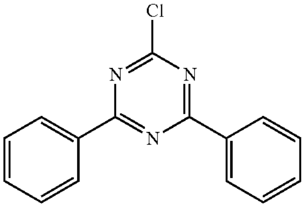 [SMILES: Clc1nc(-c2ccccc2)nc(-c2ccccc2)n1] |
| 366 | 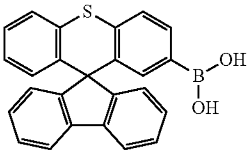 [SMILES: OB(O)c1ccc2c(c1)C1(c3ccccc3S2)c2ccccc2-c2ccccc21] | 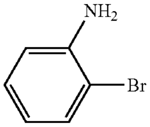 | 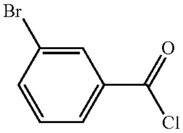 | 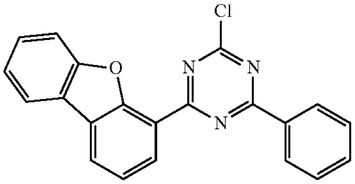 [SMILES: Clc1nc(-c2ccccc2)nc(-c2cccc3c2oc2ccccc23)n1] |
| 389 | 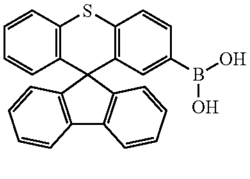 [SMILES: OB(O)c1ccc2c(c1)C1(c3ccccc3S2)c2ccccc2-c2ccccc21] | 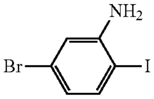 | 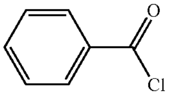 | 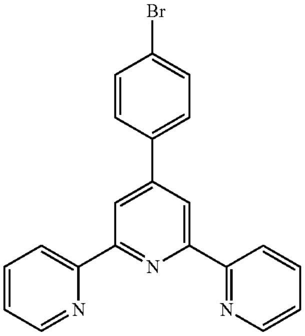 [SMILES: Brc1ccc(-c2cc(-c3ccccn3)nc(-c3ccccn3)c2)cc1] |

TABLE 1-continued
| | | | | |
|---|---|---|---|---|
| 423 | 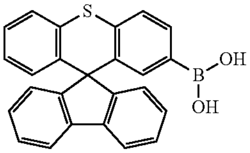 [SMILES: OB(O)c1ccc2c(c1)C1(c3ccccc3S2)c2ccccc2-c2ccccc21] | 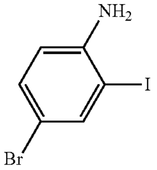 | 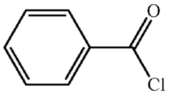 | 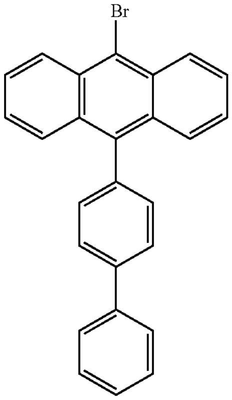 [SMILES: Brc1c2ccccc2c(-c2ccc(-c3ccccc3)cc2)c2ccccc12] |
| 461 | 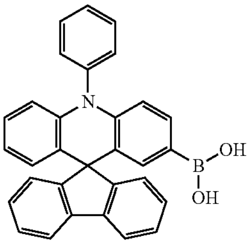 [SMILES: OB(O)c1ccc2c(c1)C1(c3ccccc3-c3ccccc31)c1ccccc1N2c1ccccc1] | 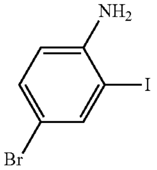 | 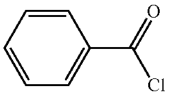 | 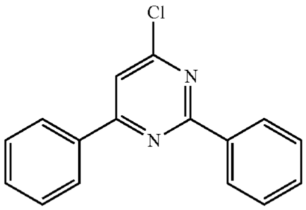 [SMILES: Clc1cc(-c2ccccc2)nc(-c2ccccc2)n1] |
| 546 | 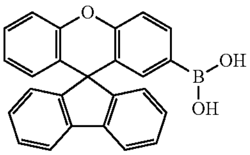 [SMILES: OB(O)c1ccc2c(c1)C1(c3ccccc3O2)c2ccccc2-c2ccccc21] | 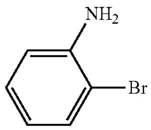 | 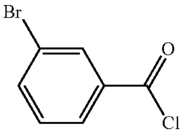 | 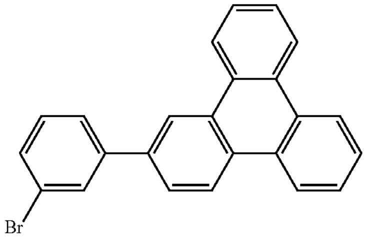 [SMILES: Brc1cccc(-c2ccc3c4ccccc4c4ccccc4c3c2)c1] |
| 547 | 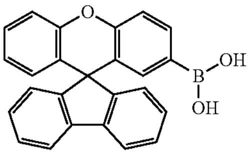 [SMILES: OB(O)c1ccc2c(c1)C1(c3ccccc3O2)c2ccccc2-c2ccccc21] | 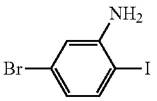 | 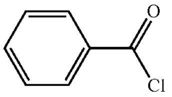 | 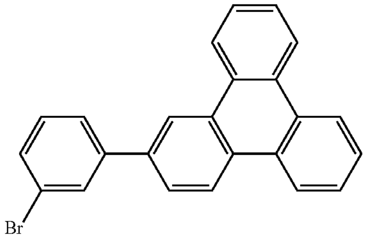 [SMILES: Brc1cccc(-c2ccc3c4ccccc4c4ccccc4c3c2)c1] |
| Compound | Target Compound | Yield |
|---|---|---|
| 6 | 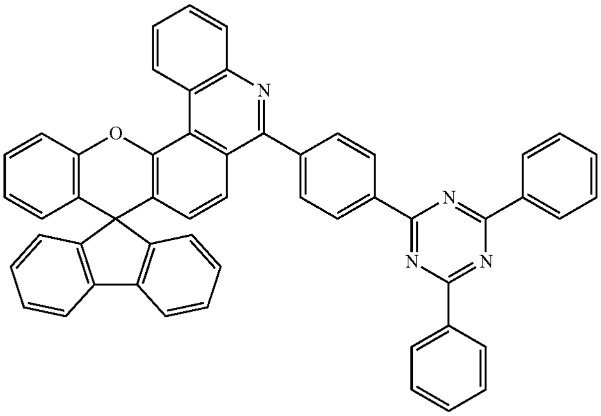 [SMILES: c1ccc(-c2nc(-c3ccccc3)nc(-c3ccc(-c4nc5ccccc5c5c6c(ccc45)C4(c5ccccc5O6)c5ccccc5-c5ccccc54)cc3)n2)cc1] | 74% |

TABLE 1-continued
| | | |
|---|---|---|
| 11 | 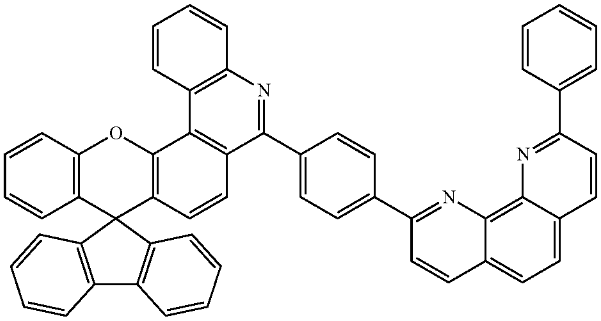 [SMILES: c1ccc(-c2ccc3ccc4ccc(-c5ccc(-c6nc7ccccc7c7c8c(ccc67)C6(c7ccccc7O8)c7ccccc7-c7ccccc76)cc5)nc4c3n2)cc1] | 72% |
| 12 | 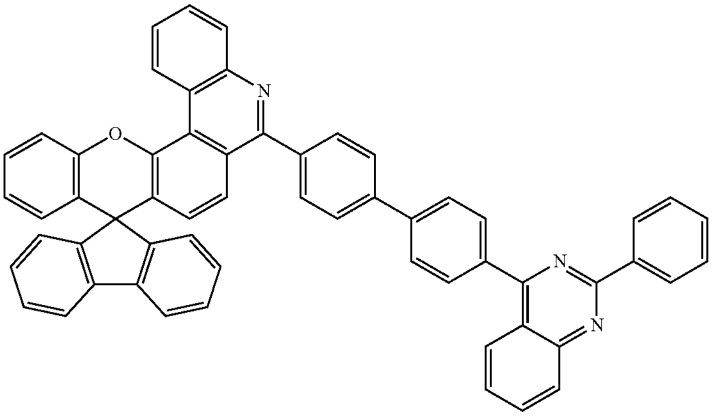 [SMILES: c1ccc(-c2nc(-c3ccc(-c4ccc(-c5nc6ccccc6c6c7c(ccc56)C5(c6ccccc6O7)c6ccccc6-c6ccccc65)cc4)cc3)c3ccccc3n2)cc1] | 81% |
| 15 | 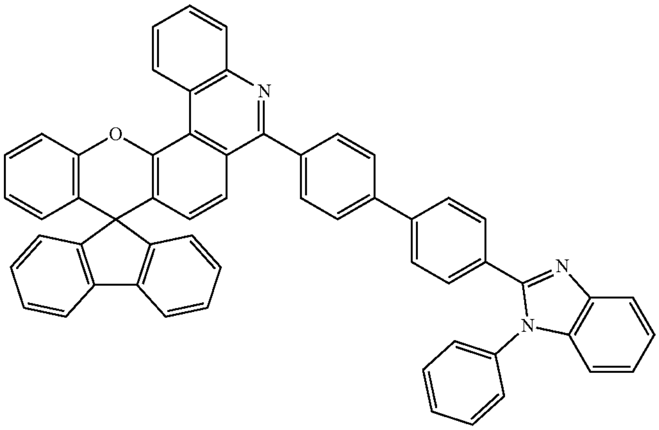 [SMILES: c1ccc(-n2c(-c3ccc(-c4ccc(-c5nc6ccccc6c6c7c(ccc56)C5(c6ccccc6O7)c6ccccc6-c6ccccc65)cc4)cc3)nc3ccccc32)cc1] | 77% |
| 23 | 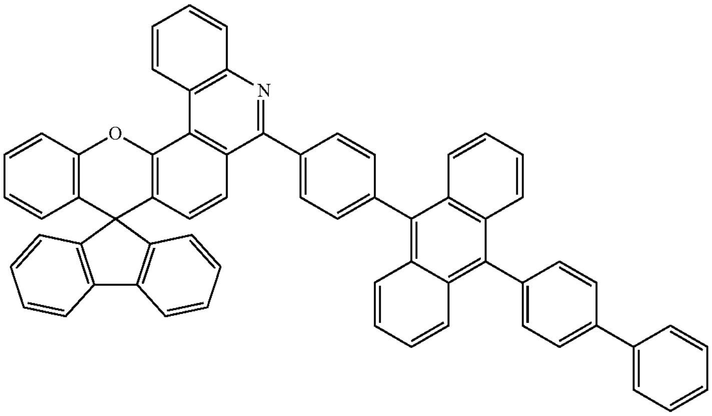 [SMILES: c1ccc(-c2ccc(-c3c4ccccc4c(-c4ccc(-c5nc6ccccc6c6c7c(ccc56)C5(c6ccccc6O7)c6ccccc6-c6ccccc65)cc4)c4ccccc34)cc2)cc1] | 72% |

TABLE 1-continued
| | | |
|---|---|---|
| 26 | 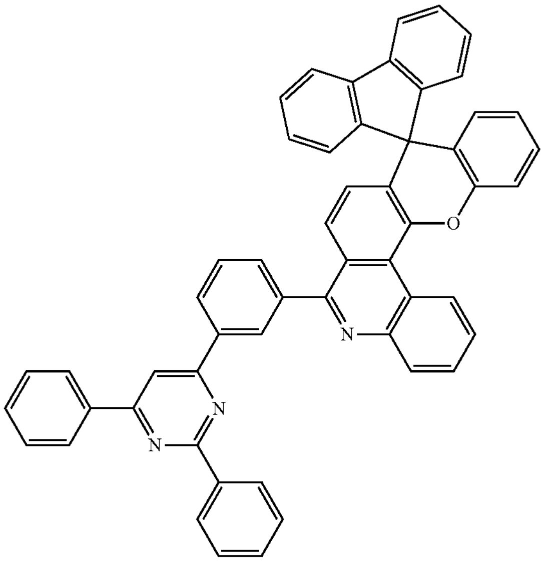 [SMILES: c1ccc(-c2cc(-c3cccc(-c4nc5ccccc5c5c6c(ccc45)C4(c5ccccc5O6)c5ccccc5-c5ccccc54)c3)nc(-c3ccccc3)n2)cc1] | 67% |
| 31 | 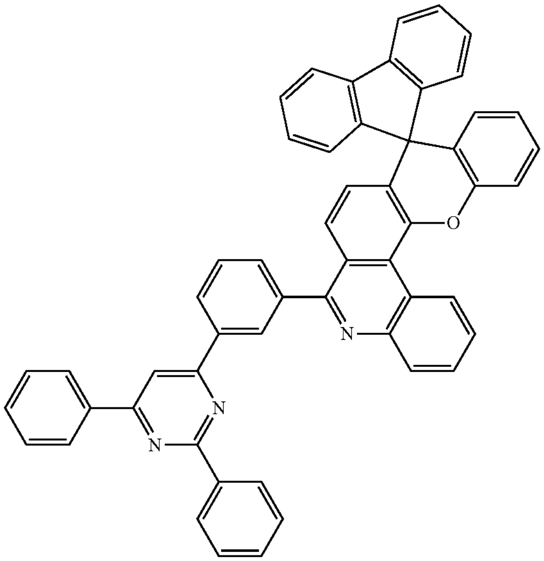 [SMILES: c1ccc(-c2cc(-c3cccc(-c4nc5ccccc5c5c6c(ccc45)C4(c5ccccc5O6)c5ccccc5-c5ccccc54)c3)nc(-c3ccccc3)n2)cc1] | 64% |

TABLE 1-continued
| | | |
|---|---|---|
| 36 | 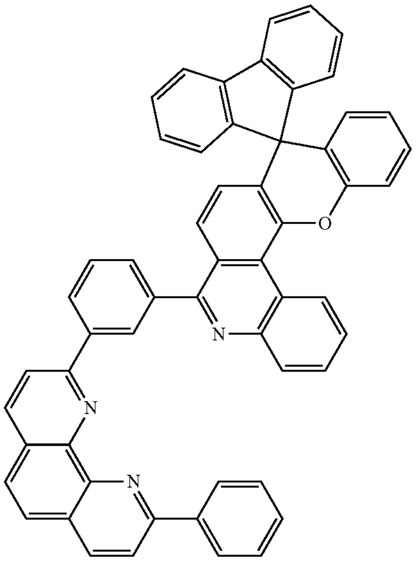 [SMILES: c1ccc(-c2ccc3ccc4ccc(-c5cccc(-c6nc7ccccc7c7c8c(ccc67)C6(c7ccccc7O8)c7ccccc7-c7ccccc76)c5)nc4c3n2)cc1] | 69% |
| 42 | 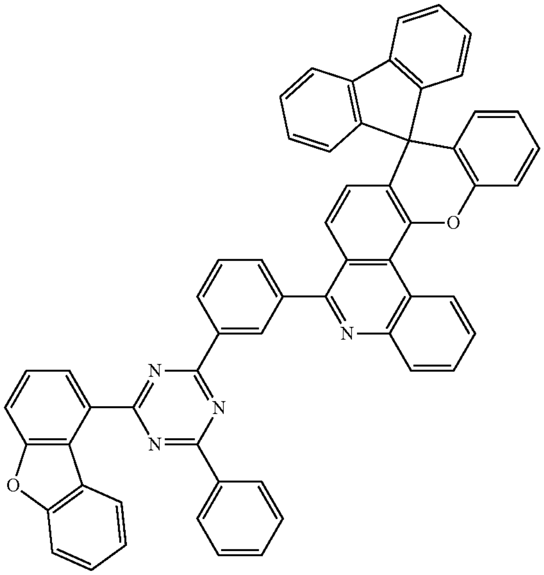 [SMILES: c1ccc(-c2nc(-c3cccc(-c4nc5ccccc5c5c6c(ccc45)C4(c5ccccc5O6)c5ccccc5-c5ccccc54)c3)nc(-c3cccc4oc5ccccc5c34)n2)cc1] | 75% |
| 56 | 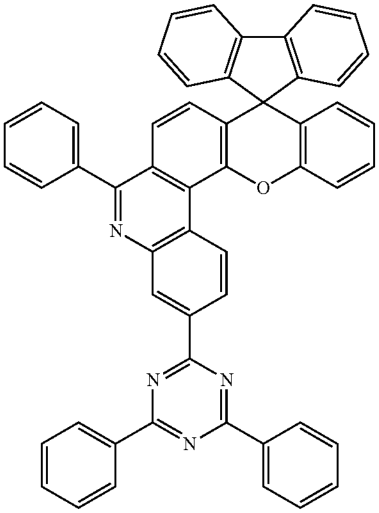 [SMILES: c1ccc(-c2nc(-c3ccccc3)nc(-c3ccc4c(c3)nc(-c3ccccc3)c3ccc5c(c34)Oc3ccccc3C53c4ccccc4-c4ccccc43)n2)cc1] | 77% |

TABLE 1-continued
| | | |
|---|---|---|
| 62 | 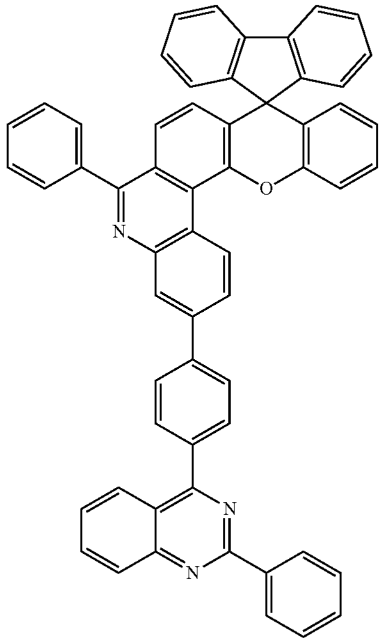 [SMILES: c1ccc(-c2nc(-c3ccc(-c4ccc5c(c4)nc(-c4ccccc4)c4ccc6c(c45)Oc4ccccc4C64c5ccccc5-c5ccccc54)cc3)c3ccccc3n2)cc1] | 70% |
| 71 | 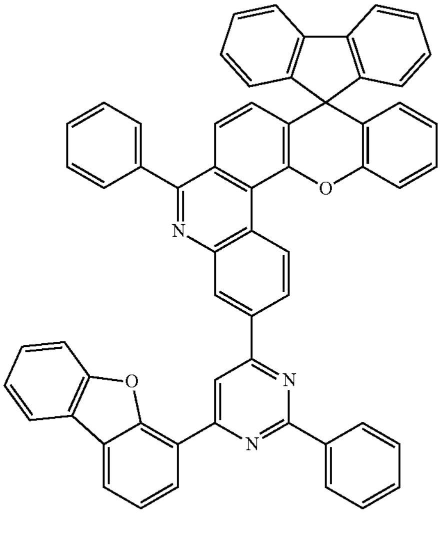 [SMILES: c1ccc(-c2nc(-c3ccc4c(c3)nc(-c3ccccc3)c3ccc5c(c34)Oc3ccccc3C53c4ccccc4-c4ccccc43)cc(-c3cccc4c3oc3ccccc34)n2)cc1] | 68% |

TABLE 1-continued
| | | |
|---|---|---|
| 77 | 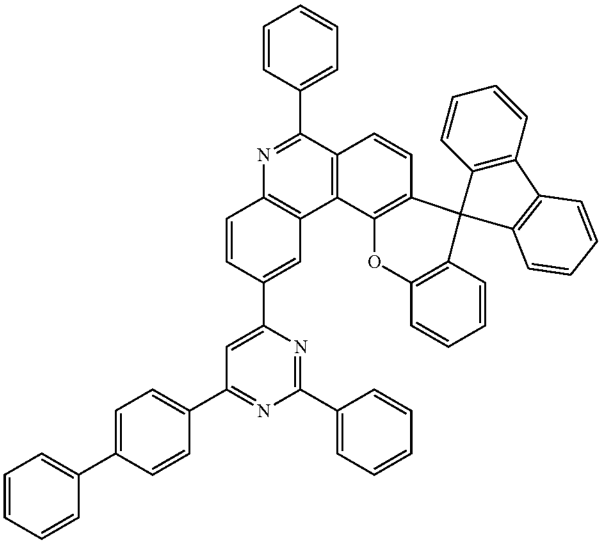 [SMILES: c1ccc(-c2ccc(-c3cc(-c4ccc5nc(-c6ccccc6)c6ccc7c(c6c5c4)Oc4ccccc4C74c5ccccc5-c5ccccc54)nc(-c4ccccc4)n3)cc2)cc1] | 82% |
| 91 | 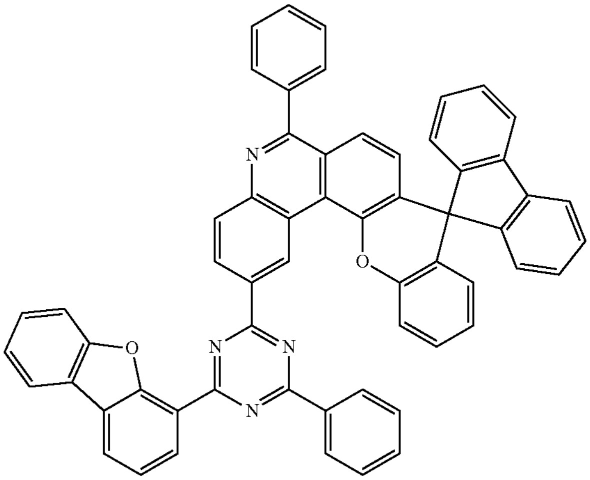 [SMILES: c1ccc(-c2nc(-c3ccc4nc(-c5ccccc5)c5ccc6c(c5c4c3)Oc3ccccc3C63c4ccccc4-c4ccccc43)nc(-c3cccc4c3sc3ccccc34)n2)cc1] | 77% |
| 93 | 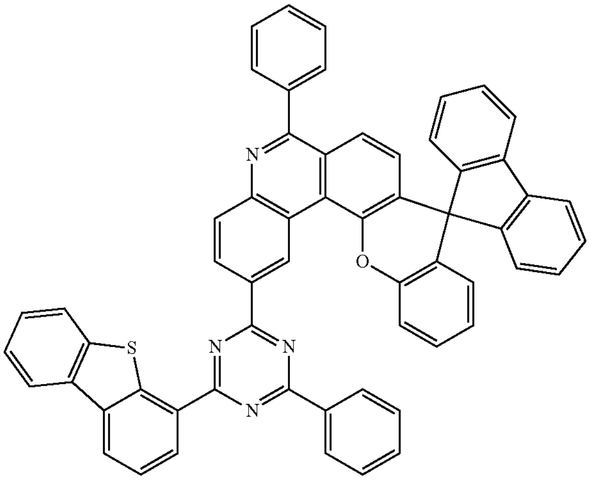 | 62% |

TABLE 1-continued
104 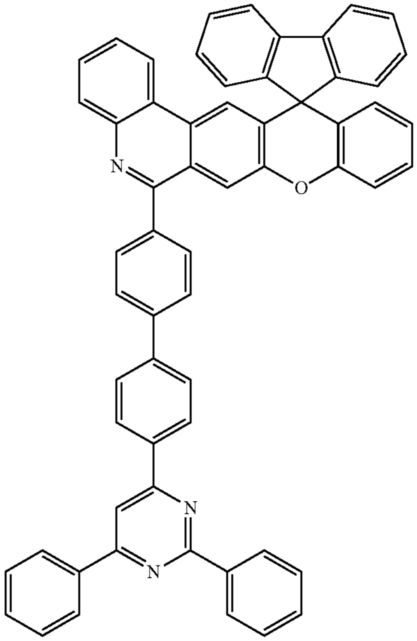 [SMILES: c1ccc(-c2cc(-c3ccc(-c4ccc(-c5nc6ccccc6c6cc7c(cc56)Oc5ccccc5C75c6ccccc6-c6ccccc65)cc4)cc3)nc(-c3ccccc3)n2)cc1] 66%
105 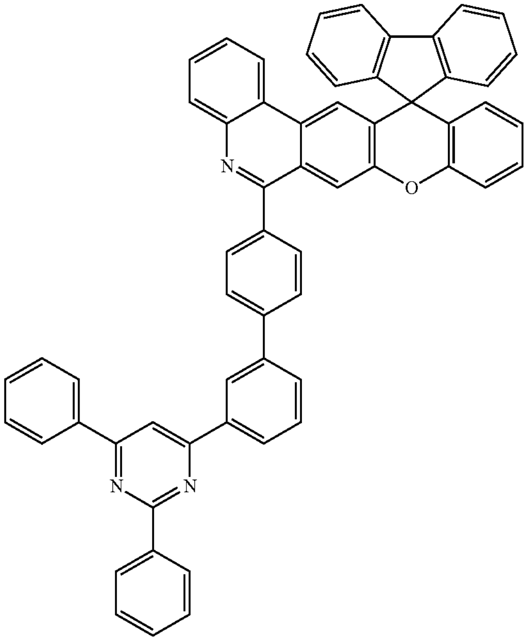 [SMILES: c1ccc(-c2cc(-c3cccc(-c4ccc(-c5nc6ccccc6c6cc7c(cc56)Oc5ccccc5C75c6ccccc6-c6ccccc65)cc4)c3)nc(-c3ccccc3)n2)cc1] 72%

TABLE 1-continued
111 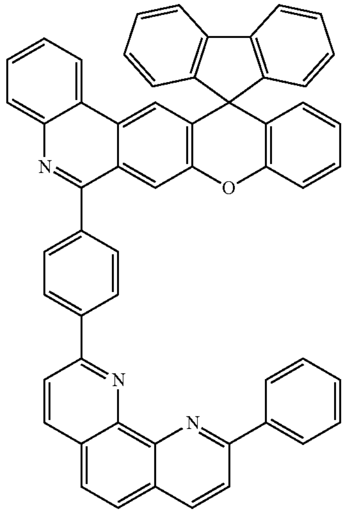 [SMILES: c1ccc(-c2ccc3ccc4ccc(-c5ccc(-c6nc7ccccc7c7cc8c(cc67)Oc6ccccc6C86c7ccccc7-c7ccccc76)cc5)nc4c3n2)cc1] 66%
124 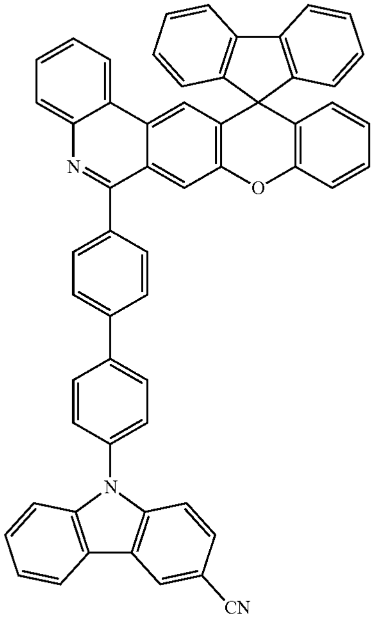 [SMILES: N#Cc1ccc2c(c1)c1ccccc1n2-c1ccc(-c2ccc(-c3nc4ccccc4c4cc5c(cc34)Oc3ccccc3C53c4ccccc4-c4ccccc43)cc2)cc1] 70%

TABLE 1-continued
| | | |
|---|---|---|
| 134 | 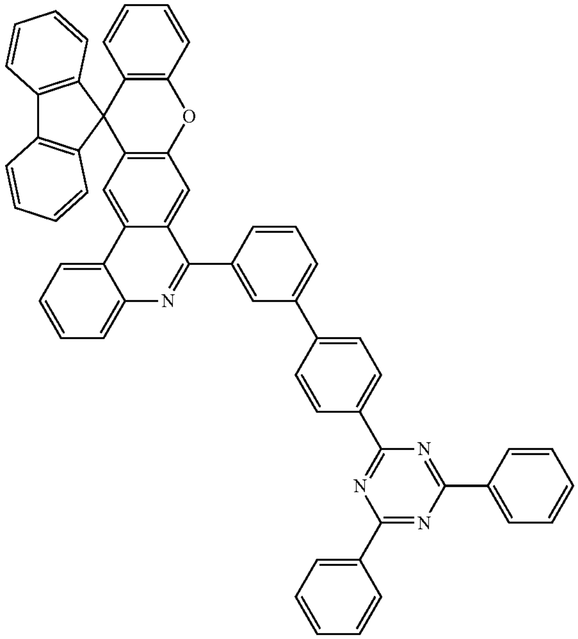 [SMILES: c1ccc(-c2nc(-c3ccccc3)nc(-c3ccc(-c4cccc(-c5nc6ccccc6c6cc7c(cc56)Oc5ccccc5C75c6ccccc6-c6ccccc65)c4)cc3)n2)cc1] | 59% |
| 146 | 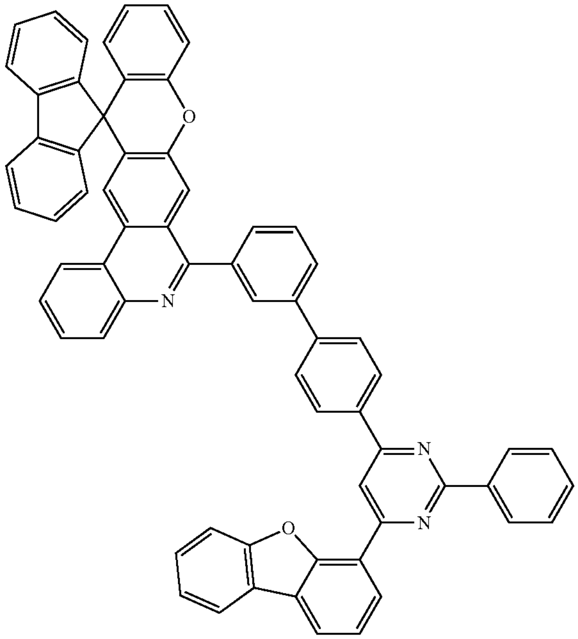 [SMILES: c1ccc(-c2nc(-c3ccc(-c4cccc(-c5nc6ccccc6c6cc7c(cc56)Oc5ccccc5C75c6ccccc6-c6ccccc65)c4)cc3)cc(-c3cccc4c3oc3ccccc34)n2)cc1] | 62% |

TABLE 1-continued
151 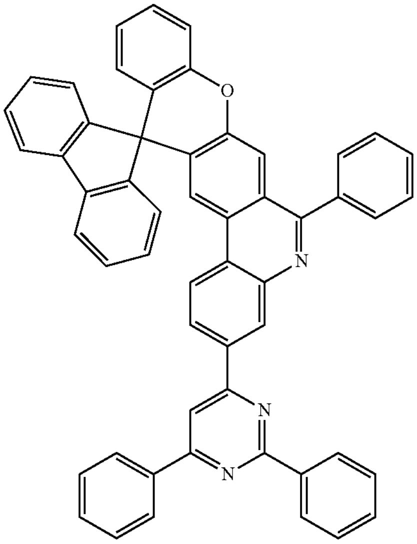 [SMILES: c1ccc(-c2cc(-c3ccc4c(c3)nc(-c3ccccc3)c3cc5c(cc34)C3(c4ccccc4O5)c4ccccc4-c4ccccc43)nc(-c3ccccc3)n2)cc1] 64%
156 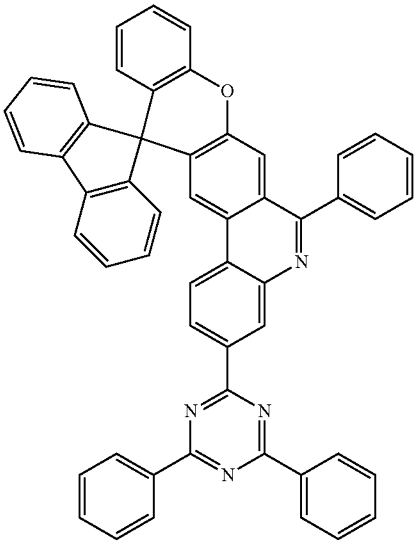 [SMILES: c1ccc(-c2nc(-c3ccccc3)nc(-c3ccc4c(c3)nc(-c3ccccc3)c3cc5c(cc34)C3(c4ccccc4O5)c4ccccc4-c4ccccc43)n2)cc1] 64%
161 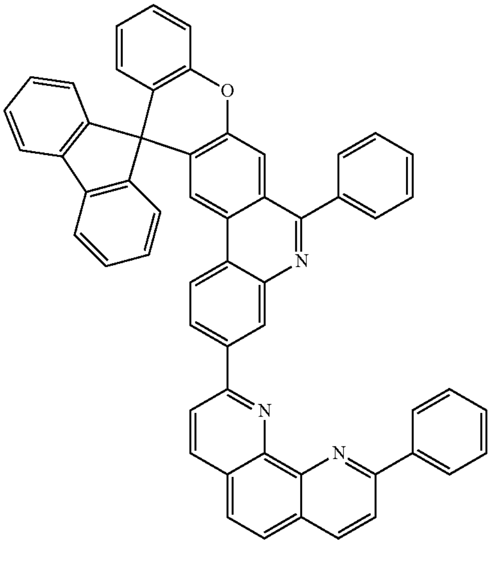 [SMILES: c1ccc(-c2ccc3ccc4ccc(-c5ccc6c(c5)nc(-c5ccccc5)c5cc7c(cc56)C5(c6ccccc6O7)c6ccccc6-c6ccccc65)nc4c3n2)cc1] 71%

TABLE 1-continued
168
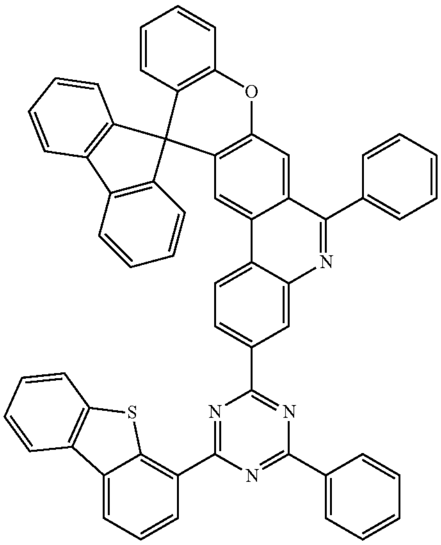 [SMILES: c1ccc(-c2nc(-c3ccc4c(c3)nc(-c3ccccc3)c3cc5c(cc34)C3(c4ccccc4O5)c4ccccc4-c4ccccc43)nc(-c3cccc4c3sc3ccccc34)n2)cc1]
73%
179
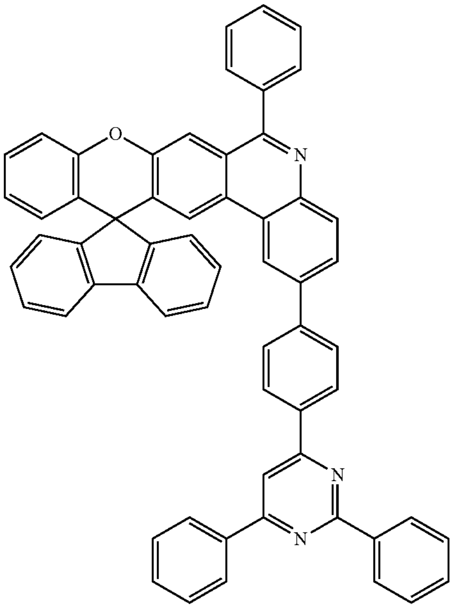 [SMILES: c1ccc(-c2cc(-c3ccc(-c4ccc5nc(-c6ccccc6)c6cc7c(cc6c5c4)C4(c5ccccc5O7)c5ccccc5-c5ccccc54)cc3)nc(-c3ccccc3)n2)cc1]
77%

TABLE 1-continued
183 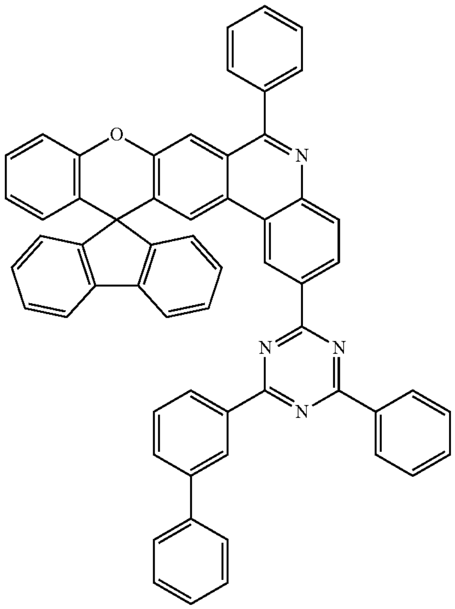 [SMILES: c1ccc(-c2cccc(-c3nc(-c4ccccc4)nc(-c4ccc5nc(-c6ccccc6)c6cc7c(cc6c5c4)C4(c5ccccc5O7)c5ccccc5-c5ccccc54)n3)c2)cc1] 75%
215 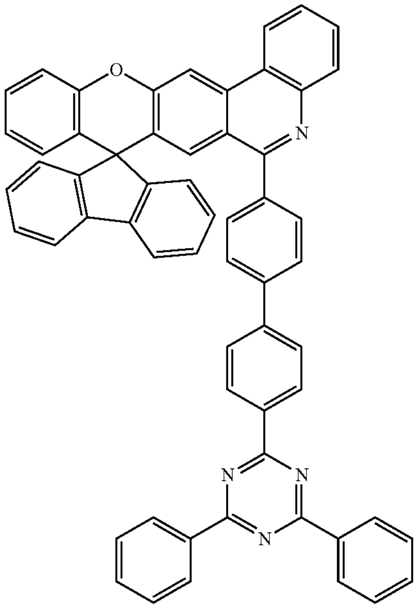 [SMILES: c1ccc(-c2nc(-c3ccccc3)nc(-c3ccc(-c4ccc(-c5nc6ccccc6c6cc7c(cc56)C5(c6ccccc6O7)c6ccccc6-c6ccccc65)cc4)cc3)n2)cc1] 72%

TABLE 1-continued
| | | |
|---|---|---|
| 251 | 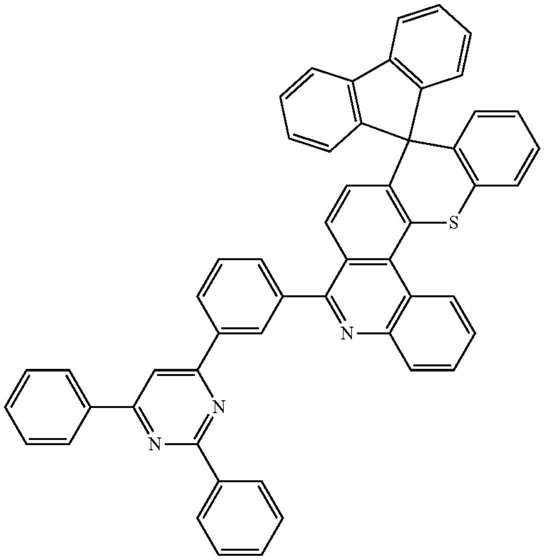 | 78% |
| 256 | 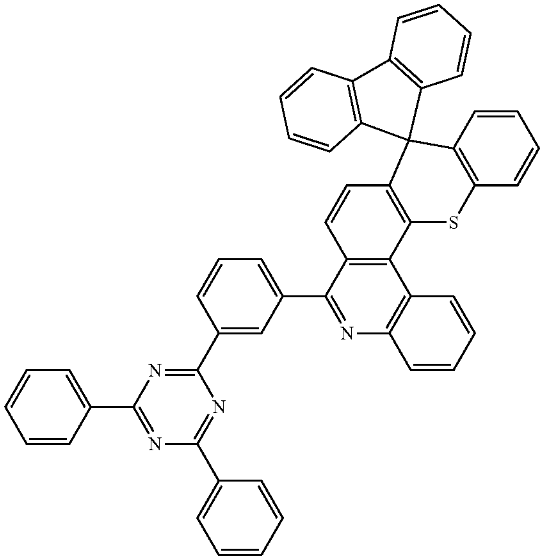 [SMILES: c1ccc(-c2nc(-c3ccccc3)nc(-c3cccc(-c4nc5ccccc5c5c6c(ccc45)C4(c5ccccc5S6)c5ccccc5-c5ccccc54)c3)n2)cc1] | 69% |

TABLE 1-continued
| | | |
|---|---|---|
| 266 | 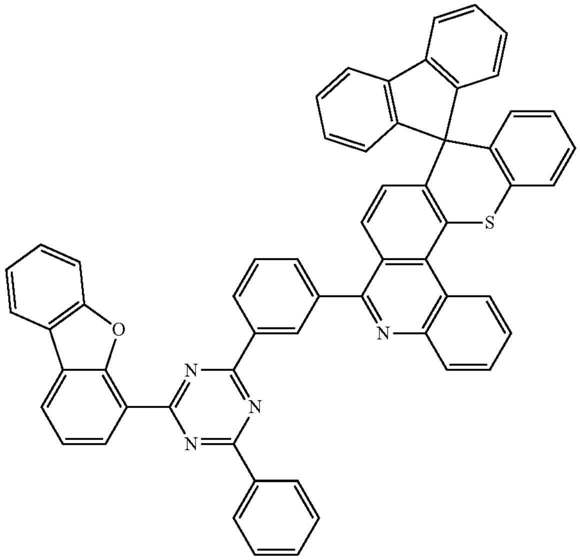 | 67% |
| 268 | 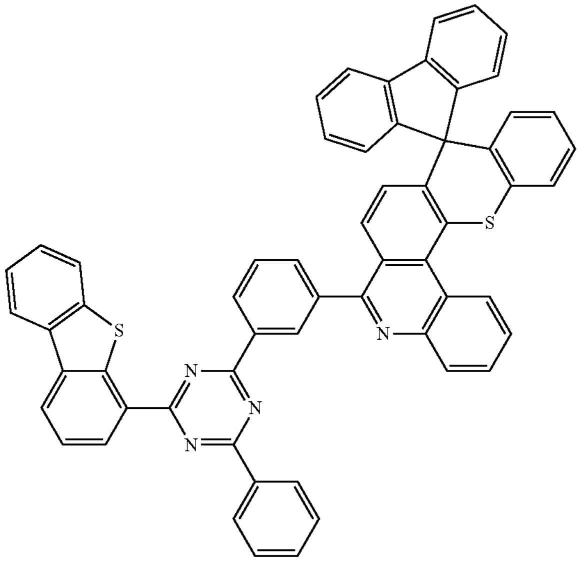 [SMILES: c1ccc(-c2nc(-c3cccc(-c4nc5ccccc5c5c6c(ccc45)C4(c5ccccc5S6)c5ccccc5-c5ccccc54)c3)nc(-c3cccc4c3sc3ccccc34)n2)cc1] | 81% |

TABLE 1-continued
| | | |
|---|---|---|
| 279 | 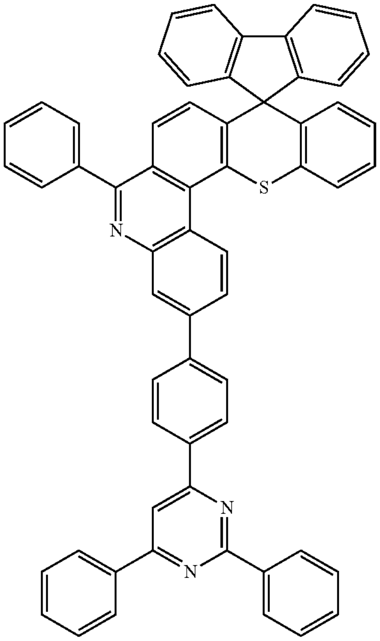 [SMILES: c1ccc(-c2cc(-c3ccc(-c4ccc5c(c4)nc(-c4ccccc4)c4ccc6c(c45)Sc4ccccc4C64c5ccccc5-c5ccccc54)cc3)nc(-c3ccccc3)n2)cc1] | 77% |
| 284 | 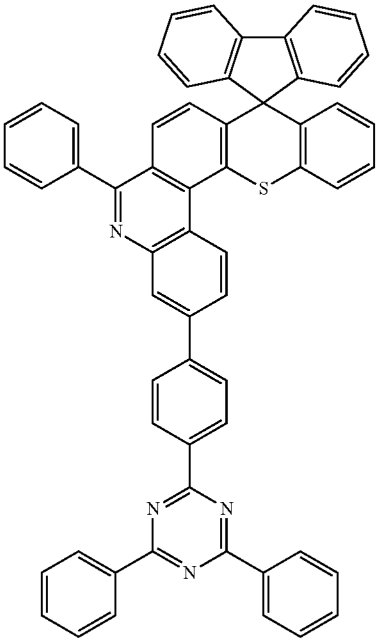 [SMILES: c1ccc(-c2nc(-c3ccccc3)nc(-c3ccc(-c4ccc5c(c4)nc(-c4ccccc4)c4ccc6c(c45)Sc4ccccc4C64c5ccccc5-c5ccccc54)cc3)n2)cc1] | 72% |

TABLE 1-continued
| | | |
|---|---|---|
| 288 | 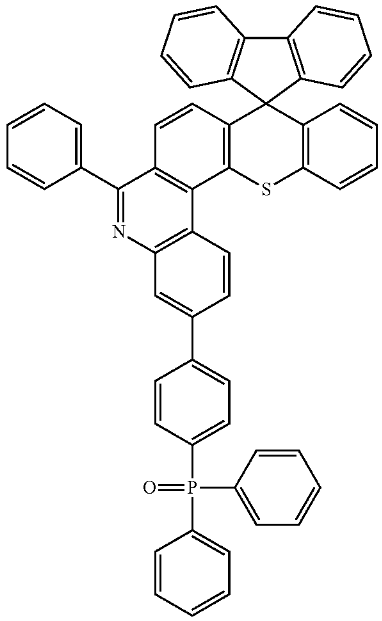 [SMILES: O=P(c1ccccc1)(c1ccccc1)c1ccc(-c2ccc3c(c2)nc(-c2ccccc2)c2ccc4c(c23)Sc2ccccc2C42c3ccccc3-c3ccccc32)cc1] | 67% |
| 307 | 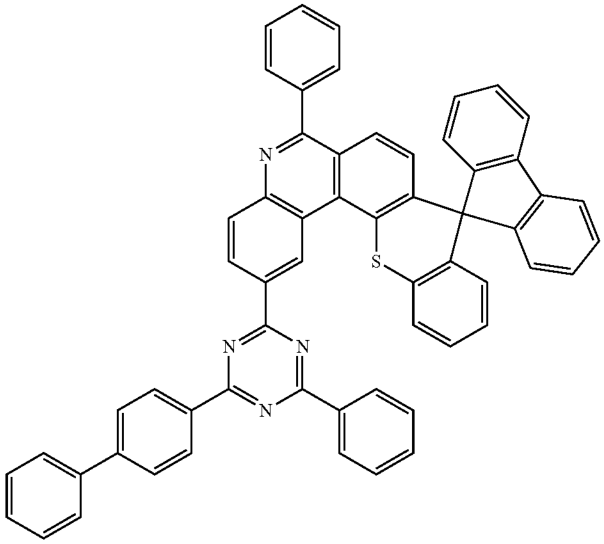 | 64% |

TABLE 1-continued
324 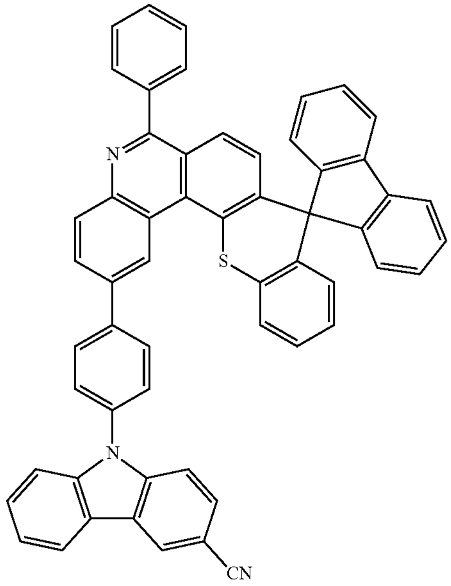 [SMILES: N#Cc1ccc2c(c1)c1ccccc1n2-c1ccc(-c2ccc3nc(-c4ccccc4)c4ccc5c(c4c3c2)Sc2ccccc2C52c3ccccc3-c3ccccc32)cc1] 69%
336 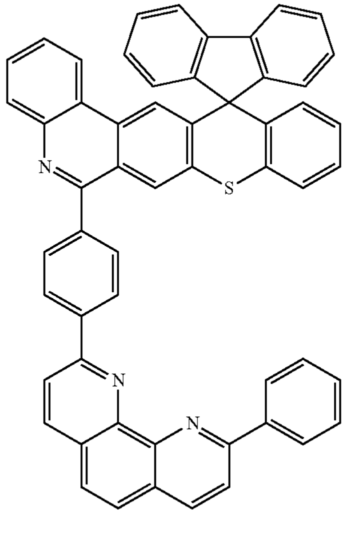 [SMILES: c1ccc(-c2ccc3ccc4ccc(-c5ccc(-c6nc7ccccc7c7cc8c(cc67)Sc6ccccc6C86c7ccccc7-c7ccccc76)cc5)nc4c3n2)cc1] 81%

TABLE 1-continued
| | | |
|---|---|---|
| 337 | 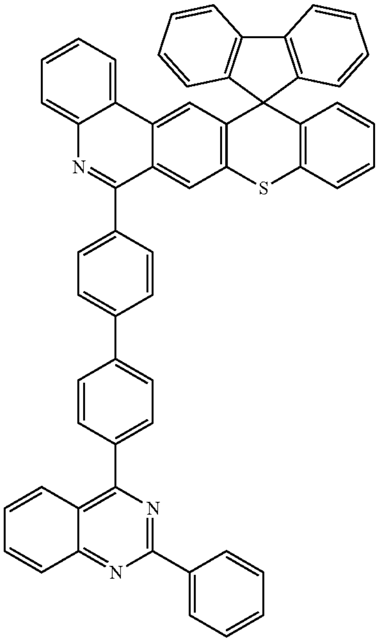 [SMILES: c1ccc(-c2nc(-c3ccc(-c4ccc(-c5nc6ccccc6c6cc7c(cc56)Sc5ccccc5C75c6ccccc6-c6ccccc65)cc4)cc3)c3ccccc3n2)cc1] | 77% |
| 351 | 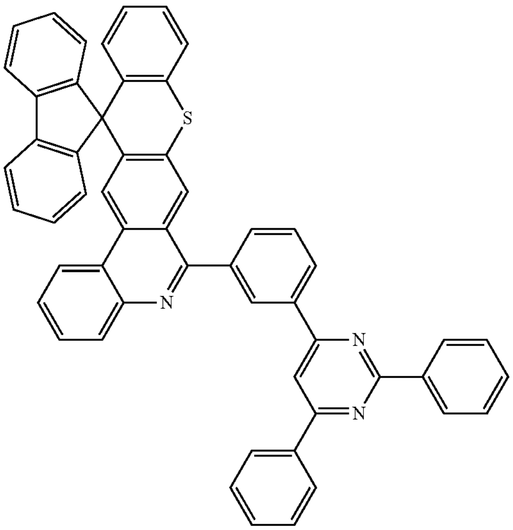 [SMILES: c1ccc(-c2cc(-c3cccc(-c4nc5ccccc5c5cc6c(cc45)Sc4ccccc4C64c5ccccc5-c5ccccc54)c3)nc(-c3ccccc3)n2)cc1] | 72% |

TABLE 1-continued
| | | |
|---|---|---|
| 356 | 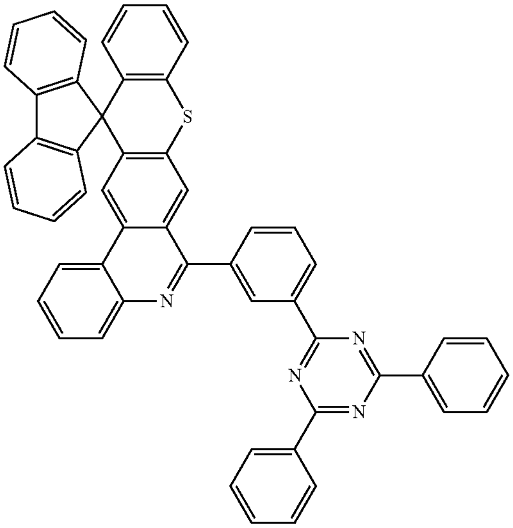 [SMILES: c1ccc(-c2nc(-c3ccccc3)nc(-c3cccc(-c4nc5ccccc5c5cc6c(cc45)Sc4ccccc4C64c5ccccc5-c5ccccc54)c3)n2)cc1] | 67% |
| 366 | 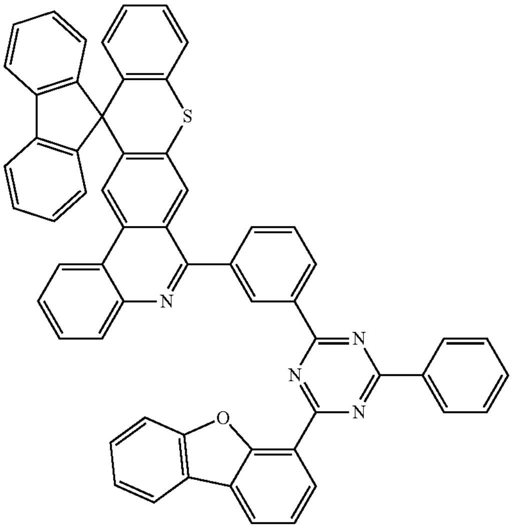 [SMILES: c1ccc(-c2nc(-c3cccc(-c4nc5ccccc5c5cc6c(cc45)Sc4ccccc4C64c5ccccc5-c5ccccc54)c3)nc(-c3cccc4c3oc3ccccc34)n2)cc1] | 64% |

TABLE 1-continued
| | | |
|---|---|---|
| 389 | 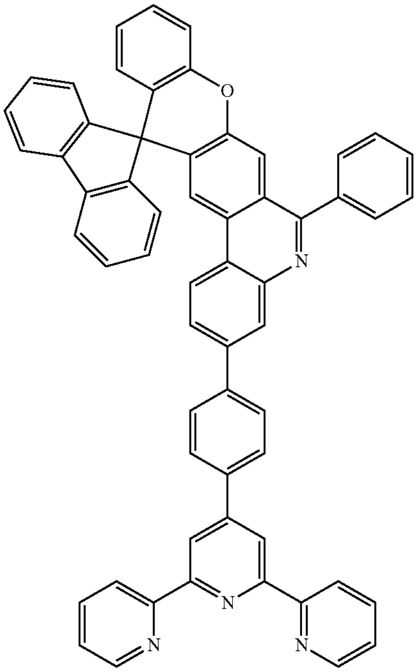 [SMILES: c1ccc(-c2nc3cc(-c4ccc(-c5cc(-c6ccccn6)nc(-c6ccccn6)c5)cc4)ccc3c3cc4c(cc23)Oc2ccccc2C42c3ccccc3-c3ccccc32)cc1] | 69% |
| 423 | 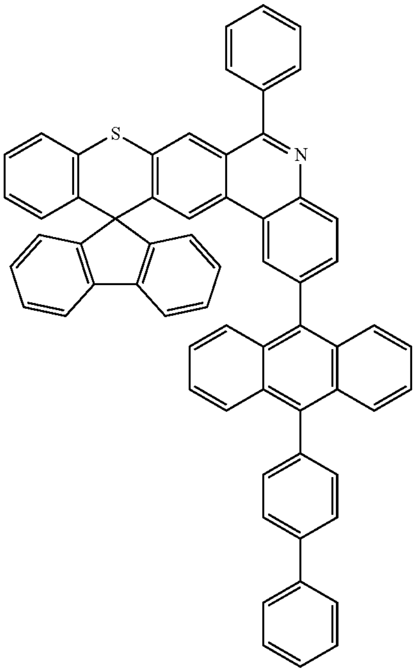 [SMILES: c1ccc(-c2ccc(-c3c4ccccc4c(-c4ccc5nc(-c6ccccc6)c6cc7c(cc6c5c4)C4(c5ccccc5S7)c5ccccc5-c5ccccc54)c4ccccc34)cc2)cc1] | 75% |

TABLE 1-continued
| | | |
|---|---|---|
| 461 | 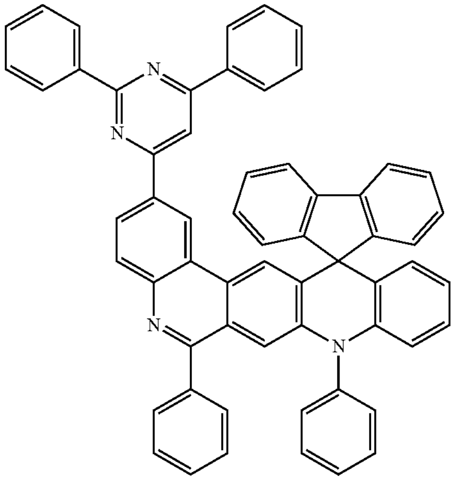 [SMILES: c1ccc(-c2cc(-c3ccc4nc(-c5ccccc5)c5cc6c(cc5c4c3)C3(c4ccccc4-c4ccccc43)c3ccccc3N6c3ccccc3)nc(-c3ccccc3)n2)cc1] | 77% |
| 546 | 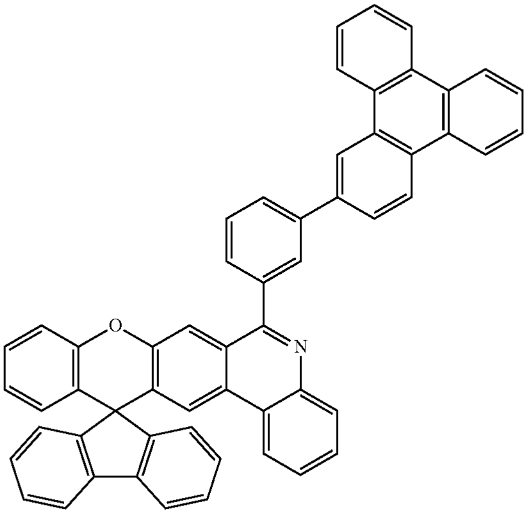 [SMILES: c1cc(-c2ccc3c4ccccc4c4ccccc4c3c2)cc(-c2nc3ccccc3c3cc4c(cc23)Oc2ccccc2C42c3ccccc3-c3ccccc32)c1] | 70% |
| 547 | 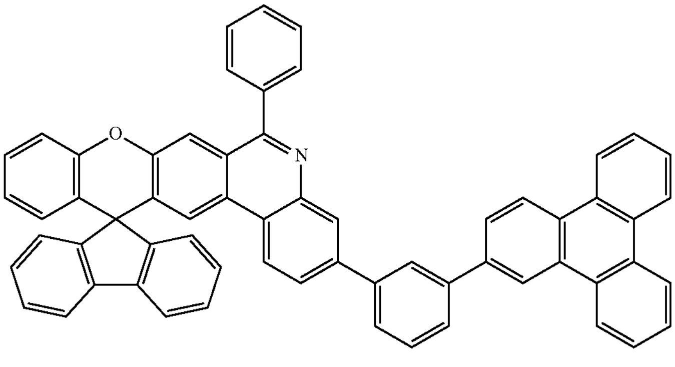 [SMILES: c1ccc(-c2nc3cc(-c4cccc(-c5ccc6c7ccccc7c7ccccc7c6c5)c4)ccc3c3cc4c(cc23)Oc2ccccc2C42c3ccccc3-c3ccccc32)cc1] | 68% |

The following Table 2 and Table 3 present 1H NMR data and FD-MS data of the synthesized compounds, and through the following data, syntheses of target compounds may be identified.

TABLE 2

| NO | $^1H$ NMR ($CDCl_3$, 300 Mz) |
|---|---|
| 1 | 8.69 (2H, dd), 8.38-8.28 (4H, m), 8.23 (1H, s), 8.14 (1H, dd), 7.96-7.84 (5H, m), 7.75 (1H, ddd), 7.58-7.25 (16H, m), 7.19-7.08 (2H, m), 6.95 (1H, ddd) |
| 6 | 8.69 (2H, dd), 8.40-8.31 (4H, m), 8.25 (2H, dd), 8.14 (1H, dd), 7.92-7.84 (3H, m), 7.75 (1H, ddd), 7.61-7.50 (10H, m), 7.48-7.25 (6H, m), 7.19-7.09 (2H, m), 6.95 (1H, ddd) |
| 11 | 8.69 (4H, s), 8.39-8.31 (4H, m), 8.14 (1H, dd), 7.92-7.84 (4H, m), 7.75 (1H, ddd), 7.61-7.25 (16H, m), 7.19-7.09 (2H, m), 6.95 (1H, ddd) |
| 12 | 8.69 (2H, dd), 8.37-8.28 (4H, m), 8.16-8.12 (2H, m), 7.93-7.72 (10H, m), 7.58-7.48 (8H, m), 7.42-7.25 (6H, m), 7.19-7.09 (2H, m), 6.95 (1H, ddd) |
| 15 | 8.69 (2H, dd), 8.56 (1H, dd), 8.25 (2H, dd), 8.14 (1H, dd), 7.93-7.72 (7H, m), 7.65-7.14 (21H, m), 6.95 (1H, ddd) |
| 23 | 8.69 (2H, dd), 8.23-8.12 (5H, m), 7.92-7.84 (3H, m), 7.78-7.72 (3H, m), 7.57-7.15 (24H, m), 6.95 (1H, ddd) |
| 26 | 8.37-8.31 (4H, m), 8.23 (1H, s), 8.14 (1H, dd), 7.96-7.78 (6H, m), 7.77-7.69 (2H, m), 7.60-7.26 (16H, m), 7.19-7.09 (2H, m), 6.95 (1H, ddd) |
| 31 | 8.40-8.31 (7H, m), 8.14 (1H, dd), 7.92-7.84 (3H, m), 7.77-7.69 (2H, m), 7.61-7.48 (10H, m), 7.42-7.25 (6H, m), 7.19-7.09 (2H, m), 6.95 (1H, ddd) |
| 36 | 8.72 (1H, dd), 8.39-8.31 (6H, m), 8.14 (1H, dd), 7.92-7.84 (4H, m), 7.77-7.69 (2H, m), 7.58-7.24 (16H, m), 7.19-7.08 (2H, m), 6.95 (1H, ddd) |
| 42 | 8.38-8.31 (5H, m), 8.14 (1H, dd), 7.98 (1H, dd), 7.92-7.83 (3H, m), 7.77-7.68 (2H, m), 7.63-7.26 (19H, m), 7.19-7.09 (2H, m), 6.95 (1H, ddd) |
| 56 | 8.39-8.33 (5H, m), 8.19 (2H, ddd), 8.05 (1H, d), 7.92-7.88 (3H, m), 7.65 (2H, ddd), 7.58-7.47 (10H, m), 7.42-7.26 (6H, m), 7.19-7.08 (2H, m), 6.95 (1H, ddd) |
| 62 | 8.37-8.09 (9H, m), 7.87-7.80 (4H, m), 7.67-7.25 (17H, m), 7.19-7.08 (2H, m), 6.95 (1H, ddd) |
| 71 | 8.39-8.33 (3H, m), 8.25-8.17 (3H, m), 8.10-7.87 (6H, m), 7.77-7.25 (20H, m), 7.19-7.08 (2H, m), 6.95 (1H, ddd) |
| 77 | 8.37-8.27 (5H, m), 8.25-8.17 (3H, m), 8.10-8.05 (2H, m), 7.93-7.83 (4H, m), 7.75 (2H, dd), 7.65 (2H, ddd), 7.57-7.26 (16H, m), 7.20-7.09 (2H, m), 6.95 (1H, ddd) |
| 91 | 8.38-8.32 (3H, m), 8.19 (2H, dd), 8.11-8.05 (3H, m), 7.99-7.88 (3H, m), 7.68-7.22 (20H, m), 7.19-7.08 (2H, m), 6.95 (1H, ddd) |
| 93 | 8.55 (1H, dd), 8.45 (1H, dd), 8.39-8.32 (3H, m), 8.19 (2H, dd), 8.10-8.06 (2H, m), 7.92-7.84 (3H, m), 7.68-7.25 (19H, m), 7.19-7.08 (2H, m), 6.95 (1H, ddd) |
| 104 | 8.69 (2H, d), 8.37-8.27 (4H, m), 8.23 (1H, s), 8.14 (1H, dd), 7.96-7.84 (9H, m), 7.75 (1H, ddd), 7.60-7.46 (9H, m), 7.41-7.22 (6H, m), 7.19-7.08 (3H, m), 6.95 (1H, ddd) |
| 105 | 8.69 (2H, d), 8.38-8.32 (2H, m), 8.23 (1H, s), 8.14 (1H, dd), 7.97-7.83 (9H, m), 7.78-7.69 (2H, m), 7.64-7.45 (10H, m), 7.41-7.25 (6H, m), 7.19-7.08 (3H, m), 6.95 (1H, ddd) |
| 111 | 8.69 (4H, s), 8.41-8.31 (4H, m), 8.14 (1H, dd), 7.92-7.82 (4H, m), 7.75 (1H, ddd), 7.61-7.47 (7H, m), 7.41-7.25 (8H, m), 7.19-7.08 (3H, m), 6.95 (1H, ddd) |
| 124 | 8.69 (2H, d), 8.55 (1H, dd), 8.22-8.11 (3H, m), 7.96-7.82 (8H, m), 7.75 (1H, ddd), 7.61-7.52 (5H, m), 7.40-7.22 (7H, m), 7.19-7.07 (5H, m), 6.95 (1H, ddd) |
| 134 | 8.39-8.31 (6H, m), 8.25 (2H, d), 8.14 (1H, dd), 7.92-7.83 (3H, m), 7.78-7.69 (2H, m), 7.63-7.47 (10H, m), 7.41-7.22 (8H, m), 7.19-7.08 (3H, m), 6.95 (1H, ddd) |
| 146 | 8.37-8.31 (4H, m), 8.23 (1H, s), 8.17-8.06 (2H, m), 8.01-7.87 (5H, m), 7.77-7.68 (3H, m), 7.61-7.22 (16H, m), 7.19-7.09 (3H, m), 6.95 (1H, ddd) |
| 151 | 8.39-8.32 (3H, m), 8.25-8.17 (3H, m), 7.28 (1H, d), 7.97-7.88 (5H, m), 7.68-7.46 (11H, m), 7.41-7.25 (6H, m), 7.20-7.08 (3H, m), 6.95 (1H, ddd) |
| 156 | 8.41-8.32 (5H, m), 8.19 (2H, dd), 7.28 (1H, d), 7.92-7.88 (3H, m), 7.65 (2H, ddd), 7.58-7.47 (9H, m), 7.41-7.26 (6H, m), 7.19-7.14 (3H, m), 6.95 (1H, ddd) |
| 161 | 8.76 (1H, d), 8.39-8.26 (5H, m), 8.19 (2H, dd), 7.28 (1H, d), 7.92-7.83 (3H, m), 7.68-7.22 (17H, m), 7.19-7.08 (3H, m), 6.95 (1H, ddd) |

TABLE 2-continued

| NO | $^1H$ NMR ($CDCl_3$, 300 Mz) |
|---|---|
| 168 | 8.55 (1H, dd), 8.45 (1H, dd), 8.40-8.33 (3H, m), 8.19 (2H, dd), 8.05 (1H, d), 7.92-7.84 (4H, m), 7.68-7.45 (11H, m), 7.41-7.23 (7H, m), 7.19-7.08 (3H, m), 6.95 (1H, ddd) |
| 179 | 8.43-8.27 (5H, m), 8.25-8.16 (3H, m), 7.97-7.82 (7H, m), 7.75 (1H, d), 7.68-7.47 (11H, m), 7.41-7.23 (6H, m), 7.19-7.09 (3H, m), 6.95 (1H, ddd) |
| 183 | 8.40-8.32 (4H, m), 8.19 (2H, dd), 8.11-8.05 (2H, m), 7.97-7.86 (3H, m), 7.79-7.25 (21H, m), 7.19-7.08 (3H, m), 6.95 (1H, ddd) |
| 215 | 8.69 (2H, dd), 8.40-8.32 (2H, m), 8.25 (2H, dd), 8.14 (1H, dd), 7.93-7.82 (5H, m), 7.75 (1H, ddd), 7.61-7.48 (9H, m), 7.43-7.22 (8H, m), 7.20-7.09 (2H, m), 7.02-6.93 (2H, m) |
| 251 | 8.38-8.31 (4H, m), 8.23 (1H, s), 8.14 (1H, dd), 7.97-7.83 (6H, m), 7.77-7.67 (3H, m), 7.58-7.47 (10H, m), 7.41-7.25 (6H, m), 6.99-6.93 (2H, m) |
| 256 | 8.38-8.31 (7H, m), 8.14 (1H, dd), 7.92-7.83 (3H, m), 7.77-7.66 (3H, m), 7.61-7.47 (10H, m), 7.41-7.25 (6H, m), 6.99-6.93 (2H, m) |
| 266 | 8.41-8.31 (5H, m), 8.15-8.05 (2H, m), 8.01-7.88 (4H, m), 7.78-7.26 (21H, m), 6.99-6.94 (2H, m) |
| 268 | 8.55 (1H, dd), 8.41-8.30 (5H, m), 8.14 (1H, dd), 7.92-7.83 (4H, m), 7.78-7.48 (13H, m), 7.41-7.25 (7H, m), 6.99-6.93 (2H, m) |
| 279 | 8.38-8.16 (8H, m), 8.11 (1H, d), 7.96-7.82 (6H, m), 7.71-7.46 (14H, m), 7.41-7.25 (6H, m), 6.99-6.93 (2H, m) |
| 284 | 8.39-8.33 (4H, m), 8.27-8.16 (5H, m), 8.11 (1H, d), 7.90 (2H, dd), 7.71-7.62 (3H, m), 7.58-7.46 (11H, m), 7.41-7.25 (8H, m), 6.99-6.92 (2H, m) |
| 288 | 8.29-8.04 (12H, m), 7.90 (2H, dd), 7.75-7.47 (14H, m), 7.36-7.25 (6H, m) |
| 307 | 8.39-8.32 (3H, m), 8.27-8.16 (4H, m), 8.11-8.05 (2H, m), 7.90 (2H, dd), 7.77-7.62 (5H, m), 7.58-7.22 (18H, m), 6.99-6.93 (2H, m) |
| 324 | 8.55 (1H, dd), 8.41 (1H, d), 8.23-8.15 (4H, m), 7.97-7.85 (6H, m), 7.77-7.25 (17H, m), 7.18-7.08 (2H, m), 6.99-6.93 (2H, m) |
| 336 | 8.69 (4H, s), 8.39-8.31 (4H, m), 8.14 (1H, dd), 7.92-7.84 (4H, m), 7.77-7.66 (2H, m), 7.61-7.47 (8H, m), 7.41-7.25 (8H, m), 6.99-6.94 (2H, m) |
| 337 | 8.69 (2H, dd), 8.37-8.27 (4H, m), 8.16-8.11 (2H, m), 7.93-7.66 (11H, m), 7.61-7.47 (8H, m), 7.41-7.26 (6H, m), 6.99-6.93 (2H, m) |
| 351 | 8.38-8.31 (4H, m), 8.23(1H, s), 8.14 (1H, dd), 7.97-7.83 (6H, m), 7.78-7.66 (3H, m), 7.58-7.25 (10H, m), 7.41-7.25 (6H, m), 7.00-6.93 (2H, m) |
| 356 | 8.41-8.30 (7H, m), 8.14 (1H, dd), 7.92-7.84 (3H, m), 7.76-7.66 (3H, m), 7.61-7.25 (10H, m), 7.41-7.25 (6H, m), 6.99-6.92 (2H, m) |
| 366 | 8.39-8.31 (5H, m), 8.17-8.05 (2H, m), 8.01-7.85 (4H, m), 7.78-7.25 (21H, m), 6.99-6.93 (2H, m) |
| 423 | 8.41 (1H, d), 8.24-8.16 (6H, m), 7.97-7.88 (3H, m), 7.78-7.63 (6H, m), 7.58-7.25 (21H, m), 6.99-6.93 (2H, m), |
| 461 | 8.38-8.32 (3H, m), 8.26-8.16 (3H, m), 8.11-8.05 (2H, m), 7.97-7.88 (4H, m), 7.68-7.45 (11H, m), 7.38 (2H, ddd), 7.30-7.22 (4H, m), 7.18-6.97 (6H, m), 6.91-6.82(2H, m), 6.76 (1H, s) |
| 546 | 9.60 (1H, dd), 9.27 (1H, d), 8.40-8.27 (5H, m), 8.14 (1H, dd), 7.93-7.84 (3H, m), 7.73-7.50 (12H, m), 7.41-7.22 (6H, m), 7.20-7.09 (3H, m), 6.95 (1H, ddd) |
| 547 | 9.60 (1H, dd), 9.27 (1H, d), 8.39-8.08 (7H, m), 7.97-7.87 (3H, m), 7.74-7.47 (15H, m), 7.41-7.22 (6H, m), 7.20-7.08 (3H, m), 6.95 (1H, ddd) |

TABLE 3

| Compound | FD-MS | Compound | FD-MS |
|---|---|---|---|
| 1 | m/z = 739.88 (C54H36N3O = 739.26) | 6 | m/z = 740.87 (C53H32N4O = 740.26) |
| 11 | m/z = 763.90 (C56H33N3O = 763.26) | 12 | m/z = 789.94 (C58H35N3O = 789.28) |
| 15 | m/z = 777.93 (C57H35N3O = 777.28) | 23 | m/z = 838.02 (C64H39NO = 837.30) |
| 26 | m/z = 739.88 (C54H33N3O = 739.26) | 31 | m/z = 740.87 (C53H32N4O = 740.26) |
| 36 | m/z = 763.90 (C56H33N3O = 763.26) | 42 | m/z = 830.95 (C59H34N4O2 = 830.27) |
| 56 | m/z = 740.87 (C53H32N4O = 740.26) | 62 | m/z = 789.94 (C58H35N3O = 789.28) |
| 71 | m/z = 829.96 (C60H35N3O2 = 829.27) | 77 | m/z = 815.98 (C60H37N3O = 815.29) |
| 91 | m/z = 830.95 (C59H34N4O2 = 830.27) | 93 | m/z = 847.01 (C59H34N4OS = 846.25) |
| 104 | m/z = 815.98 (C60H37N3O = 815.29) | 105 | m/z = 815.98 (C60H37N3O = 815.29) |
| 111 | m/z = 763.90 (C56H33N3O = 763.26) | 124 | m/z = 775.91 (C57H33N3O = 775.26) |
| 134 | m/z = 816.96 (C59H36N4O = 816.29) | 146 | m/z = 829.96 (C60H35N3O2 = 829.27) |
| 151 | m/z = 739.88 (C54H33N3O = 739.26) | 156 | m/z = 740.87 (C53H32N4O = 740.26) |
| 161 | m/z = 763.90 (C56H33N3O = 763.26) | 168 | m/z = 847.01 (C59H34N4OS = 846.25) |
| 179 | m/z = 815.98 (C60H37N3O = 815.29) | 183 | m/z = 816.96 (C59H36N4O = 816.29) |
| 215 | m/z = 816.96 (C59H36N4O = 816.29) | 251 | m/z = 755.94 (C54H33N3S = 755.24) |
| 256 | m/z = 756.93 (C53H32N4S = 756.23) | 266 | m/z = 847.01 (C59H34N4OS = 846.25) |
| 268 | m/z = 863.07 (C59H34N4S2 = 862.22) | 279 | m/z = 832.04 (C60H37N3S = 831.27) |
| 284 | m/z = 833.03 (C59H36N4S = 832.27) | 288 | m/z = 801.94 (C56H36NOPS = 801.23) |
| 307 | m/z = 833.03 (C59H36N4S = 832.27) | 324 | m/z = 791.97 (C57H33N3S = 791.24) |
| 336 | m/z = 779.96 (C56H33N3S = 779.24) | 337 | m/z = 806.00 (C58H35N3S = 805.26) |
| 351 | m/z = 755.94 (C54H33N3S = 755.24) | 356 | m/z = 756.93 (C53H32N4S = 756.23) |
| 366 | m/z = 847.01 (C59H34N4OS = 846.25) | 389 | m/z = 833.03 (C59H36N4S = 832.27) |
| 423 | m/z = 854.08 (C64H39NS = 853.28) | 461 | m/z = 814.99 (C60H38N4 = 814.31) |
| 546 | m/z = 735.89 (C56H33NO = 735.26) | 547 | m/z = 811.98 (C62H37NO = 811.29) |

<Experimental Example 1> Manufacture of Organic Light Emitting Device

1) Manufacture of Organic Light Emitting Device

Comparative Examples 1-1 to 1-3 and Examples 1 to 41

A transparent indium tin oxide (ITO) electrode thin film obtained from glass for an organic light emitting device (OLED) (manufactured by Samsung-Corning Co., Ltd.) was ultrasonic cleaned using trichloroethylene, acetone, ethanol and distilled water consecutively for 5 minutes each, stored in isopropanol, and used.

Next, an ITO substrate was installed in a substrate folder of a vacuum deposition apparatus, and the following 4,4',4"-tris (N,N-(2-naphthyl)-phenylamino)triphenylamine (2-TNATA) was introduced to a cell in the vacuum deposition apparatus.

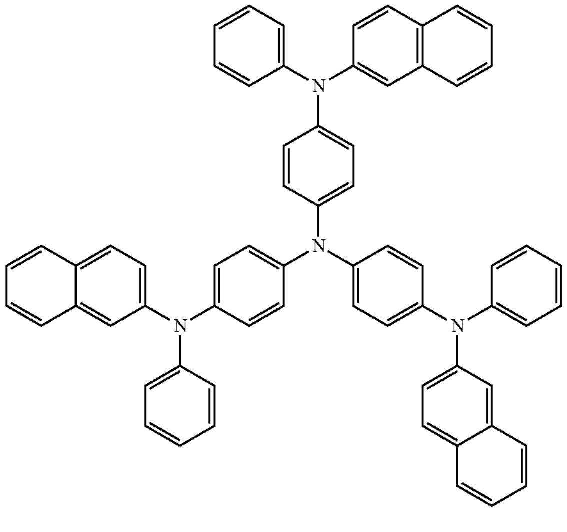

2-TNATA

Subsequently, the chamber was evacuated until the degree of vacuum therein reached $10^{-6}$ torr, and then 2-TNATA was evaporated by applying a current to the cell to deposit a hole injection layer having a thickness of 600 Å on the ITO substrate.

To another cell of the vacuum deposition apparatus, the following N,N'-bis(α-naphthyl)-N,N'-diphenyl-4,4'-diamine (NPB) was introduced, and evaporated by applying a current to the cell to deposit a hole transfer layer having a thickness of 300 Å on the hole injection layer.

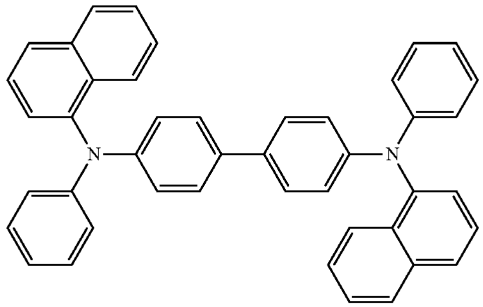

NPB

After forming the hole injection layer and the hole transfer layer as above, a blue light emitting material having a structure as below was deposited thereon as a light emitting layer. Specifically, in one side cell in the vacuum deposition apparatus, H1, a blue light emitting host material, was vacuum deposited to a thickness of 200 Å, and D1, a blue light emitting dopant material, was vacuum deposited thereon by 5% with respect to the host material.

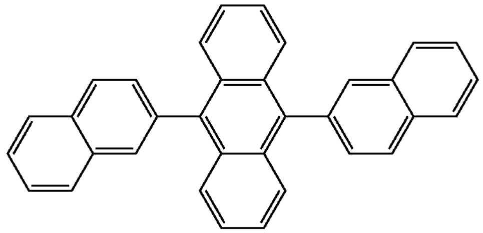

H1

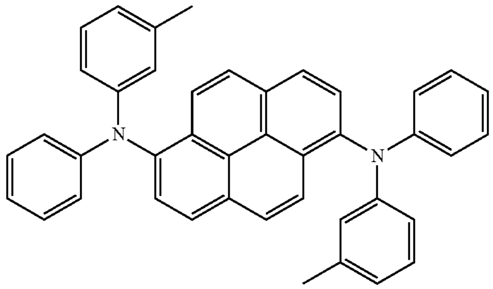

D1

Subsequently, a compound presented in the following Table 4 and LiQ were deposited in a weight ratio of 2:1 to a thickness of 300 Å to form an electron transfer layer.

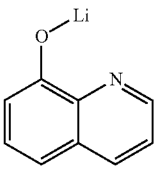

LiQ

-continued

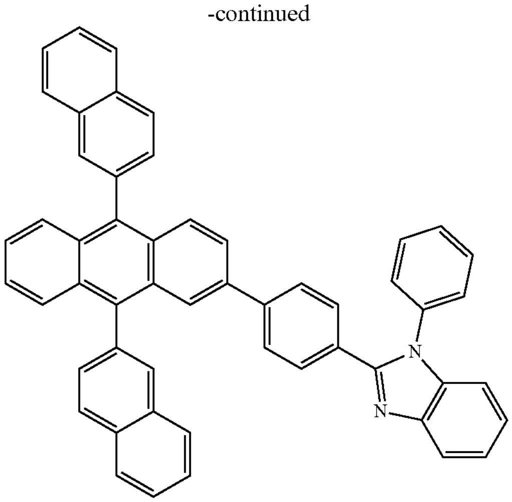

E1

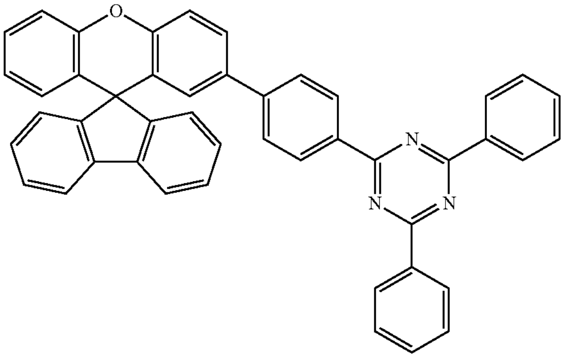

E2

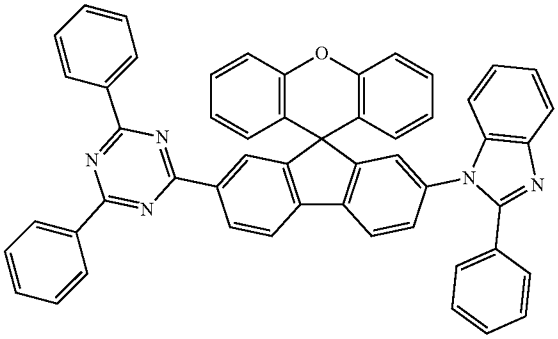

E3

As an electron injection layer, lithium fluoride (LiF) was deposited to a thickness of 10 Å, and an Al cathode was employed to a thickness of 1,000 Å, and as a result, an OLED was manufactured.

Meanwhile, all the organic compounds required to manufacture the OLED were vacuum sublimation purified under $10^{-6}$ torr to $10^{-8}$ torr by each material to be used in the OLED manufacture.

2) Driving Voltage and Light Emission Efficiency of Organic Light Emitting Device For the organic light emitting devices manufactured as above, electroluminescent (EL) properties were measured using M7000 manufactured by McScience Inc., and with the measurement results, $T_{95}$ when standard luminance was 700 cd/m$^2$ was measured using a lifetime measurement system (M6000) manufactured by McScience Inc. Results of measuring driving voltage, light emission efficiency, color coordinate (CIE) and lifetime of the blue organic light emitting devices manufactured according to the present disclosure are as shown in the following Table 4.

TABLE 4

| | Compound | Driving Voltage (V) | Light Emission Efficiency (cd/A) | CIE (x, y) | Life-time ($T_{95}$) |
|---|---|---|---|---|---|
| Example 1 | 1 | 5.11 | 7.11 | (0.134, 0.101) | 87 |
| Example 2 | 6 | 4.96 | 6.84 | (0.134, 0.102) | 91 |
| Example 3 | 12 | 5.14 | 6.79 | (0.134, 0.101) | 61 |
| Example 4 | 15 | 4.99 | 6.88 | (0.134, 0.103) | 62 |
| Example 5 | 23 | 5.45 | 6.12 | (0.134, 0.102) | 65 |
| Example 6 | 26 | 5.43 | 6.49 | (0.134, 0.101) | 61 |
| Example 7 | 31 | 5.72 | 6.92 | (0.134, 0.102) | 59 |
| Example 8 | 42 | 5.32 | 6.33 | (0.134, 0.101) | 59 |
| Example 9 | 56 | 5.40 | 6.13 | (0.134, 0.101) | 62 |
| Example 10 | 62 | 5.30 | 6.72 | (0.134, 0.100) | 67 |
| Example 11 | 71 | 5.37 | 6.35 | (0.134, 0.101) | 54 |
| Example 12 | 77 | 5.38 | 6.41 | (0.134, 0.100) | 55 |
| Example 13 | 91 | 5.27 | 6.42 | (0.134, 0.100) | 60 |
| Example 14 | 93 | 5.48 | 6.21 | (0.134, 0.100) | 59 |
| Example 15 | 104 | 4.72 | 7.39 | (0.134, 0.100) | 59 |
| Example 16 | 105 | 5.45 | 6.68 | (0.134, 0.100) | 61 |
| Example 17 | 124 | 5.22 | 6.28 | (0.134, 0.102) | 44 |
| Example 18 | 134 | 5.12 | 6.20 | (0.134, 0.101) | 58 |
| Example 19 | 146 | 5.09 | 6.77 | (0.134, 0.102) | 61 |
| Example 20 | 151 | 5.42 | 6.88 | (0.134, 0.100) | 63 |
| Example 21 | 156 | 5.21 | 5.45 | (0.134, 0.103) | 59 |
| Example 22 | 168 | 5.38 | 6.66 | (0.134, 0.100) | 62 |
| Example 23 | 179 | 5.40 | 6.36 | (0.134, 0.100) | 63 |
| Example 24 | 183 | 5.56 | 5.91 | (0.134, 0.100) | 58 |
| Example 25 | 215 | 5.19 | 7.15 | (0.134, 0.100) | 82 |
| Example 26 | 251 | 5.42 | 6.88 | (0.134, 0.100) | 62 |
| Example 27 | 256 | 5.42 | 6.56 | (0.134, 0.102) | 65 |
| Example 28 | 266 | 5.46 | 6.81 | (0.134, 0.101) | 62 |
| Example 29 | 268 | 5.30 | 6.72 | (0.134, 0.102) | 63 |
| Example 30 | 279 | 5.37 | 6.35 | (0.134, 0.100) | 58 |
| Example 31 | 284 | 5.42 | 6.34 | (0.134, 0.100) | 59 |
| Example 32 | 288 | 5.49 | 6.68 | (0.134, 0.100) | 63 |
| Example 33 | 307 | 5.42 | 6.77 | (0.134, 0.100) | 62 |
| Example 34 | 324 | 5.56 | 6.18 | (0.134, 0.100) | 45 |
| Example 35 | 337 | 5.12 | 6.20 | (0.134, 0.100) | 59 |
| Example 36 | 351 | 5.09 | 6.97 | (0.134, 0.100) | 64 |
| Example 37 | 356 | 5.41 | 6.76 | (0.134, 0.100) | 60 |
| Example 38 | 366 | 5.21 | 5.45 | (0.134, 0.100) | 56 |
| Example 39 | 389 | 5.42 | 6.88 | (0.134, 0.102) | 56 |
| Example 40 | 423 | 4.96 | 6.84 | (0.134, 0.101) | 57 |
| Example 41 | 461 | 5.14 | 6.79 | (0.134, 0.102) | 57 |
| Comparative Example 1-1 | E1 | 5.69 | 6.11 | (0.134, 0.100) | 52 |
| Comparative Example 1-2 | E2 | 5.62 | 6.07 | (0.134, 0.101) | 55 |
| Comparative Example 1-3 | E3 | 5.89 | 4.87 | (0.134, 0.101) | 49 |

As seen from the results of Table 4, the organic light emitting device using the electron transfer layer material of the blue organic light emitting device of the present disclosure had lower driving voltage and significantly improved light emission efficiency and lifetime compared to the Comparative Examples 1-1 to 1-3. Particularly, it was identified that Compounds 1, 6, 215 and 284 were superior in all aspects of driving voltage, light emission efficiency and lifetime. It was identified that the organic light emitting device had a lowered driving voltage, and enhanced light emission efficiency and lifetime compared to Comparative Example 1-2 by, due to the heteroring formed in the spirofluorene structure, having an enhanced electron transfer ability and thereby having an improved balance between electrons and holes in the light emitting layer.

Such a result is considered to be due to the fact that, when using the disclosed compound having proper length and strength, and flatness as an electron transfer layer, a compound in an excited state is made by receiving electrons under a specific condition, and particularly when a hetero-skeleton site of the compound is formed in an excited state, excited energy moves to a stable state before the excited hetero-skeleton site goes through other reactions, and a relatively stabilized compound is capable of efficiently transferring electrons without the compound being decomposed or destroyed. For reference, compounds that are stable when excited are considered to be aryl or acene-based compounds or polycyclic hetero-compounds. Accordingly, it is considered that excellent results in all aspects of driving, efficiency and lifetime were obtained by the compound of the present disclosure enhancing enhanced electron-transfer properties or improved stability.

<Experimental Example 2> Manufacture of Organic Light Emitting Device

1) Manufacture of Organic Light Emitting Device

Comparative Example 2

A transparent indium tin oxide (ITO) electrode thin film obtained from glass for an organic light emitting device (OLED) (manufactured by Samsung-Corning Co., Ltd.) was ultrasonic cleaned using trichloroethylene, acetone, ethanol and distilled water consecutively for 5 minutes each, stored in isopropanol, and used.

Next, an ITO substrate was installed in a substrate folder of a vacuum deposition apparatus, and the following 4,4',4"-tris (N,N-(2-naphthyl)-phenylamino)triphenylamine (2-TNATA) was introduced to a cell in the vacuum deposition apparatus.

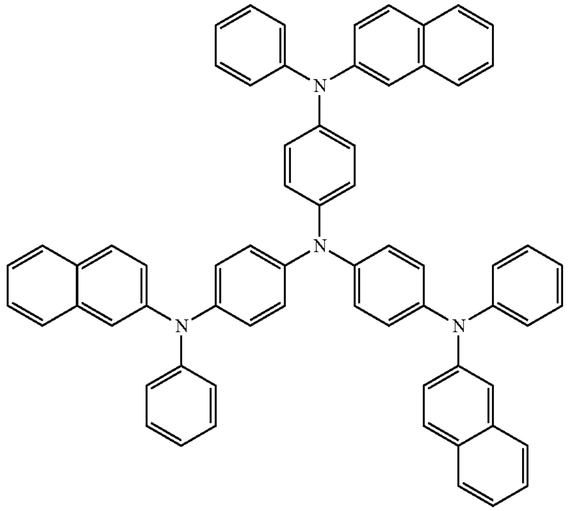

2-TNATA

Subsequently, the chamber was evacuated until the degree of vacuum therein reached $10^{-6}$ torr, and then 2-TNATA was evaporated by applying a current to the cell to deposit a hole injection layer having a thickness of 600 Å on the ITO substrate.

To another cell of the vacuum deposition apparatus, the following N,N'-bis(α-naphthyl)-N,N'-diphenyl-4,4'-diamine (NPB) was introduced, and evaporated by applying a current to the cell to deposit a hole transfer layer having a thickness of 300 Å on the hole injection layer.

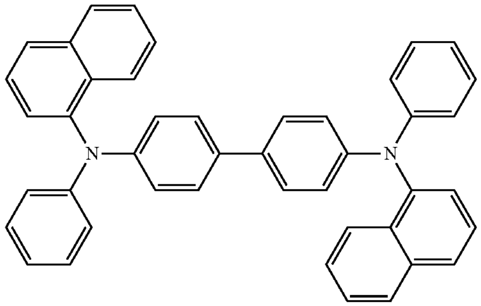

NPB

After forming the hole injection layer and the hole transfer layer as above, a blue light emitting material having a structure as below was deposited thereon as a light emitting layer. Specifically, in one side cell in the vacuum deposition apparatus, H1, a blue light emitting host material, was vacuum deposited to a thickness of 200 Å, and D1, a blue light emitting dopant material, was vacuum deposited thereon by 5% with respect to the host material.

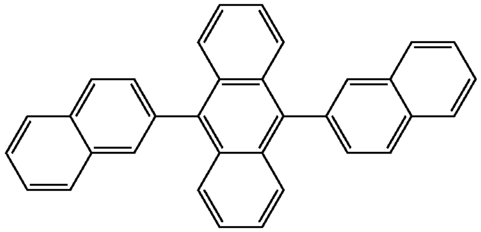

H1

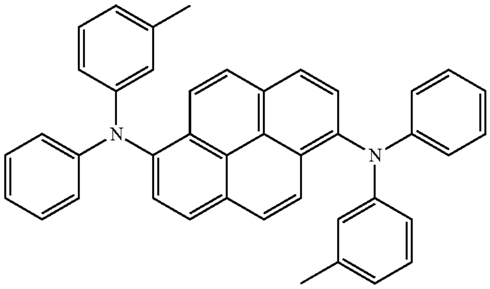

D1

Subsequently, the following structural formula E1 and LiQ were deposited in a weight ratio of 2:1 to a thickness of 300 Å to form an electron transfer layer.

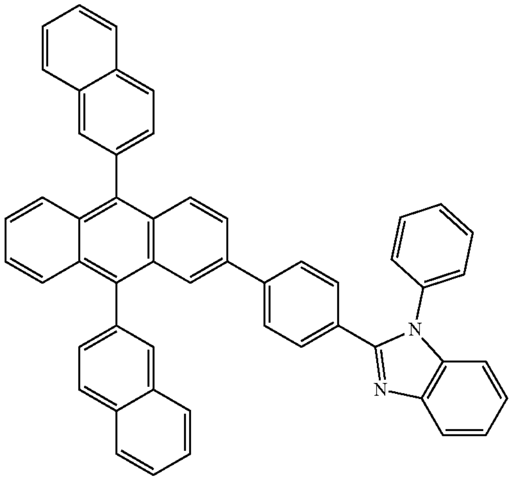

E1

As an electron injection layer, lithium fluoride (LiF) was deposited to a thickness of 10 Å, and an Al cathode was employed to a thickness of 1,000 Å, and as a result, an OLED was manufactured.

Meanwhile, all the organic compounds required to manufacture the OLED were vacuum sublimation purified under $10^{-6}$ torr to $10^{-8}$ torr by each material to be used in the OLED manufacture.

Examples 42 to 45

Organic light emitting devices were manufactured in the same manner as in Comparative Example 2 except that the electron transfer layer E1 was formed to a thickness of 250 Å, and then a hole blocking layer was formed on the electron transfer layer using a compound presented in the following Table 5 to a thickness of 50 Å.

Results of measuring driving voltage, light emission efficiency, color coordinate (CIE) and lifetime of the blue organic light emitting devices manufactured according to the present disclosure are as shown in the following Table 5.

TABLE 5

| | Compound | Driving Voltage (V) | Light Emission Efficiency (cd/A) | CIE (x, y) | Life-time ($T_{95}$) |
|---|---|---|---|---|---|
| Example 42 | 23 | 4.87 | 6.27 | (0.134, 0.101) | 90 |
| Example 43 | 423 | 4.73 | 6.57 | (0.134, 0.102) | 92 |
| Example 44 | 546 | 5.11 | 6.55 | (0.134, 0.101) | 95 |
| Example 45 | 547 | 4.87 | 6.53 | (0.134, 0.103) | 89 |
| Comparative Example 2 | — | 5.50 | 5.57 | (0.134, 0.100) | 50 |

As seen from the results of Table 5, the organic light emitting device using the hole blocking layer material of the blue organic light emitting device of the present disclosure had lower driving voltage and significantly improved light emission efficiency and lifetime compared to Comparative Example 2.

<Experimental Example 3> Manufacture of Organic Light Emitting Device

1) Manufacture of Organic Light Emitting Device

Comparative Example 3 and Examples 46 to 51

A transparent indium tin oxide (ITO) electrode thin film obtained from glass for an organic light emitting device (OLED) (manufactured by Samsung-Corning Co., Ltd.) was ultrasonic cleaned using trichloroethylene, acetone, ethanol and distilled water consecutively for 5 minutes each, stored in isopropanol, and used.

On the transparent ITO electrode (anode), organic materials were formed in a 2-stack white organic light emitting device (WOLED) structure. As for the first stack, TAPC was thermal vacuum deposited first to a thickness of 300 Å to form a hole transfer layer. After forming the hole transfer layer, a light emitting layer was thermal vacuum deposited thereon as follows. As the light emitting layer, TCz1, a host, was 8% doped with FIrpic, a blue phosphorescent dopant, and deposited to 300 Å. After forming an electron transfer layer to 400 Å using TmPyPB, the compound described in the following Table 6 was 20% doped with $Cs_2CO_3$ to form a charge generation layer to 100 Å.

As for the second stack, $MoO_3$ was thermal vacuum deposited first to a thickness of 50 Å to form a hole injection layer. A hole transfer layer, a common layer, was formed to 100 Å by 20% doping $MoO_3$ to TAPC and then depositing TAPC to 300 Å. A light emitting layer was formed by 8% doping $Ir(ppy)_3$, a green phosphorescent dopant, to TCz1, a host, and depositing the result to 300 Å, and then an electron transfer layer was formed to 600 Å using TmPyPB. Lastly, an electron injection layer was formed on the electron transfer layer by depositing lithium fluoride (LiF) to a thickness of 10 Å, and then a cathode was formed on the electron injection layer by depositing an aluminum (Al) cathode to a thickness of 1,200 Å, and as a result, an organic light emitting device was manufactured.

Meanwhile, all the organic compounds required to manufacture the OLED were vacuum sublimation purified under $10^{-6}$ torr to $10^{-8}$ torr for each material to be used in the OLED manufacture.

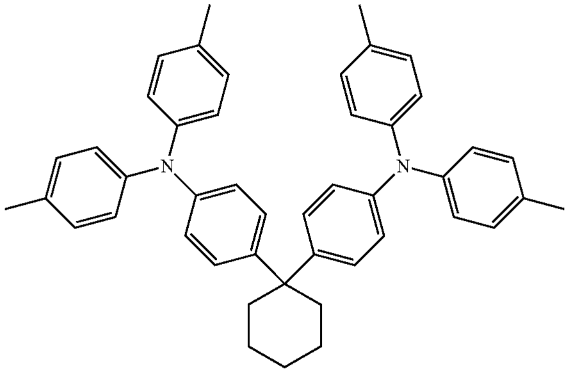

TAPC

-continued

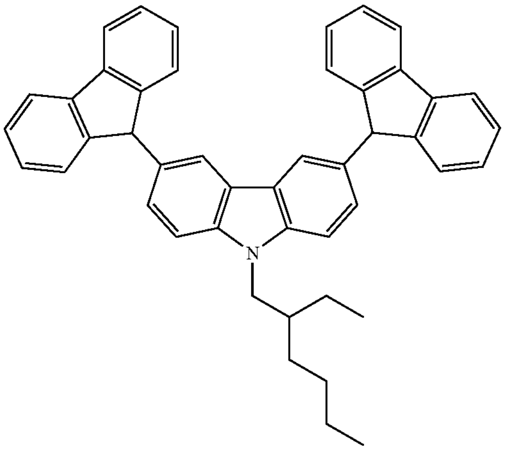

TCz1

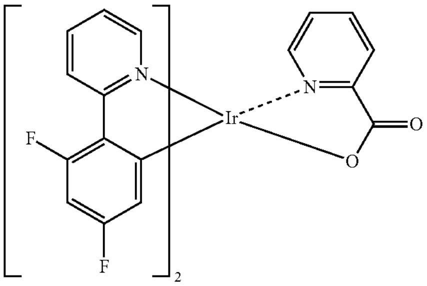

FIrpic

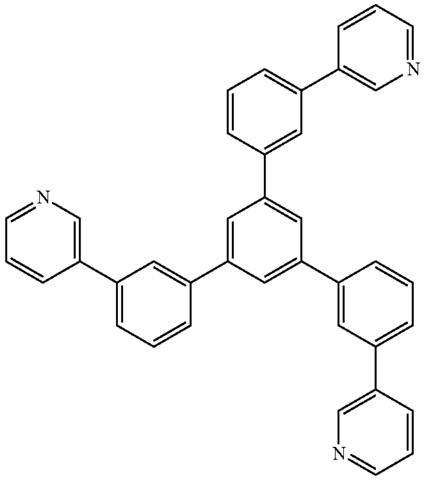

TmPyPB

-continued

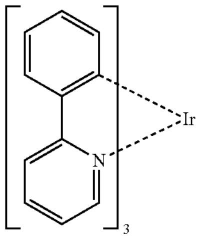

Ir(ppy)3

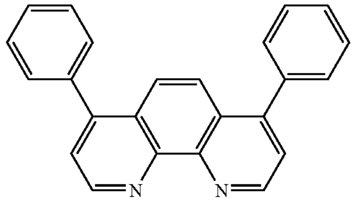

BPhen

Results of measuring driving voltage, light emission efficiency, color coordinate (CIE) and lifetime of the white organic light emitting devices manufactured according to the present disclosure are as shown in the following Table 6.

TABLE 6

| | Compound | Driving Voltage (V) | Light Emission Efficiency (cd/A) | CIE (x, y) | Life-time ($T_{95}$) |
|---|---|---|---|---|---|
| Example 46 | 11 | 6.78 | 58.24 | (0.213, 0.430) | 48 |
| Example 47 | 36 | 6.84 | 60.44 | (0.212, 0.421) | 42 |
| Example 48 | 111 | 6.44 | 66.32 | (0.211, 0.433) | 49 |
| Example 49 | 161 | 6.92 | 59.68 | (0.214, 0.439) | 52 |
| Example 50 | 336 | 6.27 | 67.99 | (0.212, 0.424) | 53 |
| Example 51 | 389 | 6.82 | 59.18 | (0.214, 0.437) | 48 |
| Comparative Example 3 | BPhen | 7.54 | 54.23 | (0.213, 0.430) | 37 |

As seen from the results of Table 6, the organic light emitting device using the charge generation layer material of the 2-stack white organic light emitting device of the present disclosure had lower driving voltage and improved light emission efficiency compared to Comparative Example 3. Such a result is considered to be due to the fact that the compound of the present disclosure used as an N-type charge generation layer formed with the disclosed skeleton having proper length and strength, and flatness and a proper hetero-compound capable of binding to metals forms a gap state in the N-type charge generation layer by doping an alkali metal or an alkaline earth metal, and electrons produced from a P-type charge generation layer are readily injected into an electron transfer layer through the gap state produced in the N-type charge generation layer. Accordingly, the P-type charge generation layer may favorably inject and transfer electrons to the N-type charge generation layer, and as a result, driving voltage was lowered, and light emission efficiency and lifetime were improved in the organic light emitting device.

The invention claimed is:

1. A heterocyclic compound represented by one of the following Chemical Formulae 6 to 8:

[Chemical Formula 6]

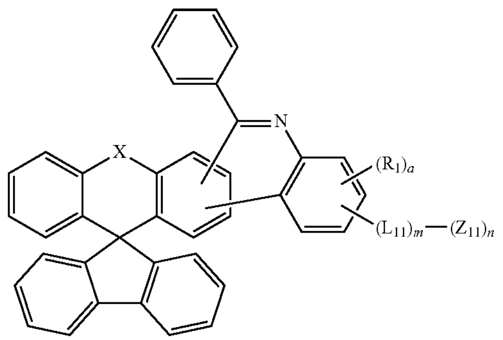

[Chemical Formula 7]

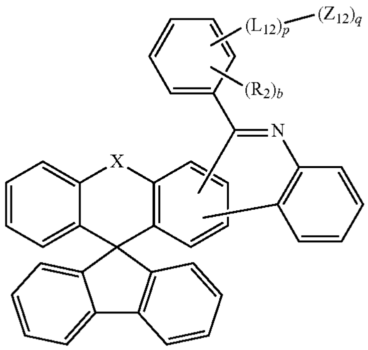

[Chemical Formula 8]

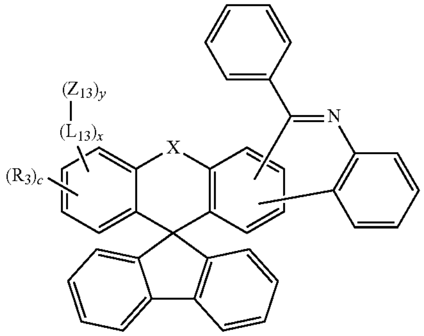

in Chemical Formulae 6 to 8,

X is O; S; or $NR_{21}$, $R_1$ to $R_3$ are the same as or different from each other, and are each independently selected from the group consisting of hydrogen; deuterium; a halogen group; a cyano group; a substituted or unsubstituted alkyl group; a substituted or unsubstituted alkenyl group; a substituted or unsubstituted alkynyl group; a substituted or unsubstituted alkoxy group; a substituted or unsubstituted cycloalkyl group; a substituted or unsubstituted heterocycloalkyl group; a substituted or unsubstituted aryl group; a substituted or unsubstituted heteroaryl group; a substituted or unsubstituted phosphine oxide group; and a substituted or unsubstituted amine group, $R_{21}$ is hydrogen; or a substituted or unsubstituted aryl group, m, p, x, n, q and y are each an integer of 1 to 5, a is an integer of 1 to 3, b is an integer of 1 to 4, c is an integer of 1 to 3, when m, p, x, n, q, y, a, b and c are an integer of 2 or greater, substituents in the parentheses are the same as or different from each other, $L_{11}$ to $L_{13}$ are the same as or different from each other, and are each independently a direct bond; a substituted or unsubstituted arylene group; or a substituted or unsubstituted heteroarylene group; and $Z_{11}$ to $Z_{13}$ are the same as or different from each other, and are each independently selected from the group consisting of an anthracene group unsubstituted or substituted with a biphenyl group; a triphenylene group; a triazine group unsubstituted or substituted with one or more substituents selected from the group consisting of a phenyl group, a biphenyl group, a dibenzofuran group and a dibenzothiophene group; a pyrimidine group unsubstituted or substituted with one or more substituents selected from the group consisting of a phenyl group, a biphenyl group, a dibenzofuran group and a dibenzothiophene group; a pyridine group unsubstituted or substituted with a pyridine group; a carbazole group unsubstituted or substituted with a cyano group; a quinazoline group unsubstituted or substituted with a phenyl group; a quinoxaline group unsubstituted or substituted with a phenyl group; an imidazole group unsubstituted or substituted with a phenyl group; a phenanthroline group unsubstituted or substituted with a phenyl group; a benzo [4,5] thieno [3,2-d]pyrimidine group unsubstituted or substituted with a phenyl group; and a phosphine oxide group unsubstituted or substituted with a phenyl group.

2. The heterocyclic compound of claim 1, wherein $R_1$ to $R_3$ are hydrogen.

3. An organic light emitting device comprising:

a first electrode;

a second electrode; and one or more organic material layers provided between the first electrode and the second electrode, wherein one or more of the one or more organic material layers comprise the heterocyclic compound of claim 1.

4. The organic light emitting device of claim 3, wherein the one or more organic material layers comprise an electron transfer layer, and the electron transfer layer comprises the heterocyclic compound.

5. The organic light emitting device of claim 3, wherein the one or more organic material layers comprise a hole blocking layer, and the hole blocking layer comprises the heterocyclic compound.

6. The organic light emitting device of claim 3, further comprising one, two or more layers selected from the group consisting of a light emitting layer, a hole injection layer, a hole transfer layer, an electron injection layer, an electron transfer layer, an electron blocking layer and a hole blocking layer.

7. The organic light emitting device of claim 3, wherein the one or more organic material layers comprise a first stack, a charge generation layer and a second stack, wherein the first stack is provided on the first electrode and comprises a first light emitting layer;

wherein the charge generation layer is provided on the first stack; and wherein the second stack is provided on the charge generation layer and comprises a second light emitting layer.

8. The organic light emitting device of claim 7, wherein the charge generation layer comprises the heterocyclic compound represented by one of the Chemical Formulae 6 to 8.

9. The organic light emitting device of claim 7, wherein the charge generation layer is an N-type charge generation layer, and the charge generation layer comprises the heterocyclic compound represented by one of the Chemical Formulae 6 to 8.

10. A heterocyclic compound represented by any one of the following compounds:

1

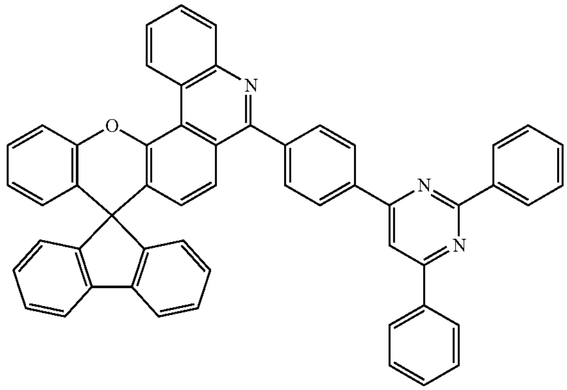

2

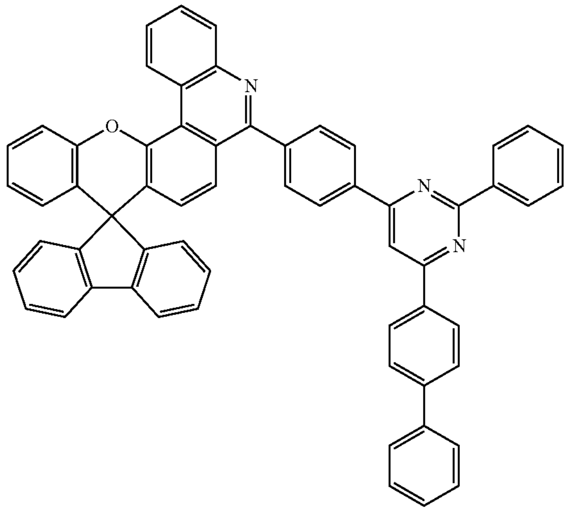

-continued

3

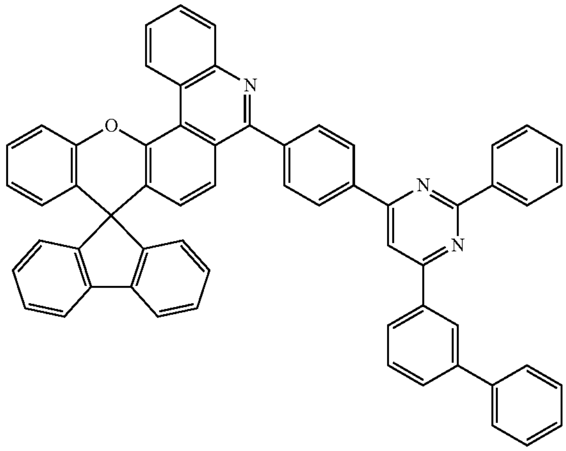

4

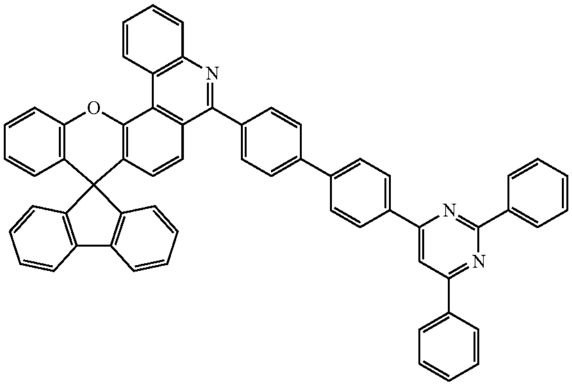

5

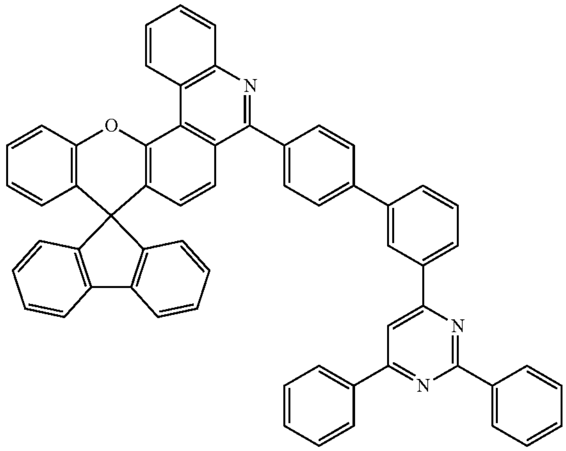

-continued
6
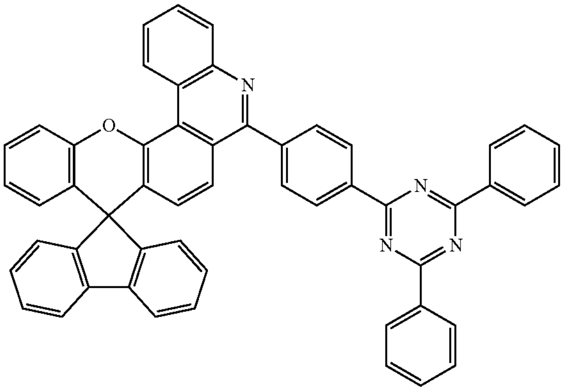
7
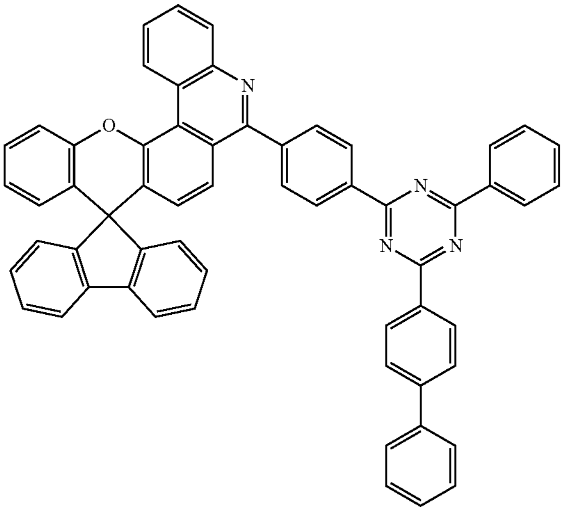
8
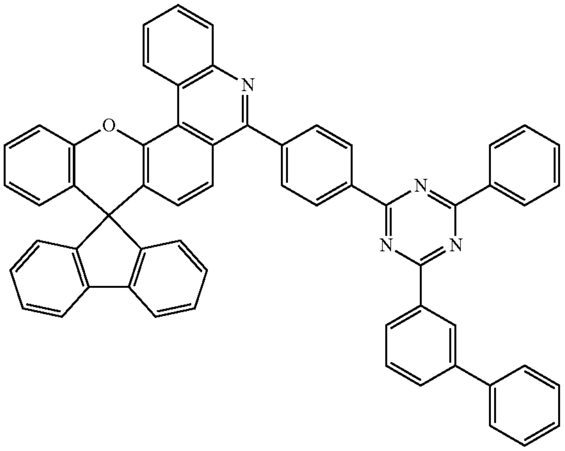
-continued
9
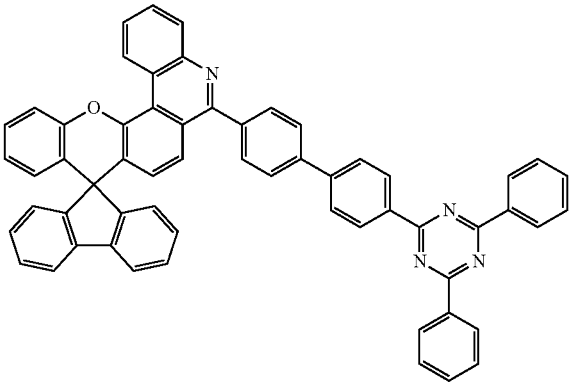
10
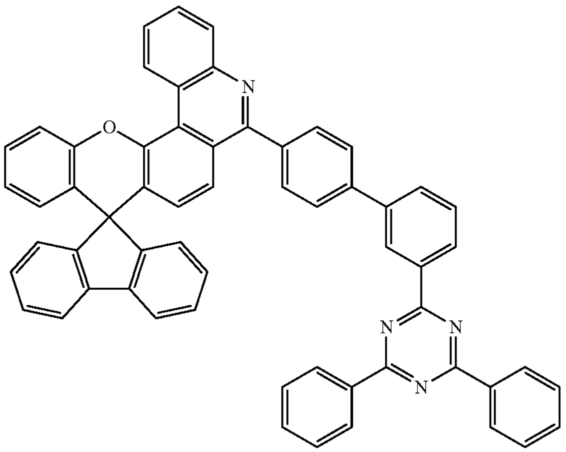
11
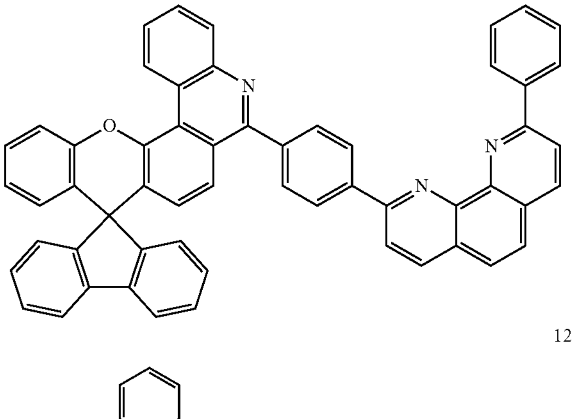
12
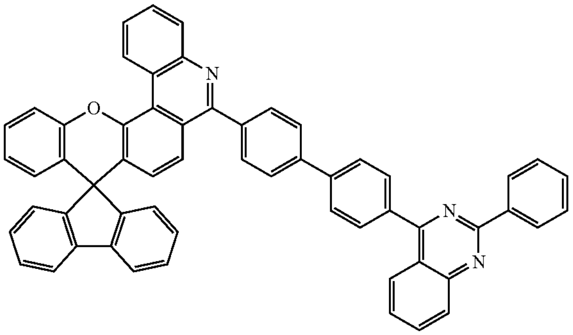

-continued
13
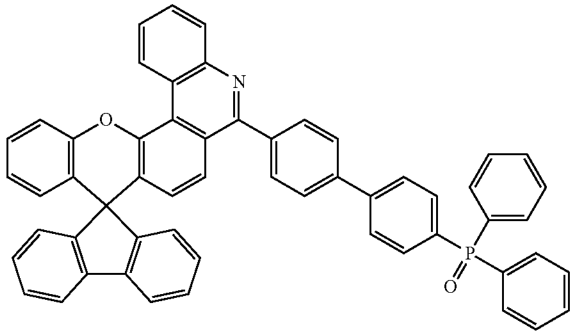
14
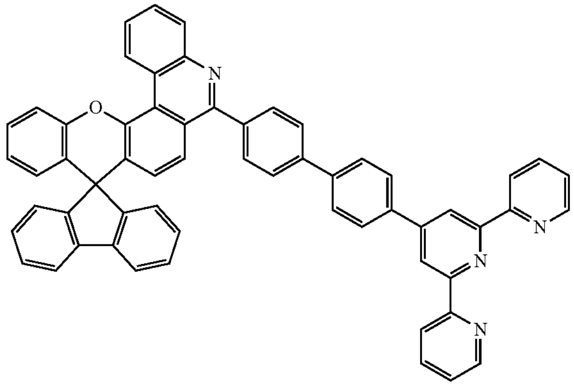
15
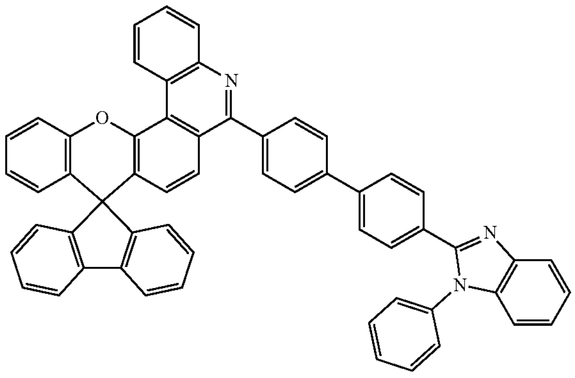
16
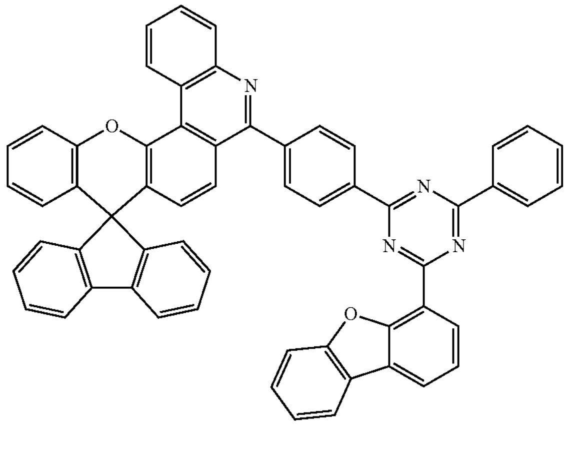
-continued
17
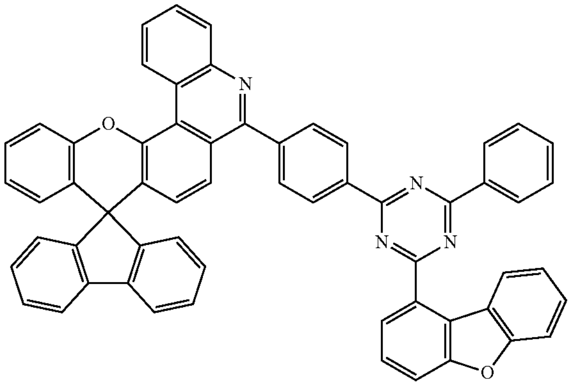
18
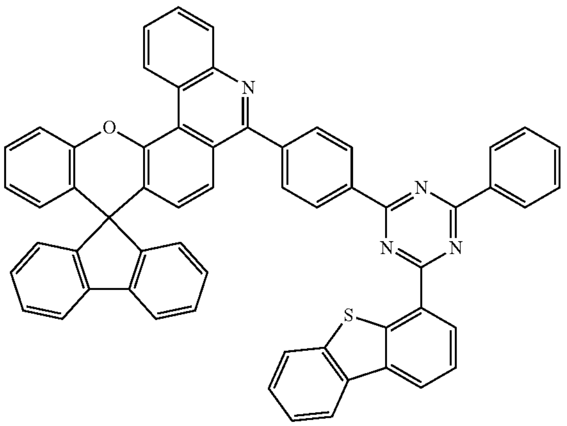
19
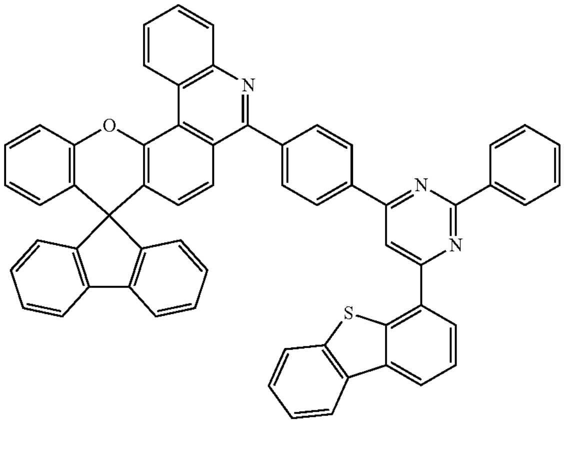

-continued
20
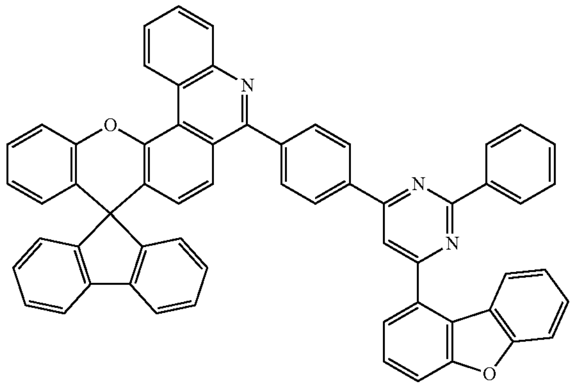
21
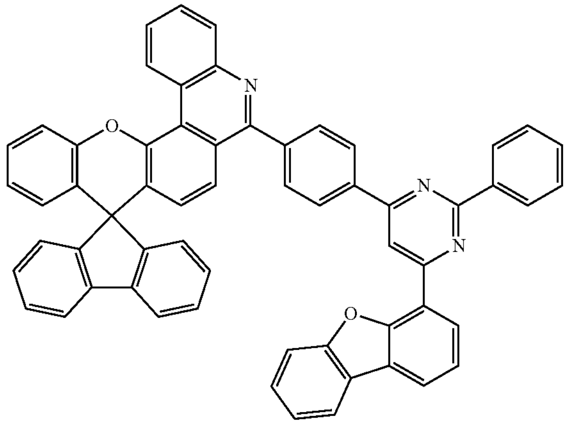
22
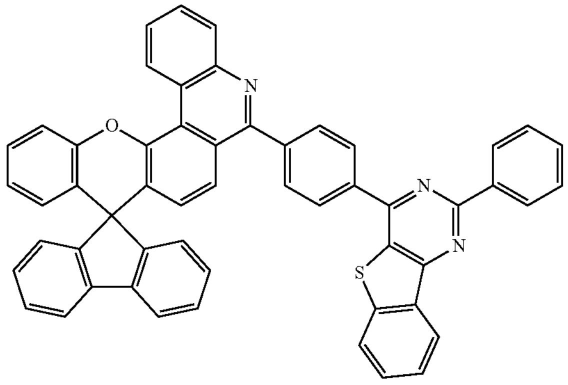
23
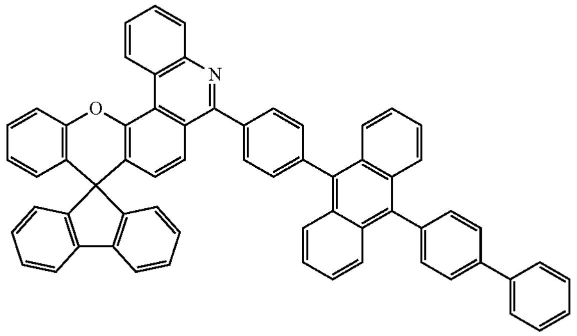
-continued
24
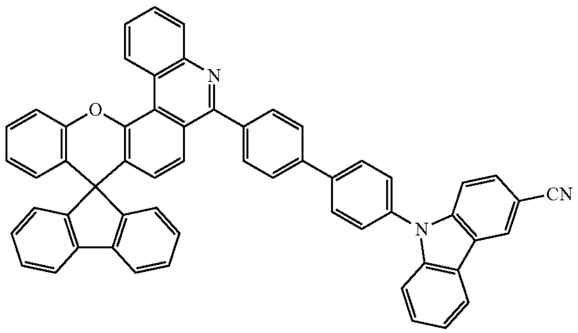
25
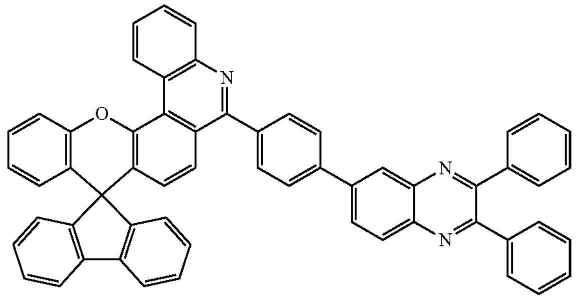
26
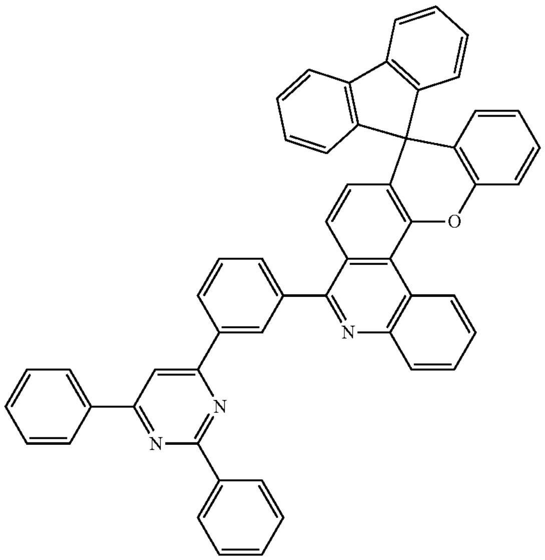

-continued
27
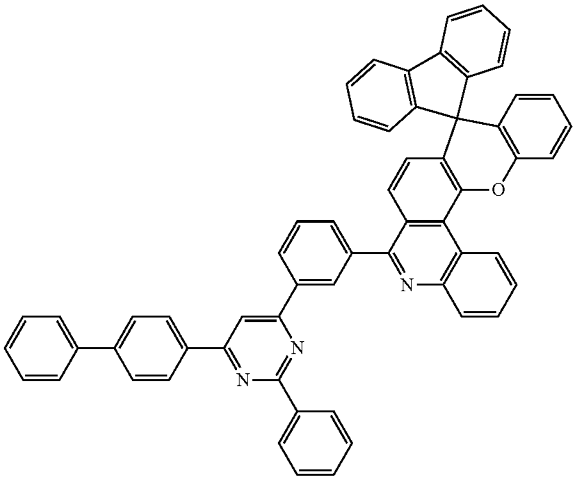
28
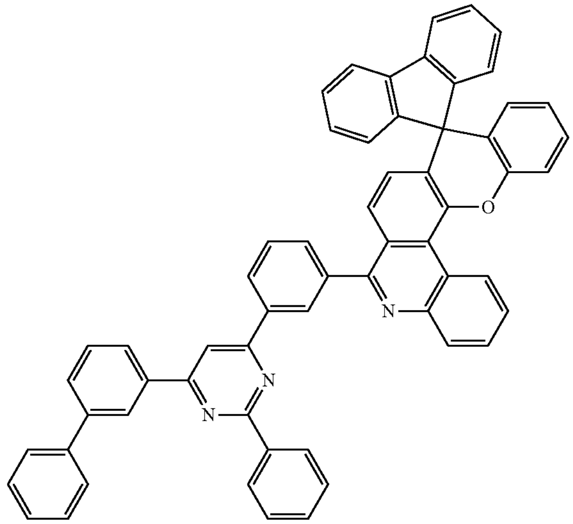
29
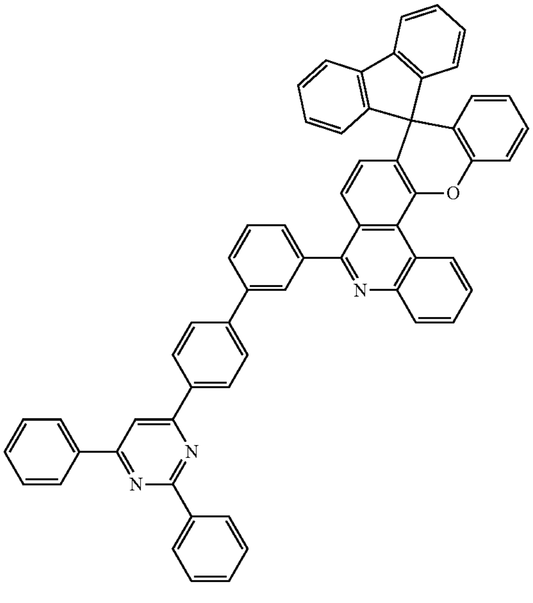
-continued
30
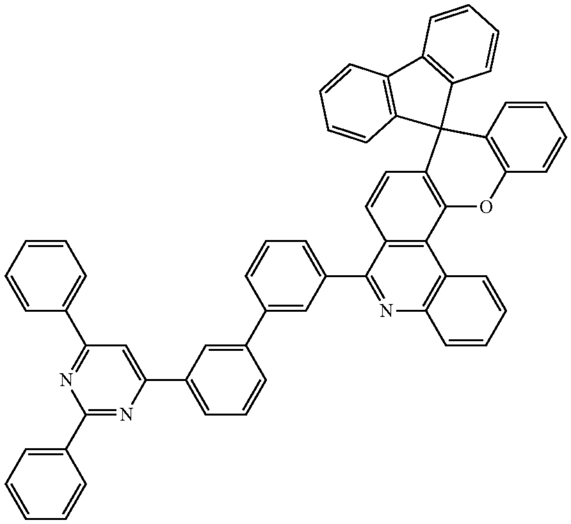
31
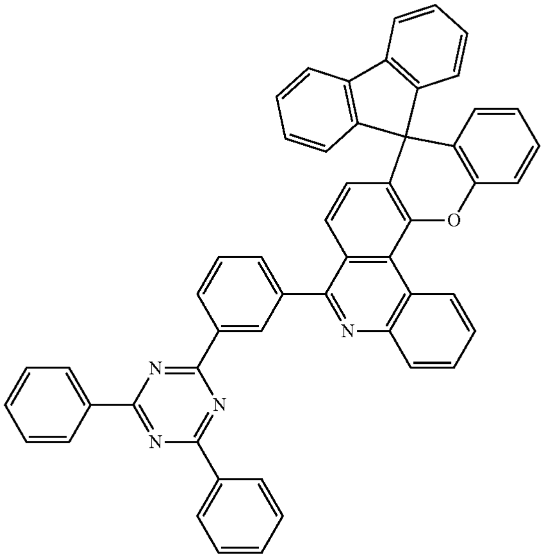
32
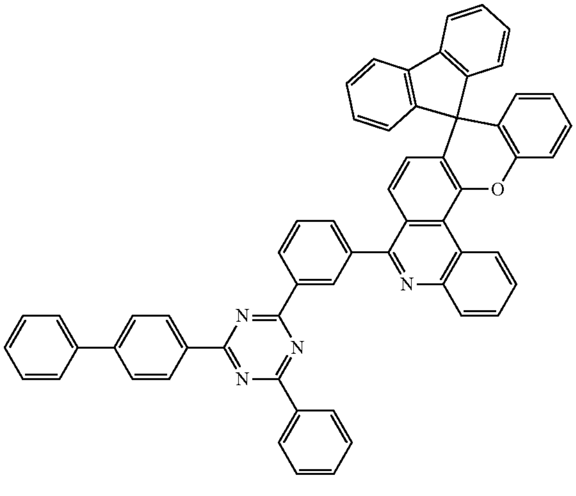

-continued
33
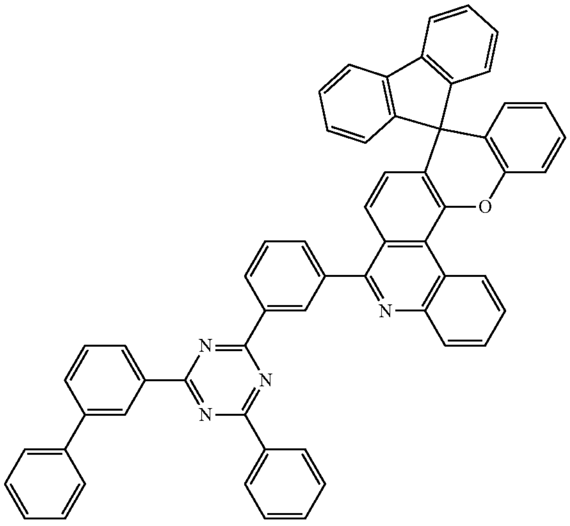
34
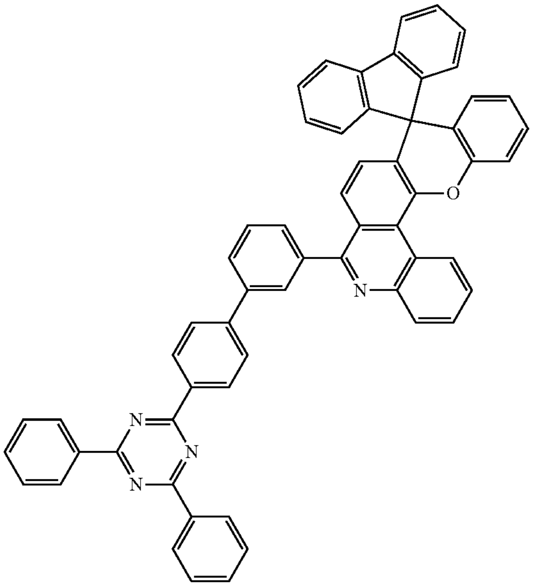
-continued
35
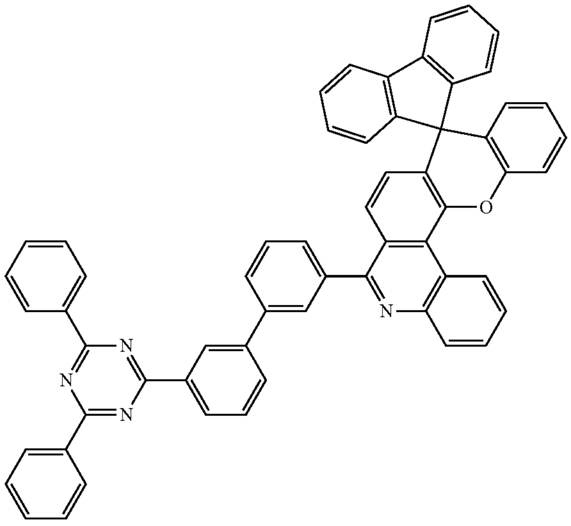
36
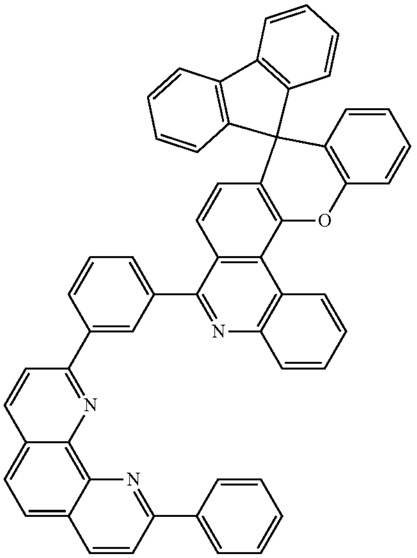

-continued
37
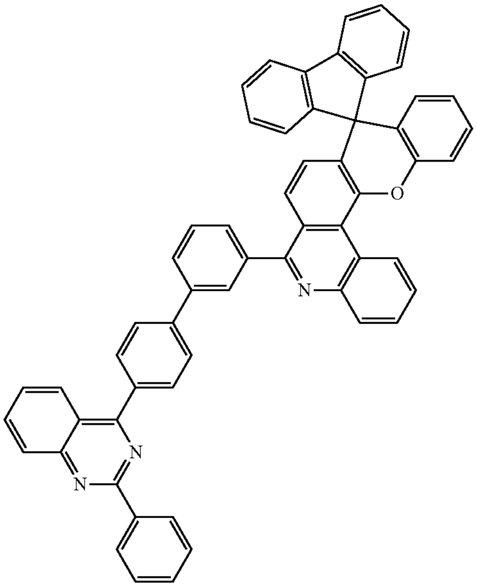
38
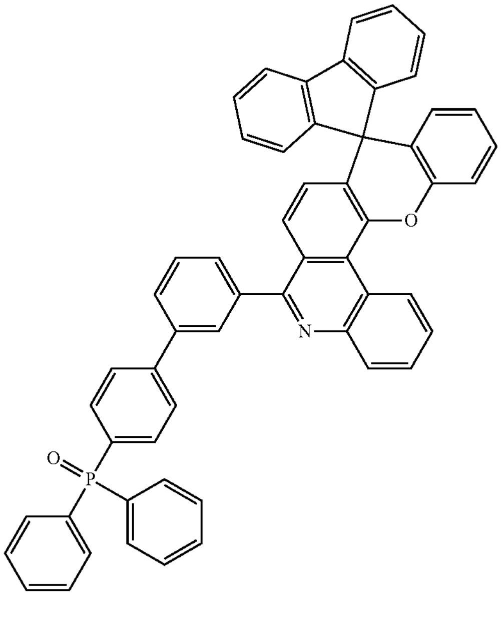
-continued
39
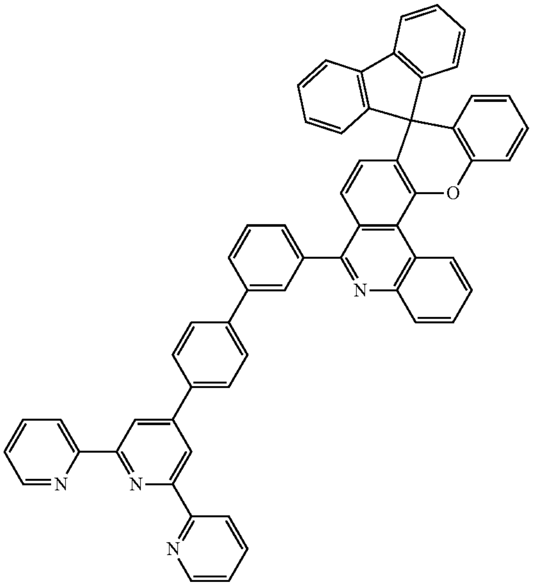
40
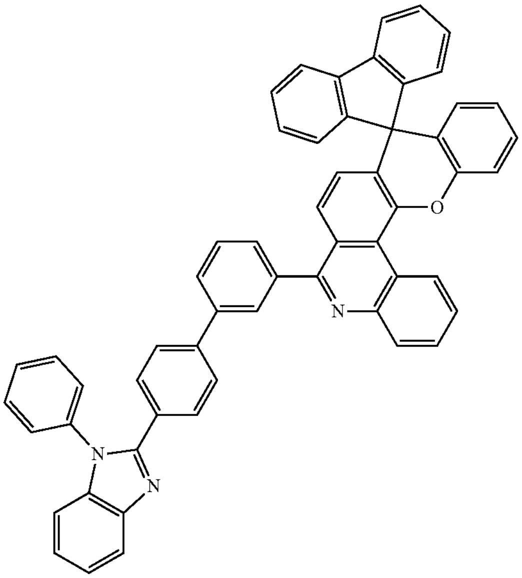

-continued
41
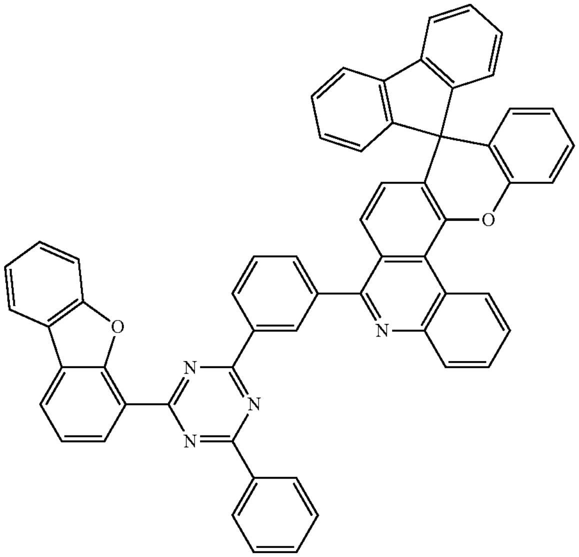
42
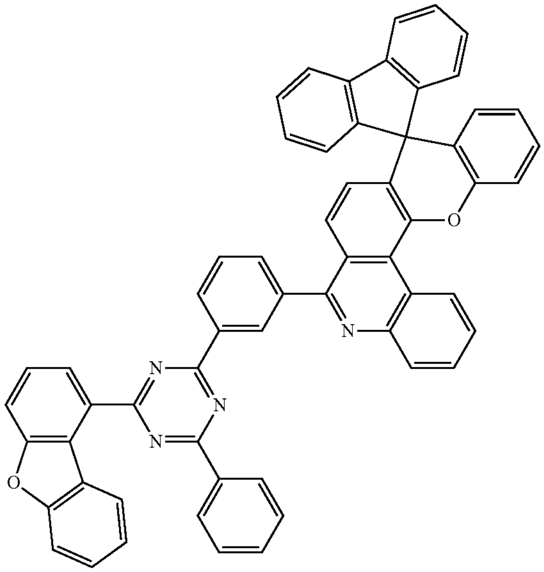
-continued
43
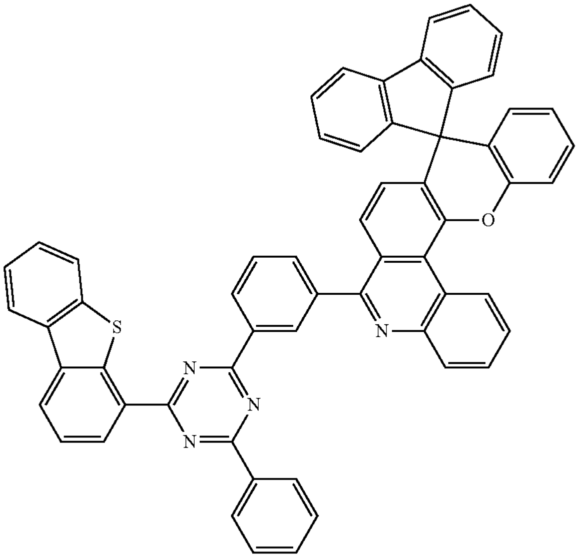
44
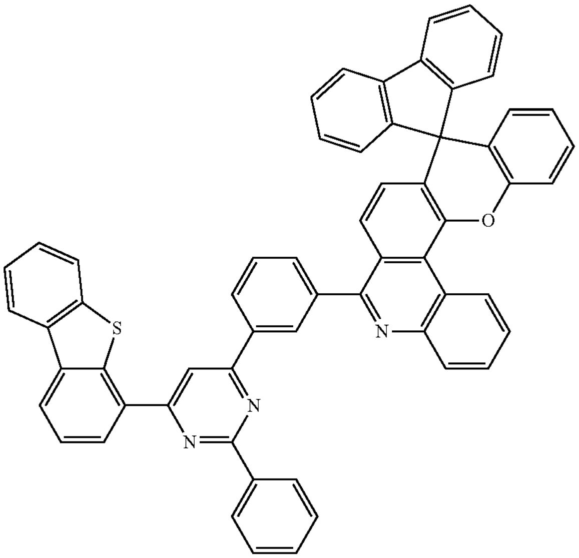

-continued
45
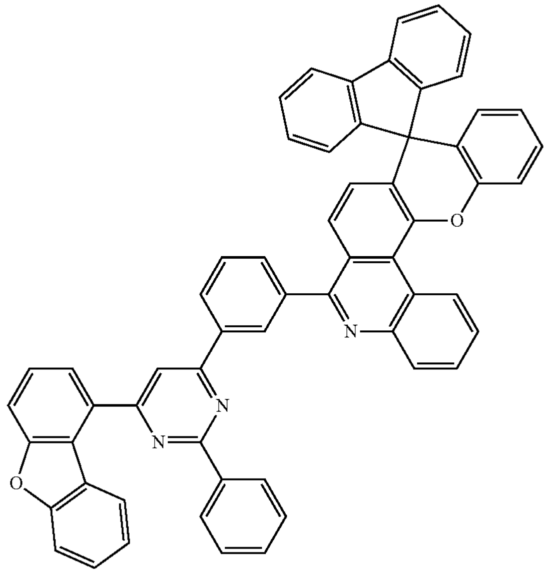
-continued
47
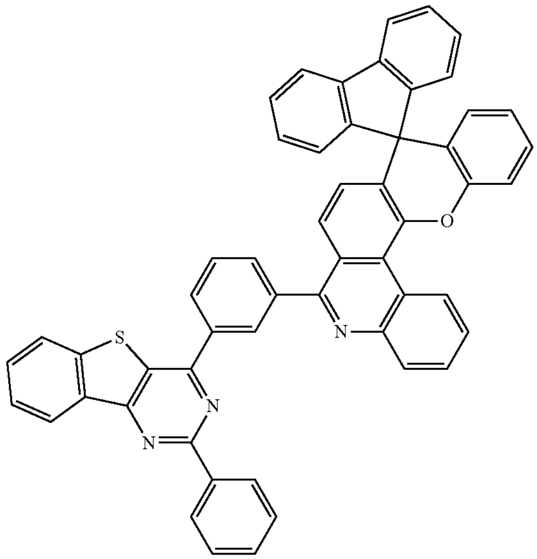
46
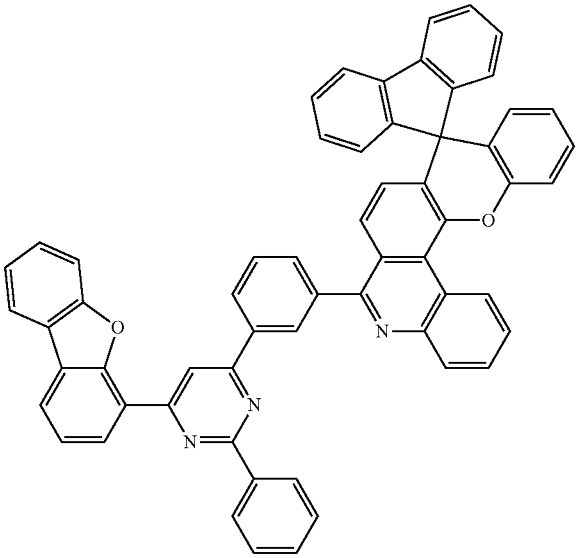
48
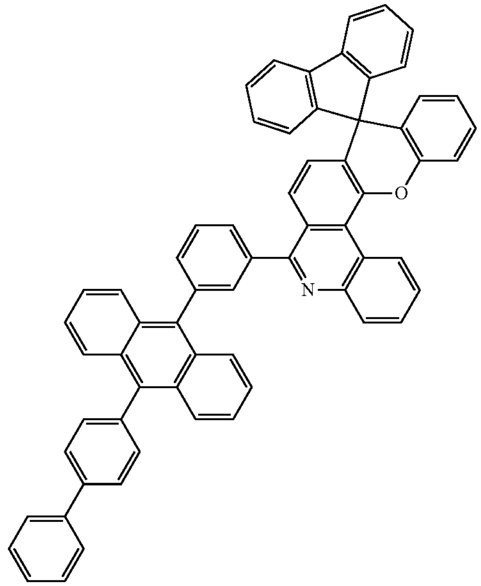

-continued
49
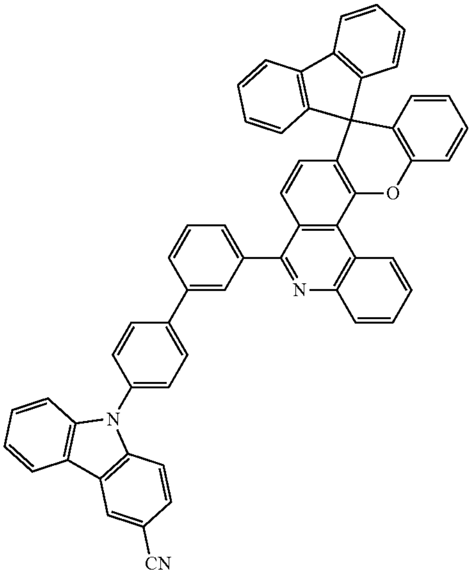
50
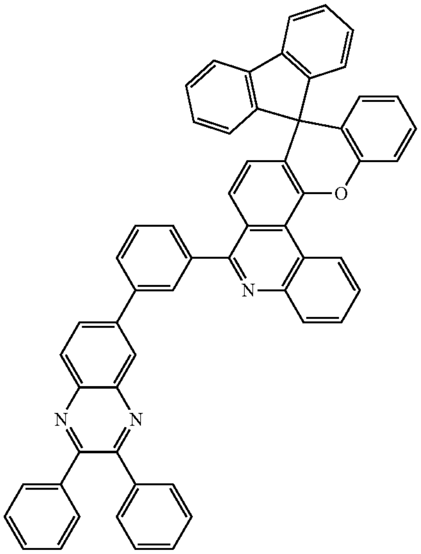
51
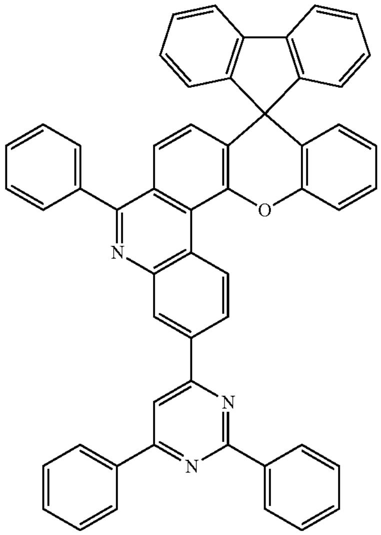
-continued
52
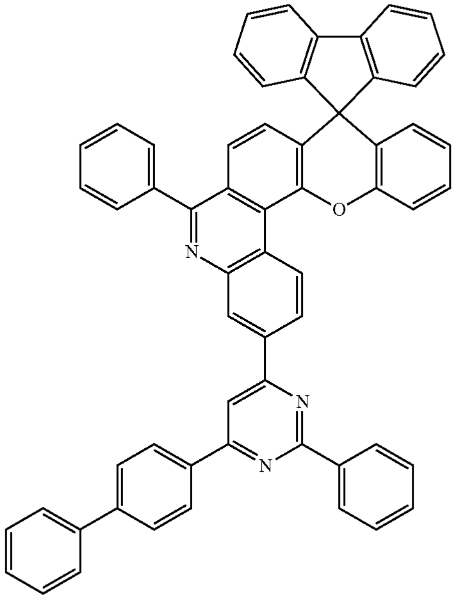
53
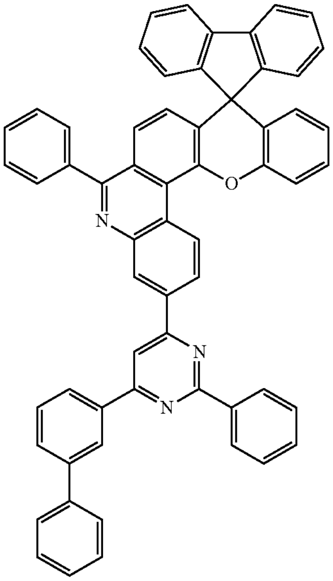

-continued
54
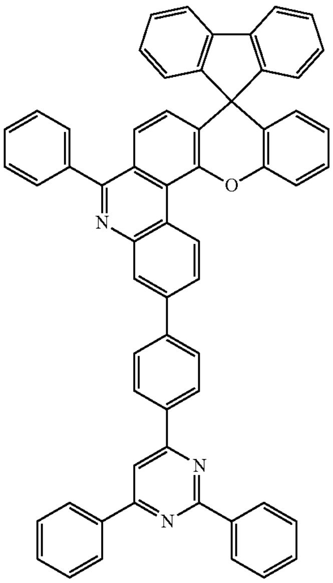
55
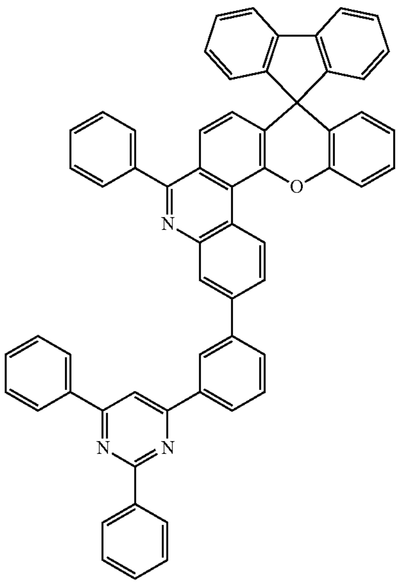
-continued
56
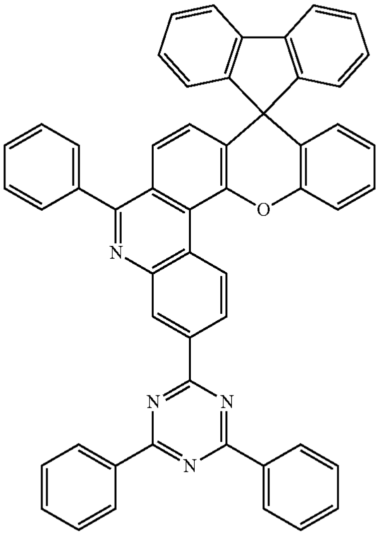
57
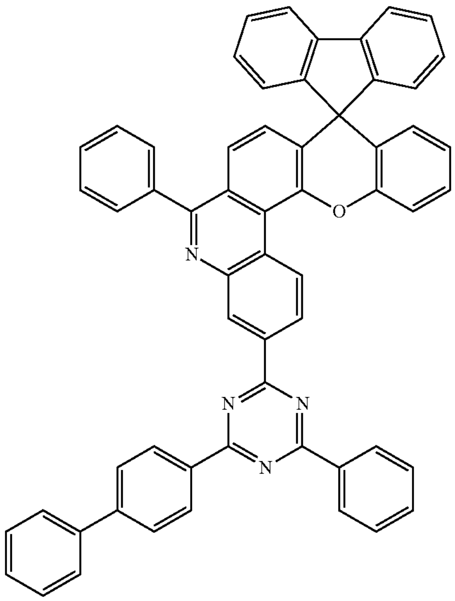

-continued
58
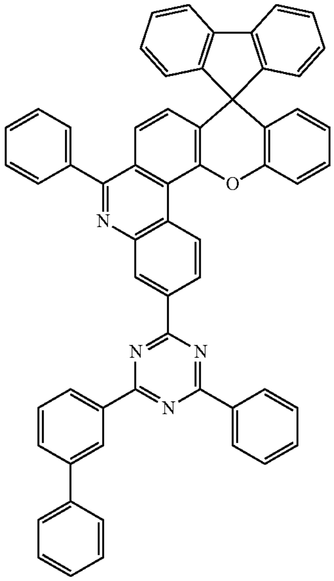
59
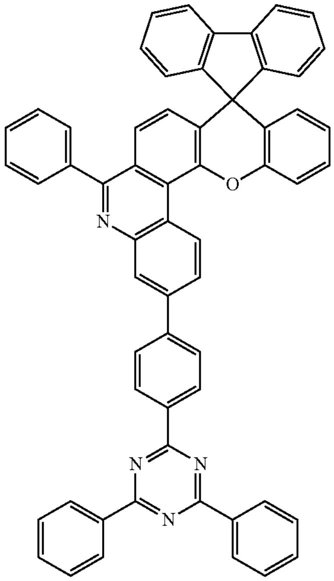
-continued
60
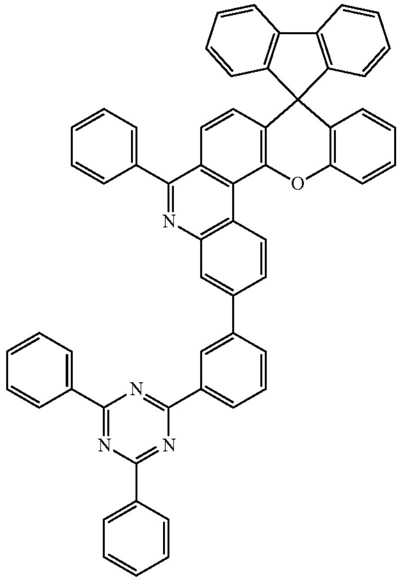
61
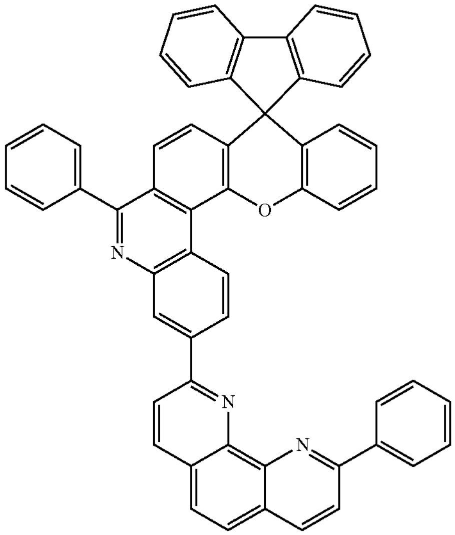

-continued
62
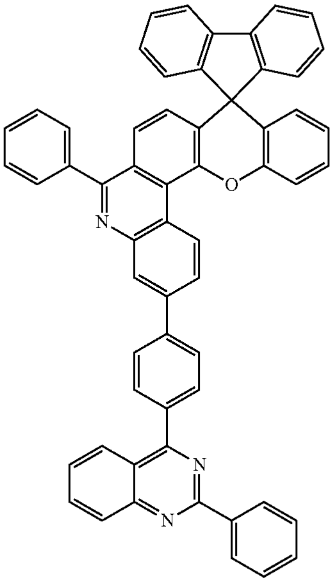
63
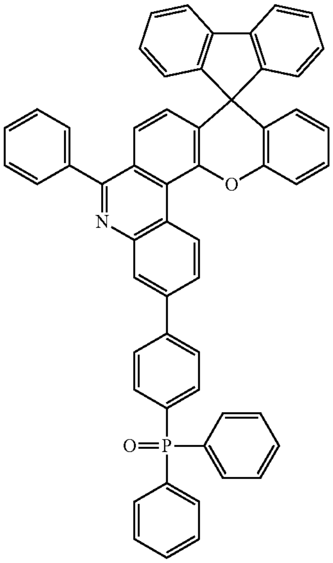
-continued
64
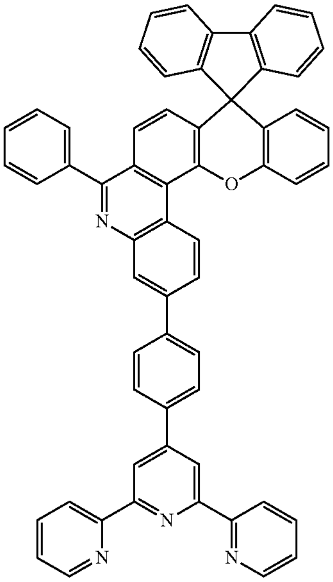
65
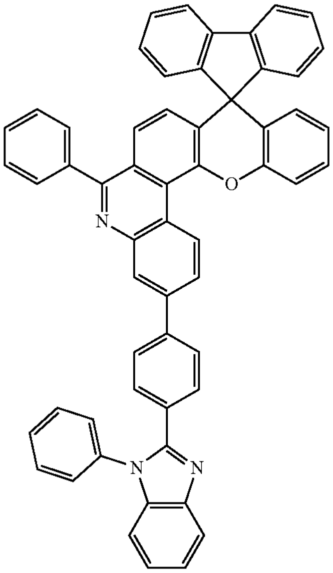

66
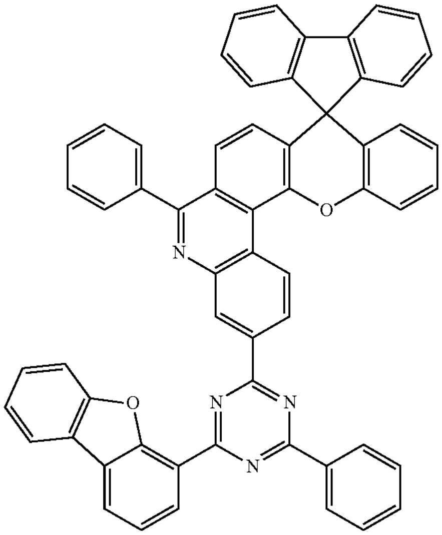
67
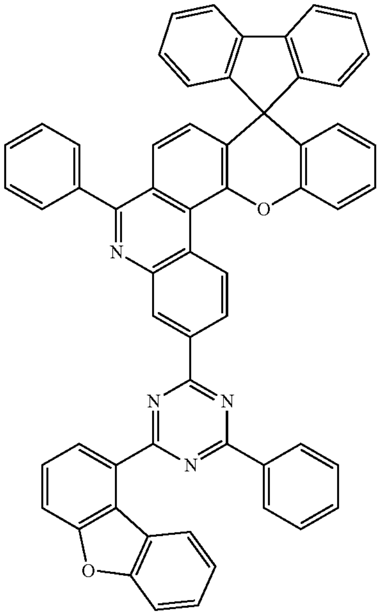
68
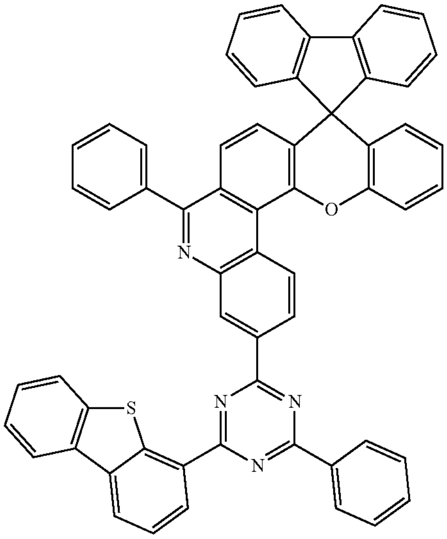
69
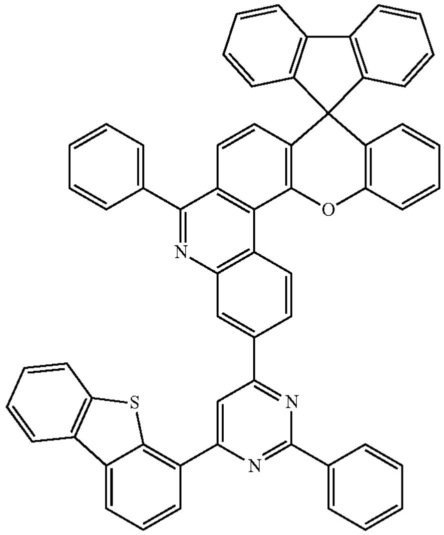

-continued
70
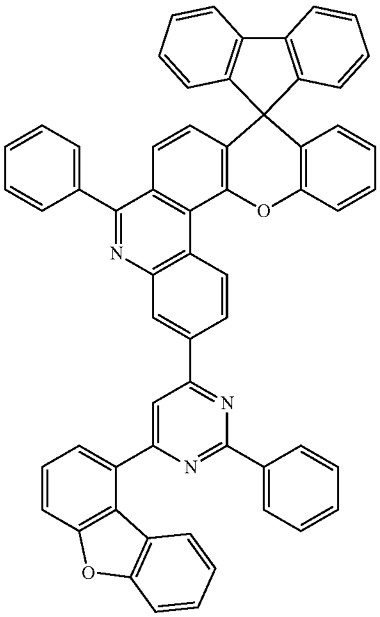
71
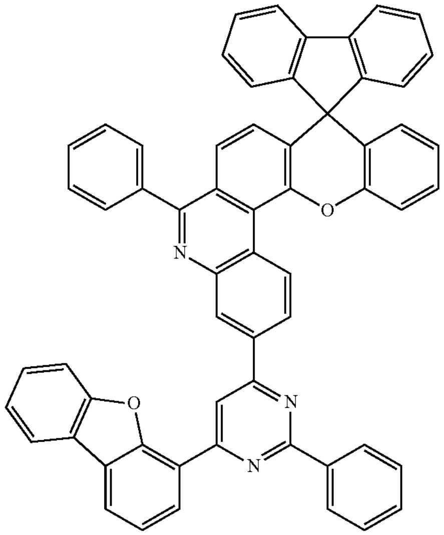
-continued
72
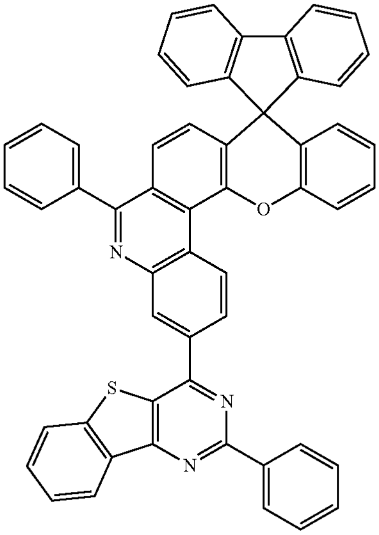
73
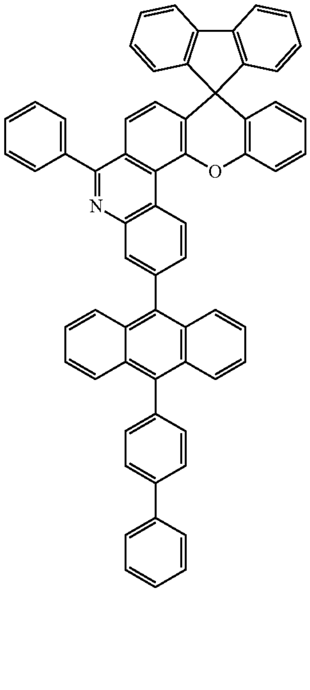

-continued
74
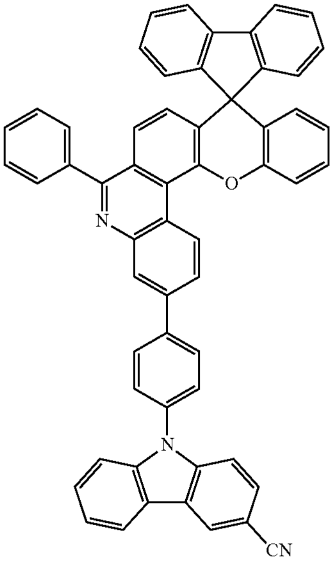
76
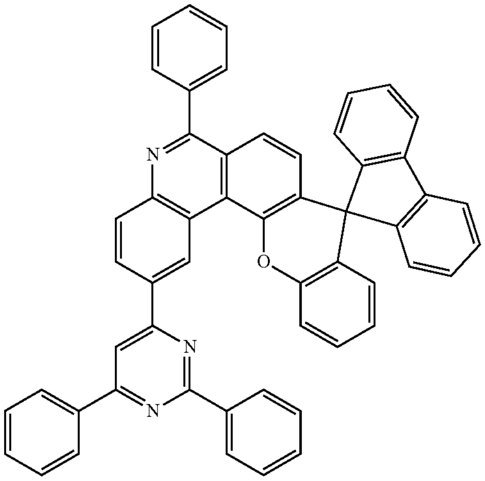
77
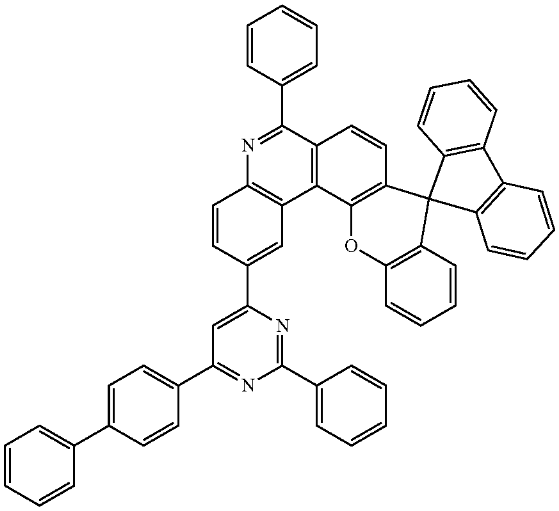
75
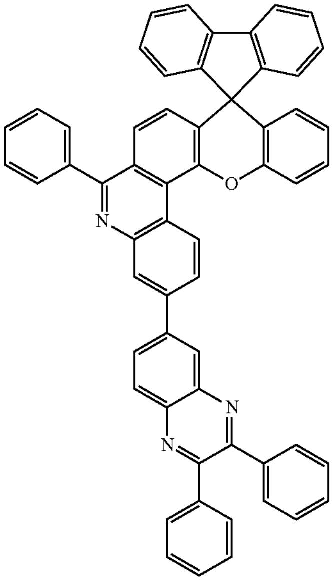
78
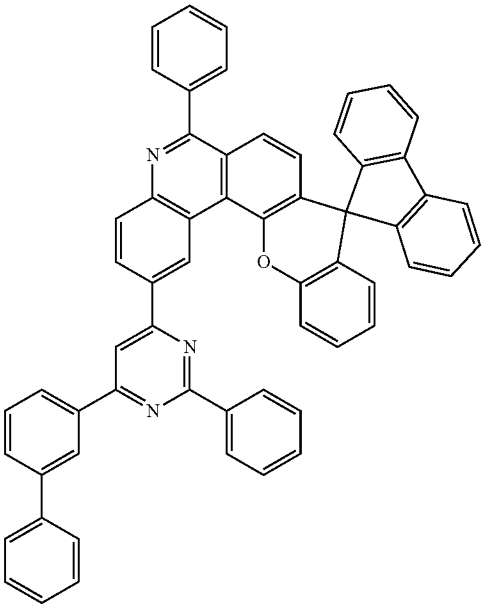

-continued
79
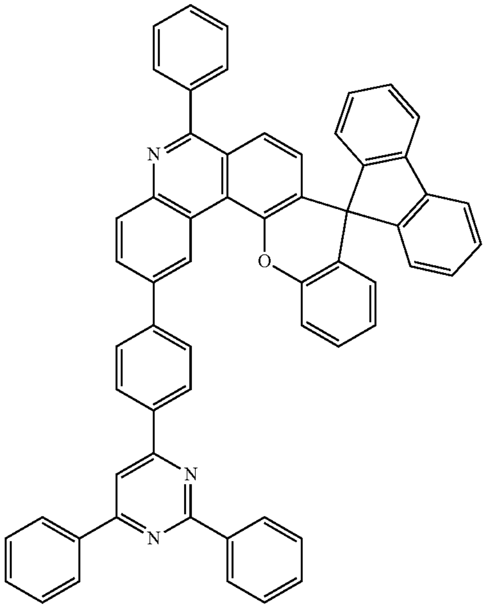
80
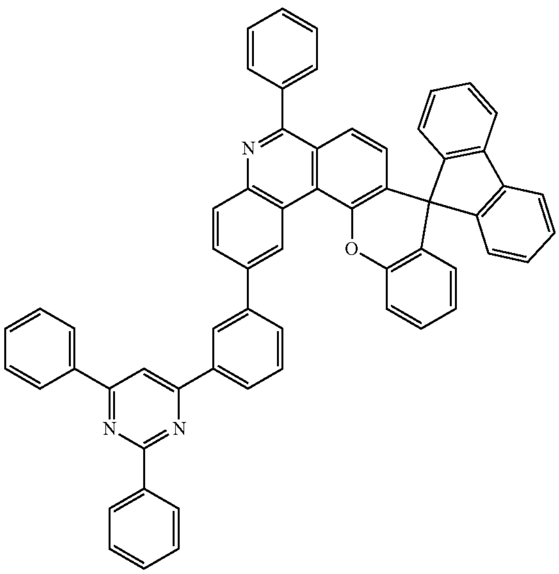
-continued
81
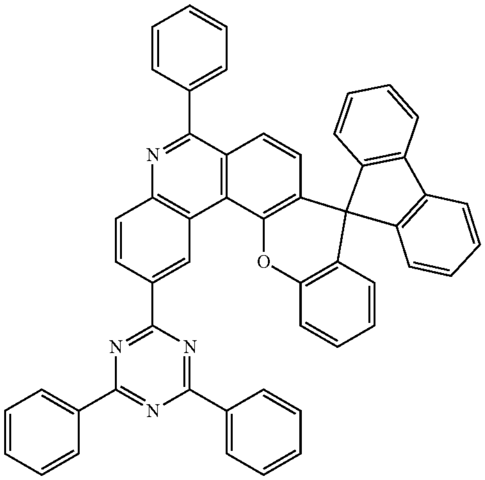
82
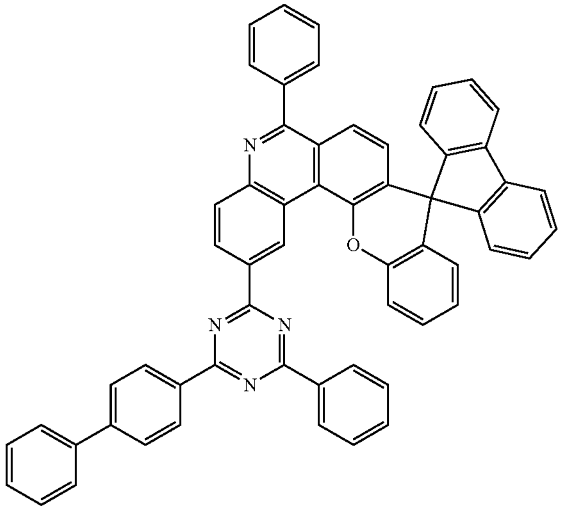
83
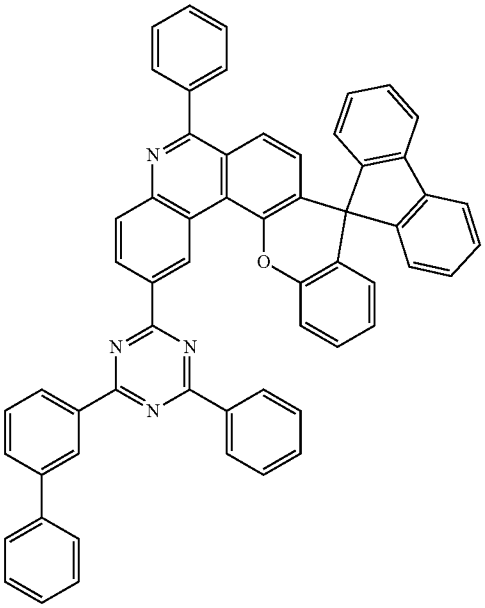

-continued
84
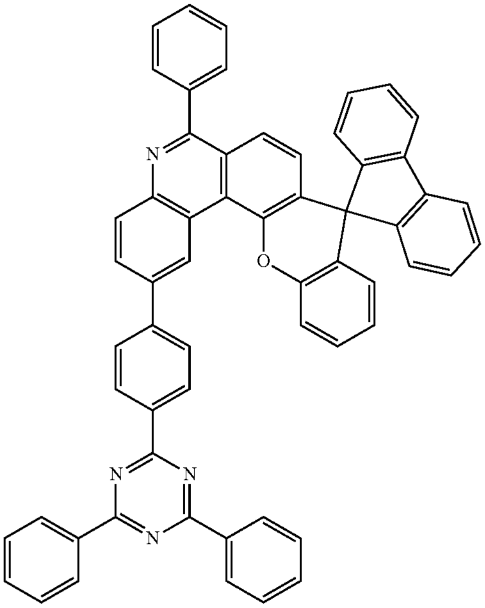
85
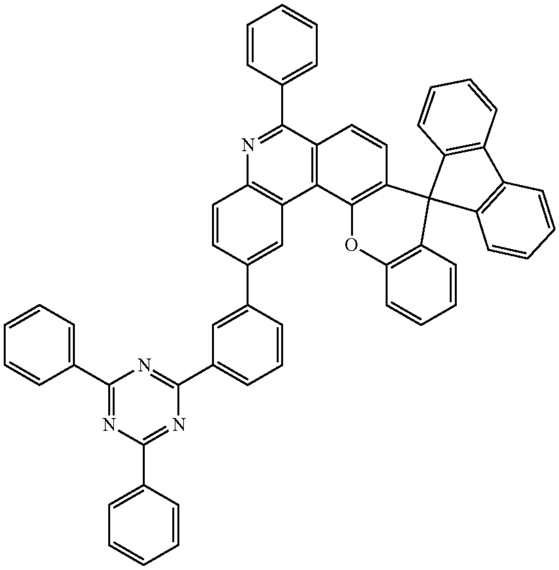
86
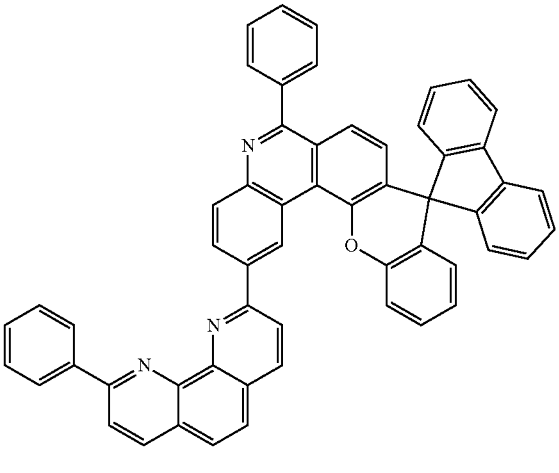
-continued
87
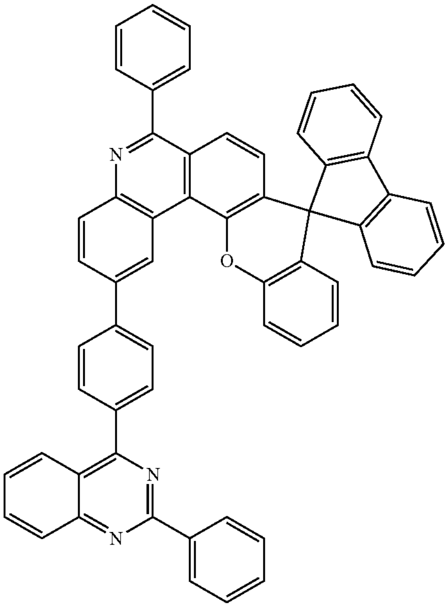
88
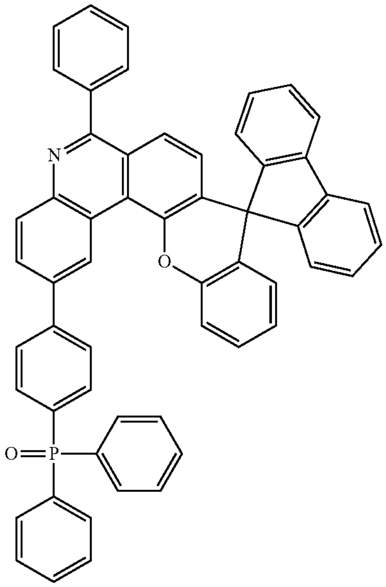

-continued
89
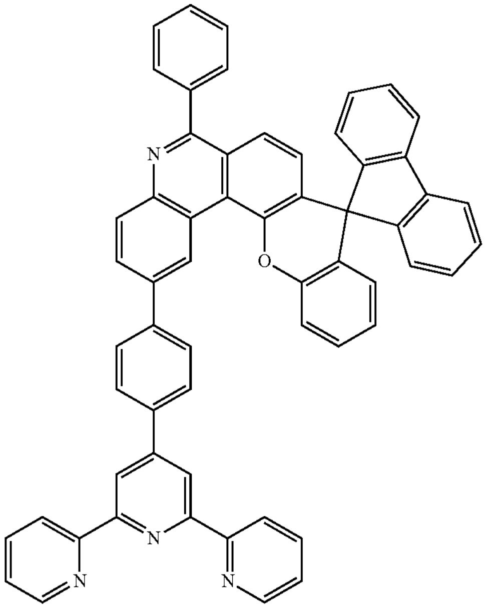
90
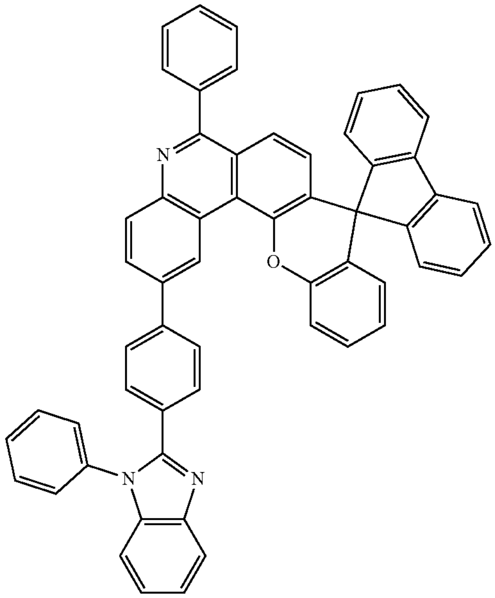
-continued
91
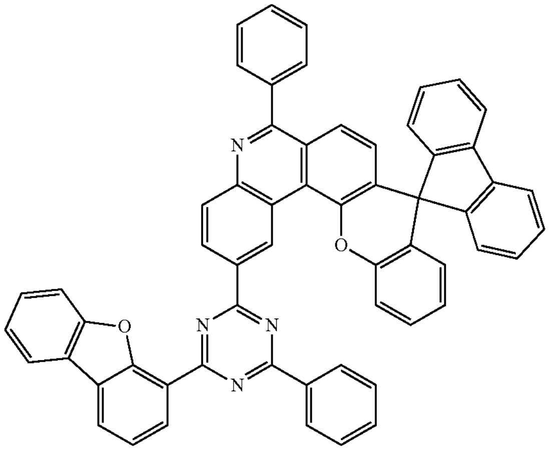
92
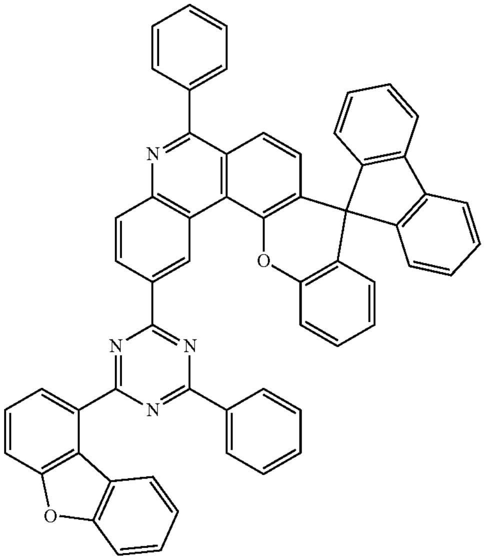
93
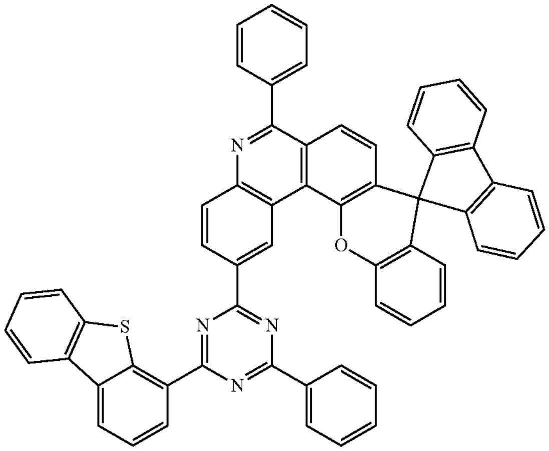

-continued
94
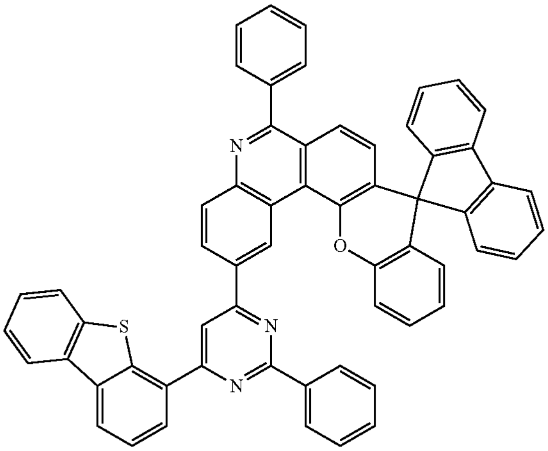
95
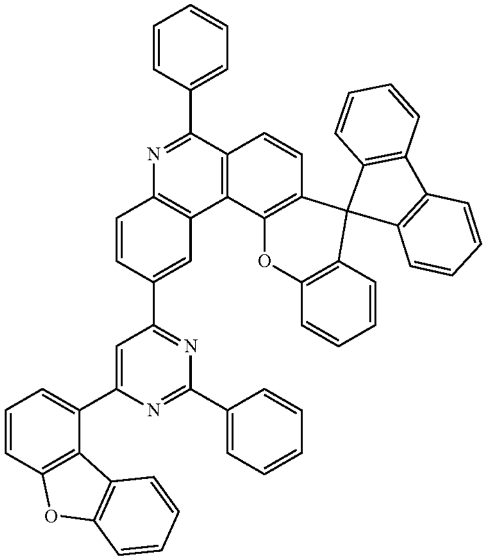
96
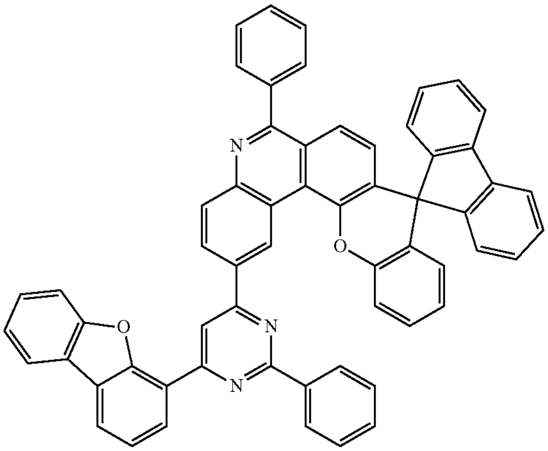
-continued
97
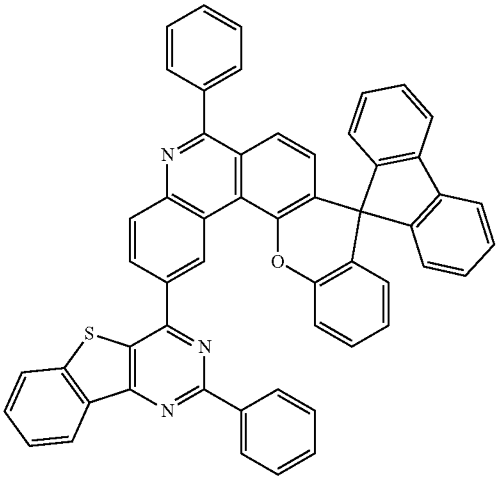
98
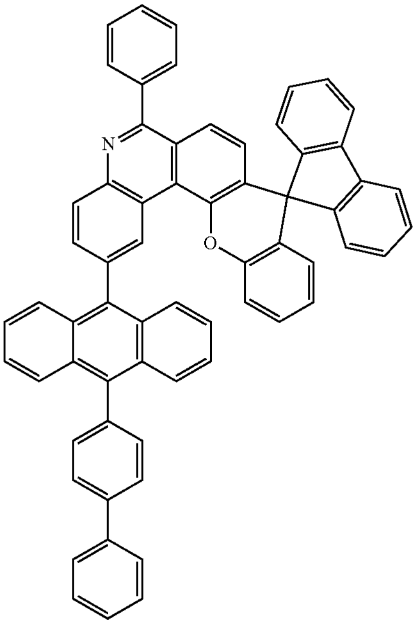

99
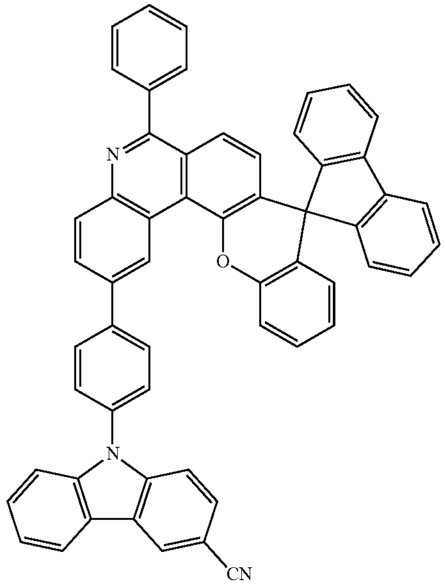
100
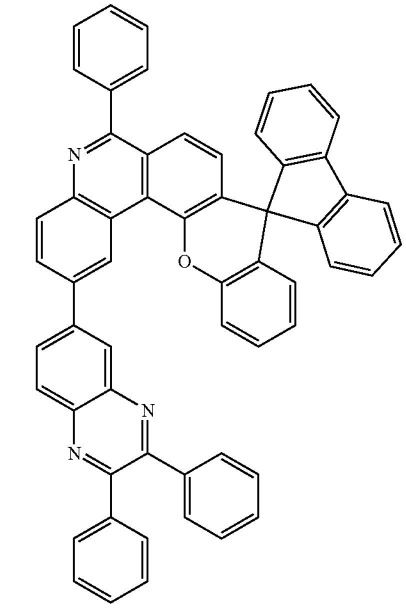
101
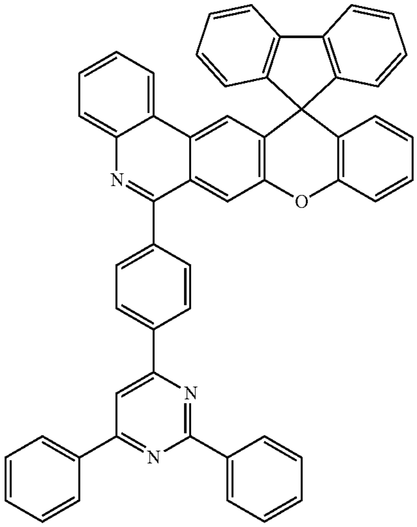
102
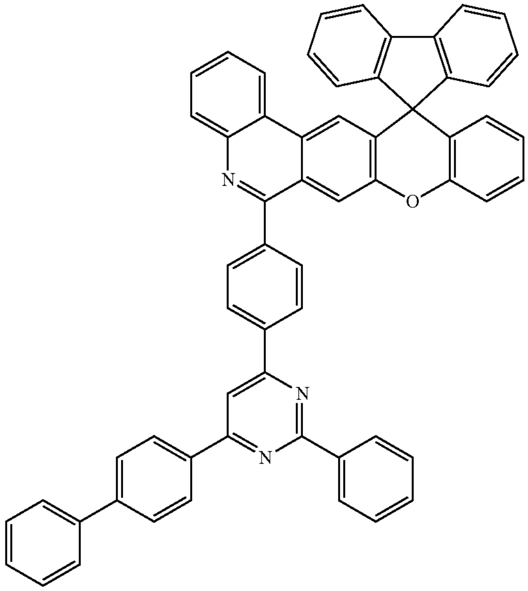

-continued
103
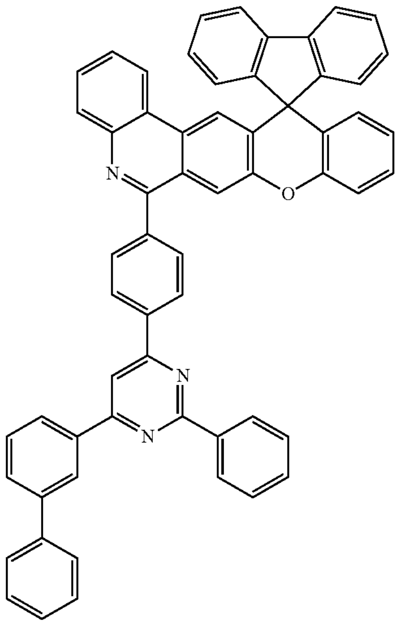
104
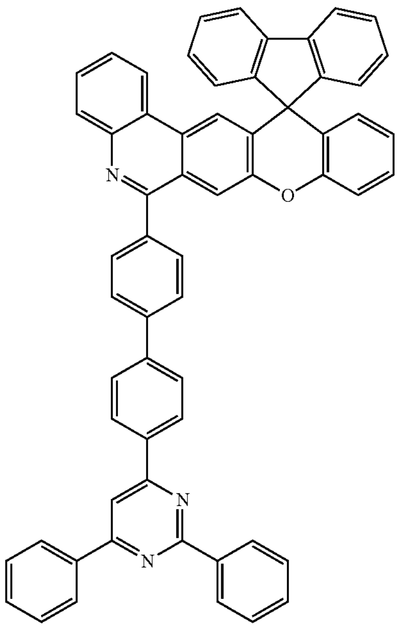
-continued
105
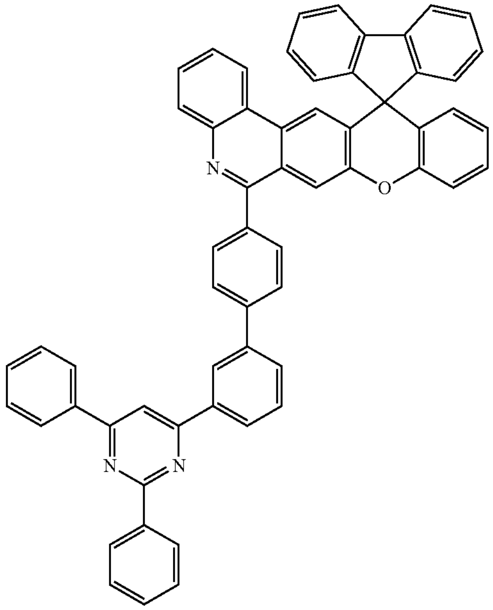
106
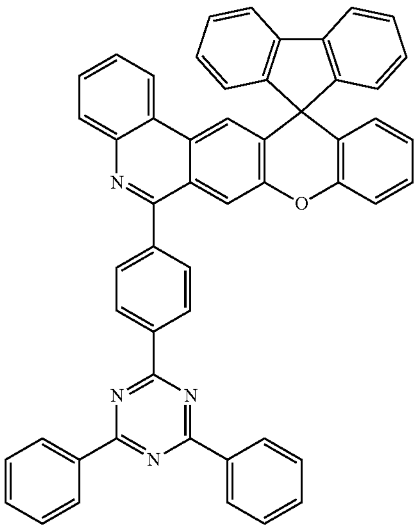

-continued
107
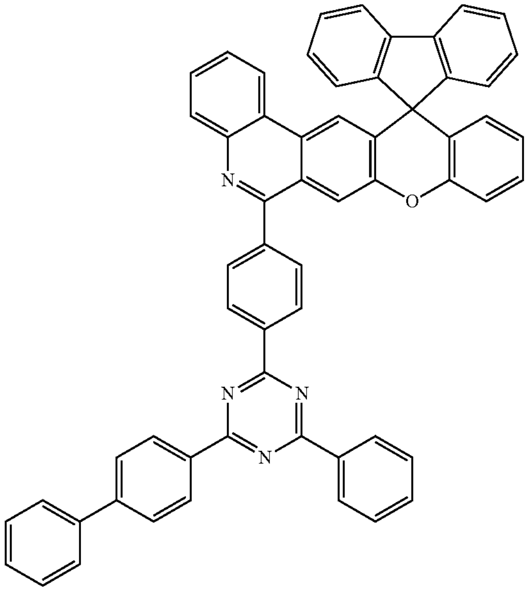
108
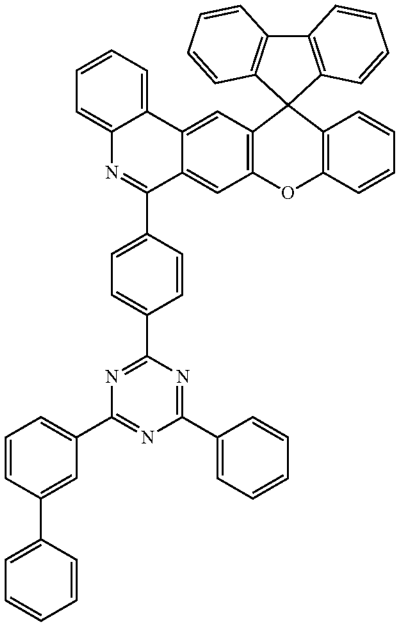
-continued
109
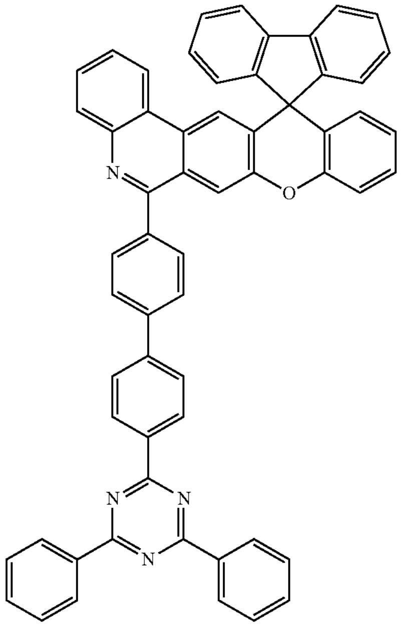
110
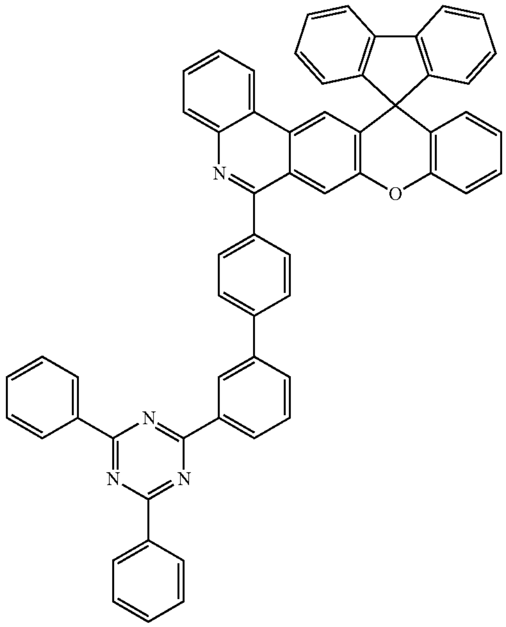

-continued
111
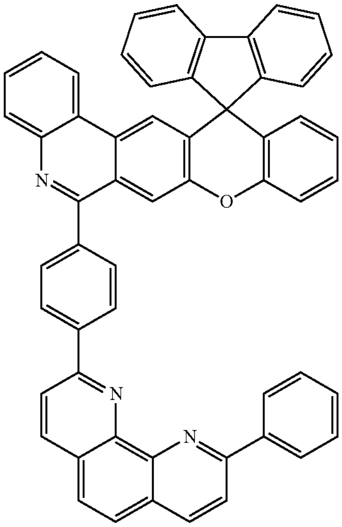
112
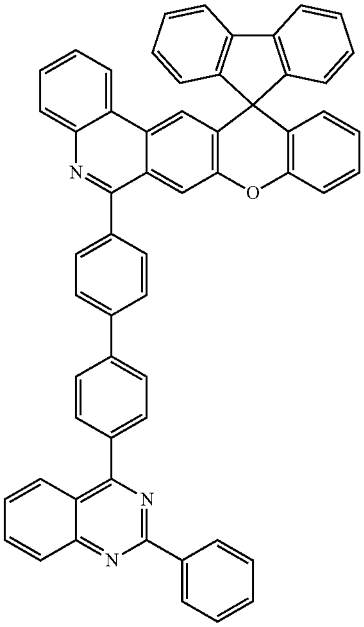
-continued
113
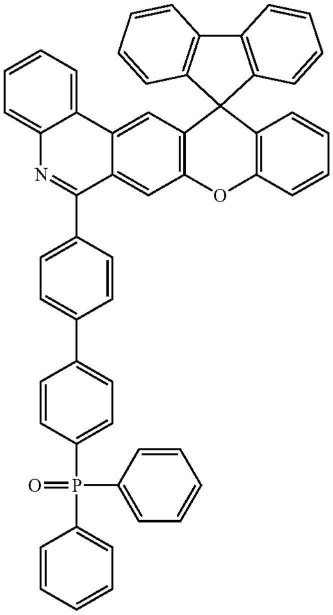
114
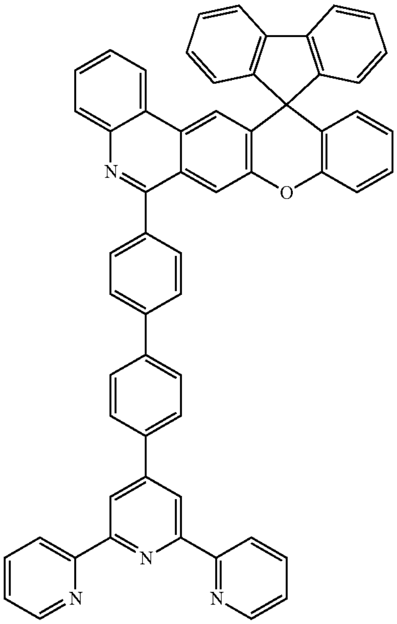

-continued
115
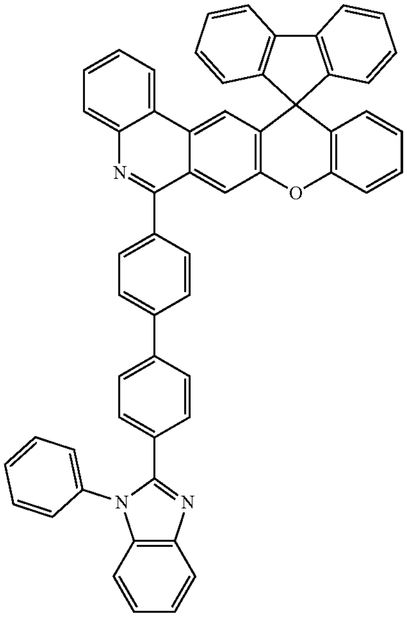
117
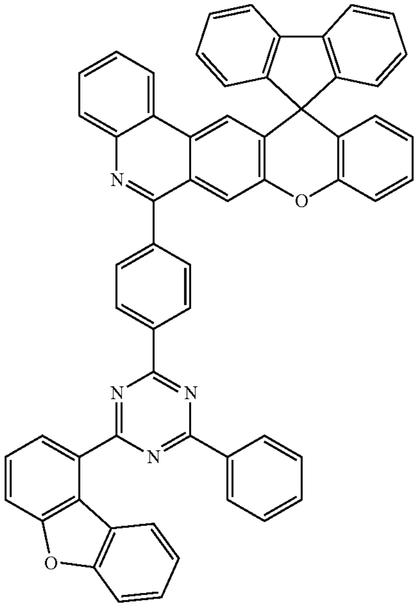
116
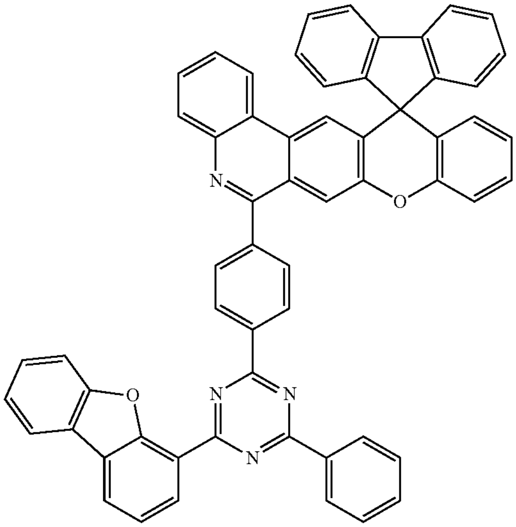
118
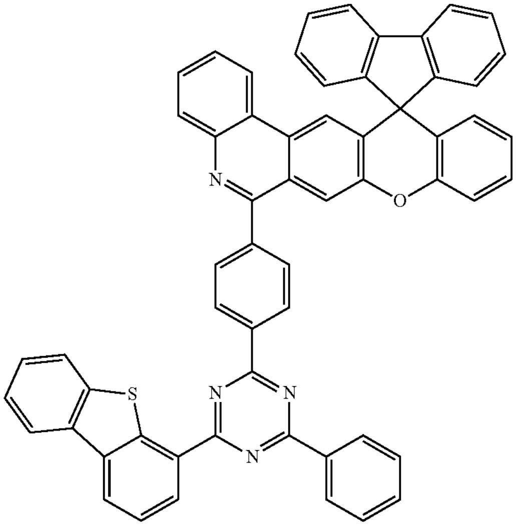

119
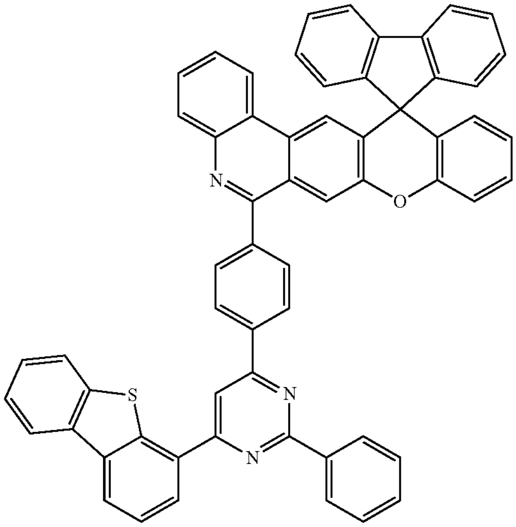
120
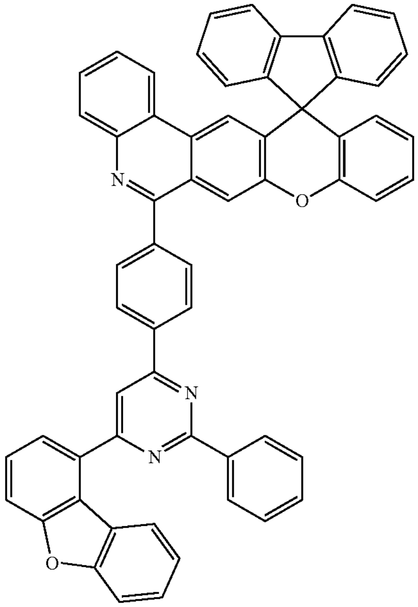
121
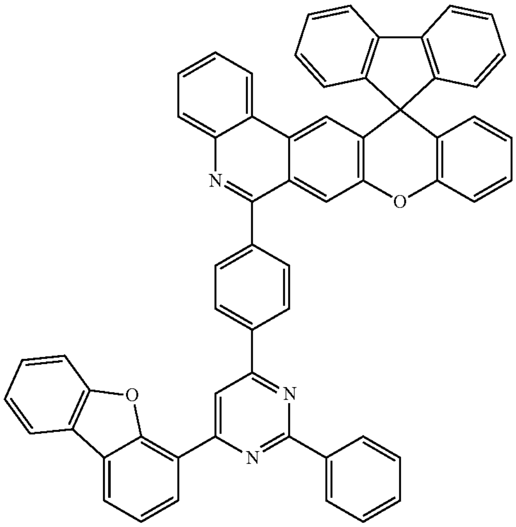
122
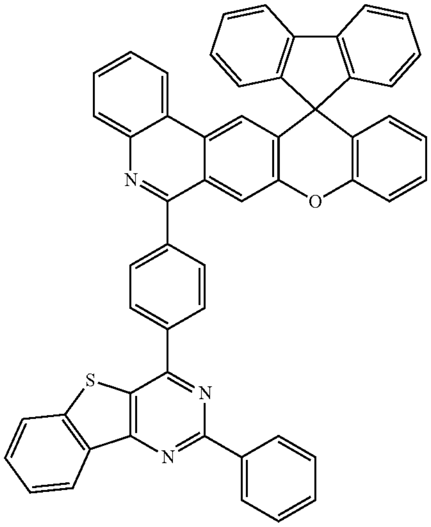

-continued
123
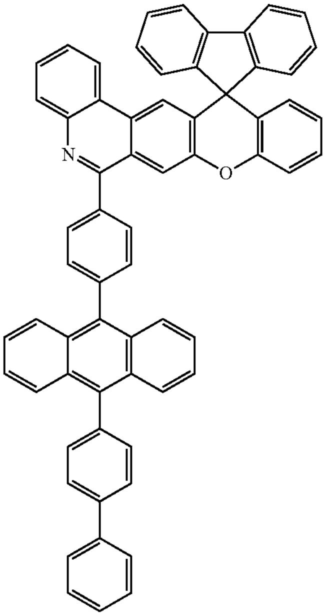
124
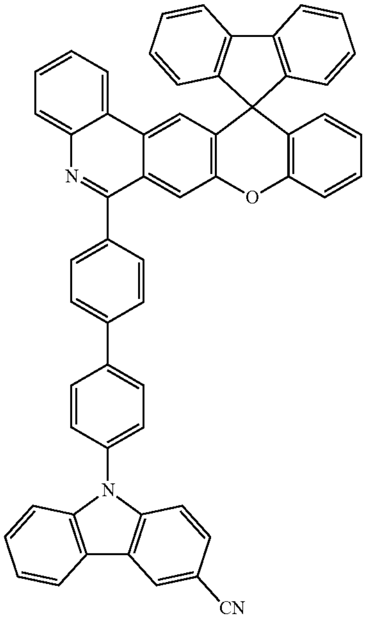
-continued
125
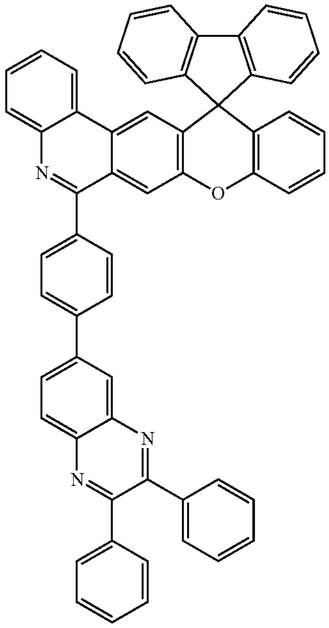
126
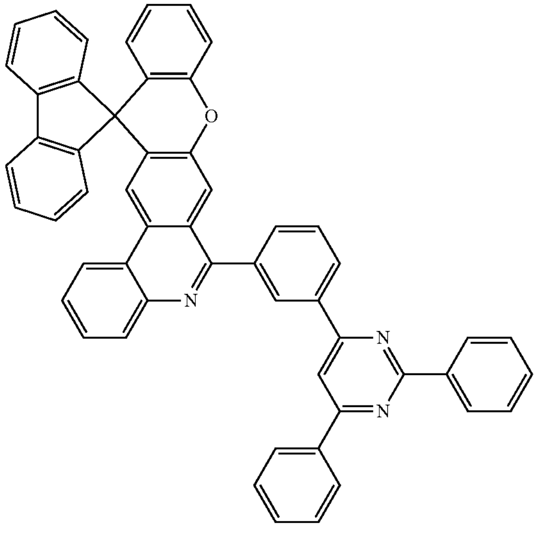

-continued
127
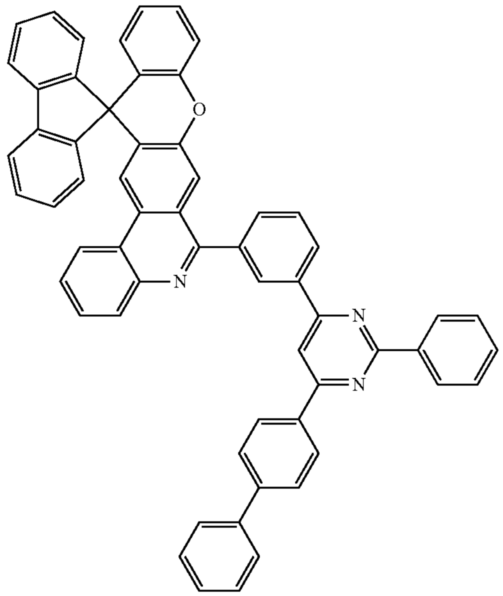
128
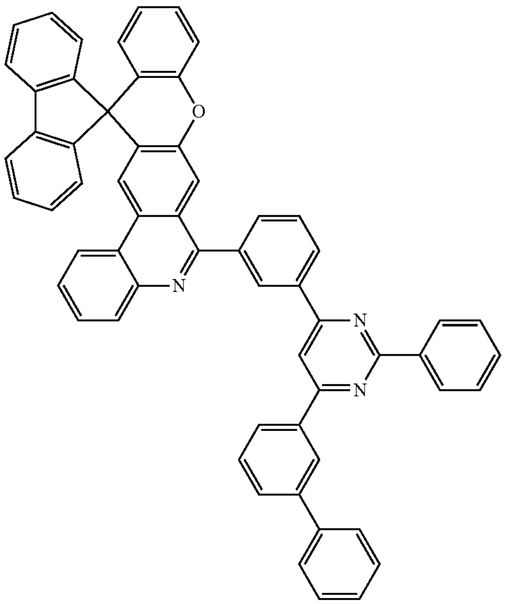
-continued
129
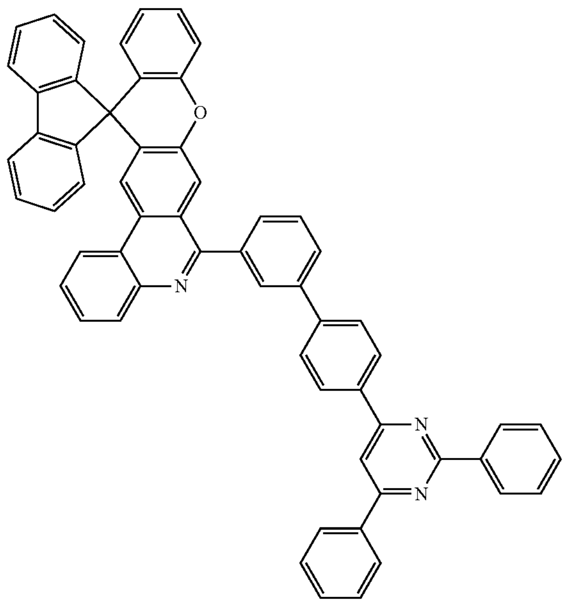
130
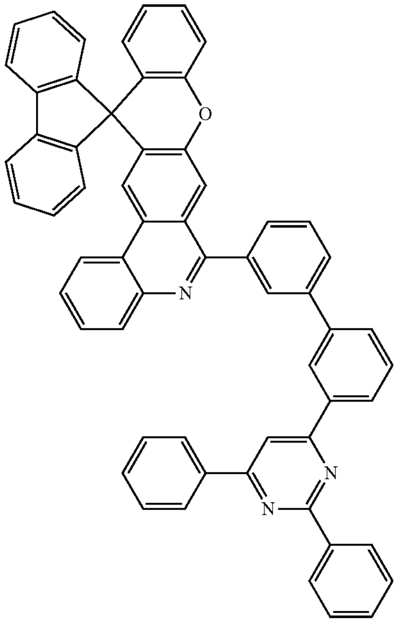

-continued
131
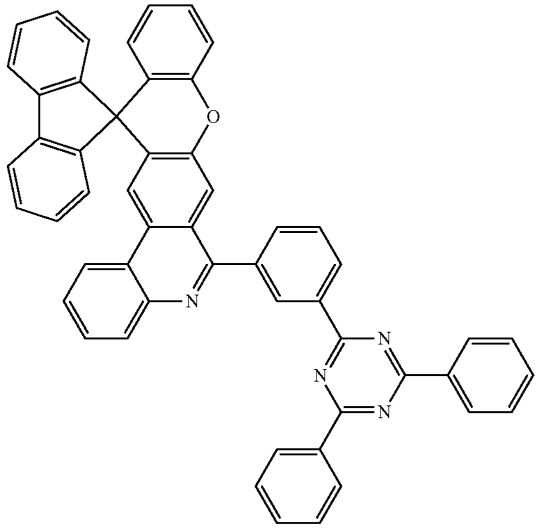
132
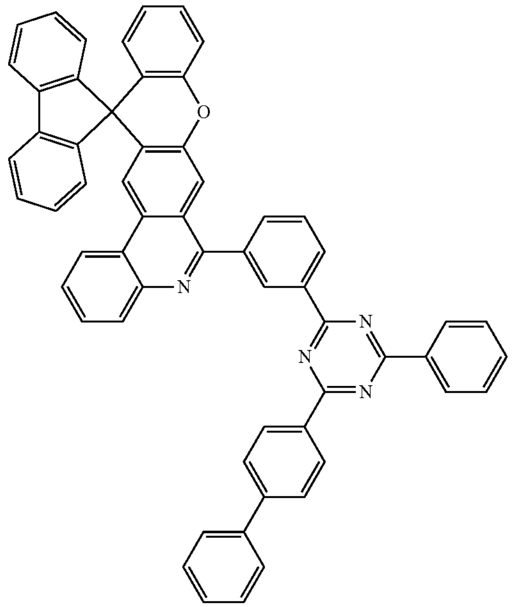
-continued
133
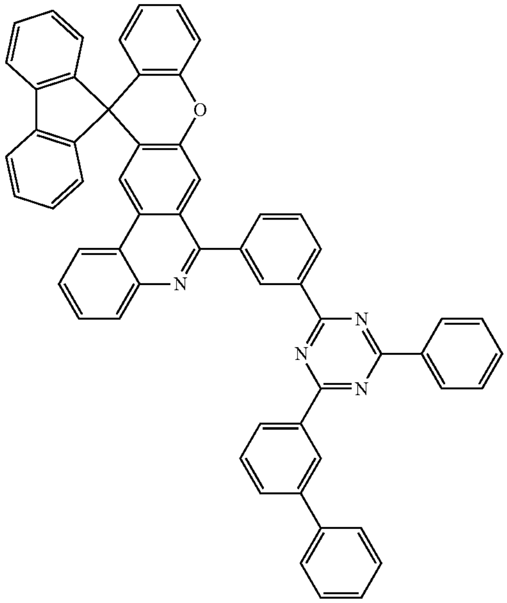
134
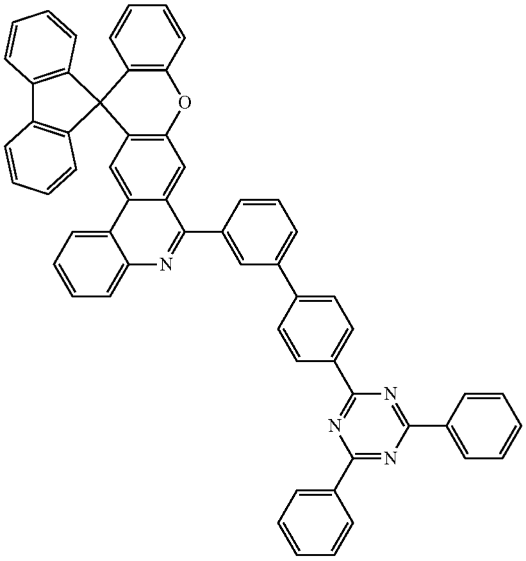

-continued
135
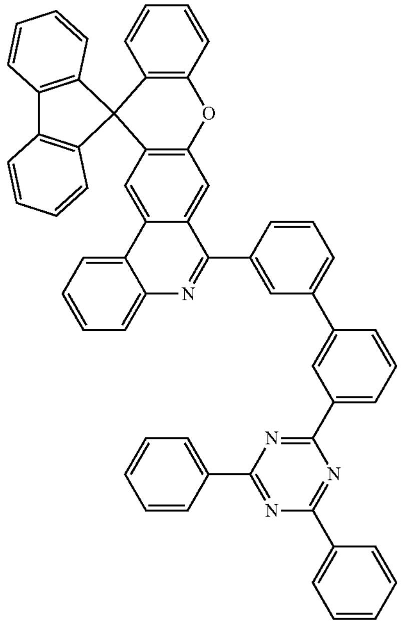
136
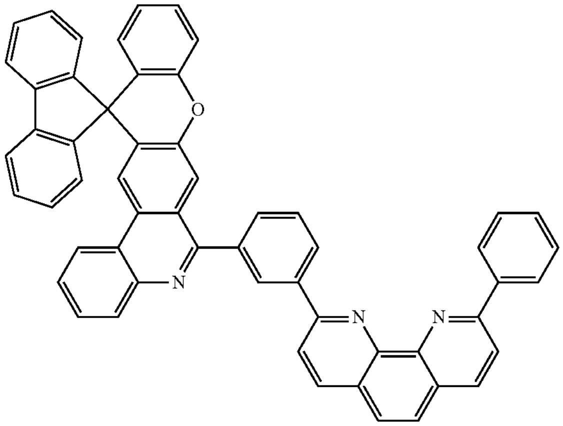
137
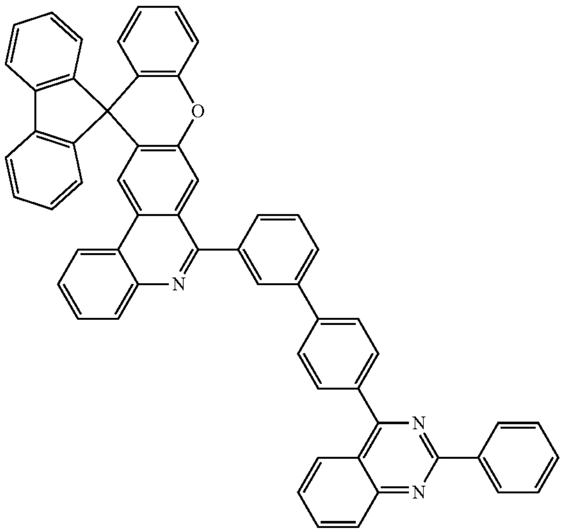
-continued
138
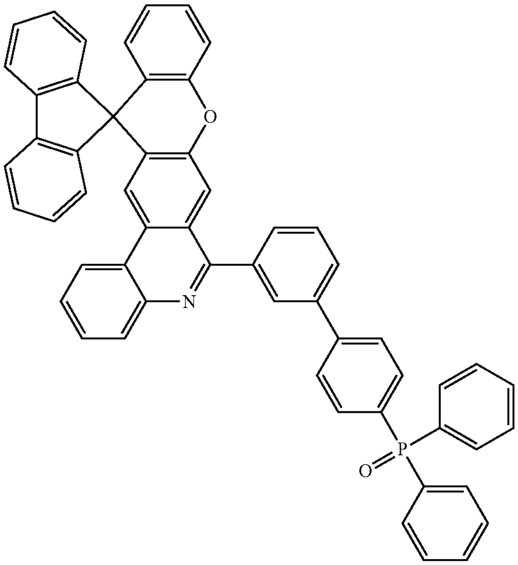
139
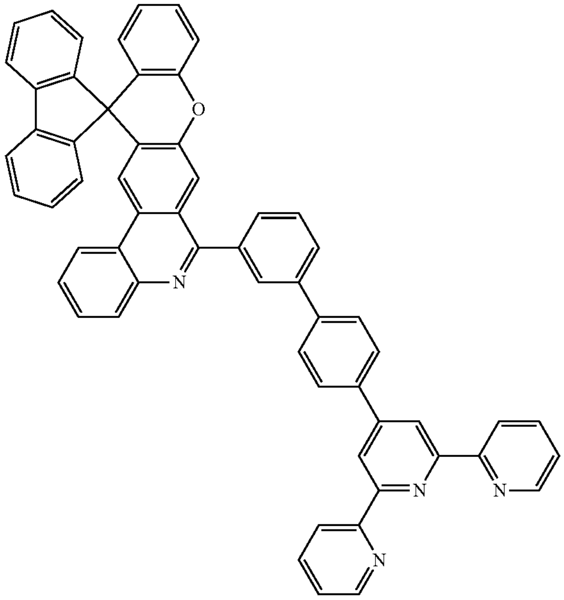

-continued
140
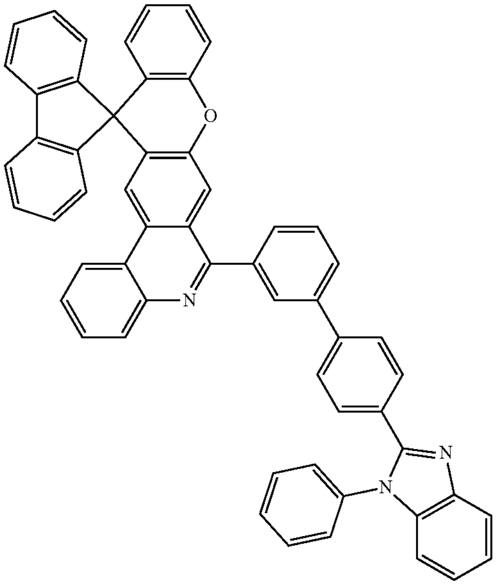
141
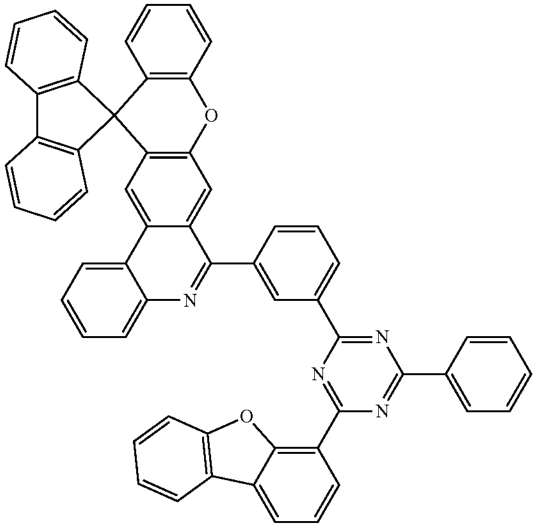
-continued
142
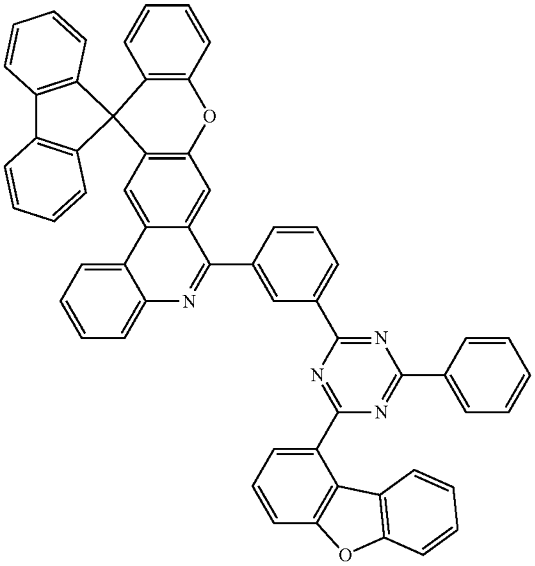
143
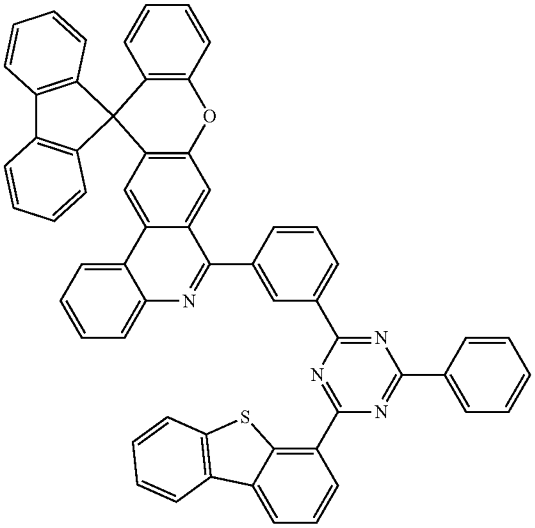

144
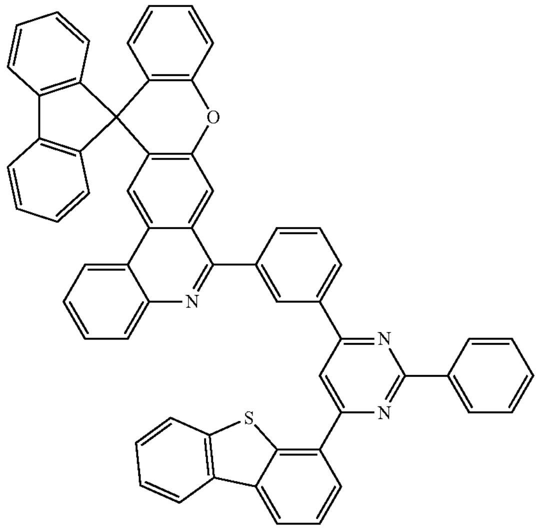
145
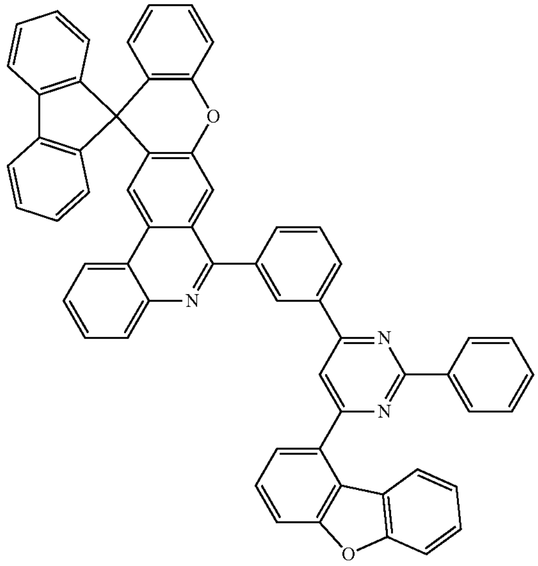
146
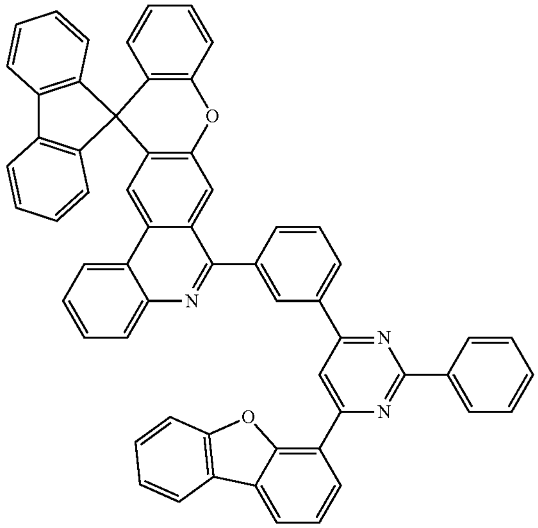
147
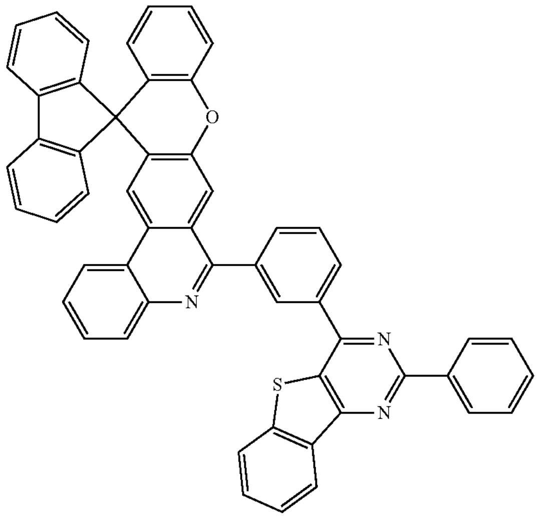

-continued
148
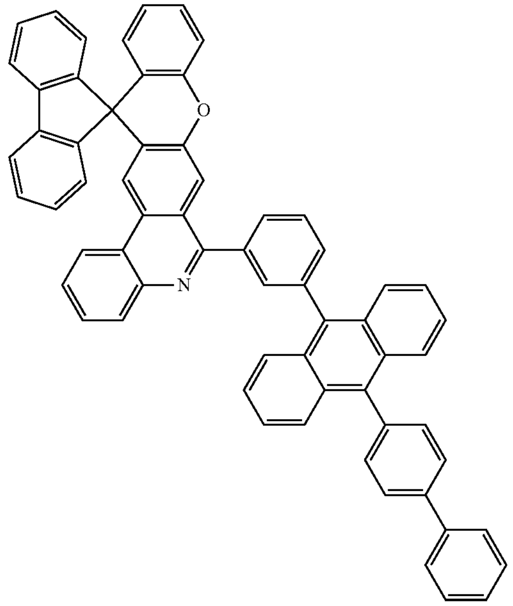
150
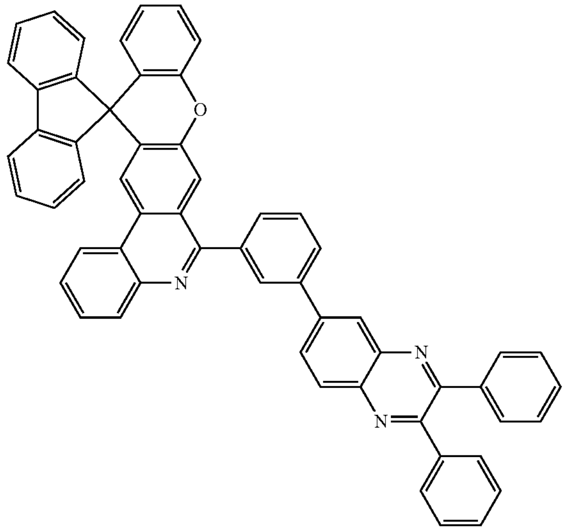
149
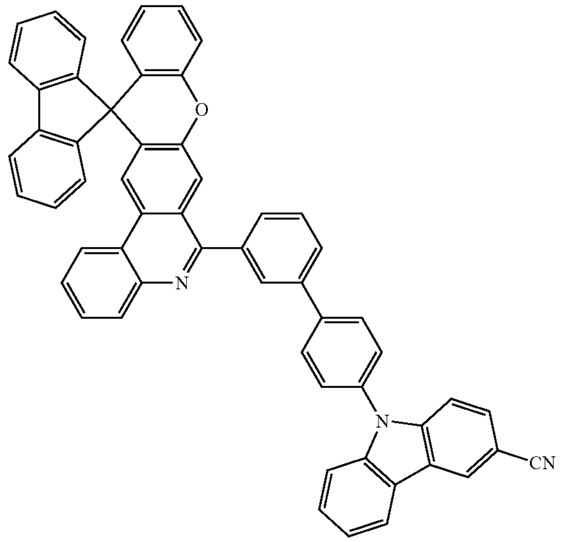
151
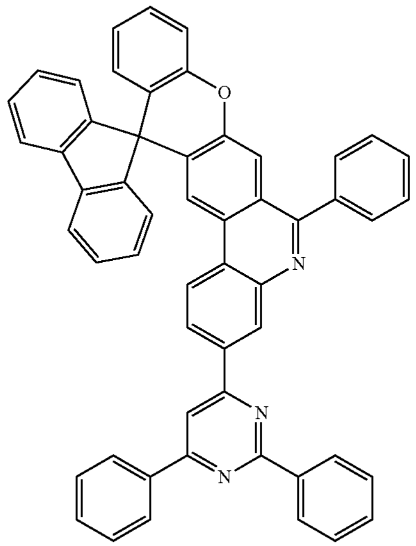

-continued
152
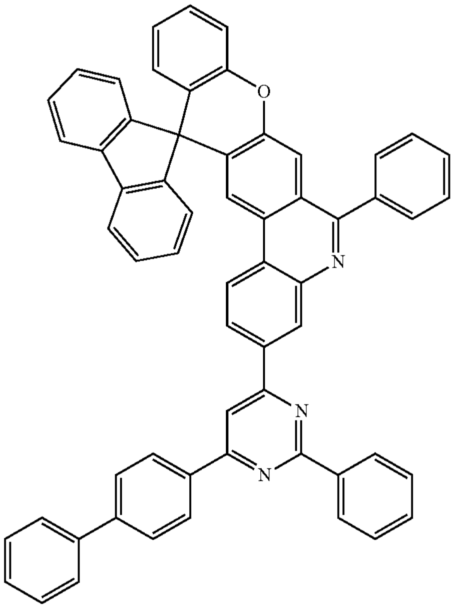
153
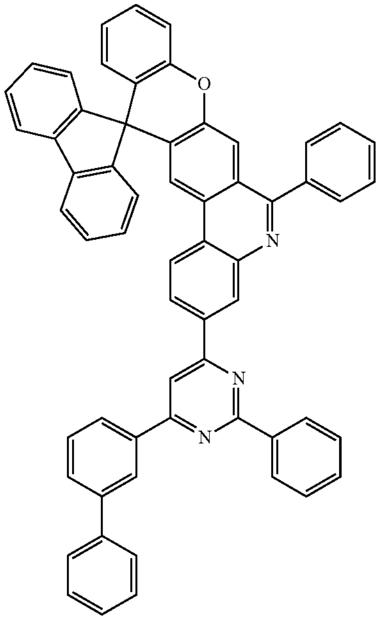
-continued
154
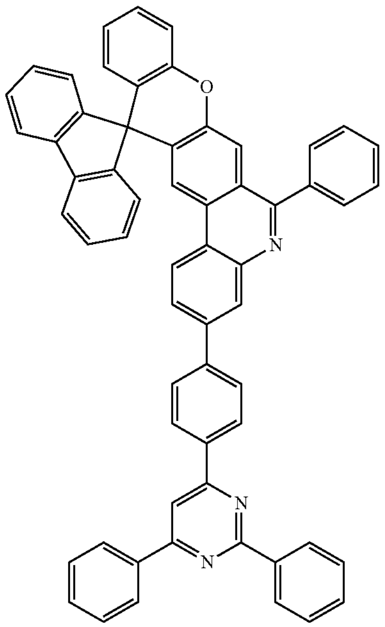
155
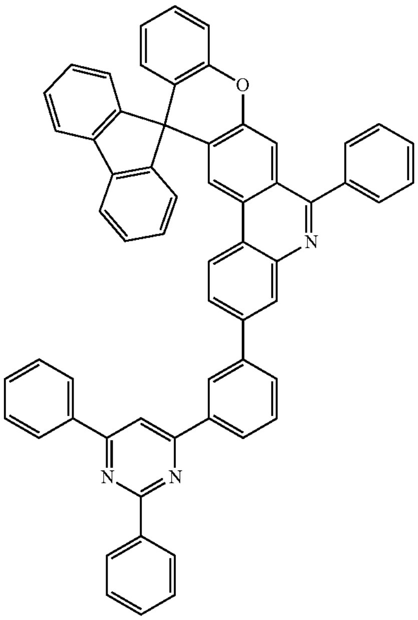

-continued
156
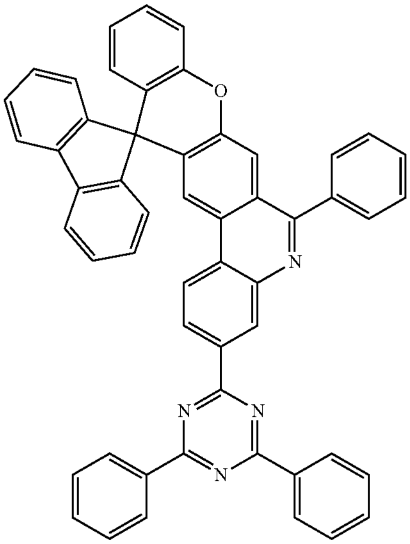
157
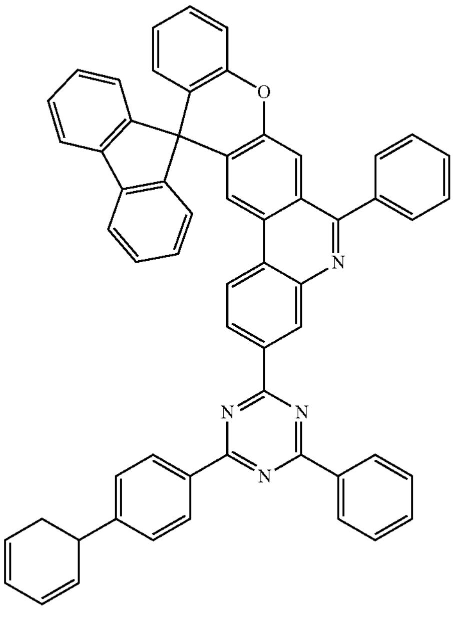
-continued
158
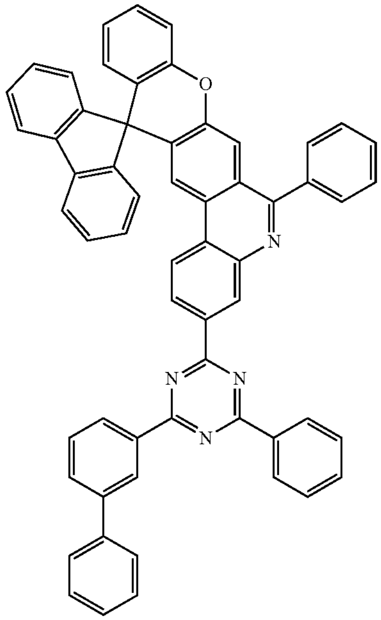
159
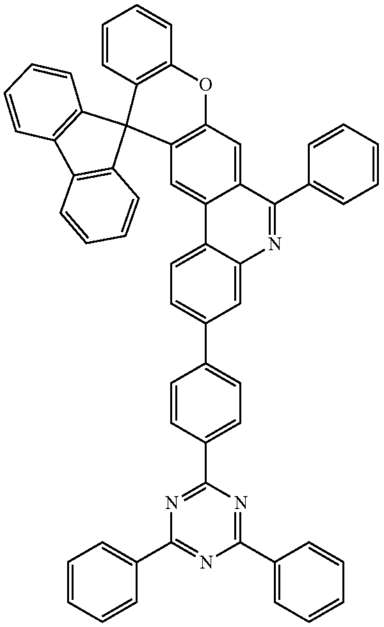

-continued
160
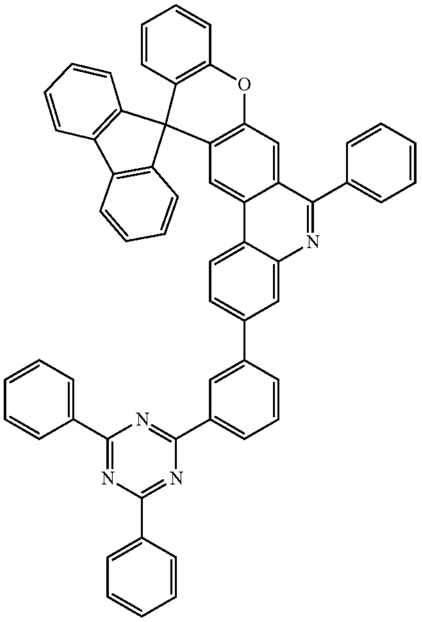
161
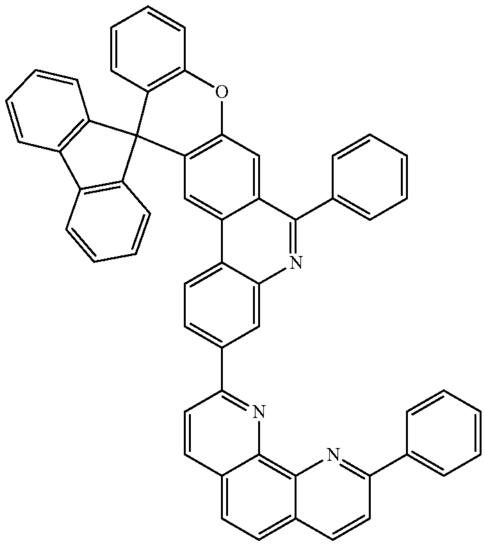
-continued
162
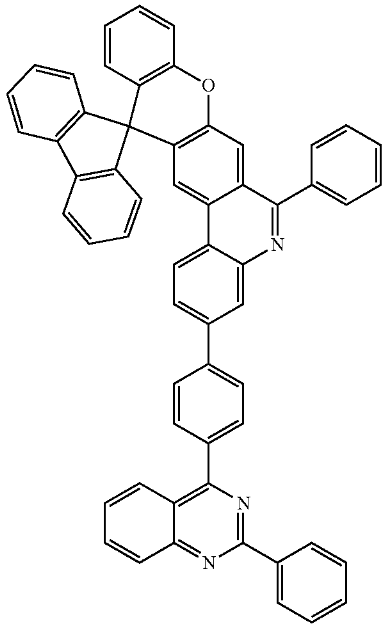
163
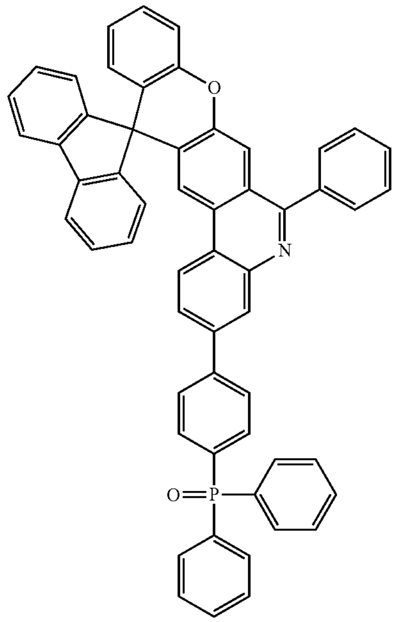

-continued
164
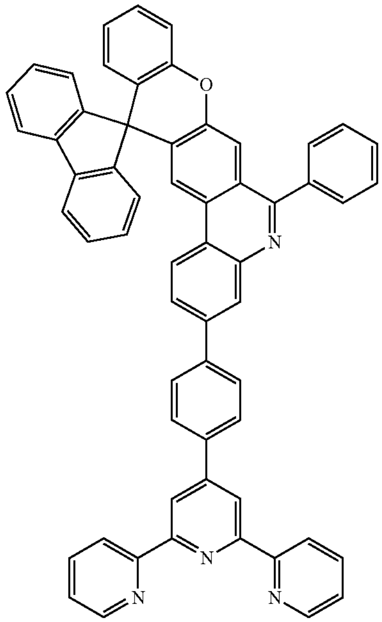
165
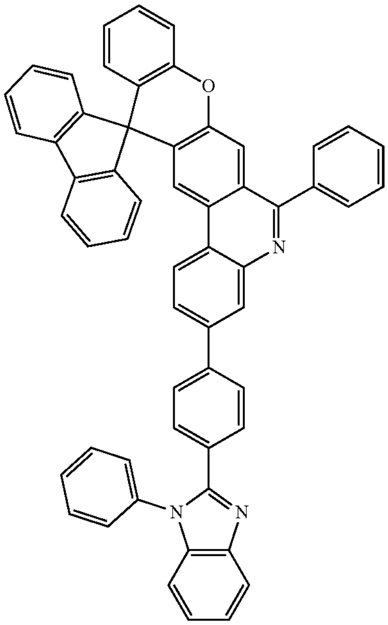
-continued
166
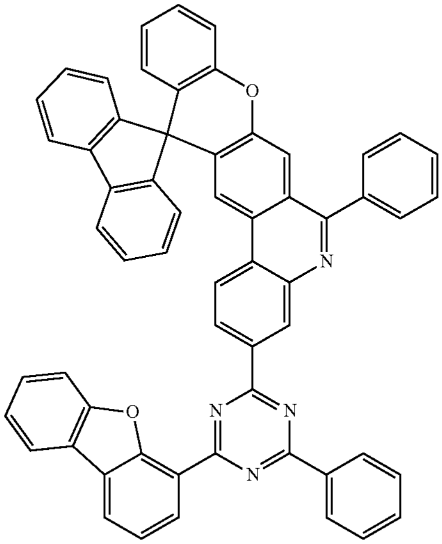
167
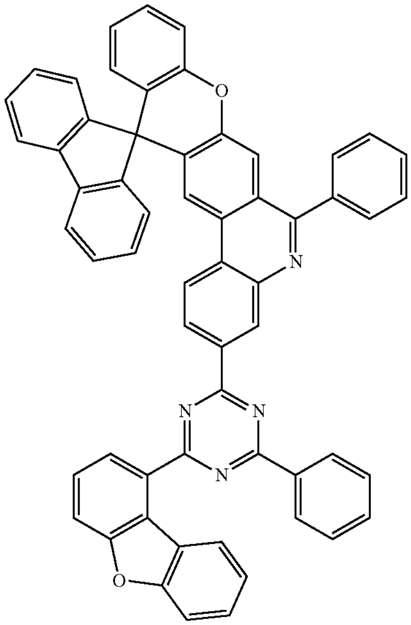

-continued
168
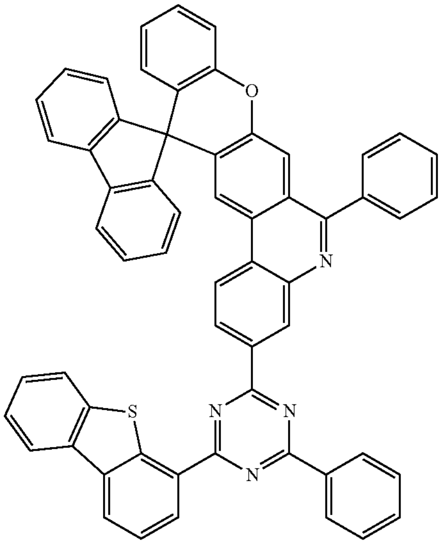
170
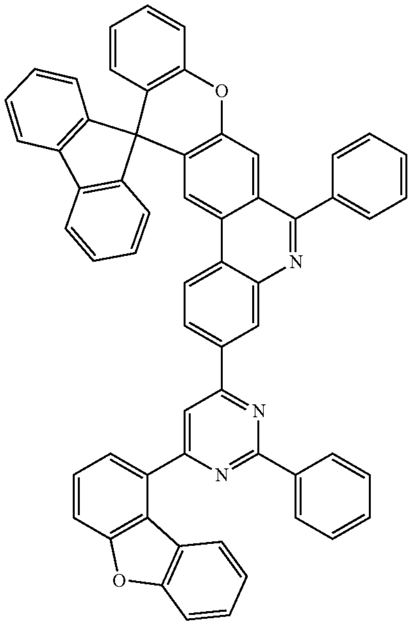
169
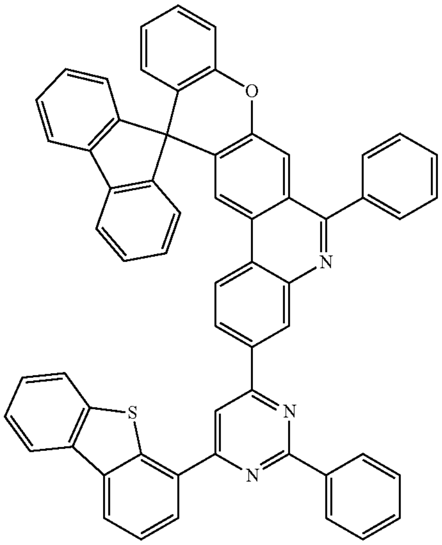
171
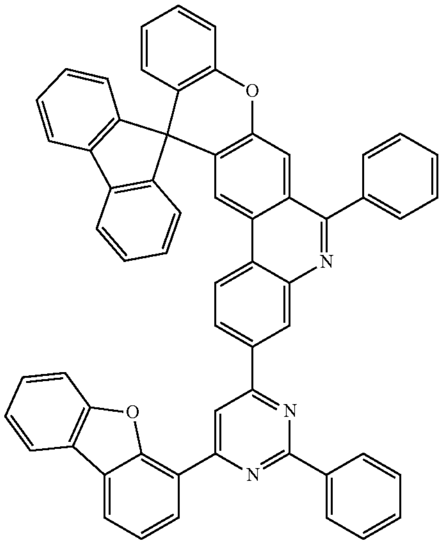

-continued
172
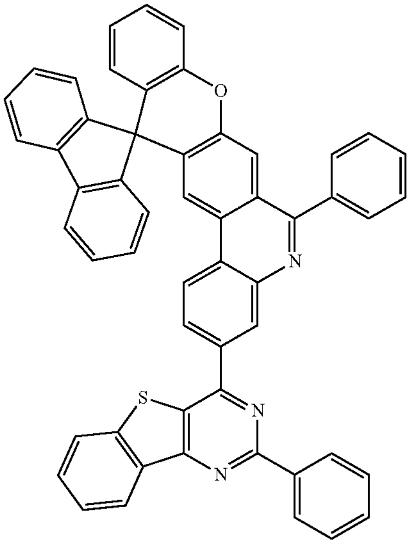
173
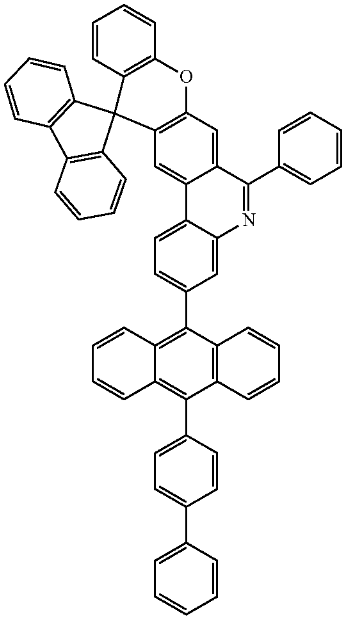
-continued
174
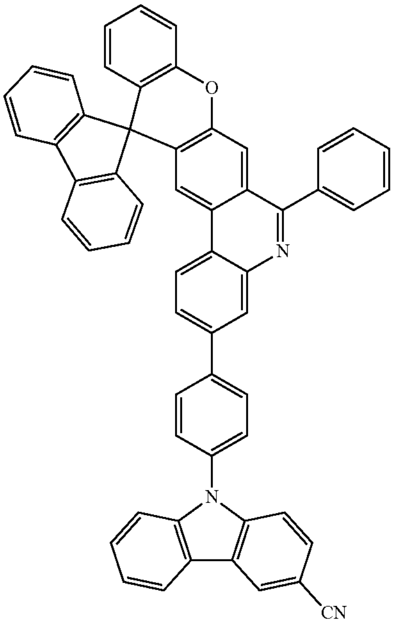
175
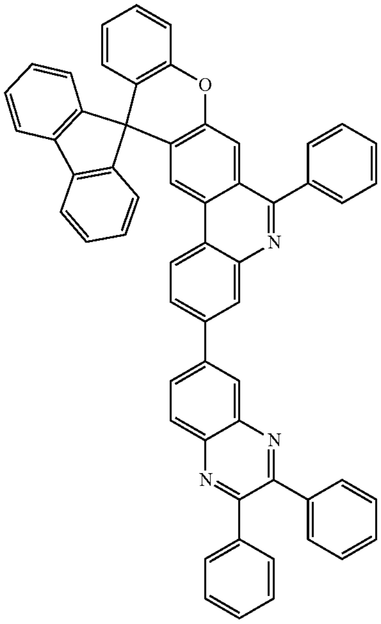

176
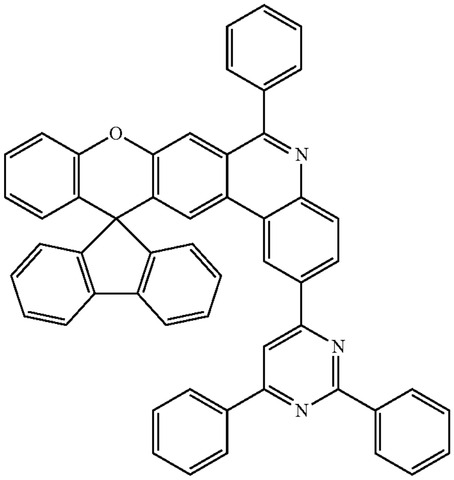
177
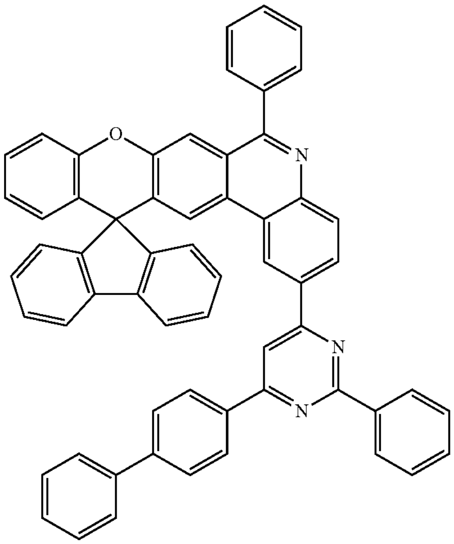
178
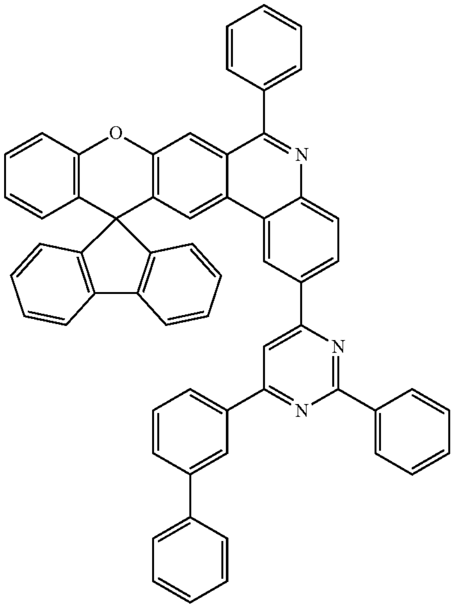
-continued
179
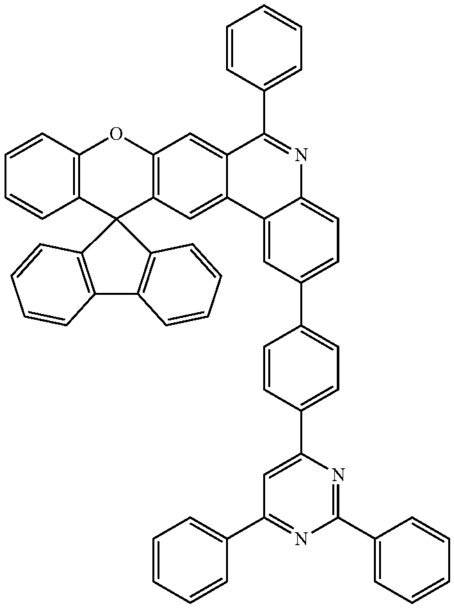
180
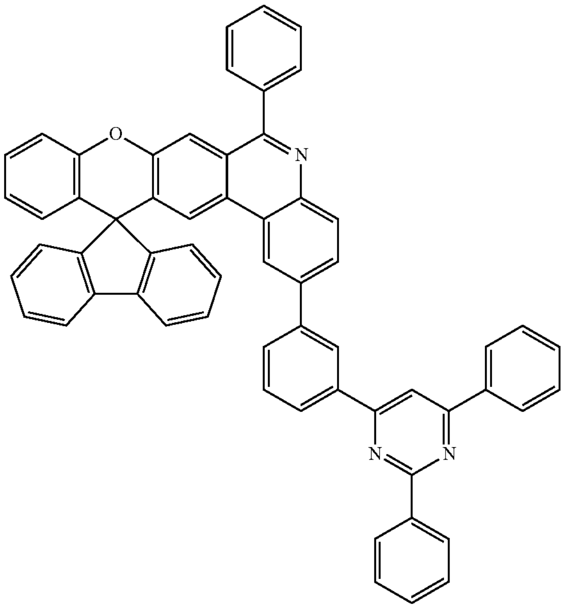

-continued
181
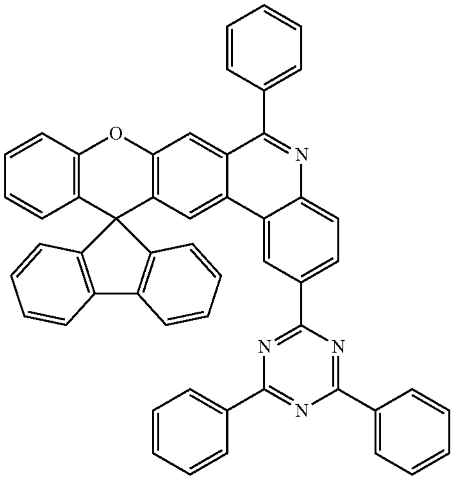
182
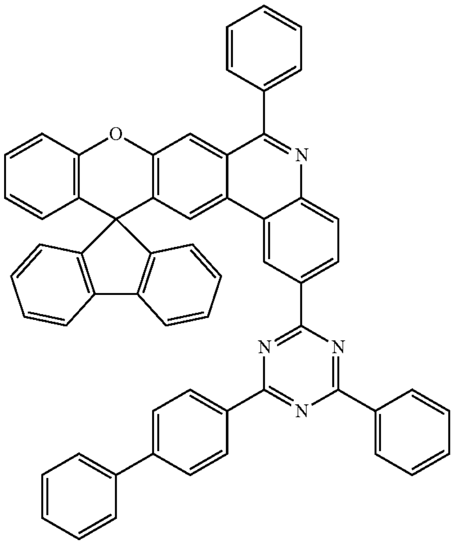
183
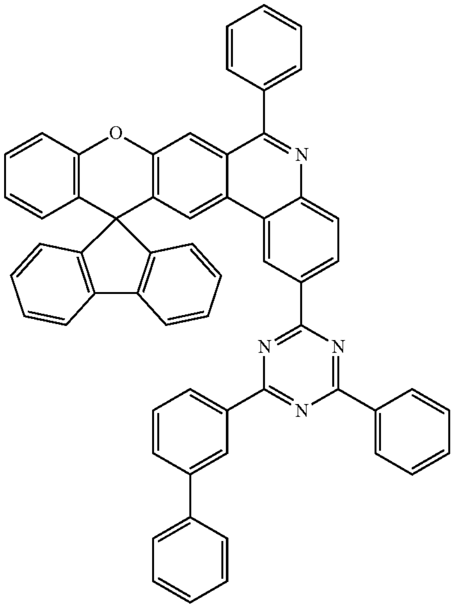
-continued
184
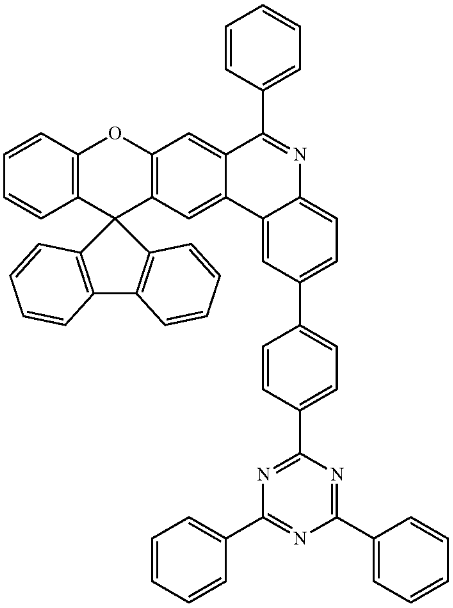
185
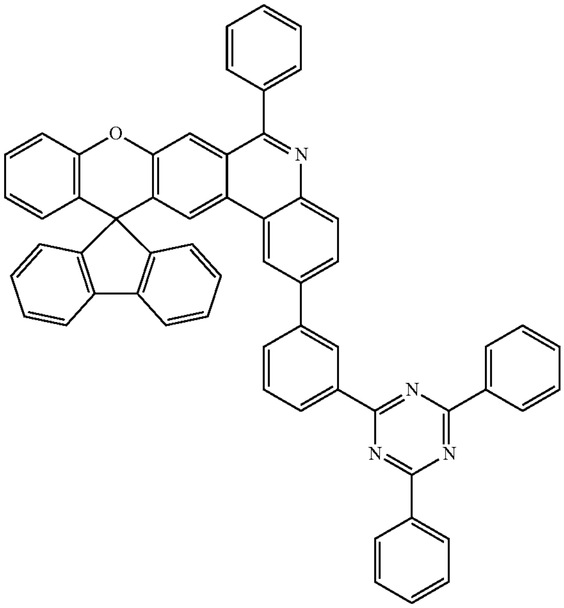

-continued
186
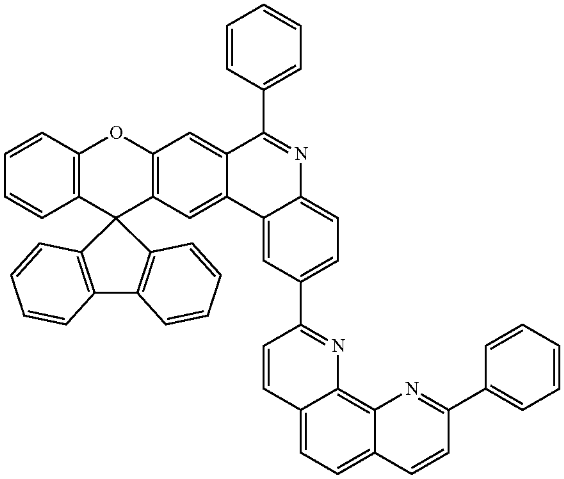
187
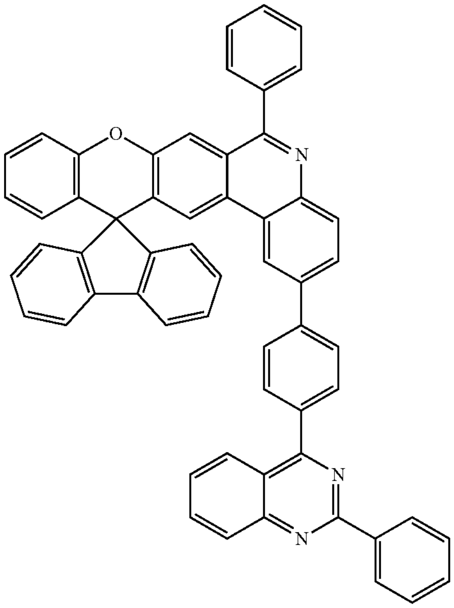
-continued
188
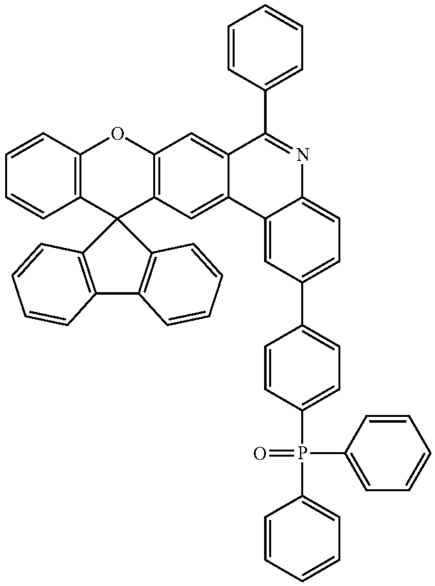
189
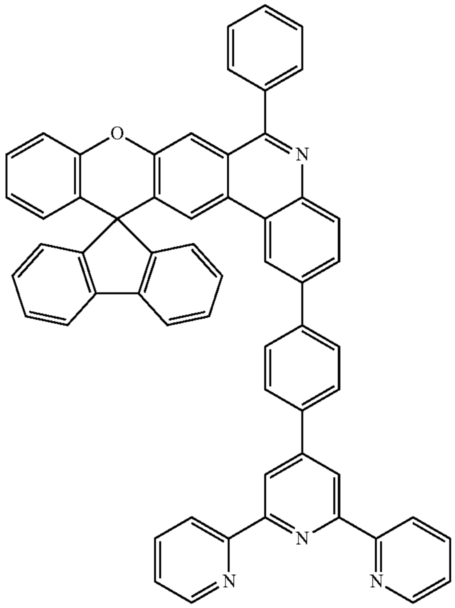

-continued
190
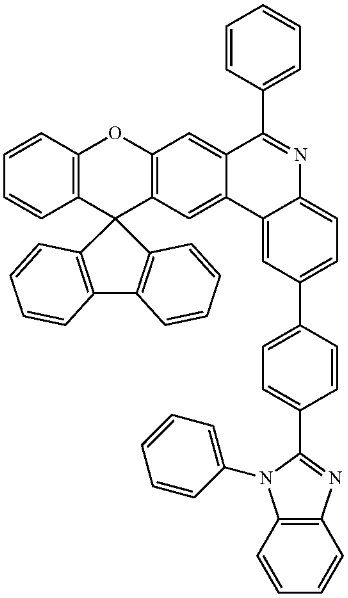
191
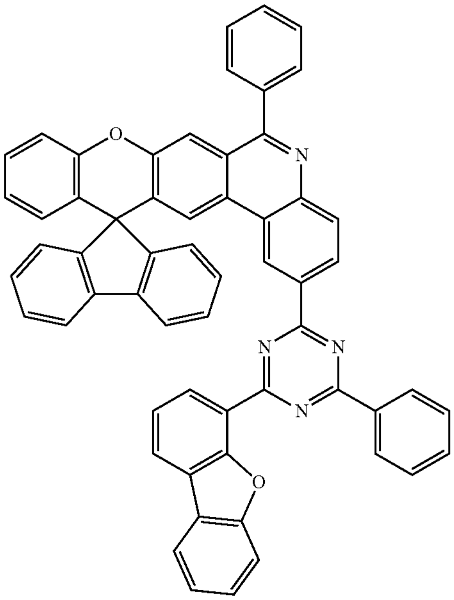
-continued
192
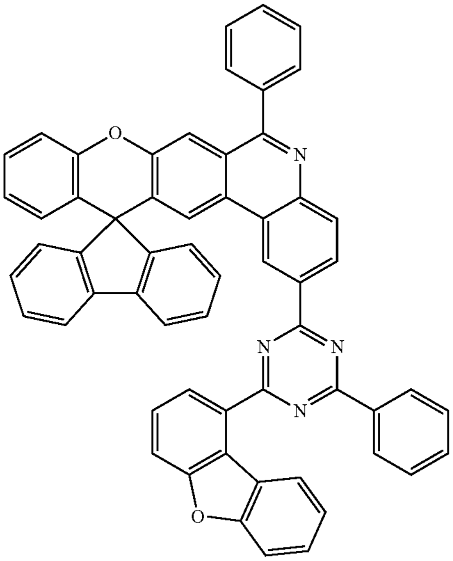
193
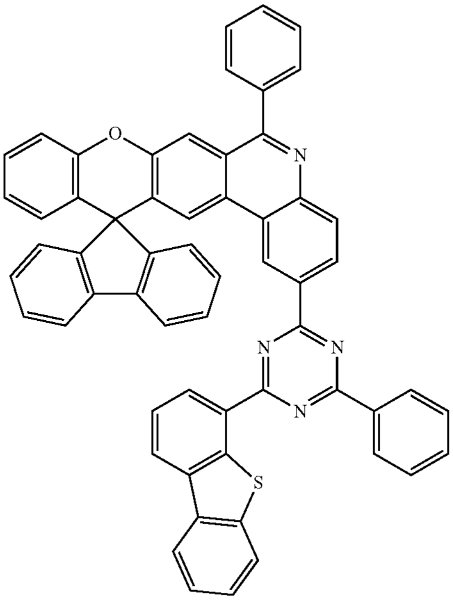

-continued
194
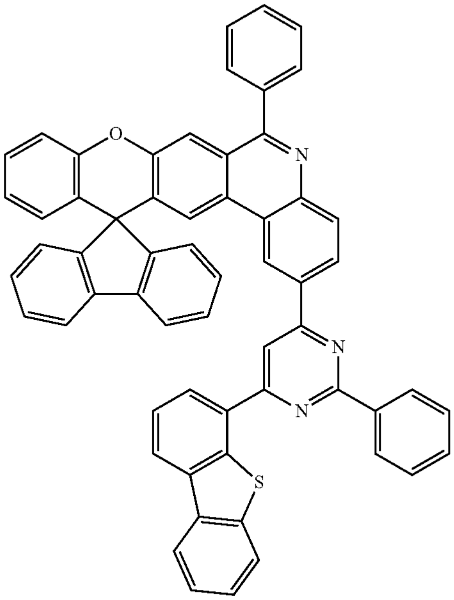
195
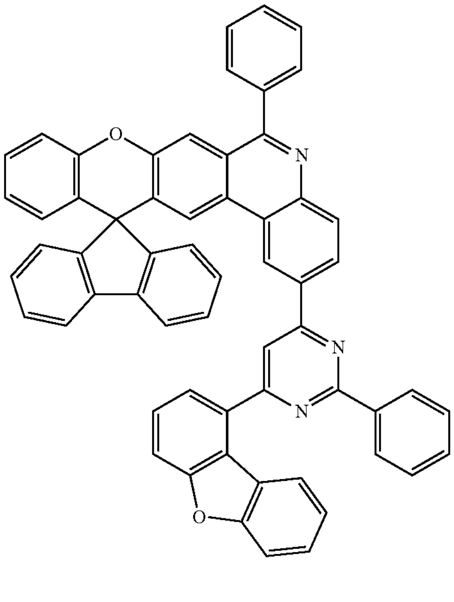
-continued
196
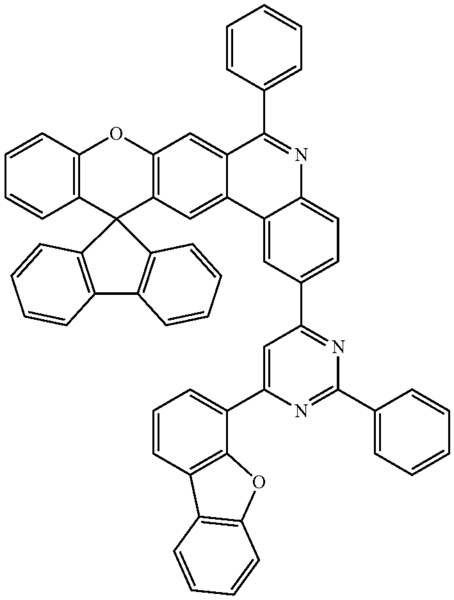
197
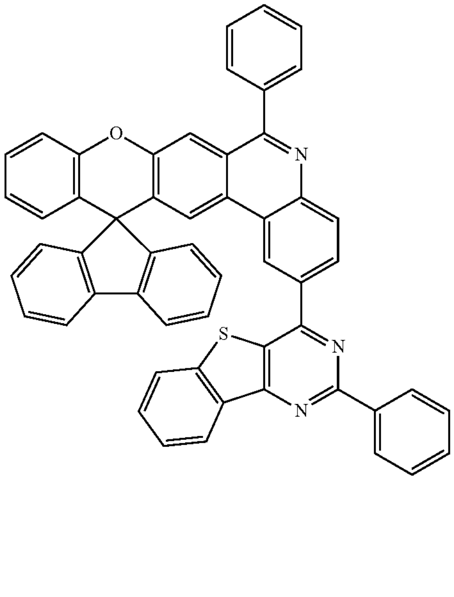

198
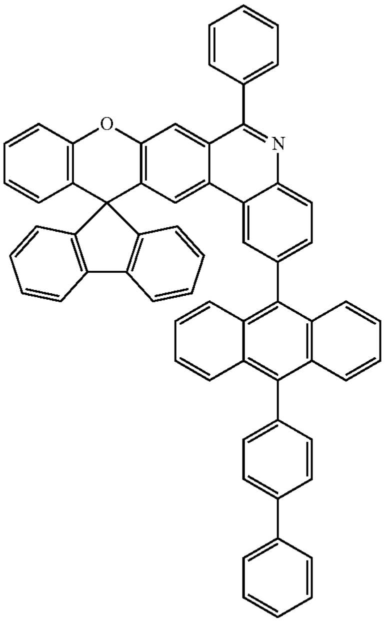
199
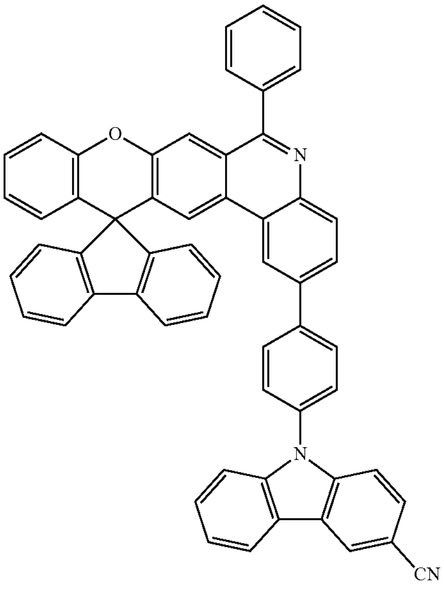
200
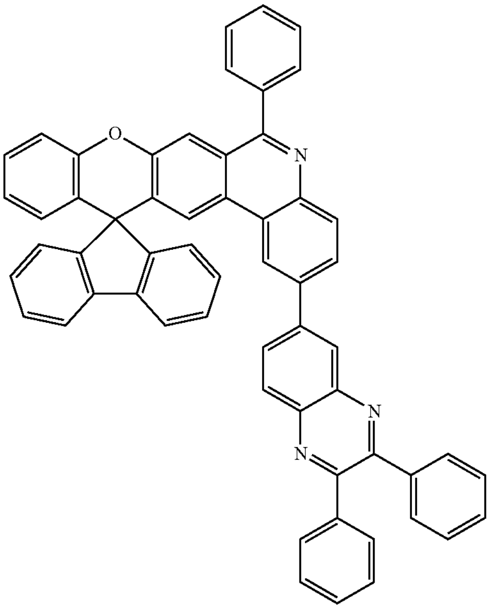
201
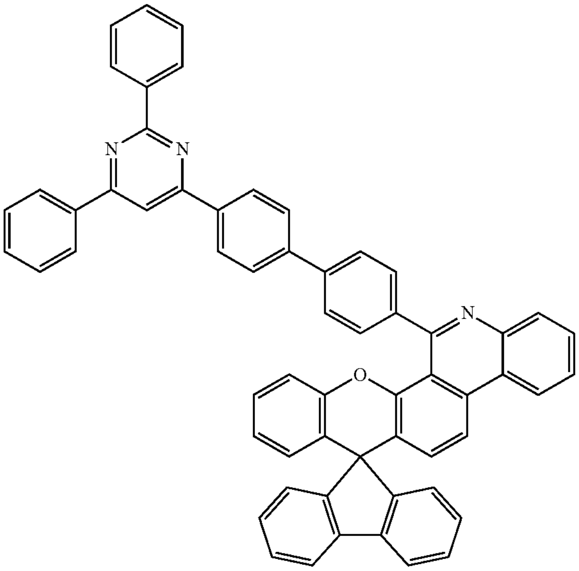

-continued
202
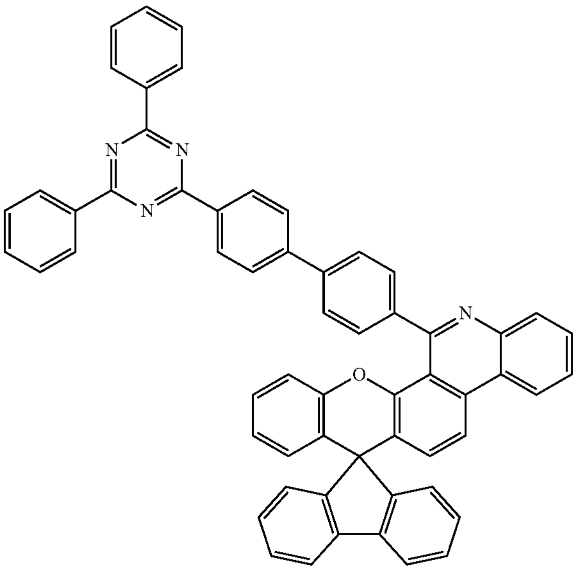
203
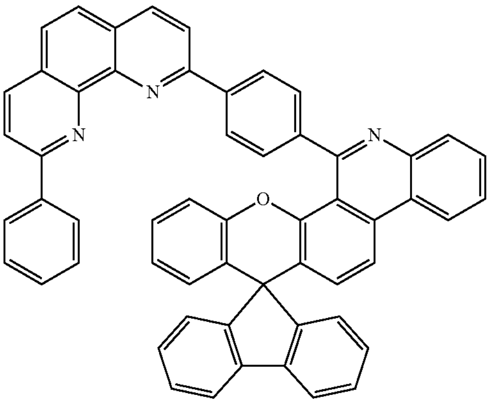
204
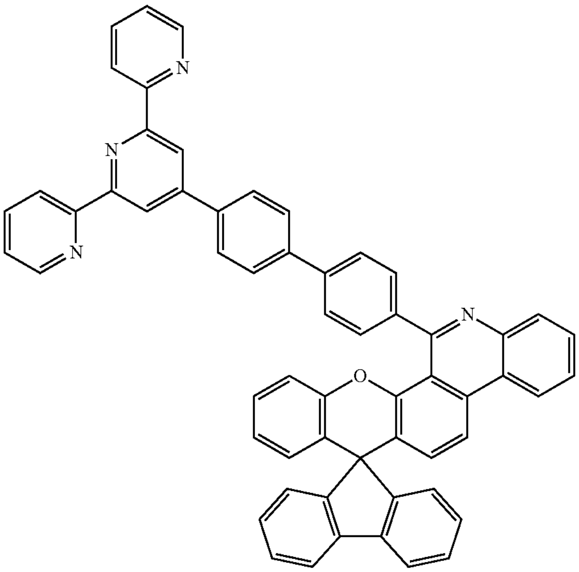
-continued
205
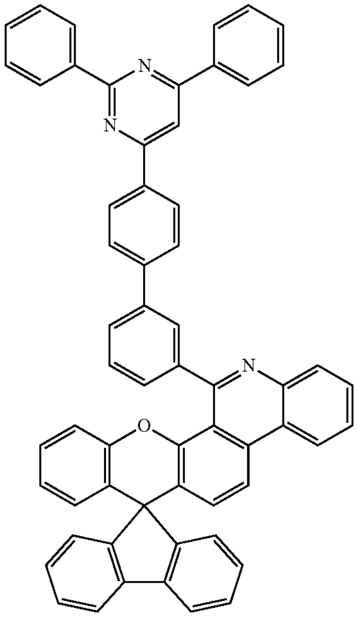
206
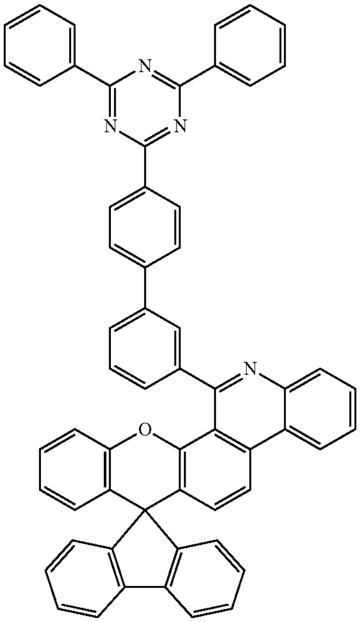

-continued
207
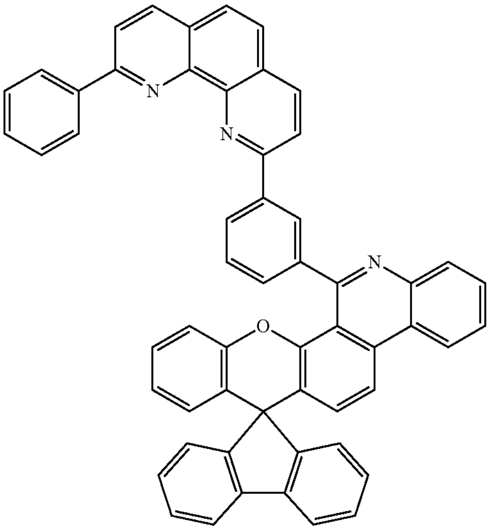
208
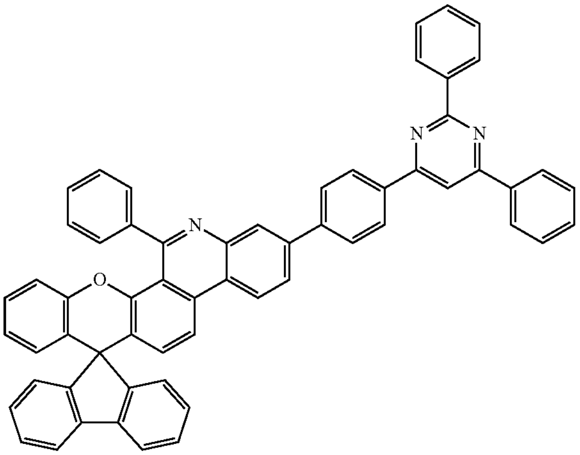
209
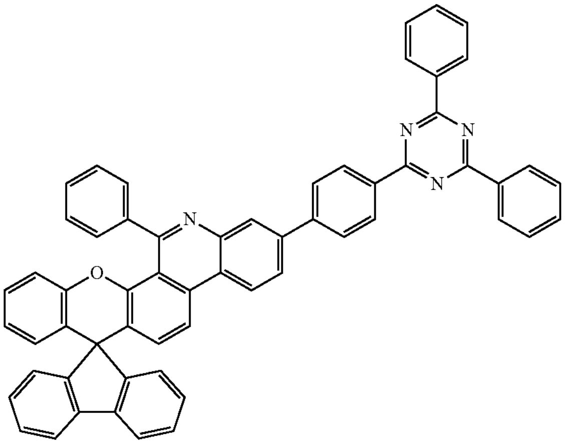
-continued
210
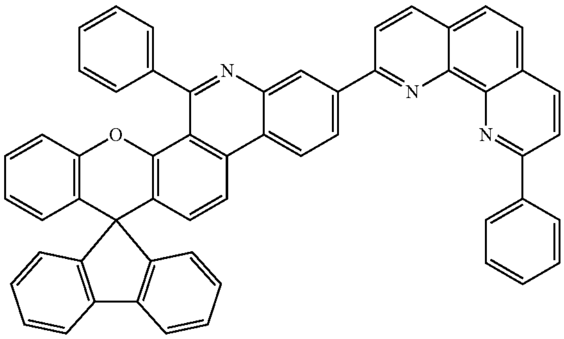
211
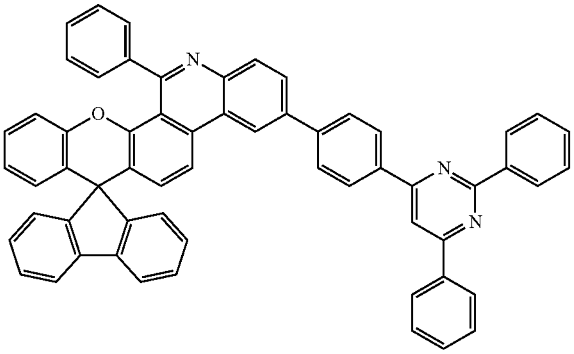
212
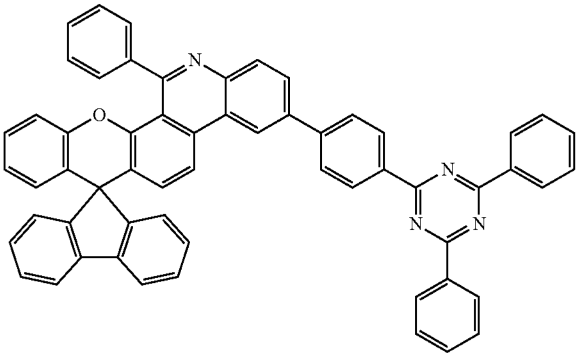
213
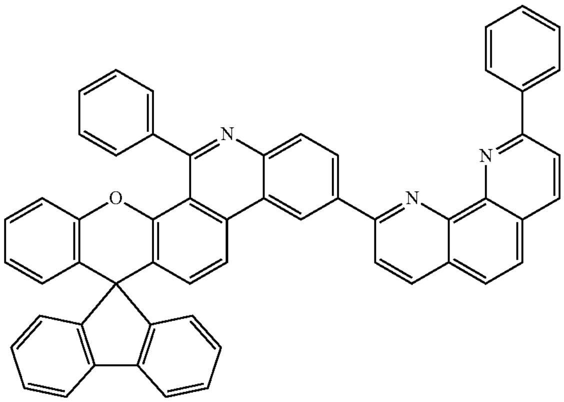

-continued
214
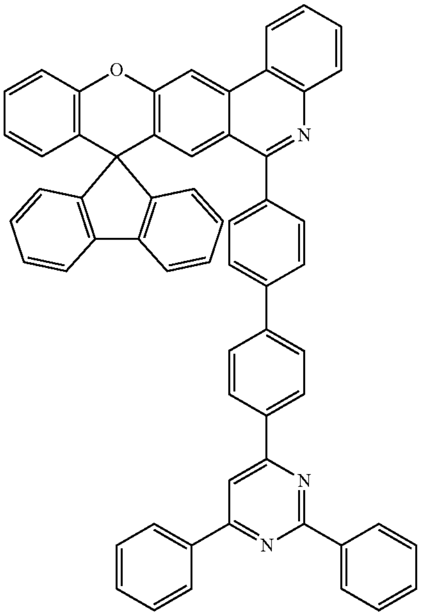
215
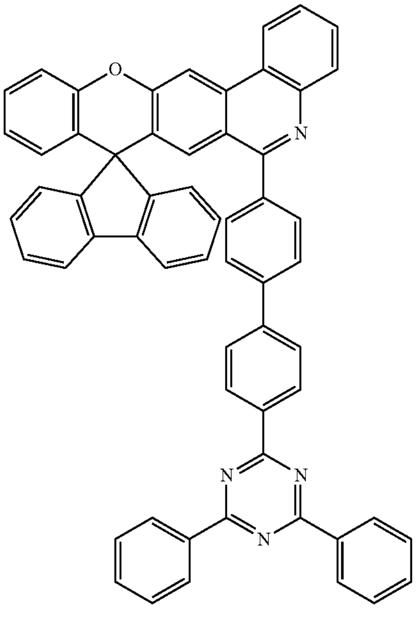
-continued
216
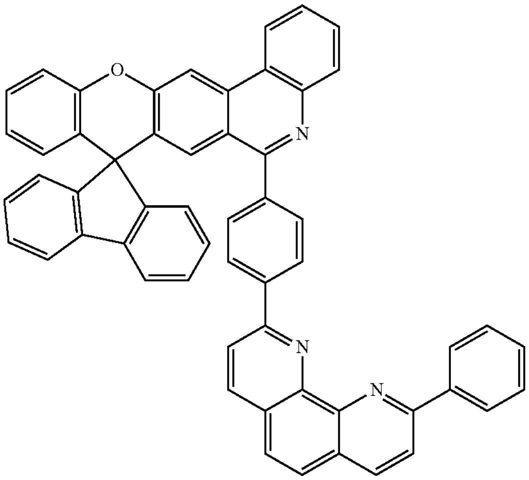
217
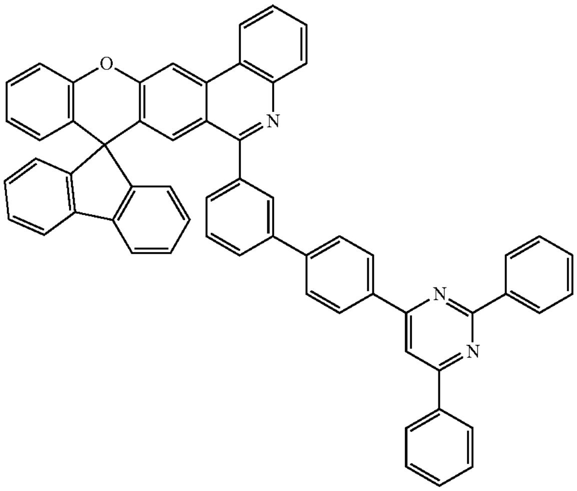
218
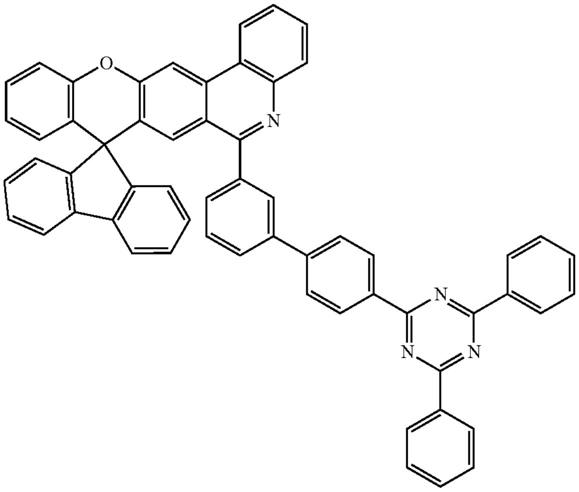

-continued
219
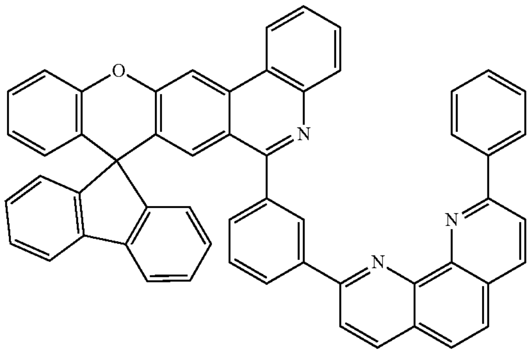
220
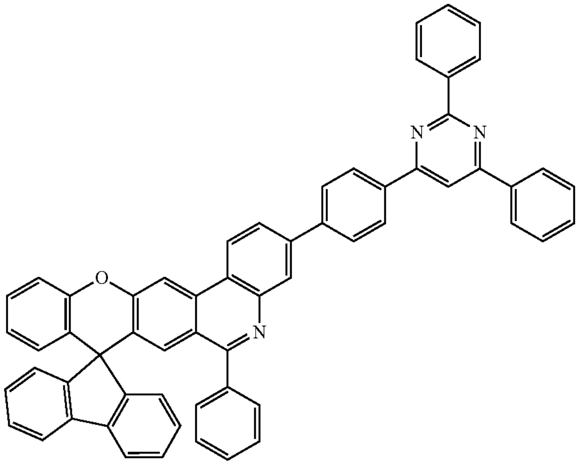
221
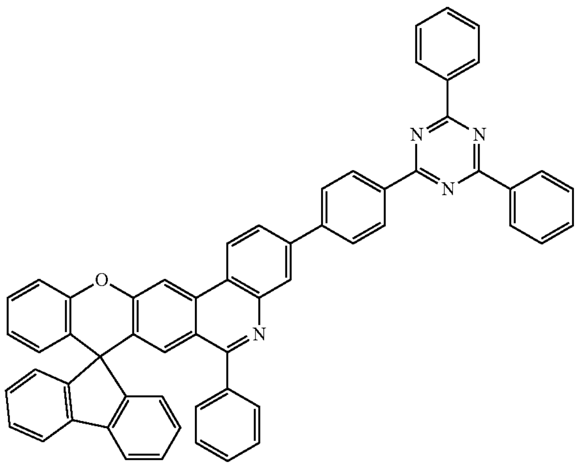
-continued
222
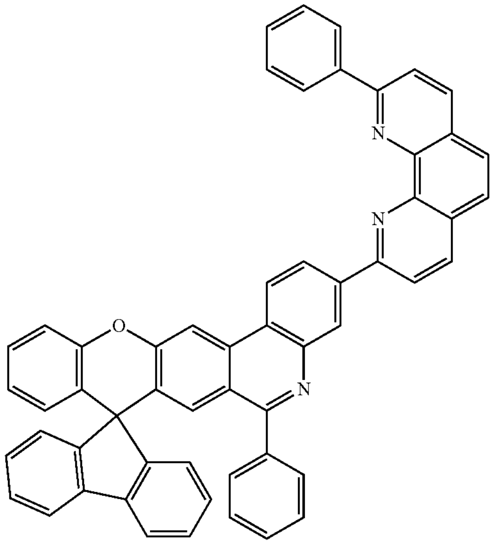
223
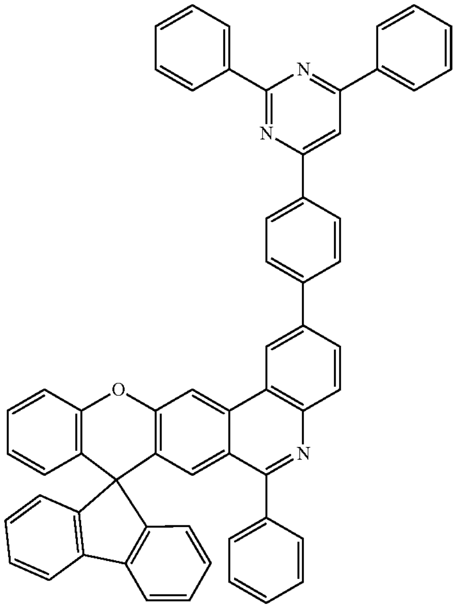

-continued
224
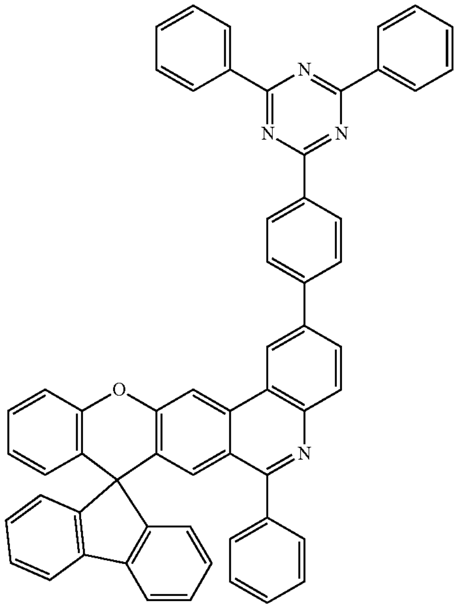
225
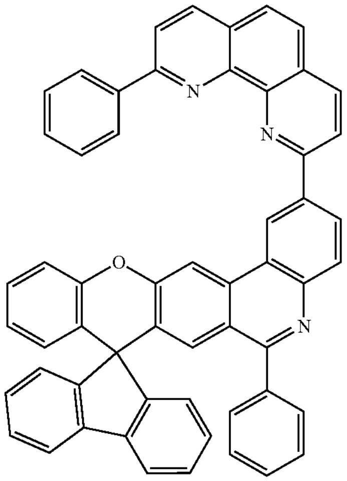
226
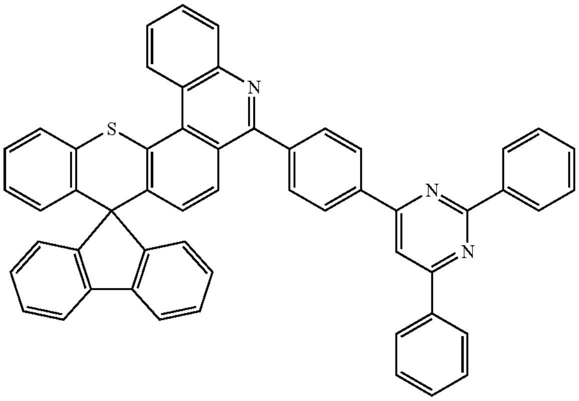
-continued
227
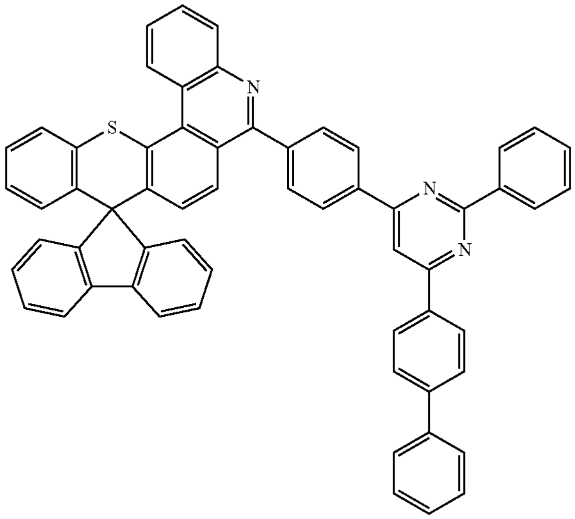
228
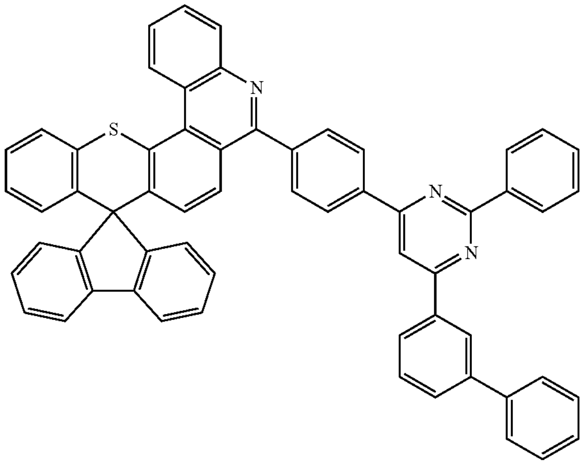
229
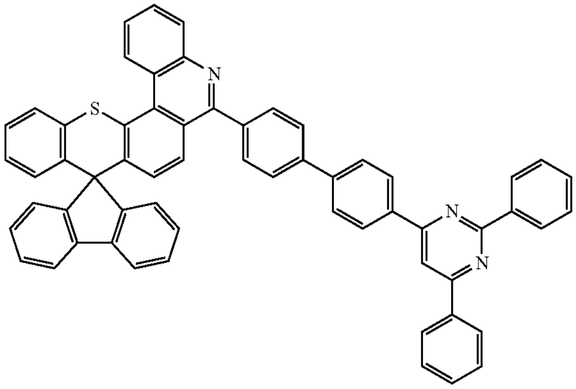

-continued
230
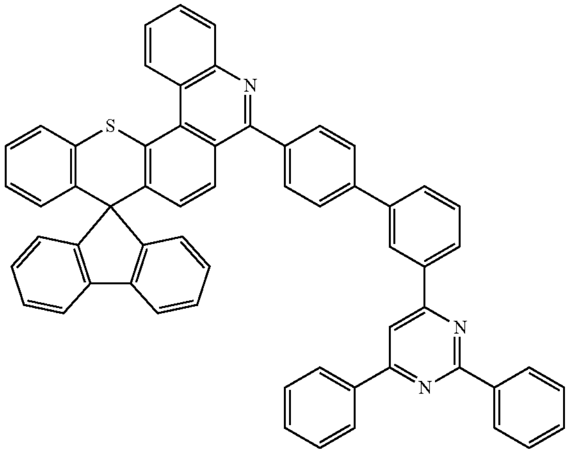
231
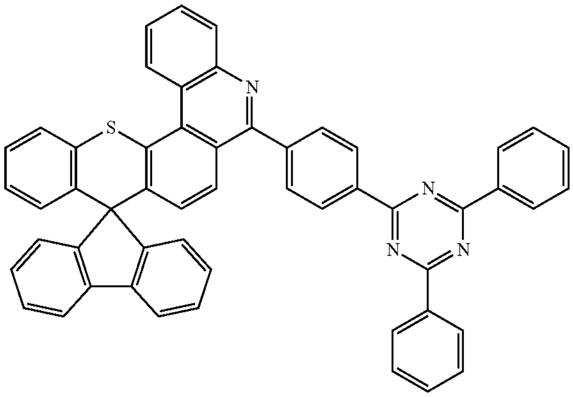
232
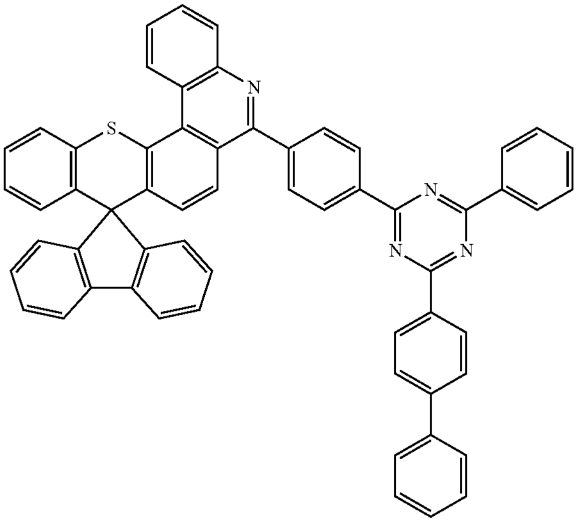
-continued
233
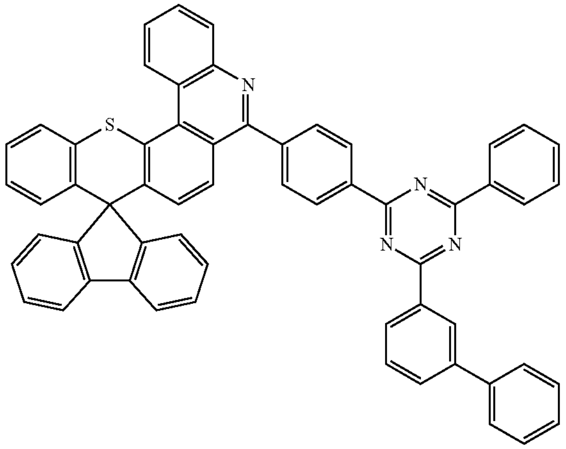
234
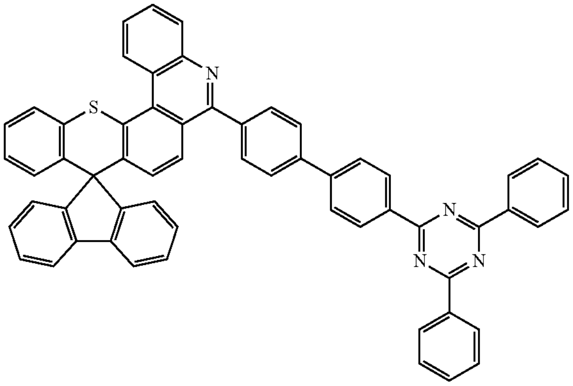
235
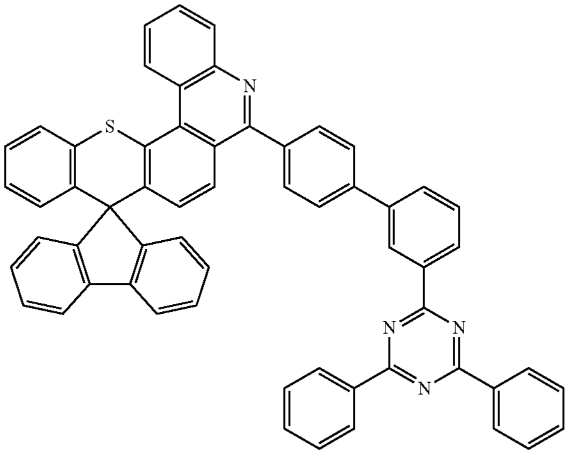

-continued
236
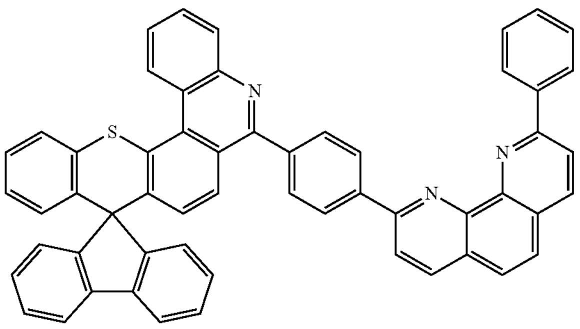
237
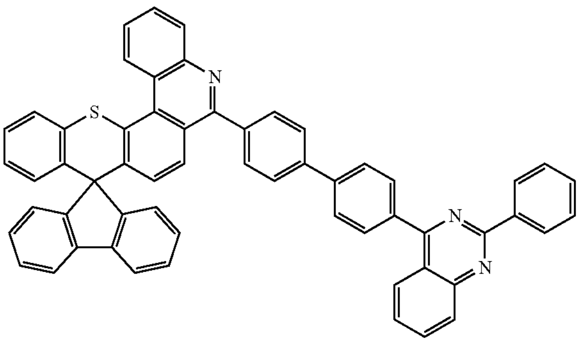
238
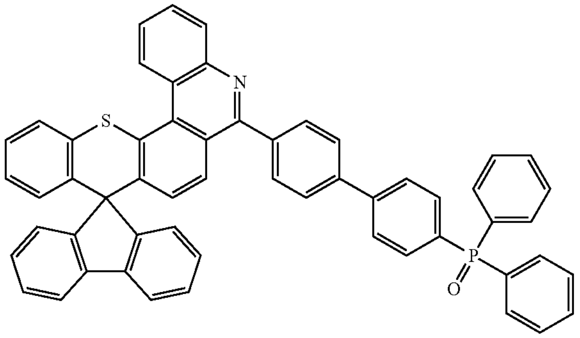
239
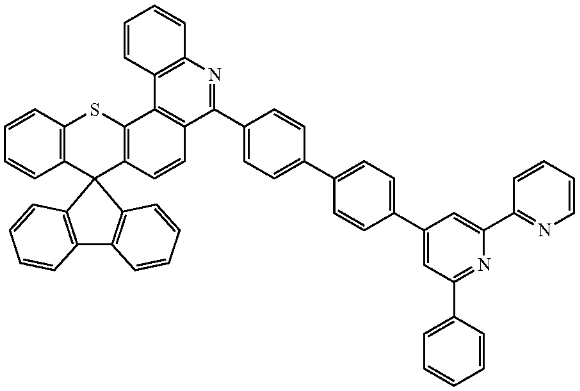
-continued
240
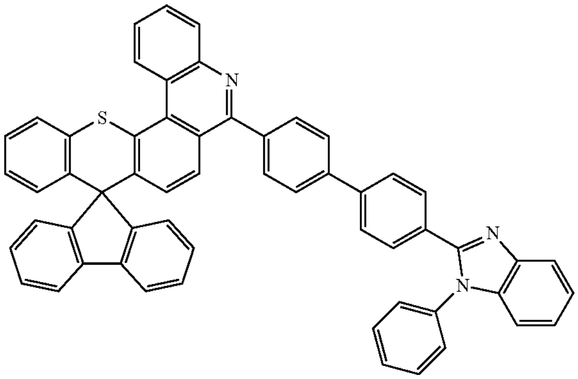
241
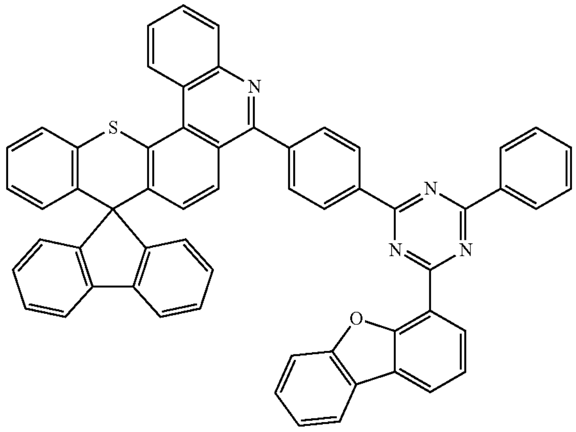
242
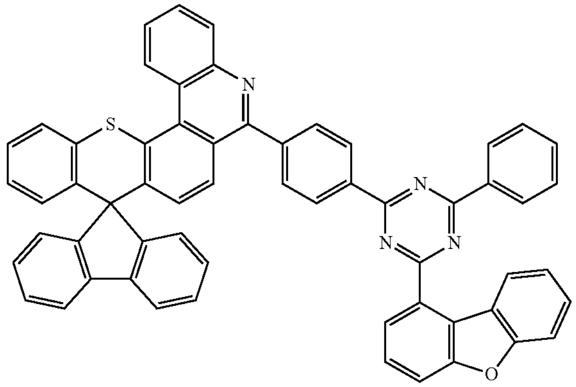

-continued
243
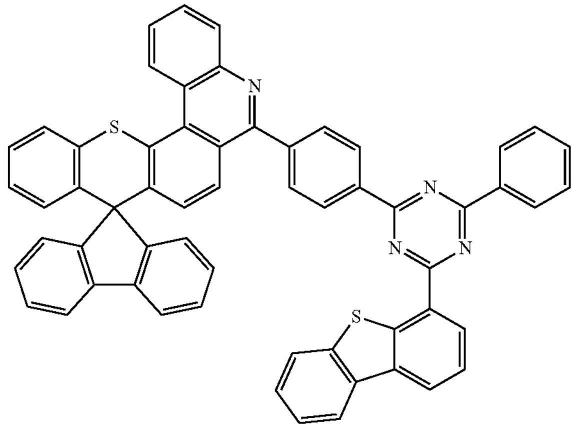
244
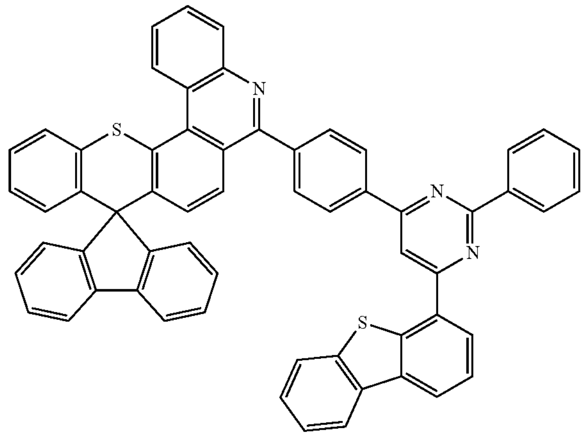
245
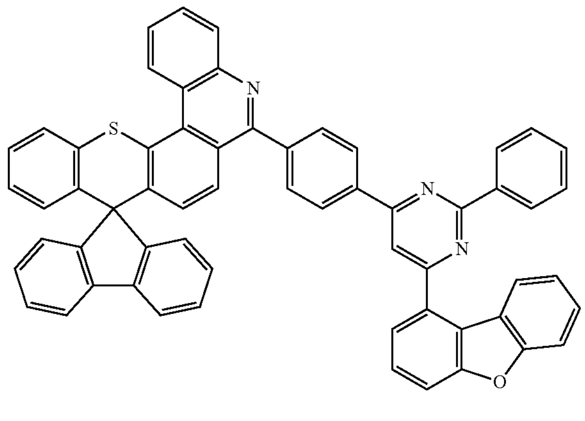
-continued
246
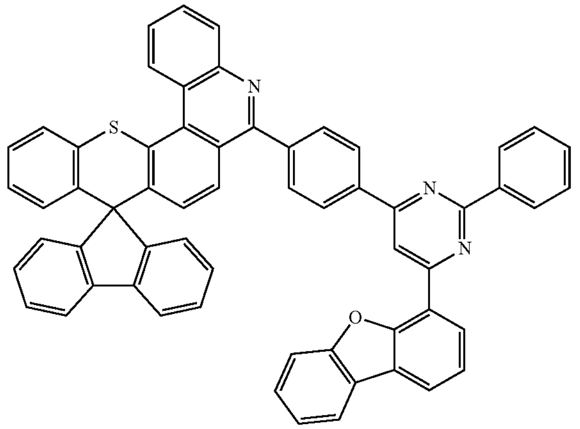
247
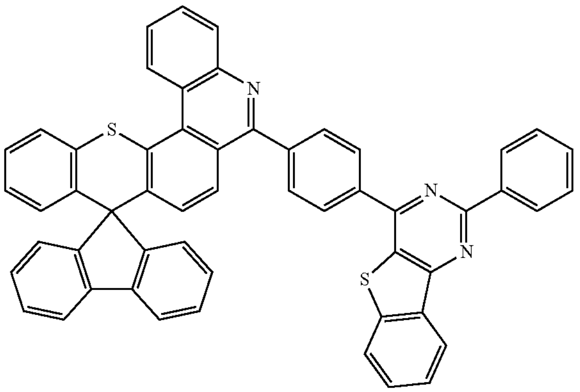
248
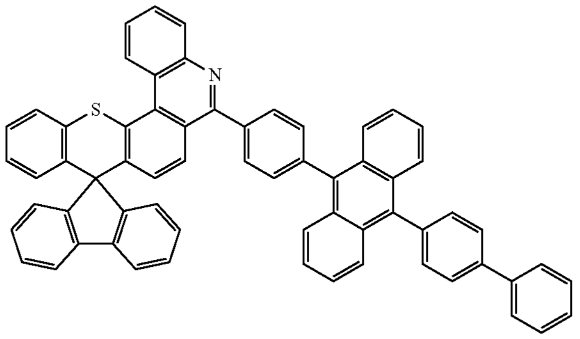
249
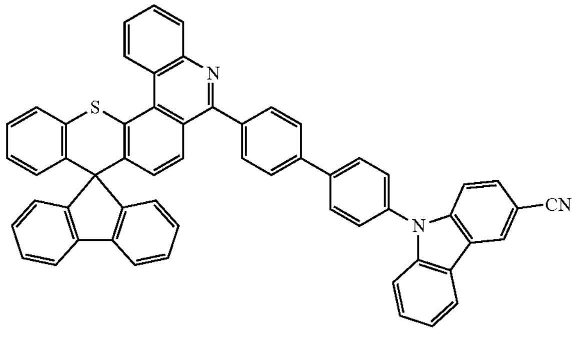

-continued
250
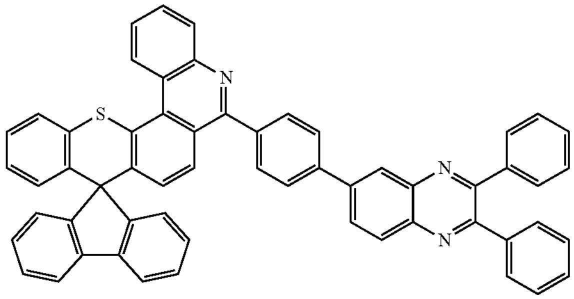
251
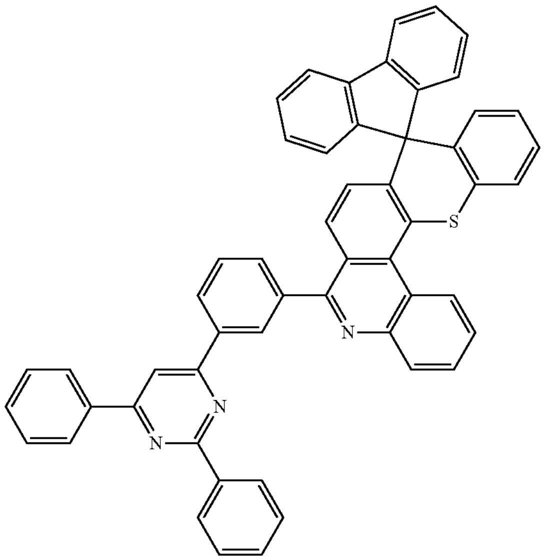
252
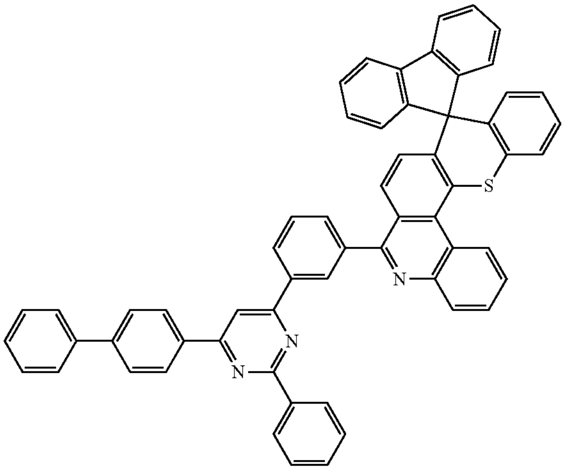
-continued
253
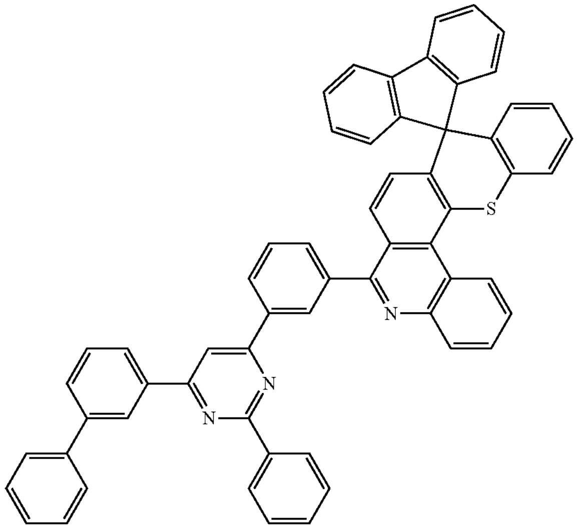
254
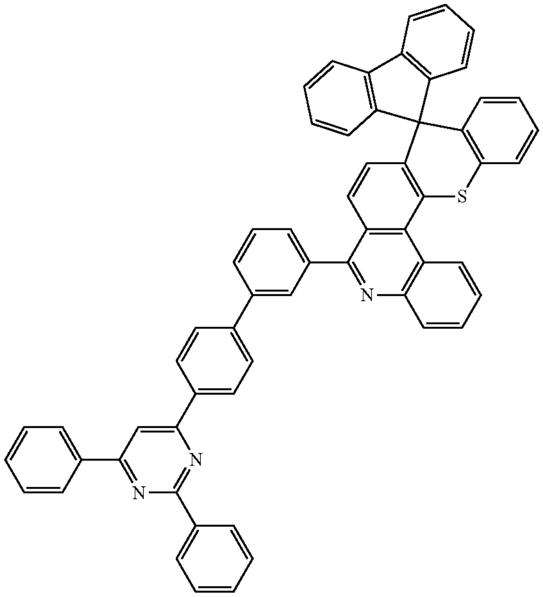

-continued
255
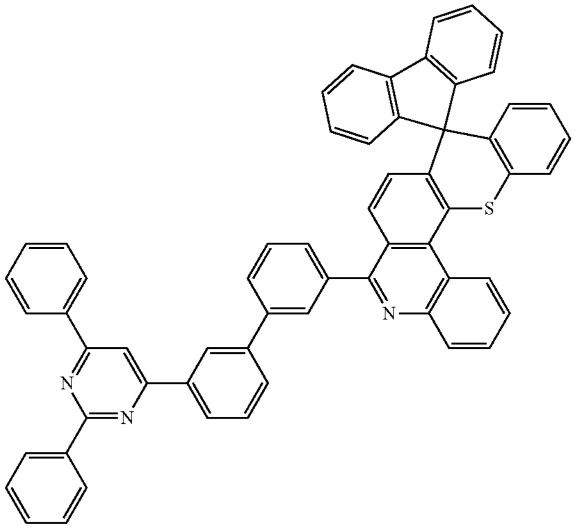
256
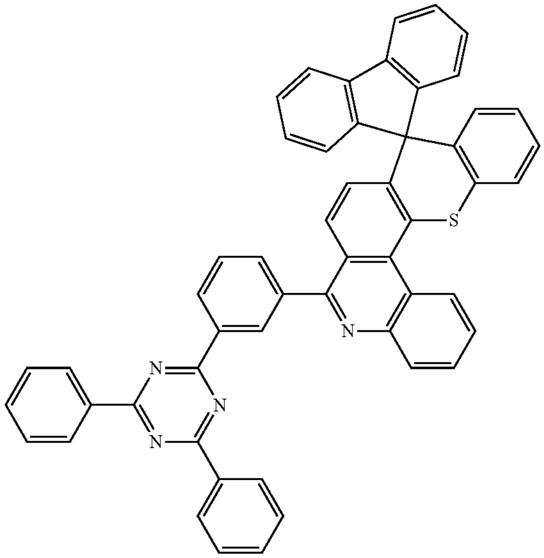
257
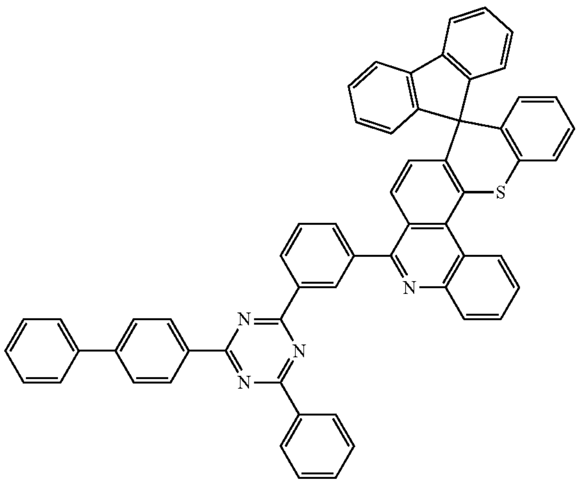
-continued
258
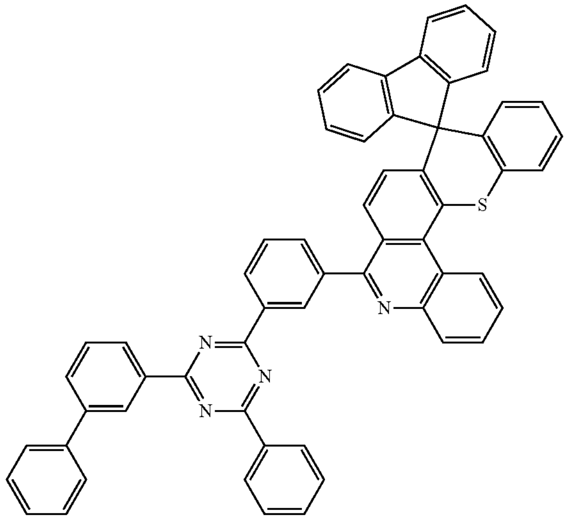
259
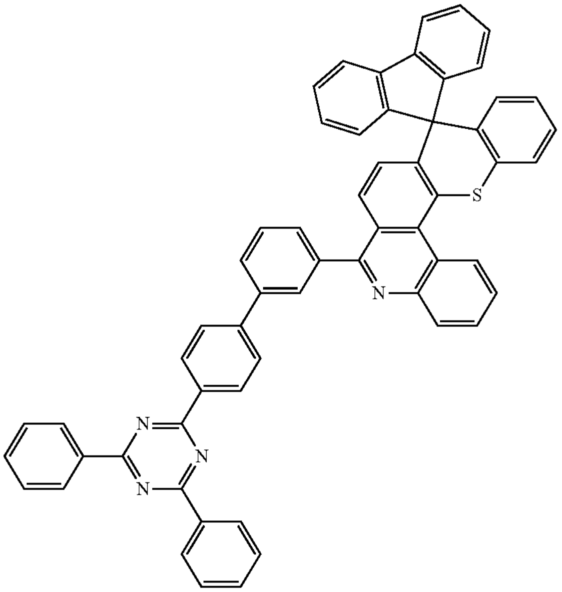

-continued
260
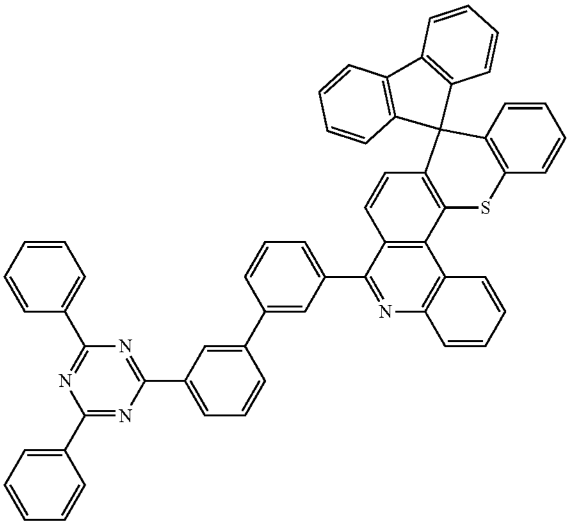
-continued
262
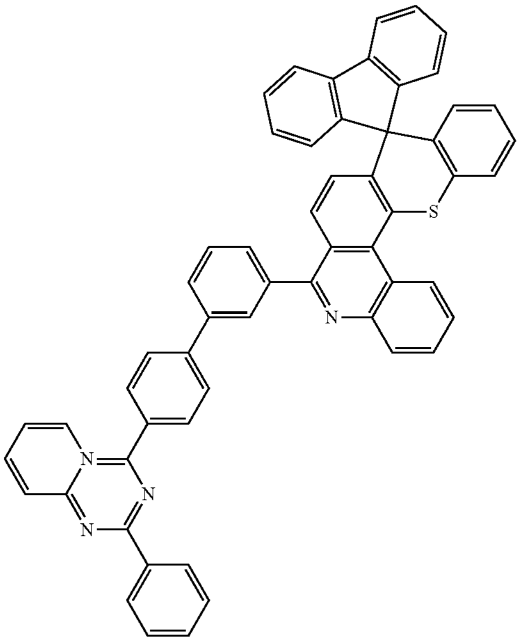
261
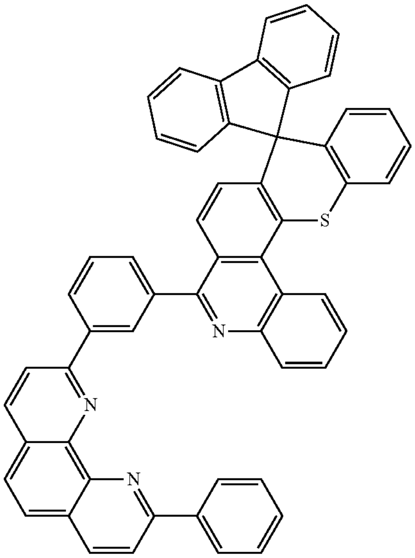
263
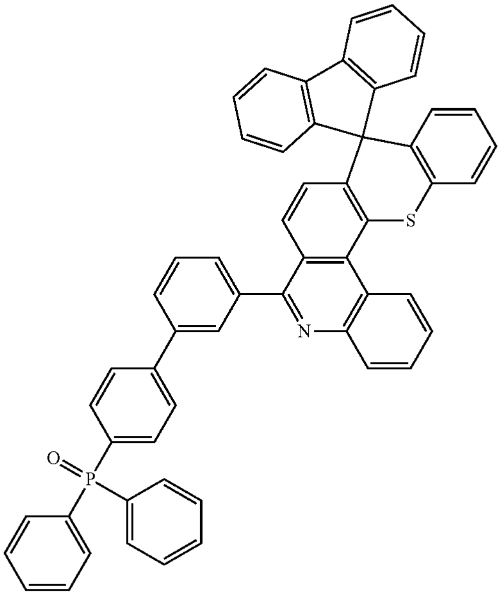

-continued
264
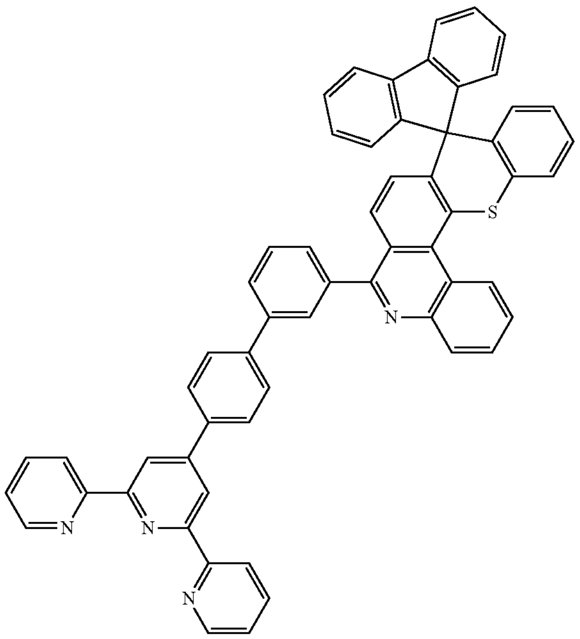
265
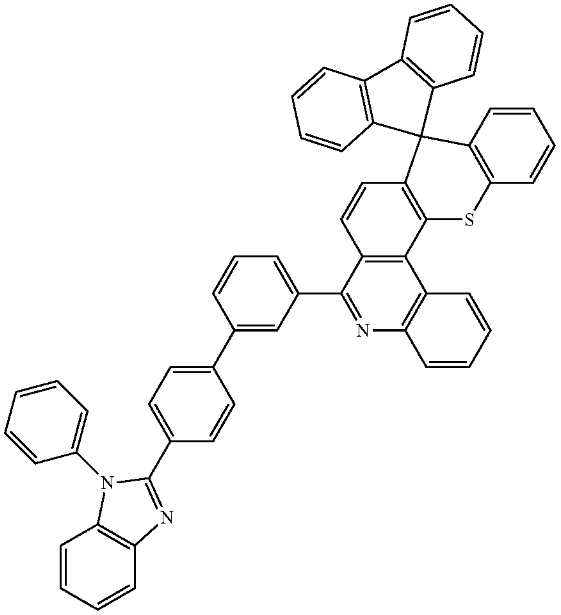
-continued
266
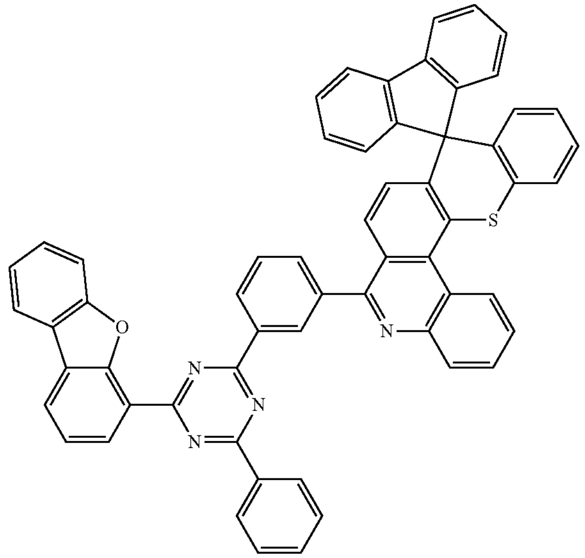
267
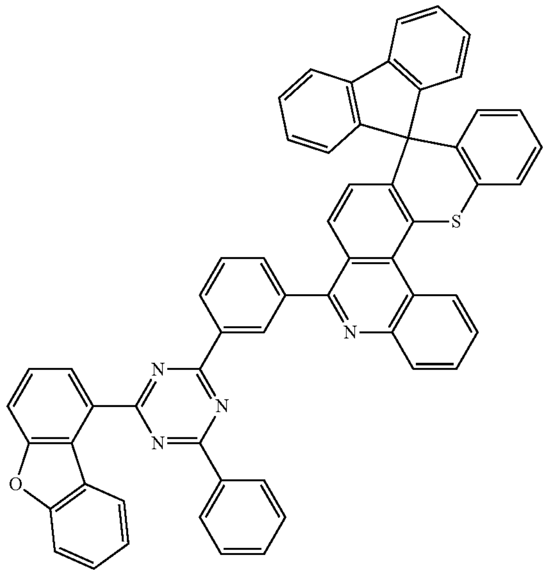

-continued
268
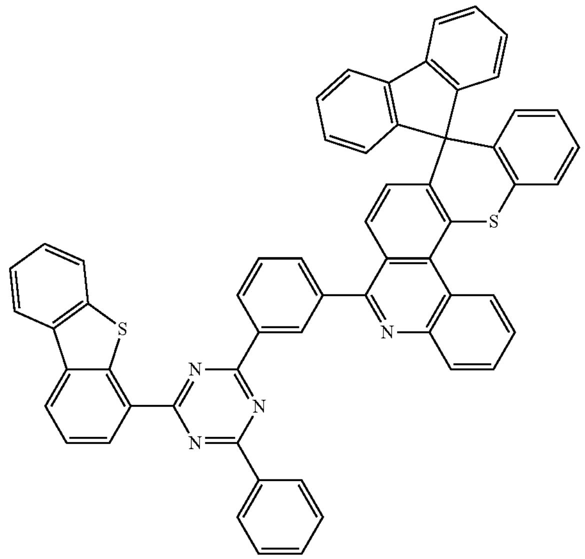
-continued
270
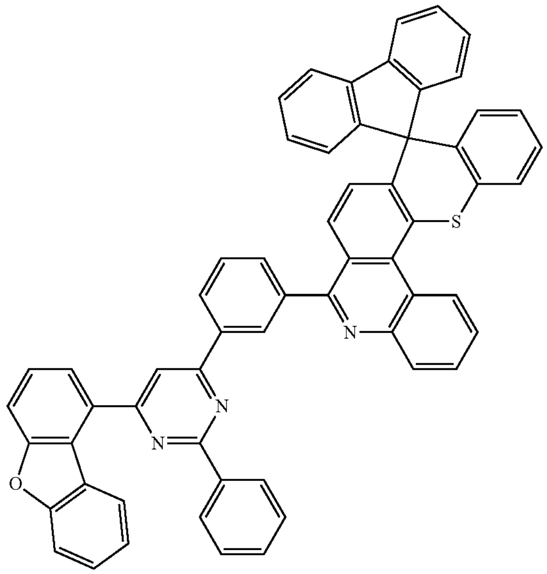
269
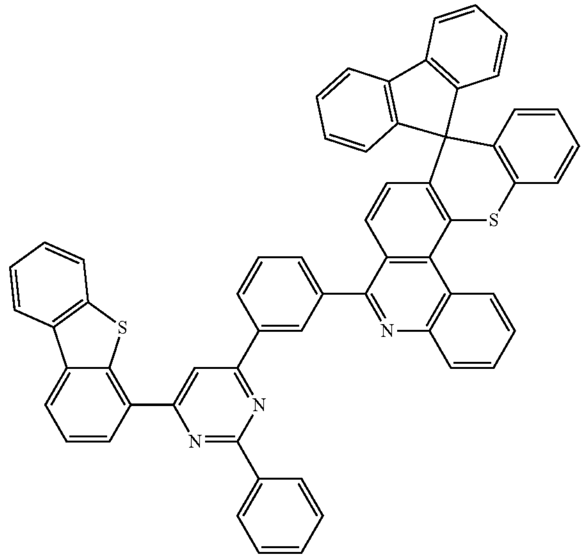
271
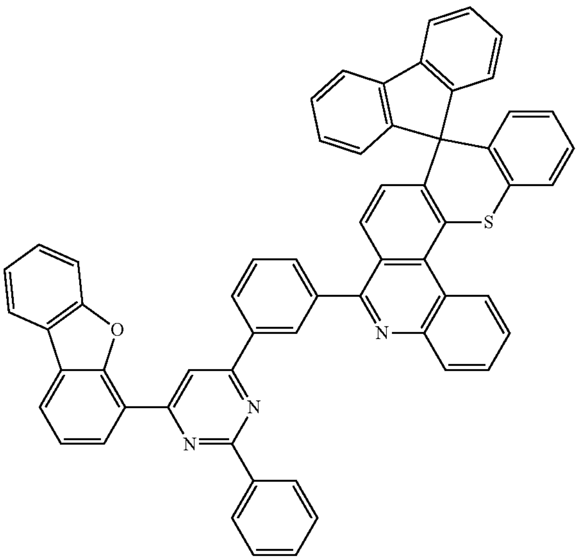

272
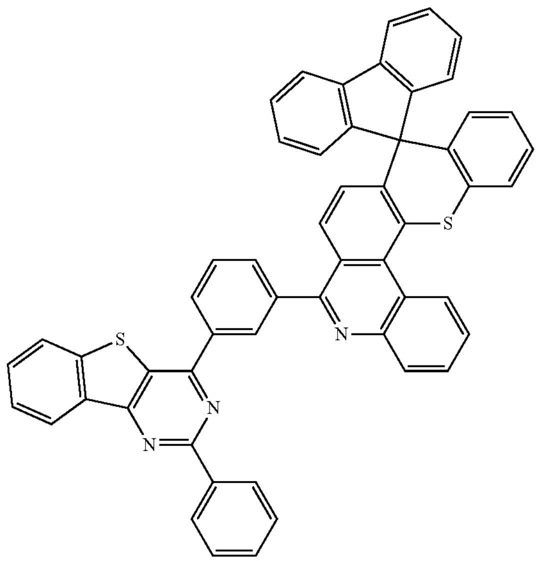
273
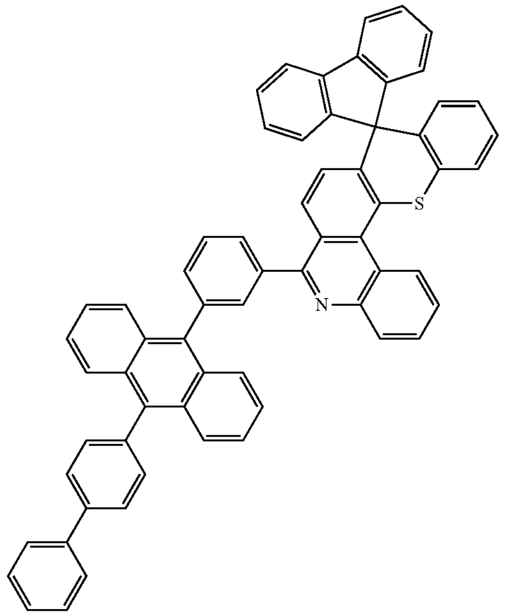
274
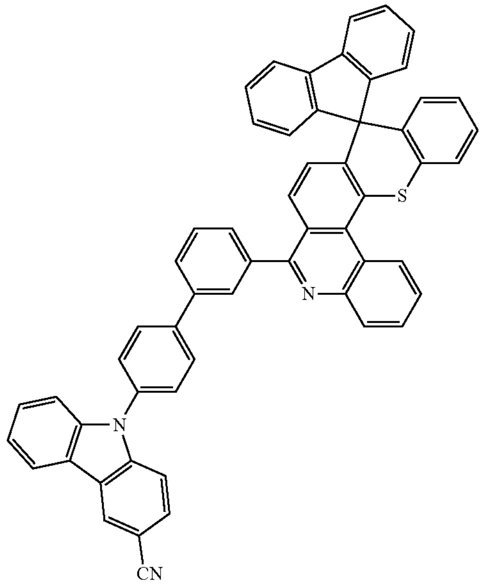
275
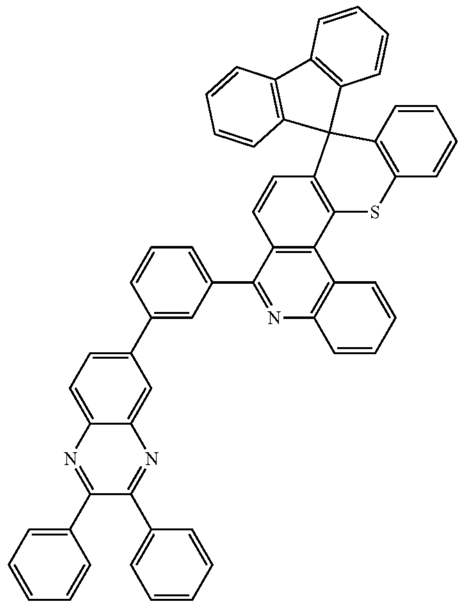

-continued
276
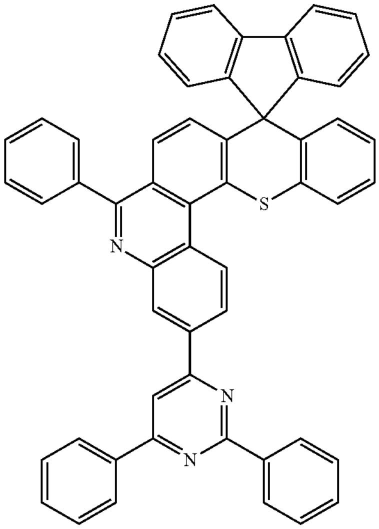
277
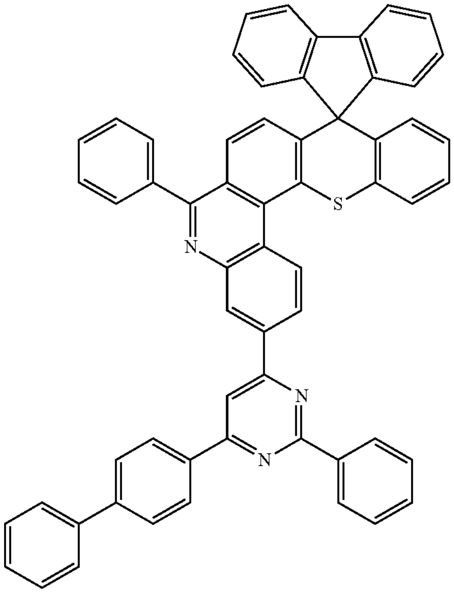
278
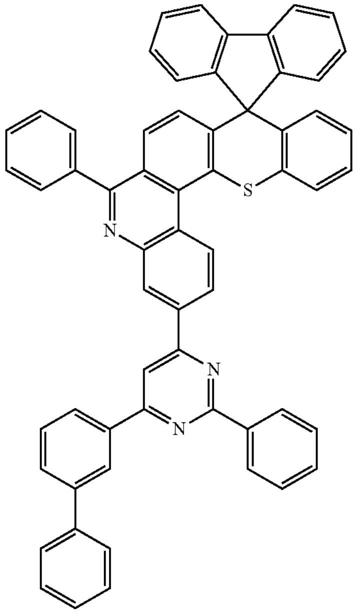
279
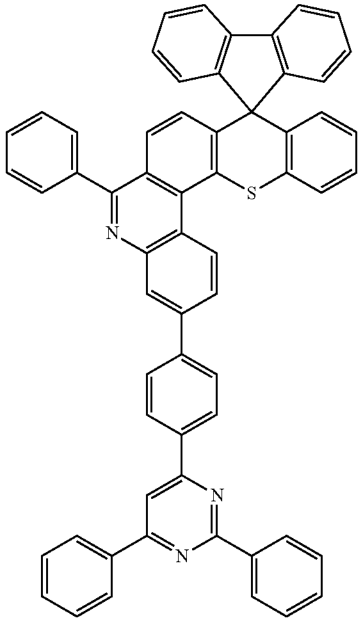

-continued
280
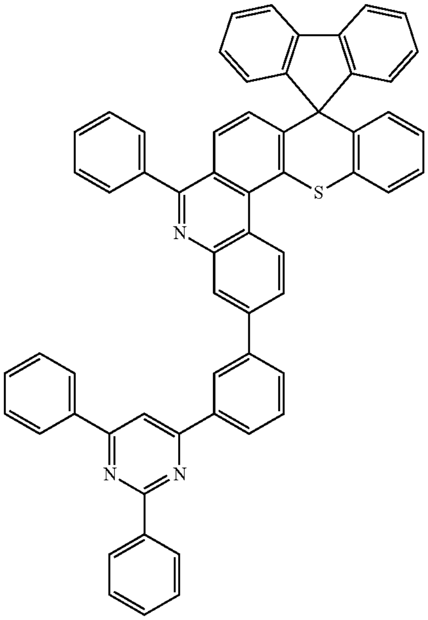
281
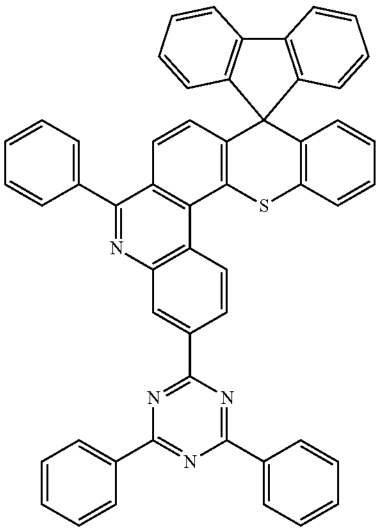
-continued
282
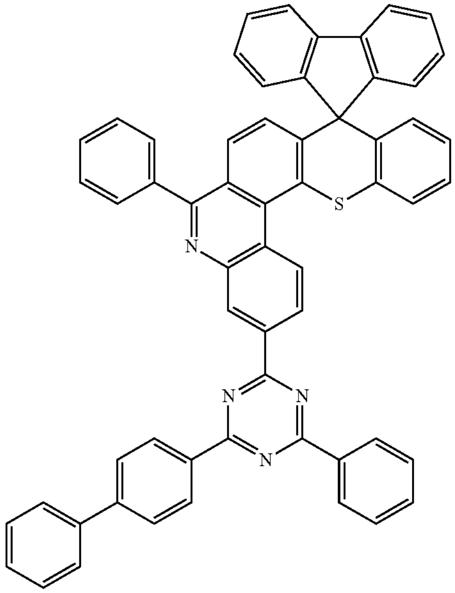
283
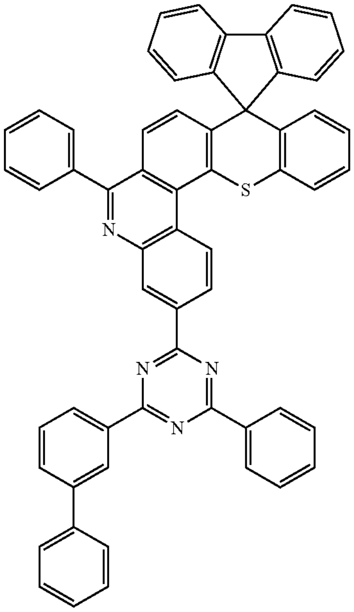

-continued
284
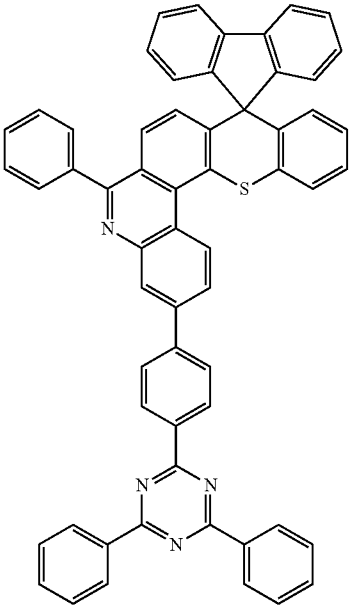
285
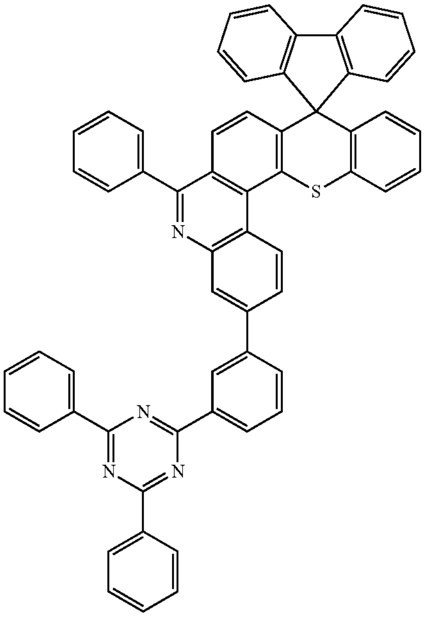
-continued
286
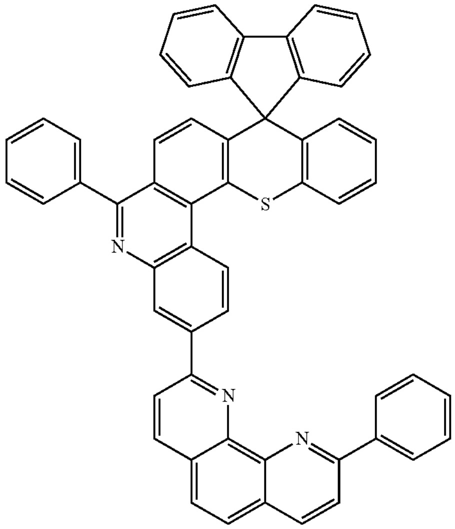
287
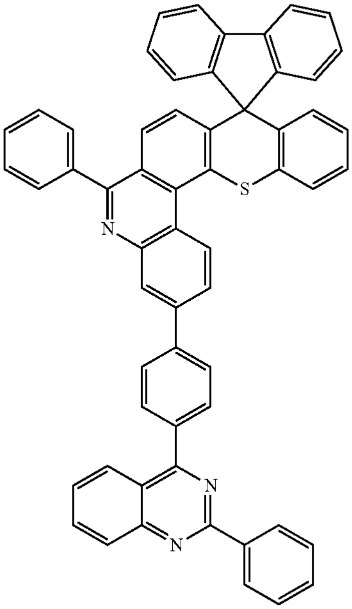

-continued
288
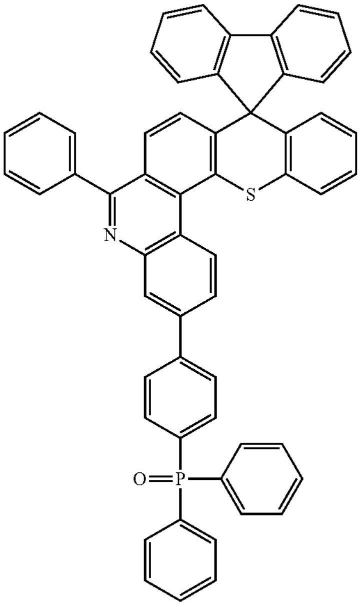
289
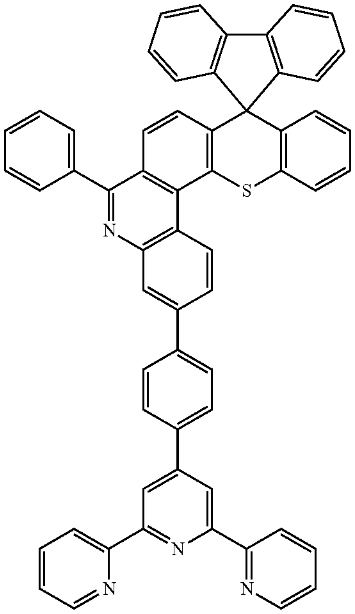
-continued
290
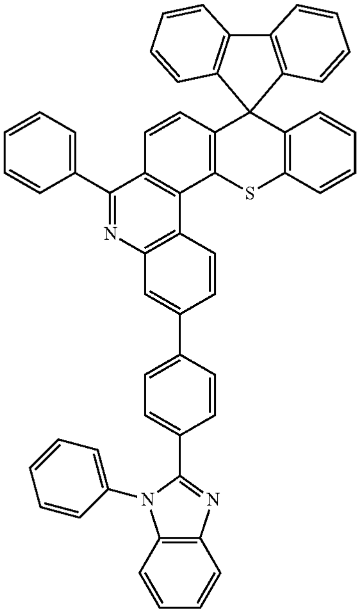
291
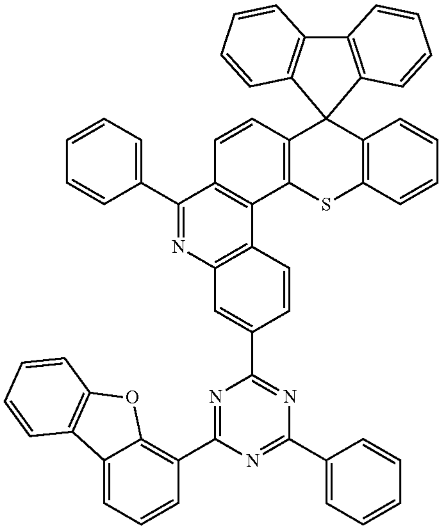

-continued
292
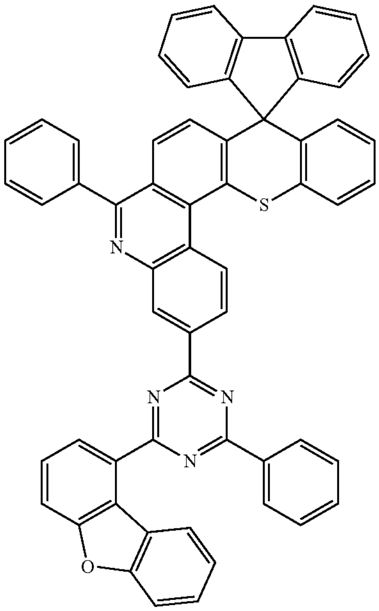
293
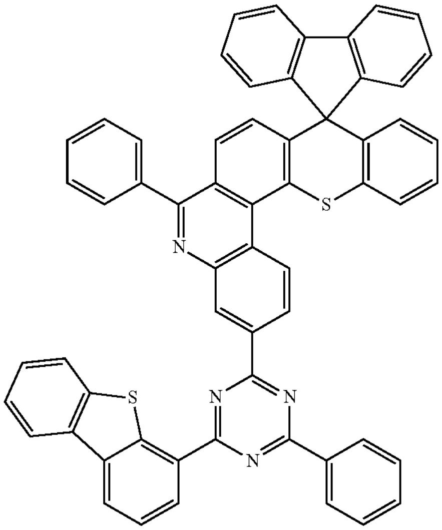
294
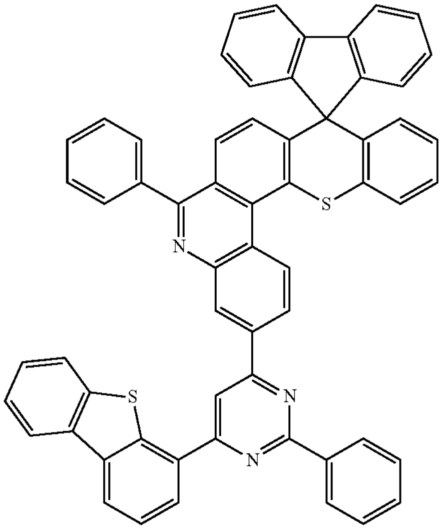
-continued
295
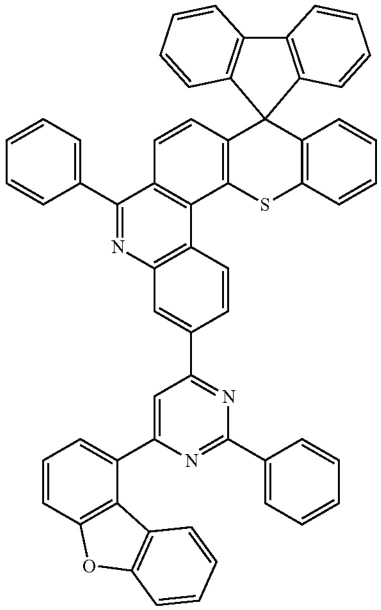
296
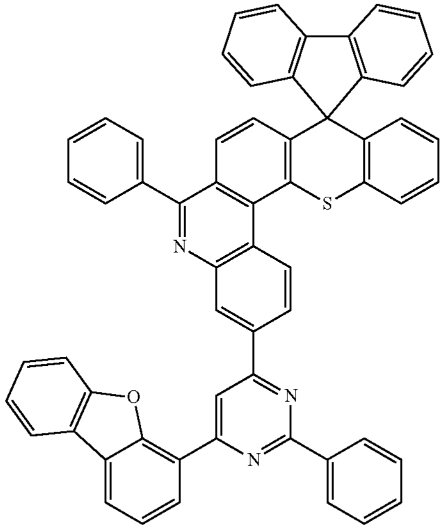
297
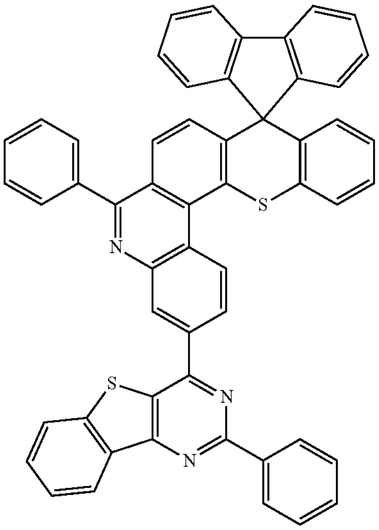

-continued
298
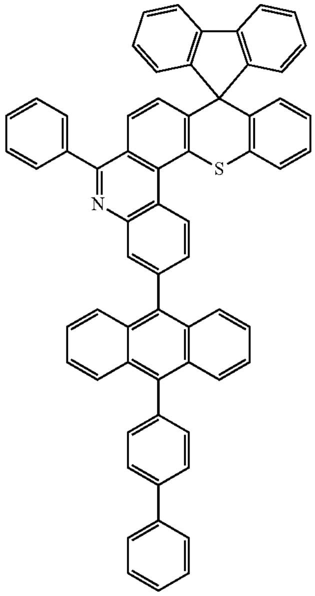
299
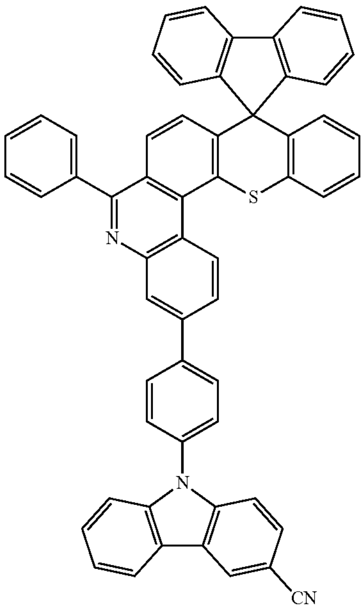
-continued
300
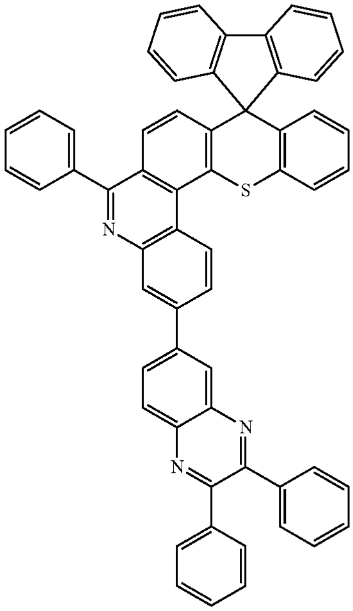
301
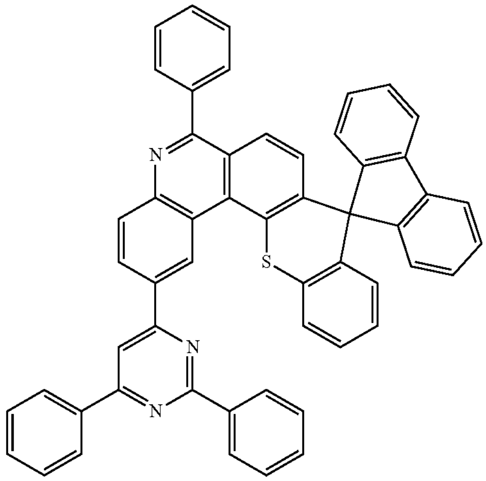
302
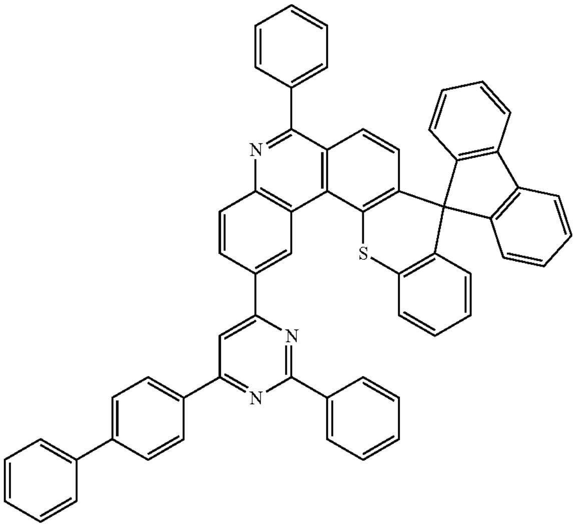

-continued
303
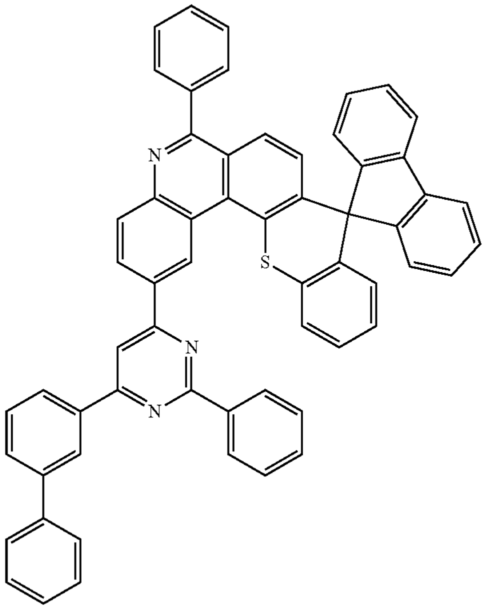
304
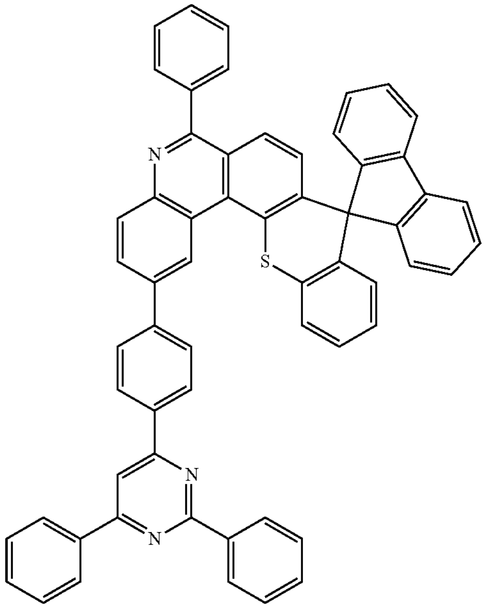
-continued
305
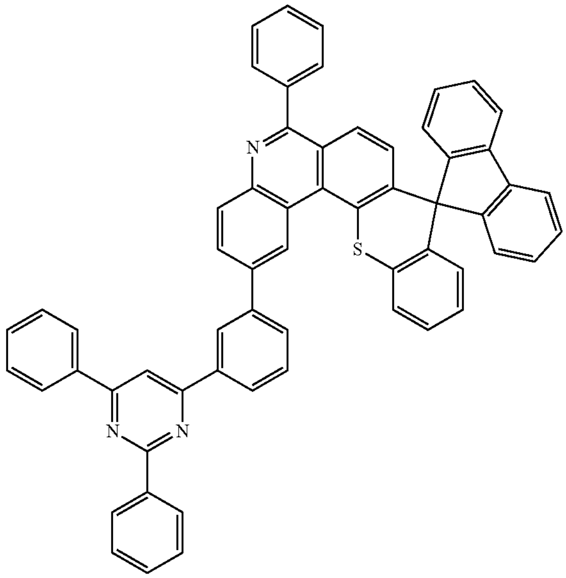
306
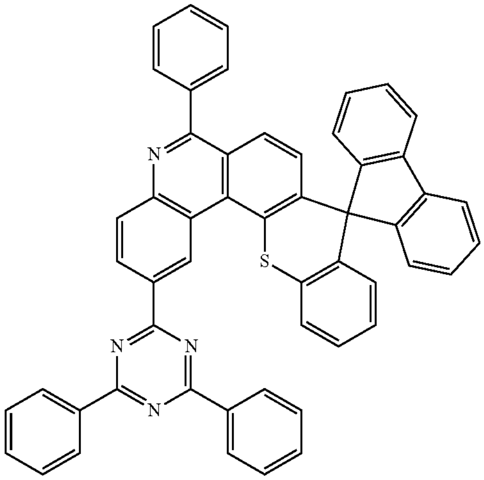
307
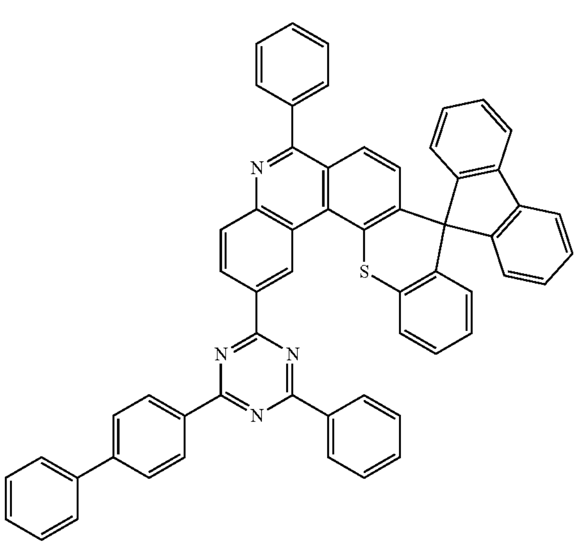

-continued
308
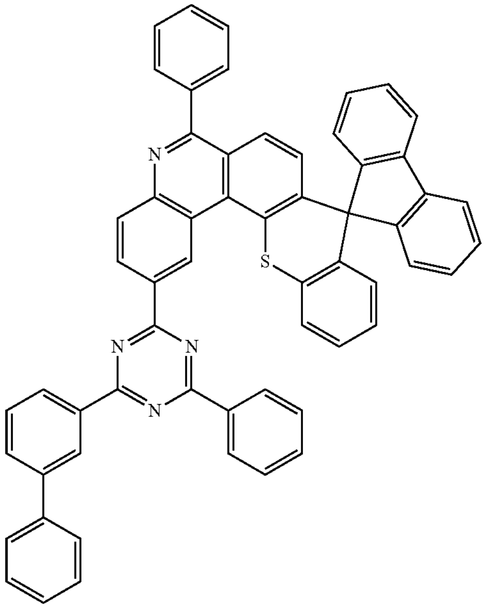
309
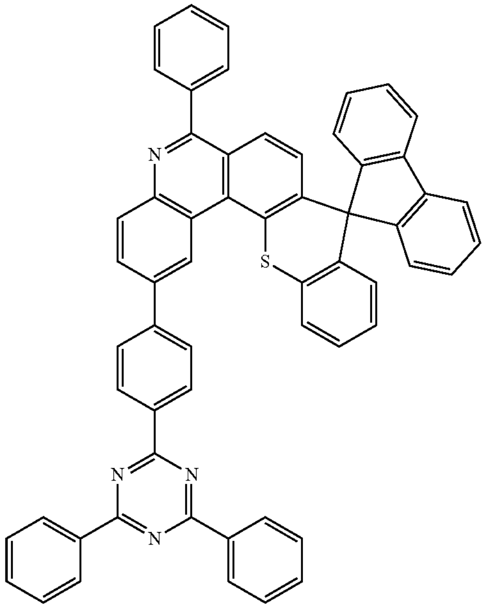
-continued
310
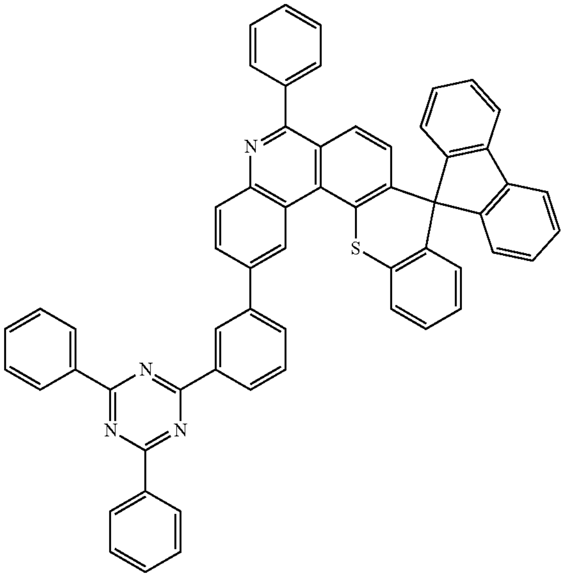
311
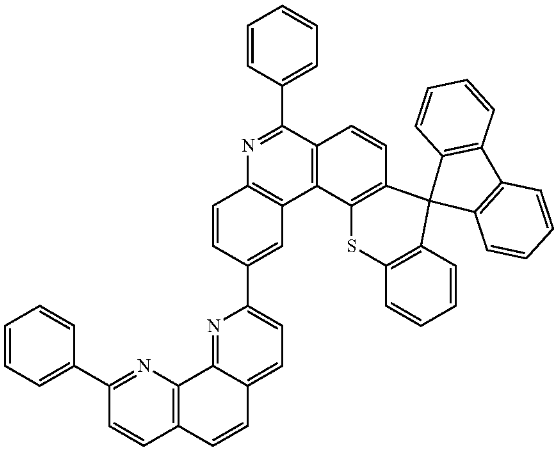

-continued
312
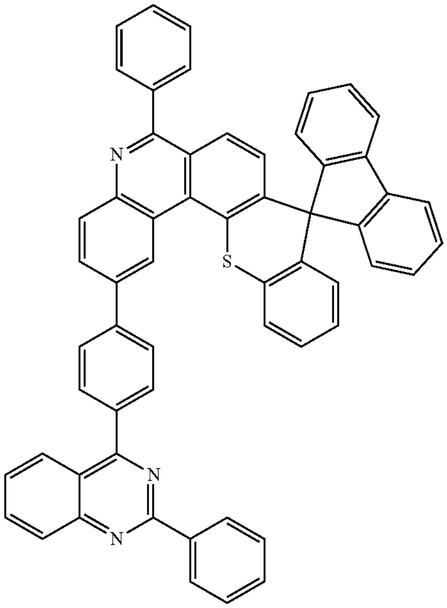
314
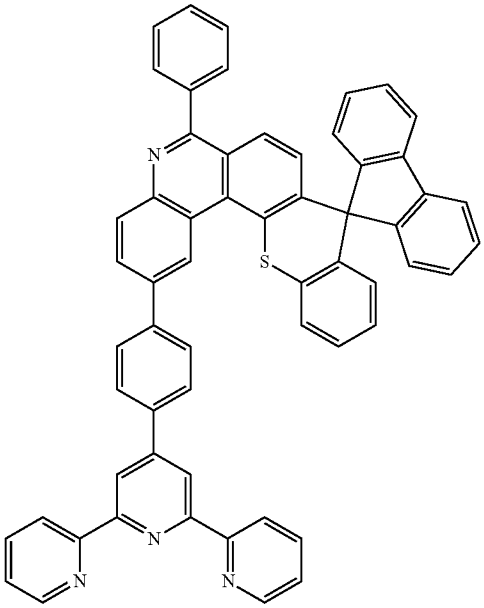
313
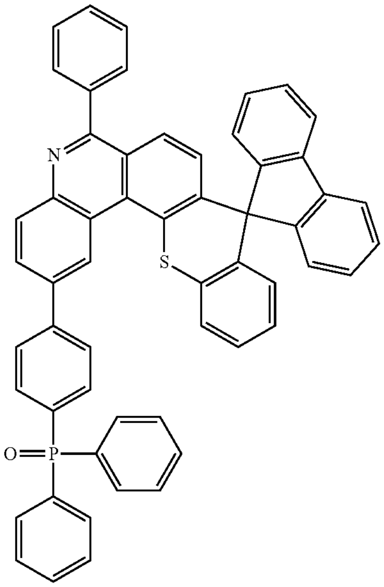
315
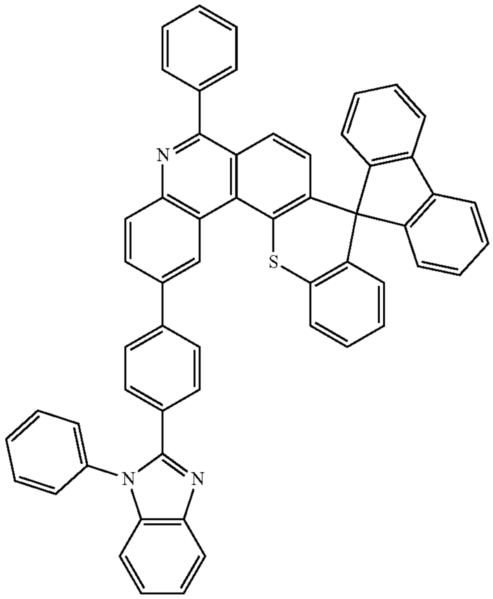

-continued
316
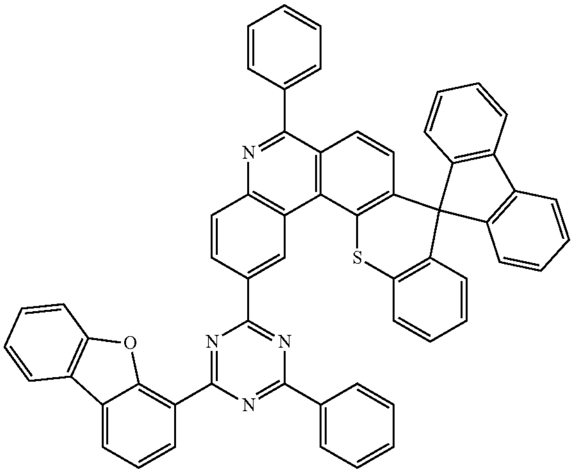
317
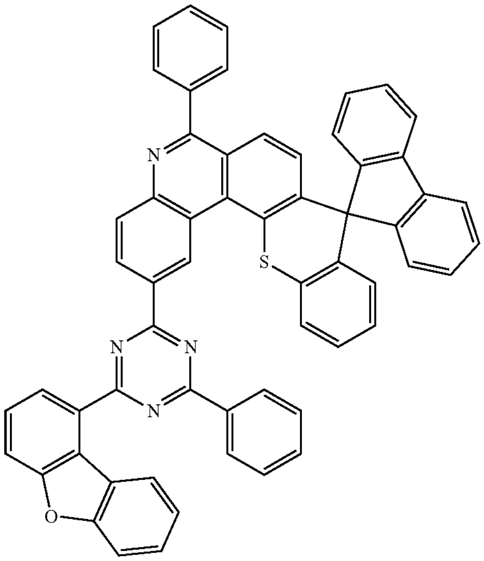
318
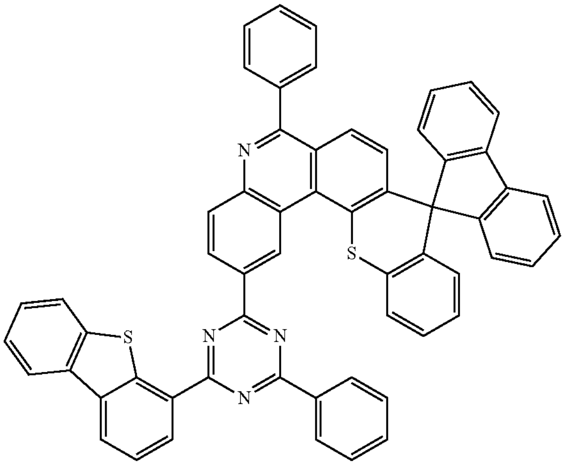
-continued
319
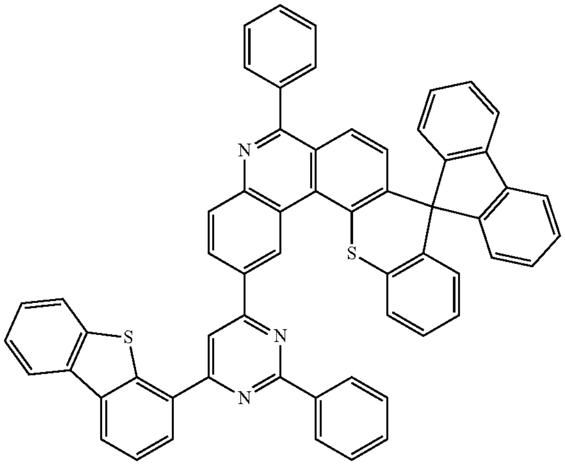
320
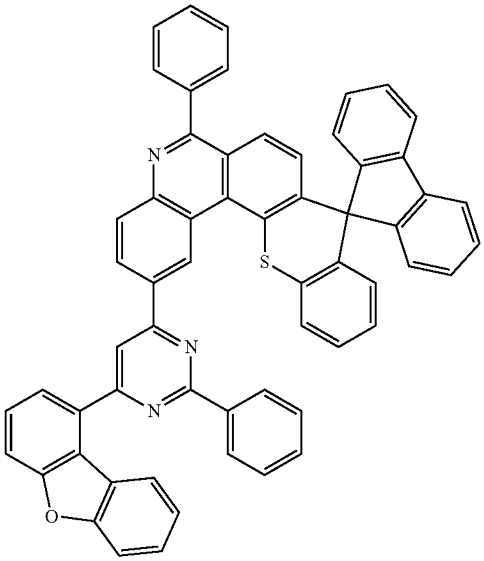
321
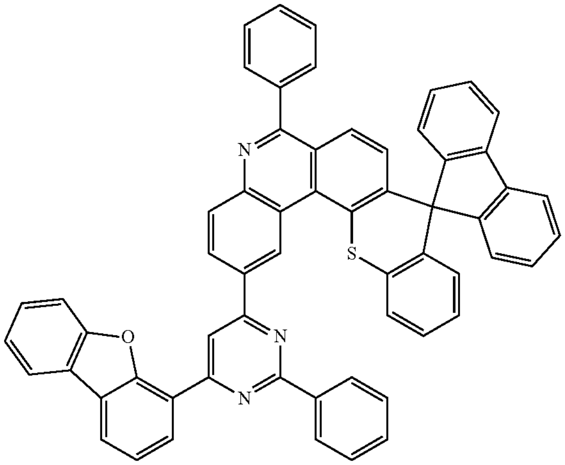

322
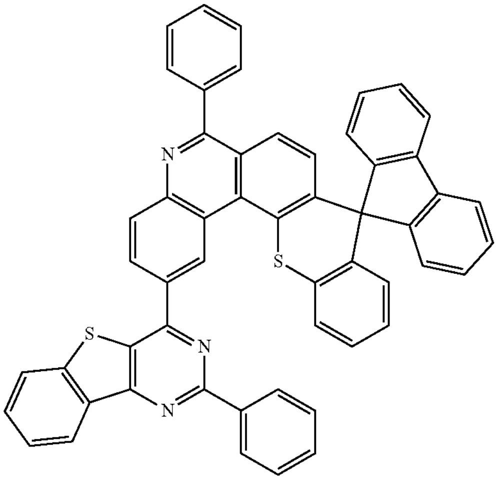
323
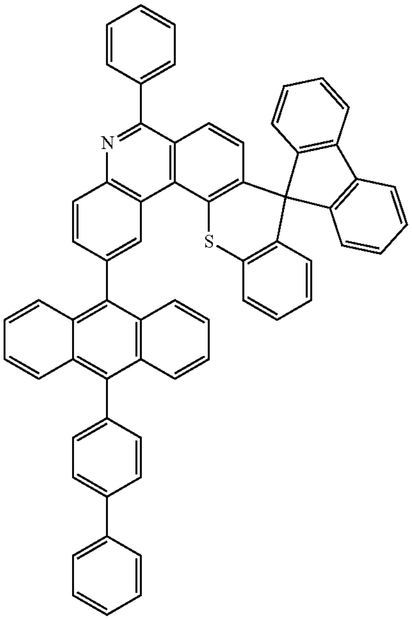
324
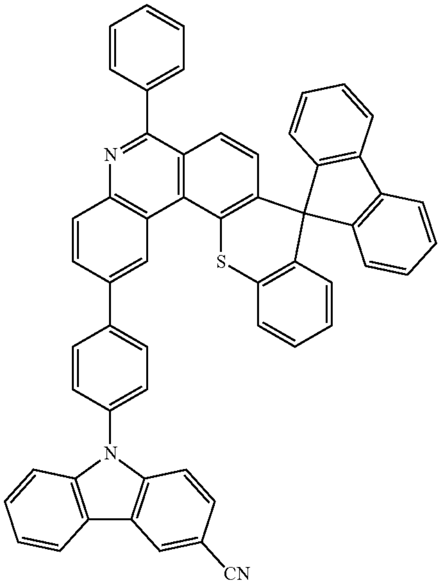
325
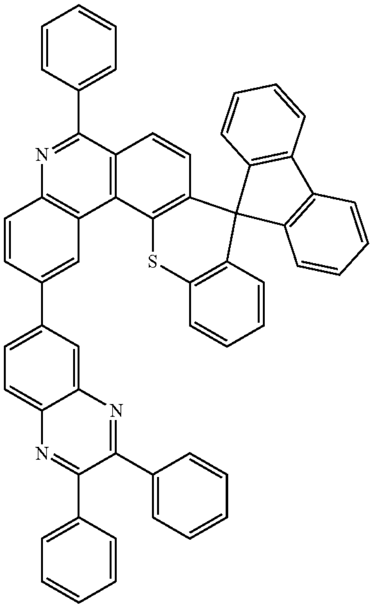

-continued
326
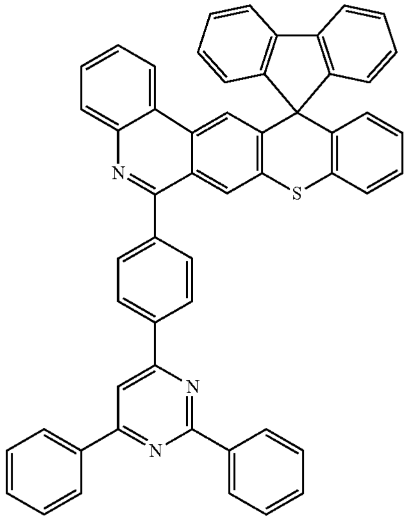
327
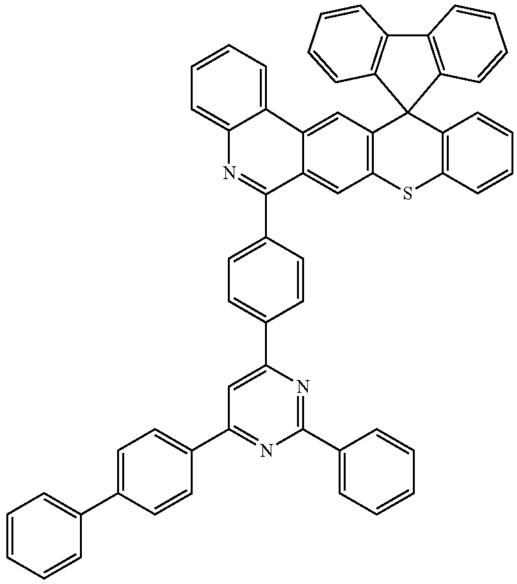
-continued
328
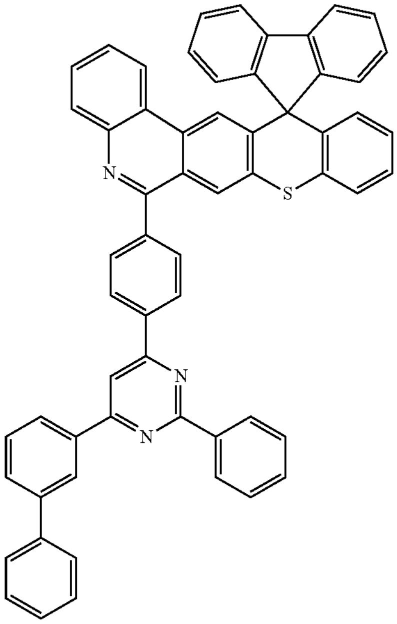
329
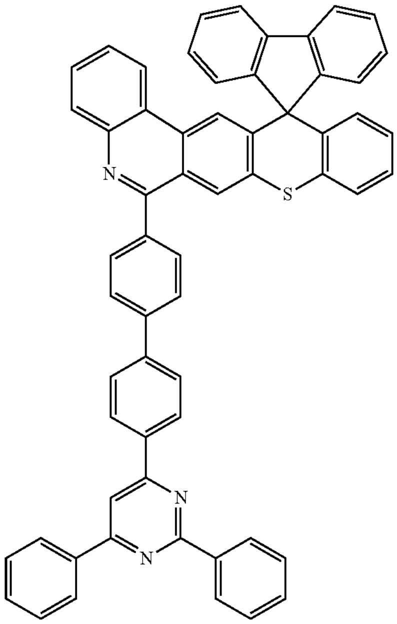

-continued
330
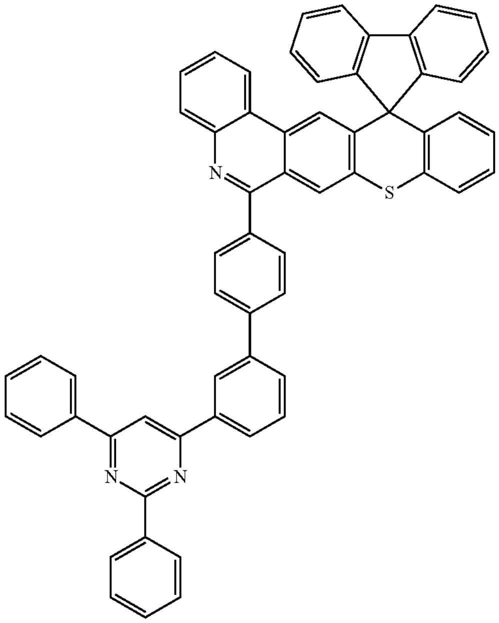
331
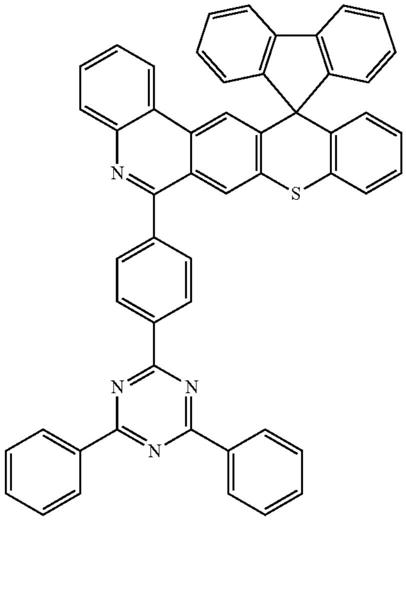
-continued
332
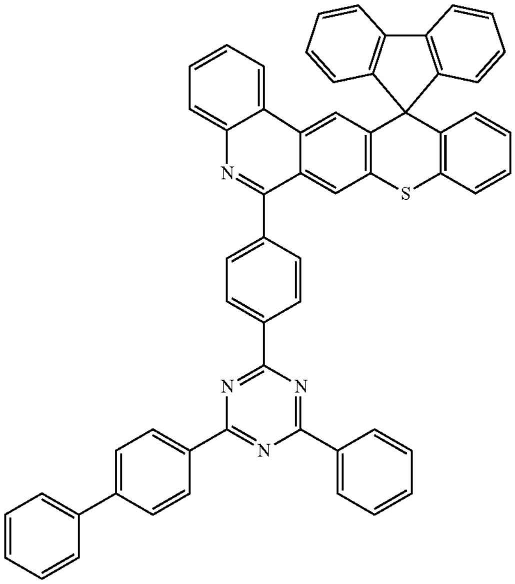
333
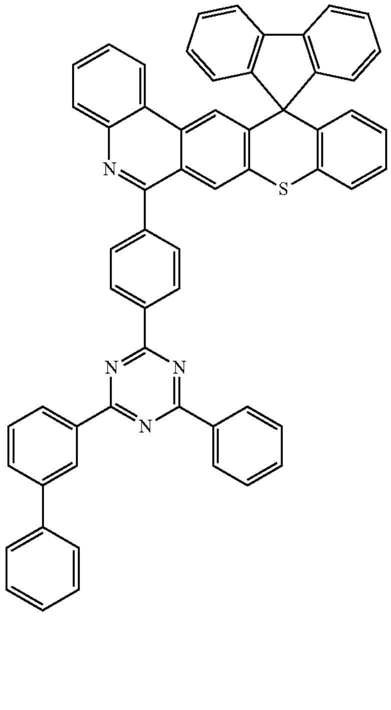

-continued
334
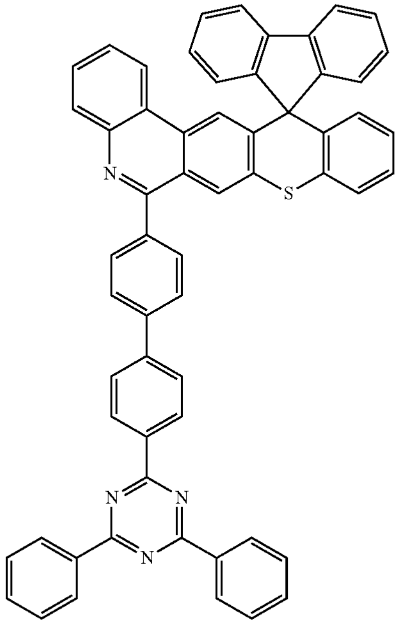
335
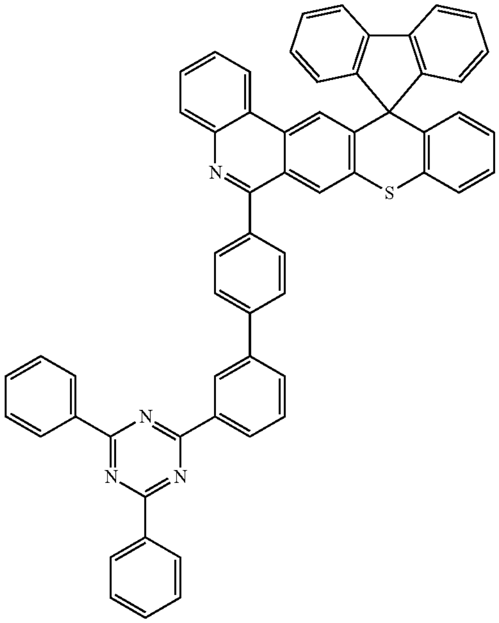
-continued
336
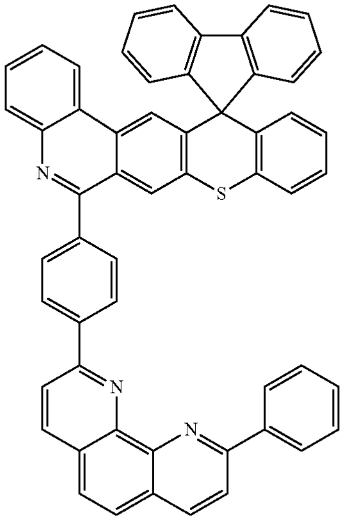
337
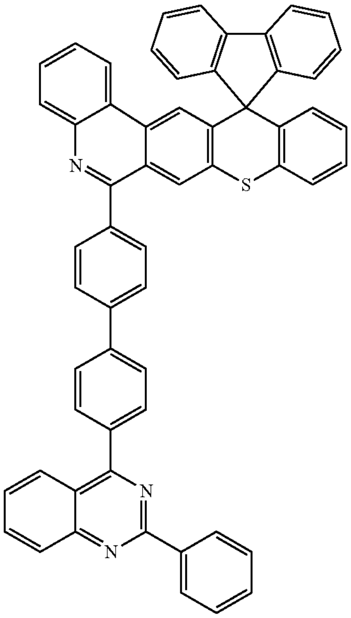

-continued
338
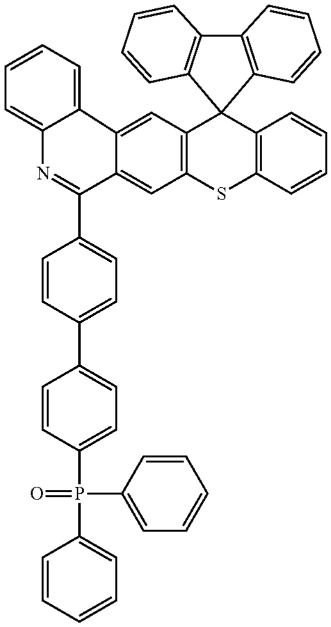
339
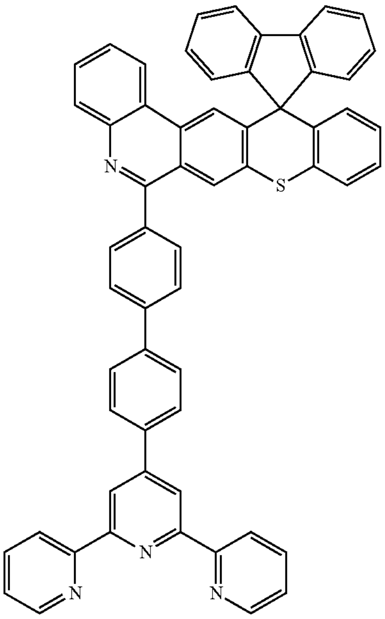
-continued
340
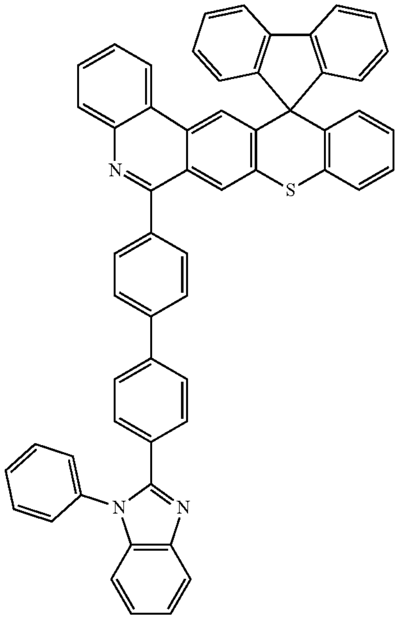
341
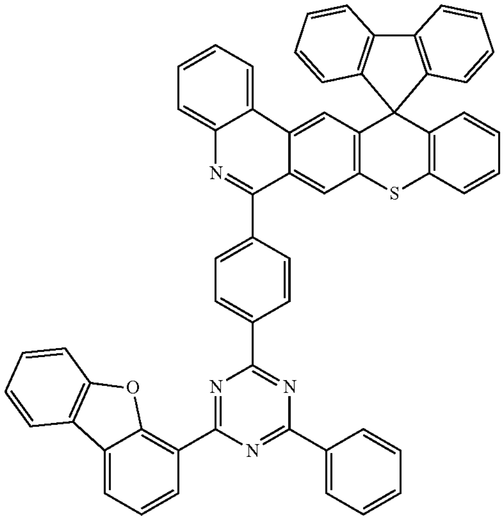

-continued
342
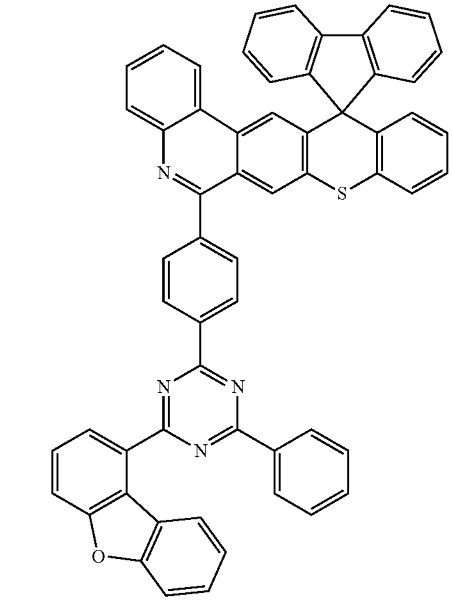
343
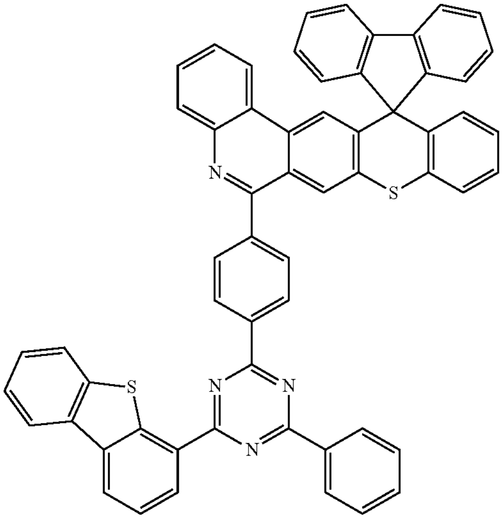
344
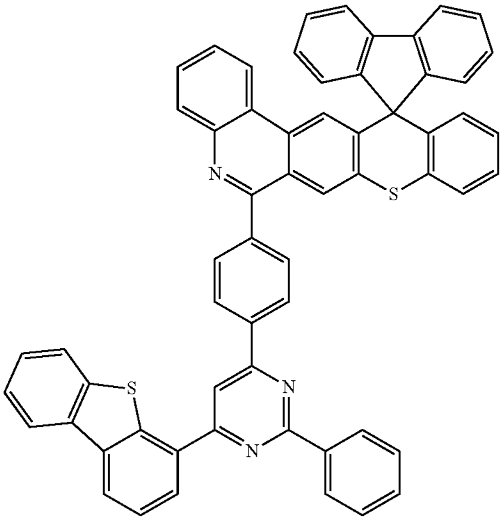
-continued
345
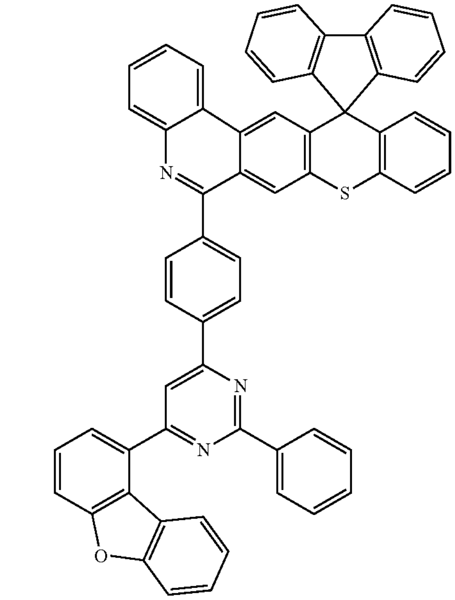
346
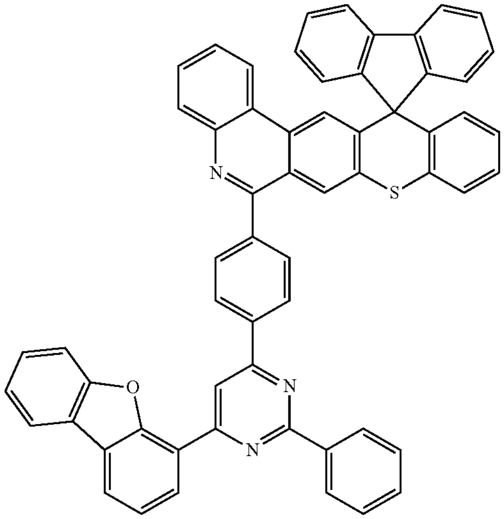
347
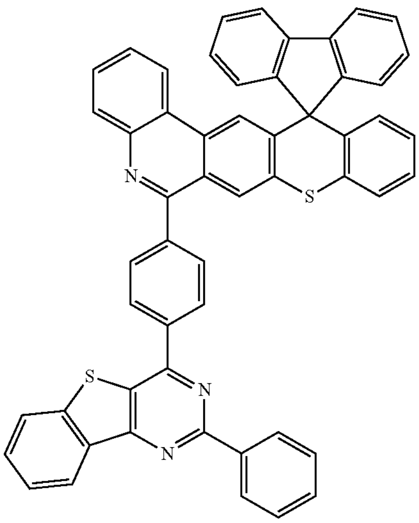

-continued
348
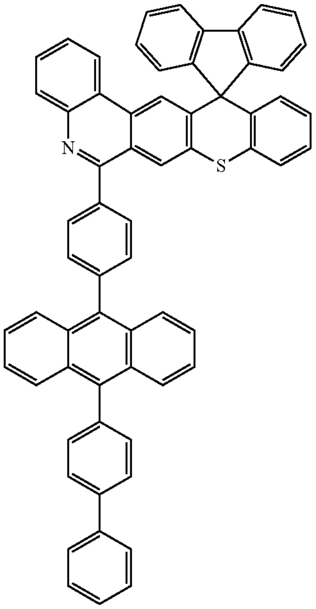
349
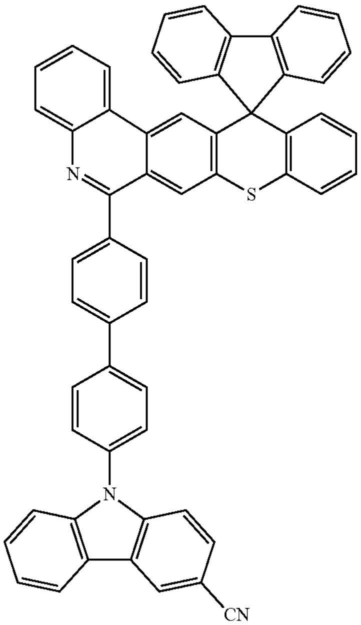
-continued
350
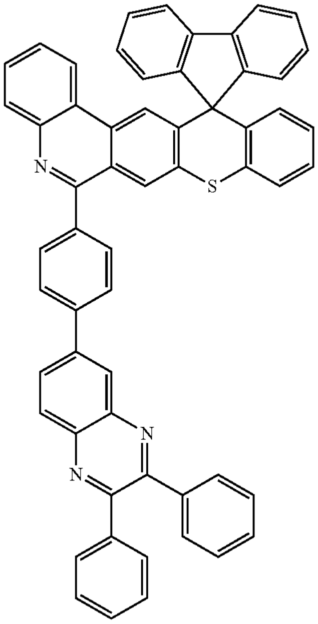
351
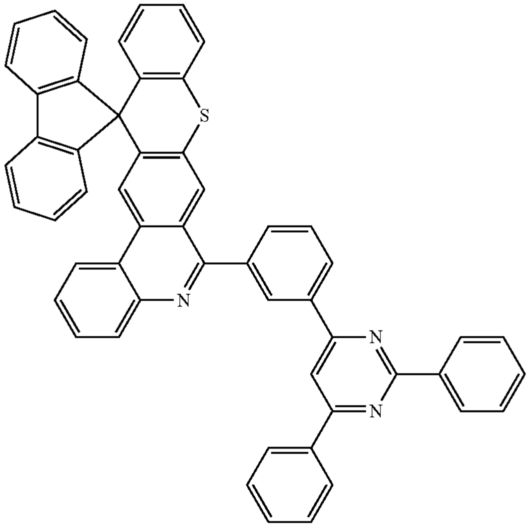

-continued
352
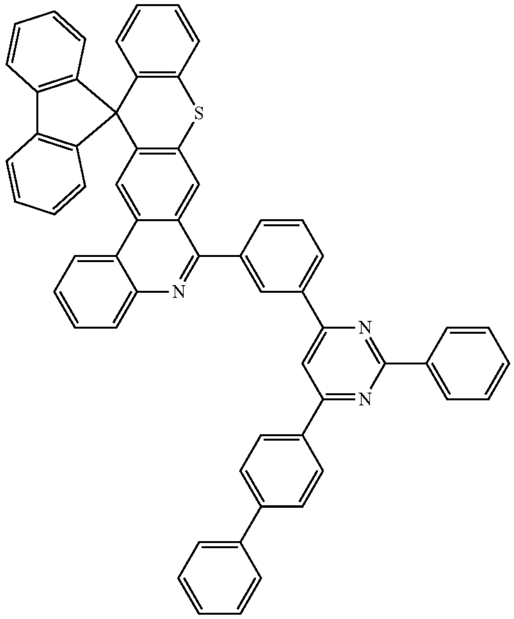
354
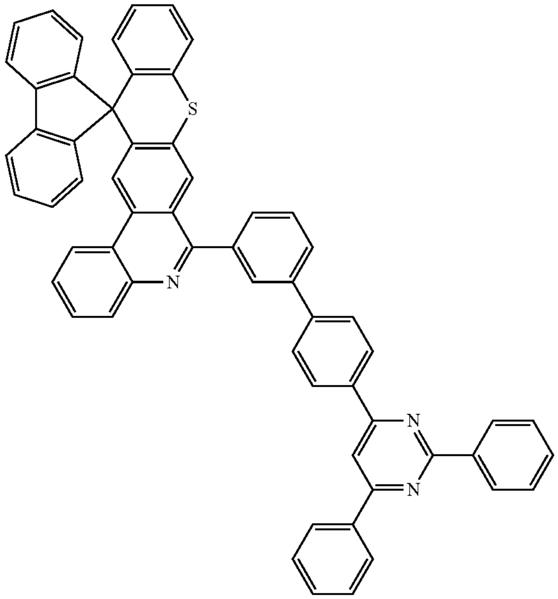
353
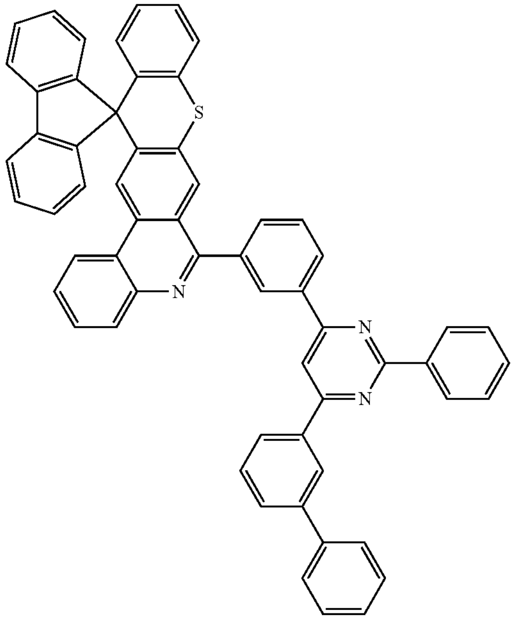
355
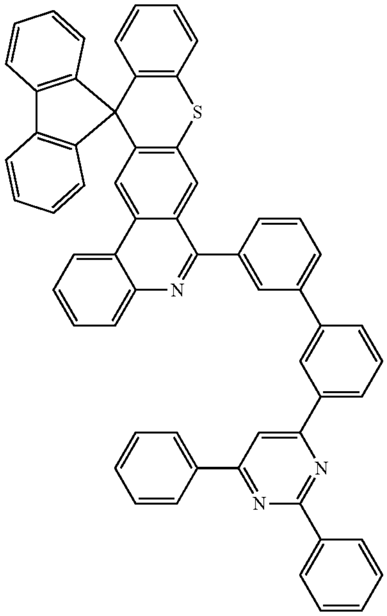

-continued
356
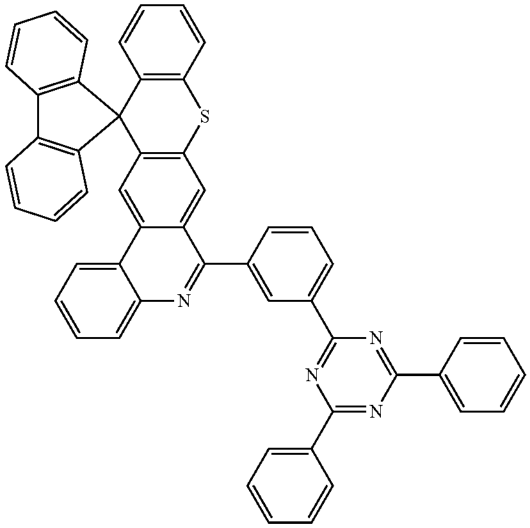
357
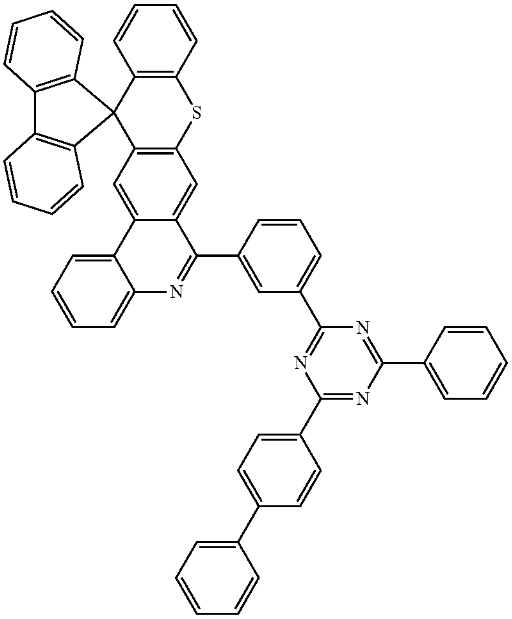
-continued
358
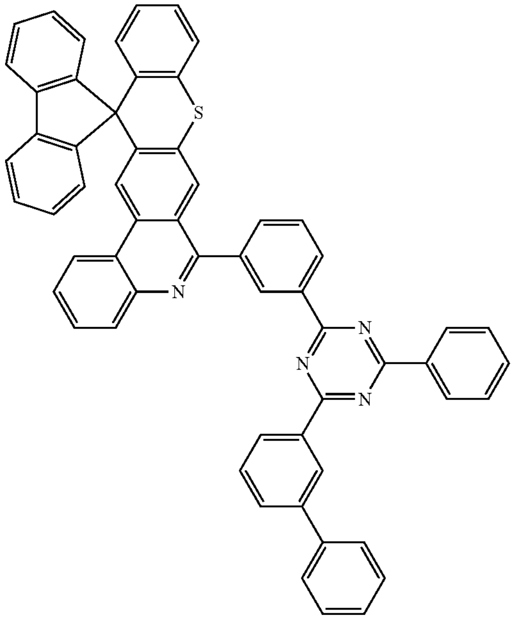
359
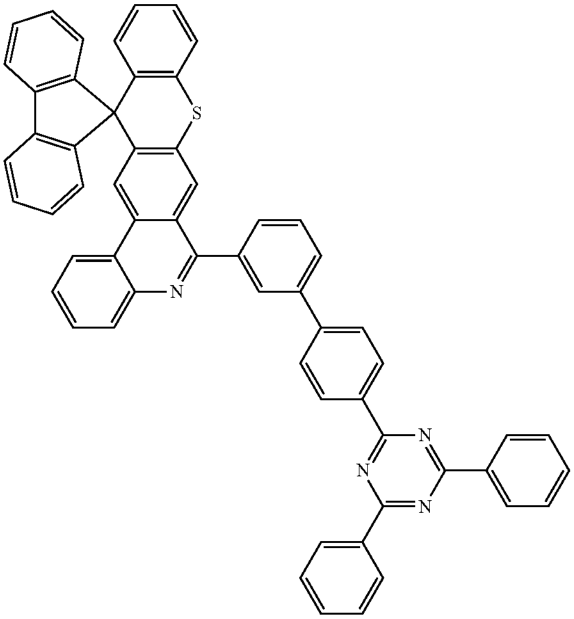

-continued
360
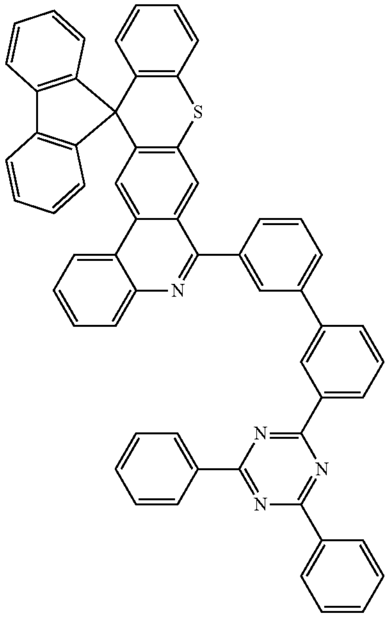
361
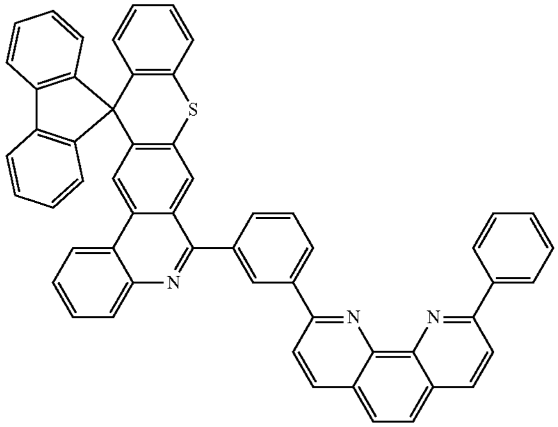
362
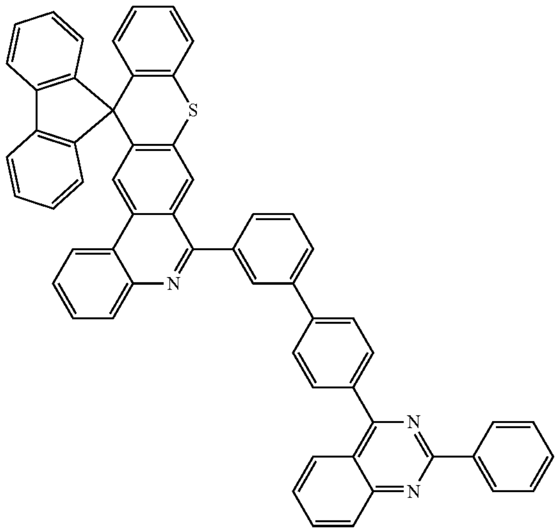
-continued
363
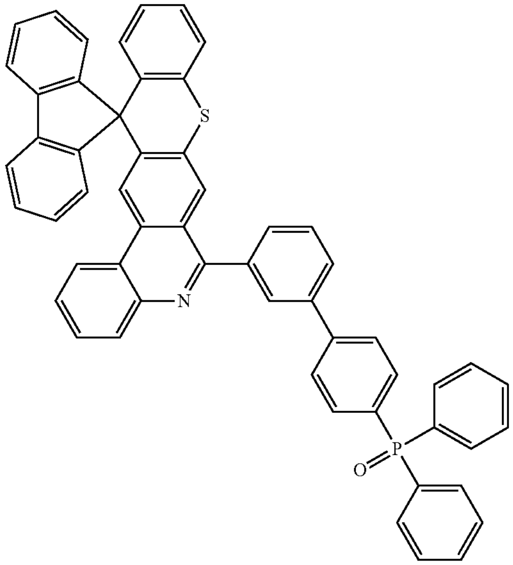
364
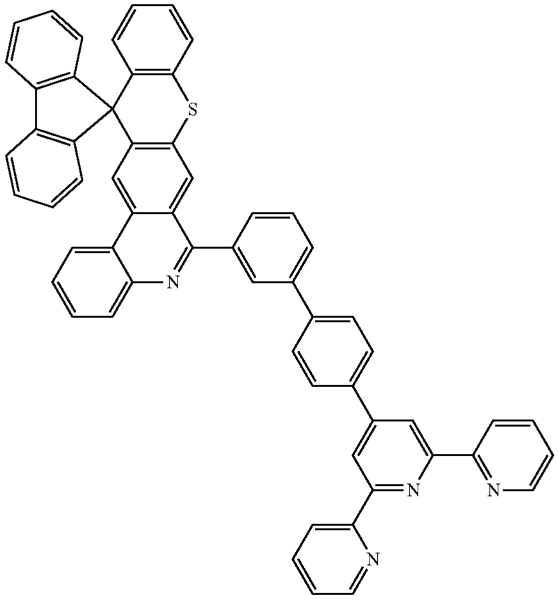

-continued
365
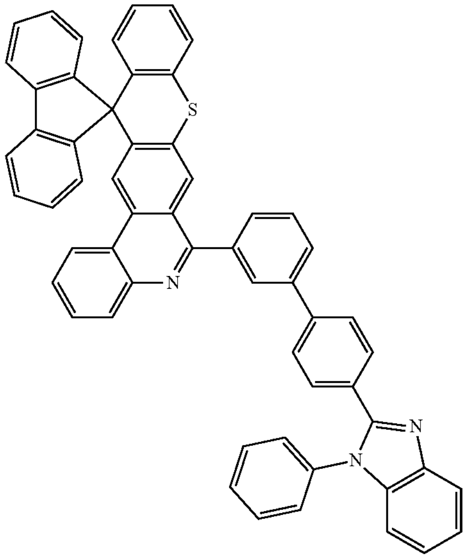
366
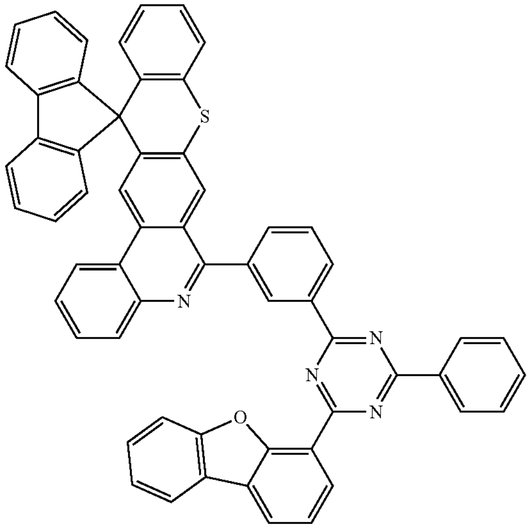
-continued
367
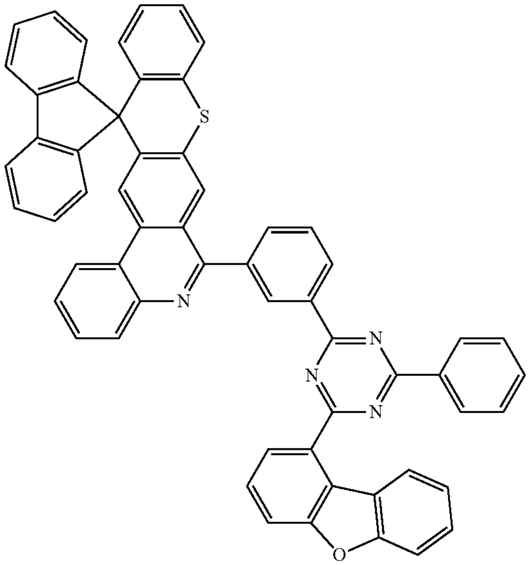
368
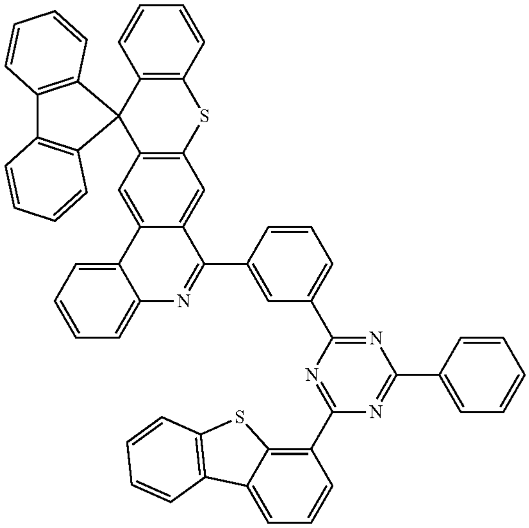

-continued
369
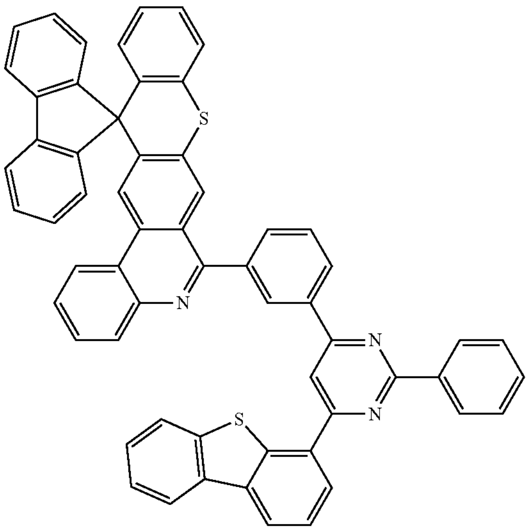
370
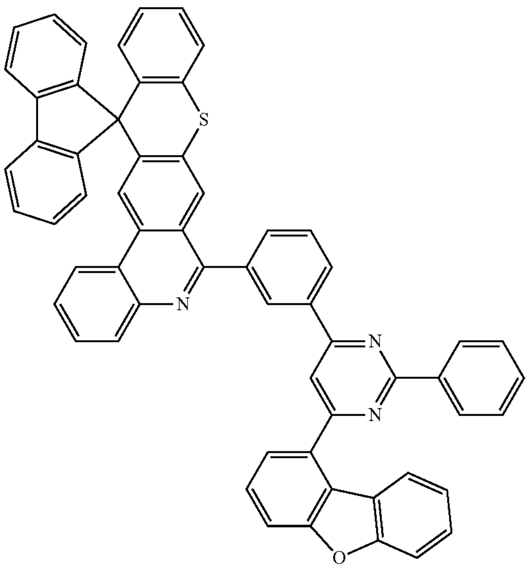
371
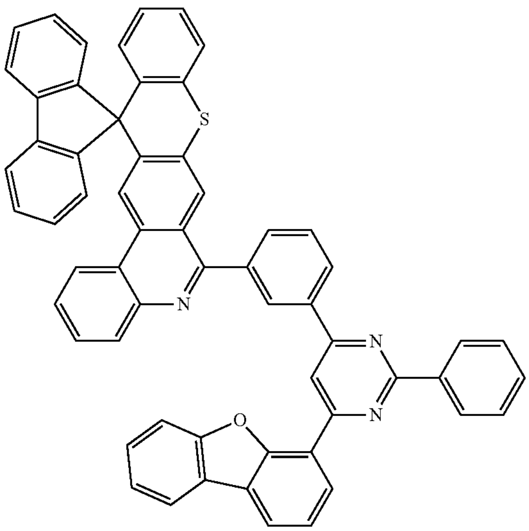
372
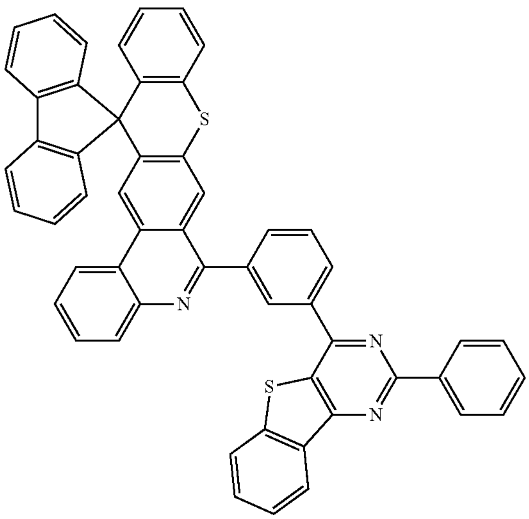

-continued
373
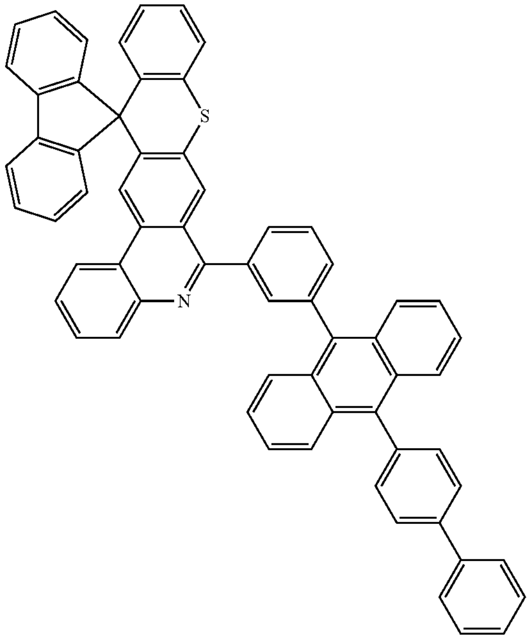
374
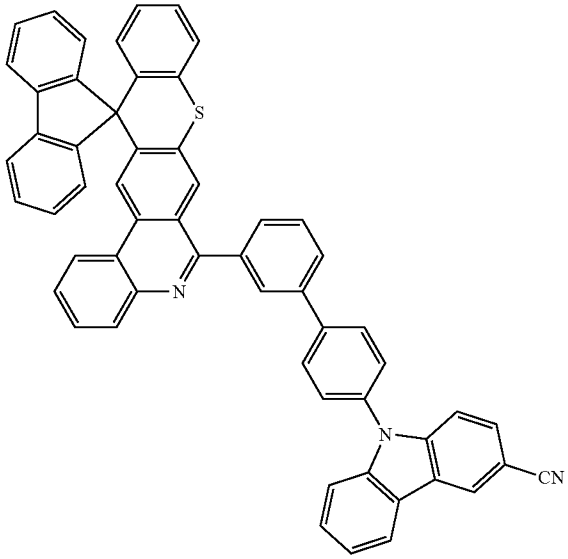
-continued
375
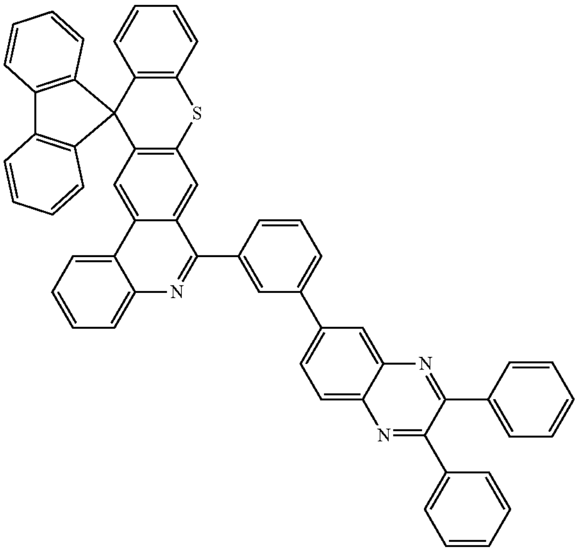
376
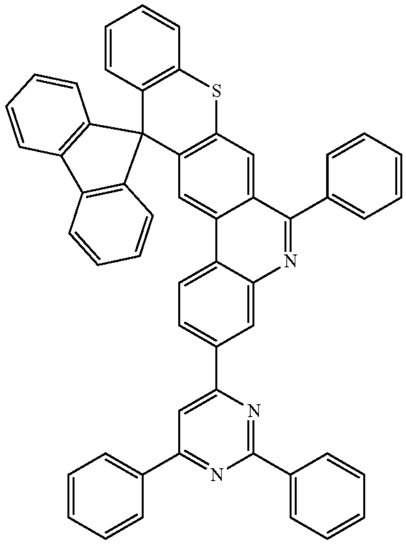

-continued
377
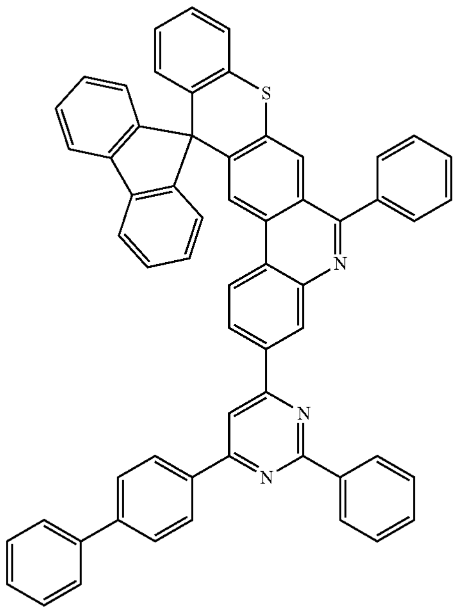
378
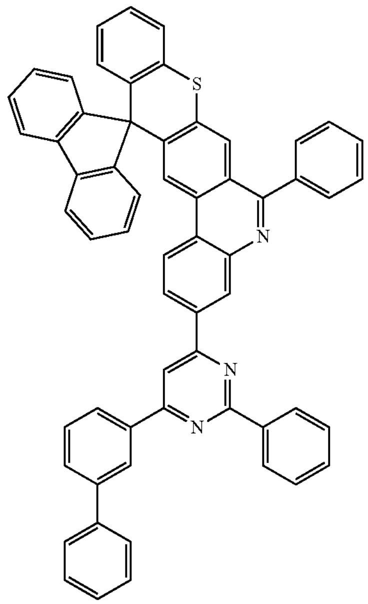
-continued
379
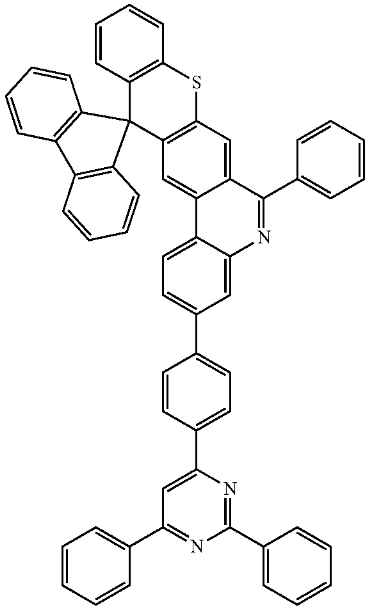
380
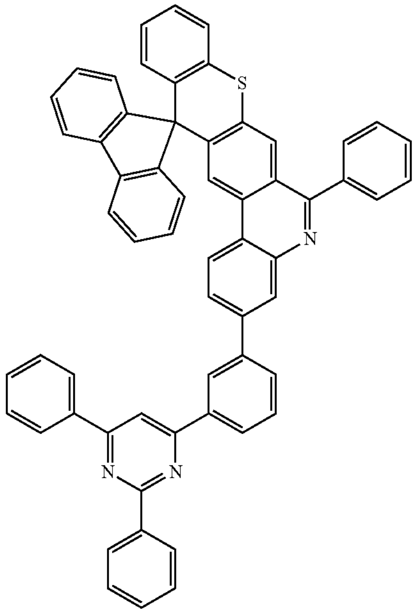

-continued
381
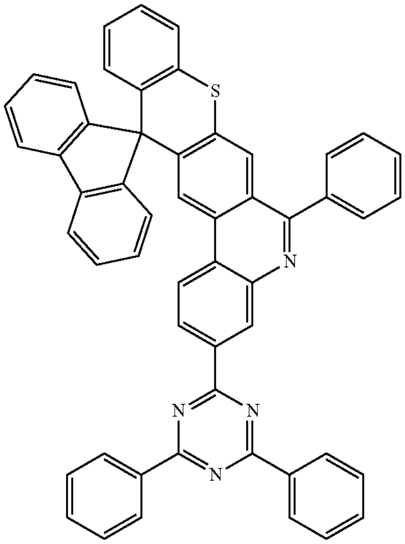
382
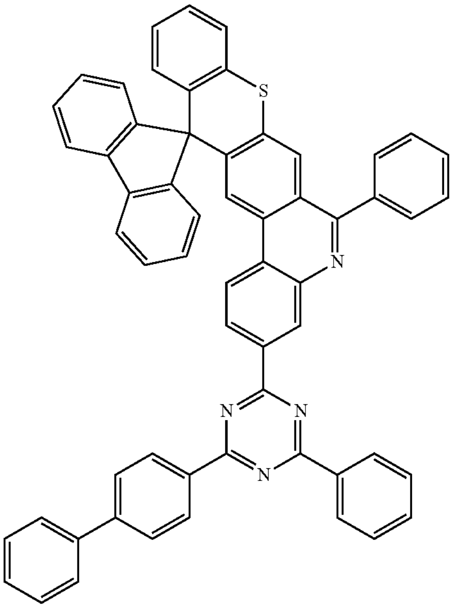
-continued
383
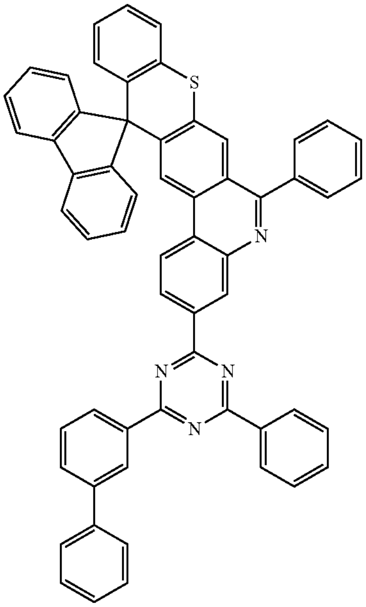
384
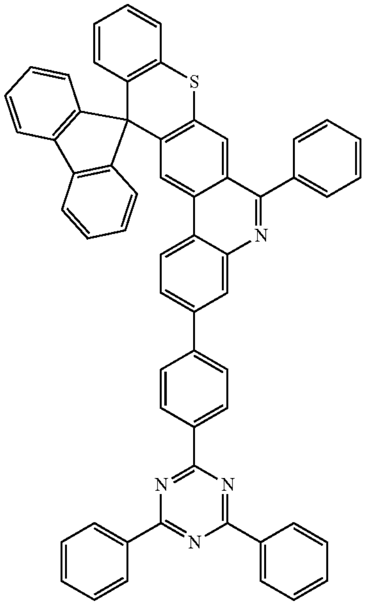

-continued
385
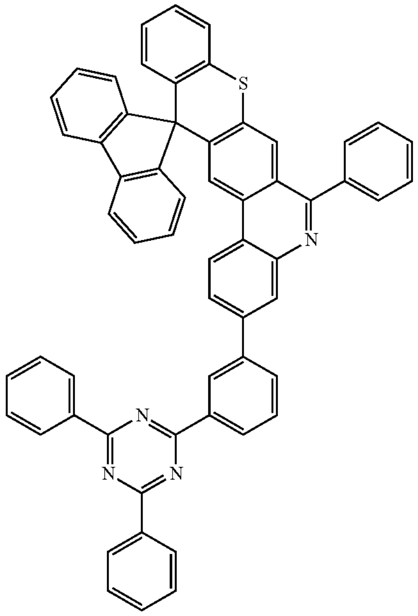
386
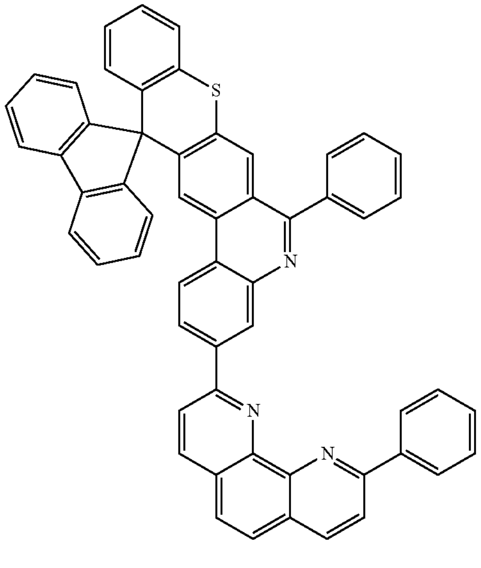
-continued
387
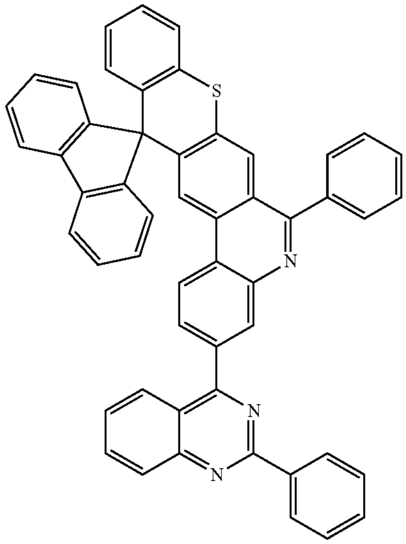
388
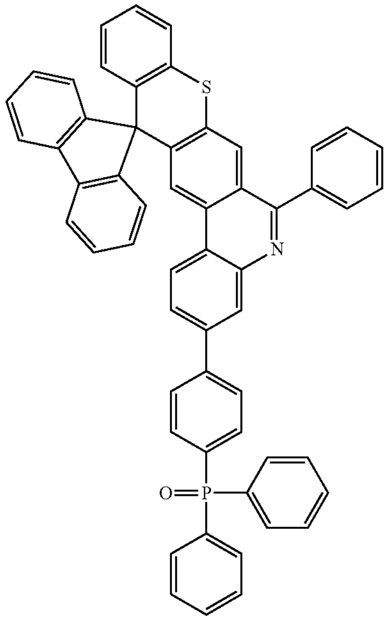

389
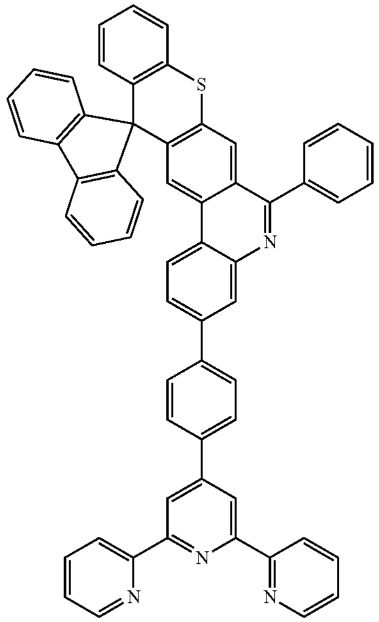
390
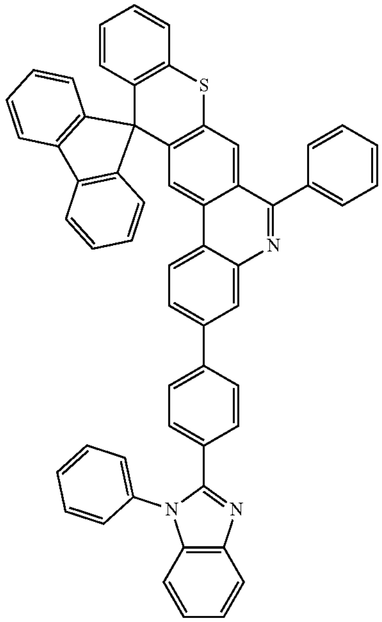
391
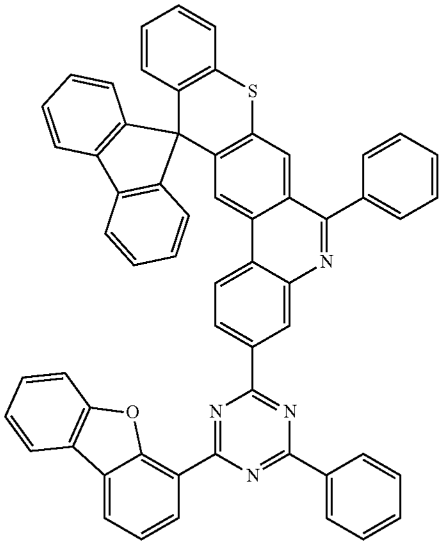
392
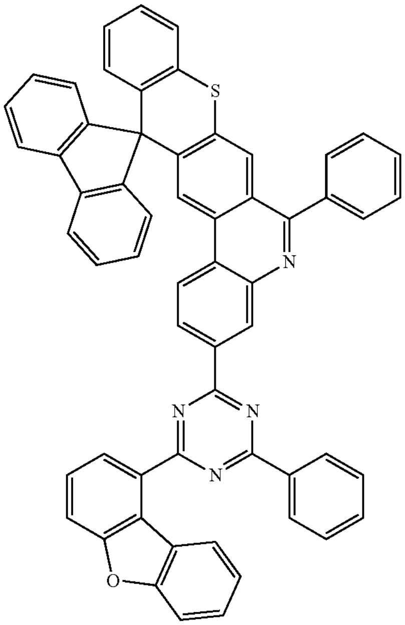

-continued
393
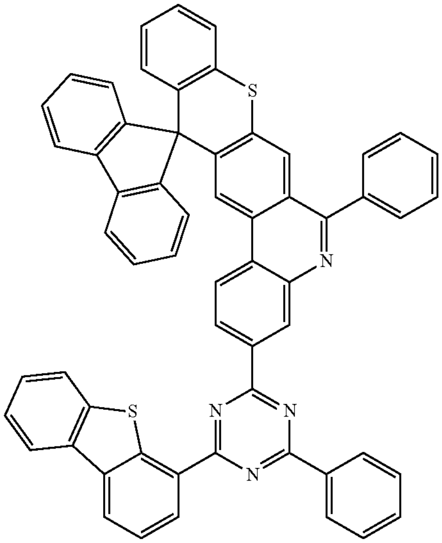
394
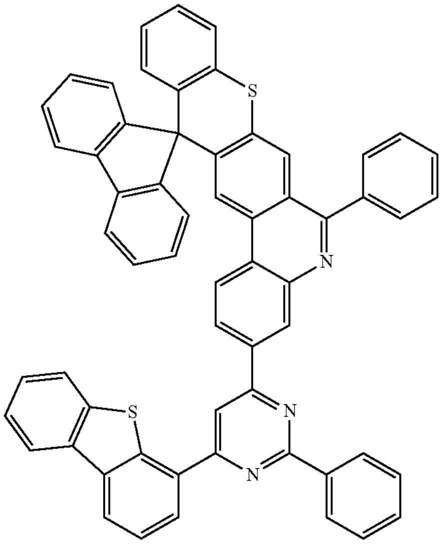
-continued
395
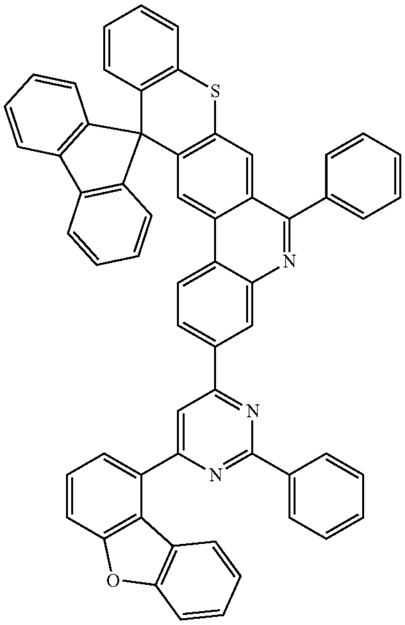
396
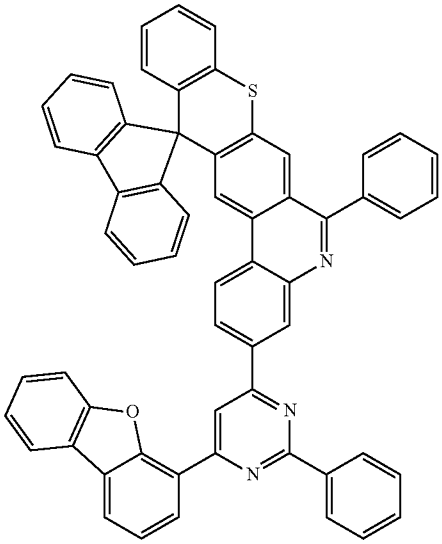

-continued
397
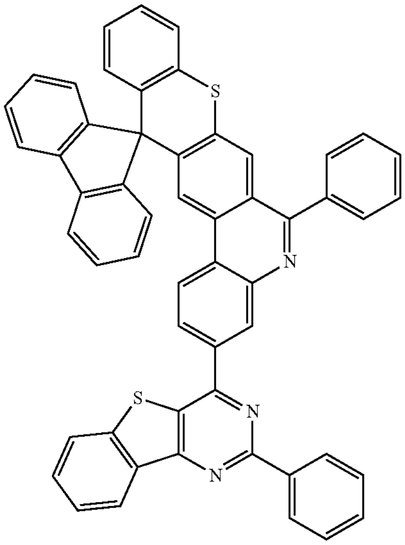
-continued
399
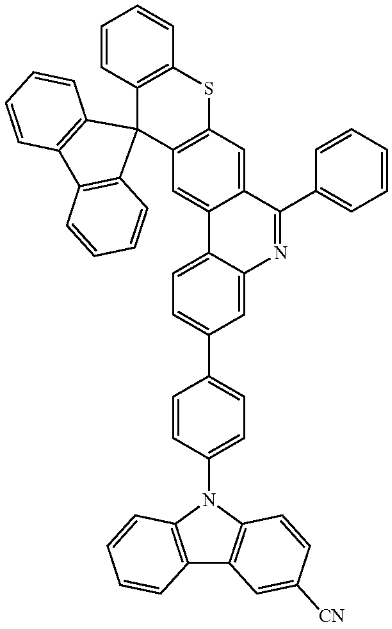
398
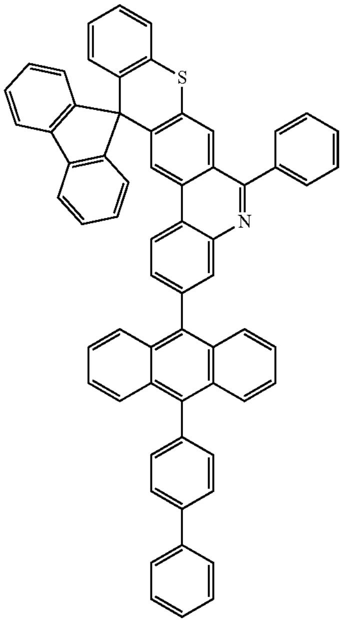
400
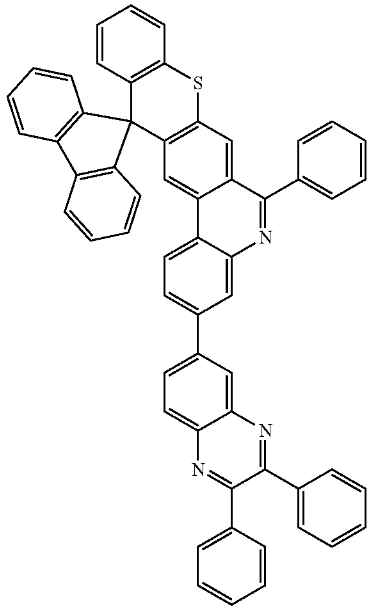

-continued
401
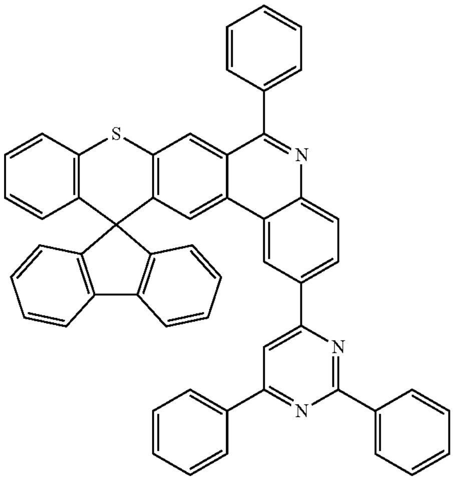
402
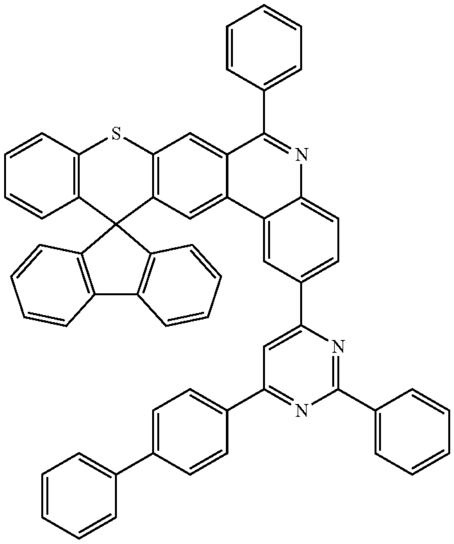
403
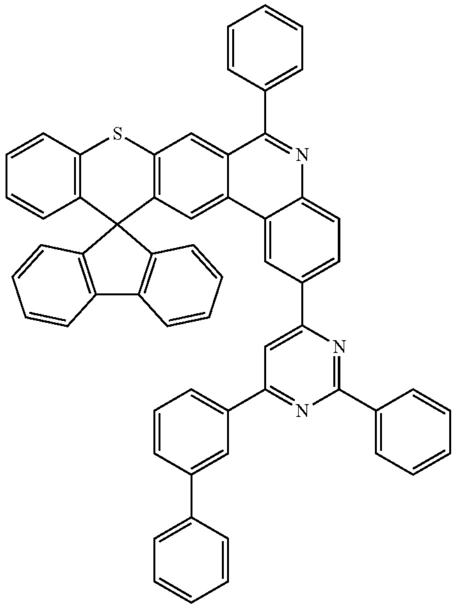
404
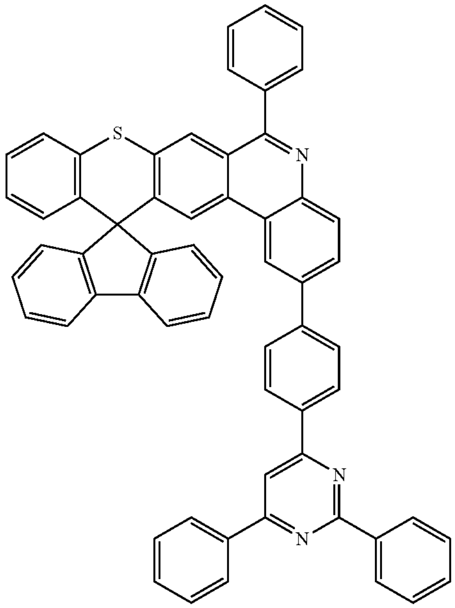

-continued
405
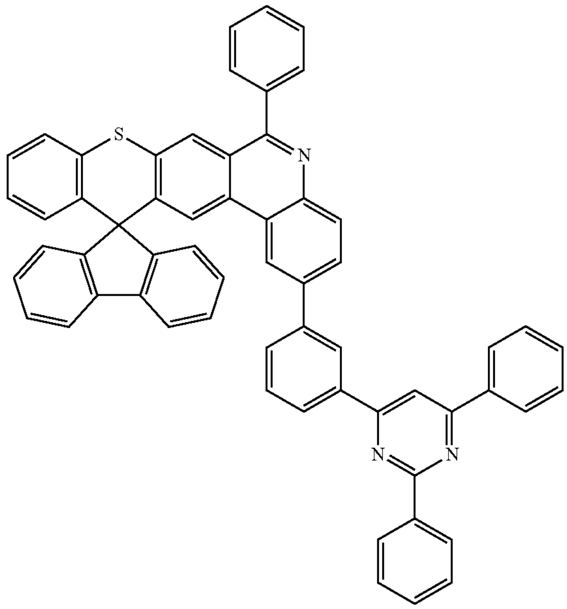
406
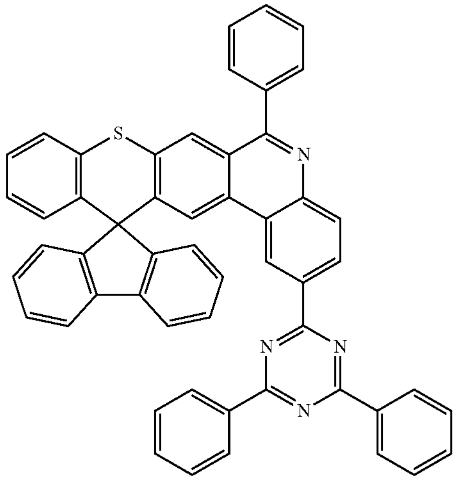
-continued
407
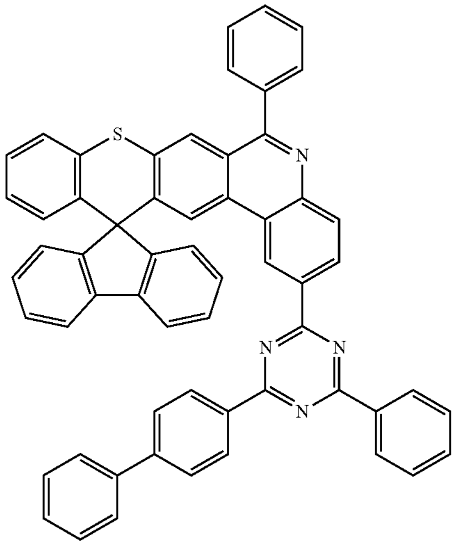
408
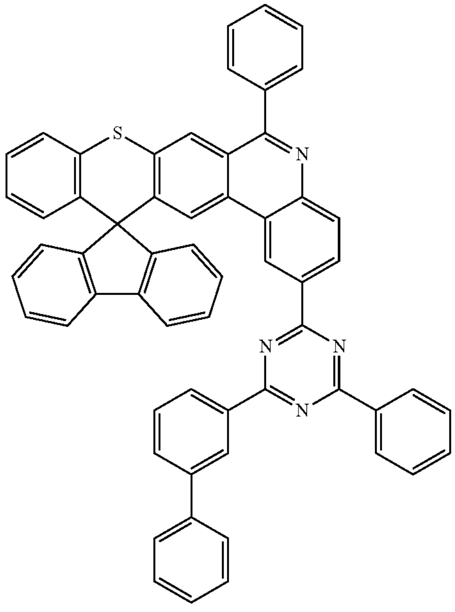

-continued
409
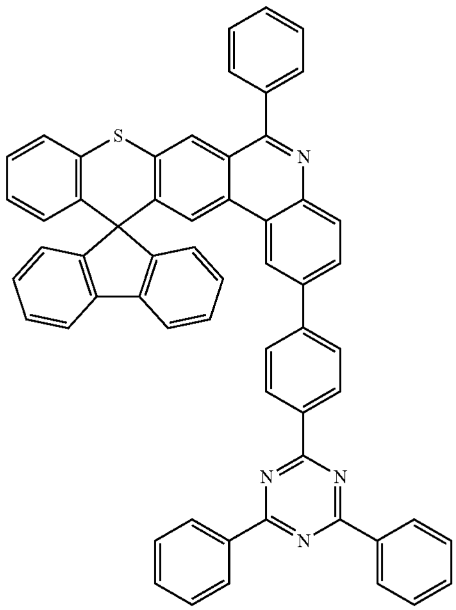
410
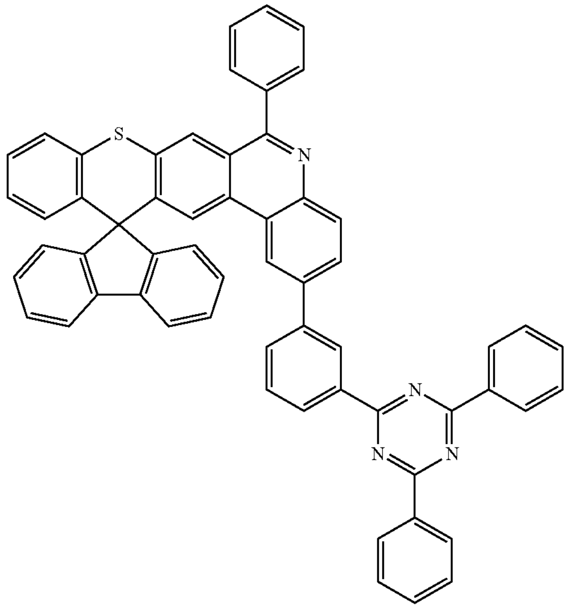
-continued
411
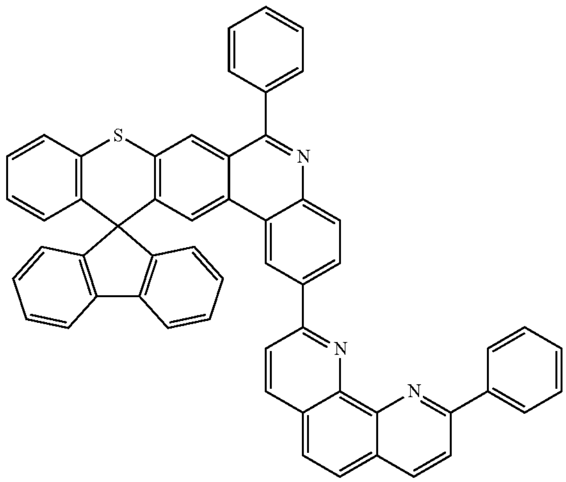
412
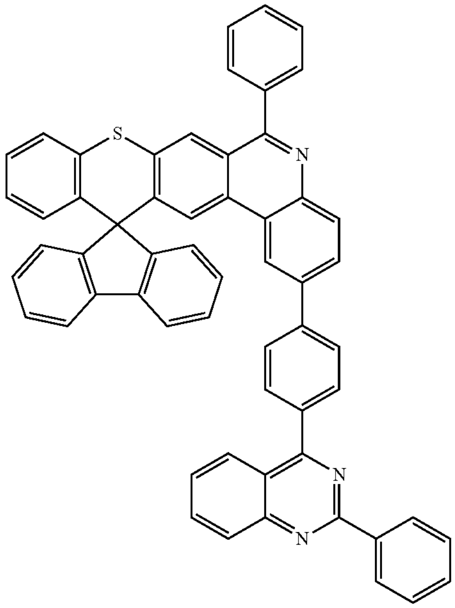

-continued
413
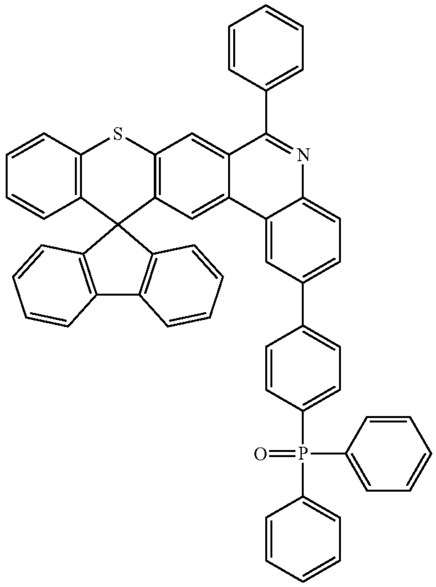
414
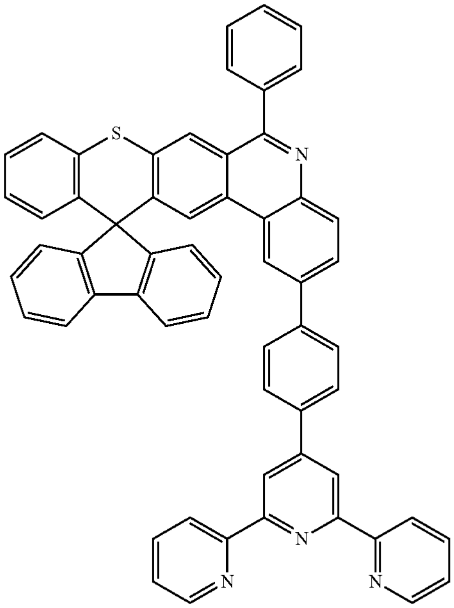
-continued
415
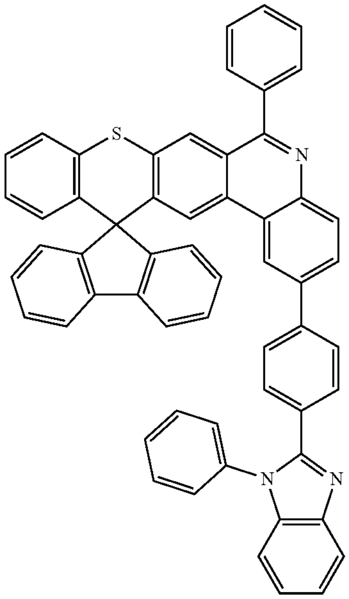
416
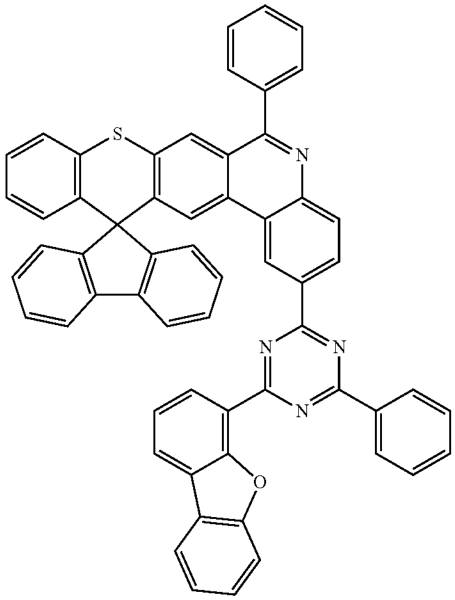

-continued
417
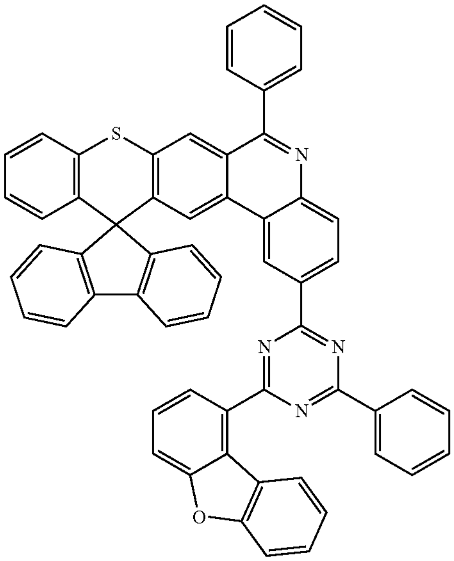
418
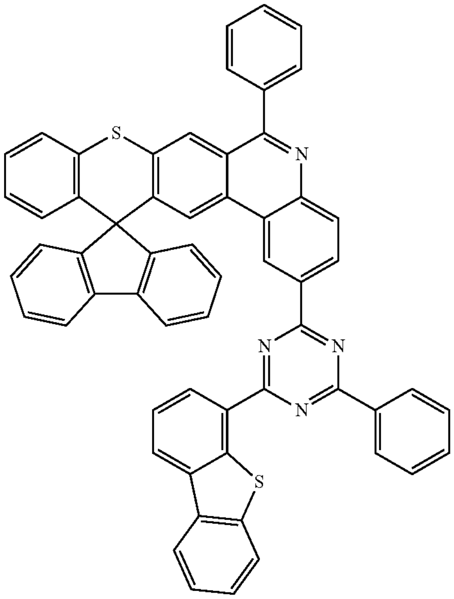
-continued
419
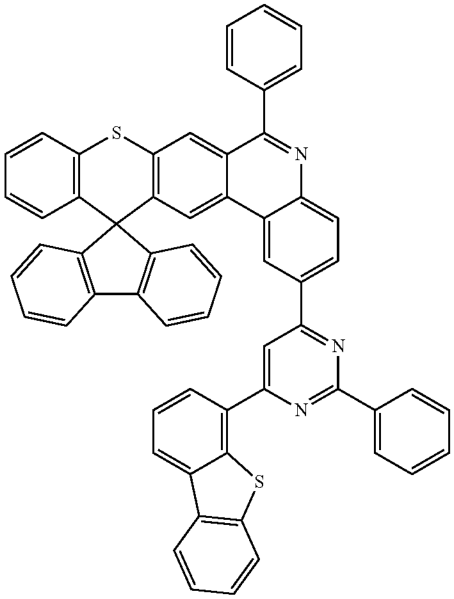
420
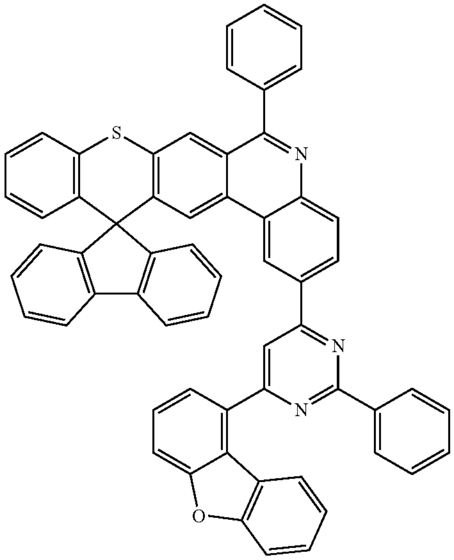

-continued
421
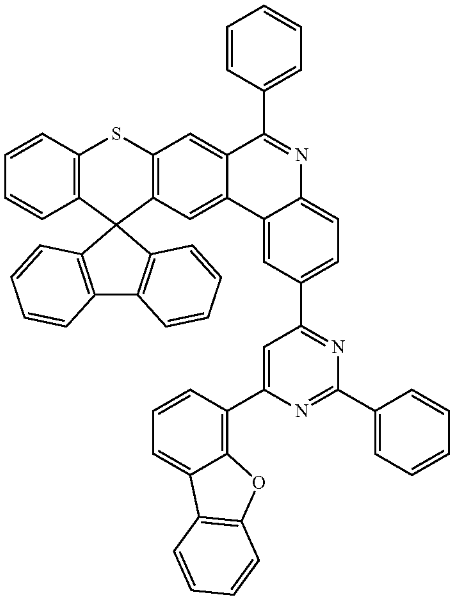
422
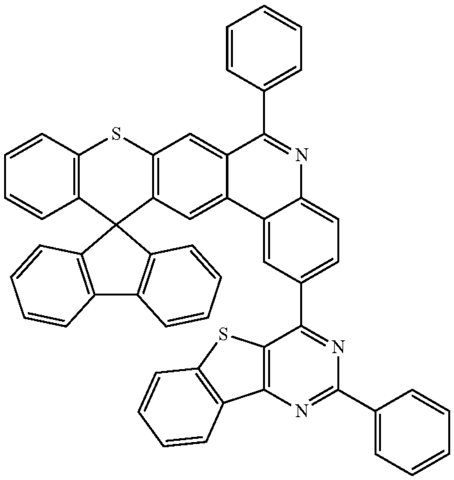
-continued
423
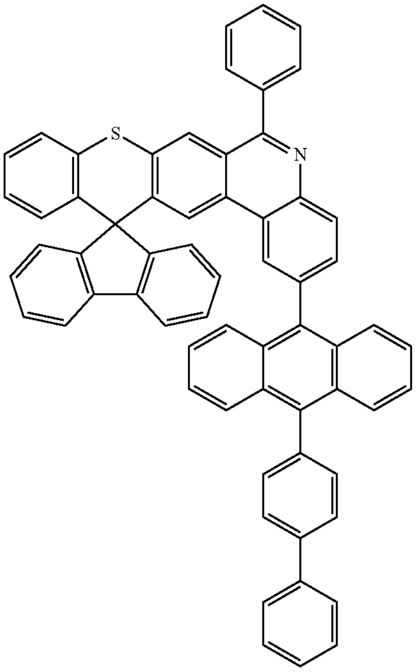
424
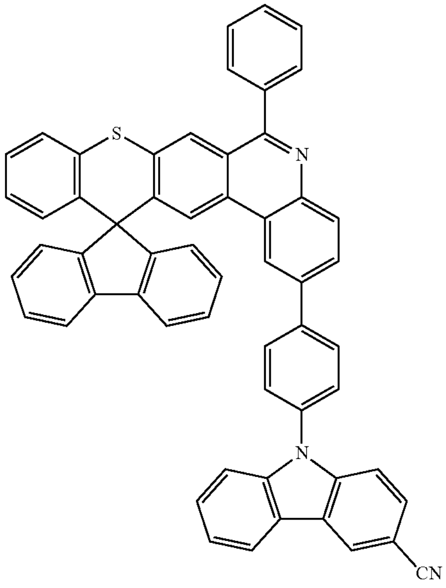

-continued
425
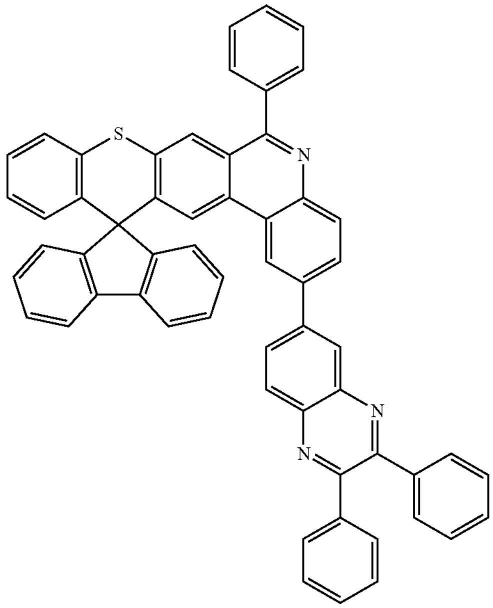
426
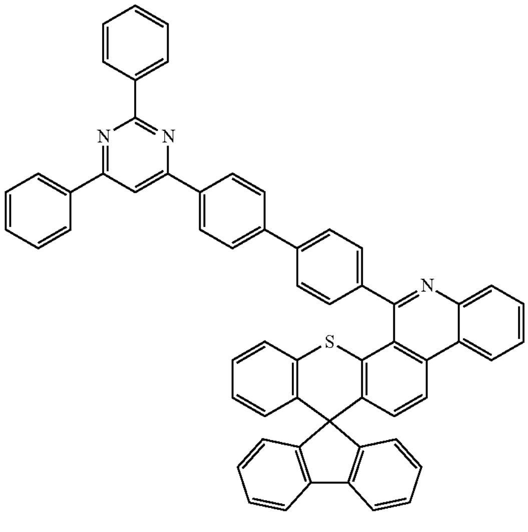
-continued
427
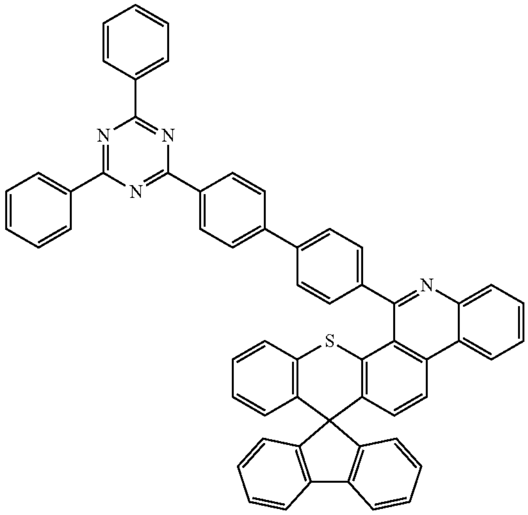
428
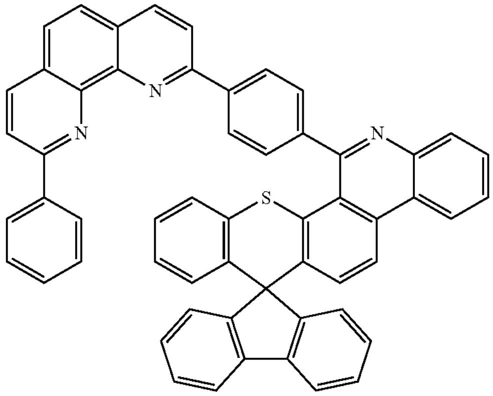
429
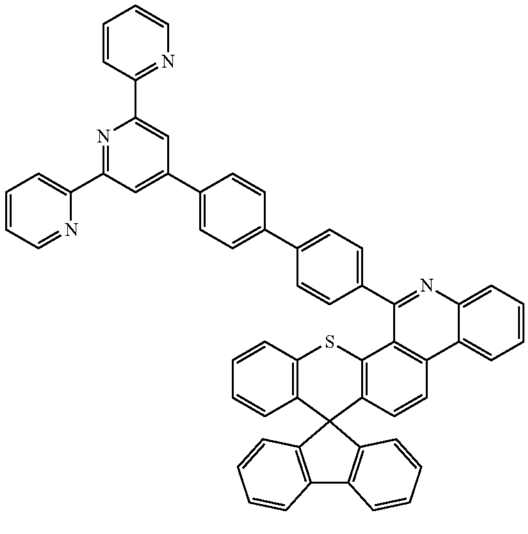

-continued
430
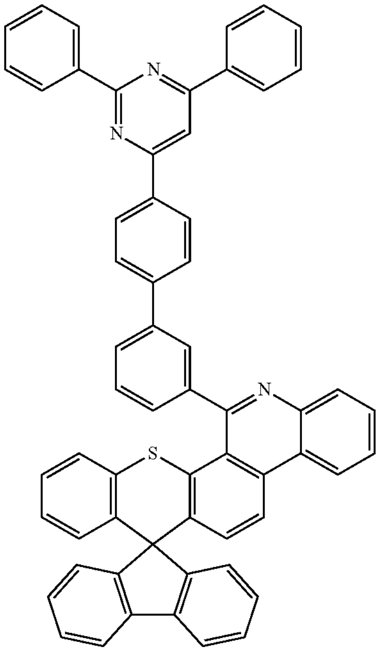
431
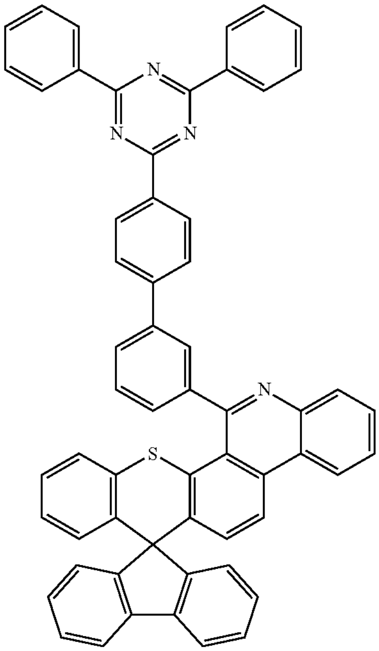
-continued
432
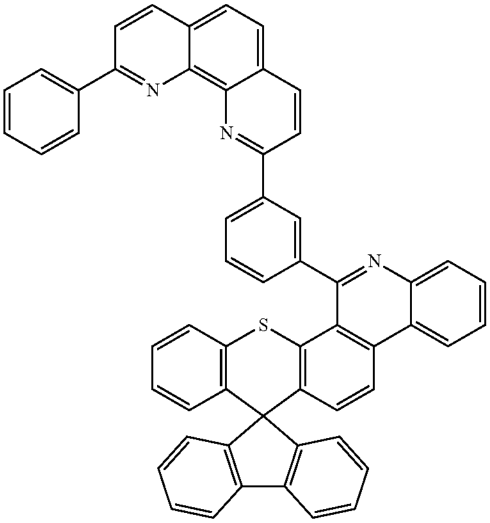
433
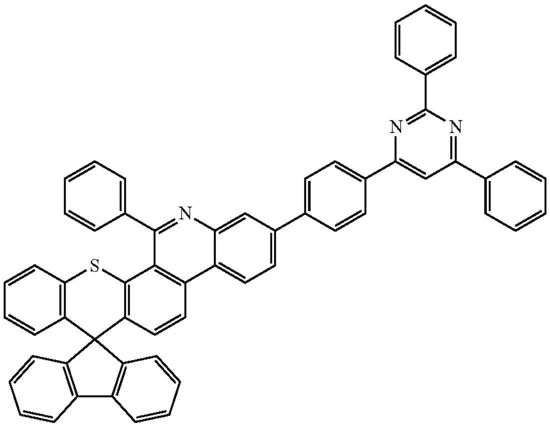
434
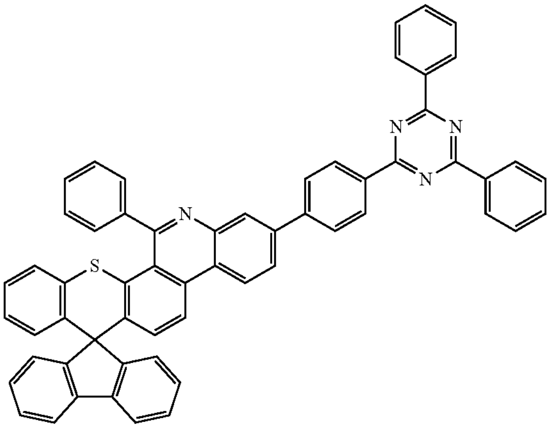

-continued
435
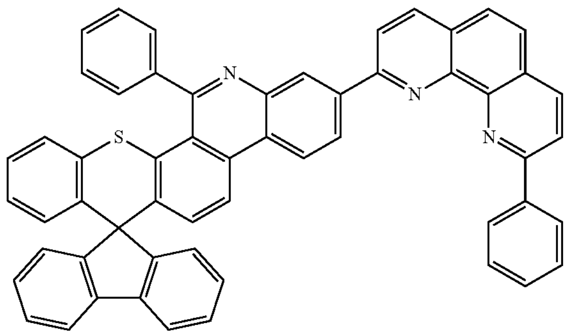
436
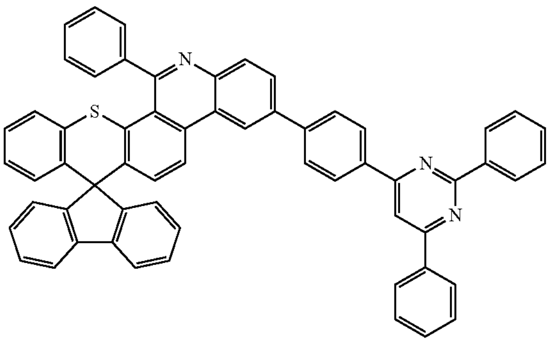
437
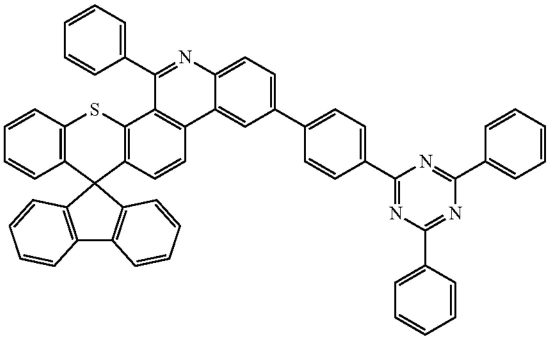
438
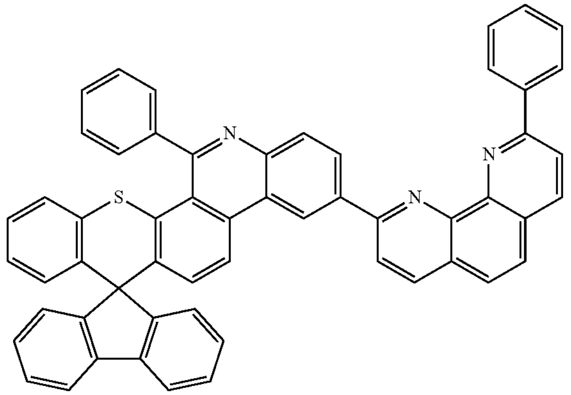
-continued
439
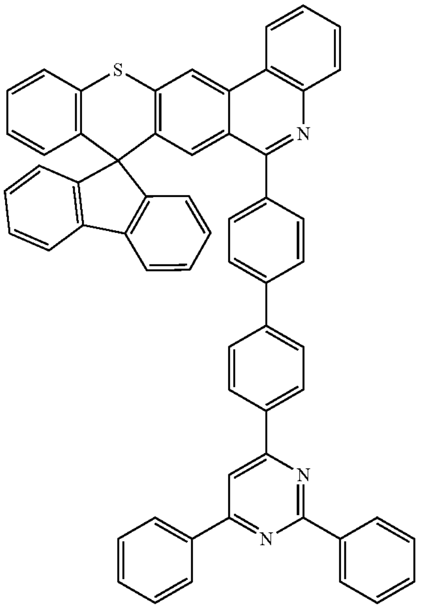
440
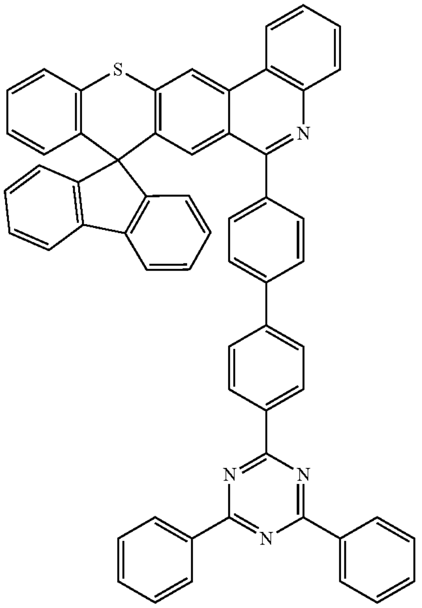

-continued
441
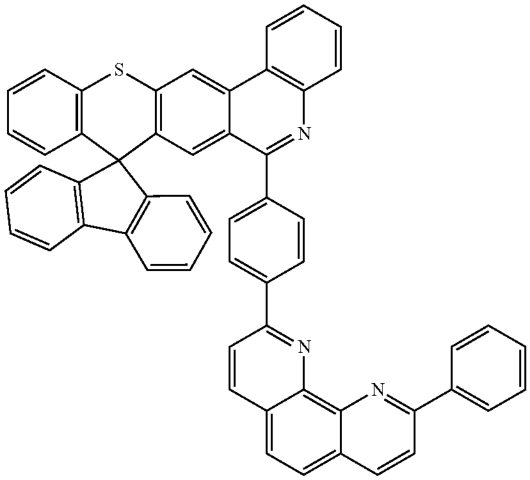
442
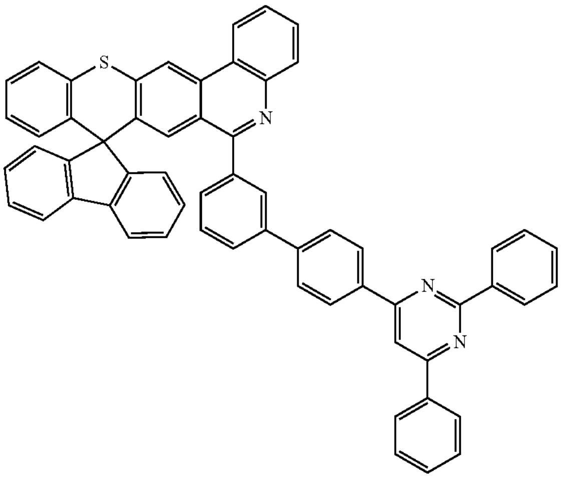
443
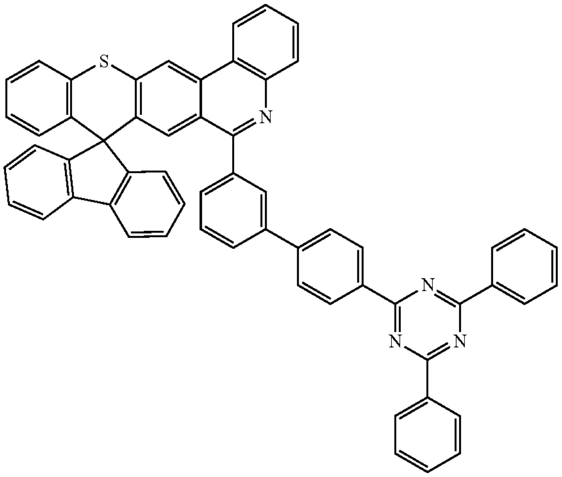
-continued
444
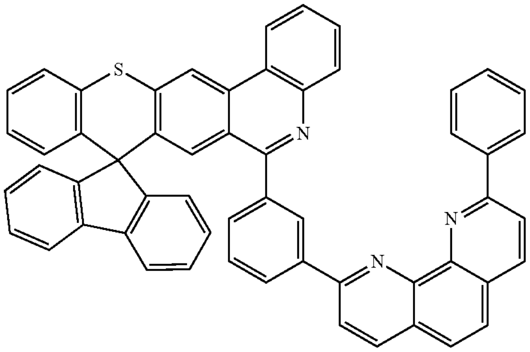
445
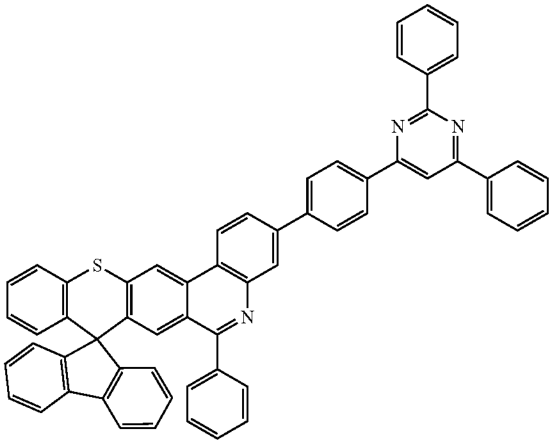
446
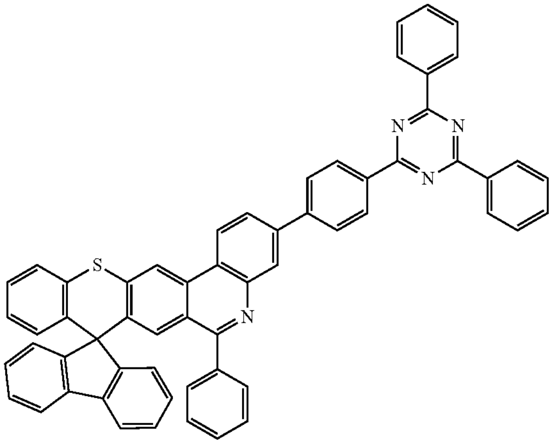

447
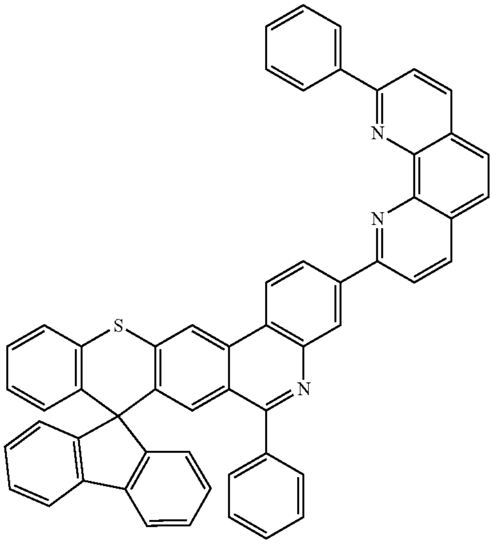
448
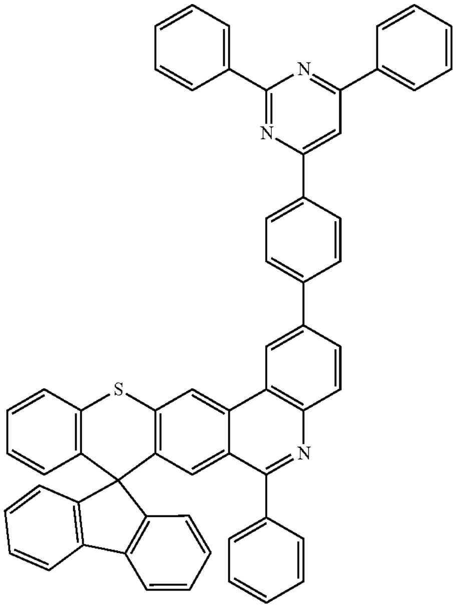
449
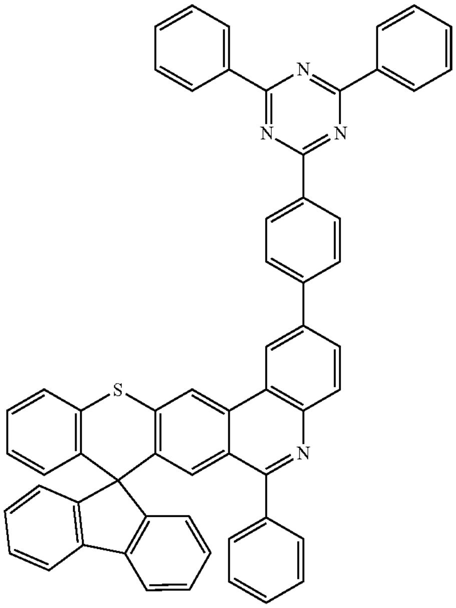
450
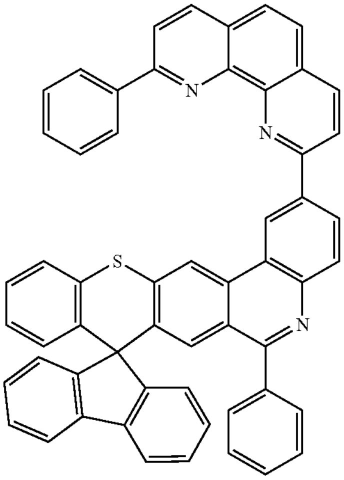
451
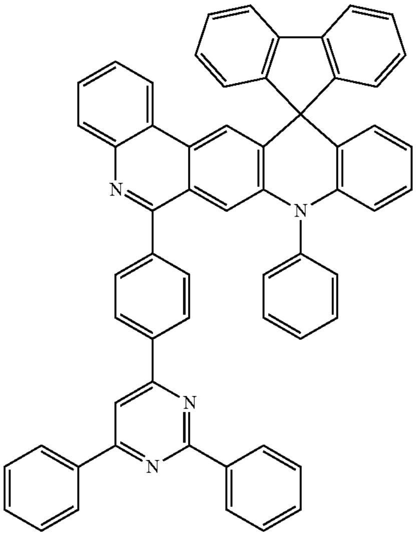

-continued
452
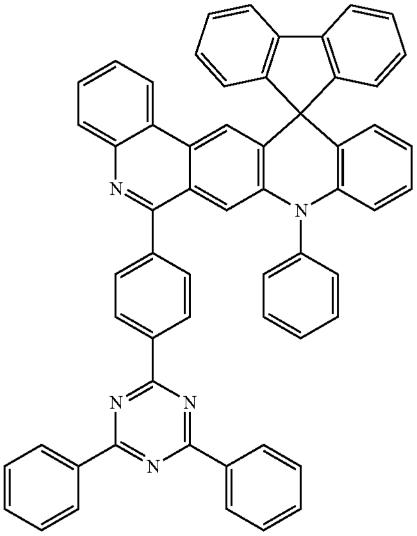
453
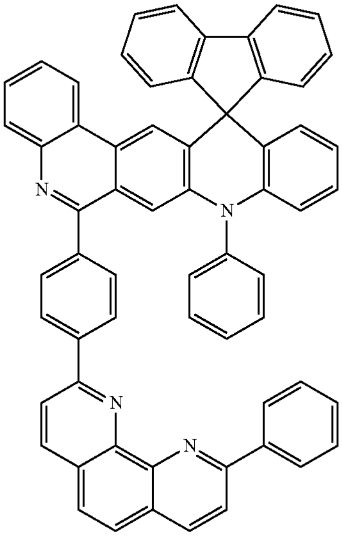
454
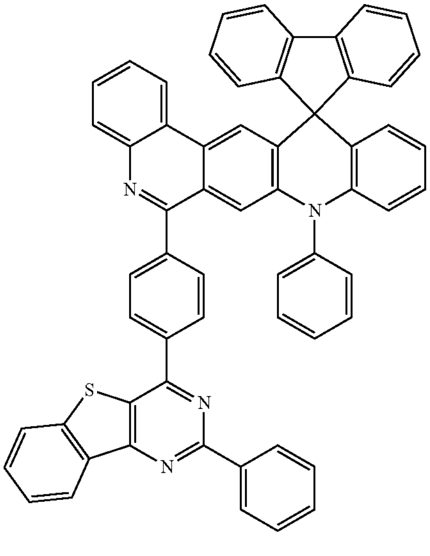
-continued
455
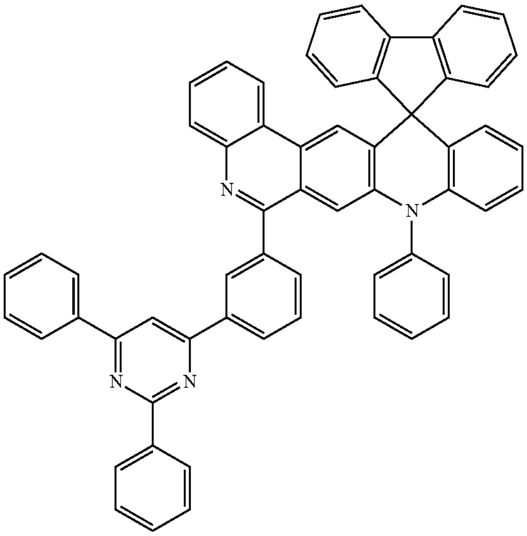
456
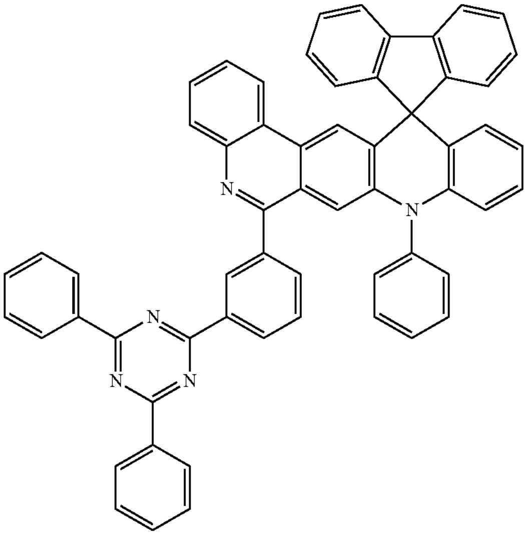

-continued
457
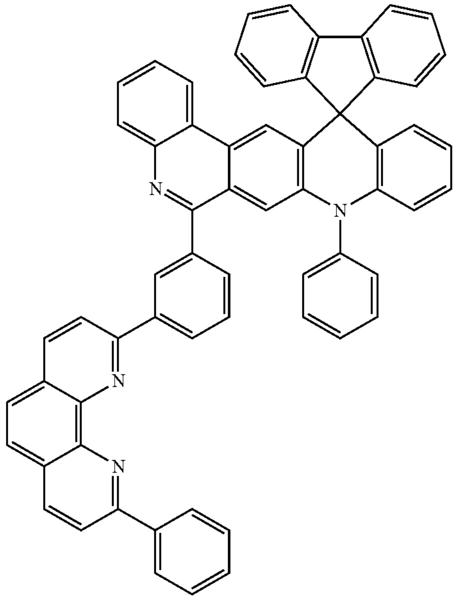
458
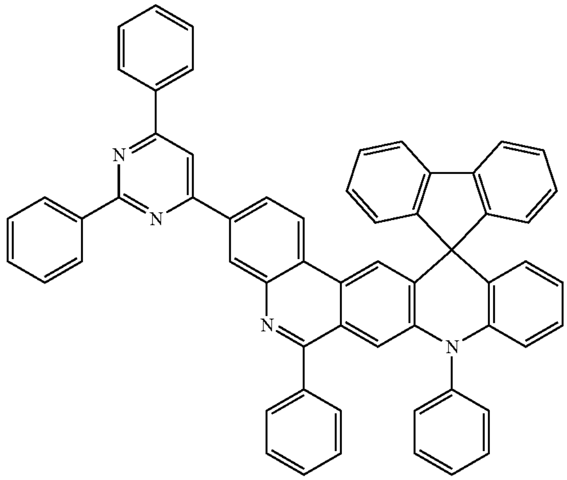
459
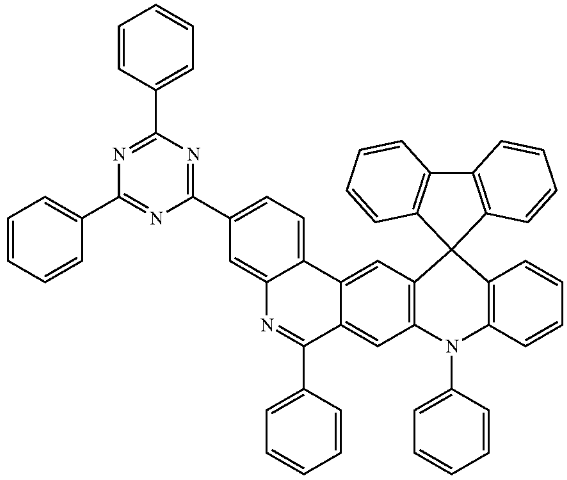
-continued
460
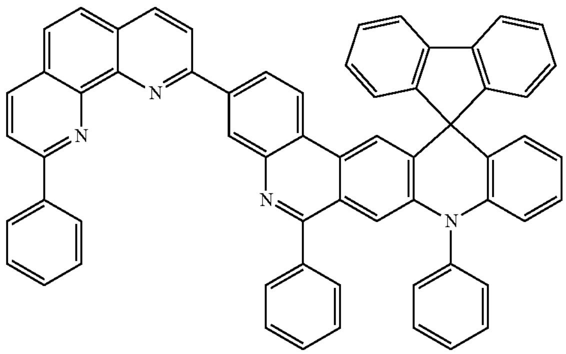
461
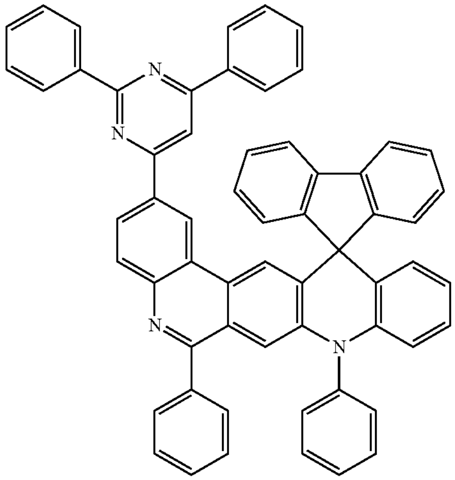
462
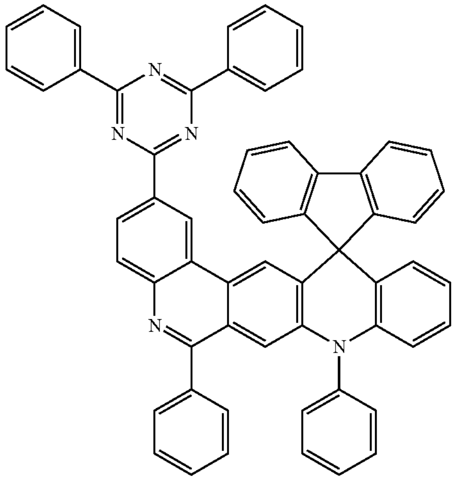

-continued
463
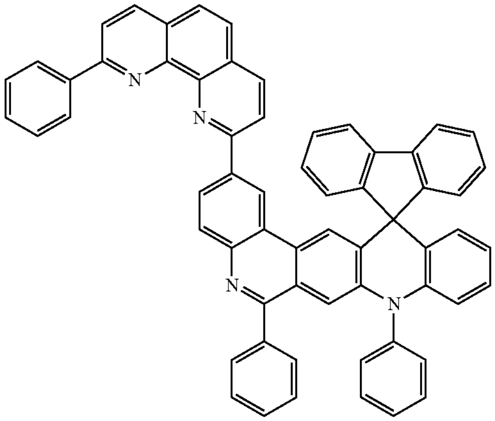
464
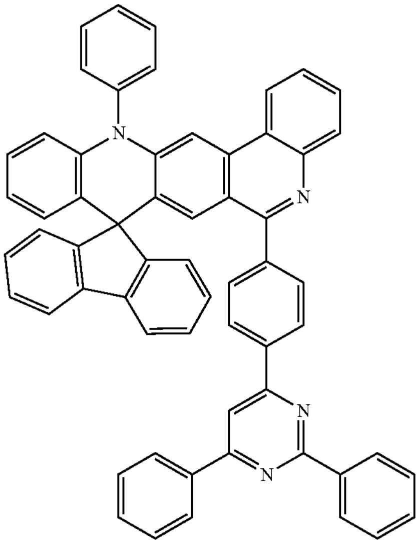
465
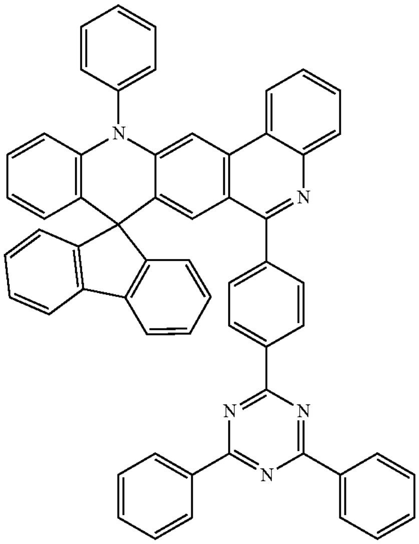
-continued
466
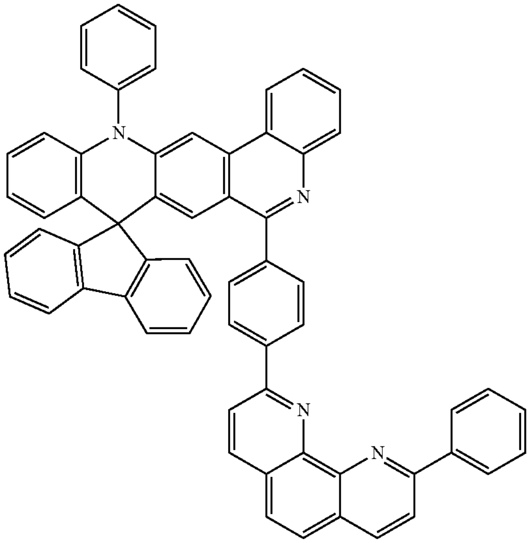
467
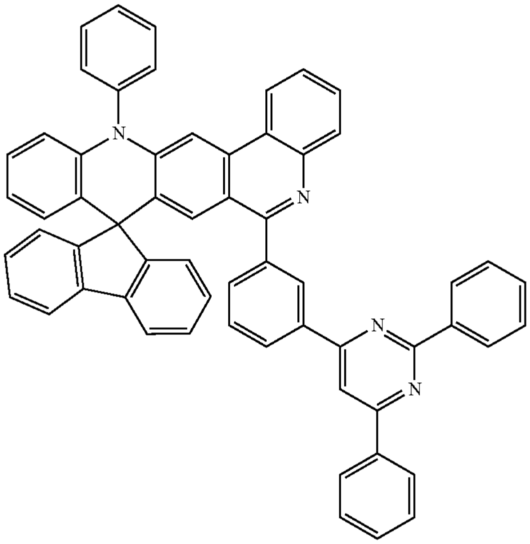
468
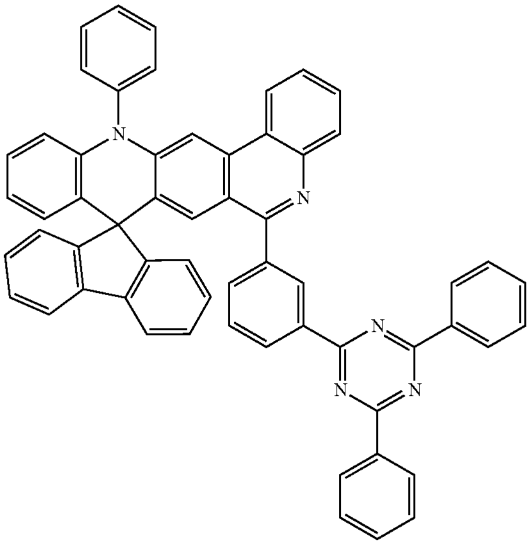

-continued
469
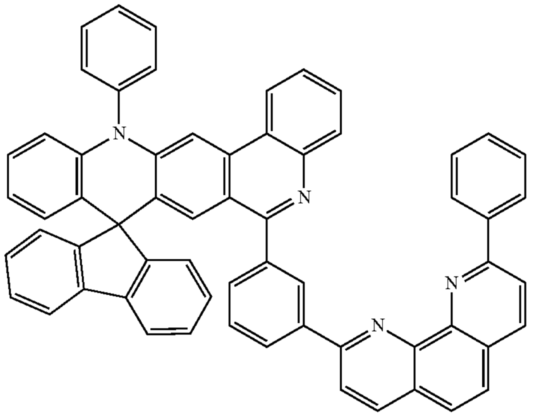
470
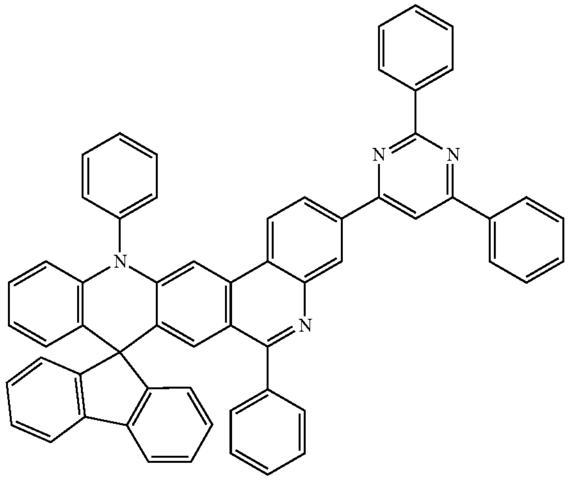
471
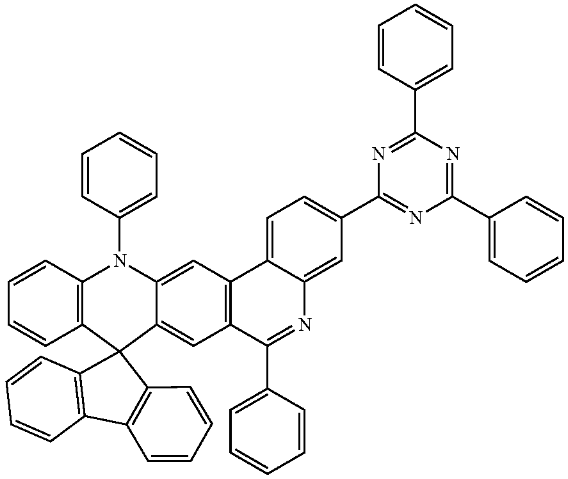
-continued
472
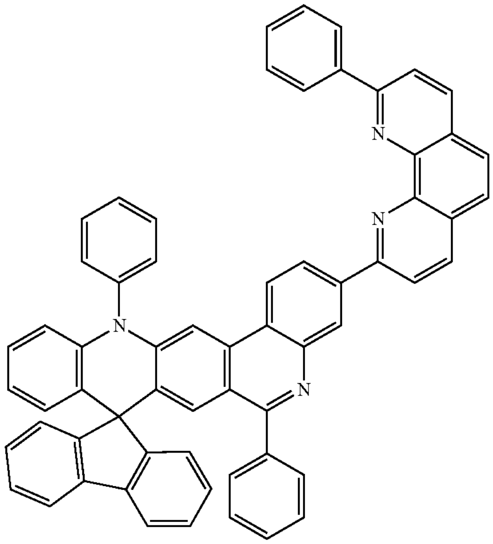
473
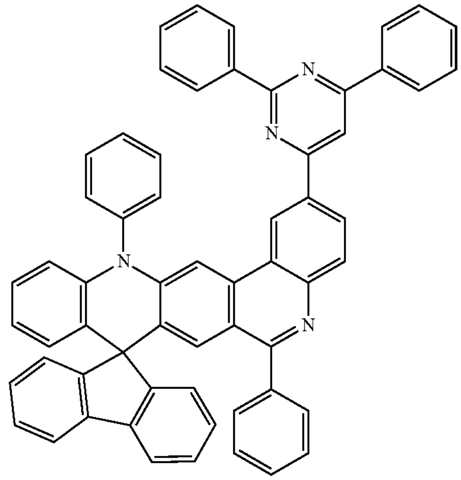
474
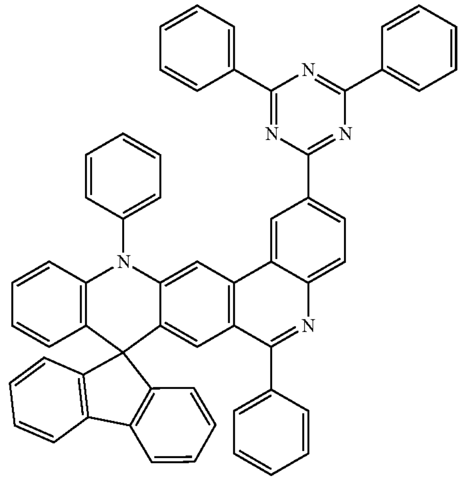

-continued
475
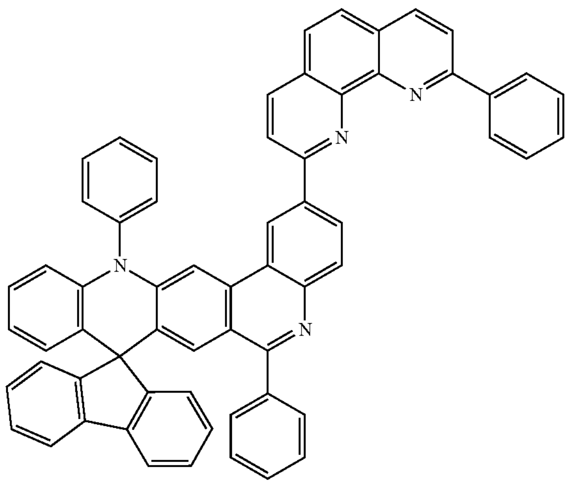
-continued
477
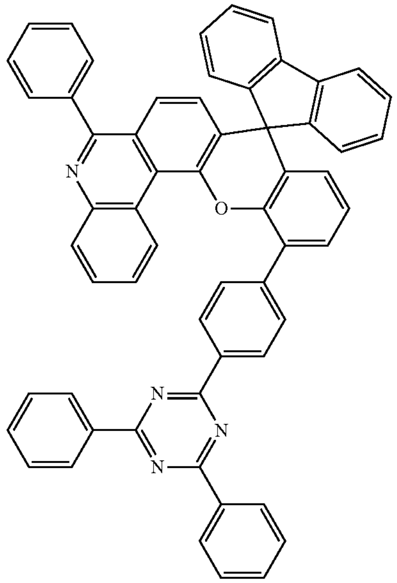
478
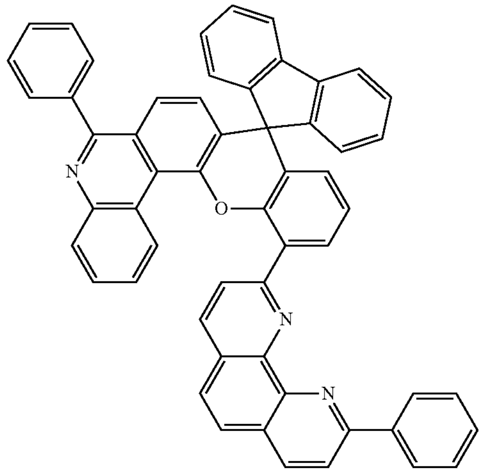
476
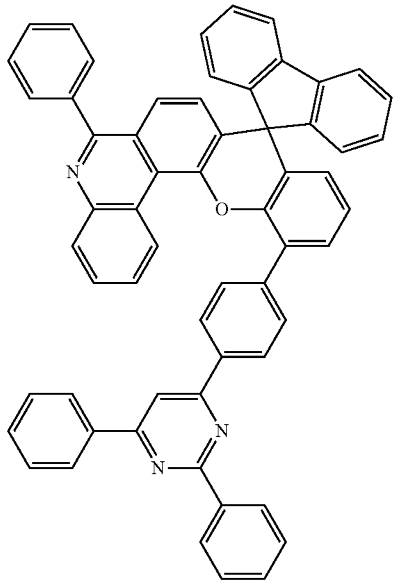
479
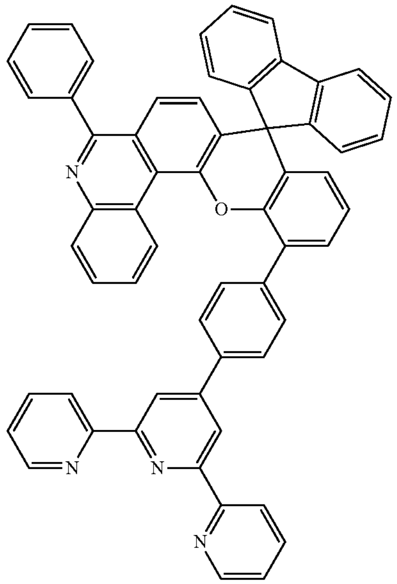

-continued
480
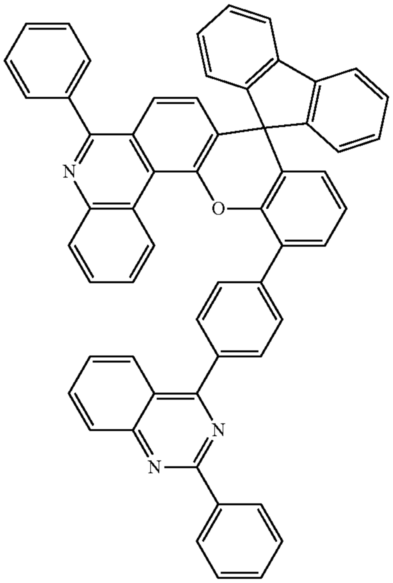
481
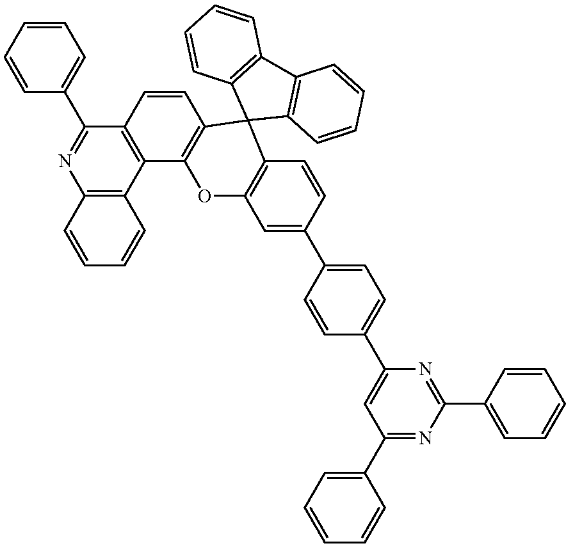
-continued
482
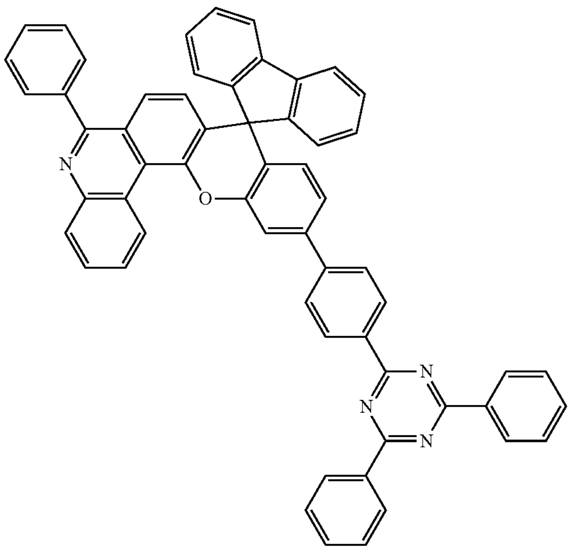
483
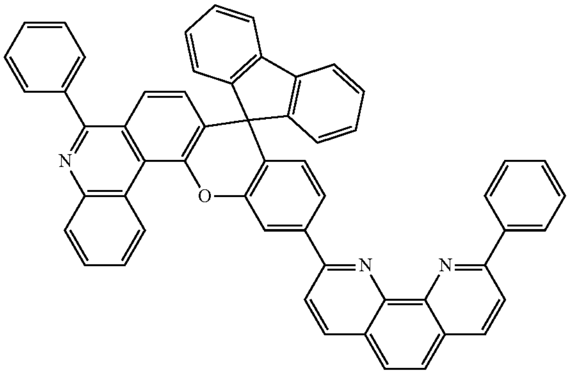
484
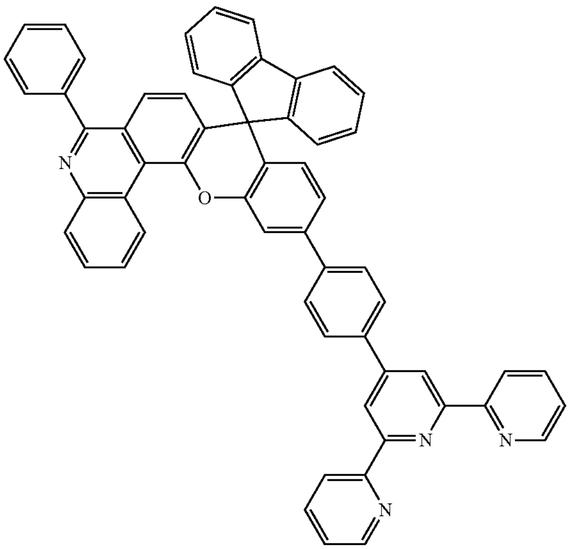

-continued
485
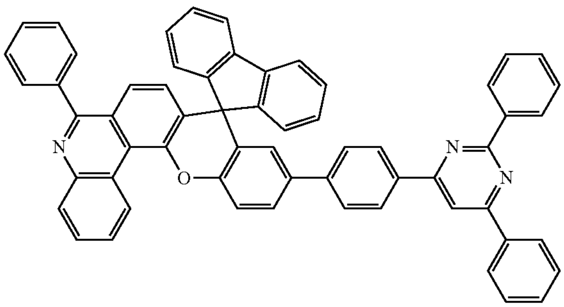
486
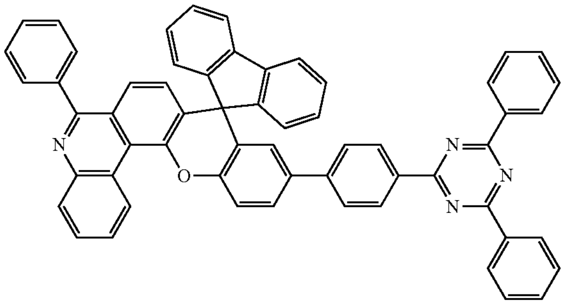
487
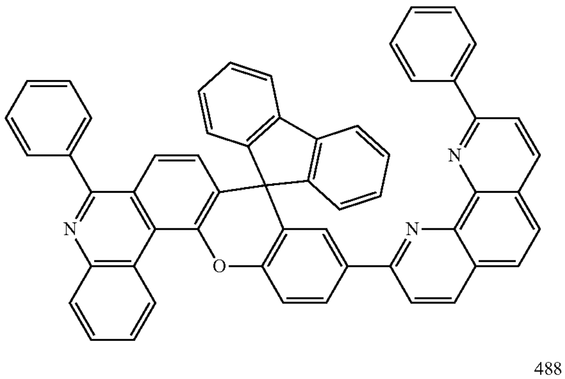
488
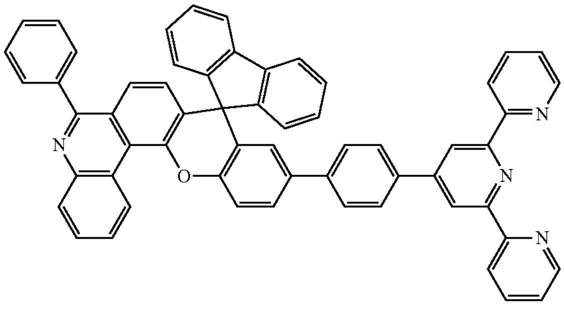
-continued
489
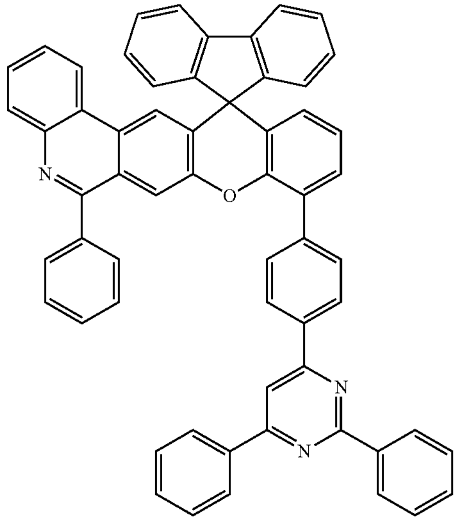
490
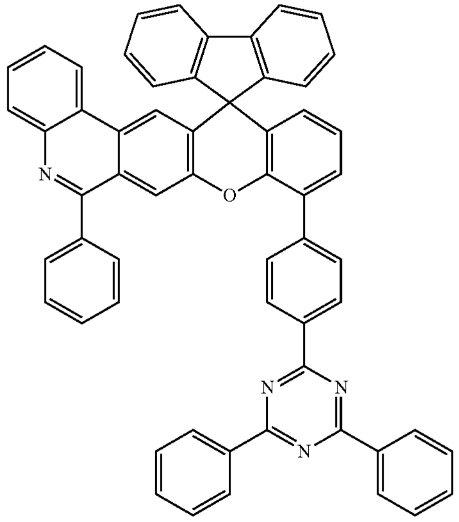
491
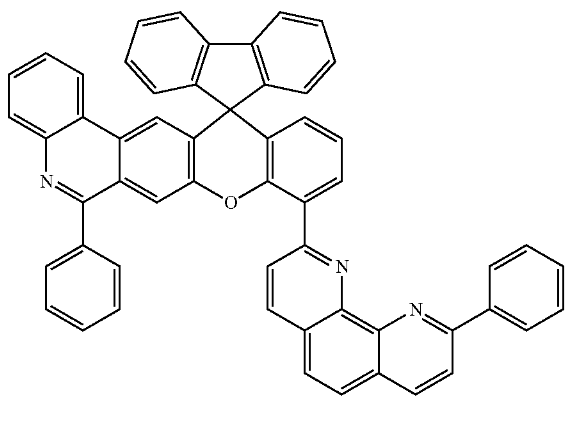

-continued
492
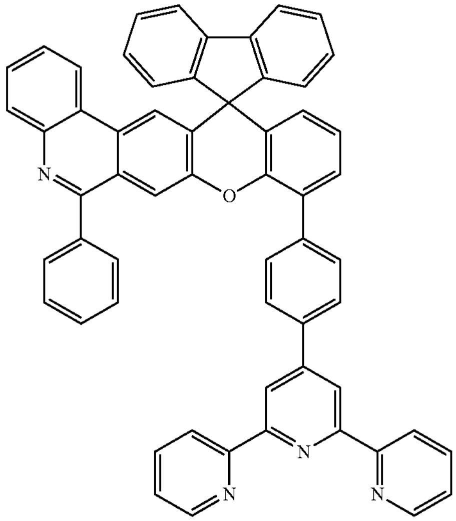
493
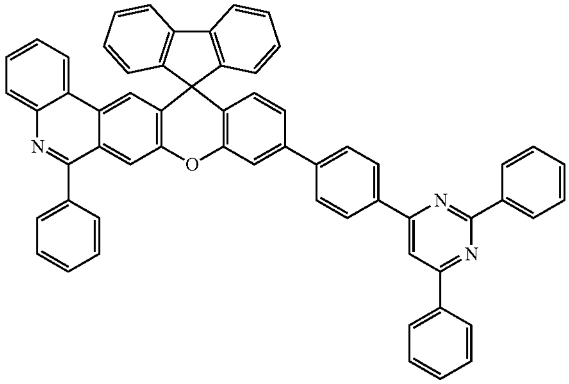
494
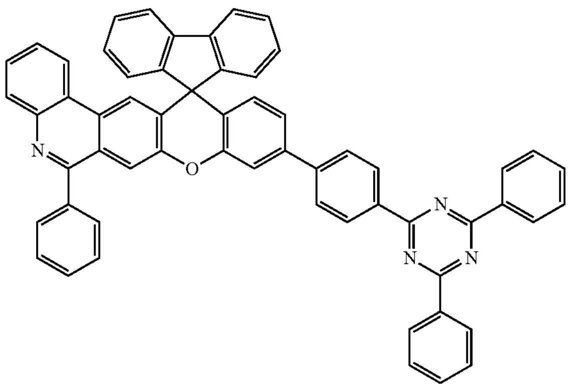
-continued
495
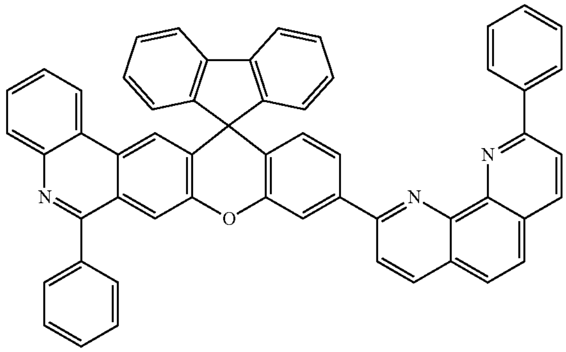
496
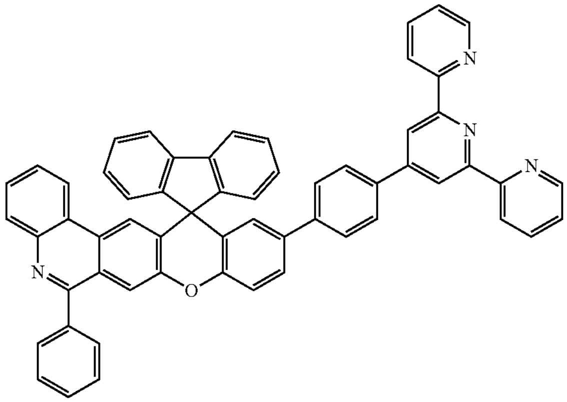
497
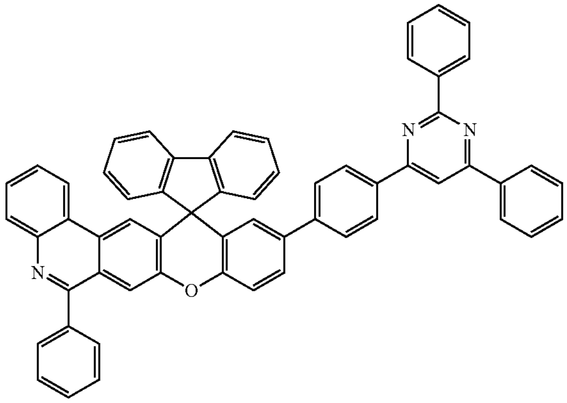
498
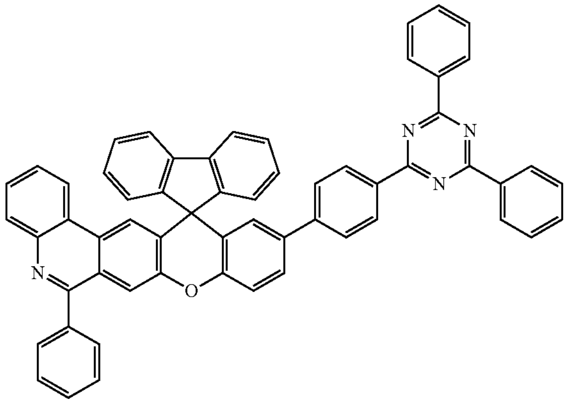

499
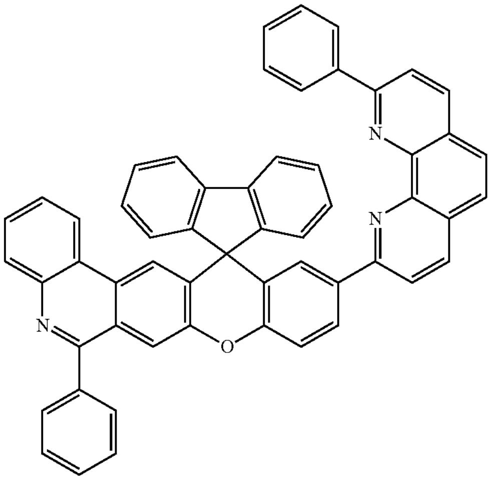
500
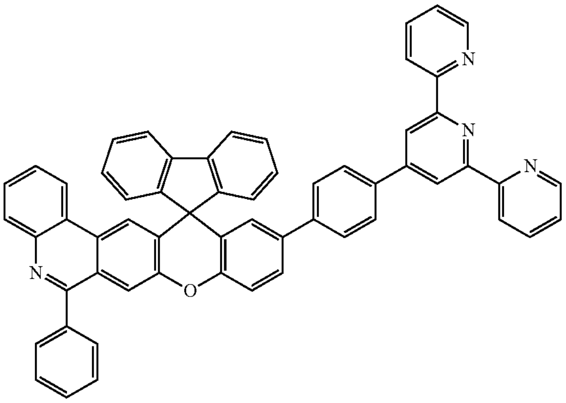
501
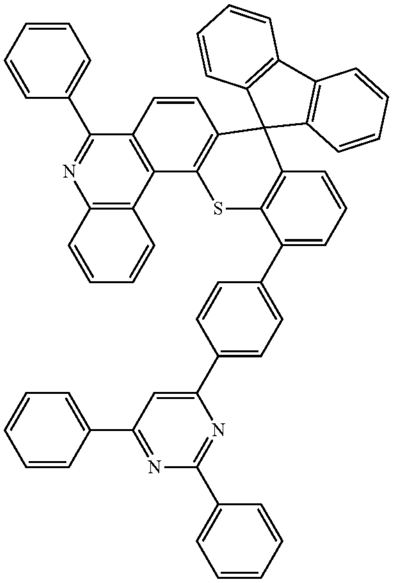
502
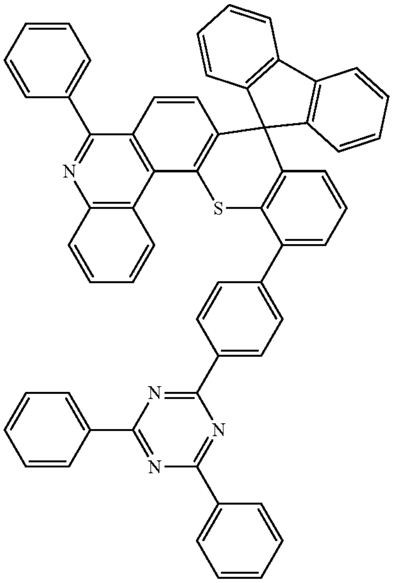
503
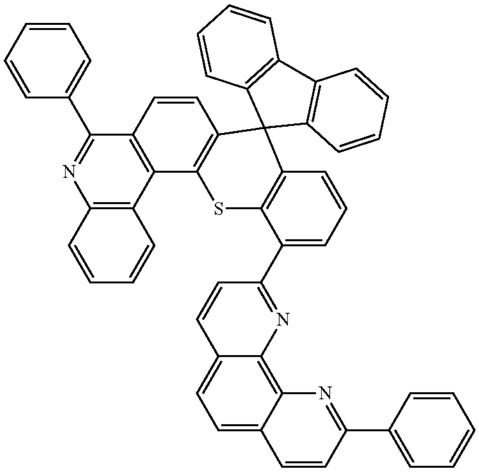
504
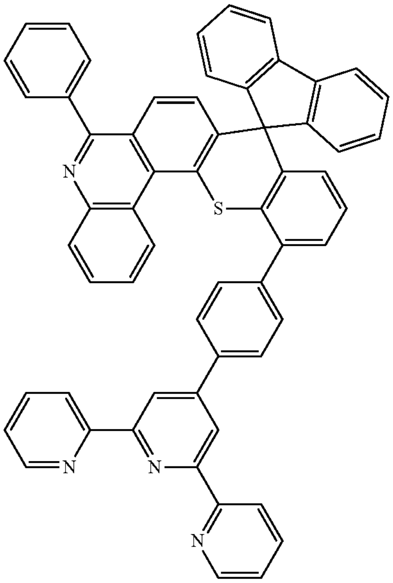

505
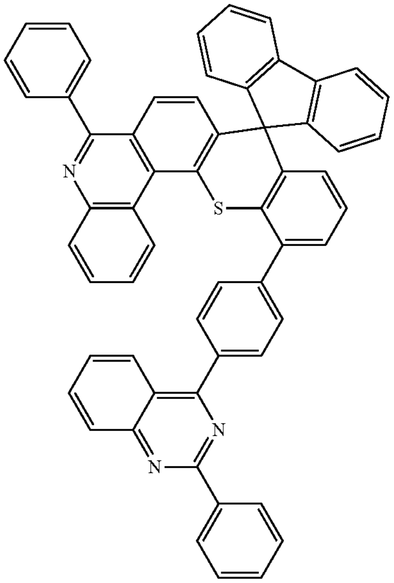
506
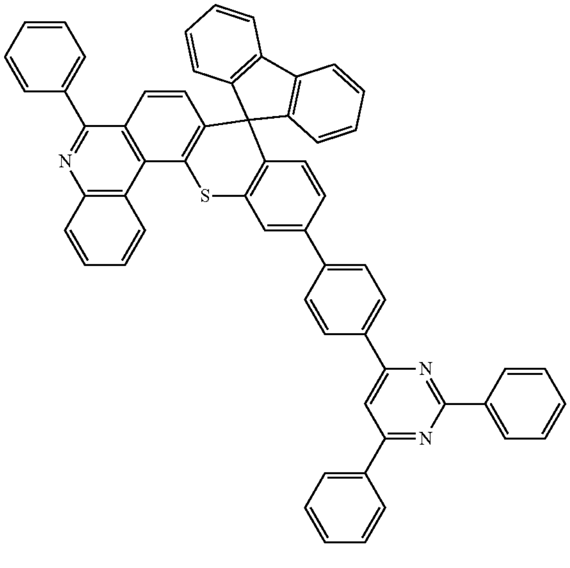
507
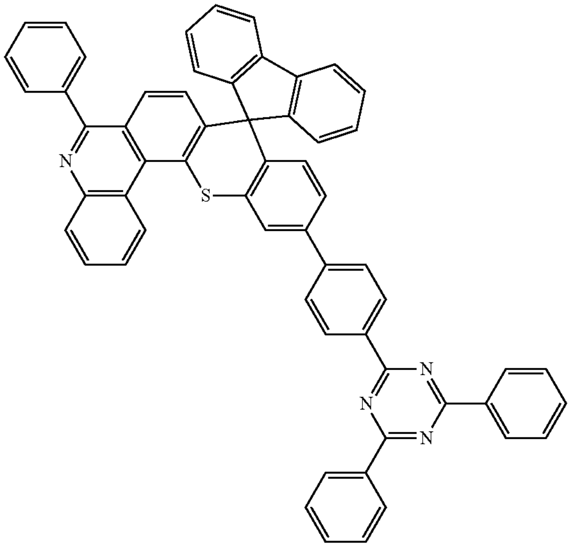
508
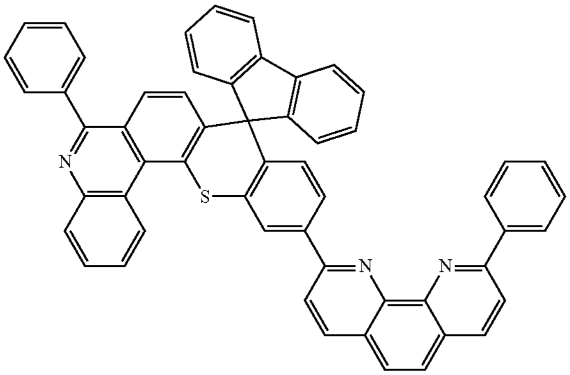
509
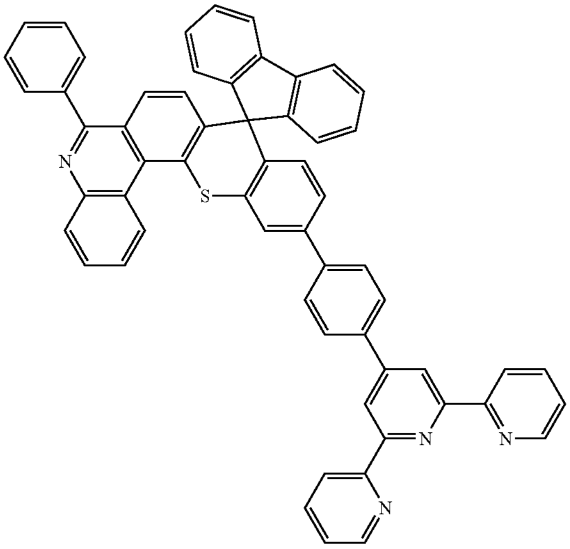

-continued
510
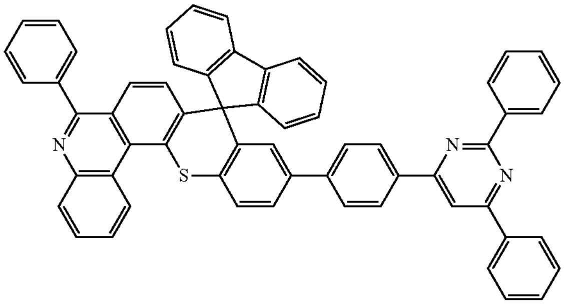
511
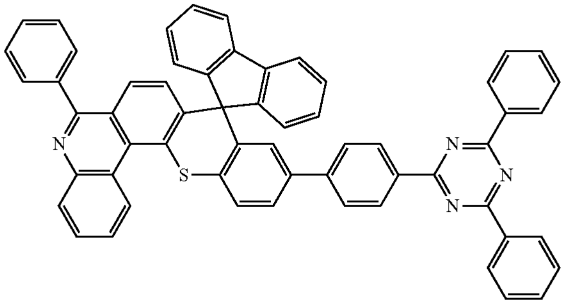
512
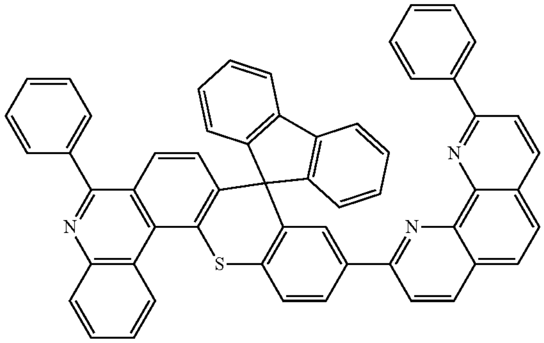
513
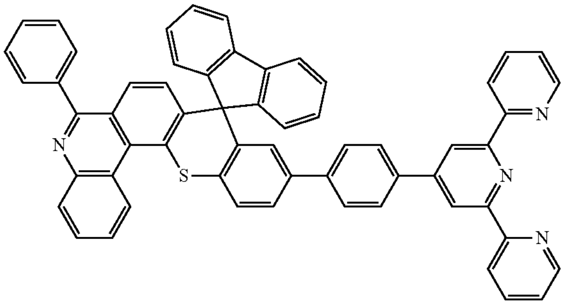
-continued
514
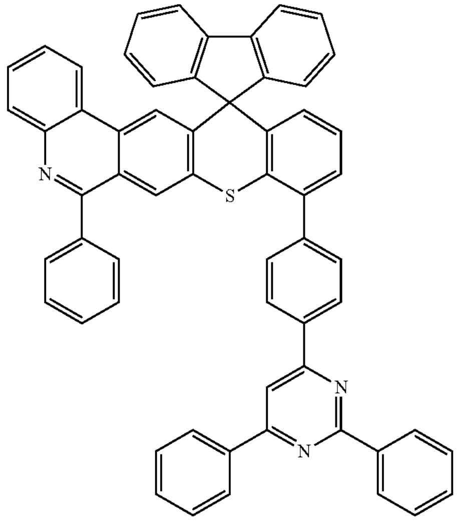
515
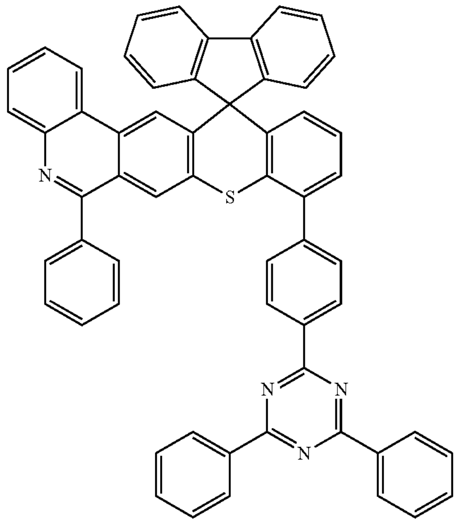
516
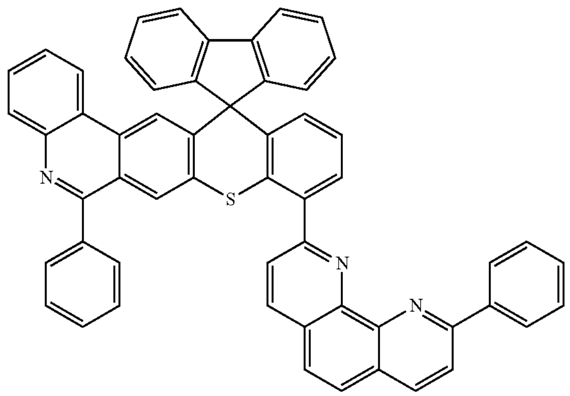

-continued
517
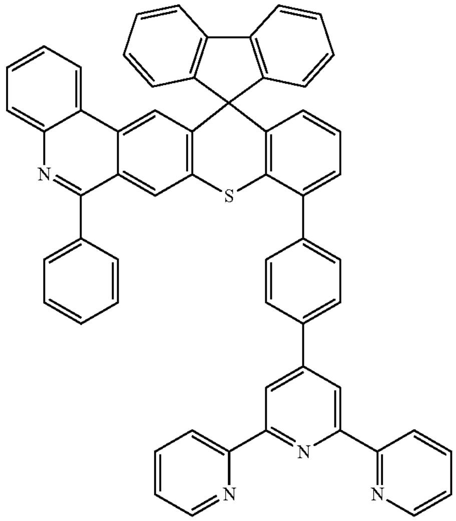
518
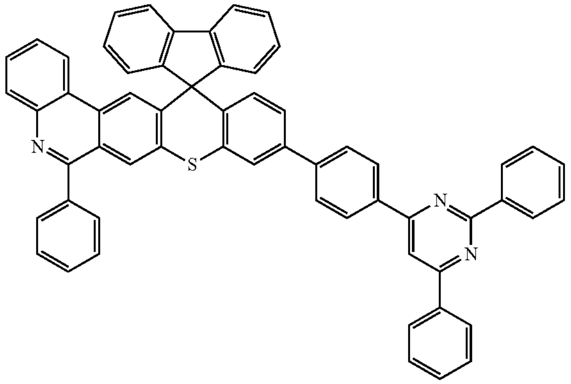
519
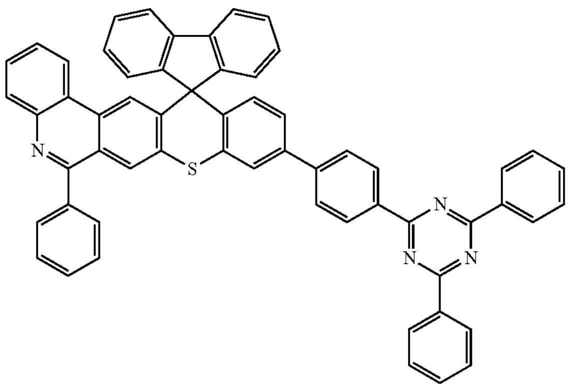
-continued
520
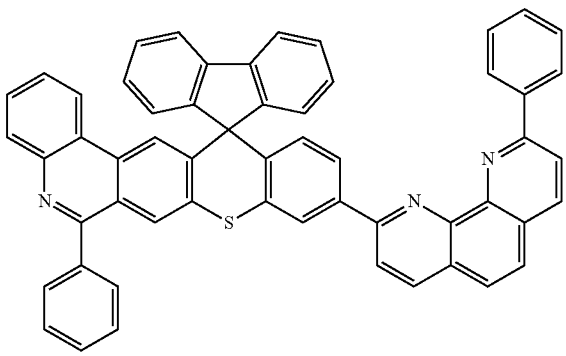
521
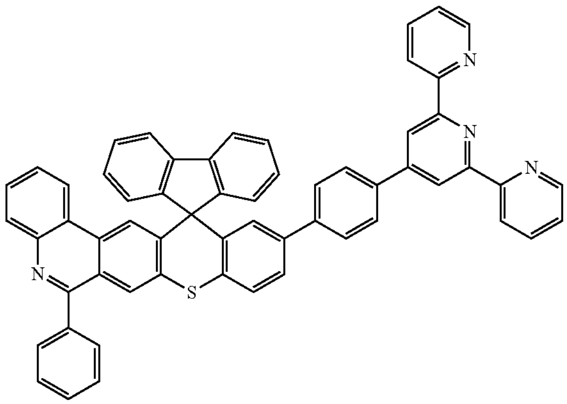
522
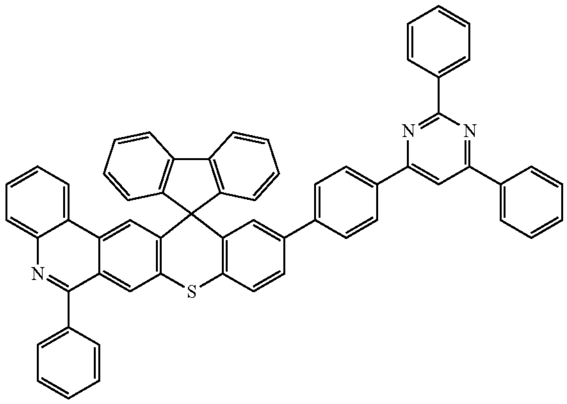
523
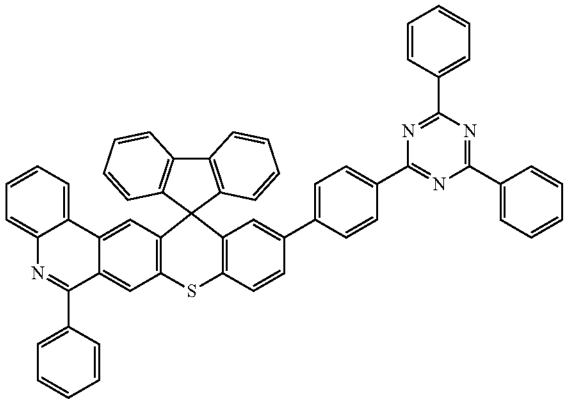

524
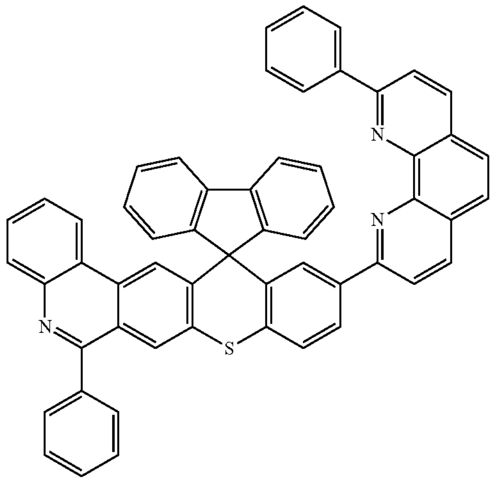
525
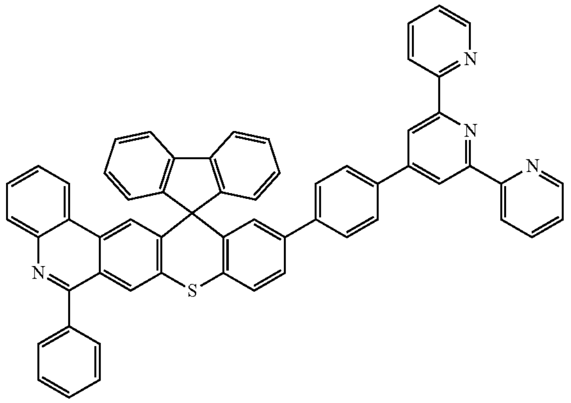
526
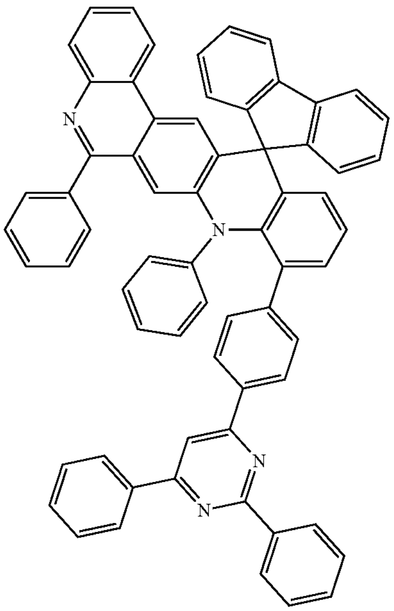
527
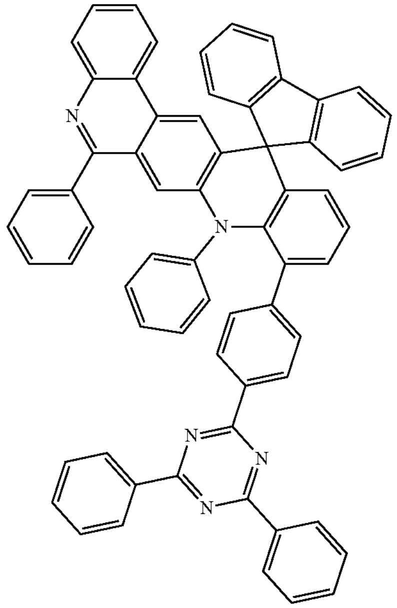
528
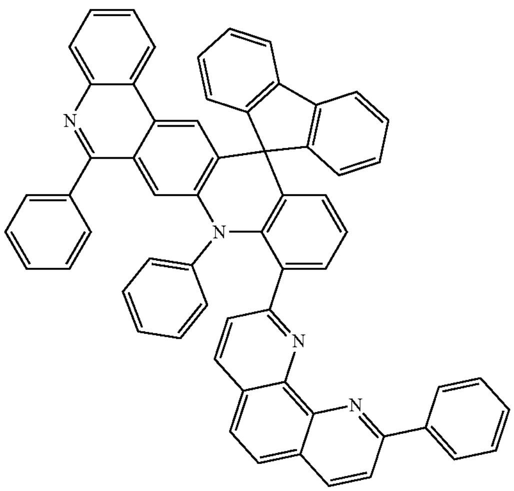

-continued
529
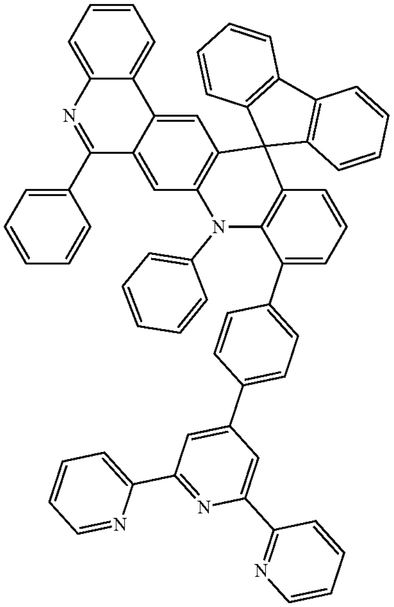
-continued
531
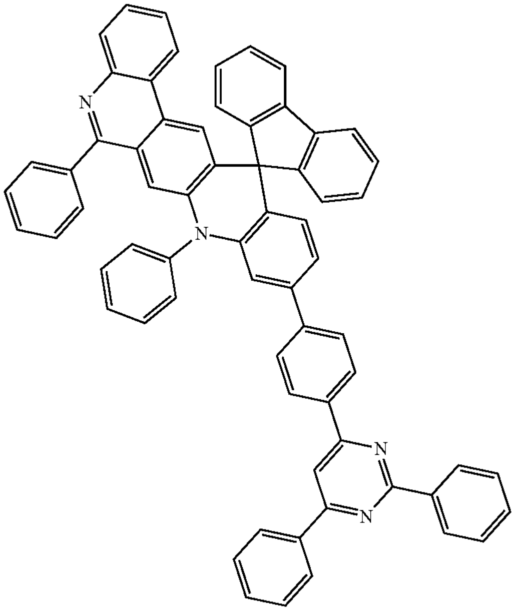
530
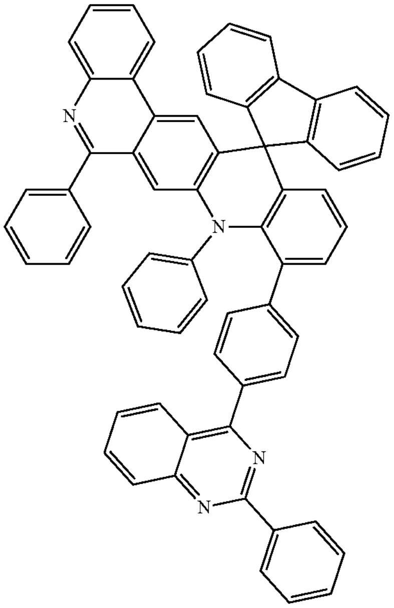
532
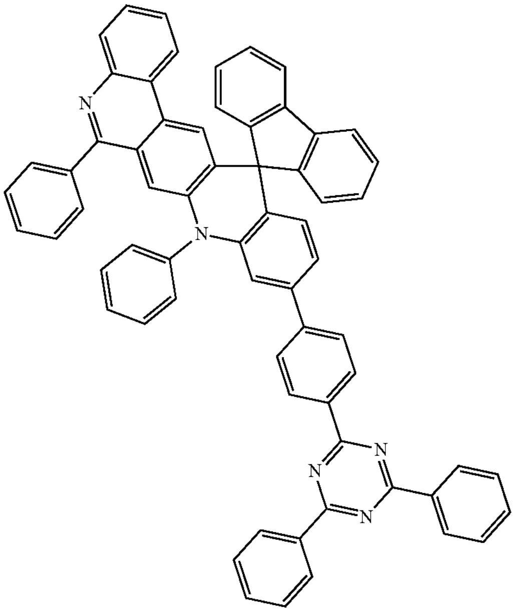

-continued
533
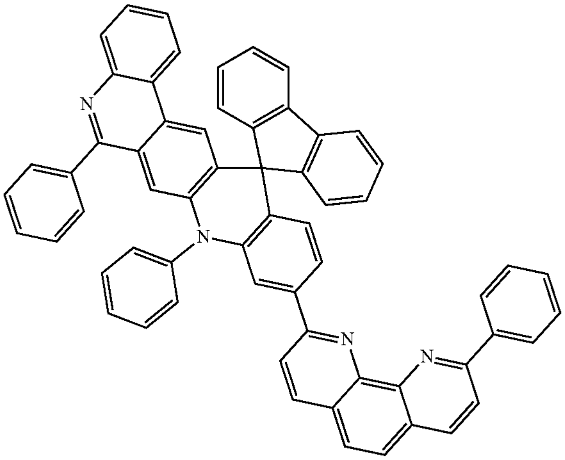
534
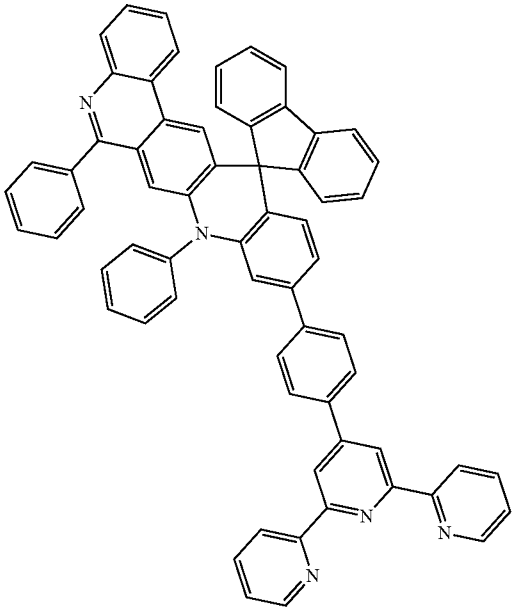
-continued
535
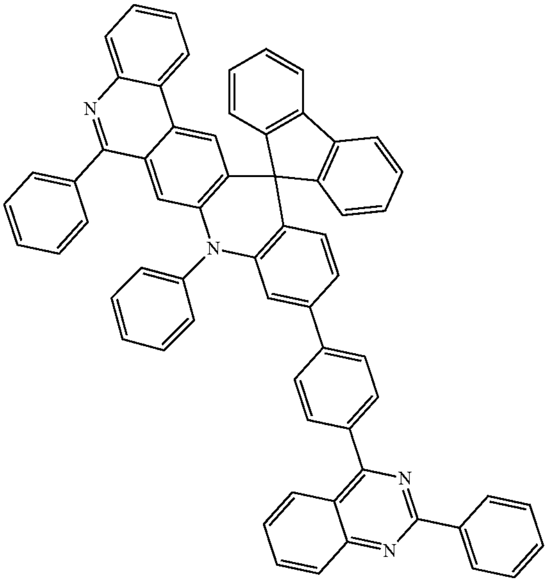
536
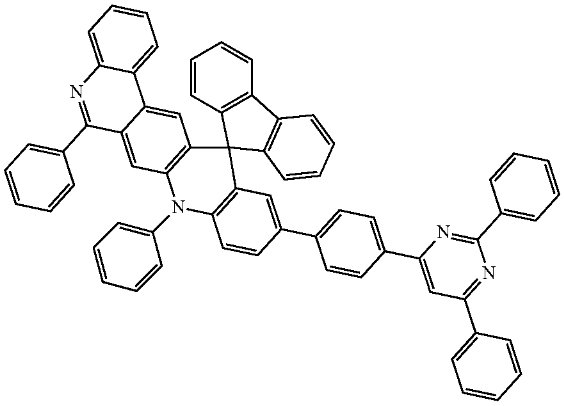
537
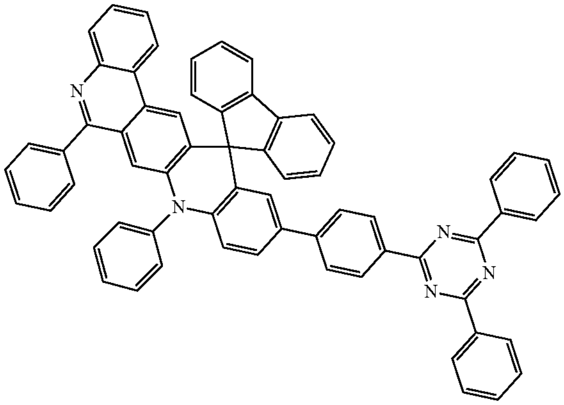

-continued
538
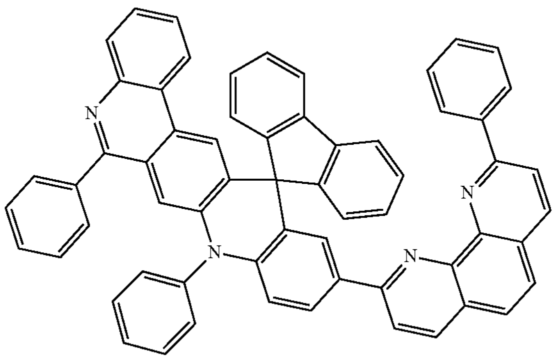
539
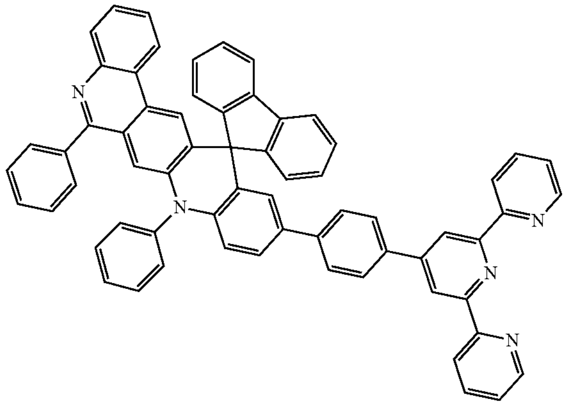
540
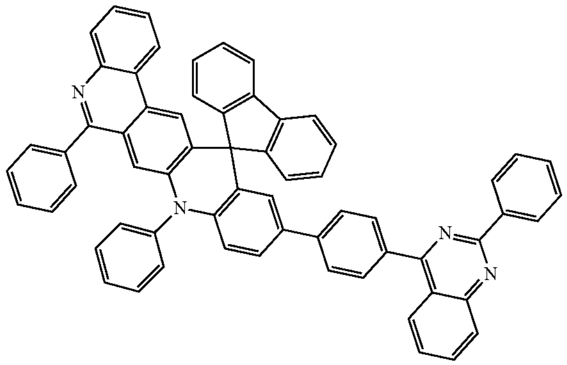
541
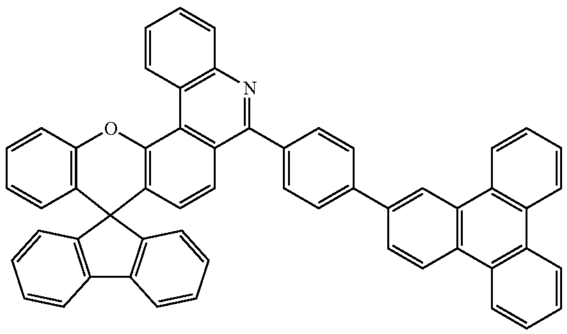
-continued
542
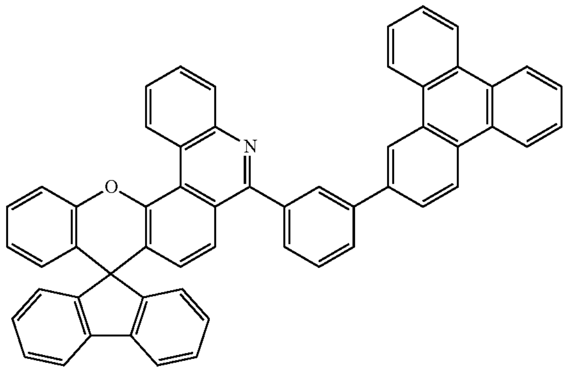
543
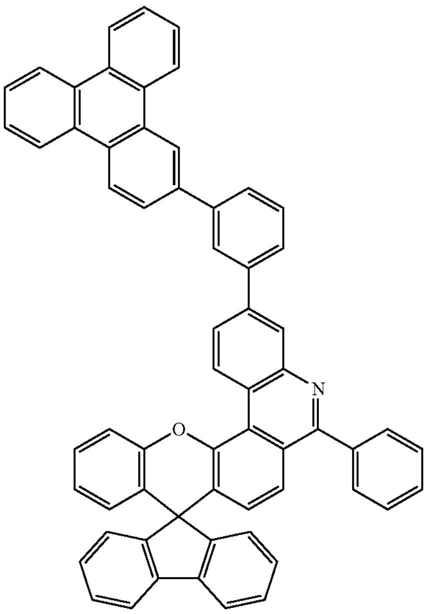
544
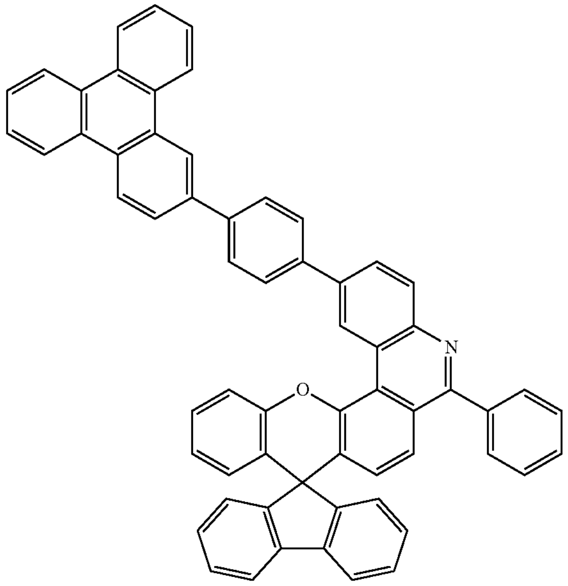

-continued
545
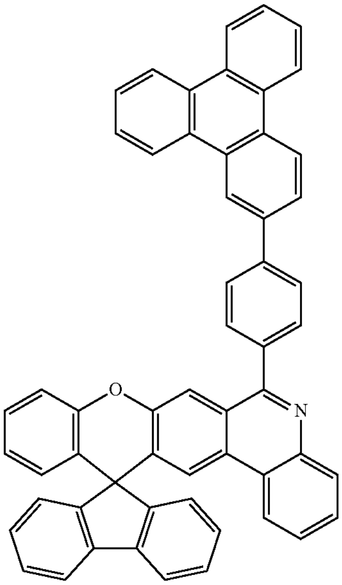
546
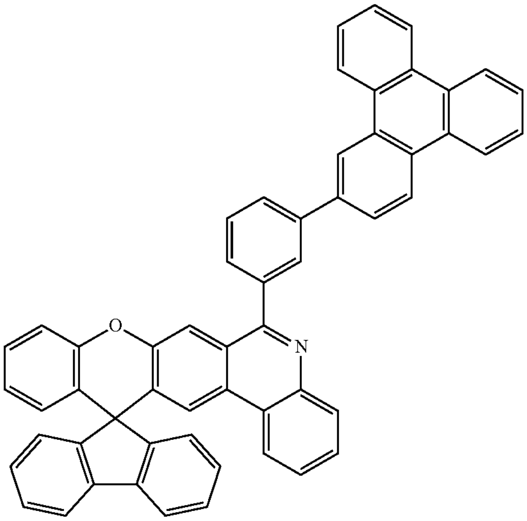
547
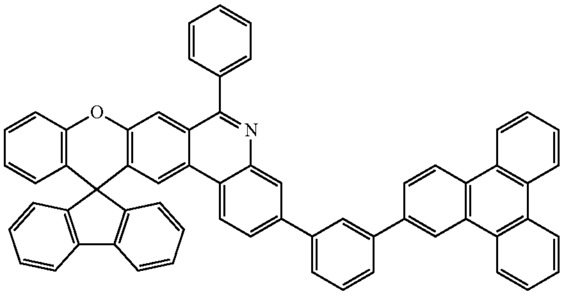
-continued
548
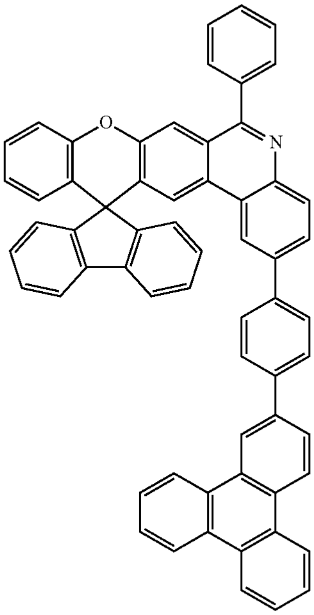
549
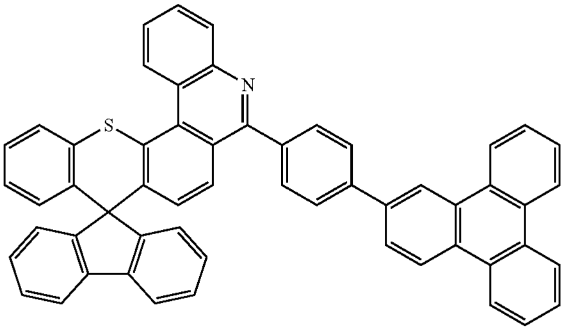
550
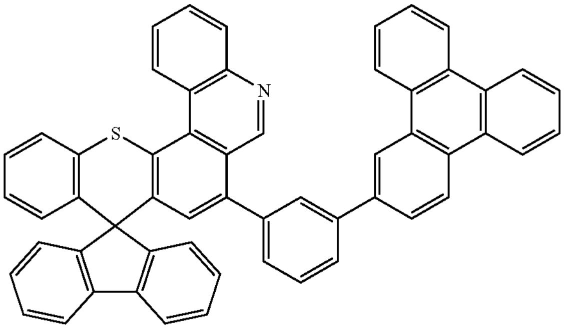

-continued

551

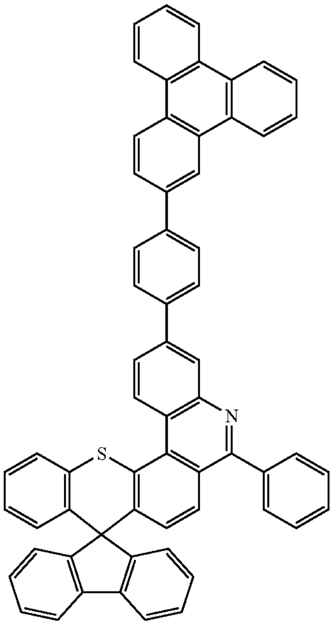

552

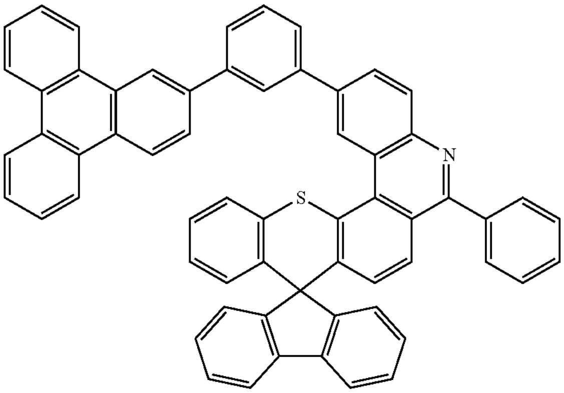

553

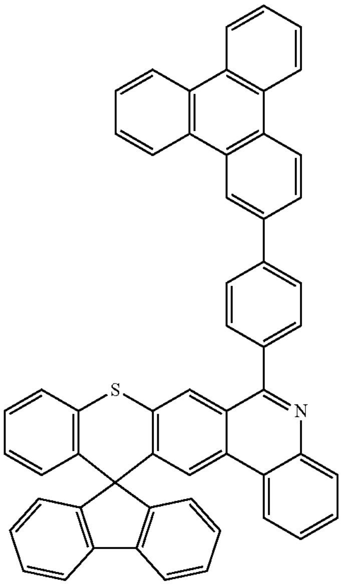

-continued

554

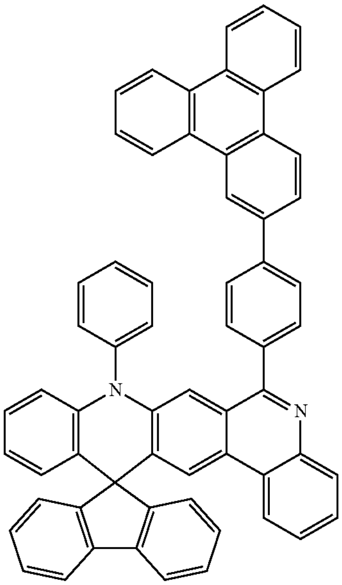

555

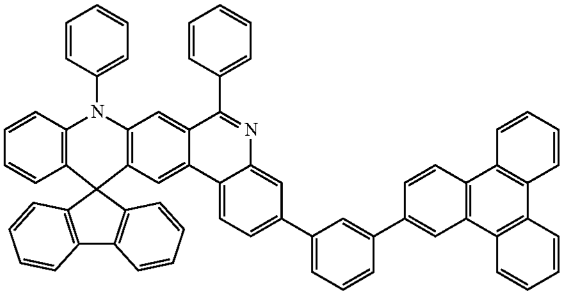

.

11. An organic light emitting device comprising:

a first electrode;

a second electrode; and one or more organic material layers provided between the first electrode and the second electrode, wherein one or more of the one or more organic material layers comprise the heterocyclic compound of claim 10.

12. The organic light emitting device of claim 11, wherein the one or more organic material layers comprise an electron transfer layer, and the electron transfer layer comprises the heterocyclic compound.

13. The organic light emitting device of claim 11, wherein the one or more organic material layers comprise a hole blocking layer, and the hole blocking layer comprises the heterocyclic compound.

14. The organic light emitting device of claim 11, further comprising one, two or more layers selected from the group consisting of a light emitting layer, a hole injection layer, a hole transfer layer, an electron injection layer, an electron transfer layer, an electron blocking layer and a hole blocking layer.

15. The organic light emitting device of claim 11, wherein the one or more organic material layers comprise a first stack, a charge generation layer and a second stack, wherein the first stack is provided on the first electrode and comprises a first light emitting layer;

wherein the charge generation layer is provided on the first stack; and wherein the second stack is provided on the charge generation layer and comprises a second light emitting layer.

16. The organic light emitting device of claim 15, wherein the charge generation layer comprises the heterocyclic compound.

17. The organic light emitting device of claim 15, wherein the charge generation layer is an N-type charge generation layer, and the charge generation layer comprises the heterocyclic compound.

* * * * *